United States Patent
Wittrup et al.

(10) Patent No.: US 11,459,389 B2
(45) Date of Patent: Oct. 4, 2022

(54) MONOCLONAL ANTIBODIES THAT BIND HUMAN CD161

(71) Applicants: Massachusetts Institute of Technology, Cambridge, MA (US); Dana-Farber Cancer Institute, Inc., Boston, MA (US)

(72) Inventors: Karl Dane Wittrup, Boston, MA (US); Kai Wucherpfennig, Brookline, MA (US); Byong Ha Kang, Cambridge, MA (US); Nathan D. Mathewson, Boston, MA (US)

(73) Assignees: Massachusetts Institute of Technology, Cambridge, MA (US); Dana-Farber Cancer Institute, Inc., Boston, MA (US)

(*) Notice: Subject to any disclaimer, the term of this patent is extended or adjusted under 35 U.S.C. 154(b) by 43 days.

(21) Appl. No.: 17/001,031

(22) Filed: Aug. 24, 2020

(65) Prior Publication Data

US 2021/0122826 A1  Apr. 29, 2021

Related U.S. Application Data

(60) Provisional application No. 62/925,663, filed on Oct. 24, 2019.

(51) Int. Cl.
*C07K 16/28* (2006.01)

(52) U.S. Cl.
CPC ...... *C07K 16/2851* (2013.01); *C07K 2317/21* (2013.01); *C07K 2317/33* (2013.01); *C07K 2317/565* (2013.01); *C07K 2317/622* (2013.01); *C07K 2317/74* (2013.01); *C07K 2317/76* (2013.01); *C07K 2317/92* (2013.01)

(58) Field of Classification Search
CPC ............ C07K 16/2851; C07K 2317/21; C07K 2317/33; C07K 2317/565; C07K 2317/622; C07K 2317/74; C07K 2317/76; C07K 2317/92
See application file for complete search history.

(56) References Cited

U.S. PATENT DOCUMENTS

| | | |
|---|---|---|
| 3,710,795 A | 1/1973 | Higuchi et al. |
| 3,773,919 A | 11/1973 | Boswell et al. |
| 4,863,457 A | 9/1989 | Lee |
| 5,223,409 A | 6/1993 | Ladner et al. |
| 5,403,484 A | 4/1995 | Ladner et al. |
| 5,427,908 A | 6/1995 | Dower et al. |
| 5,501,856 A | 3/1996 | Ohtori et al. |

FOREIGN PATENT DOCUMENTS

WO  2019/094983 A1  5/2019

OTHER PUBLICATIONS

Paul, WE (1993) Fundamental Immunology, 3rd ed. Raven Press, NY, Chap. 9, pp. 292-295.*
Rudikoff, S et al. (1982) Proc. Natl. Acad. Sci. USA, 79:1979-1983.*
Colman, PM (1994) Research in Immunology, Elsevier, NY, 145(1):33-36.*
International Search Report and Written Opinion, PCT/US2020/047627, dated Dec. 4, 2020, 13 pages.
Nigro, et al. (2019) Ann Transl Med 7:105.
Nuttall et al., (2000) Curr. Pharm. Biotech. 1:253-263.
Ohtsuka et al., Biol. Chem. 260:2605-2608, 1985.
Ossipow, et al. (2014) Humana Press p. 151-181.
Paes et al., J. Am. Chem. Soc. 131 (20): 6952-6954 (2009).
Pardoll, D., Nature. 12: 252-264, 2012.
Patel, et al. (2014) Science 344:1396-1401.
Pavisic et al. (2010) Int J Pharm 387(1-2):110-119.
Pearson & Lipman, Proc. Nat'l. Acad. Sci. USA 85:2444 (1988).
Pereboev et al. (2001) J Virol 75:7107-7113.
Persic et al. (1997) Gene 187:9-18.
Burton et al. (1994) Advances in Immunology 57:191-280.
Picelli, et al. (2014) Nat. Protoc. 9:171-181.
Poljak, (1994) Structure 2(12):1121-1123.
Pollock et al. (1999) J Immunol Methods 231(1-2):147-157.
Reardon, et al. (2019) 5th Quadrennial Meeting of the World Federation of Neuro-Oncology Societies Neuro-Oncol 19 (suppl 3), abstract OS103.
Reichmann et al., (1999) J. Immunol. Meth. 231:25-38.
Reineke et al., Curr. Opin. Biotechnol. 12: 59-64, 2001.
Robbie et al., Antimicrob. Agents Chemother, 2013, 57(12):6147.
Robbins, et al. (2008) J. Immunol. 180:6116-6131.
Roberts et al. (2002) Advanced Drug Delivery Reviews 54:459-476

Rockberg et al., Nature Methods 5: 1039-1045, 2008.
Rogers et al. (1997) J Nucl Med 38:1221-1229.
Rondon and Marasco, (1997) Annu. Rev. Microbiol. 51:257-283.
Rosen et al. (2005) J. Immunol. 175:7796-7799.
Rossolini et al., Mol. Cell. Probes 8:91-98, 1994.
Sarver et al. (1982) Proc Natl Acad Sci USA, 79:7147.
Schaffitzel et al. (1999) J Immunol Methods 231:119-135.
Schoonbroodt et al. (2005) Nucleic Acids Res 33(9):e81.
Shi et al. (2010) JMB 397:385-396.
Shiraishi et al. (2007) Nucleic Acids Symposium Series 51(1):129-130.
Shopes (1992) Immunol 148:2918-2922.
Sidman et al., Biopolymers, 22:547-556 (1983).
Smith & Waterman, Adv. Appl. Math. 2:482 (1981).
Songsivilai & Lachmann, (1990) Clin. Exp. Immunol. 79:315-321.
Southern and Berg (1982) Mol Appl Genet 1:327.
Stahli et al., Methods in Enzymology 9:242 (1983).
Stubbington, et al. (2016) Nat Methods 13:329-332.
Suckau et al., Proc. Natl. Acad. Sci. USA 87: 9848-9852, 1990.

(Continued)

*Primary Examiner* — Robert S Landsman
(74) *Attorney, Agent, or Firm* — McDonnell Boehnen Hulbert & Berghoff LLP

(57) ABSTRACT

The present disclosure relates to, inter alia, compounds (e.g., antibodies, or antigen-binding fragments thereof) that bind to an epitope of CD161 an inhibit the interaction between CD161 and CLEC2D, and the use of the compounds in methods for treating, or ameliorating one or more symptoms of, cancer.

16 Claims, 29 Drawing Sheets

Specification includes a Sequence Listing.

(56) References Cited

OTHER PUBLICATIONS

Tirosh et al. (2016) Nature 539:309-313.
Todorovska et al., (2001) J. Immunol. Methods 248(1):47-66.
Trowsdale, et al. (2001) J Immunol Rev 181:20-38.
Van de Water et al., Clin. Immunol. Immunopathol. 1997, 85(3): 229-235, 1997.
Van Gurp et al. (2008) Am J Transplantation 8(8):1711-1718.
Van Kuik-Romeijn et al. (2000) Transgenic Res 9(2):155-159.
Venteicher et al. (2017) Science 355:eaai8478.
Wang et al. (2015) Frontiers Immunol 6:368.
Wei, S. et al. Cancer Discovery (2018) 8:1069.
Wherry & Kurachi (2015) Nat Rev Immunol 15(8):486-99.
Wigler et al. (1979) Cell 16:77.
Woroniecka et al. (2018) Clin Cancer Res 24:4175-4186.
Wright et al. (1991) EMBO J 10(10):2717-2723.
Wunsch (J. Mol. Biol. (48):444-453 (1970).
Xu et al. (2013) Protein Eng Des Sel (2013) 26:663-670.
Yeung et al. (2002) Biotechnol Prog 18:212-220.
Yi et al., (2 010) Immunology 129(4):474-481.
Yokoyama et al. (2003) Nat Rev Immunol 3:304-316.
Zhang, et al. (2018) Nature 564:268-272.
Zheng, et al. (2017) Cell 169:1342-1356.
Neftel, et al. (2019) Cell 178:835-849.
Hetherington et al. (2006) Antimicrobial Agents and Chemotherapy 50(10): 3499-3500.
Hou et al. (1998) Cytokine 10:319-30.
Houdebine (2002) Curr Opin Biotechnol 13(6):625-629.
Hudson and Kortt, (1999) J. Immunol. Methods 231(1):177-189.
Jerby-Amon, et al. (2018) Cell 175:984-997.
Johnnson, B., et al. (1991) Anal. Biochem. 198:268-277.
Johnson et al. (1999) J Med Chem 42:4640-4649.
Johnsson, B., et al. (1995) J. Mol. Recognit. 8:125-131.
Jonsson, U., et al. (1991) Biotechniques 11:620-627.
Jonsson, U., et al. (1993) Ann. Biol. Clin. 51:19-26.
Kaszubska et al. (2000) Protein Expression and Purification 18:213-220.
Needleman & Wunsch, J. Mol. Biol. 48:443 (1970).
Kelley et al. (2005) PLoS Genet 1:129-139.
Kelly, et al. (2018) J Mol Biol 430:119-130.
Kettleborough et al. (1994) Eur J Immunol 24:952-958.
Kieke et al. (1997) Protein Eng 10:1303-1310.
Kinstler et al. (2002) Advanced Drug Deliveries Reviews 54:477-485.
Kirkland et al., J. Immunol. 137:3614 (1986).
Klemm et al. (2000) Microbiology 146:3025-3032.
Kostelny et al., (1992) J. Immunol. 148:1547-1553.
Langer et al., J. Biomed. Mater. Res., 15: 167-277 (1981).
Langer, Chem. Tech., 12:98-105 (1982).
Langmead, et al. (2009) Genome Biol 10:R25.
Lanier, et al. (1994) J Immunol 153:2417-2428.
Lee et al. (1999) Bioconjug Chem 10(6): 973-8.
Lefranc (2005) Nucl Acids Res 33:D593-D597.
Lefranc, M.-P., "The IMGT unique numbering for immunoglobulins, T cell Receptors and Ig-like domains", The Immunologist, 7, 132-136 (1999).
Lodmell et al. (2000) Vaccine 18:1059-1066.
Lonberg & Huszar, (1995) Intern. Rev. Immunol. 13:65-93.
Lonberg (2005) Nature Biotech. 23(9):1117-1125.
Lonberg et al., (1994) Nature 368(6474): 856-859.
Lonberg, (1994) Handbook of Experimental Pharmacology 113:49-101.
Long (1999) Annu Rev Immunol 17:875-904.
Lusky and Botchan (1981) Nature 293:79.
Maggi et al. (2010) Eur. J. Immunol. 40:2174-2181.
Mayrose et al., (2007) Bioinformatics 23:3244-3246.
Meilhoc et al. (1990) Bio/Technology 8:223-227.
Merz et al. (1995) J Neurosci Methods 62(1-2):213-9.
Meyers and W. Miller (CABIOS, 4:11-17 (1989).
Michael et al. (1995) Gene Ther 2:660-668.
Moldenhauer et al., Scand. J. Immunol. 32:77 (1990).
Morel et al., Mol. Immunol. 25(1):7 (1988).
Moretta, et al. (2004) Curr Opin Immunol 16:626-633.
Motz & Coukos, (2013).
Mueller et al. (1997) Mol Immunol 34(6):441-452.
Mulligan and Berg (1981) Proc Natl Acad Sci USA 78:2072.
Muyldermans et al., (2001) Trends Biochem. Sci. 26:230-235.

* cited by examiner

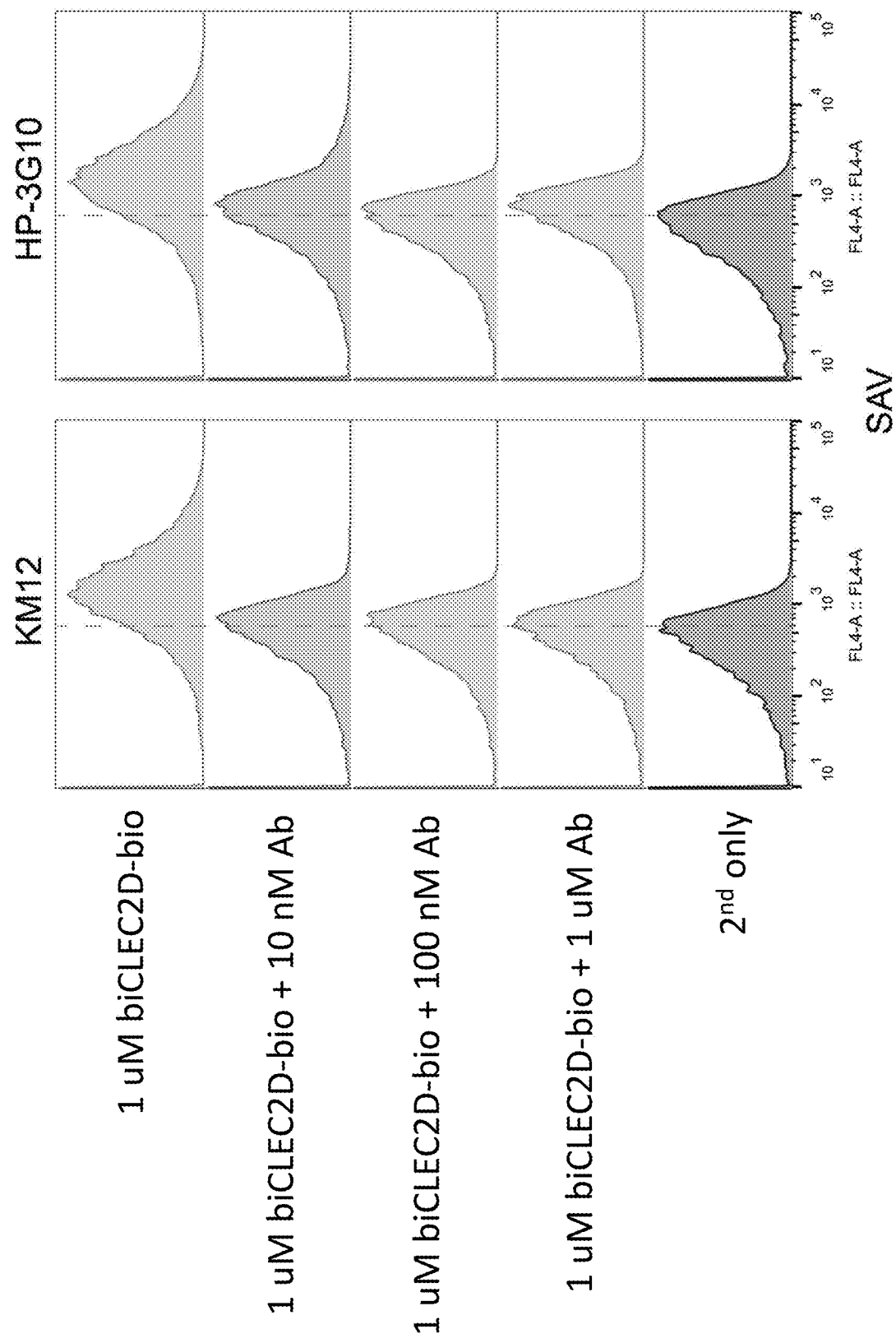

MONOCLONAL ANTIBODIES THAT BIND HUMAN CD161

CROSS-REFERENCE TO RELATED APPLICATIONS

This application claims the benefit of U.S. Provisional Patent Application Ser. No. 62/925,663, filed Oct. 24, 2019. The entire contents of which is incorporated herein by reference.

GOVERNMENT FUNDING

This invention was made with Government support under Grant Nos. R01 CA096504 and L30 CA231679 awarded by the National Institutes of Health (NIH). The Government has certain rights in the invention.

REFERENCE TO SEQUENCE LISTING

The instant application contains a Sequence Listing which has been submitted electronically in ASCII format via EFS-Web and is hereby incorporated by reference in its entirety. Said ASCII copy, created Dec. 14, 2020, is named "MITN-055_Sequence-Listing.txt" and is 313529 bytes in size.

BACKGROUND

In recent years, an increasing body of evidence suggests the immune system operates as a significant barrier to tumor formation and progression. The principle that naturally-occurring T cells with anti-tumor potential or activity exist in a patient with cancer has rationalized the development of immunotherapeutic approaches in oncology Immune cells, such as T cells, macrophages, and natural killer cells, can exhibit anti-tumor activity and effectively control the occurrence and growth of malignant tumors. Tumor-specific or -associated antigens can induce immune cells to recognize and eliminate malignancies (Chen & Mellman, (2013) *Immunity* 39(1):1-10). In spite of the existence of tumor-specific immune responses, malignant tumors often evade or avoid immune attack through a variety of immunomodulatory mechanisms resulting in the failure to control tumor occurrence and progression (Motz & Coukos, (2013) *Immunity* 39(1):61-730). Indeed, an emerging hallmark of cancer is the exploitation of these immunomodulatory mechanisms and the disablement of anti-tumor immune responses, resulting in tumor evasion and escape from immunological killing (Hanahan and Weinberg (2011) *Cell* 144(5):646-674).

Novel approaches in the immunotherapy of cancer involve counteracting these immune evasion and escape mechanisms and inducing the endogenous immune system to reject tumors. Endogenous or therapy-induced T cell responses typically target a diverse set of tumor antigens, offering the possibility of treating tumors through T cell-mediated immunity. However, suppressive mechanisms in the tumor often inhibit or block anti-tumor T cell responses, particularly through inhibitory signaling pathways that prevent T cell activation. Blockade of the inhibitory PD-1 and/or CTLA-4 receptors on T cells for example, has been a major therapeutic advance in a number of human cancer types. However, not all tumors respond to PD-1 therapy (see, e.g., Filley et al (2017) *Oncotarget* 8:91779-91794; Reardon, et al (2019) 5th Quadrennial Meeting of the World Federation of Neuro-Oncology Societies Neuro-Oncol 19 (suppl 3), abstract OS103). Thus, there remains a need to identify additional immunosuppressive mechanisms that inhibit or block anti-tumor T cell responses and targets that are subject to therapeutic manipulation.

SUMMARY OF THE DISCLOSURE

The present disclosure pertains to human monoclonal antibodies that bind to human CD161, and antigen binding fragments thereof, for use in treating or delaying progression of cancer or reducing or inhibiting tumor growth in a subject. The disclosure is based, at least in part, on gene expression analysis of human glioma samples, wherein it was discovered that inhibitory NK cell receptors are expressed on tumor-infiltrating T cells, in particular the KLRB1 gene encoding CD161. CD161 was found to be expressed by both CD8 and CD4 T cell populations, while the CD161 ligand CLEC2D was found to be expressed by tumor cells and tumor-infiltrating myeloid cells. Without being bound by theory, it is thought that CLEC2D within the tumor functions to suppress tumor-infiltrating T cells, thereby blocking their anti-tumor potential. Functional experiments described herein support this understanding, wherein inactivation of KLRB1 in primary human T cells resulted in increased anti-tumor function of these T cells when evaluated both in vitro and in vivo. Additionally, CD161 (KLRB1) was found to be expressed by tumor-infiltrating T cells in multiple human cancer samples. Thus, the present disclosure identifies CD161 as a target for immunotherapy of diffuse gliomas and other diverse human cancer types. Accordingly, the present disclosure provides agents (e.g., monoclonal antibodies) that inhibit interaction of CD161 with its ligand CLEC2D.

In some aspects, the present disclosure provides fully-human monoclonal antibodies that bind to human CD161 and are effective for blocking or inhibiting the CD161-CLEC2D interaction. While the disclosure is not bound by any particular theory or mechanism of action, inhibition of the CD161-CLEC2D interaction by the anti-CD161 antibodies disclosed herein is believed to derive in part from the epitope on human CD161 recognized by the antibodies of the disclosure and/or the binding affinity to human CD161 of the antibodies of the disclosure. Without being bound by theory, in some embodiments, the anti-CD161 antibodies of the disclosure are believed to bind to an epitope on human CD161 that overlaps the ligand binding site, thereby directly blocking CLEC2D binding to CD161. While in some embodiments, the anti-CD161 antibodies of the disclosure are believed to bind to an epitope on human CD161, wherein binding alters the conformation of the ligand binding site and/or sterically blocks the ligand binding site, thereby blocking CLEC2D binding to CD161. In some embodiments, the anti-CD161 antibodies of the disclosure have binding affinity (e.g., sub-nanomolar equilibrium dissociation constant ($K_D$)) for CD161 that greatly exceeds the affinity of CLEC2D for CD161 ($K_D$ of 48 µM as reported by Kamishikiryo, et al (2011) 286:23823-23830), thereby inhibiting or preventing competitive binding of CLEC2D to CD161. As described herein, the use of the antibodies of the disclosure to block the CD161-CLEC2D interaction is effective for increasing the activation of primary human T cells in response to target tumor cells when evaluated in vitro. Moreover, the antibodies of the disclosure demonstrate low cross-reactivity to other human proteins in the C-type lectin family that share structural homology with human CD161.

Accordingly, in some aspects, the disclosure provides an isolated human monoclonal antibody that specifically binds to human CD161, or antigen binding portion thereof, wherein the antibody or antigen binding portion: (i) binds human CD161 with an affinity ($K_D$) of about 50-300 pM; (ii) inhibits the interaction between human CD161 and CLEC2D; and (iii) binds to an epitope on human CD161 comprising one or more amino acid residues selected from I96, D121, K125, E126, R146, L151, Y198, E200, and E205 of SEQ ID NO: 335.

In some aspects, the disclosure provides an isolated human monoclonal antibody that specifically binds to human CD161, or antigen binding portion thereof, wherein the antibody or antigen binding portion: (i) binds human CD161 with an affinity ($K_D$) of about 50-300 pM; (ii) inhibits the interaction between human CD161 and CLEC2D; or (iii) binds to an epitope on human CD161 comprising one or more amino acid residues selected from I96, D121, K125, E126, R146, L151, Y198, E200, and E205 of SEQ ID NO: 335.

In any of the foregoing or related aspects, the epitope comprises D121 of SEQ ID NO: 335. In some aspects, the epitope comprises D121, I96, K125, and E126 of SEQ ID NO: 335. In some aspects, the epitope comprises I96 and K125 of SEQ ID NO: 335. In some aspects, the epitope comprises R146 of SEQ ID NO: 335. In some aspects, the epitope comprises L151, Y198, E200, or E205 of SEQ ID NO: 335. In some aspects, the epitope comprises L151, Y198, E200, and E205 of SEQ ID NO: 335.

In any of the foregoing or related aspects, the antibody or antigen binding portion binds to an epitope on human CD161, wherein the epitope comprises 1, 2, 3, 4, 5, 6, 7, 8, 9, 10, 11, 12, 13, 14, 15, 16, 17, 18, 19 or 20 amino acid residues, or 1-3, 3-6, 6-9, 9-12, 12-15, 15-20, or 20-25 amino acid residues. In some aspects, the epitope is a non-linear or discontinuous epitope.

In any of the foregoing or related aspects, the antibody or antigen binding portion binds human CD161 and does not significantly cross-react with other human proteins in the C-type lectin family.

In any of the foregoing or related aspects, the antibody or antigen binding portion binds human CD161 and does not significantly cross-react with cynomolgus CD161. In some aspects, the antibody or antigen binding portion binds to human CD161 with about 5-10 fold, 5-15 fold, 5-20 fold, 10-20 fold, 10-25 fold, 10-30, 10-40, or 10-50 fold higher binding affinity than to cynomolgus CD161.

In any of the foregoing or related aspects, the antibody or antigen binding portion binds to human CD161 with substantially equivalent affinity to cynomolgus CD161. In some aspects, the antibody or antigen binding portion binds to human CD161 with binding affinity ($K_D$) that is at least 80, 85, 90, 95, 100, 105, 110, 115, 120, 125, or 130% of its binding affinity ($K_D$) to cynomolgus CD161. In some aspects, the antibody or antigen binding portion binds to human CD161 with binding affinity ($K_D$) that is at least 60, 65, 70, 75, 80, 85, 90, 95, 100, 105, 110, 115, 120, 125, 130, 135, 140, 145, 150, 155, 160, 165, 170, 175, or 180% of its binding affinity ($K_D$) to cynomolgus CD161.

In some aspects, the disclosure provides an isolated human monoclonal antibody that specifically binds to human CD161, or antigen binding portion thereof, wherein the antibody or antigen binding portion binds human CD161 with an affinity ($K_D$) of about 50-300 pM and binds to an epitope on human CD161 comprising one or more amino acid residues are selected from I96, D121, K125, E126, R146, L151, Y198, E200, and E205 of SEQ ID NO: 335. In some aspects, the epitope comprises 1, 2, 3, 4, 5, 6, 7, 8, 9, 10, 11, 12, 13, 14, 15, 16, 17, 18, 19 or 20 amino acid residues, wherein one or more amino acid residues are selected from I96, D121, K125, E126, R146, L151, Y198, E200, and E205 of SEQ ID NO: 335. In some aspects, the epitope is at least 1, 2, 3, 4, 5, 6, 7, 8, 9, or 10 amino acid residues, wherein one or more amino acid residues are selected from I96, D121, K125, E126, R146, L151, Y198, E200, and E205 of SEQ ID NO: 335. In some aspects, the epitope is fewer than 25, 24, 23, 22, 21, 20, 19, 18, 17, 16, 15, 14, 13, 12, 11, or 10 amino acid residues, wherein one or more amino acid residues are selected from I96, D121, K125, E126, R146, L151, Y198, E200, and E205 of SEQ ID NO: 335.

In some aspects, the disclosure provides an isolated human monoclonal antibody that specifically binds human CD161, or antigen binding portion thereof, comprising a heavy chain CDR3 selected from:
  (a) a heavy chain CDR3 comprising the amino acid sequence ARGGX$_1$X$_2$PX$_3$X$_4$FX$_5$Y (SEQ ID NO: 307), wherein X$_1$ is selected from L or Y, X$_2$ is selected from I or L, X$_3$ is selected from S or D, X$_4$ is selected from G or A, and X$_5$ is selected from D or G;
  (b) a heavy chain CDR3 comprising the amino acid sequence ARGGLIPSGFX$_1$Y (SEQ ID NO: 308), wherein X$_1$ is any amino acid;
  (c) a heavy chain CDR3 comprising the amino acid sequence ARGPGX$_1$MYLYGDSFFX$_2$Y (SEQ ID NO: 309), wherein X$_1$ is any amino acid, and wherein X$_2$ is any amino acid;
  (d) a heavy chain CDR3 comprising the amino acid sequence ARDYYLX$_1$DYITQTSFDY (SEQ ID NO: 310), wherein X$_1$ is any amino acid; and
  (e) a heavy chain CDR3 comprising the amino acid sequence ARGYSDSYX$_1$YGPYYTFDY (SEQ ID NO: 311), wherein X$_1$ is any amino acid.

In any of the foregoing or related aspects, the isolated human monoclonal antibody or antigen binding portion thereof comprises a heavy chain CDR3 selected from:
  (a) a heavy chain CDR3 comprising the amino acid sequence ARGGLIPSGFX$_1$Y (SEQ ID NO: 308), wherein X$_1$ is selected from D or G;
  (b) a heavy chain CDR3 comprising the amino acid sequence ARGPGX$_1$MYLYGDSFFX$_2$Y (SEQ ID NO: 309), wherein X$_1$ is selected from D or Y and X$_2$ is selected from D or E;
  (c) a heavy chain CDR3 comprising the amino acid sequence ARDYYLX$_1$DYITQTSFDY (SEQ ID NO: 310), wherein X$_1$ is selected from S, F or Y;
  (d) a heavy chain CDR3 comprising the amino acid sequence ARGYSDSYX$_1$YGPYYTFDY (SEQ ID NO: 311), wherein X$_1$ is selected from Y or F.

In some aspects, the disclosure provides an isolated human monoclonal antibody that specifically binds to human CD161, or antigen binding portion thereof, wherein the antibody or antigen binding portion binds human CD161 with an affinity ($K_D$) of about 50-300 pM and binds to an epitope on human CD161 comprising D121 of SEQ ID NO: 335. In some aspects, the epitope comprises D121, I96, K125, and E126 of SEQ ID NO: 335. In some aspects, the foregoing isolated human monoclonal antibody or antigen binding portion thereof comprises a heavy chain CDR3 comprising the amino acid sequence ARGGX$_1$X$_2$PX$_3$X$_4$FX$_5$Y (SEQ ID NO: 307), wherein X$_1$ is selected from L or Y, X$_2$ is selected from I or L, X$_3$ is selected from S or D, X$_4$ is selected from G or A, and X$_5$ is selected from D or G. In some aspects, the foregoing isolated human monoclonal antibody or antigen binding portion thereof comprises a heavy chain CDR3 comprising the amino acid sequence ARGGLIPSGFX$_1$Y (SEQ ID NO:

308), wherein X₁ is any amino acid, or wherein X₁ is selected from D or G. In some aspects, the foregoing isolated human monoclonal antibody or antigen binding portion thereof comprises a heavy chain CDR3 comprising an amino acid sequence selected from ARGGLIPSGFDY (SEQ ID NO: 141), ARGGLIPSGFGY (SEQ ID NO: 142), or ARGGYLPDAFDY (SEQ ID NO: 143).

In some aspects, the disclosure provides an isolated human monoclonal antibody that specifically binds to human CD161, or antigen binding portion thereof, wherein the antibody or antigen binding portion binds human CD161 with an affinity ($K_D$) of about 50-300 pM and binds to an epitope on human CD161 comprising R146 of SEQ ID NO: 335. In some aspects, the foregoing isolated human monoclonal antibody or antigen binding portion thereof comprises a heavy chain CDR3 comprising the amino acid sequence ARGPGX₁MYLYGDSFFX₂Y (SEQ ID NO: 309), wherein X₁ is any amino acid, or wherein X₁ is selected from D or Y, and wherein X₂ is any amino acid, or wherein X₂ is selected from D or E. In some aspects, the foregoing isolated human monoclonal antibody or antigen binding portion thereof comprises the heavy chain CDR3 comprising an amino acid sequence selected from: ARGPGDMYLYGDSFFDY (SEQ ID NO: 144), ARGPGYMYLYGDSFFDY (SEQ ID NO: 145), or ARGPGYMYLYGDSFFEY (SEQ ID NO: 146).

In some aspects, the disclosure provides an isolated human monoclonal antibody that specifically binds to human CD161, or antigen binding portion thereof, wherein the antibody or antigen binding portion binds human CD161 with an affinity ($K_D$) of about 50-300 pM and binds to an epitope on human CD161 comprising L151, Y198, E200, and E205 of SEQ ID NO: 335. In some aspects, the foregoing isolated human monoclonal antibody or antigen binding portion thereof comprises a heavy chain CDR3 comprising the amino acid sequence ARDYYLX₁DYITQTSFDY (SEQ ID NO: 310), wherein X₁ is any amino acid, or wherein X₁ is selected from S, F or Y. In some aspects, the foregoing isolated human monoclonal antibody or antigen binding portion thereof comprises a heavy chain CDR3 comprising an amino acid sequence selected from ARDYYLSDYITQTSFDY (SEQ ID NO: 147), ARDYYLFDYITQTSFDY (SEQ ID NO: 148), or ARDYYLYDYITQTSFDY (SEQ ID NO: 149).

In some aspects, the disclosure provides an isolated human monoclonal antibody that specifically binds to human CD161, or antigen binding portion thereof, wherein the antibody or antigen binding portion binds human CD161 with an affinity ($K_D$) of about 50-300 pM and binds to an epitope on human CD161 comprising I96 and K125 of SEQ ID NO: 335. In some aspects, the foregoing isolated human monoclonal antibody or antigen binding portion thereof comprises a heavy chain CDR3 comprising the amino acid sequence ARGYSDSYX₁YGPYYTFDY (SEQ ID NO: 311), wherein X₁ is any amino acid, or wherein X₁ is selected from Y or F. In some aspects, the foregoing isolated human monoclonal antibody or antigen binding portion thereof comprises a heavy chain CDR3 comprising an amino acid sequence selected from ARGYSDSYYYGPYYTFDY (SEQ ID NO: 150) or ARGYSDSYFYGPYYTFDY (SEQ ID NO: 151).

In some aspects, the disclosure provides an isolated human monoclonal antibody that specifically binds human CD161, or antigen binding portion thereof, comprising heavy and light chain CDRs selected from:
  (a) heavy chain CDR1, CDR2, and CDR3 comprising amino acid sequences set forth in SEQ ID NOs: 299, 303, and 307 respectively, and light chain CDR1, CDR2, and CDR3 comprising amino acid sequences set forth in SEQ ID NOs: 312, 316, and 317 respectively;
  (b) heavy chain CDR1, CDR2, and CDR3 comprising amino acid sequences set forth in SEQ ID NOs: 299, 303, and 307 respectively, and light chain CDR1, CDR2, and CDR3 comprising amino acid sequences set forth in SEQ ID NOs: 312, 316, and 318 respectively;
  (c) heavy chain CDR1, CDR2, and CDR3 comprising amino acid sequences set forth in SEQ ID NOs: 300, 304, and 307 respectively, and light chain CDR1, CDR2, and CDR3 comprising amino acid sequences set forth in SEQ ID NOs: 312, 316, and 317 respectively;
  (d) heavy chain CDR1, CDR2, and CDR3 comprising amino acid sequences set forth in SEQ ID NOs: 300, 304, and 307 respectively, and light chain CDR1, CDR2, and CDR3 comprising amino acid sequences set forth in SEQ ID NOs: 312, 316, and 318 respectively;
  (e) heavy chain CDR1, CDR2, and CDR3 comprising amino acid sequences set forth in SEQ ID NOs: 300, 304, and 308 respectively, and light chain CDR1, CDR2, and CDR3 comprising amino acid sequences set forth in SEQ ID NOs: 312, 316, and 317 respectively;
  (f) heavy chain CDR1, CDR2, and CDR3 comprising amino acid sequences set forth in SEQ ID NOs: 300, 304, and 308 respectively, and light chain CDR1, CDR2, and CDR3 comprising amino acid sequences set forth in SEQ ID NOs: 312, 316, and 318 respectively;
  (g) heavy chain CDR1, CDR2, and CDR3 comprising amino acid sequences set forth in SEQ ID NOs: 299, 303, and 309 respectively, and light chain CDR1, CDR2, and CDR3 comprising amino acid sequences set forth in SEQ ID NOs: 312, 316, and 317 respectively;
  (h) heavy chain CDR1, CDR2, and CDR3 comprising amino acid sequences set forth in SEQ ID NOs: 299, 303, and 309 respectively, and light chain CDR1, CDR2, and CDR3 comprising amino acid sequences set forth in SEQ ID NOs: 313, 316, and 319 respectively;
  (i) heavy chain CDR1, CDR2, and CDR3 comprising amino acid sequences set forth in SEQ ID NOs: 300, 304, and 309 respectively, and light chain CDR1, CDR2, and CDR3 comprising amino acid sequences set forth in SEQ ID NOs: 312, 316, and 317 respectively;
  (j) heavy chain CDR1, CDR2, and CDR3 comprising amino acid sequences set forth in SEQ ID NOs: 300, 304, and 309 respectively, and light chain CDR1, CDR2, and CDR3 comprising amino acid sequences set forth in SEQ ID NOs: 313, 316, and 319 respectively;
  (k) heavy chain CDR1, CDR2, and CDR3 comprising amino acid sequences set forth in SEQ ID NOs: 299, 303, and 310 respectively, and light chain CDR1, CDR2, and CDR3 comprising amino acid sequences set forth in SEQ ID NOs: 315, 316, and 321 respectively;
  (l) heavy chain CDR1, CDR2, and CDR3 comprising amino acid sequences set forth in SEQ ID NOs: 301, 305, and 310 respectively, and light chain CDR1, CDR2, and CDR3 comprising amino acid sequences set forth in SEQ ID NOs: 315, 316, and 321 respectively;

(m) heavy chain CDR1, CDR2, and CDR3 comprising amino acid sequences set forth in SEQ ID NOs: 299, 303, and 311 respectively, and light chain CDR1, CDR2, and CDR3 comprising amino acid sequences set forth in SEQ ID NOs: 312, 316, and 317 respectively;

(n) heavy chain CDR1, CDR2, and CDR3 comprising amino acid sequences set forth in SEQ ID NOs: 299, 303, and 311 respectively, and light chain CDR1, CDR2, and CDR3 comprising amino acid sequences set forth in SEQ ID NOs: 314, 316, and 320 respectively;

(o) heavy chain CDR1, CDR2, and CDR3 comprising amino acid sequences set forth in SEQ ID NOs: 302, 306, and 311 respectively, and light chain CDR1, CDR2, and CDR3 comprising amino acid sequences set forth in SEQ ID NOs: 312, 316, and 317 respectively; and (p) heavy chain CDR1, CDR2, and CDR3 comprising amino acid sequences set forth in SEQ ID NOs: 302, 306, and 311 respectively, and light chain CDR1, CDR2, and CDR3 comprising amino acid sequences set forth in SEQ ID NOs: 314, 316, and 320 respectively.

In some aspects, the disclosure provides an isolated human monoclonal antibody that specifically binds human CD161, or antigen binding portion thereof, wherein the antibody or antigen binding portion comprises heavy and light chain CDRs selected from:

(a) heavy chain CDR1, CDR2, and CDR3 comprising amino acid sequences set forth in SEQ ID NOs: 127, 132, and 141 respectively, and light chain CDR1, CDR2, and CDR3 comprising amino acid sequences set forth in SEQ ID NOs: 273, 279, and 281 respectively;

(b) heavy chain CDR1, CDR2, and CDR3 comprising amino acid sequences set forth in SEQ ID NOs: 127, 132, and 141 respectively, and light chain CDR1, CDR2, and CDR3 comprising amino acid sequences set forth in SEQ ID NOs: 273, 279, and 282 respectively;

(c) heavy chain CDR1, CDR2, and CDR3 comprising amino acid sequences set forth in SEQ ID NOs: 127, 132, and 141 respectively, and light chain CDR1, CDR2, and CDR3 comprising amino acid sequences set forth in SEQ ID NOs: 273, 279, and 283 respectively;

(d) heavy chain CDR1, CDR2, and CDR3 comprising amino acid sequences set forth in SEQ ID NOs: 127, 132, and 141 respectively, and light chain CDR1, CDR2, and CDR3 comprising amino acid sequences set forth in SEQ ID NOs: 273, 279, and 284 respectively;

(e) heavy chain CDR1, CDR2, and CDR3 comprising amino acid sequences set forth in SEQ ID NOs: 127, 132, and 142 respectively, and light chain CDR1, CDR2, and CDR3 comprising amino acid sequences set forth in SEQ ID NOs: 273, 279, and 281 respectively;

(f) heavy chain CDR1, CDR2, and CDR3 comprising amino acid sequences set forth in SEQ ID NOs: 128, 132, and 141 respectively, and light chain CDR1, CDR2, and CDR3 comprising amino acid sequences set forth in SEQ ID NOs: 273, 279, and 283

(g) heavy chain CDR1, CDR2, and CDR3 comprising amino acid sequences set forth in SEQ ID NOs: 129, 132, and 141 respectively, and light chain CDR1, CDR2, and CDR3 comprising amino acid sequences set forth in SEQ ID NOs: 273, 279, and 283 respectively;

(h) heavy chain CDR1, CDR2, and CDR3 comprising amino acid sequences set forth in SEQ ID NOs: 127, 132, and 143 respectively, and light chain CDR1, CDR2, and CDR3 comprising amino acid sequences set forth in SEQ ID NOs: 273, 279, and 281 respectively;

(i) heavy chain CDR1, CDR2, and CDR3 comprising amino acid sequences set forth in SEQ ID NOs: 127, 132, and 143 respectively, and light chain CDR1, CDR2, and CDR3 comprising amino acid sequences set forth in SEQ ID NOs: 273, 279, and 283 respectively;

(j) heavy chain CDR1, CDR2, and CDR3 comprising amino acid sequences set forth in SEQ ID NOs: 127, 133, and 143 respectively, and light chain CDR1, CDR2, and CDR3 comprising amino acid sequences set forth in SEQ ID NOs: 273, 279, and 283 respectively;

(k) heavy chain CDR1, CDR2, and CDR3 comprising amino acid sequences set forth in SEQ ID NOs: 129, 132, and 143 respectively, and light chain CDR1, CDR2, and CDR3 comprising amino acid sequences set forth in SEQ ID NOs: 273, 279, and 283 respectively;

(l) heavy chain CDR1, CDR2, and CDR3 comprising amino acid sequences set forth in SEQ ID NOs: 127, 132, and 144 respectively, and light chain CDR1, CDR2, and CDR3 comprising amino acid sequences set forth in SEQ ID NOs: 273, 279, and 281 respectively;

(m) heavy chain CDR1, CDR2, and CDR3 comprising amino acid sequences set forth in SEQ ID NOs: 127, 132, and 145 respectively, and light chain CDR1, CDR2, and CDR3 comprising amino acid sequences set forth in SEQ ID NOs: 273, 279, and 281 respectively;

(n) heavy chain CDR1, CDR2, and CDR3 comprising amino acid sequences set forth in SEQ ID NOs: 127, 132, and 145 respectively, and light chain CDR1, CDR2, and CDR3 comprising amino acid sequences set forth in SEQ ID NOs: 273, 279, and 285 respectively;

(o) heavy chain CDR1, CDR2, and CDR3 comprising amino acid sequences set forth in SEQ ID NOs: 127, 132, and 145 respectively, and light chain CDR1, CDR2, and CDR3 comprising amino acid sequences set forth in SEQ ID NOs: 274, 279, and 281 respectively;

(p) heavy chain CDR1, CDR2, and CDR3 comprising amino acid sequences set forth in SEQ ID NOs: 127, 132, and 145 respectively, and light chain CDR1, CDR2, and CDR3 comprising amino acid sequences set forth in SEQ ID NOs: 275, 279, and 285 respectively;

(q) heavy chain CDR1, CDR2, and CDR3 comprising amino acid sequences set forth in SEQ ID NOs: 127, 134, and 146 respectively, and light chain CDR1, CDR2, and CDR3 comprising amino acid sequences set forth in SEQ ID NOs: 273, 279, and 281 respectively;

(r) heavy chain CDR1, CDR2, and CDR3 comprising amino acid sequences set forth in SEQ ID NOs: 127, 134, and 146 respectively, and light chain CDR1, CDR2, and CDR3 comprising amino acid sequences set forth in SEQ ID NOs: 275, 279, and 281 respectively;

(s) heavy chain CDR1, CDR2, and CDR3 comprising amino acid sequences set forth in SEQ ID NOs: 127, 132, and 147 respectively, and light chain CDR1, CDR2, and CDR3 comprising amino acid sequences set forth in SEQ ID NOs: 277, 280, and 289 respectively;

(t) heavy chain CDR1, CDR2, and CDR3 comprising amino acid sequences set forth in SEQ ID NOs: 127, 132, and 148 respectively, and light chain CDR1, CDR2, and CDR3 comprising amino acid sequences set forth in SEQ ID NOs: 277, 280, and 289 respectively;

(u) heavy chain CDR1, CDR2, and CDR3 comprising amino acid sequences set forth in SEQ ID NOs: 127, 132, and 148 respectively, and light chain CDR1, CDR2, and CDR3 comprising amino acid sequences set forth in SEQ ID NOs: 277, 280, and 290 respectively;

(v) heavy chain CDR1, CDR2, and CDR3 comprising amino acid sequences set forth in SEQ ID NOs: 127, 132, and 149 respectively, and light chain CDR1, CDR2, and CDR3 comprising amino acid sequences set forth in SEQ ID NOs: 277, 280, and 289 respectively;

(w) heavy chain CDR1, CDR2, and CDR3 comprising amino acid sequences set forth in SEQ ID NOs: 127, 132, and 149 respectively, and light chain CDR1, CDR2, and CDR3 comprising amino acid sequences set forth in SEQ ID NOs: 277, 280, and 290

(x) heavy chain CDR1, CDR2, and CDR3 comprising amino acid sequences set forth in SEQ ID NOs: 127, 132, and 149 respectively, and light chain CDR1, CDR2, and CDR3 comprising amino acid sequences set forth in SEQ ID NOs: 277, 280, and 291 respectively;

(y) heavy chain CDR1, CDR2, and CDR3 comprising amino acid sequences set forth in SEQ ID NOs: 127, 132, and 149 respectively, and light chain CDR1, CDR2, and CDR3 comprising amino acid sequences set forth in SEQ ID NOs: 277, 280, and 292 respectively;

(z) heavy chain CDR1, CDR2, and CDR3 comprising amino acid sequences set forth in SEQ ID NOs: 127, 132, and 149 respectively, and light chain CDR1, CDR2, and CDR3 comprising amino acid sequences set forth in SEQ ID NOs: 278, 280, and 289 respectively;

(aa) heavy chain CDR1, CDR2, and CDR3 comprising amino acid sequences set forth in SEQ ID NOs: 127, 135, and 149 respectively, and light chain CDR1, CDR2, and CDR3 comprising amino acid sequences set forth in SEQ ID NOs: 277, 280, and 289 respectively;

(bb) heavy chain CDR1, CDR2, and CDR3 comprising amino acid sequences set forth in SEQ ID NOs: 127, 136, and 149 respectively, and light chain CDR1, CDR2, and CDR3 comprising amino acid sequences set forth in SEQ ID NOs: 277, 280, and 291 respectively;

(cc) heavy chain CDR1, CDR2, and CDR3 comprising amino acid sequences set forth in SEQ ID NOs: 127, 136, and 149 respectively, and light chain CDR1, CDR2, and CDR3 comprising amino acid sequences set forth in SEQ ID NOs: 277, 280, and 292 respectively;

(dd) heavy chain CDR1, CDR2, and CDR3 comprising amino acid sequences set forth in SEQ ID NOs: 127, 136, and 149 respectively, and light chain CDR1, CDR2, and CDR3 comprising amino acid sequences set forth in SEQ ID NOs: 277, 280, and 293 respectively;

(ee) heavy chain CDR1, CDR2, and CDR3 comprising amino acid sequences set forth in SEQ ID NOs: 127, 136, and 149 respectively, and light chain CDR1, CDR2, and CDR3 comprising amino acid sequences set forth in SEQ ID NOs: 277, 280, and 294 respectively;

(ff) heavy chain CDR1, CDR2, and CDR3 comprising amino acid sequences set forth in SEQ ID NOs: 130, 132, and 149 respectively, and light chain CDR1, CDR2, and CDR3 comprising amino acid sequences set forth in SEQ ID NOs: 277, 280, and 290 respectively;

(gg) heavy chain CDR1, CDR2, and CDR3 comprising amino acid sequences set forth in SEQ ID NOs: 127, 132, and 150 respectively, and light chain CDR1, CDR2, and CDR3 comprising amino acid sequences set forth in SEQ ID NOs: 273, 279, and 281 respectively;

(hh) heavy chain CDR1, CDR2, and CDR3 comprising amino acid sequences set forth in SEQ ID NOs: 127, 132, and 150 respectively, and light chain CDR1, CDR2, and CDR3 comprising amino acid sequences set forth in SEQ ID NOs: 275, 279, and 286 respectively;

(ii) heavy chain CDR1, CDR2, and CDR3 comprising amino acid sequences set forth in SEQ ID NOs: 127, 132, and 151 respectively, and light chain CDR1, CDR2, and CDR3 comprising amino acid sequences set forth in SEQ ID NOs: 273, 279, and 286 respectively;

(jj) heavy chain CDR1, CDR2, and CDR3 comprising amino acid sequences set forth in SEQ ID NOs: 127, 137, and 150 respectively, and light chain CDR1, CDR2, and CDR3 comprising amino acid sequences set forth in SEQ ID NOs: 273, 279, and 281 respectively;

(kk) heavy chain CDR1, CDR2, and CDR3 comprising amino acid sequences set forth in SEQ ID NOs: 127, 138, and 150 respectively, and light chain CDR1, CDR2, and CDR3 comprising amino acid sequences set forth in SEQ ID NOs: 273, 279, and 281 respectively;

(ll) heavy chain CDR1, CDR2, and CDR3 comprising amino acid sequences set forth in SEQ ID NOs: 127, 138, and 150 respectively, and light chain CDR1, CDR2, and CDR3 comprising amino acid sequences set forth in SEQ ID NOs: 273, 279, and 286 respectively;

(mm) heavy chain CDR1, CDR2, and CDR3 comprising amino acid sequences set forth in SEQ ID NOs: 127, 138, and 150 respectively, and light chain CDR1, CDR2, and CDR3 comprising amino acid sequences set forth in SEQ ID NOs: 276, 279, and 281 respectively;

(nn) heavy chain CDR1, CDR2, and CDR3 comprising amino acid sequences set forth in SEQ ID NOs: 127, 138, and 151 respectively, and light chain CDR1, CDR2, and CDR3 comprising amino acid sequences set forth in SEQ ID NOs: 273, 279, and 286

(oo) heavy chain CDR1, CDR2, and CDR3 comprising amino acid sequences set forth in SEQ ID NOs: 127, 138, and 151 respectively, and light chain CDR1, CDR2, and CDR3 comprising amino acid sequences set forth in SEQ ID NOs: 273, 279, and 287 respectively;

(pp) heavy chain CDR1, CDR2, and CDR3 comprising amino acid sequences set forth in SEQ ID NOs: 127, 138, and 151 respectively, and light chain CDR1, CDR2, and CDR3 comprising amino acid sequences set forth in SEQ ID NOs: 273, 279, and 288 respectively;

(qq) heavy chain CDR1, CDR2, and CDR3 comprising amino acid sequences set forth in SEQ ID NOs: 127, 138, and 151 respectively, and light chain CDR1, CDR2, and CDR3 comprising amino acid sequences set forth in SEQ ID NOs: 275, 279, and 286 respectively;

(rr) heavy chain CDR1, CDR2, and CDR3 comprising amino acid sequences set forth in SEQ ID NOs: 127, 140, and 151 respectively, and light chain CDR1, CDR2, and CDR3 comprising amino acid sequences set forth in SEQ ID NOs: 273, 279, and 286 respectively;

(ss) heavy chain CDR1, CDR2, and CDR3 comprising amino acid sequences set forth in SEQ ID NOs: 131, 132, and 151 respectively, and light chain CDR1, CDR2, and CDR3 comprising amino acid sequences set forth in SEQ ID NOs: 273, 279, and 281 respectively;

(tt) heavy chain CDR1, CDR2, and CDR3 comprising amino acid sequences set forth in SEQ ID NOs: 131, 132, and 150 respectively, and light chain CDR1, CDR2, and CDR3 comprising amino acid sequences set forth in SEQ ID NOs: 273, 279, and 281 respectively; and (uu) heavy chain CDR1, CDR2, and CDR3 comprising amino acid sequences set forth in SEQ ID NOs: 131, 139, and 151 respectively, and light chain CDR1, CDR2, and CDR3 comprising amino acid sequences set forth in SEQ ID NOs: 273, 279, and 286 respectively.

In some aspects, the disclosure provides an isolated human monoclonal antibody that specifically binds to human CD161, or antigen binding portion thereof, wherein the antibody or antigen binding portion:

(i) binds human CD161 with an affinity ($K_D$) of about 50-300 pM;

(ii) inhibits the interaction between human CD161 and CLEC2D; and (iii) comprises a heavy chain CDR3 with an amino acid sequence ARGGX$_1$X$_2$PX$_3$X$_4$FX$_5$Y (SEQ ID NO: 307), wherein X$_1$ is selected from L or Y, X$_2$ is selected from I or L, X$_3$ is selected from S or D, X$_4$ is selected from G or A, and X$_5$ is any amino acid. In some aspects, X$_1$ is L, X$_2$ is I, X$_3$ is S, X$_4$ is G, and X$_5$ is any amino acid. In some aspects, X$_1$ is L, X$_2$ is I, X$_3$ is S, X$_4$ is G, and X$_5$ is selected from D or G. In some aspects, the heavy chain CDR1, CDR2, and CDR3 comprise GSTFSSYA (SEQ ID NO: 129), ISGSGGST (SEQ ID NO: 132), and ARGGLIPSGFDY (SEQ ID NO: 141) respectively. In some aspects, the heavy chain CDR1, CDR2, and CDR3 comprise GFTFSSYA (SEQ ID NO: 127), ISGSGGST (SEQ ID NO: 132), and ARGGLIPSGFDY (SEQ ID NO: 141) respectively. In some aspects, the heavy chain CDR1, CDR2, and CDR3 comprise GFTFSSYA (SEQ ID NO: 127), ISGSGGST (SEQ ID NO: 132), and ARGGYLPDAFDY (SEQ ID NO: 143) respectively. In some aspects, the light chain CDR1, CDR2, and CDR3 comprise QSISSY (SEQ ID NO: 273), AAS (SEQ ID NO: 279), and QQTYSTPLT (SEQ ID NO: 283) respectively. In some aspects, the light chain CDR1, CDR2, and CDR3 comprise QSISSY (SEQ ID NO: 273), AAS (SEQ ID NO: 279), and QQTYSAPLT (SEQ ID NO: 284) respectively.

In any of the foregoing or related aspects, the isolated human monoclonal antibody or antigen binding portion thereof comprises heavy and light chain variable regions, wherein the heavy and light chain variable regions comprise the amino acid sequences set forth in SEQ ID NOs: 15 and 165, respectively. In some aspects, the heavy and light chain variable regions comprise the nucleotide sequences set forth in SEQ ID NOs: 16 and 166, respectively.

In any of the foregoing or related aspects, the isolated human monoclonal antibody or antigen binding portion thereof comprises heavy and light chain variable regions, wherein the heavy and light chain variable regions comprise the amino acid sequences set forth in SEQ ID NOs: 8 and 167, respectively. In some aspects, the heavy and light chain variable regions comprise the nucleotide sequences set forth in SEQ ID NOs: 9 and 168, respectively.

In any of the foregoing or related aspects, the isolated human monoclonal antibody or antigen binding portion thereof comprises heavy and light chain variable regions, wherein the heavy and light chain variable regions comprise amino acid sequences set forth in SEQ ID NOs: 22 and 185, respectively. In some aspects, the heavy and light chain variable regions comprise nucleotide sequences set forth in SEQ ID NOs: 24 and 186, respectively.

In any of the foregoing or related aspects, the antibody or antigen binding portion thereof binds to an epitope on human CD161 comprising one or more amino acid residues selected from I96, D121, K125, E126, R146, L151, Y198, E200, and E205 of SEQ ID NO: 335. In some aspects, the amino acid residue is D121 of SEQ ID NO: 335. In some aspects, the amino acid residues are D121, I96, K125, and E126 of SEQ ID NO: 335. In some aspects, the antibody or antigen binding portion does not significantly cross-react with other human proteins in the C-type lectin family. In some aspects, the antibody or antigen binding portion binds to human CD161 with substantially equivalent affinity to cynomolgus CD161. In some aspects, the antibody or antigen binding portion binds to human CD161 with binding affinity ($K_D$) that is at least 80, 85, 90, 95, 100, 105, 110, 115, 120, 125, or 130% of its binding affinity to cynomolgus CD161. In some aspects, the antibody or antigen binding portion binds to human CD161 with binding affinity ($K_D$) that is at least 60, 65, 70, 75, 80, 85, 90, 95, 100, 105, 110, 115, 120, 125, 130, 135, 140, 145, 150, 155, 160, 165, 170, 175, or 180% of its binding affinity to cynomolgus CD161.

In some aspects, the disclosure provides an isolated human monoclonal antibody that specifically binds to human CD161, or antigen binding portion thereof, wherein the antibody or antigen binding portion:

(i) binds human CD161 with an affinity ($K_D$) of about 50-300 pM;

(ii) inhibits the interaction between human CD161 and CLEC2D; and (iii) comprises a heavy chain CDR3 with an amino acid sequence ARGYSDSYX$_1$YGPYYTFDY (SEQ ID NO: 311), wherein X$_1$ is any amino acid. In some aspects, X$_1$ is selected from Y or F. In some aspects, the heavy chain CDR1, CDR2, and CDR3 comprise amino acid sequences GFTFSSYA (SEQ ID NO: 127), ISGSGGSI (SEQ ID NO: 138), and ARGYSDSYFYGPYYTFDY (SEQ ID NO: 151) respectively, and the light chain CDR1, CDR2, and CDR3 comprise amino acid sequences QSISSY (SEQ ID NO: 273), AAS (SEQ ID NO: 279), and QQSYDTPLT (SEQ ID NO: 287) respectively. In some aspects, the antibody or antigen binding portion thereof comprises heavy and light chain variable regions, wherein the heavy and light chain variable regions comprise the amino acid sequences set forth in SEQ ID NOs: 117 and 235 respectively. In some aspects, the heavy and light chain variable regions comprise the nucleotide sequences set forth in SEQ ID NOs: 118 and 236 respectively.

In any of the foregoing or related aspects, the isolated human monoclonal antibody or antigen binding portion thereof binds to an epitope on human CD161 comprising amino acid residues 196 and K125 of SEQ ID NO: 335. In some aspects, the antibody or antigen binding portion does not significantly cross-react with other human proteins in the C-type lectin family In some aspects, the antibody or antigen binding portion binds to human CD161 with binding affinity ($K_D$) that is at least 60, 65, 70, 75, 80, 85, 90, 95, or 100% of its binding affinity ($K_D$) to cynomolgus CD161.

In some aspects, the disclosure provides an isolated human monoclonal antibody that specifically binds to human CD161, or antigen binding portion thereof, comprising heavy and light chain variable regions, wherein the heavy and light chain variable regions comprise amino acid sequences which are at least 90%, at least 95%, or at least 100% identical to the amino acid sequences selected from:

(a) SEQ ID NOs: 1 and 152, respectively;
(b) SEQ ID NOs: 1 and 155, respectively;
(c) SEQ ID NOs: 1 and 157, respectively;
(d) SEQ ID NOs: 4 and 152, respectively;
(e) SEQ ID NOs: 6 and 152, respectively;
(f) SEQ ID NOs: 8 and 157, respectively;
(g) SEQ ID NOs: 8 and 167, respectively;
(h) SEQ ID NOs: 11 and 160, respectively;
(i) SEQ ID NOs: 13 and 162, respectively;
(j) SEQ ID NOs: 15 and 165, respectively;
(k) SEQ ID NOs: 15 and 171, respectively;
(l) SEQ ID NOs: 15 and 173, respectively;
(m) SEQ ID NOs: 18 and 169, respectively;
(n) SEQ ID NOs: 20 and 295, respectively;
(o) SEQ ID NOs: 22 and 152, respectively;
(p) SEQ ID NOs: 22 and 160, respectively;
(q) SEQ ID NOs: 22 and 162, respectively;
(r) SEQ ID NOs: 22 and 175, respectively;
(s) SEQ ID NOs: 22 and 179, respectively;
(t) SEQ ID NOs: 22 and 183, respectively;
(u) SEQ ID NOs: 22 and 185, respectively;
(v) SEQ ID NOs: 29 and 177, respectively;
(w) SEQ ID NOs: 31 and 181, respectively;
(x) SEQ ID NOs: 33 and 160, respectively;
(y) SEQ ID NOs: 35 and 187, respectively;
(z) SEQ ID NOs: 37 and 187, respectively;
(aa) SEQ ID NOs: 39 and 160, respectively;
(bb) SEQ ID NOs: 41 and 190, respectively;
(cc) SEQ ID NOs: 43 and 152, respectively;
(dd) SEQ ID NOs: 43 and 192, respectively;
(ee) SEQ ID NOs: 45 and 194, respectively;
(ff) SEQ ID NOs: 47 and 152, respectively;
(gg) SEQ ID NOs: 47 and 202, respectively;
(hh) SEQ ID NOs: 50 and 196, respectively;
(ii) SEQ ID NOs: 52 and 152, respectively;
(jj) SEQ ID NOs: 52 and 208, respectively;
(kk) SEQ ID NOs: 54 and 196, respectively;
(ll) SEQ ID NOs: 56 and 199, respectively;
(mm) SEQ ID NOs: 56 and 206, respectively;
(nn) SEQ ID NOs: 59 and 204, respectively;
(oo) SEQ ID NOs: 61 and 245, respectively;
(pp) SEQ ID NOs: 66 and 258, respectively;
(qq) SEQ ID NOs: 63 and 250, respectively;
(rr) SEQ ID NOs: 63 and 245, respectively;
(ss) SEQ ID NOs: 66 and 248, respectively;
(tt) SEQ ID NOs: 70 and 252, respectively;
(uu) SEQ ID NOs: 68 and 245, respectively;
(vv) SEQ ID NOs: 66 and 250, respectively;
(ww) SEQ ID NOs: 66 and 254, respectively;
(xx) SEQ ID NOs: 72 and 256, respectively;
(yy) SEQ ID NOs: 74 and 260, respectively;
(zz) SEQ ID NOs: 76 and 297, respectively;
(aaa) SEQ ID NOs: 78 and 262, respectively;
(bbb) SEQ ID NOs: 78 and 267, respectively;
(ccc) SEQ ID NOs: 78 and 269, respectively;
(ddd) SEQ ID NOs: 80 and 264, respectively;
(eee) SEQ ID NOs: 82 and 271, respectively;
(fff) SEQ ID NOs: 84 and 264, respectively;
(ggg) SEQ ID NOs: 86 and 254, respectively;
(hhh) SEQ ID NOs: 88 and 152, respectively;
(iii) SEQ ID NOs: 90 and 210, respectively;
(jjj) SEQ ID NOs: 92 and 212, respectively;
(kkk) SEQ ID NOs: 94 and 215, respectively;
(lll) SEQ ID NOs: 94 and 217, respectively;
(mmm) SEQ ID NOs: 96 and 152, respectively;
(nnn) SEQ ID NOs: 98 and 230, respectively;
(ooo) SEQ ID NOs: 98 and 152, respectively;
(ppp) SEQ ID NOs: 101 and 219, respectively;
(qqq) SEQ ID NOs: 103 and 221, respectively;
(rrr) SEQ ID NOs: 105 and 225, respectively;
(sss) SEQ ID NOs: 105 and 223, respectively;
(ttt) SEQ ID NOs: 107 and 225, respectively;
(uuu) SEQ ID NOs: 109 and 212, respectively;
(vvv) SEQ ID NOs: 111 and 230, respectively;
(www) SEQ ID NOs: 113 and 228, respectively;
(xxx) SEQ ID NOs: 113 and 212, respectively;
(yyy) SEQ ID NOs: 113 and 225, respectively;
(zzz) SEQ ID NOs: 113 and 239, respectively;
(aaaa) SEQ ID NOs: 113 and 243, respectively;
(bbbb) SEQ ID NOs: 115 and 233, respectively;
(cccc) SEQ ID NOs: 117 and 235, respectively;
(dddd) SEQ ID NOs: 119 and 237, respectively;
(eeee) SEQ ID NOs: 121 and 219, respectively;
(ffff) SEQ ID NOs: 123 and 225, respectively; and
(gggg) SEQ ID NOs: 125 and 241, respectively.

In any of the foregoing or related aspects, the isolated human monoclonal antibody or antigen binding portion thereof binds to human CD161 with an affinity ($K_D$) of about 50-70 pM, 50-80 pM, 50-90 pM, 50-100 pM, 50-150 pM, 100-150 pM, 50-200 pM, 100-200 pM, 150-200 pM, 100-300 pM, 150-300 pM, 200-300 pM, or 250-300 pM.

In any of the foregoing or related aspects, the antibody is selected from the group consisting of: an IgG1, an IgG2, an IgG3, an IgG4, an IgM, an IgA1, an IgA2, an IgD, and an IgE antibody. In some aspects, the antibody is an IgG1 antibody or an IgG4 antibody.

In any of the foregoing or related aspects, the antibody comprises a human IgG1 or human IgG4 heavy chain constant region. In some aspects, the antibody comprises a mutant IgG1 heavy chain constant region. In some aspects, the mutant IgG1 heavy chain comprises a substitution at Leu234, Leu235 and Pro329. In some aspects, the mutant IgG1 heavy chain comprises a substitution at Leu234, Leu235 and Pro329, determined by EU numbering. In some aspects, the mutant IgG1 heavy chain comprises a substitution of Leu234 to alanine, a substitution of Leu235 to alanine, and a substitution of Pro329 to glycine. In some aspects, the mutant IgG1 heavy chain comprises a substitution of Leu234 to alanine, a substitution of Leu235 to alanine, and a substitution of Pro329 to glycine, determined by EU numbering. In some aspects, the mutant IgG1 heavy chain has reduced Fc-gamma receptor binding relative to wild-type IgG1 heavy chain. In some aspects, the mutant IgG1 heavy chain is derived from a wild-type IgG1 heavy chain and has reduced Fc-gamma receptor binding relative to wild-type IgG1 heavy chain. In some aspects, the isolated human monoclonal antibody or antigen binding portion thereof comprises a mutant IgG4 heavy chain constant region. In some aspects, the isolated human monoclonal antibody or antigen binding portion thereof comprises a mutant IgG4 heavy chain constant region derived from a wild-type IgG4 heavy chain constant region. In some aspects, the mutant IgG4 heavy chain comprises a substitution at Ser228, Leu325, and Pro329, determined by EU numbering. In some aspects, the mutant IgG4 heavy chain comprises a substitution of Ser228 to proline, Leu325 to glutamate, and Pro329 to glycine, determined by EU numbering.

In any of the foregoing or related aspects, the isolated human monoclonal antibody or antigen binding portion thereof binds to a ligand-binding region of human CD161. In some aspects, the antibody or antigen binding portion thereof blocks the CLEC2D-binding region of human CD161, thereby inhibiting the interaction between human CD161 and CLEC2D.

In any of the foregoing or related aspects, the isolated human monoclonal antibody or antigen binding portion thereof binds to a non-ligand binding region of human CD161. In some aspects, the antibody or antigen binding portion thereof alters the conformation of the CLEC2D binding region of human CD161, thereby inhibiting the interaction between human CD161 and CLEC2D.

In any of the foregoing or related aspects, the isolated human monoclonal antibody or antigen binding portion thereof does not significantly cross-react with human proteins of the C-type lectin family selected from: KLRF1, CD94, KLRF2, Clec12B, Clec7A, KLRG1, OLR1, Clec5A, Clec9A, CD209, Clec4E, or Clec10A.

In any of the foregoing or related aspects, the isolated human monoclonal antibody or antigen binding portion thereof, exhibits at least one or more of the following properties selected from the group consisting of:
  (a) induces or increases activation of CD161-expressing human T cells in response to antigen-expressing target cells;
  (b) induces or increases cytokine production by CD161-expressing human T cells in response to antigen-expressing target cells;
  (c) induces or increases granzyme B expression by CD161-expressing human T cells in response to antigen-expressing target cells;
  (d) reduces exhaustion of CD161-expressing human T cells in response to antigen-expressing target cells;
  (e) reduces expression of the PD-1 receptor in human T cells in response to antigen-expressing target cells; and
  (f) any combination of (a)-(e).

In some aspects, the disclosure provides a pharmaceutical composition comprising an isolated monoclonal human antibody or antigen binding portion thereof, as described herein, and a pharmaceutically acceptable carrier.

In some aspects, the disclosure provides a nucleic acid comprising a nucleotide sequence encoding a light chain comprising the CDRs or light chain variable region of an isolated monoclonal antibody, or antigen binding portion thereof, described herein; a heavy chain comprising the CDRs or heavy chain variable region of an isolated monoclonal antibody, or antigen binding portion thereof, described herein; or both.

In any of the foregoing or related aspects, the heavy and light chain variable regions comprise nucleotide sequences which are at least 90%, at least 95%, or at least 100% identical to the nucleotide sequences selected from:
  (a) SEQ ID NOs: 2 and 153, respectively;
  (b) SEQ ID NOs: 23 and 153, respectively;
  (c) SEQ ID NOs: 44 and 153, respectively;
  (d) SEQ ID NOs: 62 and 246, respectively;
  (e) SEQ ID NOs: 89 and 153, respectively;
  (f) SEQ ID NOs: 2 and 156, respectively;
  (g) SEQ ID NOs: 3 and 159, respectively;
  (h) SEQ ID NOs: 5 and 153, respectively;
  (i) SEQ ID NOs: 7 and 153, respectively;
  (j) SEQ ID NOs: 10 and 158, respectively;
  (k) SEQ ID NOs: 10 and 168, respectively;
  (l) SEQ ID NOs: 9 and 168, respectively;
  (m) SEQ ID NOs: 12 and 161, respectively;
  (n) SEQ ID NOs: 14 and 163, respectively;
  (o) SEQ ID NOs: 16 and 166, respectively;
  (p) SEQ ID NOs: 17 and 172, respectively;
  (q) SEQ ID NOs: 16 and 174, respectively;
  (r) SEQ ID NOs: 19 and 170, respectively;
  (s) SEQ ID NOs: 21 and 296, respectively;
  (t) SEQ ID NOs: 23 and 161, respectively;
  (u) SEQ ID NOs: 28 and 161, respectively;
  (v) SEQ ID NOs: 27 and 164, respectively;
  (w) SEQ ID NOs: 25 and 176, respectively;
  (x) SEQ ID NOs: 23 and 180, respectively;
  (y) SEQ ID NOs: 26 and 184, respectively;
  (z) SEQ ID NOs: 24 and 186, respectively;
  (aa) SEQ ID NOs: 30 and 178, respectively;
  (bb) SEQ ID NOs: 32 and 182, respectively;
  (cc) SEQ ID NOs: 34 and 161, respectively;
  (dd) SEQ ID NOs: 36 and 188, respectively;
  (ee) SEQ ID NOs: 38 and 189, respectively;
  (ff) SEQ ID NOs: 40 and 161, respectively;
  (gg) SEQ ID NOs: 42 and 191, respectively;
  (hh) SEQ ID NOs: 44 and 193, respectively;
  (ii) SEQ ID NOs: 46 and 195, respectively;
  (jj) SEQ ID NOs: 48 and 153, respectively;
  (kk) SEQ ID NOs: 49 and 203, respectively;
  (ll) SEQ ID NOs: 51 and 197, respectively;
  (mm) SEQ ID NOs: 53 and 153, respectively;
  (nn) SEQ ID NOs: 53 and 209, respectively;
  (oo) SEQ ID NOs: 55 and 198, respectively;
  (pp) SEQ ID NOs: 57 and 200, respectively;
  (qq) SEQ ID NOs: 57 and 201, respectively;
  (rr) SEQ ID NOs: 58 and 207, respectively;
  (ss) SEQ ID NOs: 60 and 205, respectively;
  (tt) SEQ ID NOs: 67 and 259, respectively;
  (uu) SEQ ID NOs: 64 and 246, respectively;
  (vv) SEQ ID NOs: 65 and 251, respectively;
  (ww) SEQ ID NOs: 65 and 246, respectively;
  (xx) SEQ ID NOs: 67 and 249, respectively;
  (yy) SEQ ID NOs: 71 and 253, respectively;
  (zz) SEQ ID NOs: 69 and 247, respectively;
  (aaa) SEQ ID NOs: 67 and 251, respectively;
  (bbb) SEQ ID NOs: 67 and 255, respectively;
  (ccc) SEQ ID NOs: 73 and 257, respectively;

(ddd) SEQ ID NOs: 75 and 261, respectively;
(eee) SEQ ID NOs: 77 and 298, respectively;
(fff) SEQ ID NOs: 79 and 263, respectively;
(ggg) SEQ ID NOs: 79 and 268, respectively;
(hhh) SEQ ID NOs: 79 and 270, respectively;
(iii) SEQ ID NOs: 81 and 265, respectively;
(jjj) SEQ ID NOs: 83 and 272, respectively;
(kkk) SEQ ID NOs: 85 and 266, respectively;
(lll) SEQ ID NOs: 87 and 255, respectively;
(mmm) SEQ ID NOs: 91 and 211, respectively;
(nnn) SEQ ID NOs: 93 and 213, respectively;
(ooo) SEQ ID NOs: 95 and 216, respectively;
(ppp) SEQ ID NOs: 95 and 218, respectively;
(qqq) SEQ ID NOs: 97 and 153, respectively;
(rrr) SEQ ID NOs: 99 and 154, respectively;
(sss) SEQ ID NOs: 100 and 232, respectively;
(ttt) SEQ ID NOs: 102 and 220, respectively;
(uuu) SEQ ID NOs: 104 and 222, respectively;
(vvv) SEQ ID NOs: 106 and 226, respectively;
(www) SEQ ID NOs: 106 and 224, respectively;
(xxx) SEQ ID NOs: 108 and 226, respectively;
(yyy) SEQ ID NOs: 110 and 214, respectively;
(zzz) SEQ ID NOs: 112 and 231, respectively;
(aaaa) SEQ ID NOs: 114 and 229, respectively;
(bbbb) SEQ ID NOs: 114 and 214, respectively;
(cccc) SEQ ID NOs: 114 and 226, respectively;
(dddd) SEQ ID NOs: 114 and 240, respectively;
(eeee) SEQ ID NOs: 114 and 244, respectively;
(ffff) SEQ ID NOs: 116 and 234, respectively;
(gggg) SEQ ID NOs: 118 and 236, respectively;
(hhhh) SEQ ID NOs: 120 and 238, respectively;
(iiii) SEQ ID NOs: 122 and 220, respectively;
(jjjj) SEQ ID NOs: 124 and 227, respectively; and
(kkkk) SEQ ID NOs: 126 and 242, respectively.

In some aspects, the disclosure provides an expression vector comprising a nucleic acid described herein. In some aspects, the disclosure provides a cell transformed with an expression vector comprising a nucleic acid described herein.

In some aspects, the disclosure provides a method for producing a human monoclonal antibody or antigen binding portion thereof that specifically binds to human CD161, the method comprising maintaining a cell transformed with an expression vector comprising a nucleic acid described herein under conditions permitting expression of the human monoclonal antibody or antigen binding portion thereof. In some aspects, the method further comprises obtaining the human monoclonal antibody or antigen binding portion thereof.

In some aspects, the disclosure provides a method for inhibiting or blocking the interaction between human CD161 and CLEC2D in a subject, comprising administering to a subject in need thereof, an isolated human monoclonal antibody or antigen binding portion described herein or a pharmaceutical composition described herein.

In some aspects, the disclosure provides a method for inducing or enhancing immune cell activation in a subject, comprising administering to a subject in need thereof, an isolated human monoclonal antibody or antigen binding portion disclosed herein or a pharmaceutical composition disclosed herein. In some aspects, the immune cell activation occurs in a tumor microenvironment. In some aspects, the immune cell is a T cell or a NK cell. In some aspects, the T cell is cytotoxic T cell.

In some aspects, the disclosure provides a method for inducing or enhancing a cytotoxic T cell effector response in a subject, comprising administering to a subject in need thereof, an isolated human monoclonal antibody or antigen binding portion disclosed herein or a pharmaceutical composition disclosed herein. In some aspects, the T cell effector response is in a tumor microenvironment. In some aspects, the T cell effector response is cytokine production. In some aspects, the cytokine is IL-2, TNFα, IFNγ or a combination thereof. In some aspects, the T cell effector response is secretion of granzyme B.

In some aspects, the disclosure provides a method for reducing T cell exhaustion in a subject, comprising administering to a subject in need thereof, an isolated human monoclonal antibody or antigen binding portion described herein or a pharmaceutical composition described herein. In some aspects, the T cell exhaustion occurs in a tumor microenvironment. In some aspects, the reduction of T cell exhaustion comprises a decrease in expression of a cell surface marker selected from: TIGIT and PD-1.

In some aspects, the disclosure provides a method for treating a disorder mediated by human CD161 in a subject, comprising administering to a subject in need thereof, an isolated human monoclonal antibody or antigen binding portion described herein or a pharmaceutical composition described herein.

In some aspects, the disclosure provides a method for reducing or inhibiting tumor growth, comprising administering to a subject in need thereof, an isolated human monoclonal antibody or antigen binding portion described herein or a pharmaceutical composition described herein.

In some aspects, the disclosure provides a method for treating cancer in a subject, comprising administering to a subject in need thereof, an isolated human monoclonal antibody or antigen binding portion described herein or a pharmaceutical composition described herein.

In any of the foregoing aspects, the method further comprises administering one or more additional therapies selected from: a tumor-targeting antibody, a chemotherapy, or an immune checkpoint inhibitor. In some aspects, the immune checkpoint inhibitor is an antibody or antigen binding portion thereof that binds to PD-1, PD-L1, CTLA-4, or LAG3.

In any of the foregoing aspects, the cancer is selected from a group consisting of: melanoma, lung, glioma, colorectal, or liver. In some aspects, the tumor is a cancer selected from: melanoma, lung, glioma, colorectal, or liver.

In some aspects, the disclosure provides a method for detecting the presence or absence of human CD161 in a biological sample, comprising:
 (i) contacting a biological sample with the isolated human monoclonal antibody or antigen binding portion described herein, wherein the antibody or antigen binding portion is labeled with a detectable substance; and
 (ii) detecting the antibody or antigen binding portion bound to human CD161 to thereby detect the presence or absence of human CD161 in the biological sample.

In some aspects, the disclosure provides a kit comprising a container comprising an isolated human monoclonal antibody or antigen binding portion thereof described herein, and an optional pharmaceutically acceptable carrier, or a pharmaceutical composition described herein, and a package insert comprising instructions for administration of the antibody or pharmaceutical composition, for treating or delaying progression of cancer or reducing or inhibiting tumor growth in a subject in need thereof.

In some aspects, the disclosure provides a kit comprising a container comprising an isolated human monoclonal antibody or antigen binding portion thereof described herein, and an optional pharmaceutically acceptable carrier, or a pharmaceutical composition described herein, and a package insert comprising instructions for administration of the antibody or pharmaceutical composition alone or in combination with another agent, for treating or delaying progression of cancer or reducing or inhibiting tumor growth in a subject in need thereof.

In some aspects, the disclosure provides use of an isolated human monoclonal antibody or antigen binding portion thereof described herein, for use in treating or delaying progression of cancer or reducing or inhibiting tumor growth in a subject in need thereof.

In some aspects, the disclosure provides an isolated human monoclonal antibody or antigen binding portion thereof described herein, in the manufacture of a medicament for treating or delaying progression of cancer or reducing or inhibiting tumor growth in a subject in need thereof. In some aspects, the disclosure provides an isolated human monoclonal antibody or antigen binding portion thereof described herein, for use as a medicament.

BRIEF DESCRIPTION OF THE FIGURES

FIG. 3G provides a dot plot showing tumor bioluminescence signal measured on indicated days as quantified by tumor bioluminescence imaging for each experimental group. FIG. 3H provides a line graph showing survival of mice in the three experimental groups.

FIGS. 5A-5C provide sequences of heavy chains (FIG. 5A, clone KW1, SEQ ID NO: 1; clone KW7, SEQ ID NO: 22; clone KW9, SEQ ID NO: 43; clone KW17, SEQ ID NO: 61; and KM12, SEQ ID NO: 88), kappa light chains (FIG. 5B, clone KW1, KW7, KW9, and KM12, SEQ ID NO: 152) or lambda light chains (FIG. 5C, clone KW17, SEQ ID NO: 245) of five CD161-binding parental antibody clones identified by yeast display technology, with amino acid sequence numbering according to the IMGT numbering system.

FIGS. 5D-5E provide sequences of heavy chains (FIG. 5D, clone KW1.2.1, SEQ ID NO: 15; clone KW1.3.12, SEQ ID NO: 8; clone KW7.2.2, SEQ ID NO: 22; clone KW7.3.7, SEQ ID NO: 41; clone KM12.4.7, SEQ ID NO: 117) and kappa light chains (FIG. 5E, clone KW1.2.1, SEQ ID NO: 165; clone KW1.3.12, SEQ ID NO: 393; clone KW7.2.2, SEQ ID NO: 185; clone KW7.3.7, SEQ ID NO: 190; clone KM12.4.7, SEQ ID NO: 395) of CD161-binding antibodies that were affinity matured from parental anti-CD161 antibodies identified by yeast display.

FIGS. 6C-6D provide histograms depicting binding of biotinylated bivalent CLEC2D Fc fusion protein (biCLEC2D-bio) to Jurkat cells expressing human CD161 alone or in the presence of increasing concentrations of parental human anti-CD161 antibodies identified by yeast display (clones KW1, KW7, KW9, or KW17 in FIG. 6C and clone KM12 in FIG. 6D) or a mouse anti-human CD161 antibody (HP-3G10, FIG. 6D) as measured by flow cytometry, with background staining determined by staining with secondary detection reagent only.

DETAILED DESCRIPTION

Figure 1A:
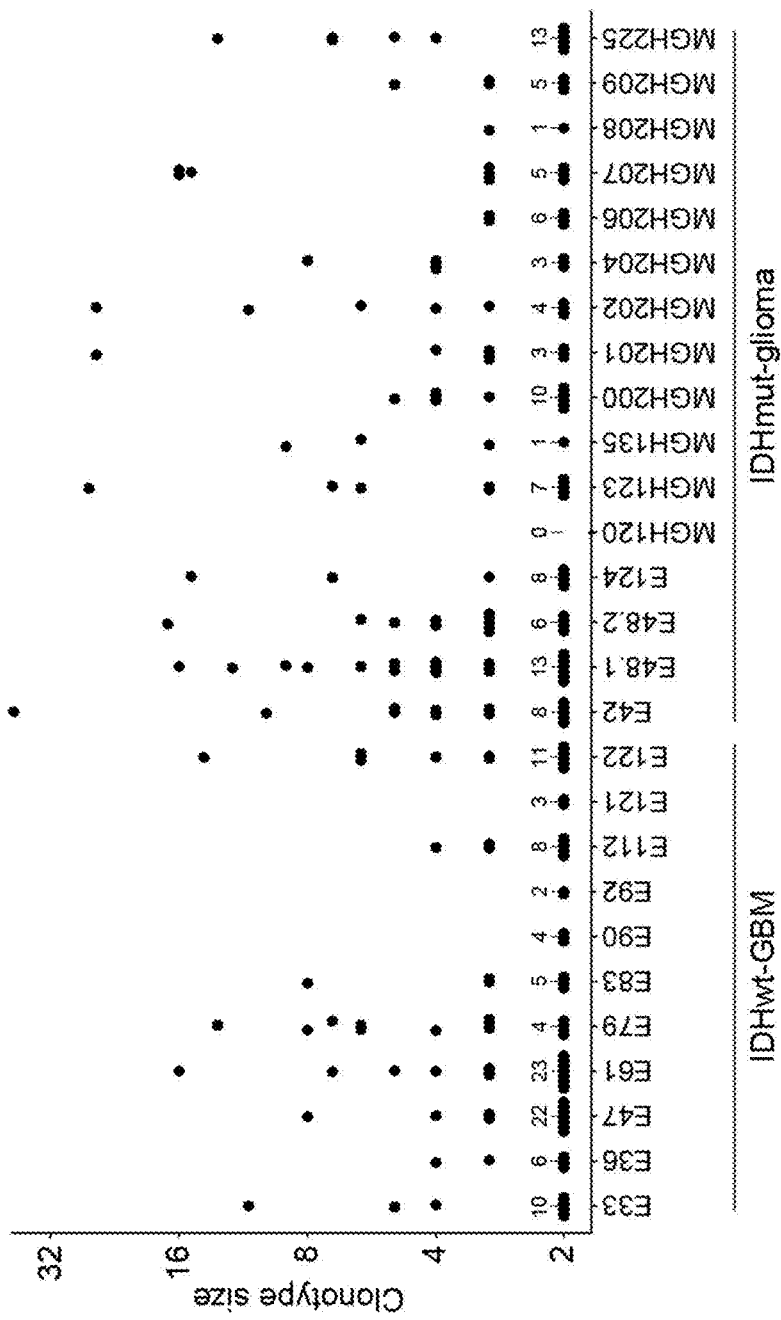
FIG. 1A provides a bee swarm plot of the quantification of clonally expanded T cells from human glioma samples (glioblastoma, isocitrate dehydrogenase (IDH) wildtype (IDHwt-GBM) or astrocytoma, IDH mutant or oligodendroglioma IDH mutant, ip/19g co-depleted (collectively IDHmut-glioma) samples). TCR sequences were used to identify T cells with identical TCR sequences (clonotypes). For each tumor sample, the number of T cells belonging to each clonotype (clonotype size) is shown; the number of clonotypes composed of two T cells is also indicated.

The present disclosure provides isolated human monoclonal antibodies that specifically bind to human CD161, and antigen binding portions thereof. In some embodiments, the disclosure provides human monoclonal antibodies or antigen binding portions thereof that specifically bind to human CD161 and inhibit the interaction of CD161 with CLEC2D. CD161 is encoded by the gene known as Killer Cell Lectin Like receptor (KLRB1). The CD161 receptor binds to a ligand known as C-type Lectin Domain Family 2 Member D (CLEC2D). Previous reports have shown that CD161 is expressed by NK cells and functions as a regulatory receptor that inhibits NK cell cytotoxic function. Additionally, CD161 has also been found to be expressed by subset of T cells, including tumor-infiltrating T cells. As disclosed herein, blocking the CD161-CLEC2D interaction (e.g., by inactivation of KLRB1 or by blocking CLEC2D binding using a CD161 binding antibody of the disclosure) promotes activation of T cells in response to tumor cells. Moreover, the T cells demonstrate reduced exhaustion in response to tumor cells following blocking of the CD161-CLEC2D interaction, as measured by reduced PD-1 expression.

Accordingly, in some aspects, the CD161 binding antibodies or antigen binding portions thereof of the disclosure induce or promote activation and cytokine production of T cells (e.g., tumor-reactive T cells or T cells specific to cancer antigens). In some embodiments, the CD161 binding antibodies or antigen binding portions thereof induce or promote activation and cytokine production of CD8+ T cells within the tumor microenvironment. In some embodiments, the CD161 binding antibodies or antigen binding portions thereof reduce or prevent exhaustion of T cells following chronic exposure to antigen, as measured by expression of PD-1. In some embodiments, the CD161 binding antibodies or antigen binding portions thereof induce or promote protective anti-tumor immunity.

In some aspects, the disclosure provides methods for administering CD161 binding antibodies, or antigen binding portions thereof, to treat or delay progression of cancer or reduce or inhibit tumor growth in a subject. In some embodiments, CD161 binding antibodies, or antigen binding portions thereof are administered alone (e.g., as a monotherapy) or in combination with one or more additional therapies (e.g., as a combination therapy) to induce or promote protective anti-tumor immunity and/or for the treatment of cancer.

CD161 Binding Antibodies and Antigen-Binding Portions Thereof

In some embodiments, CD161 binding antibodies or antigen binding portions thereof and compositions thereof are used for the treatment of diseases characterized via expression of KLRB1 by immune cells. Human KLRB1 encodes the CD161 receptor, which is a 225 amino acid transmembrane polypeptide receptor. Specifically, CD161 is a NK cell receptor that is expressed by the majority of human natural killer (NK) cells (Lanier et al. (1994) *J. Immunol.* 153:2417-2428). As used herein, the term "NK cell receptor" refers to activating receptors and inhibitory receptors expressed by natural killer (NK) cells. Most NK cell receptors belong to two large gene families that include the immunoglobulin (Ig) superfamily (e.g., Ig-like receptors) and the C-type lectin superfamily (CLSF) (e.g., C-type lectin-like receptors). The Ig superfamily comprises killer cell Ig-like receptors (KIRs) (see, e.g., Long (1999) *Annu Rev Immunol* 17:875-904 and Moretta, et al (2004) *Curr Opin Immunol* 16:626-633). The CLSF comprises proteins comprising a C-type lectin-like domain (CTLD) (see, e.g., Bartel et al (2013) *Front Immunol* 4:362; Hao et al (2006) *PNAS* 103:3192-3197). In humans, genes encoding NK cell receptor proteins of the CLSF are clustered in a single region, the NK receptor gene complex (NKC) located on chromosome 12p13 (see, e.g., Kelley et al (2005) *PLoS Genet* 1:129-139; Trowsdale, et al (2001) *J Immunol Rev* 181:20-38; Yokoyama et al (2003) *Nat Rev Immunol* 3:304-316).

The CD161 protein is alternatively referred to as C-type lectin domain family 5 member B (CLEC5B), Natural killer cell surface protein HA (NKR-P1A), and HNKR-P1a. An amino acid sequence of full-length human CD161 can be found using the UniProtKB database (Ref #: Q12918; Name: KLRB1_HUMAN) and is further identified by SEQ ID NO: 335. The sequence comprises a cytoplasmic domain (amino acid residues 1-45 of SEQ ID NO: 335), transmembrane domain (amino acid residues 46-66 of SEQ ID NO: 335), and extracellular domain (amino acid residues 67-225 of SEQ ID NO: 335). A nucleic acid sequence of full-length human CD161, including Kozak sequence, cytoplasmic domain, transmembrane domain, and extracellular domains is set forth by SEQ ID NO: 382.

Homologous receptors in other species include cynomolgus C-type lectin domain-containing protein (SEQ ID NO: 336; UniProt Ref #A0A2K5WYI1; UniProt Name: A0A2K5WYI1_MACFA), mouse Killer cell lectin-like receptor subfamily B member 1B allele B (UniProt Ref #Q99JB4; UniProt Name: KRBBB_MOUSE), and rat killer cell lectin-like receptor subfamily B member 1B allele B (UniProt Ref #Q5NKN4; UniProt Name: KRBBB_RAT). The cynomolgus gene homolog of human KLRB1 is referred to herein as "cynomolgus KLRB1" or "cynoKLRB1". The cynomolgus protein homolog of human CD161 (protein product of the KLRB1 gene) is referred to herein as "cynomolgus CD161" or "cynoCD161".

CD161 binds to the ligand C-type lectin domain family 2 member D (CLEC2D). CLEC2D is also known as lectin-like transcript 1 (LLT1). The amino acid sequence of the CLEC2D protein is identified in the UniProtKB database (Ref #: Q9UHP7; Name: CLC2D_HUMAN) and set forth by SEQ ID NO: 337. The CLEC2D protein comprises a cytoplasmic domain (amino acid residues 1-38 of SEQ ID NO: 337), a transmembrane domain (amino acid residues 39-59 of SEQ ID NO: 337), and extracellular domain (amino acid residues 60-191 of SEQ ID NO: 337).

The CD161-CLEC2D interaction is known to reduce or inhibit cytolytic function of CD161-expressing NK cells, and further prevent NK cell-mediated lysis of target cells expressing CLEC2D (Germain, et al (2010) *J. Biol. Chem.* 285:36207-36215; Germain et al, (2011) *J. Biol. Chem.*, 286:37964-37975; Rosen et at (2005) *J. Immunol*, 175: 7796-7799), Additionally, CD161 has been found to be expressed by a subset of human T cells, including γδ and αβ TCR-expressing subsets (Maggi et al (2010) *Eur. J. Immunol.* 40:2174-2181) and NK-T cells. Moreover, it has been recently demonstrated that CD161 is highly expressed by T cells isolated from a tumor microenvironment, and that reduced CD161 expression due to inactivation of KLRB1 in human primary T cells results in increased anti-tumor activity as described further by PCT Application No. PCT/US2018/060857 (WO2019/094983), the entire contents of which are expressly incorporated herein by reference. Accordingly, without being bound by theory, the CD161-CLEC2D interaction is thought to be an important regulator of T cell function. Specifically, the CD161-CLEC2D interaction is thought to protect target cells (e.g., tumor cells) expressing CLEC2D from CD161-expressing T cells (e.g., tumor-infiltrating CD161-expressing T cells).

Accordingly, in some embodiments, the disclosure provides isolated monoclonal antibodies or antigen binding portions thereof, that bind to CD161 and block, inhibit or antagonize binding of CLEC2D. In some embodiments, the disclosure provides isolated monoclonal antibodies or antigen binding portions thereof, that bind to CD161 and induces or promotes activation of immune cells. In some embodiments the immune cell is any immune cell expressing CD161. In some embodiments the immune cell is an NK cell. In some embodiments, the immune cell is a T cell. In some embodiments, the disclosure provides isolated monoclonal antibodies or antigen binding portions thereof, that bind to CD161 and reduce or prevent exhaustion of T cells.

As used herein, the term "anti-CD161 antibody" (used interchangeably with "anti-CD161 monoclonal antibody") refers to an antibody that specifically binds to CD161 (e.g., human CD161) and inhibits or blocks the binding of CD161 to CLEC2D.

In some embodiments, an isolated anti-CD161 monoclonal antibody or antigen binding portion thereof of the disclosure has one or more of the following properties or characteristics:
 a) binds to human CD161;
 b) binds to human and cynomolgus CD161;
 c) binds to human CD161 and induces or promotes activation of human NK or T cells;

d) binds to cynomolgus CD161 and induces or promotes activation of cynomolgus NK or T cells;
e) binds to human CD161 and reduces or prevents human T cell exhaustion; and
f) binds to cynomolgus CD161 and reduces or prevents cynomolgus T cell exhaustion.

In some embodiments, an isolated anti-CD161 monoclonal antibody or antigen binding portion thereof of the disclosure binds to CD161 and induces or promotes activation of immune cell effector function, wherein the immune cell is any CD161-expressing immune cell, or wherein the immune cell is a CD161-expressing T cell, a CD161-expressing NK cell, or a combination thereof. In some embodiments, an antibody or antigen binding portion of the disclosure bind to CD161 and induces or promotes activation, proliferation, cytokine production, cytolytic function or any combination thereof of a CD161-expressing T cell or a CD161-expressing NK cell. In some embodiments, an antibody or antigen binding portion of the disclosure bind to CD161 and induces or promotes T cell activation, a cytotoxic T lymphocyte (CTL) response, T cell proliferation, cytokine production, or a combination thereof.

In some embodiments, an isolated anti-CD161 monoclonal antibody or antigen binding portion thereof of the disclosure binds to CD161 and induces or promotes activation, proliferation, cytokine production, cytolytic function or any combination thereof of a CD161-expressing T cell that is a tumor-reactive T cell or a T cell specific to a cancer antigen. In some embodiments, an antibody or antigen binding portion of the disclosure bind to CD161 and induces or promotes T cell activation, a cytotoxic T lymphocyte (CTL) response, T cell proliferation, cytokine production, or a combination thereof in a tumor microenvironment. In some embodiments, an antibody or antigen binding portion of the disclosure bind to CD161 and induces or promotes T cell activation, a cytotoxic T lymphocyte (CTL) response, T cell proliferation, cytokine production, or a combination thereof in response to stimulation by a cancer antigen. In some embodiments, an antibody or antigen binding portion of the disclosure bind to CD161 and induces or promotes production of IFNγ. In some embodiments, an antibody or antigen binding portion of the disclosure hind to CD161 and induces or promotes production of IL-2, TNF-α, IFNγ, or a combination thereof. In some embodiments, an antibody or antigen binding portion of the disclosure hind to CD161 and induces or promotes production of granzyme B.

In some embodiments, an isolated anti-CD161 monoclonal antibody or antigen binding portion thereof of the disclosure binds to CD161 and reduces or prevents T cell exhaustion. In some embodiments, an antibody or antigen binding portion of the disclosure bind to CD161 and reduces or prevents T cell exhaustion in a tumor microenvironment. In some embodiments, an antibody or antigen binding portion of the disclosure bind to CD161 and reduces or prevents exhaustion of a tumor-reactive T cell or T cell specific to a cancer antigen. In some embodiments, an antibody or antigen binding portion of the disclosure binds to CD161 and reduces or prevents PD-1 expression.

In some embodiments, an isolated anti-CD161 monoclonal antibody or antigen binding portion thereof of the disclosure binds to and blocks CD1.61 binding to CLEC2D. In some embodiments, blocking of CD161 is measured by determining ligand (e.g., CLEC2D) binding. Methods of measuring ligand binding are known in the art and used in the Examples. In some embodiments, an antibody or antigen-binding portion of the disclosure binds to a ligand-binding region of CD161 (e.g., a CLEC2D-binding region). In some embodiments, an antibody or antigen-binding portion of the disclosure binds to a region of CD161 that significantly overlaps with a ligand-binding region of CD161 (e.g., a CLEC2D-binding region). In some embodiments, an antibody or antigen-binding portion of the disclosure binds to a non-ligand binding region of CD161. In some embodiments, an antibody or antigen-binding portion of the disclosure binds to CD161 and blocks the ligand-binding region of CD161. In some embodiments, an antibody or antigen-binding portion of the disclosure binds to CD161 and blocks the CLEC2D-binding region of CD161. In some embodiments, an antibody or antigen-binding portion of the disclosure binds to CD161 and alters the conformation of a ligand binding region of CD161 (e.g., CLEC2D-binding region), thereby preventing or inhibiting ligand binding.

In some embodiments, an antibody or antigen-binding portion of the disclosure binds to and blocks CD161, wherein blocking of CD161 is measured by determining the concentration of cytokines produced by CD161-expressing immune cells (e.g., CD161-expressing T cells, e.g., CD161-expressing NK cells). In some embodiments, blocking of CD161 is measured by determining concentration of cytokines produced by CD161-expressing T cells in response to a target cell (e.g., tumor cell). In some embodiments, an increase in cytokine production by immune cells indicates blocking of CD161. In some embodiments, blocking of CD161 is measured by analyzing proliferation of CD161-expressing immune cells (e.g., CD161-expressing T cells, e.g., CD161-expressing NK In some embodiments, an increase in immune cell proliferation indicates blocking of CD161. In some embodiments, blocking of CD161 is measured by measuring the level of cell signaling either by quantification of phosphorylation of relevant molecules or expression of a gene reporter induced by a relevant transcription factor. In some embodiments, increased cell signaling indicates blocking of CD161. In some embodiments, blocking of CD161 is measured by measuring the volume of a tumor. In some embodiments, a decrease or reduction in the volume of a tumor indicates blocking of CD161.

In some embodiments, an antibody or antigen binding portion of the disclosure binds to human CD161 with substantially equivalent affinity to cynomolgus CD161. As used herein, the term "substantially equivalent affinity" as it applies to an antibody or antigen binding portion refers to binding affinity for one antigen (e.g., human CD161) that is at least 60, 65, 70, 75, 80, 85, 90, 95, 100, 105, 110, 115, 120, 125, 130, 135, 140, 145, 150, 155, 160, 165, 170, 175, or 180% of its binding affinity to a second antigen (e.g., cynomolgus CD161). In some embodiments, an antibody or antigen binding portion of the disclosure binds to human CD161 with binding affinity ($K_D$) that is at least 60, 65, 70, 75, 80, 85, 90, 95, 100, 105, 110, 115, 120, 125, 130, 135, 140, 145, 150, 155, 160, 165, 170, 175 or 180% of its binding affinity to cynomolgus CD161. In some embodiments, an antibody or antigen binding portion of the disclosure binds to human CD161 with binding affinity that is about 70-80, 70-90, 70-100, 80-90, 80-100, 80-110, 90-100, 90-110, 90-120, 100-110, 100-120, 100-130, 110-120, 110-130, 110-140, 120-130, 120-140, 120-150, 120-160, 130-160, 130-170, 140-170, 140-180, or 150-180% of its binding affinity to cynomolgus CD161. In some embodiments, an anti-CD161 antibody or antigen binding portion thereof disclosed herein has a binding affinity for human CD161 that is no more than 1.1, 1.15, 1.2, 1.25, 1.3, 1.35, 1.4, 1.45, 1.5, 1.55, 1.6, 1.65, 1.7, 1.75, 1.8, 1.85, 1.9, 1.95, or 2-fold higher than its binding affinity to cynomolgus CD161.

In some embodiments, an antibody or antigen binding portion of the disclosure binds to human CD161, but not to cynomolgus CD161. In some embodiments, an antibody or antigen binding portion of the disclosure does not significantly cross-react with cynomolgus CD161. An antibody that "does not significantly cross-react" or "does not bind with a physiologically-relevant affinity" refers to one that will not appreciably bind to an off-target antigen (e.g., a non-CD161 polypeptide) or epitope. For example, in some embodiments, an antibody that specifically binds to human CD161 will exhibit at least a one, two, three, or four or more order(s) of magnitude better binding affinity (i.e., binding exhibiting a one, two, three, or four or more order(s) of magnitude lower KD value) for CD161 than, e.g., a protein other than CD161. While in some embodiments, an antibody that specifically binds to human CD161 will exhibit at least a 5-fold, 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, or 100-fold better binding affinity (i.e., binding exhibiting a 5-fold, 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, or 100-fold lower KD value) for CD161 than, e.g., a protein other than CD161. Methods of measuring cross-reactive binding are known in the art and are further described herein, and include for example, measurements according to Biacore analysis, bio-layer interferometry, and/or competitive (competition) binding assays.

In some embodiments, an antibody or antigen binding portion of the disclosure binds to human CD161 with higher affinity than to cynomolgus CD161. In some embodiments, an antibody or antigen binding portion of the disclosure binds with about 5-10 fold, 5-15 fold, 5-20 fold, 10-20 fold, 10-25 fold, 10-30, 10-40, or 10-50 fold higher binding affinity ($K_D$) to human CD161 than to cynomolgus CD161. In some embodiments, an antibody or antigen binding portion of the disclosure binds with about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40-fold higher binding affinity ($K_D$) to human CD161 than to cynomolgus CD161.

In some embodiments, an antibody or antigen binding portion of the disclosure specifically binds to human CD161. In some embodiments, an antibody or antigen binding portion of the disclosure specifically binds to human CD161 and cynomolgus CD161. In some embodiments, an antibody or antigen binding portion of the disclosure does not significantly cross-react with other human proteins in the C-type lectin receptor superfamily. In some embodiments, an antibody or antigen binding portion of the disclosure does not significantly cross-react with other human proteins that are proteins in the C-type lectin receptor superfamily that are expressed by NK cells (e.g., NK cell receptors, e.g., NK lectin-like receptors). In some embodiments, an antibody or antigen binding portion of the disclosure binds to human CD161, but does not significantly cross-react with other human proteins in the C-type lectin receptor superfamily that share at least 60%, 65%, 70%, 75%, 80%, 85%, 90%, 91%, 92%, 93%, 94%, or 95% sequence similarity with human CD161 (e.g., SEQ ID NO: 335).

Non-limiting examples of human proteins in the C-type lectin superfamily include those identified in Table 1.

TABLE 1

Human proteins in the C-type lectin superfamily

| Protein Name | Gene Name | Amino acid sequence (SEQ ID NO) | UniProtKB Reference Number |
|---|---|---|---|
| Natural killer cells antigen CD94 (CD94) | KLRD1 | 338 | Q13241 |
| Killer cell lectin-like receptor subfamily F member 2 (KLRF2) | KLRF2 | 339 | D3W0D1 |
| C-type lectin domain family 2 member B (CLEC2B) | CLEC2B | 340 | Q92478 |
| C-type lectin domain family 7 member A (CLEC7A) | CLEC7A | 341 | Q9BXN2 |
| Killer cell lectin-like receptor subfamily G member 1 (KLRG1) | KLRG1 | 342 | Q96E93 |
| Oxidized low-density lipoprotein receptor 1 (OLR1) | OLR1 | 343 | P78380 |
| C-type lectin domain family 5 member A (CLEC5A) | CLEC5A | 344 | Q9NY25 |
| C-type lectin domain family 9 member A (CLEC9A) | CLEC9A | 345 | Q6UXN8 |
| CD209 | CD209 | 346 | Q9NNX6 |
| C-type lectin domain family 4 member E (CLEC4E) | CLEC4E | 347 | Q9ULY5 |
| C-type lectin domain family 10 member A (CLEC10A) | CLEC10A | 348 | Q8IUN9 |
| Killer cell lectin-like receptor subfamily F member 1 (KLRF1) | KLRF1 | 349 | Q9NZS2 |

In some embodiments, an antibody or antigen binding portion of the disclosure binds to human CD161 with higher affinity than other human proteins in the C-type lectin receptor family. In some embodiments, an antibody or antigen binding portion of the disclosure binds to human CD161, but not to other human proteins identified in Table 1. In some embodiments, an antibody or antigen binding portion of the disclosure does not significantly cross-react with other human proteins identified in Table 1, as measured by an antigen binding assay described herein. In some embodiments, an antibody or antigen binding portion of the disclosure binds to human CD161 with higher affinity than other human proteins identified in Table 1. In some embodiments, an antibody or antigen binding portion of the disclosure binds human CD161 with binding affinity that is at least 1, 2, 3, 4 or more orders of magnitude higher than its binding affinity for other human proteins in the C-type lectin receptor family or a human protein identified in Table 1. In some embodiments, an antibody or antigen binding portion of the disclosure binds with about 5-10 fold, 5-15 fold, 5-20 fold, 10-20 fold, 10-25 fold, 10-30, 10-40, 10-50, 10-60, 10-70, 10-80, 10-90, 10-100, 50-100, 50-200, 50-300, 100-200, 100-300, 100-400, or 100-500 fold higher binding affinity ($K_D$) to human CD161 than to other human proteins in the C-type lectin receptor family or a human protein identified in Table 1. In some embodiments, an antibody or antigen binding portion of the disclosure binds with about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40-fold higher binding affinity ($K_D$) to human CD161 than to other human proteins in the C-type lectin receptor family or a human protein identified in Table 1. In some embodiments, an antibody or antigen binding portion of the disclosure binds to human CD161, but does not bind appreciably to other human proteins in the C-type lectin receptor family or a human protein identified in Table 1 as determined by an antigen binding assay described herein.

Affinity for CD161

In some embodiments, an isolated monoclonal antibody or antigen binding portion thereof of the disclosure binds to human CD161 with an affinity ($K_D$) of about 50-500 pM (e.g., between about 50 pM and about 500 pM or between about 50 pM and about 300 pM). Methods of measuring affinity ($K_D$) are further described herein.

Affinity is the strength of binding of a single molecule to its ligand. Conventionally, the term "affinity" as it applies to an antibody-antigen interaction refers to the binding energy of e.g., a monovalent antigen-binding portion of an antibody and a single antigen epitope, while the term "avidity" refers to more complex binding interactions between, e.g., antibodies comprising multiple binding sites and one or more antigens. However, as used herein, "affinity" is used to describe in general the binding energy between an antibody (e.g., single or multiple antigen binding sites) and bound antigen.

Binding affinity is typically measured and reported by the equilibrium dissociation constant ($K_D$), which is used to evaluate and rank strengths of bimolecular interactions. As used herein the term "KD" or "$K_D$" refers to the equilibrium dissociation constant of a binding reaction between an antibody and an antigen. The value of $K_D$ is a numeric representation of the ratio of the antibody off-rate constant (kd) to the antibody on-rate constant (ka). The value of $K_D$ is inversely related to the binding affinity of an antibody to an antigen. The smaller the $K_D$ value the greater the affinity of the antibody for its antigen.

As used herein, the term "kd" or "$k_d$" (alternatively "koff" or "$k_{off}$") is intended to refer to the off-rate constant for the dissociation of an antibody from an antibody/antigen complex. The value of kd is a numeric representation of the fraction of complexes that decay or dissociate per second, and is expressed in units $sec^{-1}$. As used herein, the term "ka" or "$k_a$" (alternatively "kon" or "$k_{on}$") is intended to refer to the on-rate constant for the association of an antibody with an antigen. The value of ka is a numeric representation of the number of antibody/antigen complexes formed per second in a 1 molar (1M) solution of antibody and antigen, and is expressed in units $M^{-1} sec^{-1}$.

In some embodiments, an antibody or antigen binding portion of the disclosure binds to human CD161 with an affinity ($K_D$) that is no greater than 2000, 1500, 1000, 900, 800, 700, 600, 500, 450, 400, 350, 300, 250, 200, 250, 200, 175, 150, 125, 110, 100, 90, 80, 70, 60, 50, 40, 30, 20, 10, 9, 8, 7, 6, 5, 4, 3, 2, or 1 nM. In some embodiments, an antibody or antigen binding portion of the disclosure binds to human CD161 with an affinity ($K_D$) that is no greater than 2000, 1500, 1000, 900, 800, 700, 600, 500, 450, 400, 350, 300, 250, 200, 250, 200, 175, 150, 125, 110, 100, 90, 80, 70, 60, or 50 pM. The affinity of the antibody is the strength of binding to a single CD161 polypeptide. In some embodiments, affinity is indicated by the equilibrium dissociation constant ($K_D$). The value of $K_D$ is inversely related to the binding affinity of an antibody to an antigen. Accordingly, the smaller the $K_D$ value, the greater the affinity of the antibody for its antigen.

In some embodiments, the anti-CD161 antibodies or antigen binding portions thereof bind to human CD161 with an affinity ($K_D$) of about 1-2000 nM (e.g., between about 1 nM and about 2000 nM or between about 500 nM and about 2000 nM or between about 1000 nM and about 2000 nM). In some embodiments, the antibodies or antigen binding portions of the disclosure bind human CD161 with an affinity ($K_D$) of about 100-2000 nM. In some embodiments, the antibodies or antigen binding portions of the disclosure bind human CD161 with an affinity ($K_D$) of about 1-10 nM, 1-20 nM, 10-20 nM, 10-30 nM, 10-40 nM, 20-40 nM, 20-50 nM, 20-60 nM, 30-60 nM, 30-70 nM, 30-80 nM, 40-80 nM, 40-90 nM, 50-90 nM, 50-100 nM, 60-100 nM, 70-100 nM, 80-100 nM, 100-200 nM, 100-300 nM, 100-400 nM, 100-500 nM, 200-500 nM, 200-600 nM, 200-700 nM, 300-500 nM, 300-600 nM, 300-700 nM, 300-800 nM, 400-500 nM, 400-600 nM, 400-700 nM, 400-800 nM, 500-600 nM, 500-700 nM, 500-800 nM, 500-900 nM, 500-1000 nM, 500-1500 nM, 1000-1500 nM, 1000-2000 nM or 1500-2000 nM.

In some embodiments, the anti-CD161 antibodies or antigen binding portions thereof bind to human CD161 with an affinity ($K_D$) of about 50-1000 pM (e.g., between about 50 pM and about 1000 pM, or between about 50 pM and about 500 pM, or between about 50 pM and about 300 pM). In some embodiments, the antibodies or antigen binding portions of the disclosure bind human CD161 with an affinity ($K_D$) of about 50-300 pM. In some embodiments, the antibodies or antigen binding portions of the disclosure bind human CD161 with an affinity ($K_D$) of about 50-60 pM, 50-70 pM, 50-80 pM, 50-90 pM, 50-100 pM, 90-100 pM, 90-110 pM, 90-120 pM, 100-150 pM, 100-200 pM, 150-200 pM, 150-250 pM, 200-300 pM, 250-300 pM, 250-400 pM, 300-400 pM, 350-400 pM, 350-500 pM, 400-500 pM, 450-500 pM, 400-600 pM, 500-600 pM, 500-700 pM, 500-800 pM, 600-800 pM, 600-900 pM, 700-900 pM, 800-900 pM, 800-1000 pM, 900-1000 pM, or 950-1000 pM.

In some embodiments, the anti-CD161 antibodies or antigen binding portions thereof bind to human CD161 with an affinity ($K_D$) of about 50-90 pM. In some embodiments, the anti-CD161 antibodies or antigen binding portions thereof bind to human CD161 with an affinity ($K_D$) of about 60-90 pM. In some embodiments, the anti-CD161 antibodies or antigen binding portions thereof bind to human CD161 with an affinity ($K_D$) of about 60-100 pM. In some embodiments, the anti-CD161 antibodies or antigen binding portions thereof bind to human CD161 with an affinity ($K_D$) of about 90-120 pM. In some embodiments, the anti-CD161 antibodies or antigen binding portions thereof bind to human CD161 with an affinity ($K_D$) of about 100-150 pM. In some embodiments, the anti-CD161 antibodies or antigen binding portions thereof bind to human CD161 with an affinity ($K_D$) of about 100-200 pM. In some embodiments, the anti-CD161 antibodies or antigen binding portions thereof bind to human CD161 with an affinity ($K_D$) of about 150-200 pM. In some embodiments, the anti-CD161 antibodies or antigen binding portions thereof bind to human CD161 with an affinity ($K_D$) of about 150-250 pM. In some embodiments, the anti-CD161 antibodies or antigen binding portions thereof bind to human CD161 with an affinity ($K_D$) of about 200-250 pM. In some embodiments, the anti-CD161 antibodies or antigen binding portions thereof bind to human CD161 with an affinity ($K_D$) of about 200-300 pM. In some embodiments, the anti-CD161 antibodies or antigen binding portions thereof bind to human CD161 with an affinity ($K_D$) of about 200-400 pM. In some embodiments, the anti-CD161 antibodies or antigen binding portions thereof bind to human CD161 with an affinity ($K_D$) of about 200-500 pM. In some embodiments, the anti-CD161 antibodies or antigen binding portions thereof bind to human CD161 with an affinity ($K_D$) of about 300-500 pM. In some embodiments, the anti-CD161 antibodies or antigen binding portions thereof bind to human CD161 with an affinity ($K_D$) of about 400-500 pM.

In some embodiments, the anti-CD161 antibodies or antigen binding portions thereof bind to human CD161 with an affinity ($K_D$) of about 50 pM, about 51 pM, about 52 pM, about 53 pM, about 54 pM, about 55 pM, about 56 pM, about 57 pM, about 58 pM, about 59 pM, about 60 pM, about 61 pM, about 62 pM, about 63 pM, about 64 pM, about 65 pM, about 66 pM, about 67 pM, about 68 pM, about 69 pM, about 70 pM, about 71 pM, about 72 pM, about 73 pM, about 74 pM, about 75 pM, about 77 pM, about 77 pM, about 78 pM, about 79 pM, about 80 pM, about 81 pM, about 82 pM, about 83 pM, about 84 pM, about 85 pM, about 88 pM, about 87 pM, about 88 pM, about 89 pM, about 90 pM, about 91 pM, about 92 pM, about 93 pM, about 94 pM, about 95 pM, about 99 pM, about 97 pM, about 98 pM, about 99 pM, about 100 pM, about 101 pM, about 102 pM, about 103 pM, about 104 pM, about 105 pM, about 1010 pM, about 107 pM, about 108 pM, about 109 pM, about 110 pM, about 111 pM, about 112 pM, about 113 pM, about 114 pM, about 115 pM, about 116 pM, about 117 pM, about 118 pM, about 119 pM, about 120 pM, about 121 pM, about 122 pM, about 123 pM, about 124 pM, about 125 pM, about 126 pM, about 127 pM, about 128 pM, about 129 pM, or about 130 pM.

In some embodiments, the anti-CD161 antibodies or antigen binding portions thereof bind to human CD161 with an affinity ($K_D$) of at least 50 pM but less than about 70 pM, at least 50 pM but less than about 80 pM, at least 50 pM but less than about 90 pM, at least 50 pM but less than about 100 pM, at least 60 pM but less than about 90 pM, at least 60 pM but less than about 100 pM, at least 80 pM but less than about 110 pM, at least 90 pM but less than about 120 pM, at least 100 pM but less than about 120 pM, at least 100 pM but less than about 130 pM, at least 100 pM but less than about 140 pM, at least 100 pM but less than about 150 pM, at least 110 pM but less than about 150 pM, at least 120 pM but less than about 150 pM, at least 120 pM but less than about 160 pM, at least 130 pM but less than about 160 pM, at least 140 pM but less than about 160 pM, at least 150 pM but less than about 170 pM, at least 150 pM but less than about 180 pM, at least 150 pM but less than about 190 pM, at least 150 pM but less than about 200 pM, at least 150 pM but less than about 250 pM, at least 200 pM but less than about 250 pM, at least 200 pM but less than about 300 pM, at least 250 pM but less than about 350 pM, at least 250 pM but less than about 400 pM, at least 300 pM but less than about 400 pM, at least 350 pM but less than about 400 pM, at least 350 pM but less than about 450 pM, at least 400 pM but less than about 500 pM, or at least 450 pM but less than about 500 pM.

CD161 Epitope Binding

In some embodiments, an isolated monoclonal antibody or antigen binding portions thereof of the disclosure specifically binds to an epitope on human CD161 comprising one or more amino acid residues (e.g., one, two, three, four, five, six, seven, eight, nine, 10, 11, 12, 13, 14, 15, 16, 17, 18, 19, 20, 21, 22, 23, 24, 25, 26, 27, 28, 29, or 30 amino acid residues) selected from amino acid residues 96-205 of SEQ ID NO: 335. In some embodiments, an isolated monoclonal antibody or antigen binding portion thereof of the disclosure specifically binds to an epitope on human CD161 comprising one or more amino acid residues (e.g., one, two, three, four, five, six, seven, eight, nine, 10, 11, 12, 13, 14, 15, 16, 17, 18, 19, 20, 21, 22, 23, 24, 25, 26, 27, 28, 29, 30, 31, 32, 33, or all 34 amino acid residues) selected from amino acid residues 96-130 of SEQ ID NO: 335. In some embodiments, an isolated monoclonal antibody or antigen binding portion thereof of the disclosure specifically binds to an epitope on human CD161 comprising one or more amino acid residues (e.g., one, two, three, four, five, six, seven, eight, nine, 10, 11, 12, 13, 14, 15, 16, 17, 18, 19, 20, 21, 22, 23, 24, 25, 26, 27, 28, 29, or all 30 amino acid residues) selected from amino acid residues 120-150 of SEQ ID NO: 335. In some embodiments, an isolated monoclonal antibody or antigen binding portion thereof of the disclosure specifically binds to an epitope on human CD161 comprising one or more amino acid residues (e.g., one, two, three, four, five, six, seven, eight, nine, 10, 11, 12, 13, 14, 15, 16, 17, 18, 19, 20, 21, 22, 23, 24, 25, 26, 27, 28, 29, 30, 31, 32, 33, 34 or 35 amino acid residues) selected from amino acid residues 150-205 of SEQ ID NO: 335.

In some embodiments, an isolated monoclonal antibody or antigen binding portion thereof of the disclosure specifically binds to an epitope on human CD161 comprising one or more amino acid residues selected from: I96, D121, K125, E126, R146, L151, Y198, E200, or E205 of SEQ ID NO: 335. In some embodiments, an isolated monoclonal antibody or antigen binding portion thereof of the disclosure specifically binds to an epitope on human CD161 comprising one or more amino acid residues selected from: I96, D121, K125, E126, R146, L151, Y198, E200, and E205 of SEQ ID NO: 335. In some embodiments, an isolated monoclonal antibody or antigen binding portion thereof of the disclosure specifically binds to an epitope on human CD161 comprising amino acid residue I96 of SEQ ID NO: 335. In some embodiments, an isolated monoclonal antibody or antigen binding portion thereof of the disclosure specifically binds to an epitope on human CD161 comprising amino acid residue D121 of SEQ ID NO: 335. In some embodiments, an isolated monoclonal antibody or antigen binding portion thereof of the disclosure specifically binds to an epitope on human CD161 comprising amino acid residue K125 of SEQ ID NO: 335. In some embodiments, an isolated monoclonal antibody or antigen binding portion thereof of the disclosure specifically binds to an epitope on human CD161 comprising amino acid residue E126 of SEQ ID NO: 335. In some embodiments, an isolated monoclonal antibody or antigen binding portion thereof of the disclosure specifically binds to an epitope on human CD161 comprising amino acid residue R146 of SEQ ID NO: 335. In some embodiments, an isolated monoclonal antibody or antigen binding portion thereof of the disclosure specifically binds to an epitope on human CD161 comprising amino acid residue L151 of SEQ ID NO: 335. In some embodiments, an isolated monoclonal antibody or antigen binding portion thereof of the disclosure specifically binds to an epitope on human CD161 comprising amino acid residue Y198 of SEQ ID NO: 335. In some embodiments, an isolated monoclonal antibody or antigen binding portion thereof of the disclosure specifically binds to an epitope on human CD161 comprising amino acid residue E200 of SEQ ID NO: 335, or amino acid residue E205 of SEQ ID NO: 335.

In some embodiments, an isolated monoclonal antibody or antigen binding portion thereof of the disclosure specifically binds to an epitope on human CD161 comprising amino acid residues I96, D121, K125, and E126 of SEQ ID NO: 335. In some embodiments, an isolated monoclonal antibody or antigen binding portion thereof of the disclosure specifically binds to an epitope on human CD161 comprising amino acid residues I96 and K125 of SEQ ID NO: 335. In some embodiments, an isolated monoclonal antibody or antigen binding portion thereof of the disclosure specifically binds to an epitope on human CD161 comprising L151, Y198, E200, or E205 of SEQ ID NO: 335. In some embodiments, an isolated monoclonal antibody or antigen binding portion thereof of the disclosure specifically binds to an epitope on human CD161 comprising L151, Y198, E200, and E205 of SEQ ID NO: 335.

In some embodiments, the disclosure provides an anti-CD161 antibody or antigen binding portion thereof that binds to human CD1.61, wherein binding affinity is abrogated or reduced when one or more amino acid residues of human CD161 is mutated to alanine. Methods of measuring binding of an antibody or antigen binding portion thereof to an antigen are known in the art and further described in the Examples. In some embodiments, the disclosure provides an anti-CD161 antibody or antigen binding portion thereof that binds to human CD161, wherein binding to mutated human CD161 is not more than about 1%, about 5%, about 10%, about 15%, about 20%, about 25%, about 30%, about 35%, about 40%, about 45%, about 50%, about 55%, or about 60% of binding to wild type human CD161. In some embodiments, the disclosure provides an anti-CD161 antibody or antigen binding portion thereof that binds to human CD161, wherein binding to mutated human CD161 is not more than about 1-10%, about 1-20%, about 10-30%, about 10-40%, about 20-30%, 20-40%, 20-50%, 30-50%, 30-60%, 40-50%, or 40-60% of binding to wild type human CD161.

In some embodiments, an isolated monoclonal antibody or antigen binding portion thereof of the disclosure specifically binds to human CD161 with abrogated or reduced binding affinity when one or more amino acid residues is mutated to alanine, wherein the one or more amino acid residues are selected from:
 a) amino acid residue I96 of SEQ ID NO: 335;
 b) amino acid residue R102 of SEQ ID NO: 335;
 c) amino acid residue E103 of SEQ ID NO: 335;
 d) amino acid residue D121 of SEQ ID NO: 335;
 e) amino acid residue K125 of SEQ ID NO: 335;
 f) amino acid residue E126 of SEQ ID NO: 335;
 g) amino acid residue R133 of SEQ ID NO: 335;
 h) amino acid residue K135 of SEQ ID NO: 335;
 i) amino acid residue R146 of SEQ ID NO: 335;
 j) amino acid residue K148 of SEQ ID NO: 335;
 k) amino acid residue K163 of SEQ ID NO: 335;
 l) amino acid residue L151 of SEQ ID NO: 335;
 m) amino acid residue Y198 of SEQ ID NO: 335;
 n) amino acid residue E200 of SEQ ID NO: 335; and
 o) amino acid residue E205 of SEQ ID NO: 335.

In some embodiments, an isolated monoclonal antibody or antigen binding portion thereof of the disclosure specifically binds to human CD161 with abrogated or reduced binding affinity when one or more amino acid residues is mutated to alanine, wherein the one or more amino acid residues comprise D121 of SEQ ID NO: 335. In some embodiments, an isolated monoclonal antibody or antigen binding portion thereof of the disclosure specifically binds to human CD161 with abrogated or reduced binding affinity when one or more amino acid residues is mutated to alanine, wherein the one or more amino acid residues comprise I96, D121, K125, E126, and K148 of SEQ ID NO: 335. In some embodiments, an isolated monoclonal antibody or antigen binding portion thereof of the disclosure specifically binds to human CD161 with abrogated or reduced binding affinity when one or more amino acid residues is mutated to alanine, wherein the one or more amino acid residues comprise K125 and R146 of SEQ ID NO: 335. In some embodiments, an isolated monoclonal antibody or antigen binding portion thereof of the disclosure specifically binds to human CD161 with abrogated or reduced binding affinity when one or more amino acid residues is mutated to alanine, wherein the one or more amino acid residues comprise K125, L151, Y198, E200, and E205 of SEQ ID NO: 335. In some embodiments, an isolated monoclonal antibody or antigen binding portion thereof of the disclosure specifically binds to human CD161 with abrogated or reduced binding affinity when one or more amino acid residues is mutated to alanine, wherein the one or more amino acid residues comprise 196, R102, E103, D121, K125, R133, K135, R146, K148, and K163 of SEQ ID NO: 335.

In some embodiments, an isolated monoclonal antibody or antigen binding portion thereof of the disclosure specifically binds to an epitope on human CD161 comprising one or more amino acid residues corresponding to amino acid positions 96-205 of SEQ ID NO: 335, wherein the epitope comprises at least amino acid residue D121, and wherein the antibody or antigen binding portion thereof binds to cynomolgus CD161. In some embodiments, an isolated monoclonal antibody or antigen binding portion thereof of the disclosure specifically binds to an epitope on human CD161 comprising one or more amino acid residues corresponding to amino acid positions 96-205 of SEQ ID NO: 335, wherein the epitope comprises at least amino acid residues I96, D121, K125, and E126 and wherein the antibody or antigen binding portion thereof binds to cynomolgus CD161. In some embodiments, an isolated monoclonal antibody or antigen binding portion thereof of the disclosure specifically binds to an epitope on human CD161 comprising one or more amino acid residues corresponding to amino acid positions 96-205 of SEQ ID NO: 335, wherein the epitope comprises at least amino acid residues 196 and K125, and wherein the antibody or antigen binding portion thereof binds to cynomolgus CD161.

In some embodiments, an isolated monoclonal antibody or antigen binding portion thereof of the disclosure specifically binds to an epitope on human CD161 comprising one or more amino acid residues corresponding to amino acid positions 96-205 of SEQ ID NO: 335, wherein the epitope comprises at least amino acid residue R146 and wherein the antibody or antigen binding portion thereof does not significantly bind to cynomolgus CD161. In some embodiments, an isolated monoclonal antibody or antigen binding portion thereof of the disclosure specifically binds to an epitope on human CD161 comprising one or more amino acid residues corresponding to amino acid positions 96-205 of SEQ ID NO: 335, wherein the epitope comprises at least amino acid residues L151, Y198, E200, and E205 and wherein the antibody or antigen binding portion thereof does not bind to cynomolgus CD161. In some embodiments, binding of an isolated monoclonal antibody or antigen binding portion thereof described herein to human CD161 or cynomolgus CD161 is determined by binding to CD161-expressing cells (e.g., as measured by flow cytometry or microscopy) or by surface plasmon resonance (SPR).

In some embodiments, an isolated monoclonal antibody or antigen binding portion thereof of the disclosure specifically binds to an epitope on human CD161 with an affinity that is at least 10, 20, 30, 40, 50, 100, 200, 500 or 1000 times greater than the antibody's affinity for cynomolgus CD161. In some embodiments, an isolated monoclonal antibody or antigen binding portion thereof of the disclosure specifically binds to an epitope on human CD161 with an affinity that is at least 10, 20, 30, 40, 50, 100, 200, 500 or 1000 times greater than the antibody's affinity for a CD161 polypeptide that does not comprise an arginine at position 102 or 146 of SEQ ID NO: 335. In some embodiments, an isolated monoclonal antibody or antigen binding portion thereof of the disclosure specifically binds to an epitope on human CD161 with an affinity that is at least 10, 20, 30, 40, 50, 100, 200, 500 or 1000 times greater than the antibody's affinity for a CD161 polypeptide that does not comprise a leucine at position 151 of SEQ ID NO: 335.

In some embodiments, an isolated monoclonal antibody or antigen binding portion thereof of the disclosure specifically binds to an epitope on human CD161 that comprises all or a portion of an epitope recognized by one or more particular reference antibodies described herein (e.g., KW1, KW7, KW9, KM12, KW17, or HP-3G10). In some embodiments, anti-CD161 antibodies or antigen binding portion thereof of the disclosure bind human CD161 with an equilibrium dissociation constant $K_D$ of about 500-1000, 500-1500, or 500-2000 nM and compete with a reference antibody (e.g., KW1, KW7, KW9, KM12, KW17, or HP-3G10) for binding to an epitope on human CD161. In some embodiments, anti-CD161 antibodies or antigen binding portion thereof of the disclosure bind human CD161 with an equilibrium dissociation constant $K_D$ of less than 500, 400, 300, 200, 100, 50, 40, 30, 20, 10, 5, 4, 3, 2, 1, 0.5, 0.1, or 0.05 nM and compete with a reference antibody (e.g., KW1, KW7, KW9, KM12, KW17, or HP-3G10) for binding to an epitope on human CD161. In some embodiments, the anti-CD161 antibodies or antigen binding portion thereof bind to an epitope on CD161, wherein one or more mutations to the epitope inhibit, reduce, or block binding to both the antibodies and a reference antibody (e.g., HP-3G10). In some embodiments, the reference antibody is the HP-3G10 antibody. In some embodiments, the reference antibody is KW1, KW7, KW9, KM12, or KW17. In some embodiments, the reference antibody is any one antibody provided in Table 20.

In some embodiments, the epitope bound by the anti-CD161 antibodies described herein is at least 3 amino acid residues. In some embodiments, the epitope bound by the anti-CD161 antibodies described herein is at least 4 amino acid residues. In some embodiments, the epitope bound by the anti-CD161 antibodies described herein is at least 5 amino acid residues. In some embodiments, the epitope bound by the anti-CD161 antibodies described herein is at least 6 amino acid residues. In some embodiments, the epitope bound by the anti-CD161 antibodies described herein is at least 7 amino acid residues. In some embodiments, the epitope bound by the anti-CD161 antibodies described herein is at least 8 amino acid residues. In some embodiments, the epitope bound by the anti-CD161 antibodies described herein is at least 9 amino acid residues. In some embodiments, the epitope bound by the anti-CD161 antibodies described herein is at least 10 amino acid residues. In some embodiments, the epitope bound by the anti-CD161 antibodies described herein is at least 12 amino acid residues. In some embodiments, the epitope bound by the anti-CD161 antibodies described herein is at least 3 amino acid residues. In some embodiments, the epitope bound by the anti-CD161 antibodies described herein is at least 13 amino acid residues. In some embodiments, the epitope bound by the anti-CD161 antibodies described herein is at least 14 amino acid residues. In some embodiments, the epitope bound by the anti-CD161 antibodies described herein is at least 15 amino acid residues.

In some embodiments, the epitope bound by the anti-CD161 antibodies described herein is fewer than 25 amino acid residues. In some embodiments, the epitope bound by the anti-CD161 antibodies described herein is fewer than 24 amino acid residues. In some embodiments, the epitope bound by the anti-CD161 antibodies described herein is fewer than 23 amino acid residues. In some embodiments, the epitope bound by the anti-CD161 antibodies described herein is fewer than 22 amino acid residues. In some embodiments, the epitope bound by the anti-CD161 antibodies described herein is fewer than 21 amino acid residues. In some embodiments, the epitope bound by the anti-CD161 antibodies described herein is fewer than 20 amino acid residues. In some embodiments, the epitope bound by the anti-CD161 antibodies described herein is fewer than 19 amino acid residues. In some embodiments, the epitope bound by the anti-CD161 antibodies described herein is fewer than 18 amino acid residues. In some embodiments, the epitope bound by the anti-CD161 antibodies described herein is fewer than 17 amino acid residues. In some embodiments, the epitope bound by the anti-CD161 antibodies described herein is fewer than 16 amino acid residues. In some embodiments, the epitope bound by the anti-CD161 antibodies described herein is fewer than 15 amino acid residues. In some embodiments, the epitope bound by the anti-CD161 antibodies described herein is fewer than 14 amino acid residues. In some embodiments, the epitope bound by the anti-CD161 antibodies described herein is fewer than 13 amino acid residues. In some embodiments, the epitope bound by the anti-CD161 antibodies described herein is fewer than 12 amino acid residues. In some embodiments, the epitope bound by the anti-CD161 antibodies described herein is fewer than 11 amino acid residues. In some embodiments, the epitope bound by the anti-CD161 antibodies described herein is fewer than 10 amino acid residues. In some embodiments, the epitope bound by the anti-CD161 antibodies described herein is fewer than 9 amino acid residues. In some embodiments, the epitope bound by the anti-CD161 antibodies described herein is fewer than 8 amino acid residues. In some embodiments, the epitope bound by the anti-CD161 antibodies described herein is fewer than 7 amino acid residues. In some embodiments, the epitope bound by the anti-CD161 antibodies described herein is fewer than 6 amino acid residues. In some embodiments, the epitope bound by the anti-CD161 antibodies described herein is fewer than 5 amino acid residues.

In some embodiments, the anti-CD161 antibodies described herein bind to an epitope of fewer than 25, 24, 23, 22, 21, 20, 19, 18, 17, 16, 15, 14, 13, 12, 11, 10, 9, 8, 7, 6 or 5 amino acids and comprises one or more amino acid residue selected from: I96, D121, K125, E126, R146, L151, Y198, E200, or E205 of SEQ ID NO: 335. In some embodiments, the anti-CD161 antibodies described herein bind to an epitope of fewer than 25, 24, 23, 22, 21, 20, 19, 18, 17, 16, 15, 14, 13, 12, 11, 10, 9, 8, 7, 6 or 5 amino acids and comprises amino acid residue D121 of SEQ ID NO: 335. In some embodiments, the anti-CD161 antibodies described herein bind to an epitope of fewer than 25, 24, 23, 22, 21, 20, 19, 18, 17, 16, 15, 14, 13, 12, 11, 10, 9, 8, 7, 6 or 5 amino acids and comprises amino acid residues D121, I96, K125, and E126 of SEQ ID NO: 335. In some embodiments, the anti-CD161 antibodies described herein bind to an epitope of fewer than 25, 24, 23, 22, 21, 20, 19, 18, 17, 16, 15, 14, 13, 12, 11, 10, 9, 8, 7, 6 or 5 amino acids and comprises amino acid residues I96 and K125 of SEQ ID NO: 335. In some embodiments, the anti-CD161 antibodies described herein bind to an epitope of fewer than 25, 24, 23, 22, 21, 20, 19, 18, 17, 16, 15, 14, 13, 12, 11, 10, 9, 8, 7, 6 or 5 amino acids and comprises amino acid residue R146 of SEQ ID NO: 335. In some embodiments, the anti-CD161 antibodies described herein bind to an epitope of fewer than 25, 24, 23, 22, 21, 20, 19, 18, 17, 16, 15, 14, 13, 12, 11, 10, 9, 8, 7, 6 or 5 amino acids and comprises amino acid residues L151, Y198, E200, or E205 of SEQ ID NO: 335.

In some embodiments, the anti-CD161 antibodies described herein bind to an epitope on human CD161 and compete for binding when compared to one or more reference antibodies, wherein the one or more reference antibodies comprises KW1. In some embodiments, the anti-CD161 antibodies described herein bind to an epitope on human CD161 and compete for binding when compared to one or more reference antibodies, wherein the one or more reference antibodies comprises KW7. In some embodiments, the anti-CD161 antibodies described herein bind to an epitope on human CD161 and compete for binding when compared to one or more reference antibodies, wherein the one or more reference antibodies comprises KW1 and KW7. In some embodiments, the anti-CD161 antibodies described herein bind to an epitope on human CD161 and compete for binding when compared to one or more reference antibodies, wherein the one or more reference antibodies comprises KW9. In some embodiments, the anti-CD161 antibodies described herein bind to an epitope on human CD161 and compete for binding when compared to one or more reference antibodies, wherein the one or more reference antibodies comprises KW1 and KW9. In some embodiments, the anti-CD161 antibodies described herein bind to an epitope on human CD161 and compete for binding when compared to one or more reference antibodies, wherein the one or more reference antibodies comprises KW7 and KW9. In some embodiments, the anti-CD161 antibodies described herein bind to an epitope on human CD161 and compete for binding when compared to one or more reference antibodies, wherein the one or more reference antibodies comprises KW1, KW7 and KW9. In some embodiments, the anti-CD161 antibodies described herein bind to an epitope on human CD161 and compete for binding when compared to one or more reference antibodies, wherein the one or more reference antibodies comprises KW17. In some embodiments, the anti-CD161 antibodies described herein bind to an epitope on human CD161 and compete for binding when compared to one or more reference antibodies, wherein the one or more reference antibodies comprises KW9 and KW17. In some embodiments, the anti-CD161 antibodies described herein bind to an epitope on human CD161 and compete for binding when compared to one or more reference antibodies, wherein the one or more reference antibodies comprises KM12. In some embodiments, the anti-CD161 antibodies described herein bind to an epitope on human CD161 and compete for binding when compared to one or more reference antibodies, wherein the one or more reference antibodies comprises HP-3G10. In some embodiments, the anti-CD161 antibodies described herein bind to an epitope on human CD161 and compete for binding when compared to one or more reference antibodies, wherein the one or more reference antibodies comprises KM12 and HP-3G10. In some embodiments, the anti-CD161 antibodies described herein bind to an epitope on human CD161 and compete for binding when compared to one or more reference antibodies, wherein the one or more reference antibodies comprises KW9 and HP-3G10. In some embodiments, the anti-CD161 antibodies described herein bind to an epitope on human CD161 and compete for binding when compared to one or more reference antibodies, wherein the one or more reference antibodies comprises KW17 and HP-3G10. In some embodiments, the anti-CD161 antibodies described herein bind to an epitope on human CD161 and compete for binding when compared to one or more reference antibodies, wherein the one or more reference antibodies comprises KW9, KW17 and HP-3G10.

Variable Regions

In some embodiments, the disclosure provides isolated monoclonal antibodies or antigen binding portion thereof that bind human CD161 and comprise heavy and light chain variable sequences.

In some embodiments, a variable domain of the antibodies described herein comprises three complementarity determining regions (CDRs), each of which is flanked by a framework region (FW). For example, a VH domain may comprise a set of three heavy chain CDRs: HCDR1, HCDR2, and HCDR3. A VL domain may comprise a set of three light chain CDRs: LCDR1, LCDR2, and LCDR3. A set of HCDRs can be provided in a VH domain that is used in combination with a VL domain A VH domain may be provided with a set of HCDRs, and if such a VH domain is paired with a VL domain, then the VL domain may be provided with a set of LCDRs disclosed herein.

CDR Numbering

In some embodiments, the anti-CD161 antibodies and antigen-binding fragments thereof described herein are numbered according to numbering conventions known in the art. In some embodiments, the heavy and light chain CDRs of the anti-CD161 antibodies and antigen-binding fragments thereof described herein are numbered according to IMGT unique numbering.

The IMGT (INTERNATIONAL IMMUNOGENETICS INFORMATION SYSTEM) numbering of variable regions is the numbering of the residues in an immunoglobulin variable heavy or light chain according to the methods of the IMGT, as described in Lefranc, M.-P., "The IMGT unique numbering for immunoglobulins, T cell Receptors and Ig-like domains", The Immunologist, 7, 132-136 (1999), and is expressly incorporated herein in its entirety by reference. As used herein, "IMGT sequence numbering" or "numbered according to IMGT," refers to numbering of the sequence encoding a variable region according to the IMGT. For the heavy chain variable domain, when numbered according to IMGT, the hypervariable region ranges from amino acid positions 27 to 38 for CDR1, amino acid positions 56 to 65 for CDR2, and amino acid positions 105 to 117 for CDR3. For the light chain variable domain, when numbered according to IMGT, the hypervariable region ranges from amino acid positions 27 to 38 for CDR1, amino acid positions 56 to 65 for CDR2, and amino acid positions 105 to 117 for CDR3. When the CDRs are numbered according to IMGT, the heavy chain framework (FR) residues are positioned about at residues 1-26 (HC-FR1), 39-55 (HC-FR2), 66-104 (HC-FR3), and 118-128 (HCFR4) in the heavy chain residues and the light chain FR residues are positioned at about residues 1-26 (LC-FR1), 39-55 (LC-FR2), 66-104 (LC-FR3), and 118-128 (LC-FR4).

Other CDR numbering systems are known in the art and the heavy and light chain CDRs of the anti-CD161 antibodies of the disclosure are numbered according to a numbering system other than IMGT. In one embodiment, the heavy and light chain CDRs of the anti-CD161 antibodies of the disclosure are numbered according to the system described by Kabat, also referred to as "numbered according to Kabat," "Kabat numbering", and "Kabat definitions" provides an residue numbering system applicable to any variable domain of an antibody, and provides precise residue boundaries defining the three CDRs of each chain. (Kabat et al., Sequences of Proteins of Immunological Interest, National Institutes of Health, Bethesda, Md. (1987) and (1991), the contents of which are incorporated by reference in their entirety. Heavy and light chain CDRs of the anti-CD161 antibodies of the disclosure numbered according to Kabat are also referred to as Kabat CDRs. The "EU index as in Kabat" refers to the residue numbering of the human IgG1 EU antibody.

In other embodiments, the heavy and light chain CDRs of the anti-CD161 antibodies of the disclosure are numbered according Chothia et al. Chothia and coworkers identified sub-portions within Kabat CDRs that adopt nearly identical peptide backbone conformations, despite having great diversity at the level of amino acid sequence. (Chothia et al. (1987) J. Mol. Biol. 196: 901-917; and Chothia et al. (1989) Nature 342: 877-883). These sub-portions were designated as L1, L2, and L3 or H1, H2, and H3 where the "L" and the "H" designates the light chain and the heavy chains regions, respectively. Heavy and light chain CDRs of the anti-CD161 antibodies of the disclosure numbered according to Chothia et al. are referred to as "Chothia CDRs," "Chothia numbering," or "numbered according to Chothia."

An antibody of the disclosure having the same CDRs (e.g., CDR3) as a reference antibody, or antigen-binding portion thereof, means that the two antibodies have the same amino acid sequence in that CDR region as determined by the same methodology (e.g., IMGT numbering, Kabat numbering, Chothia numbering).

Heavy Chain CDR3

In some embodiments, anti-CD161 antibodies or antigen binding portions thereof of the disclosure comprise a heavy chain CDR3, wherein the heavy chain CDR3 comprises the amino acid sequence ARGGX$_1$X$_2$PX$_3$X$_4$FX$_5$Y (SEQ ID NO: 307), wherein X$_1$ is selected from L or Y, X$_2$ is selected from I or L, X$_3$ is selected from S or D, X$_4$ is selected from G or A, and X$_5$ is any amino acid. In some embodiments, the heavy chain CDR3 comprises the amino acid sequence ARGGX$_1$X$_2$PX$_3$X$_4$FX$_5$Y (SEQ ID NO: 307), wherein X$_1$ is selected from L or Y, X$_2$ is selected from I or L, X$_3$ is selected from S or D, X$_4$ is selected from G or A, and X$_5$ is selected from D or G. In some embodiments, the heavy chain CDR3 comprises the amino acid sequence ARGGX$_1$X$_2$PX$_3$X$_4$FX$_5$Y (SEQ ID NO: 307), wherein X$_1$ is L, X$_2$ is I, X$_3$ is S, X$_4$ is G, and X$_5$ is any amino acid. In some embodiments, the heavy chain CDR3 comprises the amino acid sequence ARGGX$_1$X$_2$PX$_3$X$_4$FX$_5$Y (SEQ ID NO: 307), wherein X$_1$ is L, X$_2$ is I, X$_3$ is S, X$_4$ is G, and X$_5$ is D or G. In some embodiments, the heavy chain CDR3 comprises the amino acid sequence ARGGLIPSGFX$_1$Y (SEQ ID NO: 308), wherein X$_1$ is any amino acid. In some embodiments, the heavy chain CDR3 comprises the amino acid sequence ARGGLIPSGFX$_1$Y (SEQ ID NO: 308), wherein X$_1$ is D or G. In some embodiments, the heavy chain CDR3 comprises the amino acid sequence selected from: ARGGLIPSGFDY (SEQ ID NO: 141), ARGGLIPSGFGY (SEQ ID NO: 142), and ARGGYLPDAFDY (SEQ ID NO: 143).

In some embodiments, anti-CD161 antibodies or antigen binding portions thereof of the disclosure comprise a heavy chain CDR3, wherein the heavy chain CDR3 comprises the amino acid sequence ARGPGX$_1$MYLYGDSFFX$_2$Y (SEQ ID NO: 309), wherein X$_1$ is any amino acid, and wherein X$_2$ is any amino acid. In some embodiments, the heavy chain CDR3 comprises the amino acid sequence ARGPGX$_1$MYLYGDSFFX$_2$Y (SEQ ID NO: 309), wherein X$_1$ is selected from D or Y and X$_2$ is selected from D or E. In some embodiments, the heavy chain CDR3 comprises the amino acid sequence selected from: ARGPGDMYLYGDSFFDY (SEQ ID NO: 144), ARGPGYMYLYGDSFFDY (SEQ ID NO: 145), and ARGPGYMYLYGDSFFEY (SEQ ID NO: 146).

In some embodiments, anti-CD161 antibodies or antigen binding portions thereof of the disclosure comprise a heavy chain CDR3, wherein the heavy chain CDR3 comprises the amino acid sequence ARDYYLX$_1$DYITQTSFDY (SEQ ID NO: 310), wherein X$_1$ is any amino acid. In some embodiments, the heavy chain CDR3 comprises the amino acid sequence ARDYYLX$_1$DYITQTSFDY (SEQ ID NO: 310), wherein X$_1$ is selected from S, F or Y. In some embodiments, the heavy chain CDR3 comprises the amino acid sequence selected from: ARDYYLSDYITQTSFDY (SEQ ID NO: 147), ARDYYLFDYITQTSFDY (SEQ ID NO: 148), and ARDYYLYDYITQTSFDY (SEQ ID NO: 149).

In some embodiments, anti-CD161 antibodies or antigen binding portions thereof of the disclosure comprise a heavy chain CDR3, wherein the heavy chain CDR3 comprises the amino acid sequence ARGYSDSYX$_1$YGPYYTFDY (SEQ ID NO: 311), wherein X$_1$ is any amino acid. In some embodiments, the heavy chain CDR3 comprises the amino acid sequence ARGYSDSYX$_1$YGPYYTFDY (SEQ ID NO: 311), wherein X$_1$ is selected from Y or F. In some embodiments, the heavy chain CDR3 comprises an amino acid sequence selected from: ARGYSDSYYYGPYYTFDY (SEQ ID NO: 150) and ARGYSDSYFYGPYYTFDY (SEQ ID NO: 151).

In some embodiments, anti-CD161 antibodies or antigen binding portions thereof of the disclosure comprise a heavy chain CDR3, wherein the heavy chain CDR3 comprises the amino acid sequence selected from a sequence set forth in Table 21.

CDR Combinations

In some embodiments, anti-CD161 antibodies or antigen binding portions thereof of the disclosure comprise heavy and light chain CDRs selected from:

(a) heavy chain CDR1, CDR2, and CDR3 comprise amino acid sequences set forth in SEQ ID NOs: 299, 303, and 307 respectively, and wherein light chain CDR1, CDR2, and CDR3 comprise amino acid sequences set forth in SEQ ID NOs: 312, 316, and 317 respectively;

(b) heavy chain CDR1, CDR2, and CDR3 comprise amino acid sequences set forth in SEQ ID NOs: 299, 303, and 307 respectively, and wherein light chain CDR1, CDR2, and CDR3 comprise amino acid sequences set forth in SEQ ID NOs: 312, 316, and 318 respectively;

(c) heavy chain CDR1, CDR2, and CDR3 comprise amino acid sequences set forth in SEQ ID NOs: 300, 304, and 307 respectively, and wherein light chain CDR1, CDR2, and CDR3 comprise amino acid sequences set forth in SEQ ID NOs: 312, 316, and 317 respectively;

(d) heavy chain CDR1, CDR2, and CDR3 comprise amino acid sequences set forth in SEQ ID NOs: 300, 304, and 307 respectively, and wherein light chain CDR1, CDR2, and CDR3 comprise amino acid sequences set forth in SEQ ID NOs: 312, 316, and 318 respectively;

(e) heavy chain CDR1, CDR2, and CDR3 comprise amino acid sequences set forth in SEQ ID NOs: 300, 304, and 308 respectively, and wherein light chain CDR1, CDR2, and CDR3 comprise amino acid sequences set forth in SEQ ID NOs: 312, 316, and 317 respectively;

(f) heavy chain CDR1, CDR2, and CDR3 comprise amino acid sequences set forth in SEQ ID NOs: 300, 304, and 308 respectively, and wherein light chain CDR1, CDR2, and CDR3 comprise amino acid sequences set forth in SEQ ID NOs: 312, 316, and 318 respectively;
(g) heavy chain CDR1, CDR2, and CDR3 comprise amino acid sequences set forth in SEQ ID NOs: 299, 303, and 309 respectively, and wherein light chain CDR1, CDR2, and CDR3 comprise amino acid sequences set forth in SEQ ID NOs: 312, 316, and 317 respectively;
(h) heavy chain CDR1, CDR2, and CDR3 comprise amino acid sequences set forth in SEQ ID NOs: 299, 303, and 309 respectively, and wherein light chain CDR1, CDR2, and CDR3 comprise amino acid sequences set forth in SEQ ID NOs: 313, 316, and 319 respectively;
(i) heavy chain CDR1, CDR2, and CDR3 comprise amino acid sequences set forth in SEQ ID NOs: 300, 304, and 309 respectively, and wherein light chain CDR1, CDR2, and CDR3 comprise amino acid sequences set forth in SEQ ID NOs: 312, 316, and 317 respectively;
(j) heavy chain CDR1, CDR2, and CDR3 comprise amino acid sequences set forth in SEQ ID NOs: 300, 304, and 309 respectively, and wherein light chain CDR1, CDR2, and CDR3 comprise amino acid sequences set forth in SEQ ID NOs: 313, 316, and 319 respectively;
(k) heavy chain CDR1, CDR2, and CDR3 comprise amino acid sequences set forth in SEQ ID NOs: 299, 303, and 310 respectively, and wherein light chain CDR1, CDR2, and CDR3 comprise amino acid sequences set forth in SEQ ID NOs: 315, 316, and 321 respectively;
(l) heavy chain CDR1, CDR2, and CDR3 comprise amino acid sequences set forth in SEQ ID NOs: 301, 305, and 310 respectively, and wherein light chain CDR1, CDR2, and CDR3 comprise amino acid sequences set forth in SEQ ID NOs: 315, 316, and 321 respectively;
(m) heavy chain CDR1, CDR2, and CDR3 comprise amino acid sequences set forth in SEQ ID NOs: 299, 303, and 311 respectively, and wherein light chain CDR1, CDR2, and CDR3 comprise amino acid sequences set forth in SEQ ID NOs: 312, 316, and 317 respectively;
(n) heavy chain CDR1, CDR2, and CDR3 comprise amino acid sequences set forth in SEQ ID NOs: 299, 303, and 311 respectively, and wherein light chain CDR1, CDR2, and CDR3 comprise amino acid sequences set forth in SEQ ID NOs: 314, 316, and 320 respectively;
(o) heavy chain CDR1, CDR2, and CDR3 comprise amino acid sequences set forth in SEQ ID NOs: 302, 306, and 311 respectively, and wherein light chain CDR1, CDR2, and CDR3 comprise amino acid sequences set forth in SEQ ID NOs: 312, 316, and 317 respectively; and
(p) heavy chain CDR1, CDR2, and CDR3 comprise amino acid sequences set forth in SEQ ID NOs: 302, 306, and 311 respectively, and wherein light chain CDR1, CDR2, and CDR3 comprise amino acid sequences set forth in SEQ ID NOs: 314, 316, and 320 respectively.

In some embodiments, anti-CD161 antibodies or antigen binding portions thereof of the disclosure comprise heavy and light chain CDRs selected from:
(a) heavy chain CDR1, CDR2, and CDR3 comprise amino acid sequences set forth in SEQ ID NOs: 127, 132, and 141 respectively; and light chain CDR1, CDR2, and CDR3 comprise amino acid sequences set forth in SEQ ID NOs: 273, 279, and 281 respectively;
(b) heavy chain CDR1, CDR2, and CDR3 comprise amino acid sequences set forth in SEQ ID NOs: 127, 132, and 141 respectively; and light chain CDR1, CDR2, and CDR3 comprise amino acid sequences set forth in SEQ ID NOs: 273, 279, and 282 respectively;
(c) heavy chain CDR1, CDR2, and CDR3 comprise amino acid sequences set forth in SEQ ID NOs: 127, 132, and 141 respectively; and light chain CDR1, CDR2, and CDR3 comprise amino acid sequences set forth in SEQ ID NOs: 273, 279, and 283 respectively;
(d) heavy chain CDR1, CDR2, and CDR3 comprise amino acid sequences set forth in SEQ ID NOs: 127, 132, and 141 respectively; and light chain CDR1, CDR2, and CDR3 comprise amino acid sequences set forth in SEQ ID NOs: 273, 279, and 284 respectively;
(e) heavy chain CDR1, CDR2, and CDR3 comprise amino acid sequences set forth in SEQ ID NOs: 127, 132, and 142 respectively; and light chain CDR1, CDR2, and CDR3 comprise amino acid sequences set forth in SEQ ID NOs: 273, 279, and 281 respectively;
(f) heavy chain CDR1, CDR2, and CDR3 comprise amino acid sequences set forth in SEQ ID NOs: 128, 132, and 141 respectively; and light chain CDR1, CDR2, and CDR3 comprise amino acid sequences set forth in SEQ ID NOs: 273, 279, and 283 respectively;
(g) heavy chain CDR1, CDR2, and CDR3 comprise amino acid sequences set forth in SEQ ID NOs: 129, 132, and 141 respectively; and light chain CDR1, CDR2, and CDR3 comprise amino acid sequences set forth in SEQ ID NOs: 273, 279, and 283 respectively;
(h) heavy chain CDR1, CDR2, and CDR3 comprise amino acid sequences set forth in SEQ ID NOs: 127, 132, and 143 respectively; and light chain CDR1, CDR2, and CDR3 comprise amino acid sequences set forth in SEQ ID NOs: 273, 279, and 281 respectively;
(i) heavy chain CDR1, CDR2, and CDR3 comprise amino acid sequences set forth in SEQ ID NOs: 127, 132, and 143 respectively; and light chain CDR1, CDR2, and CDR3 comprise amino acid sequences set forth in SEQ ID NOs: 273, 279, and 283 respectively;
(j) heavy chain CDR1, CDR2, and CDR3 comprise amino acid sequences set forth in SEQ ID NOs: 127, 133, and 143 respectively; and light chain CDR1, CDR2, and CDR3 comprise amino acid sequences set forth in SEQ ID NOs: 273, 279, and 283 respectively;
(k) heavy chain CDR1, CDR2, and CDR3 comprise amino acid sequences set forth in SEQ ID NOs: 129, 132, and 143 respectively; and light chain CDR1, CDR2, and CDR3 comprise amino acid sequences set forth in SEQ ID NOs: 273, 279, and 283 respectively;
(l) heavy chain CDR1, CDR2, and CDR3 comprise amino acid sequences set forth in SEQ ID NOs: 127, 132, and 144 respectively; and light chain CDR1, CDR2, and CDR3 comprise amino acid sequences set forth in SEQ ID NOs: 273, 279, and 281 respectively;
(m) heavy chain CDR1, CDR2, and CDR3 comprise amino acid sequences set forth in SEQ ID NOs: 127, 132, and 145 respectively; and light chain CDR1, CDR2, and CDR3 comprise amino acid sequences set forth in SEQ ID NOs: 273, 279, and 281 respectively;
(n) heavy chain CDR1, CDR2, and CDR3 comprise amino acid sequences set forth in SEQ ID NOs: 127, 132, and 145 respectively; and light chain CDR1, CDR2, and CDR3 comprise amino acid sequences set forth in SEQ ID NOs: 273, 279, and 285 respectively;
(o) heavy chain CDR1, CDR2, and CDR3 comprise amino acid sequences set forth in SEQ ID NOs: 127, 132, and 145 respectively; and light chain CDR1, CDR2, and CDR3 comprise amino acid sequences set forth in SEQ ID NOs: 274, 279, and 281 respectively;
(p) heavy chain CDR1, CDR2, and CDR3 comprise amino acid sequences set forth in SEQ ID NOs: 127, 132, and 145 respectively; and light chain CDR1, CDR2, and CDR3 comprise amino acid sequences set forth in SEQ ID NOs: 275, 279, and 285 respectively;
(q) heavy chain CDR1, CDR2, and CDR3 comprise amino acid sequences set forth in SEQ ID NOs: 127, 134, and 146 respectively; and light chain CDR1, CDR2, and CDR3 comprise amino acid sequences set forth in SEQ ID NOs: 273, 279, and 281 respectively;
(r) heavy chain CDR1, CDR2, and CDR3 comprise amino acid sequences set forth in SEQ ID NOs: 127, 134, and 146 respectively; and light chain CDR1, CDR2, and CDR3 comprise amino acid sequences set forth in SEQ ID NOs: 275, 279, and 281 respectively;
(s) heavy chain CDR1, CDR2, and CDR3 comprise amino acid sequences set forth in SEQ ID NOs: 127, 132, and 147 respectively; and light chain CDR1, CDR2, and CDR3 comprise amino acid sequences set forth in SEQ ID NOs: 277, 280, and 289 respectively;
(t) heavy chain CDR1, CDR2, and CDR3 comprise amino acid sequences set forth in SEQ ID NOs: 127, 132, and 148 respectively; and light chain CDR1, CDR2, and CDR3 comprise amino acid sequences set forth in SEQ ID NOs: 277, 280, and 289 respectively;
(u) heavy chain CDR1, CDR2, and CDR3 comprise amino acid sequences set forth in SEQ ID NOs: 127, 132, and 148 respectively; and light chain CDR1, CDR2, and CDR3 comprise amino acid sequences set forth in SEQ ID NOs: 277, 280, and 290 respectively;
(v) heavy chain CDR1, CDR2, and CDR3 comprise amino acid sequences set forth in SEQ ID NOs: 127, 132, and 149 respectively; and light chain CDR1, CDR2, and CDR3 comprise amino acid sequences set forth in SEQ ID NOs: 277, 280, and 289 respectively;
(w) heavy chain CDR1, CDR2, and CDR3 comprise amino acid sequences set forth in SEQ ID NOs: 127, 132, and 149 respectively; and light chain CDR1, CDR2, and CDR3 comprise amino acid sequences set forth in SEQ ID NOs: 277, 280, and 290 respectively;
(x) heavy chain CDR1, CDR2, and CDR3 comprise amino acid sequences set forth in SEQ ID NOs: 127, 132, and 149 respectively; and light chain CDR1, CDR2, and CDR3 comprise amino acid sequences set forth in SEQ ID NOs: 277, 280, and 291 respectively;
(y) heavy chain CDR1, CDR2, and CDR3 comprise amino acid sequences set forth in SEQ ID NOs: 127, 132, and 149 respectively; and light chain CDR1, CDR2, and CDR3 comprise amino acid sequences set forth in SEQ ID NOs: 277, 280, and 292 respectively;
(z) heavy chain CDR1, CDR2, and CDR3 comprise amino acid sequences set forth in SEQ ID NOs: 127, 132, and 149 respectively; and light chain CDR1, CDR2, and CDR3 comprise amino acid sequences set forth in SEQ ID NOs: 278, 280, and 289 respectively;
(aa) heavy chain CDR1, CDR2, and CDR3 comprise amino acid sequences set forth in SEQ ID NOs: 127, 135, and 149 respectively; and light chain CDR1, CDR2, and CDR3 comprise amino acid sequences set forth in SEQ ID NOs: 277, 280, and 289 respectively;
(bb) heavy chain CDR1, CDR2, and CDR3 comprise amino acid sequences set forth in SEQ ID NOs: 127, 136, and 149 respectively; and light chain CDR1, CDR2, and CDR3 comprise amino acid sequences set forth in SEQ ID NOs: 277, 280, and 291 respectively;
(cc) heavy chain CDR1, CDR2, and CDR3 comprise amino acid sequences set forth in SEQ ID NOs: 127, 136, and 149 respectively; and light chain CDR1, CDR2, and CDR3 comprise amino acid sequences set forth in SEQ ID NOs: 277, 280, and 292 respectively;
(dd) heavy chain CDR1, CDR2, and CDR3 comprise amino acid sequences set forth in SEQ ID NOs: 127, 136, and 149 respectively; and light chain CDR1, CDR2, and CDR3 comprise amino acid sequences set forth in SEQ ID NOs: 277, 280, and 293 respectively;
(ee) heavy chain CDR1, CDR2, and CDR3 comprise amino acid sequences set forth in SEQ ID NOs: 127, 136, and 149 respectively; and light chain CDR1, CDR2, and CDR3 comprise amino acid sequences set forth in SEQ ID NOs: 277, 280, and 294 respectively;
(ff) heavy chain CDR1, CDR2, and CDR3 comprise amino acid sequences set forth in SEQ ID NOs: 130, 132, and 149 respectively; and light chain CDR1, CDR2, and CDR3 comprise amino acid sequences set forth in SEQ ID NOs: 277, 280, and 290 respectively;
(gg) heavy chain CDR1, CDR2, and CDR3 comprise amino acid sequences set forth in SEQ ID NOs: 127, 132, and 150 respectively; and light chain CDR1, CDR2, and CDR3 comprise amino acid sequences set forth in SEQ ID NOs: 273, 279, and 281 respectively;
(hh) heavy chain CDR1, CDR2, and CDR3 comprise amino acid sequences set forth in SEQ ID NOs: 127, 132, and 150 respectively; and light chain CDR1, CDR2, and CDR3 comprise amino acid sequences set forth in SEQ ID NOs: 275, 279, and 286 respectively;
(ii) heavy chain CDR1, CDR2, and CDR3 comprise amino acid sequences set forth in SEQ ID NOs: 127, 132, and 151 respectively; and light chain CDR1, CDR2, and CDR3 comprise amino acid sequences set forth in SEQ ID NOs: 273, 279, and 286 respectively;
(jj) heavy chain CDR1, CDR2, and CDR3 comprise amino acid sequences set forth in SEQ ID NOs: 127, 137, and 150 respectively; and light chain CDR1, CDR2, and CDR3 comprise amino acid sequences set forth in SEQ ID NOs: 273, 279, and 281 respectively;
(kk) heavy chain CDR1, CDR2, and CDR3 comprise amino acid sequences set forth in SEQ ID NOs: 127, 138, and 150 respectively; and light chain CDR1, CDR2, and CDR3 comprise amino acid sequences set forth in SEQ ID NOs: 273, 279, and 281 respectively;
(ll) heavy chain CDR1, CDR2, and CDR3 comprise amino acid sequences set forth in SEQ ID NOs: 127, 138, and 150 respectively; and light chain CDR1, CDR2, and CDR3 comprise amino acid sequences set forth in SEQ ID NOs: 273, 279, and 286 respectively;
(mm) heavy chain CDR1, CDR2, and CDR3 comprise amino acid sequences set forth in SEQ ID NOs: 127, 138, and 150 respectively; and light chain CDR1, CDR2, and CDR3 comprise amino acid sequences set forth in SEQ ID NOs: 276, 279, and 281 respectively;
(nn) heavy chain CDR1, CDR2, and CDR3 comprise amino acid sequences set forth in SEQ ID NOs: 127, 138, and 151 respectively; and light chain CDR1, CDR2, and CDR3 comprise amino acid sequences set forth in SEQ ID NOs: 273, 279, and 286 respectively;
(oo) heavy chain CDR1, CDR2, and CDR3 comprise amino acid sequences set forth in SEQ ID NOs: 127, 138, and 151 respectively; and light chain CDR1, CDR2, and CDR3 comprise amino acid sequences set forth in SEQ ID NOs: 273, 279, and 287 respectively;

(pp) heavy chain CDR1, CDR2, and CDR3 comprise amino acid sequences set forth in SEQ ID NOs: 127, 138, and 151 respectively; and light chain CDR1, CDR2, and CDR3 comprise amino acid sequences set forth in SEQ ID NOs: 273, 279, and 288 respectively;
(qq) heavy chain CDR1, CDR2, and CDR3 comprise amino acid sequences set forth in SEQ ID NOs: 127, 138, and 151 respectively; and light chain CDR1, CDR2, and CDR3 comprise amino acid sequences set forth in SEQ ID NOs: 275, 279, and 286 respectively;
(rr) heavy chain CDR1, CDR2, and CDR3 comprise amino acid sequences set forth in SEQ ID NOs: 127, 140, and 151 respectively; and light chain CDR1, CDR2, and CDR3 comprise amino acid sequences set forth in SEQ ID NOs: 273, 279, and 286 respectively;
(ss) heavy chain CDR1, CDR2, and CDR3 comprise amino acid sequences set forth in SEQ ID NOs: 131, 132, and 151 respectively; and light chain CDR1, CDR2, and CDR3 comprise amino acid sequences set forth in SEQ ID NOs: 273, 279, and 281 respectively;
(tt) heavy chain CDR1, CDR2, and CDR3 comprise amino acid sequences set forth in SEQ ID NOs: 131, 132, and 150 respectively; and light chain CDR1, CDR2, and CDR3 comprise amino acid sequences set forth in SEQ ID NOs: 273, 279, and 281 respectively;
(uu) heavy chain CDR1, CDR2, and CDR3 comprise amino acid sequences set forth in SEQ ID NOs: 131, 139, and 151 respectively; and light chain CDR1, CDR2, and CDR3 comprise amino acid sequences set forth in SEQ ID NOs: 273, 279, and 286 respectively.

In some embodiments, anti-CD161 antibodies or antigen binding portions thereof of the disclosure comprise heavy and light chain CDRs, wherein the amino acid sequences of the heavy chain CDR1, heavy chain CDR2, heavy chain CDR3, light chain CDR1, light chain CDR2, and light chain CDR3 are set forth in Table 22. In some embodiments, anti-CD161 antibodies or antigen binding portions thereof of the disclosure comprise heavy and light chain CDRs, wherein the amino acid sequences of the heavy chain CDR1, heavy chain CDR2, heavy chain CDR3, light chain CDR1, light chain CDR2, and light chain CDR3 are set forth in Table 20.

Variable Heavy and Light Chain Regions

In some embodiments, the anti-CD161 antibodies or antigen binding portions thereof described herein comprise heavy and light chain variable regions, wherein the heavy chain variable region comprises an amino acid sequence that is at least 85%, at least 86%, at least 87%, at least 88%, at least 89%, at least 90%, at least 91%, at least 92%, at least 93%, at least 94%, at least 95%, at least 96% identical, at least 97%, at least 98%, at least 99%, or at least 100% identical to an amino acid sequence selected from SEQ ID NOs: 1, 4, 6, 8, 11, 13, 15, 18, 20, 22, 29, 31, 33, 35, 37, 39, 41, 43, 45, 47, 50, 52, 54, 56, 59, 61, 63, 66, 68, 70, 72, 74, 76, 78, 80, 82, 84, 86, 88, 90, 92, 94, 96, 98, 101, 103, 105, 107, 109, 111, 113, 115, 117, 119, 121, 123 and 125; and wherein the light chain variable region comprises an amino acid sequence that is at least 85%, at least 86%, at least 87%, at least 88%, at least 89%, at least 90%, at least 91%, at least 92%, at least 93%, at least 94%, at least 95%, at least 96% identical, at least 97%, at least 98%, at least 99%, or at least 100% identical to an amino acid sequence selected from SEQ ID NOs: 152, 155, 157, 160, 162, 165, 167, 169, 171, 173, 175, 177, 179, 181, 183, 185, 187, 190, 192, 194, 196, 199, 202, 204, 206, 208, 210, 212, 215, 217, 219, 221, 223, 225, 228, 230, 233, 235, 237, 239, 241, 243, 245, 248, 250, 252, 254, 256, 258, 260, 262, 264, 267, 269, 271, 295, and 297.

In some embodiments, the anti-CD161 antibodies or antigen binding portions thereof described herein comprise heavy and light chain variable regions, wherein the heavy chain variable region comprises an amino acid sequence that is at least 85%, 86%, 87%, 88%, 89%, 90%, 91%, 92%, 93%, 94%, 95%, 96%, 97%, 98%, 99%, or 100% identical to an amino acid sequence selected from a sequence set forth in Table 18. In some embodiments, the anti-CD161 antibodies or antigen binding portions thereof described herein comprise heavy and light chain variable regions, wherein the light chain variable region comprises an amino acid sequence that is at least 85%, 86%, 87%, 88%, 89%, 90%, 91%, 92%, 93%, 94%, 95%, 96%, 97%, 98%, 99%, or 100% identical to an amino acid sequence selected from a sequence set forth in Table 19.

In some embodiments, the anti-CD161 antibodies or antigen binding portions thereof described herein comprise heavy and light chain variable regions, wherein the heavy and light chain variable regions comprise amino acid sequences that are at least 85%, at least 86%, at least 87%, at least 88%, at least 89%, at least 90%, at least 91%, at least 92%, at least 93%, at least 94%, at least 95%, at least 96% identical, at least 97%, at least 98%, at least 99%, or at least 100% identical to amino acid sequences selected from:
(a) SEQ ID NOs: 1 and 152, respectively;
(b) SEQ ID NOs: 1 and 155, respectively;
(c) SEQ ID NOs: 1 and 157, respectively;
(d) SEQ ID NOs: 4 and 152, respectively;
(e) SEQ ID NOs: 6 and 152, respectively;
(f) SEQ ID NOs: 8 and 157, respectively;
(g) SEQ ID NOs: 8 and 167, respectively;
(h) SEQ ID NOs: 11 and 160, respectively;
(i) SEQ ID NOs: 13 and 162, respectively;
(j) SEQ ID NOs: 15 and 165, respectively;
(k) SEQ ID NOs: 15 and 171, respectively;
(l) SEQ ID NOs: 15 and 173, respectively;
(m) SEQ ID NOs: 18 and 169, respectively;
(n) SEQ ID NOs: 20 and 295, respectively;
(o) SEQ ID NOs: 22 and 152, respectively;
(p) SEQ ID NOs: 22 and 160, respectively;
(q) SEQ ID NOs: 22 and 162, respectively;
(r) SEQ ID NOs: 22 and 175, respectively;
(s) SEQ ID NOs: 22 and 179, respectively;
(t) SEQ ID NOs: 22 and 183, respectively;
(u) SEQ ID NOs: 22 and 185, respectively;
(v) SEQ ID NOs: 29 and 177, respectively;
(w) SEQ ID NOs: 31 and 181, respectively;
(x) SEQ ID NOs: 33 and 160, respectively;
(y) SEQ ID NOs: 35 and 187, respectively;
(z) SEQ ID NOs: 37 and 187, respectively;
(aa) SEQ ID NOs: 39 and 160, respectively;
(bb) SEQ ID NOs: 41 and 190, respectively;
(cc) SEQ ID NOs: 43 and 152, respectively;
(dd) SEQ ID NOs: 43 and 192, respectively;
(ee) SEQ ID NOs: 45 and 194, respectively;
(ff) SEQ ID NOs: 47 and 152, respectively;
(gg) SEQ ID NOs: 47 and 202, respectively;
(hh) SEQ ID NOs: 50 and 196, respectively;
(ii) SEQ ID NOs: 52 and 152, respectively;
(jj) SEQ ID NOs: 52 and 208, respectively;
(kk) SEQ ID NOs: 54 and 196, respectively;
(ll) SEQ ID NOs: 56 and 199, respectively;
(mm) SEQ ID NOs: 56 and 206, respectively;
(nn) SEQ ID NOs: 59 and 204, respectively;

(oo) SEQ ID NOs: 61 and 245, respectively;
(pp) SEQ ID NOs: 66 and 258, respectively;
(qq) SEQ ID NOs: 63 and 250, respectively;
(rr) SEQ ID NOs: 63 and 245, respectively;
(ss) SEQ ID NOs: 66 and 248, respectively;
(tt) SEQ ID NOs: 70 and 252, respectively;
(uu) SEQ ID NOs: 68 and 245, respectively;
(vv) SEQ ID NOs: 66 and 250, respectively;
(ww) SEQ ID NOs: 66 and 254, respectively;
(xx) SEQ ID NOs: 72 and 256, respectively;
(yy) SEQ ID NOs: 74 and 260, respectively;
(zz) SEQ ID NOs: 76 and 297, respectively;
(aaa) SEQ ID NOs: 78 and 262, respectively;
(bbb) SEQ ID NOs: 78 and 267, respectively;
(ccc) SEQ ID NOs: 78 and 269, respectively;
(ddd) SEQ ID NOs: 80 and 264, respectively;
(eee) SEQ ID NOs: 82 and 271, respectively;
(fff) SEQ ID NOs: 84 and 264, respectively;
(ggg) SEQ ID NOs: 86 and 254, respectively;
(hhh) SEQ ID NOs: 88 and 152, respectively;
(iii) SEQ ID NOs: 90 and 210, respectively;
(jjj) SEQ ID NOs: 92 and 212, respectively;
(kkk) SEQ ID NOs: 94 and 215, respectively;
(lll) SEQ ID NOs: 94 and 217, respectively;
(mmm) SEQ ID NOs: 96 and 152, respectively;
(nnn) SEQ ID NOs: 98 and 230, respectively;
(ooo) SEQ ID NOs: 98 and 152, respectively;
(ppp) SEQ ID NOs: 101 and 219, respectively;
(qqq) SEQ ID NOs: 103 and 221, respectively;
(rrr) SEQ ID NOs: 105 and 225, respectively;
(sss) SEQ ID NOs: 105 and 223, respectively;
(ttt) SEQ ID NOs: 107 and 225, respectively;
(uuu) SEQ ID NOs: 109 and 212, respectively;
(vvv) SEQ ID NOs: 111 and 230, respectively;
(www) SEQ ID NOs: 113 and 228, respectively;
(xxx) SEQ ID NOs: 113 and 212, respectively;
(yyy) SEQ ID NOs: 113 and 225, respectively;
(zzz) SEQ ID NOs: 113 and 239, respectively;
(aaaa) SEQ ID NOs: 113 and 243, respectively;
(bbbb) SEQ ID NOs: 115 and 233, respectively;
(cccc) SEQ ID NOs: 117 and 235, respectively;
(dddd) SEQ ID NOs: 119 and 237, respectively;
(eeee) SEQ ID NOs: 121 and 219, respectively;
(ffff) SEQ ID NOs: 123 and 225, respectively; and
(gggg) SEQ ID NOs: 125 and 241, respectively.

In some embodiments, the anti-CD161 antibodies or antigen binding portions thereof described herein comprise heavy and light chain variable regions, wherein the heavy and light chain variable regions comprise nucleotide sequences that are at least 85%, at least 86%, at least 87%, at least 88%, at least 89%, at least 90%, at least 91%, at least 92%, at least 93%, at least 94%, at least 95%, at least 96% identical, at least 97%, at least 98%, at least 99%, or at least 100% identical to nucleotide sequences selected from:

(a) SEQ ID NOs: 2 and 153, respectively;
(b) SEQ ID NOs: 23 and 153, respectively;
(c) SEQ ID NOs: 44 and 153, respectively;
(d) SEQ ID NOs: 62 and 246, respectively;
(e) SEQ ID NOs: 89 and 153, respectively;
(f) SEQ ID NOs: 2 and 156, respectively;
(g) SEQ ID NOs: 3 and 159, respectively;
(h) SEQ ID NOs: 5 and 153, respectively;
(i) SEQ ID NOs: 7 and 153, respectively;
(j) SEQ ID NOs: 10 and 158, respectively;
(k) SEQ ID NOs: 10 and 168, respectively;
(l) SEQ ID NOs: 9 and 168, respectively;
(m) SEQ ID NOs: 12 and 161, respectively;
(n) SEQ ID NOs: 14 and 163, respectively;
(o) SEQ ID NOs: 16 and 166, respectively;
(p) SEQ ID NOs: 17 and 172, respectively;
(q) SEQ ID NOs: 16 and 174, respectively;
(r) SEQ ID NOs: 19 and 170, respectively;
(s) SEQ ID NOs: 21 and 296, respectively;
(t) SEQ ID NOs: 23 and 161, respectively;
(u) SEQ ID NOs: 28 and 161, respectively;
(v) SEQ ID NOs: 27 and 164, respectively;
(w) SEQ ID NOs: 25 and 176, respectively;
(x) SEQ ID NOs: 23 and 180, respectively;
(y) SEQ ID NOs: 26 and 184, respectively;
(z) SEQ ID NOs: 24 and 186, respectively;
(aa) SEQ ID NOs: 30 and 178, respectively;
(bb) SEQ ID NOs: 32 and 182, respectively;
(cc) SEQ ID NOs: 34 and 161, respectively;
(dd) SEQ ID NOs: 36 and 188, respectively;
(ee) SEQ ID NOs: 38 and 189, respectively;
(ff) SEQ ID NOs: 40 and 161, respectively;
(gg) SEQ ID NOs: 42 and 191, respectively;
(hh) SEQ ID NOs: 44 and 193, respectively;
(ii) SEQ ID NOs: 46 and 195, respectively;
(jj) SEQ ID NOs: 48 and 153, respectively;
(kk) SEQ ID NOs: 49 and 203, respectively;
(ll) SEQ ID NOs: 51 and 197, respectively;
(mm) SEQ ID NOs: 53 and 153, respectively;
(nn) SEQ ID NOs: 53 and 209, respectively;
(oo) SEQ ID NOs: 55 and 198, respectively;
(pp) SEQ ID NOs: 57 and 200, respectively;
(qq) SEQ ID NOs: 57 and 201, respectively;
(rr) SEQ ID NOs: 58 and 207, respectively;
(ss) SEQ ID NOs: 60 and 205, respectively;
(tt) SEQ ID NOs: 67 and 259, respectively;
(uu) SEQ ID NOs: 64 and 246, respectively;
(vv) SEQ ID NOs: 65 and 251, respectively;
(ww) SEQ ID NOs: 65 and 246, respectively;
(xx) SEQ ID NOs: 67 and 249, respectively;
(yy) SEQ ID NOs: 71 and 253, respectively;
(zz) SEQ ID NOs: 69 and 247, respectively;
(aaa) SEQ ID NOs: 67 and 251, respectively;
(bbb) SEQ ID NOs: 67 and 255, respectively;
(ccc) SEQ ID NOs: 73 and 257, respectively;
(ddd) SEQ ID NOs: 75 and 261, respectively;
(eee) SEQ ID NOs: 77 and 298, respectively;
(fff) SEQ ID NOs: 79 and 263, respectively;
(ggg) SEQ ID NOs: 79 and 268, respectively;
(hhh) SEQ ID NOs: 79 and 270, respectively;
(iii) SEQ ID NOs: 81 and 265, respectively;
(jjj) SEQ ID NOs: 83 and 272, respectively;
(kkk) SEQ ID NOs: 85 and 266, respectively;
(lll) SEQ ID NOs: 87 and 255, respectively;
(mmm) SEQ ID NOs: 91 and 211, respectively;
(nnn) SEQ ID NOs: 93 and 213, respectively;
(ooo) SEQ ID NOs: 95 and 216, respectively;
(ppp) SEQ ID NOs: 95 and 218, respectively;
(qqq) SEQ ID NOs: 97 and 153, respectively;
(rrr) SEQ ID NOs: 99 and 154, respectively;
(sss) SEQ ID NOs: 100 and 232, respectively;
(ttt) SEQ ID NOs: 102 and 220, respectively;
(uuu) SEQ ID NOs: 104 and 222, respectively;
(vvv) SEQ ID NOs: 106 and 226, respectively;
(www) SEQ ID NOs: 106 and 224, respectively;
(xxx) SEQ ID NOs: 108 and 226, respectively;
(yyy) SEQ ID NOs: 110 and 214, respectively;
(zzz) SEQ ID NOs: 112 and 231, respectively;
(aaaa) SEQ ID NOs: 114 and 229, respectively;
(bbbb) SEQ ID NOs: 114 and 214, respectively;

(cccc) SEQ ID NOs: 114 and 226, respectively;
(dddd) SEQ ID NOs: 114 and 240, respectively;
(eeee) SEQ ID NOs: 114 and 244, respectively;
(ffff) SEQ ID NOs: 116 and 234, respectively;
(gggg) SEQ ID NOs: 118 and 236, respectively;
(hhhh) SEQ ID NOs: 120 and 238, respectively;
(iiii) SEQ ID NOs: 122 and 220, respectively;
(jjjj) SEQ ID NOs: 124 and 227, respectively; and
(kkkk) SEQ ID NOs: 126 and 242, respectively.

In some embodiments, the anti-CD161 antibodies or antigen binding portions thereof described herein comprise heavy and light chain variable regions, wherein the heavy chain variable region comprises a nucleotide sequence that is at least 85%, 86%, 87%, 88%, 89%, 90%, 91%, 92%, 93%, 94%, 95%, 96%, 97%, 98%, 99%, or 100% identical to a nucleotide sequence selected from a sequence set forth in Table 18. In some embodiments, the anti-CD161 antibodies or antigen binding portions thereof described herein comprise heavy and light chain variable regions, wherein the light chain variable region comprises a nucleotide sequence that is at least 85%, 86%, 87%, 88%, 89%, 90%, 91%, 92%, 93%, 94%, 95%, 96%, 97%, 98%, 99%, or 100% identical to a nucleotide sequence selected from a sequence set forth in Table 19.

Antibody Formats

In some embodiments, the anti-CD161 antibodies or antigen binding portions thereof disclosed herein comprise a single-domain antibody, which interacts with the target antigen via only one single variable domain such as a single heavy chain domain (as opposed to traditional antibodies, which interact with the target antigen via heavy chain and light chain variable domains). In some embodiments, single domain antibodies comprise one variable domain (VH) of a heavy-chain antibody, and can be devoid of a light chain. In additional to a variable region (for example, a $V_H$), a single-domain antibody may further comprise a constant region, for example, $C_H1$, $C_H2$, $C_H3$, $C_H4$, or a combination thereof.

In some embodiments, the anti-CD161 antibodies or antigen binding portions thereof disclosed herein comprise a single chain antibody, which may comprise only one variable region (e.g., $V_H$) or comprise both a VH and a $V_L$. In some embodiments, the anti-CD161 antibodies or antigen binding portions thereof disclosed herein comprise an independent heavy chain and an independent light chain. In some embodiments, the anti-CD161 antibodies or antigen binding portions thereof disclosed herein comprise a single chain Fv (scFv) that binds to CD161 (e.g., human CD161). As used herein, the term "single-chain" refers to a molecule comprising amino acid monomers linearly linked by peptide bonds, e.g., a single chain Fv can be a VH and a $V_L$ operably linked by a linker region, e.g., a single chain Fv can be a $V_H$ and a $V_L$ connected with a short linker peptide of ten to about 25 amino acids. The linker can be rich in glycine for flexibility, as well as serine or threonine for solubility, and can either connect the N-terminus of the VH with the C-terminus of the VL, or vice versa. Other linkers include those known in the art and disclosed herein. In some embodiments, an scFv has a variable domain of light chain (VL) connected from its C-terminus to the N-terminal end of a variable domain of heavy chain (VH) by a polypeptide chain. Alternately the scFv comprises of polypeptide chain where in the C-terminal end of the VH is connected to the N-terminal end of VL by a polypeptide chain. In some embodiments the scFv constructs may be oriented in a variety of ways. For instance, the order to VH and VL in the construct may vary and alter the expression and/or activity of the scFv. In some embodiments the scFv constructs are oriented, from N to C terminus, VL-linker-VH-linker-CH2-CH3.

In some embodiments, one or more flexible linkers can be used to link two or more portions or fragments of an antibody. For example, flexible linkers can attach scFv fragments to one another, and/or to Fc domains. In some embodiments, the variable heavy and variable light chains are covalently attached using flexible linkers. In some embodiments, flexible linkers such as those containing glycine and serine are used. The scFV-FC synthesis from a typical antibody format can involve the addition of linkers. In some embodiments, the linker is (GxS)3, wherein x can be 1, 2, 3, 4, 5, 6, 7, 8, 9, or 10. In some cases, longer linkers are more effective to reduce strain and oligomerization. In some cases, it is desirable to have a linker that is 15 amino acids or greater in length, e.g., a linker that is 15 to 30 amino acids, 16-25 amino acids, 20 or to 30 amino acids in length. The (G4S)4 linker (also referred to as Linker20) is a longer linker that can reduce strain in some cases. In some embodiments the linker is (G4S)4. Preferably, any linker peptide used in the instant invention will be relatively non-immunogenic and not prevent proper folding of the constant region domains.

In some embodiments, the anti-CD161 antibodies or antigen binding portions thereof disclosed herein comprise a bifunctional antibody. As used herein, the term "bispecific" or "bifunctional antibody" refers to an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, (1990) Clin. Exp. Immunol. 79:315-321; Kostelny et al., (1992) J. Immunol. 148:1547-1553.

Constant Regions

In some embodiments, the anti-CD161 antibodies or antigen binding portions thereof disclosed herein comprise a fragment crystallizable (Fc) region. The Fc region is the tail region of an antibodies and antigen binding fragments thereof which contains constant domains (e.g., CH2 and CH3); the other region of the antibodies and antigen binding fragments thereof being the Fab region which contains a variable domain (e.g., VH) and a constant domain (e.g., CH1), the former of which defines binding specificity.

As described herein, the anti-CD161 antibodies or antigen binding portions can comprise a VH domain In some embodiments, the VH domain further comprises one or more constant domains (e.g., CH2 and/or CH3) of an Fc region and/or one or more constant domains (e.g., CH1) of a Fab region. In some embodiments, the VH domain further comprises one or more constant domains (e.g., CH2, CH3 and/or CH4) of an Fc region and a hinge region. In some embodiments, each of the one or more constant domains (e.g., CH1, CH2, CH3, CH4 and/or hinge region) can comprise or consist of portions of a constant domain. For example, in some embodiments, the constant domain comprises 99% or less, 98% or less, 97% or less, 96% or less, 95% or less, 90% or less, 80% or less, 70% or less, 60% or less, 50% or less, 40% or less, 30% or less, 20% or less, or 10% or less of the corresponding full sequence. As described herein, the anti-CD161 antibodies or antigen binding portions can comprise a VL domain. In some embodiments, the VL domain further comprises a constant domain or portion thereof (e.g., CL domain).

Immunoglobulin heavy chain and light chain constant regions useful for producing the anti-CD161 antibodies described herein may be obtained from a number of different sources. For example, the sequences of human heavy and light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. Similarly, a variety of immunoglobulin heavy chain and light chain constant regions gene sequences (e.g., mouse and human constant region gene sequences) are available in the form of publicly accessible deposits (e.g., www.bioinfo.org.uk/abs/, www.vbase2.org, or www.imgt.org).

In some embodiments, the anti-CD161 antibodies disclosed herein comprise an immunoglobulin heavy chain constant region or domain comprising a CH1 domain or a portion thereof. In some embodiments, the anti-CD161 antibodies disclosed herein comprise an immunoglobulin heavy chain constant region or domain comprising a hinge region or a portion thereof. In some embodiments, the anti-CD161 antibodies disclosed herein comprise an immunoglobulin heavy chain constant region or domain comprising a CH2 domain or a portion thereof. In some embodiments, the anti-CD161 antibodies disclosed herein comprise an immunoglobulin heavy chain constant region or domain comprising a CH3 domain or a portion thereof. In some embodiments, the anti-CD161 antibodies disclosed herein comprise an immunoglobulin heavy chain constant region or domain comprising a CH4 domain or a portion thereof. In some embodiments, the anti-CD161 antibodies disclosed herein comprise an immunoglobulin heavy chain constant region or domain comprising a hinge region or a portion thereof and a CH2 domain or portion thereof (e.g., in the hinge-CH2 orientation or CH2-hinge orientation). In some embodiments, the anti-CD161 antibodies disclosed herein comprise an immunoglobulin heavy chain constant region or domain comprising a CH2 domain or portion thereof and a CH3 domain or portion thereof (e.g., in the CH2-CH3 orientation or CH3-CH2 orientation). In some embodiments, the anti-CD161 antibodies disclosed herein comprise an immunoglobulin heavy chain constant region or domain comprising a hinge region or a portion thereof, a CH2 domain or portion thereof, and a CH3 domain or portion thereof, for example in the orientation hinge-CH2-CH3, hinge-CH3-CH2, or CH2-CH3-hinge.

In some embodiments, the anti-CD161 antibodies comprise an immunoglobulin heavy chain constant region or domain derived from one or more immunoglobulin heavy chains (e.g., an immunoglobulin heavy chain including CH1, hinge, CH2, CH3, and/or CH4 domains, although these need not be derived from the same antibody). In certain embodiments, the complete immunoglobulin heavy chain constant region or domain is derived from a human IgG immunoglobulin heavy chain (e.g., human IgG1). It is understood, however, that the immunoglobulin heavy chain constant region or domain may be derived from an immunoglobulin of another mammalian species, including for example, a rodent (e.g. a mouse, rat, rabbit, guinea pig) or non-human primate (e.g. chimpanzee, macaque) species. Moreover, the immunoglobulin heavy chains domain or portion thereof may be derived from any immunoglobulin class, including IgM, IgG, IgD, IgA, and IgE, and any immunoglobulin isotype, including IgG1, IgG2, IgG3, and IgG4.

In some embodiments, the anti-CD161 antibodies described herein comprise an immunoglobulin light chain constant region (CL or $C_L$), or a fragment thereof. The light chain region can be a naturally occurring CL, or a naturally occurring CL in which one or more amino acids have been substituted, added or deleted, provided that the CL has a desired biological property. In some embodiments, the immunoglobulin framework comprises a CL which is a kappa or lambda constant region. In some embodiments, the CL is a human kappa or lambda light chain constant region or fragment thereof. In some embodiments, the CL may comprise a C-terminal lysine.

Constant region domains comprising an immunoglobulin domain sequence can be selected lacking a particular effector function and/or with a particular modification to reduce immunogenicity. Many sequences of antibodies and antibody-encoding genes have been published and suitable immunoglobulin domain sequences (e.g. hinge, CH2, and/or CH3 sequences, or portions thereof) can be derived from these sequences using art recognized techniques. The genetic material obtained using any of the foregoing methods may then be altered or synthesized to obtain polypeptides suitable for use in the compositions and methods disclosed herein. It will further be appreciated that the scope of this invention encompasses alleles, variants and mutations of constant region DNA sequences.

The constant region domains or portions thereof making up an anti-CD161 antibody disclosed herein may be derived from different immunoglobulin molecules. For example, anti-CD161 antibody disclosed herein may comprise a CH2 domain or portion thereof derived from an IgG1 molecule and a CH3 region or portion thereof derived from an IgG4 molecule. In another example, an anti-CD161 antibody described herein may comprises a heavy chain constant region comprising a hinge domain derived, in part, from an IgG1 molecule and, in part, from an IgG4 molecule. As set forth herein, it will be understood by one of ordinary skill in the art that immunoglobulin heavy chain or light chain constant region may be altered such that it varies in amino acid sequence from a naturally occurring antibody molecule.

In certain embodiments, the anti-CD161 antibodies disclosed herein lack one or more constant region domains of a complete immunoglobulin heavy chain or light chain, i.e., they are partially or entirely deleted. In certain embodiments, the anti-CD161 disclosed herein will lack an entire CL domain In certain embodiments, the anti-CD161 disclosed herein will lack an entire CH1 domain In certain embodiments, the anti-CD161 disclosed herein will lack an entire hinge domain or region. In certain embodiments, the anti-CD161 disclosed herein will lack an entire CH2 domain. In certain embodiments, the anti-CD161 disclosed herein comprise CH2 domain-deleted Fc regions derived from a vector (e.g., from IDEC Pharmaceuticals, San Diego) encoding an IgG1 human constant region domain (see, e.g., WO02/060955A2 and WO02/096948A2). This exemplary vector is engineered to delete the CH2 domain and provide a synthetic vector expressing a domain-deleted IgG1 constant region. It will be noted that these exemplary constructs are preferably engineered to fuse a binding CH3 domain directly to a hinge region of the respective Fc domain.

In other constructs it may be desirable to provide a peptide spacer between one or more constituent immunoglobulin constant region domains. For example, a peptide spacer may be placed between a hinge region and a CH2 domain and/or between a CH2 and a CH3 domain. For example, compatible constructs could be expressed wherein the CH2 domain has been deleted and the remaining CH3 domain (synthetic or non-synthetic) is joined to the hinge region with a 1-20, 1-10, or 1-5 amino acid peptide spacer. Such a peptide spacer may be added, for instance, to ensure that the regulatory elements of the constant region domain remain free and accessible or that the hinge region remains flexible. Preferably, any linker peptide used in the instant invention will be relatively non-immunogenic and not prevent proper folding of the constant region domains.

In certain embodiments, an immunoglobulin constant region domain employed in the anti-CD161 antibodies disclosed herein is altered or modified, e.g., by amino acid mutation (e.g., addition, deletion, or substitution). As used herein, the term "Fc domain variant" refers to an Fc domain having at least one amino acid modification, such as an amino acid substitution, as compared to the wild-type Fc from which the Fc domain is derived. For example, wherein the Fc domain is derived from a human IgG1 antibody, a variant comprises at least one amino acid mutation (e.g., substitution) as compared to a wild type amino acid at the corresponding position of the human IgG1 Fc region.

In some embodiments, an Fc variant has altered antigen-dependent effector functions of the polypeptide, in particular ADCC or complement activation, e.g., as compared to a wild type Fc region. Such anti-CD161 antibodies exhibit decreased binding to FcR gamma when compared to wild-type polypeptides and, therefore, mediate reduced effector function. Fc variants with decreased FcR gamma binding affinity are expected to reduce effector function, and such molecules are also useful, for example, for treatment of conditions in which target cell destruction is undesirable, e.g., where normal cells may express target molecules, or where chronic administration of the polypeptide might result in unwanted immune system activation Amino acid mutations in the Fc domain which exhibit reduced binding to the Fc gamma receptor and Fc gamma receptor subtypes, reduced antibody dependent cell-mediated cytotoxicity, or reduced complement dependent cytotoxicity, have been described (e.g., U.S. Pat. Nos. 6,737,056; 5,624,821; U.S. 2006/0235208; 2003/0108548, each incorporated herein by reference in their entirety).

In some embodiments, the heavy chain constant region used in the antibodies described herein may comprise mutations (e.g., amino acid residue substitutions) to enhance a desired characteristic of the antibody, for example, increasing the binding activity to the neonatal Fc receptor (FcRn) and thus the serum half-life of the antibodies. It was known that binding to FcRn is critical for maintaining antibody homeostasis and regulating the serum half-life of antibodies. One or more (e.g., 1, 2, 3, 4, 5, or more) mutations (e.g., amino acid residue substitutions) may be introduced into the constant region at suitable positions (e.g., in $C_H2$ region) to enhance FcRn binding and enhance the half-life of the antibody. See, e.g., Dall'Acqua et al., J. B. C., 2006, 281:23514-23524; Robbie et al., Antimicrob. Agents Chemother, 2013, 57(12):6147; and Dall'Acqua et al., J. Immunol. 2002 169:5171-5180.

The anti-CD161 antibodies disclosed herein may also comprise an amino acid substitution which alters the glycosylation of the antibody constant region. For example, the heavy chain constant region of the anti-CD161 antibody may comprise an Fc domain having a mutation leading to reduced glycosylation (e.g., N- or O-linked glycosylation) or may comprise an altered glycoform of the wild-type Fc domain (e.g., a low fucose or fucose-free glycan). In certain embodiments, the anti-CD161 antibodies disclosed herein comprise an amino acid substitution near or within a glycosylation motif, for example, an N-linked glycosylation motif that contains the amino acid sequence NXT or NXS. Exemplary amino acid substitutions which reduce or alter glycosylation are disclosed in WO05/018572 and US2007/0111281, the contents of which are incorporated by reference herein. In certain embodiments, the anti-CD161 antibodies disclosed herein comprises at least one Fc domain having engineered cysteine residue or analog thereof which is located at the solvent-exposed surface. In certain embodiments, the anti-CD161 antibodies herein comprise an Fc domain comprising at least one engineered free cysteine residue or analog thereof that is substantially free of disulfide bonding with a second cysteine residue. Any of the above engineered cysteine residues or analogs thereof may subsequently be conjugated to a functional domain using art-recognized techniques (e.g., conjugated with a thiol-reactive heterobifunctional linker).

Exemplary CD161 Binding Antibodies

In some embodiments, an anti-CD161 antibody or antigen binding portion thereof described herein binds human CD161 with an affinity ($K_D$) of about 50-300 pM (e.g., between about 50 pM and about 300 pM). In some embodiments, an anti-CD161 antibody or antigen binding portion thereof described herein binds human CD161 and inhibits the interaction between human CD161 and the human CD161 ligand CLEC2D. In some embodiments, an anti-CD161 antibody or antigen binding portion thereof described herein does not significantly cross-react with other human proteins in the C-type lectin family. In some embodiments, an anti-CD161 antibody or antigen binding portion thereof described herein does not significantly cross-react with other human proteins in the C-type lectin family selected from Table 1. In some embodiments, an anti-CD161 antibody or antigen binding portion thereof described herein binds to an epitope on human CD161 comprising one or more amino acid residues selected from: I96, D121, K125, E126, R146, L151, Y198, E200, and E205 of SEQ ID NO: 335.

In some embodiments, an anti-CD161 antibody or antigen binding portion thereof described herein binds to an epitope on human CD161 comprising amino acid residue D121 of SEQ ID NO: 335. In some embodiments, an anti-CD161 antibody or antigen binding portion thereof described herein binds to an epitope on human CD161 comprising amino acid residues D121, I96, K125, and E126 of SEQ ID NO: 335. In some embodiments, the antibody or antigen binding portion binds to human CD161 with substantially equivalent affinity to cynomolgus CD161. In some embodiments, the antibody or antigen binding portion binds to human CD161 with binding affinity ($K_D$) that is at least 80, 85, 90, 95, 100, 105, 110, 115, 120, 125, 130, 135, 140, 145, 150, 155, 160, 165, 170, 175, or 180% of its binding affinity to cynomolgus CD161. In some embodiments, an anti-CD161 antibody or antigen binding portion thereof described herein comprises a heavy chain CDR3 with an amino acid sequence ARGGX$_1$X$_2$PX$_3$X$_4$FX$_5$Y (SEQ ID NO: 307), wherein X$_1$ is selected from L or Y, X$_2$ is selected from I or L, X$_3$ is selected from S or D, X$_4$ is selected from G or A, and X$_5$ is any amino acid. In some embodiments, an anti-CD161 antibody or antigen binding portion thereof described herein comprises a heavy chain CDR3 with an amino acid sequence ARGGX$_1$X$_2$PX$_3$X$_4$FX$_5$Y (SEQ ID NO: 307), wherein X$_1$ is L, X$_2$ is I, X$_3$ is S, X$_4$ is G, and X$_5$ is any amino acid. In some embodiments, an anti-CD161 antibody or antigen binding portion thereof described herein comprises a heavy chain CDR3 with an amino acid sequence ARGGX$_1$X$_2$PX$_3$X$_4$FX$_5$Y (SEQ ID NO: 307), wherein X$_1$ is L, X$_2$ is I, X$_3$ is S, X$_4$ is G, and X$_5$ is selected from D or G. In some embodiments, an anti-CD161 antibody or antigen binding portion thereof described herein comprises a heavy chain CDR3 with an amino acid sequence ARGGLIPSGFX$_1$Y (SEQ ID NO: 308), wherein X$_1$ is any amino acid. In some embodiments, an anti-CD161 antibody or antigen binding portion thereof described herein comprises a heavy chain CDR3 with an amino acid sequence ARGGLIPSGFX$_1$Y (SEQ ID NO: 308), wherein X$_1$ is D or G.

In some embodiments, the disclosure provides an anti-CD161 antibody or antigen binding portion thereof of Subgroup I, wherein the antibody or antigen binding portion:
(a) binds human CD161 with an affinity (K$_D$) of about 50-300 pM (e.g., between about 50 pM and about 300 pM);
(b) binds human CD161 an inhibits the interaction between human CD161 and the human CD161 ligand CLEC2D;
(c) does not significantly cross-react with other human proteins in the C-type lectin family (e.g., a human protein selected from Table 1);
(d) comprises a heavy chain CDR3 with an amino acid sequence ARGGX$_1$X$_2$PX$_3$X$_4$FX$_5$Y (SEQ ID NO: 307), wherein X$_1$ is selected from L or Y, X$_2$ is selected from I or L, X$_3$ is selected from S or D, X$_4$ is selected from G or A, and X$_5$ is any amino acid;
(e) binds to an epitope on human CD161 comprising at least one amino acid residue selected from: D121, I96, K125, and E126 of SEQ ID NO: 335; and
(f) binds to human CD161 with substantially equivalent affinity to cynomolgus CD161.

In some embodiments, an anti-CD161 antibody or antigen binding portion of Subgroup I comprises heavy and light chain CDRs that are selected from:
(a) heavy chain CDR1, CDR2, and CDR3 comprising amino acid sequences set forth in SEQ ID NOs: 299, 303, and 307 respectively, and light chain CDR1, CDR2, and CDR3 comprising amino acid sequences set forth in SEQ ID NOs: 312, 316, and 317 respectively;
(b) heavy chain CDR1, CDR2, and CDR3 comprising amino acid sequences set forth in SEQ ID NOs: 299, 303, and 307 respectively, and light chain CDR1, CDR2, and CDR3 comprising amino acid sequences set forth in SEQ ID NOs: 312, 316, and 318 respectively;
(c) heavy chain CDR1, CDR2, and CDR3 comprising amino acid sequences set forth in SEQ ID NOs: 300, 304, and 307 respectively, and light chain CDR1, CDR2, and CDR3 comprising amino acid sequences set forth in SEQ ID NOs: 312, 316, and 317 respectively;
(d) heavy chain CDR1, CDR2, and CDR3 comprising amino acid sequences set forth in SEQ ID NOs: 300, 304, and 307 respectively, and light chain CDR1, CDR2, and CDR3 comprising amino acid sequences set forth in SEQ ID NOs: 312, 316, and 318 respectively;
(e) heavy chain CDR1, CDR2, and CDR3 comprising amino acid sequences set forth in SEQ ID NOs: 300, 304, and 308 respectively, and light chain CDR1, CDR2, and CDR3 comprising amino acid sequences set forth in SEQ ID NOs: 312, 316, and 317 respectively; and
(f) heavy chain CDR1, CDR2, and CDR3 comprising amino acid sequences set forth in SEQ ID NOs: 300, 304, and 308 respectively, and light chain CDR1, CDR2, and CDR3 comprising amino acid sequences set forth in SEQ ID NOs: 312, 316, and 318 respectively.

In some embodiments, an anti-CD161 antibody or antigen binding portion of Subgroup I comprises heavy and light chain CDRs selected from:
(a) heavy chain CDR1, CDR2, and CDR3 comprising amino acid sequences set forth in SEQ ID NOs: 127, 132, and 141 respectively, and light chain CDR1, CDR2, and CDR3 comprising amino acid sequences set forth in SEQ ID NOs: 273, 279, and 281 respectively;
(b) heavy chain CDR1, CDR2, and CDR3 comprising amino acid sequences set forth in SEQ ID NOs: 127, 132, and 141 respectively, and light chain CDR1, CDR2, and CDR3 comprising amino acid sequences set forth in SEQ ID NOs: 273, 279, and 282 respectively;
(c) heavy chain CDR1, CDR2, and CDR3 comprising amino acid sequences set forth in SEQ ID NOs: 127, 132, and 141 respectively, and light chain CDR1, CDR2, and CDR3 comprising amino acid sequences set forth in SEQ ID NOs: 273, 279, and 283 respectively;
(d) heavy chain CDR1, CDR2, and CDR3 comprising amino acid sequences set forth in SEQ ID NOs: 127, 132, and 141 respectively, and light chain CDR1, CDR2, and CDR3 comprising amino acid sequences set forth in SEQ ID NOs: 273, 279, and 284 respectively;
(e) heavy chain CDR1, CDR2, and CDR3 comprising amino acid sequences set forth in SEQ ID NOs: 127, 132, and 142 respectively, and light chain CDR1, CDR2, and CDR3 comprising amino acid sequences set forth in SEQ ID NOs: 273, 279, and 281 respectively;
(f) heavy chain CDR1, CDR2, and CDR3 comprising amino acid sequences set forth in SEQ ID NOs: 128, 132, and 141 respectively, and light chain CDR1, CDR2, and CDR3 comprising amino acid sequences set forth in SEQ ID NOs: 273, 279, and 283 respectively;
(g) heavy chain CDR1, CDR2, and CDR3 comprising amino acid sequences set forth in SEQ ID NOs: 129, 132, and 141 respectively, and light chain CDR1, CDR2, and CDR3 comprising amino acid sequences set forth in SEQ ID NOs: 273, 279, and 283 respectively;
(h) heavy chain CDR1, CDR2, and CDR3 comprising amino acid sequences set forth in SEQ ID NOs: 127, 132, and 143 respectively, and light chain CDR1, CDR2, and CDR3 comprising amino acid sequences set forth in SEQ ID NOs: 273, 279, and 281 respectively;
(i) heavy chain CDR1, CDR2, and CDR3 comprising amino acid sequences set forth in SEQ ID NOs: 127, 132, and 143 respectively, and light chain CDR1, CDR2, and CDR3 comprising amino acid sequences set forth in SEQ ID NOs: 273, 279, and 283 respectively;
(j) heavy chain CDR1, CDR2, and CDR3 comprising amino acid sequences set forth in SEQ ID NOs: 127, 133, and 143 respectively, and light chain CDR1, CDR2, and CDR3 comprising amino acid sequences set forth in SEQ ID NOs: 273, 279, and 283 respectively; and
(k) heavy chain CDR1, CDR2, and CDR3 comprising amino acid sequences set forth in SEQ ID NOs: 129, 132, and 143 respectively, and light chain CDR1, CDR2, and CDR3 comprising amino acid sequences set forth in SEQ ID NOs: 273, 279, and 283 respectively.

In some embodiments, an anti-CD161 antibody or antigen binding portion of Subgroup I comprises heavy and light chain variable regions comprising amino acid sequences selected from:
(a) SEQ ID NOs: 1 and 152, respectively;
(b) SEQ ID NOs: 1 and 155, respectively;
(c) SEQ ID NOs: 1 and 157, respectively;
(d) SEQ ID NOs: 4 and 152, respectively;
(e) SEQ ID NOs: 6 and 152, respectively;
(f) SEQ ID NOs: 8 and 157, respectively;
(g) SEQ ID NOs: 8 and 167, respectively;
(h) SEQ ID NOs: 11 and 160, respectively;
(i) SEQ ID NOs: 13 and 162, respectively;
(j) SEQ ID NOs: 15 and 165, respectively;
(k) SEQ ID NOs: 15 and 171, respectively;
(l) SEQ ID NOs: 15 and 173, respectively;
(m) SEQ ID NOs: 18 and 169, respectively;
(n) SEQ ID NOs: 20 and 295, respectively;
(o) SEQ ID NOs: 22 and 152, respectively;
(p) SEQ ID NOs: 22 and 160, respectively;
(q) SEQ ID NOs: 22 and 162, respectively;
(r) SEQ ID NOs: 22 and 175, respectively;
(s) SEQ ID NOs: 22 and 179, respectively;
(t) SEQ ID NOs: 22 and 183, respectively;
(u) SEQ ID NOs: 22 and 185, respectively;
(v) SEQ ID NOs: 29 and 177, respectively;
(w) SEQ ID NOs: 31 and 181, respectively;
(x) SEQ ID NOs: 33 and 160, respectively;
(y) SEQ ID NOs: 35 and 187, respectively;
(z) SEQ ID NOs: 37 and 187, respectively;
(aa) SEQ ID NOs: 39 and 160, respectively; and
(bb) SEQ ID NOs: 41 and 190, respectively.

In some embodiments, an anti-CD161 antibody or antigen binding portion of Subgroup I comprises heavy and light chain variable regions comprising nucleotide sequences selected from:
(a) SEQ ID NOs: 2 and 153, respectively;
(b) SEQ ID NOs: 23 and 153, respectively;
(c) SEQ ID NOs: 2 and 156, respectively;
(d) SEQ ID NOs: 3 and 159, respectively;
(e) SEQ ID NOs: 5 and 153, respectively;
(f) SEQ ID NOs: 7 and 153, respectively;
(g) SEQ ID NOs: 10 and 158, respectively;
(h) SEQ ID NOs: 10 and 168, respectively;
(i) SEQ ID NOs: 9 and 168, respectively;
(j) SEQ ID NOs: 12 and 161, respectively;
(k) SEQ ID NOs: 14 and 163, respectively;
(l) SEQ ID NOs: 16 and 166, respectively;
(m) SEQ ID NOs: 17 and 172, respectively;
(n) SEQ ID NOs: 16 and 174, respectively;
(o) SEQ ID NOs: 19 and 170, respectively;
(p) SEQ ID NOs: 21 and 296, respectively;
(q) SEQ ID NOs: 23 and 161, respectively;
(r) SEQ ID NOs: 28 and 161, respectively;
(s) SEQ ID NOs: 27 and 164, respectively;
(t) SEQ ID NOs: 25 and 176, respectively;
(u) SEQ ID NOs: 23 and 180, respectively;
(v) SEQ ID NOs: 26 and 184, respectively;
(w) SEQ ID NOs: 24 and 186, respectively;
(x) SEQ ID NOs: 30 and 178, respectively;
(y) SEQ ID NOs: 32 and 182, respectively;
(z) SEQ ID NOs: 34 and 161, respectively;
(aa) SEQ ID NOs: 36 and 188, respectively;
(bb) SEQ ID NOs: 38 and 189, respectively;
(cc) SEQ ID NOs: 40 and 161, respectively; and
(dd) SEQ ID NOs: 42 and 191, respectively.

In some embodiments, an anti-CD161 antibody or antigen binding portion having a light chain variable region comprising the amino acid sequence set forth in SEQ ID NO: 167 is altered to have a light chain variable region comprising the amino acid sequence set forth in SEQ ID NO: 393. In some embodiments, an anti-CD161 antibody or antigen binding portion having a light chain variable region comprising the nucleotide sequence set forth in SEQ ID NO: 168 is altered to have a light chain variable region comprising the nucleotide sequence set forth in SEQ ID NO: 394.

In some embodiments, an anti-CD161 antibody or antigen binding portion thereof described herein binds to an epitope on human CD161 comprising amino acid residues 196 and K125 of SEQ ID NO: 335. In some embodiments, an anti-CD161 antibody or antigen binding portion of the disclosure binds to human CD161 and to cynomolgus CD161. In some embodiments, an anti-CD161 antibody or antigen binding portion of the disclosure binds to human CD161 with about 1.1-1.5 fold, 1.1-2 fold, 1.5-2 fold, 2-10 fold, 5-10 fold, 5-15 fold, 5-20 fold, 10-20 fold, 10-25 fold, 10-30, 10-40, or 10-50 fold higher binding affinity ($K_D$) than to cynomolgus CD161. In some embodiments, an anti-CD161 antibody or antigen binding portion thereof described herein comprise a heavy chain CDR3 with an amino acid sequence ARGYSDSYX$_1$YGPYYTFDY (SEQ ID NO: 311), wherein $X_1$ is any amino acid. In some embodiments, an anti-CD161 antibody or antigen binding portion thereof described herein comprise a heavy chain CDR3 with an amino acid sequence ARGYSDSYX$_1$YGPYYTFDY (SEQ ID NO: 311), wherein $X_1$ is selected from Y or F.

In some embodiments, the disclosure provides an anti-CD161 antibody or antigen binding portion thereof of Subgroup II, wherein the antibody or antigen binding portion:
(a) binds human CD161 with an affinity ($K_D$) of about 50-300 pM (e.g., between about 50 pM and about 300 pM);
(b) binds human CD161 an inhibits the interaction between human CD161 and the human CD161 ligand CLEC2D;
(c) does not significantly cross-react with other human proteins in the C-type lectin family (e.g., a human protein selected from Table 1);
(d) comprises a heavy chain CDR3 with an amino acid sequence ARGYSDSYX$_1$YGPYYTFDY (SEQ ID NO: 311), wherein $X_1$ is any amino acid;
(e) binds to an epitope on human CD161 comprising amino acid residues 196 and K125 of SEQ ID NO: 335;
(f) binds to human CD161 and cynomolgus CD161; and
(g) binds to human CD161 with binding affinity ($K_D$) that is about 1.1-1.5 fold, 1.1-2 fold, 1.5-2 fold, 2-10 fold, 5-10 fold, 5-15 fold, 5-20 fold, 10-20 fold, 10-25 fold, 10-30, 10-40, or 10-50 fold higher than its binding affinity ($K_D$) to cynomolgus CD161.

In some embodiments, an anti-CD161 antibody or antigen binding portion thereof of Subgroup II comprises heavy and light chain CDRs selected from:
(a) heavy chain CDR1, CDR2, and CDR3 comprising amino acid sequences set forth in SEQ ID NOs: 299, 303, and 311 respectively, and light chain CDR1, CDR2, and CDR3 comprising amino acid sequences set forth in SEQ ID NOs: 312, 316, and 317 respectively;
(b) heavy chain CDR1, CDR2, and CDR3 comprising amino acid sequences set forth in SEQ ID NOs: 299, 303, and 311 respectively, and light chain CDR1, CDR2, and CDR3 comprising amino acid sequences set forth in SEQ ID NOs: 314, 316, and 320 respectively;
(c) heavy chain CDR1, CDR2, and CDR3 comprising amino acid sequences set forth in SEQ ID NOs: 302, 306, and 311 respectively, and light chain CDR1, CDR2, and CDR3 comprising amino acid sequences set forth in SEQ ID NOs: 312, 316, and 317 respectively; and
(d) heavy chain CDR1, CDR2, and CDR3 comprising amino acid sequences set forth in SEQ ID NOs: 302, 306, and 311 respectively, and light chain CDR1, CDR2, and CDR3 comprising amino acid sequences set forth in SEQ ID NOs: 314, 316, and 320 respectively.

In some embodiments, an anti-CD161 antibody or antigen binding portion thereof of Subgroup II comprises heavy and light chain CDRs selected from:
(a) heavy chain CDR1, CDR2, and CDR3 comprising amino acid sequences set forth in SEQ ID NOs: 127, 132, and 150 respectively, and light chain CDR1, CDR2, and CDR3 comprising amino acid sequences set forth in SEQ ID NOs: 273, 279, and 281 respectively;
(b) heavy chain CDR1, CDR2, and CDR3 comprising amino acid sequences set forth in SEQ ID NOs: 127, 132, and 150 respectively, and light chain CDR1, CDR2, and CDR3 comprising amino acid sequences set forth in SEQ ID NOs: 275, 279, and 286 respectively;
(c) heavy chain CDR1, CDR2, and CDR3 comprising amino acid sequences set forth in SEQ ID NOs: 127, 132, and 151 respectively, and light chain CDR1, CDR2, and CDR3 comprising amino acid sequences set forth in SEQ ID NOs: 273, 279, and 286 respectively;
(d) heavy chain CDR1, CDR2, and CDR3 comprising amino acid sequences set forth in SEQ ID NOs: 127, 137, and 150 respectively, and light chain CDR1, CDR2, and CDR3 comprising amino acid sequences set forth in SEQ ID NOs: 273, 279, and 281 respectively;
(e) heavy chain CDR1, CDR2, and CDR3 comprising amino acid sequences set forth in SEQ ID NOs: 127, 138, and 150 respectively, and light chain CDR1, CDR2, and CDR3 comprising amino acid sequences set forth in SEQ ID NOs: 273, 279, and 281 respectively;
(f) heavy chain CDR1, CDR2, and CDR3 comprising amino acid sequences set forth in SEQ ID NOs: 127, 138, and 150 respectively, and light chain CDR1, CDR2, and CDR3 comprising amino acid sequences set forth in SEQ ID NOs: 273, 279, and 286 respectively;
(g) heavy chain CDR1, CDR2, and CDR3 comprising amino acid sequences set forth in SEQ ID NOs: 127, 138, and 150 respectively, and light chain CDR1, CDR2, and CDR3 comprising amino acid sequences set forth in SEQ ID NOs: 276, 279, and 281 respectively;
(h) heavy chain CDR1, CDR2, and CDR3 comprising amino acid sequences set forth in SEQ ID NOs: 127, 138, and 151 respectively, and light chain CDR1, CDR2, and CDR3 comprising amino acid sequences set forth in SEQ ID NOs: 273, 279, and 286 respectively;
(i) heavy chain CDR1, CDR2, and CDR3 comprising amino acid sequences set forth in SEQ ID NOs: 127, 138, and 151 respectively, and light chain CDR1, CDR2, and CDR3 comprising amino acid sequences set forth in SEQ ID NOs: 273, 279, and 287 respectively;
(j) heavy chain CDR1, CDR2, and CDR3 comprising amino acid sequences set forth in SEQ ID NOs: 127, 138, and 151 respectively, and light chain CDR1, CDR2, and CDR3 comprising amino acid sequences set forth in SEQ ID NOs: 273, 279, and 288 respectively;
(k) heavy chain CDR1, CDR2, and CDR3 comprising amino acid sequences set forth in SEQ ID NOs: 127, 138, and 151 respectively, and light chain CDR1, CDR2, and CDR3 comprising amino acid sequences set forth in SEQ ID NOs: 275, 279, and 286 respectively;
(l) heavy chain CDR1, CDR2, and CDR3 comprising amino acid sequences set forth in SEQ ID NOs: 127, 140, and 151 respectively, and light chain CDR1, CDR2, and CDR3 comprising amino acid sequences set forth in SEQ ID NOs: 273, 279, and 286 respectively;
(m) heavy chain CDR1, CDR2, and CDR3 comprising amino acid sequences set forth in SEQ ID NOs: 131, 132, and 151 respectively, and light chain CDR1, CDR2, and CDR3 comprising amino acid sequences set forth in SEQ ID NOs: 273, 279, and 281 respectively;
(n) heavy chain CDR1, CDR2, and CDR3 comprising amino acid sequences set forth in SEQ ID NOs: 131, 132, and 150 respectively, and light chain CDR1, CDR2, and CDR3 comprising amino acid sequences set forth in SEQ ID NOs: 273, 279, and 281 respectively; and
(o) heavy chain CDR1, CDR2, and CDR3 comprising amino acid sequences set forth in SEQ ID NOs: 131, 139, and 151 respectively, and light chain CDR1, CDR2, and CDR3 comprising amino acid sequences set forth in SEQ ID NOs: 273, 279, and 286 respectively.

In some embodiments, an anti-CD161 antibody or antigen binding portion thereof of Subgroup II comprises heavy and light chain variable regions comprising amino acid sequences selected from:
(a) SEQ ID NOs: 88 and 152, respectively;
(b) SEQ ID NOs: 90 and 210, respectively;
(c) SEQ ID NOs: 92 and 212, respectively;
(d) SEQ ID NOs: 94 and 215, respectively;
(e) SEQ ID NOs: 94 and 217, respectively;
(f) SEQ ID NOs: 96 and 152, respectively;
(g) SEQ ID NOs: 98 and 230, respectively;
(h) SEQ ID NOs: 98 and 152, respectively;
(i) SEQ ID NOs: 101 and 219, respectively;
(j) SEQ ID NOs: 103 and 221, respectively;
(k) SEQ ID NOs: 105 and 225, respectively;
(l) SEQ ID NOs: 105 and 223, respectively;
(m) SEQ ID NOs: 107 and 225, respectively;
(n) SEQ ID NOs: 109 and 212, respectively;
(o) SEQ ID NOs: 111 and 230, respectively;
(p) SEQ ID NOs: 113 and 228, respectively;
(q) SEQ ID NOs: 113 and 212, respectively;
(r) SEQ ID NOs: 113 and 225, respectively;
(s) SEQ ID NOs: 113 and 239, respectively;
(t) SEQ ID NOs: 113 and 243, respectively;
(u) SEQ ID NOs: 115 and 233, respectively;

(v) SEQ ID NOs: 117 and 235, respectively;
(w) SEQ ID NOs: 119 and 237, respectively;
(x) SEQ ID NOs: 121 and 219, respectively;
(y) SEQ ID NOs: 123 and 225, respectively; and
(z) SEQ ID NOs: 125 and 241, respectively.

In some embodiments, an anti-CD161 antibody or antigen binding portion thereof of Subgroup II comprises heavy and light chain variable regions comprising nucleotide sequences selected from:
(a) SEQ ID NOs: 89 and 153, respectively;
(b) SEQ ID NOs: 91 and 211, respectively;
(c) SEQ ID NOs: 93 and 213, respectively;
(d) SEQ ID NOs: 95 and 216, respectively;
(e) SEQ ID NOs: 95 and 218, respectively;
(f) SEQ ID NOs: 97 and 153, respectively;
(g) SEQ ID NOs: 99 and 154, respectively;
(h) SEQ ID NOs: 100 and 232, respectively;
(i) SEQ ID NOs: 102 and 220, respectively;
(j) SEQ ID NOs: 104 and 222, respectively;
(k) SEQ ID NOs: 106 and 226, respectively;
(l) SEQ ID NOs: 106 and 224, respectively;
(m) SEQ ID NOs: 108 and 226, respectively;
(n) SEQ ID NOs: 110 and 214, respectively;
(o) SEQ ID NOs: 112 and 231, respectively;
(p) SEQ ID NOs: 114 and 229, respectively;
(q) SEQ ID NOs: 114 and 214, respectively;
(r) SEQ ID NOs: 114 and 226, respectively;
(s) SEQ ID NOs: 114 and 240, respectively;
(t) SEQ ID NOs: 114 and 244, respectively;
(u) SEQ ID NOs: 116 and 234, respectively;
(v) SEQ ID NOs: 118 and 236, respectively;
(w) SEQ ID NOs: 120 and 238, respectively;
(x) SEQ ID NOs: 122 and 220, respectively;
(y) SEQ ID NOs: 124 and 227, respectively; and
(z) SEQ ID NOs: 126 and 242, respectively.

In some embodiments, an anti-CD161 antibody or antigen binding portion having a light chain variable region comprising the amino acid sequence set forth in SEQ ID NO: 235 is altered to have a light chain variable region comprising the amino acid sequence set forth in SEQ ID NO: 395. In some embodiments, an anti-CD161 antibody or antigen binding portion having a light chain variable region comprising the nucleotide sequence set forth in SEQ ID NO: 236 is altered to have a light chain variable region comprising the nucleotide sequence set forth in SEQ ID NO: 396.

In some embodiments, an anti-CD161 antibody or antigen binding portion thereof described herein binds to an epitope comprising amino acid residue R146 of SEQ ID NO: 335. In some embodiments, an anti-CD161 antibody or antigen binding portion of the disclosure does not significantly cross-react with cynomolgus CD161. In some embodiments, an anti-CD161 antibody or antigen binding portion thereof described herein comprise a heavy chain CDR3 with an amino acid sequence ARGPGX$_1$MYLYGDSFFX$_2$Y (SEQ ID NO: 309), wherein X$_1$ is any amino acid, and wherein X$_2$ is any amino acid. In some embodiments, an anti-CD161 antibody or antigen binding portion thereof described herein comprise a heavy chain CDR3 with an amino acid sequence ARGPGX$_1$MYLYGDSFFX$_2$Y (SEQ ID NO: 309), wherein X$_1$ is selected from D or Y and X$_2$ is selected from D or E.

In some embodiments, the disclosure provides an anti-CD161 antibody or antigen binding portion thereof of Subgroup III, wherein the antibody or antigen binding portion:
(a) binds human CD161 with an affinity (K$_D$) of about 50-300 pM (e.g., between about 50 pM and about 300 pM);
(b) binds human CD161 an inhibits the interaction between human CD161 and the human CD161 ligand CLEC2D;
(c) does not significantly cross-react with other human proteins in the C-type lectin family (e.g., a human protein selected from Table 1);
(d) comprises a heavy chain CDR3 with an amino acid sequence ARGPGX$_1$MYLYGDSFFX$_2$Y (SEQ ID NO: 309), wherein X$_1$ is any amino acid, and wherein X$_2$ is any amino acid;
(e) binds to an epitope on human CD161 comprising amino acid residue R146 of SEQ ID NO: 335; and
(f) does not significantly cross-react with cynomolgus CD161.

In some embodiments, an anti-CD161 antibody or antigen binding portion thereof of Subgroup III comprises heavy and light chain CDRs selected from:
(a) heavy chain CDR1, CDR2, and CDR3 comprising amino acid sequences set forth in SEQ ID NOs: 299, 303, and 309 respectively, and light chain CDR1, CDR2, and CDR3 comprising amino acid sequences set forth in SEQ ID NOs: 312, 316, and 317 respectively;
(b) heavy chain CDR1, CDR2, and CDR3 comprising amino acid sequences set forth in SEQ ID NOs: 299, 303, and 309 respectively, and light chain CDR1, CDR2, and CDR3 comprising amino acid sequences set forth in SEQ ID NOs: 313, 316, and 319 respectively;
(c) heavy chain CDR1, CDR2, and CDR3 comprising amino acid sequences set forth in SEQ ID NOs: 300, 304, and 309 respectively, and light chain CDR1, CDR2, and CDR3 comprising amino acid sequences set forth in SEQ ID NOs: 312, 316, and 317 respectively; and
(d) heavy chain CDR1, CDR2, and CDR3 comprising amino acid sequences set forth in SEQ ID NOs: 300, 304, and 309 respectively, and light chain CDR1, CDR2, and CDR3 comprising amino acid sequences set forth in SEQ ID NOs: 313, 316, and 319 respectively.

In some embodiments, an anti-CD161 antibody or antigen binding portion thereof of Subgroup III heavy and light chain CDRs selected from:
(a) heavy chain CDR1, CDR2, and CDR3 comprising amino acid sequences set forth in SEQ ID NOs: 127, 132, and 144 respectively, and light chain CDR1, CDR2, and CDR3 comprising amino acid sequences set forth in SEQ ID NOs: 273, 279, and 281 respectively;
(b) heavy chain CDR1, CDR2, and CDR3 comprising amino acid sequences set forth in SEQ ID NOs: 127, 132, and 145 respectively, and light chain CDR1, CDR2, and CDR3 comprising amino acid sequences set forth in SEQ ID NOs: 273, 279, and 281 respectively;
(c) heavy chain CDR1, CDR2, and CDR3 comprising amino acid sequences set forth in SEQ ID NOs: 127, 132, and 145 respectively, and light chain CDR1, CDR2, and CDR3 comprising amino acid sequences set forth in SEQ ID NOs: 273, 279, and 285 respectively;
(d) heavy chain CDR1, CDR2, and CDR3 comprising amino acid sequences set forth in SEQ ID NOs: 127, 132, and 145 respectively, and light chain CDR1, CDR2, and CDR3 comprising amino acid sequences set forth in SEQ ID NOs: 274, 279, and 281 respectively;
(e) heavy chain CDR1, CDR2, and CDR3 comprising amino acid sequences set forth in SEQ ID NOs: 127, 132, and 145 respectively, and light chain CDR1, CDR2, and CDR3 comprising amino acid sequences set forth in SEQ ID NOs: 275, 279, and 285 respectively;
(f) heavy chain CDR1, CDR2, and CDR3 comprising amino acid sequences set forth in SEQ ID NOs: 127, 134, and 146 respectively, and light chain CDR1, CDR2, and CDR3 comprising amino acid sequences set forth in SEQ ID NOs: 273, 279, and 281 respectively; and
(g) heavy chain CDR1, CDR2, and CDR3 comprising amino acid sequences set forth in SEQ ID NOs: 127, 134, and 146 respectively, and light chain CDR1, CDR2, and CDR3 comprising amino acid sequences set forth in SEQ ID NOs: 275, 279, and 281 respectively.

In some embodiments, an anti-CD161 antibody or antigen binding portion thereof of Subgroup III comprises heavy and light chain variable regions comprising amino acid sequences selected from:
(a) SEQ ID NOs: 43 and 152, respectively;
(b) SEQ ID NOs: 43 and 192, respectively;
(c) SEQ ID NOs: 45 and 194, respectively;
(d) SEQ ID NOs: 47 and 152, respectively;
(e) SEQ ID NOs: 47 and 202, respectively;
(f) SEQ ID NOs: 50 and 196, respectively;
(g) SEQ ID NOs: 52 and 152, respectively;
(h) SEQ ID NOs: 52 and 208, respectively;
(i) SEQ ID NOs: 54 and 196, respectively;
(j) SEQ ID NOs: 56 and 199, respectively;
(k) SEQ ID NOs: 56 and 206, respectively; and
(l) SEQ ID NOs: 59 and 204, respectively.

In some embodiments, an anti-CD161 antibody or antigen binding portion thereof of Subgroup III comprises heavy and light chain variable regions comprising nucleotide sequences selected from:
(a) SEQ ID NOs: 44 and 153, respectively;
(b) SEQ ID NOs: 44 and 193, respectively;
(c) SEQ ID NOs: 46 and 195, respectively;
(d) SEQ ID NOs: 48 and 153, respectively;
(e) SEQ ID NOs: 49 and 203, respectively;
(f) SEQ ID NOs: 51 and 197, respectively;
(g) SEQ ID NOs: 53 and 153, respectively;
(h) SEQ ID NOs: 53 and 209, respectively;
(i) SEQ ID NOs: 55 and 198, respectively;
(j) SEQ ID NOs: 57 and 200, respectively;
(k) SEQ ID NOs: 57 and 201, respectively;
(l) SEQ ID NOs: 58 and 207, respectively; and
(m) SEQ ID NOs: 60 and 205, respectively;

In some embodiments, an anti-CD161 antibody or antigen binding portion thereof described herein binds to an epitope comprising amino acid residues L151, Y198, E200, or E205 of SEQ ID NO: 335. In some embodiments, an anti-CD161 antibody or antigen binding portion of the disclosure does not significantly cross-react with cynomolgus CD161. In some embodiments, an anti-CD161 antibody or antigen binding portion thereof described herein comprise a heavy chain CDR3 with an amino acid sequence ARDYYLX$_1$DYITQTSFDY (SEQ ID NO: 310), wherein X$_1$ is any amino acid. In some embodiments, an anti-CD161 antibody or antigen binding portion thereof described herein comprise a heavy chain CDR3 with an amino acid sequence ARDYYLX$_1$DYITQTSFDY (SEQ ID NO: 310), wherein X$_1$ is selected from S, F or Y.

In some embodiments, the disclosure provides an anti-CD161 antibody or antigen binding portion thereof of Subgroup IV, wherein the antibody or antigen binding portion:
(a) binds human CD161 with an affinity (K$_D$) of about 50-300 pM (e.g., between about 50 pM and about 300 pM);
(b) binds human CD161 an inhibits the interaction between human CD161 and the human CD161 ligand CLEC2D;
(c) does not significantly cross-react with other human proteins in the C-type lectin family (e.g., a human protein selected from Table 1);
(d) comprises a heavy chain CDR3 with an amino acid sequence ARDYYLX$_1$DYITQTSFDY (SEQ ID NO: 310), wherein X$_1$ is any amino acid;
(e) binds to an epitope on human CD161 comprising amino acid residues L151, Y198, E200, or E205 of SEQ ID NO: 335; and
(f) does not significantly cross-react with cynomolgus CD161.

In some embodiments, an anti-CD161 antibody or antigen binding portion of Subgroup IV comprises heavy and light chain CDRs selected from:
(a) heavy chain CDR1, CDR2, and CDR3 comprising amino acid sequences set forth in SEQ ID NOs: 299, 303, and 310 respectively, and light chain CDR1, CDR2, and CDR3 comprising amino acid sequences set forth in SEQ ID NOs: 315, 316, and 321 respectively; and
(b) heavy chain CDR1, CDR2, and CDR3 comprising amino acid sequences set forth in SEQ ID NOs: 301, 305, and 310 respectively, and light chain CDR1, CDR2, and CDR3 comprising amino acid sequences set forth in SEQ ID NOs: 315, 316, and 321 respectively.

In some embodiments, an anti-CD161 antibody or antigen binding portion of Subgroup IV comprises heavy and light chain CDRs selected from:
(a) heavy chain CDR1, CDR2, and CDR3 comprising amino acid sequences set forth in SEQ ID NOs: 127, 132, and 147 respectively, and light chain CDR1, CDR2, and CDR3 comprising amino acid sequences set forth in SEQ ID NOs: 277, 280, and 289 respectively;
(b) heavy chain CDR1, CDR2, and CDR3 comprising amino acid sequences set forth in SEQ ID NOs: 127, 132, and 148 respectively, and light chain CDR1, CDR2, and CDR3 comprising amino acid sequences set forth in SEQ ID NOs: 277, 280, and 289 respectively;
(c) heavy chain CDR1, CDR2, and CDR3 comprising amino acid sequences set forth in SEQ ID NOs: 127, 132, and 148 respectively, and light chain CDR1, CDR2, and CDR3 comprising amino acid sequences set forth in SEQ ID NOs: 277, 280, and 290 respectively;
(d) heavy chain CDR1, CDR2, and CDR3 comprising amino acid sequences set forth in SEQ ID NOs: 127, 132, and 149 respectively, and light chain CDR1, CDR2, and CDR3 comprising amino acid sequences set forth in SEQ ID NOs: 277, 280, and 289 respectively;
(e) heavy chain CDR1, CDR2, and CDR3 comprising amino acid sequences set forth in SEQ ID NOs: 127, 132, and 149 respectively, and light chain CDR1, CDR2, and CDR3 comprising amino acid sequences set forth in SEQ ID NOs: 277, 280, and 290 respectively;
(f) heavy chain CDR1, CDR2, and CDR3 comprising amino acid sequences set forth in SEQ ID NOs: 127, 132, and 149 respectively, and light chain CDR1, CDR2, and CDR3 comprising amino acid sequences set forth in SEQ ID NOs: 277, 280, and 291 respectively;
(g) heavy chain CDR1, CDR2, and CDR3 comprising amino acid sequences set forth in SEQ ID NOs: 127, 132, and 149 respectively, and light chain CDR1, CDR2, and CDR3 comprising amino acid sequences set forth in SEQ ID NOs: 277, 280, and 292 respectively;
(h) heavy chain CDR1, CDR2, and CDR3 comprising amino acid sequences set forth in SEQ ID NOs: 127, 132, and 149 respectively, and light chain CDR1, CDR2, and CDR3 comprising amino acid sequences set forth in SEQ ID NOs: 278, 280, and 289 respectively;
(i) heavy chain CDR1, CDR2, and CDR3 comprising amino acid sequences set forth in SEQ ID NOs: 127, 135, and 149 respectively, and light chain CDR1, CDR2, and CDR3 comprising amino acid sequences set forth in SEQ ID NOs: 277, 280, and 289 respectively;
(j) heavy chain CDR1, CDR2, and CDR3 comprising amino acid sequences set forth in SEQ ID NOs: 127, 136, and 149 respectively, and light chain CDR1, CDR2, and CDR3 comprising amino acid sequences set forth in SEQ ID NOs: 277, 280, and 291 respectively;
(k) heavy chain CDR1, CDR2, and CDR3 comprising amino acid sequences set forth in SEQ ID NOs: 127, 136, and 149 respectively, and light chain CDR1, CDR2, and CDR3 comprising amino acid sequences set forth in SEQ ID NOs: 277, 280, and 292 respectively;
(l) heavy chain CDR1, CDR2, and CDR3 comprising amino acid sequences set forth in SEQ ID NOs: 127, 136, and 149 respectively, and light chain CDR1, CDR2, and CDR3 comprising amino acid sequences set forth in SEQ ID NOs: 277, 280, and 293 respectively;
(m) heavy chain CDR1, CDR2, and CDR3 comprising amino acid sequences set forth in SEQ ID NOs: 127, 136, and 149 respectively, and light chain CDR1, CDR2, and CDR3 comprising amino acid sequences set forth in SEQ ID NOs: 277, 280, and 294 respectively; and
(n) heavy chain CDR1, CDR2, and CDR3 comprising amino acid sequences set forth in SEQ ID NOs: 130, 132, and 149 respectively, and light chain CDR1, CDR2, and CDR3 comprising amino acid sequences set forth in SEQ ID NOs: 277, 280, and 290 respectively.

In some embodiments, an anti-CD161 antibody or antigen binding portion of Subgroup IV comprises heavy and light chain variable regions comprising amino acid sequences selected from:
(a) SEQ ID NOs: 61 and 245, respectively;
(b) SEQ ID NOs: 66 and 258, respectively;
(c) SEQ ID NOs: 63 and 250, respectively;
(d) SEQ ID NOs: 63 and 245, respectively;
(e) SEQ ID NOs: 66 and 248, respectively;
(f) SEQ ID NOs: 70 and 252, respectively;
(g) SEQ ID NOs: 68 and 245, respectively;
(h) SEQ ID NOs: 66 and 250, respectively;
(i) SEQ ID NOs: 66 and 254, respectively;
(j) SEQ ID NOs: 72 and 256, respectively;
(k) SEQ ID NOs: 74 and 260, respectively;
(l) SEQ ID NOs: 76 and 297, respectively;
(m) SEQ ID NOs: 78 and 262, respectively;
(n) SEQ ID NOs: 78 and 267, respectively;
(o) SEQ ID NOs: 78 and 269, respectively;
(p) SEQ ID NOs: 80 and 264, respectively;
(q) SEQ ID NOs: 82 and 271, respectively;
(r) SEQ ID NOs: 84 and 264, respectively; and
(s) SEQ ID NOs: 86 and 254, respectively.

In some embodiments, an anti-CD161 antibody or antigen binding portion of Subgroup IV comprises heavy and light chain variable regions comprising nucleotide sequences selected from:
(a) SEQ ID NOs: 62 and 246, respectively;
(b) SEQ ID NOs: 67 and 259, respectively;
(c) SEQ ID NOs: 64 and 246, respectively;
(d) SEQ ID NOs: 65 and 251, respectively;
(e) SEQ ID NOs: 65 and 246, respectively;
(f) SEQ ID NOs: 67 and 249, respectively;
(g) SEQ ID NOs: 71 and 253, respectively;
(h) SEQ ID NOs: 69 and 247, respectively;
(i) SEQ ID NOs: 67 and 251, respectively;
(j) SEQ ID NOs: 67 and 255, respectively;
(k) SEQ ID NOs: 73 and 257, respectively;
(l) SEQ ID NOs: 75 and 261, respectively;
(m) SEQ ID NOs: 77 and 298, respectively;
(n) SEQ ID NOs: 79 and 263, respectively;
(o) SEQ ID NOs: 79 and 268, respectively;
(p) SEQ ID NOs: 79 and 270, respectively;
(q) SEQ ID NOs: 81 and 265, respectively;
(r) SEQ ID NOs: 83 and 272, respectively;
(s) SEQ ID NOs: 85 and 266, respectively; and
(t) SEQ ID NOs: 87 and 255, respectively.

In some embodiments, the functional properties of an anti-CD161 antibody described herein (e.g., an anti-CD161 antibody of Subgroup I-IV) include but are not limited to:
(a) induces or increases activation of CD161-expressing human T cells in response to antigen-expressing target cells;
(b) induces or increases cytokine production by CD161-expressing human T cells in response to antigen-expressing target cells;
(c) induces or increases granzyme B expression by CD161-expressing human T cells in response to antigen-expressing target cells;
(d) reduces exhaustion of CD161-expressing human T cells in response to antigen-expressing target cells;
(e) reduces expression of the PD-1 receptor in human T cells in response to antigen-expressing target cells;
(f) does not significantly cross-react with other human proteins in the C-type lectin family (e.g., a human protein selected from Table 1); and
(g) any combination of a-f.

In some embodiments, the anti-CD161 antibodies described herein have at least the functional properties of an antibody selected from:
(a) KW1 (i.e., an antibody comprising heavy and light chain variable regions with amino acid sequences set forth by SEQ ID NOs: 1 and 152 respectively);
(b) KW1.2.1 (i.e., an antibody comprising heavy and light chain variable regions with amino acid sequences set forth by SEQ ID NOs: 15 and 165 respectively);

(c) KW1.3.12 (i.e., an antibody comprising heavy and light chain variable regions with amino acid sequences set forth by SEQ ID NOs: 8 and 167 respectively);
(d) KW7 (i.e., an antibody comprising heavy and light chain variable regions with amino acid sequences set forth by SEQ ID NOs: 22 and 152 respectively);
(e) KW7.2.2 (i.e., an antibody comprising heavy and light chain variable regions with amino acid sequences set forth by SEQ ID NOs: 22 and 185 respectively);
(f) KW7.3.7 (i.e., an antibody comprising heavy and light chain variable regions with amino acid sequences set forth by SEQ ID NOs: 41 and 190 respectively);
(g) KW9 (i.e., an antibody comprising heavy and light chain variable regions with amino acid sequences set forth by SEQ ID NOs: 43 and 152 respectively);
(h) KW9.3.3 (i.e., an antibody comprising heavy and light chain variable regions with amino acid sequences set forth by SEQ ID NOs: 56 and 206 respectively);
(i) KW17 (i.e., an antibody comprising heavy and light chain variable regions with amino acid sequences set forth by SEQ ID NOs: 61 and 245 respectively);
(j) KW17.3.4 (i.e., an antibody comprising heavy and light chain variable regions with amino acid sequences set forth by SEQ ID NOs: 78 and 267 respectively);
(k) KM12 (i.e., an antibody comprising heavy and light chain variable regions with amino acid sequences set forth by SEQ ID NOs: 88 and 152 respectively);
(l) KM12.2.3 (i.e., an antibody comprising heavy and light chain variable regions with amino acid sequences set forth by SEQ ID NOs: 105 and 223 respectively);
(m) KM12.3.2 (i.e., an antibody comprising heavy and light chain variable regions with amino acid sequences set forth by SEQ ID NOs: 113 and 212 respectively); and
(n) KM12.4.7 (i.e., an antibody comprising heavy and light chain variable regions with amino acid sequences set forth by SEQ ID NOs: 117 and 235 respectively).

In some embodiments, the anti-CD161 antibodies described herein bind human CD161 with an equilibrium dissociation constant $K_D$ at least equivalent to that of an antibody selected from:
(a) KW1 (i.e., an antibody comprising heavy and light chain variable regions with amino acid sequences set forth by SEQ ID NOs: 1 and 152 respectively);
(b) KW1.2.1 (i.e., an antibody comprising heavy and light chain variable regions with amino acid sequences set forth by SEQ ID NOs: 15 and 165 respectively);
(c) KW1.3.12 (i.e., an antibody comprising heavy and light chain variable regions with amino acid sequences set forth by SEQ ID NOs: 8 and 167 respectively);
(d) KW7 (i.e., an antibody comprising heavy and light chain variable regions with amino acid sequences set forth by SEQ ID NOs: 22 and 152 respectively);
(e) KW7.2.2 (i.e., an antibody comprising heavy and light chain variable regions with amino acid sequences set forth by SEQ ID NOs: 22 and 185 respectively);
(f) KW7.3.7 (i.e., an antibody comprising heavy and light chain variable regions with amino acid sequences set forth by SEQ ID NOs: 41 and 190 respectively);
(g) KW9 (i.e., an antibody comprising heavy and light chain variable regions with amino acid sequences set forth by SEQ ID NOs: 43 and 152 respectively);
(h) KW17 (i.e., an antibody comprising heavy and light chain variable regions with amino acid sequences set forth by SEQ ID NOs: 61 and 245 respectively);
(i) KM12 (i.e., an antibody comprising heavy and light chain variable regions with amino acid sequences set forth by SEQ ID NOs: 88 and 152 respectively); and
(j) KM12.4.7 (i.e., an antibody comprising heavy and light chain variable regions with amino acid sequences set forth by SEQ ID NOs: 117 and 235 respectively).

In some embodiments, the anti-CD161 antibodies described herein (e.g., anti-CD161 antibodies of Subgroup I-IV) comprise a human IgG1 heavy chain constant region or a human IgG4 heavy chain constant region. In some embodiments, the anti-CD161 antibodies described herein comprise a human IgG1 heavy chain constant region comprising an amino acid sequence set forth by SEQ ID NO: 322. In some embodiments, the anti-CD161 antibodies described herein comprise a human IgG4 heavy chain constant region comprising an amino acid sequence set forth by SEQ ID NO: 323. In some embodiments, the anti-CD161 antibodies described herein comprise a immunoglobulin kappa constant chain or a lambda constant chain. In some embodiments, the anti-CD161 antibodies described herein comprise an immunoglobulin kappa constant chain comprising an amino acid sequence set forth in SEQ ID NO: 324. In some embodiments, the anti-CD161 antibodies described herein comprise an immunoglobulin lambda constant chain comprising an amino acid sequence set forth in SEQ ID NO: 325.

In some embodiments, the anti-CD161 antibodies described herein (e.g., anti-CD161 antibodies of Subgroup I-IV) comprise a heavy chain constant region derived from a human IgG1 heavy chain constant region. In some embodiments, the anti-CD161 antibodies described herein (e.g., anti-CD161 antibodies of Subgroup I-IV) comprise a mutant IgG1 heavy chain constant region, wherein the mutant is derived from a human IgG1 heavy chain constant region (e.g., human IgG1 set by SEQ ID NO: 322). In some embodiments, the anti-CD161 antibodies described herein (e.g., anti-CD161 antibodies of Subgroup I-IV) comprise a mutant IgG1 heavy chain constant region, wherein the mutant comprises one or more amino acid sequence deletions, insertions, or substitutions relative to human IgG1 heavy chain constant region (e.g., human IgG1 set by SEQ ID NO: 322). In some embodiments, the mutant IgG1 heavy chain comprises a substitution at Leu234, Leu235 and Pro329. In some embodiments, the mutant IgG1 heavy chain comprises a substitution at Leu234, Leu235 and Pro329, defined by EU numbering. In some embodiments, the mutant IgG1 heavy chain comprises a substitution of Leu234 to alanine, a substitution of Leu235 to alanine, and a substitution of Pro329 to glycine. In some embodiments, the mutant IgG1 heavy chain comprises a substitution of Leu234 to alanine, a substitution of Leu235 to alanine, and a substitution of Pro329 to glycine, defined by EU numbering. In some embodiments, the mutant IgG1 heavy chain constant region comprises an amino acid sequence set forth in SEQ ID NO: 326. In some embodiments, the mutant IgG1 heavy chain has reduced Fc-gamma receptor binding relative to wild-type IgG1 heavy chain. In some embodiments, the mutant IgG heavy chains binds to Fc-gamma receptor with binding affinity (Kd) that is reduced at least 5-fold, 10-fold, 100-fold, 1000-fold or more relative to the wild-type IgG1 heavy chain. In some embodiments, the anti-CD161 antibodies described herein comprise a mutant IgG4 heavy chain constant region. In some embodiments, the mutant IgG4 heavy chain comprises one or more substitutions at amino acid positions selected from: Ser228, Leu325, and Pro329, each as defined by EU numbering. In some embodiments, the mutant IgG4 heavy chain comprises one or more substitutions selected from: Ser228 to proline, Leu325 to glutamate, and Pro329 to glycine, each as defined by EU numbering. In some embodiments, the mutant IgG4 heavy comprises the following substitutions: S228P, L325E, and P329G, each as defined by EU numbering.

Methods for Characterization of Anti-CD161 Antibodies
Methods of Measuring Antibody Binding In some embodiments, an anti-CD161 antibodies or antibody binding portions described herein (e.g., anti-CD161 antibodies of Subgroup I-IV) bind human CD161 with an affinity (KD) determined by an antigen-binding assay.

In some embodiments, the antigen-binding assay determines a binding affinity (KD) of the anti-CD161 antibody for a CD161 polypeptide. In some embodiments, the antigen-binding assay determined kinetic rate constants (e.g., kon, e.g., koff) for the binding interaction of an anti-CD161 antibody for a CD161 polypeptide. Methods of measuring binding affinity and/or kinetic rate constants using an antigen-binding assay are known in the art and include, but are not limited to, enzyme-linked immunosorbent assay (ELISA), gel-shift assays, pull-down assays, quantitative immunoblot, equilibrium dialysis, analytical ultracentrifugation, surface plasmon resonance, fluorescence anisotropy, solution equilibrium titration, kinetic exclusion assay, and isothermal titration calorimetry.

In some embodiments, an exact determination of KD is unnecessary, as it is sufficient to obtain a qualitative measurement of affinity. For example, by determining relative binding affinity of a test antibody relative to a reference antibody using a method such as ELISA or FACS analysis, e.g., determining whether affinity of the test antibody is higher (e.g., 2-fold, 3-fold, 4-fold, etc) than a reference antibody.

In some embodiments, the antigen-binding assay comprises measuring binding affinity of a labeled anti-CD161 antibody for a CD161 polypeptide expressed on a cell surface. In some embodiments, the anti-CD161 antibody is labeled with a fluorescent molecule (e.g., a fluorescent dye). In some embodiments, binding is detected using a method of fluorescence detection (e.g., flow cytometry). In some embodiments, binding of an anti-CD161 antibody disclosed herein to a cell expressing the antigen is compared relative to a reference cell lacking expression of the antigen. In some embodiments, an anti-CD161 antibody or antigen binding portion thereof described herein binds human CD161 with an affinity (KD) of about 50-2000 nM as determined using fluorescence detection of binding to a CD161-expressing cell. In some embodiments, an anti-CD161 antibody or antigen binding portion thereof described herein binds human CD161 with an affinity (KD) of about 50-500 pM as determined using fluorescence detection of binding to a CD161-expressing cell.

In some embodiments, the antigen binding assay is surface plasmon resonance. "Surface plasmon resonance" includes an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jönsson, U., et al. (1993) Ann. Biol. Clin. 51:19-26; Jönsson, U., et al. (1991) Biotechniques 11:620-627; Johnsson, B., et al. (1995) J. Mol. Recognit. 8:125-131; and Johnsson, B., et al. (1991) Anal. Biochem. 198:268-277. In some embodiments, the antigen binding assay is biolayer interferometry (BLI). The phrase "biolayer interferometry" or "BLI" includes an optical phenomenon that allows for the measurement of sub-nanometer changes in the thickness of its optical layer detection surface. In some embodiments, biomolecules binds at a sensor surface and change the optical layer thickness. The magnitude of the optical layer thickness change is proportional to the mass or molecular weight of the binding molecule. In some embodiments, CD161 is immobilized to the sensor surface to measure binding by an antibody, wherein binding creates a changes in the molecular weight to produce a corresponding change in the optical layer thickness. In some embodiments wherein CD161 is immobilized to the sensor surface, samples of the anti-CD161 antibody are prepared by serial dilution and injected, and KD values are calculated from modeling of the curve of binding relative to antibody concentration. In some embodiments, BLI is performed with an OCTET system (ForteBio).

In some embodiments, an anti-CD161 antibody or antigen binding portion thereof described herein binds human CD161 with an affinity (KD) of about 1-10 nM, 5-10 nM, 5-20 nM, 10-20 nM, 10-30 nM, 20-30 nM, 20-40 nM, 30-40 nM, 30-50 nM, 30-60 nM, 40-60 nM, 50-100 nM, about 50-200 nM, about 100-200 nM, about 100-300 nM, about 100-400 nM, about 100-500 nM, about 200-500 nM, about 300-500 nM, about 300-600 nM, about 300-700 nM, about 500-800 nM, about 500-900 nM, about 500-1000 nM, about 500-1500 nM, about 1000-1500 nM, about 1000-2000 nM, about 1500-2000 nM as measured using a method of BLI (e.g., OCTET). In some embodiments, a method of surface plasmon resonance or BLI is used to measure binding affinity (KD), wherein the measurement is made at a concentration of antibody that is near or below the antibody KD (e.g., concentration of about 5%, about 10%, about 20%, about 30%, about 40%, about 50%, about 60%, about 70%, about 80%, about 90%, about 100%, about 110%, about 120%, about 130%, about 140% or about 150% of the antibody KD). In some embodiments, a method of surface plasmon resonance or BLI is used to measure antibody binding as the sample reaches equilibrium, thereby providing a measure of the on rate of the antibody (e.g., kon). In some embodiments, a method of surface plasmon resonance or BLI is used to measure kon, wherein the measurement is made at a concentration of antibody that is significantly higher than the antibody KD (e.g, at least 2-fold, at least 3-fold, at least 4-fold, at least 5-fold, at least 6-fold, at least 7-fold, at least 8-fold, at least 9-fold, or at least 10-fold higher than the antibody KD).

In some embodiments, the antigen binding assay is a kinetic exclusion assay (KinExA). The KinExA is a solution-based method to determine equilibrium binding affinity (KD) and kinetics of binding for interactions between binding partners, particularly for binding interactions in the picomolar to subnanomolar range (see, e.g., Darling et al (2004) *Assay Drug Dev Technol* 2:647-657).

For measurement of binding affinity (KD), the KinExA assay typically comprises the following: (i) antigen (e.g., CD161) is titrated into a constant concentration of antibody or antigen binding portion thereof (e.g., anti-CD161 antibody, e.g., anti-CD161 antigen binding portion), (ii) the sample comprising the antigen (e.g., CD161) and antibody or antigen binding portion thereof (e.g., anti-CD161 antibody, e.g., anti-CD161 antigen binding portion) is allowed to equilibrate, (iii) the antibody or antigen binding portion thereof is captured using a solid-phase immobilized reagent, (iv) the quantity of antigen bound to immobilized antibody or antigen binding portion thereof is determined, (v) a binding curve of bound antigen as a function of antigen concentration titrated into the sample is used to determine the binding affinity (KD). In some embodiments, the assay comprises (ii), wherein the time for equilibration is about 1-2 hours, about 1-3 hours, about 2-4 hours, about 2-5 hours, about 3-6 hours, about 3-10 hours, about 5-10 hours, about 5-15 hours, about 10-15 hours, about 10-20 hours, about 10-25 hours, about 15-20 hours, about 15-25 hours, about 20-25 hours, about 20-30 hours, about 25-30 hours, about 25-35 hours, about 30-35 hours, about 30-40 hours, or about 35-40 hours.

In some embodiments, the assay measures binding of an antibody or antigen binding portion thereof comprising a covalently-bound tag (e.g., biotin) to an antigen linked to an Fc domain (e.g., CD161-Fc), wherein (iii) comprises capturing the antibody or antigen binding portion thereof using a reagent that binds the covalent tag (e.g., streptavidin), wherein (iv) comprises measuring bound antigen using a Fc-binding antibody comprising a label for detection (e.g., a fluorescent label, an enzymatic label, a bioluminescent label), and wherein the measurement comprises quantification of the label for detection using a method discernable to one skilled in the art (e.g., quantification of fluorescence, e.g., quantification of enzymatic product, e.g., quantification of bioluminescence).

In some embodiments, the KinExA assay comprises the following: (i) the antibody or antigen binding portion thereof (e.g., anti-CD161 antibody, e.g., anti-CD161 antigen binding portion) is titrated into a constant concentration of the antigen (e.g., CD161), (ii) the sample comprising the antigen (e.g., CD161) and antibody or antigen binding portion thereof (e.g., anti-CD161 antibody, e.g., anti-CD161 antigen binding portion) is allowed to equilibrate, (iii) the antigen is captured using a solid-phase immobilized reagent, (iv) the quantity of antibody or antigen binding portion thereof bound to immobilized antigen is determined, and (v) a binding curve of bound antibody or antigen binding portion thereof as a function of concentration of antibody or antigen binding portion thereof titrated into the sample is used to determine the binding affinity (KD).

In some embodiments, the assay measures binding of an antibody or antigen binding portion thereof to an antigen, wherein the antigen is linked to an Fc domain (e.g., CD161-Fc) and further comprises a covalently-bound tag (e.g., biotin), wherein (iii) comprises capturing the antigen (e.g., CD161-Fc) using a reagent that binds the covalent tag (e.g., streptavidin), wherein (iv) comprises measuring bound antibody or antigen binding portion thereof using an anti-species antibody that lacks significant binding to the antigen Fc domain (e.g., an anti-human antibody that binds the light chain constant region of the antibody or antigen binding portion thereof) and further comprises a label for detection (e.g., a fluorescent label, an enzymatic label, a bioluminescent label), and wherein the measurement comprises quantification of the label for detection using a method discernable to one skilled in the art (e.g., quantification of fluorescence, e.g., quantification of enzymatic product, e.g., quantification of bioluminescence).

In some embodiments, an anti-CD161 antibody or antigen binding portion thereof described herein binds human CD161 with an affinity (KD) of about 50-100 pM, about 50-200 pM, about 100-200 pM, about 100-300 pM, about 100-400 pM, about 100-500 pM, about 200-500 pM, about 300-500 pM, about 300-600 pM, about 300-700 pM, about 500-800 pM, about 500-900 pM, about 500-1000 pM, about 500-1500 pM, about 1000-1500 pM, about 1000-2000 pM, about 1500-2000 pM as measured using a kinetic exclusion assay.

Methods to Measure Ligand Binding

In some embodiments, an anti-CD161 antibody described herein binds human CD161 and blocks or inhibits binding by CLEC2D as determined by a ligand binding assay. A ligand binding assay (LBA) is an assay, or an analytic procedure, that provides a measure of the interactions that occur between two reactant molecules (e.g., a receptor and ligand polypeptides). Suitably, the LBA provides a measure of the degree of affinity between the two reactant molecules (e.g., a receptor and ligand polypeptides). For example, in some embodiments a ligand binding assay is used to determine the presence, rate, extent of binding, or combinations thereof, of a ligand molecule (e.g., CLEC2D) to a receptor (e.g., CD161). In some embodiments, to determine the presence, rate and/or extent of ligand binding to a receptor, a ligand binding assay comprises detecting the formation of a ligand:receptor complex. In some embodiments, to determine the presence, rate and/or extent of ligand binding to a receptor, a ligand binding assay comprises determining the dissociation of a ligand:receptor complex.

In some embodiments, the formation and/or dissociation of a ligand:receptor complex is determined by detection of a fluorescently-labeled ligand in complex with a receptor. In some embodiments, the formation and/or dissociation of a ligand:receptor complex is determined by detection and/or quantification of an amount of fluorescently-labeled receptor in complex with a ligand. In some embodiments, the formation and/or dissociation of a ligand:receptor complex is determined by detection and/or quantification of an amount of a fluorescently-labeled antibody that specifically binds to the ligand:receptor complex. Methods of detecting and quantifying fluorescence are known in the art and include, but are not limited to, fluorescence polarization (FP), fluorescence anisotropy (FA), flow cytometry and microscopy.

In some embodiments, the formation and/or dissociation of a ligand:receptor complex is determined by detection and/or quantification of an amount of a radioactively-labeled ligand in complex with a receptor. In some embodiments, the formation and/or dissociation of a ligand:receptor complex is determined by detection and/or quantification of an amount of radioactively-labeled receptor in complex with a ligand. In some embodiments, the formation and/or dissociation of a ligand:receptor complex is determined by detection and/or quantification of an amount of a radioactively-labeled antibody that specifically binds to the ligand:receptor complex. Methods of detecting and quantifying radioactivity are known in the art and include, but are not limited to, quantitative autoradiography and scintillation counting.

In some embodiments, the formation and/or dissociation of a ligand:receptor complex is determined by detection and/or quantification of an amount of a bioluminescently-labeled ligand in complex with a receptor. In some embodiments, the formation and/or dissociation of a ligand:receptor complex is determined by detection and/or quantification of an amount of bioluminescently-labeled receptor in complex with a ligand. In some embodiments, the formation and/or dissociation of a ligand:receptor complex is determined by detection and/or quantification of an amount of a bioluminescently-labeled antibody that specifically binds to the ligand:receptor complex. Methods of detecting and quantifying bioluminescence are known in the art and include, but are not limited to, luminometry.

In some embodiment, formation and/or dissociation of the ligand:receptor complex is determined by surface plasmon resonance (SPR) as described supra.

In some embodiments, a ligand binding assay determines if an antibody that specifically binds to a receptor (e.g., an anti-CD161 antibody) affects the formation of a ligand:receptor complex by determining the presence, rate and/or extent of ligand binding (e.g., CLEC2D) to the receptor (e.g., CD161) in the presence of the antibody. In some embodiments, an antibody (e.g., an anti-CD161 antibody) that specifically binds to a receptor (e.g., CD161) and decreases, disrupts or blocks the formation of a ligand:receptor complex (e.g., a CD161:CLEC2D complex) is known as a "ligand blocking antibody". In some embodiments, a "ligand blocking antibody" may decrease the formation of a ligand:receptor complex (e.g., a CD161:CLEC2D complex) by at least 10%, at least 20%, at least 30%, at least 40%, or at least 50%, or at least 60%, or at least 70%, or at least 80%, or at least 90% compared to the formation of the ligand:receptor complex (e.g., the CD161:CLEC2D complex) which occurs in the absence of the ligand blocking antibody. In some embodiments, a "ligand blocking antibody" may decrease the formation of a ligand:receptor complex (e.g., a CD161:CLEC2D complex) by at least 2-fold, at least 3-fold, at least 4-fold, at least 5-fold, at least 6-fold, at least 7-fold, at least 8-fold, at least 9-fold, or at least 10-fold, or at least 11-fold, or at least 12-fold, or at least 13-fold, or at least 14-fold, or at least 15-fold, or at least 16-fold, or at least 17-fold, or at least 18-fold, or at least 19-fold, or at least 20-fold compared to the formation of the ligand:receptor complex (e.g., the CD161:CLEC2D complex) which occurs in the absence of the ligand blocking antibody.

In some embodiments, an isolated anti-CD161 antibody, or antigen-binding fragment thereof, described herein, binds to CD161 and blocks CLEC2D binding as determined by a ligand binding assay, wherein the ligand binding assay comprises the following steps:
 (i) combining an anti-CD161 antibody with CD161 and CLEC2D at various concentrations, wherein CD161 and CLEC2D form a CD161:CLEC2D complex, and
 (ii) detecting the CD161:CLEC2D complex in the presence of the anti-CD161 antibody over time,
wherein a decrease in CD161:CLEC2D complex in the presence of the anti-CD161 antibody indicates the anti-CD161 antibody blocks or inhibits CEC2D binding to CD161. In some embodiments, the decrease in CD161:CLEC2D complex in the presence of the anti-CD161 antibody is at least 1.5-fold, at least 2-fold, at least 5-fold, at least 10-fold, or at least 20-fold lower than the amount CD161:CLEC2D complex in the absence of the anti-CD161 antibody. In some embodiments, the formation of a CD161:CLEC2D complex is detected by measuring formation of a complex between CD161 and fluorescently-labeled CLEC2D using a method of fluorescence detection (e.g., microscopy or flow cytometry). In some embodiments, CD161 is expressed at the cell surface by CD161-expressing cells, and formation of a CD161:CLEC2D complex is measured by detecting surface labeling of CD161-expressing cells with fluorescently-labeled CLEC2D using a method of fluorescence detection (e.g., microscopy or flow cytometry). In some embodiments, a decrease in surface labeling with fluorescently-labeled CLEC2D in the presence of the anti-CD161 antibody is at least 1.5-fold, at least 2-fold, at least 5-fold, at least 10-fold, or at least 20-fold lower than the amount of CLEC2D surface labeling in the absence of the anti-CD161 antibody.

Methods of Epitope Mapping

The disclosure provides anti-CD161 antibodies, or antigen binding fragments thereof, that specifically bind to an epitope of human CD161 and inhibit or block the interaction between human CD161 and CLEC2D. Methods to characterize, map, or otherwise elucidate the epitope of an anti-CD161 antibody can be grouped into structural, functional, or computational methods. A particularly suitable structural method to determine the precise molecular architecture of the interaction between an antibody and the corresponding antigen to which it binds is x-ray crystallography (alternatively "x-ray co-crystallography). A crystal structure of a bonded antibody-antigen pair enables very accurate determination of key interactions between individual amino acids from both side chains and main chain atoms in both the epitope of the antigen and the paratope of the antibody Amino acids that are within 4 angstroms (Å) of each other are generally considered to be contacting residues. The methodology typically involves purification of antibody and antigen, formation and purification of the complex, followed by successive rounds of crystallization screens and optimization to obtain diffraction-quality crystals. Structural solution is obtained following x-ray crystallography frequently at a synchrotron source. Accordingly, the anti-CD161 antibodies or antigen-binding portions thereof provided by the disclosure may be assessed through x-ray crystallographic analysis of a crystal structure comprising an antibody bound to human CD161, or a fragment or portion thereof. In some aspects, the epitopes that are bound by the antibodies provided by the disclosure are identified by determining the residues on the human CD161 antigen that reside or are located within 4 angstroms (Å) of an antibody paratope residue.

Other structural methods for epitope mapping include, but are not limited to, hydrogen-deuterium exchange coupled to mass spectrometry, crosslinking-coupled mass spectrometry, and nuclear magnetic resonance (NMR) (see, e.g., Epitope Mapping Protocols in Methods in Molecular Biology, Vol. 66, G. E. Morris, Ed. (1996); Abbott et al., (2014) *Immunology* 142(4):526-535).

Functional methods for epitope mapping are well known in the art and typically involve an assessment or quantification of antibody binding to whole proteins, protein fragments or peptides. Functional methods for epitope mapping can be used, for example, to identify linear or conformational epitopes and/or can be used to infer when two or more distinct antibodies bind to the same or similar epitopes. Functional methods for epitope mapping include, for example, immunoblotting assays, immunoprecipitation assays, and fluorescence-based labeling assays, wherein overlapping or contiguous peptides from CD161 are tested for reactivity with an anti-CD161 antibody (e.g., KW1, KW7, KW9, KW17, KM12 or HP-3G10). Other functional methods for epitope mapping include array-based oligopeptide scanning (alternatively known as "overlapping peptide scanning" or "pepscan analysis"), site-directed mutagenesis (e.g., alanine-scanning mutagenesis), and high-throughput mutagenesis mapping (e.g., shotgun mutagenesis mapping).

Numerous types of competitive binding assays are known, for example: solid phase direct or indirect radioimmunoassay (RIA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, *Antibodies: A Laboratory Manual*, Cold Spring Harbor Press (1988)); solid phase direct label RIA using 1-125 label (see Morel et al., *Mol. Immunol.* 25(1):7 (1988)); solid phase direct biotin-avidin EIA (Cheung et al., *Virology* 176:546 (1990)); and direct labeled RIA. (Moldenhauer et al., *Scand. J. Immunol.* 32:77 (1990)).

Typically, such assays involve the use of purified antigen bound to a solid surface (e.g., surface of a bead, e.g., surface of a cell) and either 1) an unlabeled test antigen-binding protein and a labeled reference antigen-binding protein, or 2) a labeled test antigen-binding protein and an unlabeled reference antigen-binding protein. Competitive inhibition is measured by determining the amount of label bound to the solid surface or cells in the presence of the test antigen-binding protein. Usually the test antigen-binding protein is present in excess. Antigen-binding proteins identified by competition assay (competing antigen-binding proteins) include antigen-binding proteins binding to the same epitope as the reference antigen-binding proteins (e.g., KW1, KW7, KW9, KW17, KM12 or HP-3G10) and antigen-binding proteins binding to an adjacent epitope sufficiently proximal to the epitope bound by the reference antigen-binding protein (e.g., KW1, KW7, KW9, KW17, KM12 or HP-3G10) for steric hindrance to occur. Additional details regarding methods for determining competitive binding are provided in the examples herein. Usually, when a competing antigen-binding protein is present in excess (e.g., about 1-, about 5-, about 10-, about 20-about 50-, or about 100-fold excess), it will inhibit (e.g., reduce or block) specific binding of a reference antigen-binding protein to a common antigen by at least about 40-45%, about 45-50%, about 50-55%, about 55-60%, about 60-65%, about 65-70%, about 70-75% or about 75% or more. In some instances, binding is inhibited by at least about 80-85%, about 85-90%, about 90-95%, about 95-97%, or about 97% or more.

In some embodiments, the epitope bound by an anti-CD161 antibody described herein is determined using site-directed mutagenesis or alanine scanning mutagenesis. The site-directed mutagenesis method involves targeted site-directed mutagenesis where critical amino acids are identified by systematically introducing substitutions along the protein sequence and then determining the effects of each substitution on antibody binding. This may be done by "alanine scanning mutagenesis" (Cunningham and Wells (1989) Science 244:1081-085), or some other form of point mutagenesis of amino acid residues in CD161. As described herein, alanine scanning is a technique that involves the substitution of an alanine residue for a wild-type residue in a polypeptide, followed by an assessment of the stability or function(s) (e.g., binding affinity) of the alanine-substituted derivative or mutant polypeptide and comparison to the wild-type polypeptide. Without being bound by theory, two or more antibodies (e.g., a test antibody and a reference antibody, e.g., KW1, KW7, KW9, KW17, KM12 or HP-3G10) have the same epitope if essentially all amino acid mutations in the antigen that reduce or eliminate binding of the first antibody reduce or eliminate binding of the second or more antibodies.

In some embodiments, the epitope bound by an anti-CD161 antibody described herein is determined using shotgun mutagenesis. Shotgun mutagenesis mapping utilizes a comprehensive plasmid-mutation library for the target gene, with each clone in the library bearing a unique amino acid mutation and the entire library covering every amino acid in the target protein. The clones that constitute the mutation library are individually arranged in microplates, expressed within living mammalian cells, and tested for immunoreactivity with antibodies of interest Amino acids critical for antibody epitopes are identified by a loss of reactivity and are then mapped onto a protein structure to visualize epitopes. Expression of the target protein antigen within mammalian cells often provides the native structure of the target protein antigen, which allows both linear and conformational epitope structures to be mapped on complex proteins. (Paes et al., J. Am. Chem. Soc. 131 (20): 6952-6954 (2009); Banik and Doranz, Genetic Engineering and Biotechnology News 3(2): 25-28 (2010)).

In some embodiments, the epitope bound by an anti-CD161 antibody described herein is determined using peptide scanning methods. In peptide scanning, libraries of short peptide sequences from overlapping segments of the target protein (e.g., CD161) are tested for their ability to bind antibodies of interest. The peptides are synthesized and screened for binding, e.g. using ELISA or BIACORE, or on a chip, by any of the multiple methods for solid-phase screening (Reineke et al, Curr. Opin. Biotechnol. 12: 59-64, 2001) as in the "pepscan" methodology (WO 84/03564; WO 93/09872).

A recently developed technology termed CLIPS (chemical linkage of peptides onto scaffolds) may be used to map conformational epitopes. The loose ends of the peptides are affixed onto synthetic scaffolds, so that the scaffolded peptide may be able to adopt the same spatial structure as the corresponding sequence in the intact protein. CLIPS technology is used to fix linear peptides into cyclic structures ('single-loop' format), and to bring together different parts of a protein binding site ('double-loop', 'triple-loop', etc. format), so as to create conformational epitopes that may be assayed for antibody binding. (U.S. Pat. No. 7,972,993).

The epitopes bound by antibodies provided by the disclosure may also be mapped using computational methods. In these methods, for example, libraries of peptide fragments are displayed on the surface of the phage or cell. Epitopes are then mapped by screening antibodies against these fragments using selective binding assays. A number of computational tools have been developed which allow the prediction of conformational epitopes based upon linear affinity-selected peptides obtained using phage display (Mayrose et al., (2007) Bioinformatics 23:3244-3246). Methods are also available for the detection of conformational epitopes by phage display. Microbial display systems may also be used to express properly folded antigenic fragments on the cell surface for identification of conformational epitopes (Cochran et al., J. Immunol. Meth. 287: 147-158, 2004; Rockberg et al., Nature Methods 5: 1039-1045, 2008).

Methods involving proteolysis and mass spectroscopy may also be used to determine antibody epitopes (Baerga-Ortiz et al., Protein Sci. 2002 June; 1 1 (6): 1300-1308). In limited proteolysis, the antigen is cleaved by different proteases, in the presence and in the absence of the antibody, and the fragments are identified by mass spectrometry. The epitope is the region of the antigen that becomes protected from proteolysis upon binding of the antibody (Suckau et al., Proc. Natl. Acad. Sci. USA 87: 9848-9852, 1990). Additional proteolysis based methods include, for example, selective chemical modification (Fiedler et al., Bioconjugate Chemistry 1998, 9(2): 236-234, 1998), epitope excision (Van de Water et al., Clin. Immunol. Immunopathol. 1997, 85(3): 229-235, 1997), and the recently developed method of hydrogen-deuterium (H/D) exchange (Flanagan, N., Genetic Engineering and Biotechnology News 3(2): 25-28, 2010).

In some embodiments, the anti-CD161 antibodies described herein bind to an epitope on human CD161 comprising one or more amino acid residues selected from I96, D121, K125, E126, R146, L151, Y198, E200, and E205 of SEQ ID NO: 335 as determined by mutagenesis and mammalian display. In some embodiments, the anti-CD161 antibodies described herein bind to an epitope on human CD161 comprising D121 of SEQ ID NO: 335 as determined by mutagenesis and mammalian display. In some embodiments, the anti-CD161 antibodies described herein bind to an epitope on human CD161 comprising D121, I96, K125, and E126 of SEQ ID NO: 335 as determined by mutagenesis and mammalian display. In some embodiments, the anti-CD161 antibodies described herein bind to an epitope on human CD161 comprising R146 of SEQ ID NO: 335 as determined by mutagenesis and mammalian display. In some embodiments, the anti-CD161 antibodies described herein bind to an epitope on human CD161 comprising L151, Y198, E200, or E205 of SEQ ID NO: 335 as determined by mutagenesis and mammalian display.

In some embodiments, the anti-CD161 antibodies described herein bind to an epitope on human CD161 and compete for binding when compared to one or more reference antibodies (e.g., KW1, KW7, KW9, KW17, KM12 or HP-3G10) as determined by competitive binding assay. In some embodiments, the competitive binding assay comprises measuring binding to CD161 expressed by mammalian cells of an unlabeled test anti-CD161 antibody in the presence of a labeled reference anti-CD161 antibody (e.g., KW1, KW7, KW9, KW17, KM12 or HP-3G10). In some embodiments, the unlabeled test anti-CD161 antibody is present at a concentration that is equivalent to the concentration of the reference antibody or is about 1.5-fold, about 2-fold, about 2.5-fold, about 3-fold, about 3.5-fold, about 4-fold, about 4.5-fold, about 5-fold, about 6-fold, about 7-fold, about 8-fold, about 9-fold, about 10-fold higher, about 20-fold, about 30-fold, about 40-fold, about 50-fold, or about 100-fold higher than the concentration of the reference antibody. In some embodiments, competitive binding is a reduction in binding of the reference antibody by at least about 40-45%, about 45-50%, about 50-55%, about 55-60%, about 60-65%, about 65-70%, about 70-75% or about 75% or more. In some embodiments, competitive binding is a reduction in binding of the reference antibody by at least about 80-85%, about 85-90%, about 90-95%, about 95-97%, or about 97% or more.

Methods of Measuring Cross-Reactivity

In some embodiments, the anti-CD161 antibodies or antigen binding portions thereof that bind to human CD161, but do not significantly cross-react with other human proteins in the C-type lectin family (also known as the C-type lectin superfamily). The C-type lectin family includes proteins that have a C-type lectin domain [CTLD]. Multiple groups of proteins comprise a CTLD and are divided into groups based upon domain architecture (see, e.g., Cummings, R. D. et al, C-type lectins, In: Varki, et al., editors. Essentials of Glycobiology. 2$^{nd}$ Edition. Cold Spring Harbor (N. Y.): Cold Spring Harbor Laboratory Press; 2009, Chapter 31). Non-limiting examples of human proteins in the C-type lectin family include those in or a human protein identified in Table 1. In some embodiments, the anti-CD161 antibodies or antigen binding portions thereof that bind to human CD161, but do not significantly cross-react with other human proteins comprising a CTLD. In some embodiments, the anti-CD161 antibodies or antigen binding portions thereof that bind to human CD161, but do not significantly cross-react with one or more human proteins selected from Table 1. In some embodiments, the anti-CD161 antibodies or antigen binding portions thereof that bind to human CD161, but do not significantly cross-react with non-human CD161 (e.g., cynomolgus CD161).

In some embodiments, cross-reactivity of an anti-CD161 antibody disclosed herein to an antigen (e.g., cynomolgus CD161, e.g., human protein selected from Table 1) is measured by detecting a specific reactivity, or functional interaction with, cells physiologically expressing the antigen at the cell surface as measured in a binding assay (e.g., fluorescence assay, e.g., a flow cytometry-based assay). In some embodiments, binding of an anti-CD161 antibody disclosed herein to a cell expressing the antigen is compared relative to a reference cell lacking expression of the antigen. In some embodiments, an anti-CD161 antibody of the disclosure is not significantly cross-reactive to an antigen (e.g., cynomolgus CD161, e.g., protein comprising structural and/or sequence homology with human CD161) if binding is no more than about 1%, about 2%, about 3%, about 4%, about 5%, about 10%, about 15%, about 20%, about 25%, about 30%, about 40%, or about 50% higher than binding to the reference cell as detected using a binding assay described herein (e.g, a flow cytometry-based assay). In some embodiments, "does not significantly cross-react" refers to surface-labeling of cells expressing the human protein that is no more than about 10%, about 20%, about 30%, about 40%, or about 50% higher than surface labeling of reference cells as detected using a binding assay described herein (e.g, a flow cytometry-based assay).

In some embodiments, binding of an anti-CD161 antibody described herein to an antigen is determined by an antigen binding assay, wherein the antigen binding assay comprises the following steps:
  (i) contacting antigen-expressing cells with a fluorescently-labeled anti-CD161 antibody;
  (ii) measuring the level of surface binding using a method of fluorescence detection (e.g., flow cytometry);
  (iii) comparing the level of surface binding to surface labeling of reference cells,
wherein the reference cells do not express the antigen, and wherein an increase in surface labeling of antigen-expressing cells relative to surface labeling of the reference cells indicates binding of the anti-CD161 antibody to the antigen.

In some embodiments, the antigen is human CD161. In some embodiments, an anti-CD161 antibodies described herein bind to human CD161-expressing cells with surface labeling that is about 5-fold, about 10-fold, about 20-fold, about 30-fold, about 40-fold, about 50-fold, about 100-fold, about 150-fold, or about 200-fold higher than surface labeling of reference cells.

In some embodiments, the antigen is a human protein comprising a CTLD that is not human CD161. In some embodiments, the antigen is a human protein selected from Table 1. In some embodiments, the anti-CD161 antibodies described herein bind to cells that express the antigen (e.g., human protein comprising a CTLD, e.g., human protein selected from Table 1) with substantially equivalent surface labeling compared to reference cells. In some embodiments, the anti-CD161 antibodies described herein bind to cells that express the antigen (e.g., human protein comprising a CTLD, e.g., human protein selected from Table 1) with surface labeling that is no more than about 1%, about 2%, about 3%, about 4%, about 5%, about 10%, about 15%, about 20%, about 25%, about 30%, about 35%, about 40%, about 45%, or about 50% higher than binding to the reference cell as measured by a method of fluorescence detection (e.g., flow cytometry).

Methods to Determine Immune Cell Effect

Cytokine Production

In some embodiments, an anti-CD161 antibody described herein induces or enhances cytokine production by an immune cell as determined by a cytokine assay. In some embodiments, the cytokine assay determines an amount of at least one cytokine secreted from an immune cell contacted with the anti-CD161 antibody, wherein an increase in the amount of the at least one cytokine indicates induction or enhancement of cytokine production by the anti-CD161 antibody. In some embodiments, an increase in cytokine production is at least 1.5 fold, 2 fold, 3 fold, 4 fold, 5 fold, 6 fold, 7 fold, 8 fold, 9 fold, or 10 fold higher compared to a control antibody (e.g., an equivalent antibody isotype that does not bind to CD161, e.g., and antibody that does not induce cytokine production).

In some embodiments, an anti-CD161 antibody described herein induces or enhances cytokine production by an immune cell as determined by a cytokine assay, wherein the cytokine assay comprises the following steps:
(i) contacting the immune cell with the anti-CD161 antibody;
(ii) contacting the immune cell with a target cell expressing CLEC2D; and
(iii) determining an amount of at least one cytokine produced by the immune cell,
wherein an increase in the amount of the at least one cytokine indicates the anti-CD161 antibody induces or enhances cytokine production by the immune cell. In some embodiments, the immune cell is a T cell. In some embodiments, the immune cell is a cytotoxic T cell. In some embodiments, the T cell is a tumor-reactive T cell.

In some embodiments, an anti-CD161 antibody described herein induces or enhances cytokine production by an immune cell as determined by a cytokine assay, wherein the cytokine assay comprises the following steps:
(i) contacting the immune cell with an anti-CD161 antibody;
(ii) contacting the immune cell with a target cell expressing CLEC2D;
(iii) determining an amount of at least one cytokine produced by the immune cell; and
(iv) comparing the amount of the at least one cytokine produced by the immune cell to an amount secreted from a reference immune cell,
wherein the reference immune cell is contacted with a control antibody, and wherein an increase in the amount of the at least one cytokine produced from the immune cell relative to the reference immune cell indicates induced or enhanced cytokine production resulting from blocking of the CD161-CLEC2D interaction. In some embodiments, the immune cell is a T cell. In some embodiments, the reference immune cell is a T cell. In some embodiments the T cell is a CD8+ T cell. In some embodiments the T cell is a CD4+ T cell.

In some embodiments, the at least one cytokine is selected from: IL-2, IFNγ, and TNFα. In some embodiments, the cytokine is IL-2. In some embodiments, the cytokine is IFNγ. In some embodiments, the cytokine is TNFα. In some embodiments, an anti-CD161 antibody induces or enhances IL-2 production. In some embodiments, an anti-CD161 antibody induces or enhances IFNγ production. In some embodiments, an anti-CD161 antibody induces or enhances TNFα production. In some embodiments, the cytokine produced is IL-2. In some embodiments, the cytokine produced is IFNγ. In some embodiments, the cytokine produced is TNFα. In some embodiments, the cytokines produced are IL-2 and TNFα. In some embodiments, the cytokines produced are IFNγ and TNFα. In some embodiments, the cytokines produced are IL-2 and IFNγ. In some embodiments, the cytokines produced are IL-2, IFNγ and TNFα.

Methods of measuring cytokine production are known in the art and include ELISA, ELISPOT, cytokine bead assay, and intracellular cytokine staining. In some embodiments, the cytokine assay is an intracellular cytokine staining assay. An intracellular cytokine staining assay comprises cell permeabilization and staining of intracellular cytokines with labeled reagents (e.g., cytokine-specific antibodies), followed by labeling detection using microscopy or flow cytometry.

In some embodiments, the cytokine assay is a cytokine bead array assay. A cytokine bead array assay is a bead-based immunoassay that allows for multianalyte flow cytometric determination of multiple cytokines in a sample. The use of microspheres of different size or color is the basis of a cytokine bead array assay, wherein each microsphere (or "bead") is coated with an antibody that specifically binds to an antigen (e.g., a cytokine). Antibody-coated beads are then introduced to a sample in combination with detector antibodies. The bead:antigen:detector antibody complexes are then analyzed by flow cytometry. Commercially available cytokine bead array assays include, but are not limited to, BD™ Cytometric Bead Array Systems (BD Biosciences) and Luminex® Assays (R&D Systems). In some embodiments, induction or enhancement of cytokine by blockade of CD161-CLEC2D interaction is determined by a cytokine bead array assay. In some embodiments, induction or enhancement of cytokine by blockade of CD161-CLEC2D interaction is determined by a Luminex® Assay.

In some embodiments, an anti-CD161 antibody described herein induces or enhances T cell activation as determined by a T cell activation assay. In some embodiments, the T cell activation assay determines an amount of at least one cytokine secreted from T cells contacted with an anti-CD161 antibody described herein, wherein an increase in the amount of the at least one cytokine indicates induction or enhancement of T cell activation. In some embodiments, an increase in cytokine production is at least 1.5 fold, at least 2 fold, at least 3 fold, at least 4 fold, at least 5 fold, at least 6 fold, at least 7 fold, at least 8 fold, at least 9 fold, or at least 10 fold more compared to a control antibody (e.g., an equivalent antibody isotype that does not bind to CD161, e.g., and antibody that does not induce cytokine production).

In some embodiments, an anti-CD161 antibody described herein induces or enhances activation of T cells as determined by a T cell activation assay, wherein the T cell activation assay comprises the following steps:
(i) isolating T cells from a subject;
(ii) contacting the T cell with the anti-CD161 antibody;
(iii) contacting the T cell with a target cell expressing CLEC2D; and
(iv) determining an amount of at least one cytokine produced by the T cell after (ii),
wherein an increase in the amount of the at least one cytokine indicates the anti-CD161 antibody induces or enhances T cell activation.

In some embodiments, an anti-CD161 antibody described herein induces or enhances activation of T cells as determined by a T cell activation assay, wherein the T cell activation assay comprises the following steps:
(i) isolating T cells from a subject;
(ii) contacting the T cell with the anti-CD161 antibody;
(iii) contacting the T cell with a target cell expressing CLEC2D; and
(iv) determining an amount of at least one cytokine produced by the T cell after (ii),
(v) comparing the amount of the at least one cytokines produced by the T cells to an amount or level secreted from reference T cells,
wherein the reference T cells are not contacted with the anti-CD161 antibody or are contacted with a control antibody (e.g., a non-CD161 binding antibody of equivalent isotype), and wherein an increase in the amount of the at least one cytokine T cells relative to the reference T cells indicates the anti-CD161 antibody induces or enhances T cell activation.

In some embodiments, the T cell activation assay comprises determining the level of at least one cytokine secreted by the T cells after contact with an anti-CD161 antibody disclosed herein, wherein the at least one cytokine is selected from: IL-2, IFNγ, and TNFα. In some embodiments, the cytokine is IL-2. In some embodiments, the cytokine is IFNγ. In some embodiments, the cytokine is TNFα. In some embodiments, the T cell activation assay comprises a cytokine assay, such as those described herein, to determine the amount of the at least one cytokine. In some embodiments, the cytokine produced is IL-2. In some embodiments, the cytokine produced is IFNγ. In some embodiments, the cytokine produced is TNFα. In some embodiments, the cytokines produced are IL-2 and TNFα. In some embodiments, the cytokines produced are IFNγ and TNFα. In some embodiments, the cytokines produced are IL-2 and IFNγ. In some embodiments, the cytokines produced are IL-2, IFNγ and TNFα.

In some embodiments, an anti-CD161 antibody described herein induces or enhances T cell activation as determined by a T cell activation assay, wherein the T cell activation assay comprises detecting surface expression of at least one activation marker on T cells, and wherein an increase in the expression level of the at least one activation marker indicates induction or enhancement of T cell activation. In some embodiments, "increase in surface expression" refers to at least a 5%, 10%, 15%, 20%, 25%, 30%, 35%, 40%, 45%, 50%, 55%, 60%, 65%, 70%, 75%, 80%, 85%, 90%, 95% or 100% increase in surface expression relative to surface expression in the presence of a control antibody or in the absence of an antibody.

T Cell Activation

In some embodiments, an anti-CD161 antibody described herein induces or enhances activation of T cells as determined by a T cell activation assay, wherein the T cell activation assay comprises the following steps:
(i) isolating T cells from a subject;
(ii) contacting the T cells with the anti-CD161 antibody;
(iii) contacting the T cells with a target cell expressing CLEC2D; and
(iv) determining surface expression of at least one activation marker on the T cells after (ii),
wherein an increase in the amount of expression of at least one activation marker indicates the anti-CD161 antibody induces or enhances T cell activation.

In some embodiments, an anti-CD161 antibody described herein induces or enhances activation of T cells as determined by a T cell activation assay, wherein the T cell activation assay comprises the following steps:
(i) isolating T cells from a subject;
(ii) contacting the T cells with the anti-CD161 antibody;
(iii) contacting the T cells with a target cell expressing; and
(iv) determining surface expression of at least one activation marker on the T cells after (ii),
(v) comparing the surface expression of the at least one activation marker on the T cells to surface expression of the at least one activation marker on reference T cells,
wherein the reference T cells are not contacted with the anti-CD161 antibody or are contacted with a control antibody (e.g., a non-CD161 binding antibody of equivalent isotype), and wherein an increase in expression of at least one activation marker by the T cells relative to the reference T cells indicates the anti-CD161 antibody induces or enhances T cell activation.

In some embodiments, an anti-CD161 antibody described herein induces or enhances T cell activation as determined by a T cell activation assay in vivo, wherein the T cell activation assay comprises the following steps:
(i) administering the anti-CD161 antibody to a subject;
(ii) isolating T cells from the subject; and
(iii) detecting surface expression of at least one activation marker on the T cells,
wherein an increase in surface expression of at least one activation marker indicates the anti-CD161 antibody induces or enhances T cell activation. In some embodiments, an increase in surface expression of at least one activation marker indicates the anti-CD161 antibody induces or enhances T cell activation by blocking the CD161-CLEC2D interaction.

In some embodiments, an anti-CD161 antibody described herein induces or enhances T cell activation as determined by a T cell activation assay, wherein the T cell activation assay comprises the following steps:
(i) administering the anti-CD161 antibody to a subject;
(ii) isolating T cells from the subject;
(iii) determining surface expression of at least one activation marker on the T cells after; and
(iv) comparing surface expression of the at least one activation marker on the T cells to surface expression of the at least one activation marker on reference T cells,
wherein the reference T cells are isolated from a subject not administered the anti-CD161 antibody or a subject administered a control antibody (e.g., a non-CD161 binding antibody of equivalent isotype), and wherein an increase in surface expression of the at least one activation marker on the T cells relative to the reference T cells indicates the anti-CD161 antibody induces or enhances T cell activation. In some embodiments, an increase in surface expression of the at least one activation marker on the T cells relative to the reference T cells indicates the anti-CD161 antibody induces or enhances T cell activation by blocking the CD161-CLEC2D interaction.

In some embodiments "does not induce or enhance" is intended to refer to the absence of an activity (e.g., T cell activation) or a lack of increase of an activity relative to an increase by a reference antibody.

In some embodiments, a surface expression of a T cell activation marker is equivalent to the surface expression in the absence of an antibody. In some embodiments a surface expression of a T cell activation marker is less than the surface expression in the presence of a reference antibody that induces or enhance surface expression at least 1 fold, 5 fold, 10 fold, 50 fold, or 100 fold higher compared to surface expression in the absence of an antibody.

In some embodiments, the T cell activation assay comprises determining the level of at least one activation marker by T cells after contact with an anti-CD161 antibody disclosed herein, wherein the activation marker is selected from: CD69, HLA-DR, CD40L, and CD25. In some embodiments, the activation marker is CD69. In some embodiments, the activation marker is HLA-DR. In some embodiments, the activation marker is CD25. In some embodiments, the activation marker is CD40L. In some embodiment, an increase or elevation in expression of at least one activation marker following contacting with an anti-CD161 antibody disclosed herein is indicative of increased or enhanced T cell activation resulting from blocking of the CD161-CLEC2D interaction. In some embodiments, the at least one elevated activation marker comprises CD69. In some embodiments, the at least one elevated activation marker comprises HLA-DR. In some embodiments, the at least one elevated activation marker comprises CD25. In some embodiments, the at least one elevated activation marker comprises CD40L. Methods of measuring activation markers are known in the art, and include multi-parameter flow cytometry and immunofluorescence microscopy.

T Cell Exhaustion

In some embodiments, an anti-CD161 antibody described herein protects T cells from T cell exhaustion and/or reverses T cell exhaustion as determined by a T cell exhaustion assay. Exhausted T cells can be distinguished from other T cell dysfunctions such as anergy and senescence based on their underlying molecular mechanisms (Crespo et al., (2013) Curr Opin Immunol 25(2):241-221). Whereas anergy occurs during priming due to the absence of costimulatory signals and senescence is growth arrest after extensive proliferation, exhausted T cells arise from T cells which initially gained and provided T cell effector function, but that exhibit a gradual deterioration of T cell effector function due to continuous T cell receptor (TCR) stimulation from persistent antigen and inflammatory mediators, both of which commonly occur in tumors (Wherry & Kurachi (2015) Nat Rev Immunol 15(8):486-99). Hallmarks of T cell exhaustion include, but are not limited to, continuous deterioration of in vivo and/or ex vivo T cell function, an increased expression of multiple inhibitory receptors (IRs) (e.g., PD-1, CTLA-4, LAG-3, TIM-3, CD244, CD160, TIGIT), progressive loss or decrease of effector cytokine secretion (e.g., IL-2, interferon gamma (IFNγ), tumor necrosis factor alpha (TNFα)), loss or decrease of CC chemokine (β-chemokine) production, poor responsiveness to IL-7 and IL-15, loss or decrease of proliferative capacity, loss or decrease of in vivo and/or ex vivo cytolytic activity, altered cell metabolism and a different transcriptional profile relative to non-exhausted T cells. Severely exhausted T cells can succumb to deletion (Yi et al., (2010) Immunology 129(4):474-481).

In some embodiments, an anti-CD161 antibody described herein reduces or prevents T cell exhaustion and/or reverses T cell exhaustion as determined by a T cell exhaustion assay, wherein the T cell activation assay comprises detecting surface expression of at least one exhaustion marker on T cells, and wherein a decrease in the expression level of the at least one exhaustion marker indicates reduction or prevention of T cell exhaustion. In some embodiments, "decrease in surface expression" refers to at least a 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 155%, 160%, 165%, 170%, 175%, 180%, 185%, 190%, 195%, or 200% decrease in surface expression relative to surface expression in the presence of a control antibody or in the absence of an antibody. In some embodiments, "decrease in surface expression" refers to at least a 2-fold, a 3-fold, a 4-fold, a 5-fold, a 6-fold, a 7-fold, an 8-fold, a 9-fold, or a 10-fold decrease in surface expression relative to surface expression in the presence of a control antibody or in the absence of an antibody.

In some embodiments, an anti-CD161 antibody described herein protects T cells from T cell exhaustion and/or reverses T cell exhaustion as determined by a T cell exhaustion assay wherein the T cell exhaustion assay determines an amount or level of one or more effector cytokines secreted from T cells treated with an anti-CD161 antibody described herein, wherein the amount or level of the one or more effector cytokines indicates protection from or reversion of T cell exhaustion. In some embodiments, the T cell exhaustion assay comprises the following steps:
 (i) isolating T cells from a subject;
 (ii) contacting the T cells with the anti-CD161 antibody;
 (iii) contacting the T cells with a target cell expressing CLEC2D; and
 (iv) determining an amount of one or more effector cytokines secreted from the T cells; and;
 (v) comparing the amount or level of the one or more effector cytokines secreted from the T cells to an amount or level secreted from reference T cells,
wherein the reference T cells are not contacted with the target cell antigen that induces T cell exhaustion or are contacted with a control antibody (e.g., a non-CD161 binding antibody of equivalent isotype), and wherein the difference in the amount or level of the one or more effector cytokines secreted from the T cells and reference T cells indicates protection from or reversion of T cell exhaustion.

In some embodiments, the one or more effector cytokines is selected from IL-2, IFNγ, and TNFα. In some embodiments, the amount or level of the one or more effector cytokines is determined by ELISA. ELISAs suitable for the determination of the amount or level of the one or more effector cytokines are known in the art. In some embodiments, the amount or level of the one or more effector cytokines is determined by Meso Scale Discovery. In some embodiments, the amount or level of the one or more effector cytokines is determined by any one of the cytokine production assays described herein.

The gradual dysfunction of exhausted T cells is accompanied by the expression of IRs, which transmit inhibitory signals to the nucleus upon interaction with ligands on target cells. Accordingly, in some embodiments, an anti-CD161 antibody described herein protects T cells from T cell exhaustion and/or reverses T cell exhaustion as determined by a T cell exhaustion assay wherein the T cell exhaustion assay determines an expression level of one or more inhibitory receptors on T cells treated with an anti-CD161 antibody described herein, wherein the expression level of the one or more inhibitory receptors indicates protection from or reversion of T cell exhaustion. In some embodiments, the T cell exhaustion assay comprises the following steps:
 (i) isolating T cells from a subject;
 (ii) contacting the T cells with the anti-CD161 antibody;
 (iii) contacting the T cells with a target cell expressing CLEC2D; and
 (iv) determining an expression level of one or more inhibitory receptors on T cells after (ii),
 (v) comparing the expression level of one or more inhibitory receptors on T cells to an amount or level secreted from reference T cells, wherein the reference T cells are not contacted with the antigen that induces T cell exhaustion or are contacted with a control antibody (e.g., a non-CD161 binding antibody of equivalent isotype), and wherein the difference in the expression level of one or more inhibitory receptors on T cells and reference T cells indicates protection from or reversion of T cell exhaustion.

In some embodiments, an anti-CD161 antibody described herein protects T cells from T cell exhaustion and/or reverses T cell exhaustion as determined by a T cell exhaustion assay in vivo, wherein the T cell exhaustion assay comprises the following steps:

(i) administering the anti-CD161 antibody to a subject;
(ii) isolating T cells from the subject; and
(iii) determining an expression level of one or more inhibitory receptors on T cells after (ii),
(iv) comparing the expression level of one or more inhibitory receptors on T cells to an amount or level secreted from reference T cells, wherein the reference T cells are not contacted with the antigen that induces T cell exhaustion or are contacted with a control antibody (e.g., a non-CD161 binding antibody of equivalent isotype), and wherein the difference in the expression level of one or more inhibitory receptors on T cells and reference T cells indicates protection from or reversion of T cell exhaustion. In some embodiments, a decrease in surface expression of at least one exhaustion marker indicates the anti-CD161 antibody protected T cells from T cell exhaustion and/or reverses T cell exhaustion by blocking the CD161-CLEC2D interaction.

In some embodiments, the T cell exhaustion assay comprises determining the level of at least one exhaustion marker by T cells after contact with an anti-CD161 antibody disclosed herein, wherein the exhaustion marker is selected from: CTLA-4, TIM-3, CD39, PD-1, LAG-3 or TIGIT. In some embodiments, the exhaustion marker is PD-1. In some embodiments, the exhaustion marker is TIGIT. In some embodiments, the exhaustion marker is LAG-3. In some embodiments, the exhaustion marker is TIM-3. In some embodiments, the expression level of the one or more inhibitory receptors is determined by flow cytometry. Methods to determine expression levels of inhibitory receptors on immune cells (e.g. T cells) by flow cytometry are known in the art.

In some embodiments, the amount of exhausted T cells is less than 20%, 15%, 10% or 5% of total CD8+ or CD4+ T cells in a tumor microenvironment.

Wherein the assays described herein refer to (i) isolating T cells from a subject; it is to be understood that the assay may suitably be performed on T cells previously isolated from a subject. In some embodiments, the subject is human In some embodiments, the subject is non-human. It is to be further understood that the target cell meets criteria sufficient for stimulation of T cell activation through induction of the T cell receptor (TCR), namely surface presentation of cognate antigenic peptide by a major histocompatibility antigen (e.g., MHC type I or MHC type II). In some embodiments, the T cells are edited prior to an assay described herein to express an antigen-specific TCR and/or to inhibit expression of endogenous TCR. In some embodiments, the target cells are edited prior to an assay described herein to express cognate antigen (i.e., antigen comprising a peptide epitope recognized by a particular TCR). In some embodiments, the T cells are edited to express an antigen-specific TCR and the target cells are edited to express an antigen recognized by the TCR. Methods of editing T cells isolated from a subject (e.g., inducing expression of an antigen-specific TCR and inhibiting expression of endogenous TCR) and/or target cells are further described in the Example section below.

Wherein the assays described herein refer to (i) administering the anti-CD161 antibody to a subject and (ii) isolating T cells from the subject; it is to be understood that the assay may suitably be performed on T cells previously isolated from a subject to whom the anti-CD161 antibody has been administered.

Where the assays described herein refer to 'obtaining a sample of the tumor'; it is to be understood that the assay may suitably be performed on a sample of a tumor previously isolated from a subject.

Where the assays described herein refer to (i) administering the anti-CD161 antibody to a subject having a tumor and (ii) obtaining a sample of the tumor; it is to be understood that the assay may suitably be performed a sample of a tumor previously isolated from a subject to whom the anti-CD161 antibody has been administered.

Methods for Producing CD161 Binding Antibodies and Antigen-Binding Portions Thereof The disclosure also features methods for producing any of the anti-CD161 antibodies or antigen-binding fragments thereof described herein. In some embodiments, methods for preparing an antibody described herein can include immunizing a subject (e.g., a non-human mammal) with an appropriate immunogen. Suitable immunogens for generating any of the antibodies described herein are set forth herein. For example, to generate an antibody that binds to CD161, a skilled artisan can immunize a suitable subject (e.g., a non-human mammal such as a rat, a mouse, a gerbil, a hamster, a dog, a cat, a pig, a goat, a horse, or a non-human primate) with a full-length CD161 polypeptide such as a full-length human CD161 polypeptide comprising the amino acid sequence depicted in SEQ ID NO: 335.

A suitable subject (e.g., a non-human mammal) can be immunized with the appropriate antigen along with subsequent booster immunizations a number of times sufficient to elicit the production of an antibody by the mammal. The immunogen can be administered to a subject (e.g., a non-human mammal) with an adjuvant. Adjuvants useful in producing an antibody in a subject include, but are not limited to, protein adjuvants; bacterial adjuvants, e.g., whole bacteria (BCG, *Corynebacterium parvum* or *Salmonella minnesota*) and bacterial components including cell wall skeleton, trehalose dimycolate, monophosphoryl lipid A, methanol extractable residue (MER) of tubercle *bacillus*, complete or incomplete Freund's adjuvant; viral adjuvants; chemical adjuvants, e.g., aluminum hydroxide, and iodoacetate and cholesteryl hemisuccinate. Other adjuvants that can be used in the methods for inducing an immune response include, e.g., cholera toxin and parapoxvirus proteins. See also Bieg et al. (1999) *Autoimmunity* 31(1):15-24. See also, e.g., Lodmell et al. (2000) *Vaccine* 18:1059-1066; Johnson et al. (1999) *J Med Chem* 42:4640-4649; Baldridge et al. (1999) *Methods* 19:103-107; and Gupta et al. (1995) *Vaccine* 13(14): 1263-1276.

In some embodiments, the methods include preparing a hybridoma cell line that secretes a monoclonal antibody that binds to the immunogen. For example, a suitable mammal such as a laboratory mouse is immunized with a CD161 polypeptide as described above. Antibody-producing cells (e.g., B cells of the spleen) of the immunized mammal can be isolated two to four days after at least one booster immunization of the immunogen and then grown briefly in culture before fusion with cells of a suitable myeloma cell line. The cells can be fused in the presence of a fusion promoter such as, e.g., vaccinia virus or polyethylene glycol. The hybrid cells obtained in the fusion are cloned, and cell clones secreting the desired antibodies are selected. For example, spleen cells of Balb/c mice immunized with a suitable immunogen can be fused with cells of the myeloma cell line PAI or the myeloma cell line Sp2/0-Ag 14. After the fusion, the cells are expanded in suitable culture medium, which is supplemented with a selection medium, for example HAT medium, at regular intervals in order to prevent normal myeloma cells from overgrowing the desired hybridoma cells. The obtained hybridoma cells are then screened for secretion of the desired antibodies, e.g., an antibody that binds to CD161, e.g., an antibody that binds to human CD161.

In some embodiments, a skilled artisan can identify an anti-CD161 antibody from a non-immune biased library as described in, e.g., U.S. Pat. No. 6,300,064 (to Knappik et al.; Morphosys AG) and Schoonbroodt et al. (2005) *Nucleic Acids Res* 33(9):e81.

In some embodiments, the methods described herein can involve, or be used in conjunction with, e.g., phage display technologies, bacterial display, yeast surface display, eukaryotic viral display, mammalian cell display, and cell-free (e.g., ribosomal display) antibody screening techniques (see, e.g., Etz et al. (2001) *J Bacteriol* 183:6924-6935; Cornelis (2000) *Curr Opin Biotechnol* 11:450-454; Klemm et al. (2000) *Microbiology* 146:3025-3032; Kieke et al. (1997) *Protein Eng* 10:1303-1310; Yeung et al. (2002) *Biotechnol Prog* 18:212-220; Boder et al. (2000) *Methods Enzymology* 328:430-444; Grabherr et al. (2001) *Comb Chem High Throughput Screen* 4:185-192; Michael et al. (1995) *Gene Ther* 2:660-668; Pereboev et al. (2001) *J Virol* 75:7107-7113; Schaffitzel et al. (1999) *J Immunol Methods* 231:119-135; and Hanes et al. (2000) *Nat Biotechnol* 18:1287-1292).

Methods for identifying antibodies using various phage display methods are known in the art. In phage display methods, functional antibody domains are displayed on the surface of phage particles which carry the polynucleotide sequences encoding them. Such phage can be utilized to display antigen-binding domains of antibodies, such as Fab, Fv, or disulfide-bond stabilized Fv antibody fragments, expressed from a repertoire or combinatorial antibody library (e.g., human or murine). Phage used in these methods are typically filamentous phage such as fd and M13. The antigen binding domains are expressed as a recombinantly-fused protein to any of the phage coat proteins pIII, pVIII, or pIX. See, e.g., Shi et al. (2010) *JMB* 397:385-396. Examples of phage display methods that can be used to make the immunoglobulins, or fragments thereof, described herein include those disclosed in Brinkman et al. (1995) *J Immunol Methods* 182:41-50; Ames et al. (1995) *J Immunol Methods* 184:177-186; Kettleborough et al. (1994) *Eur J Immunol* 24:952-958; Persic et al. (1997) *Gene* 187:9-18; Burton et al. (1994) *Advances in Immunology* 57:191-280; and PCT publication nos. WO 90/02809, WO 91/10737, WO 92/01047, WO 92/18619, WO 93/11236, WO 95/15982, and WO 95/20401. Suitable methods are also described in, e.g., U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

In some embodiments, the phage display antibody libraries can be generated using mRNA collected from B cells from the immunized mammals. For example, a splenic cell sample comprising B cells can be isolated from mice immunized with CD161 polypeptide as described above. mRNA can be isolated from the cells and converted to cDNA using standard molecular biology techniques. See, e.g., Sambrook et al. (1989) "Molecular Cloning: A Laboratory Manual, $2^{nd}$ Edition," Cold Spring Harbor Laboratory Press, Cold Spring Harbor, N.Y.; Harlow and Lane (1988), supra; Benny K. C. Lo (2004), supra; and Borrebaek (1995), supra. The cDNA coding for the variable regions of the heavy chain and light chain polypeptides of immunoglobulins are used to construct the phage display library. Methods for generating such a library are described in, e.g., Merz et al. (1995) *J Neurosci Methods* 62(1-2):213-9; Di Niro et al. (2005) *Biochem J* 388(Pt 3):889-894; and Engberg et al. (1995) *Methods Mol Biol* 51:355-376.

In some embodiments, a combination of selection and screening can be employed to identify an antibody of interest from, e.g., a population of hybridoma-derived antibodies or a phage display antibody library. Suitable methods are known in the art and are described in, e.g., Hoogenboom (1997) *Trends in Biotechnology* 15:62-70; Brinkman et al. (1995), supra; Ames et al. (1995), supra; Kettleborough et al. (1994), supra; Persic et al. (1997), supra; and Burton et al. (1994), supra. For example, a plurality of phagemid vectors, each encoding a fusion protein of a bacteriophage coat protein (e.g., pIII, pVIII, or pIX of M13 phage) and a different antigen-combining region are produced using standard molecular biology techniques and then introduced into a population of bacteria (e.g., *E. coli*). Expression of the bacteriophage in bacteria can, in some embodiments, require use of a helper phage. In some embodiments, no helper phage is required (see, e.g., Chasteen et al., (2006) *Nucleic Acids Res* 34(21):e145). Phage produced from the bacteria are recovered and then contacted to, e.g., a target antigen bound to a solid support (immobilized). Phage may also be contacted to antigen in solution, and the complex is subsequently bound to a solid support.

A subpopulation of antibodies screened using the above methods can be characterized for their specificity and binding affinity for a particular antigen (e.g., human CD161) using any immunological or biochemical based method known in the art. For example, specific binding of an antibody to CD161, may be determined for example using immunological or biochemical based methods such as, but not limited to, an ELISA assay, SPR assays, immunoprecipitation assay, affinity chromatography, and equilibrium dialysis as described above Immunoassays which can be used to analyze immunospecific binding and cross-reactivity of the antibodies include, but are not limited to, competitive and non-competitive assay systems using techniques such as Western blots, RIA, ELISA (enzyme linked immunosorbent assay), "sandwich" immunoassays, immunoprecipitation assays, immunodiffusion assays, agglutination assays, complement-fixation assays, immunoradiometric assays, fluorescent immunoassays, and protein A immunoassays. Such assays are routine and well known in the art.

It is understood that the above methods can also be used to determine if, e.g., an anti-CD161 antibody does not bind to full-length human CD161 and/or non-human CD161 proteins.

In embodiments where the selected CDR amino acid sequences are short sequences (e.g., fewer than 10-15 amino acids in length), nucleic acids encoding the CDRs can be chemically synthesized as described in, e.g., Shiraishi et al. (2007) *Nucleic Acids Symposium Series* 51(1):129-130 and U.S. Pat. No. 6,995,259. For a given nucleic acid sequence encoding an acceptor antibody, the region of the nucleic acid sequence encoding the CDRs can be replaced with the chemically synthesized nucleic acids using standard molecular biology techniques. The 5' and 3' ends of the chemically synthesized nucleic acids can be synthesized to comprise sticky end restriction enzyme sites for use in cloning the nucleic acids into the nucleic acid encoding the variable region of the donor antibody. Alternatively, fragments of chemically synthesized nucleic acids, together capable of encoding an antibody, can be joined together using DNA assembly techniques known in the art (e.g. Gibson Assembly).

In some embodiments, the anti-CD161 antibodies described herein comprise an altered heavy chain constant region that has reduced (or no) effector function relative to its corresponding unaltered constant region. Effector functions involving the constant region of the anti-CD161 antibody may be modulated by altering properties of the constant or Fc region. Altered effector functions include, for example, a modulation in one or more of the following activities: antibody-dependent cellular cytotoxicity (ADCC), complement-dependent cytotoxicity (CDC), apoptosis, binding to one or more Fc-receptors, and pro-inflammatory responses. Modulation refers to an increase, decrease, or elimination of an effector function activity exhibited by a subject antibody containing an altered constant region as compared to the activity of the unaltered form of the constant region. In particular embodiments, modulation includes situations in which an activity is abolished or completely absent.

An altered constant region with altered FcR binding affinity and/or ADCC activity and/or altered CDC activity is a polypeptide which has either an enhanced or diminished FcR binding activity and/or ADCC activity and/or CDC activity compared to the unaltered form of the constant region. An altered constant region which displays increased binding to an FcR binds at least one FcR with greater affinity than the unaltered polypeptide. An altered constant region which displays decreased binding to an FcR binds at least one FcR with lower affinity than the unaltered form of the constant region. Such variants which display decreased binding to an FcR may possess little or no appreciable binding to an FcR, e.g., 0 to 50% (e.g., less than 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1%) of the binding to the FcR as compared to the level of binding of a native sequence immunoglobulin constant or Fc region to the FcR. Similarly, an altered constant region that displays modulated ADCC and/or CDC activity may exhibit either increased or reduced ADCC and/or CDC activity compared to the unaltered constant region. For example, in some embodiments, the anti-CD161 antibody comprising an altered constant region can exhibit approximately 0 to 50% (e.g., less than 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1%) of the ADCC and/or CDC activity of the unaltered form of the constant region. An anti-CD161 antibody described herein comprising an altered constant region displaying reduced ADCC and/or CDC may exhibit reduced or no ADCC and/or CDC activity.

In some embodiments, an anti-CD161 antibody described herein exhibits reduced or no effector function. In some embodiments, an anti-CD161 antibody comprises a hybrid constant region, or a portion thereof, such as a G2/G4 hybrid constant region (see e.g., Burton et al. (1992) Adv Immun 51:1-18; Canfield et al. (1991) J Exp Med 173:1483-1491; and Mueller et al. (1997) Mol Immunol 34(6):441-452). See above.

In some embodiments, an anti-CD161 antibody may contain an altered constant region exhibiting enhanced or reduced complement dependent cytotoxicity (CDC). Modulated CDC activity may be achieved by introducing one or more amino acid substitutions, insertions, or deletions in an Fc region of the antibody. See, e.g., U.S. Pat. No. 6,194,551. Alternatively or additionally, cysteine residue(s) may be introduced in the Fc region, thereby allowing interchain disulfide bond formation in this region. The homodimeric antibody thus generated may have improved or reduced internalization capability and/or increased or decreased complement-mediated cell killing See, e.g., Caron et al. (1992) J Exp Med 176:1191-1195 and Shopes (1992) Immunol 148:2918-2922; PCT publication nos. WO 99/51642 and WO 94/29351; Duncan and Winter (1988) Nature 322:738-40; and U.S. Pat. Nos. 5,648,260 and 5,624,821.

Recombinant Antibody Expression and Purification

The anti-CD161 antibodies or antigen-binding fragments thereof described herein can be produced using a variety of techniques known in the art of molecular biology and protein chemistry. For example, a nucleic acid encoding one or both of the heavy and light chain polypeptides of an antibody can be inserted into an expression vector that contains transcriptional and translational regulatory sequences, which include, e.g., promoter sequences, ribosomal binding sites, transcriptional start and stop sequences, translational start and stop sequences, transcription terminator signals, polyadenylation signals, and enhancer or activator sequences. The regulatory sequences include a promoter and transcriptional start and stop sequences. In addition, the expression vector can include more than one replication system such that it can be maintained in two different organisms, for example in mammalian or insect cells for expression and in a prokaryotic host for cloning and amplification.

Several possible vector systems are available for the expression of cloned heavy chain and light chain polypeptides from nucleic acids in mammalian cells. One class of vectors relies upon the integration of the desired gene sequences into the host cell genome. Cells which have stably integrated DNA can be selected by simultaneously introducing drug resistance genes such as E. coli gpt (Mulligan and Berg (1981) Proc Natl Acad Sci USA 78:2072) or Tn5 neo (Southern and Berg (1982) Mol Appl Genet 1:327). The selectable marker gene can be either linked to the DNA gene sequences to be expressed, or introduced into the same cell by co-transfection (Wigler et al. (1979) Cell 16:77). A second class of vectors utilizes DNA elements which confer autonomously replicating capabilities to an extrachromosomal plasmid. These vectors can be derived from animal viruses, such as bovine papillomavirus (Sarver et al. (1982) Proc Natl Acad Sci USA, 79:7147), cytomegalovirus, polyoma virus (Deans et al. (1984) Proc Natl Acad Sci USA 81:1292), or SV40 virus (Lusky and Botchan (1981) Nature 293:79).

The expression vectors can be introduced into cells in a manner suitable for subsequent expression of the nucleic acid. The method of introduction is largely dictated by the targeted cell type, discussed below. Exemplary methods include CaPO$_4$ precipitation, liposome fusion, cationic liposomes, electroporation, viral infection, dextran-mediated transfection, polybrene-mediated transfection, protoplast fusion, and direct microinjection.

Appropriate host cells for the expression of anti-CD161 antibodies or antigen-binding fragments thereof described herein include yeast, bacteria, insect, plant, and mammalian cells. Of particular interest are bacteria such as E. coli, fungi such as Saccharomyces cerevisiae and Pichia pastoris, insect cells such as SF9, mammalian cell lines (e.g., human cell lines), as well as primary cell lines.

In some embodiments, an anti-CD161 antibody or antigen-binding fragment thereof described herein can be expressed in, and purified from, transgenic animals (e.g., transgenic mammals) For example, an antibody can be produced in transgenic non-human mammals (e.g., rodents) and isolated from milk as described in, e.g., Houdebine (2002) *Curr Opin Biotechnol* 13(6):625-629; van Kuik-Romeijn et al. (2000) *Transgenic Res* 9(2):155-159; and Pollock et al. (1999) *J Immunol Methods* 231(1-2):147-157.

The anti-CD161 antibodies and antigen-binding fragments thereof described herein can be produced from the cells by culturing a host cell transformed with the expression vector containing nucleic acid encoding the antibodies or fragments, under conditions, and for an amount of time, sufficient to allow expression of the proteins. Such conditions for protein expression will vary with the choice of the expression vector and the host cell, and will be easily ascertained by one skilled in the art through routine experimentation. For example, antibodies expressed in *E. coli* can be refolded from inclusion bodies (see, e.g., Hou et al. (1998) *Cytokine* 10:319-30). Bacterial expression systems and methods for their use are well known in the art (see Current Protocols in Molecular Biology, Wiley & Sons, and Molecular Cloning—A Laboratory Manual—3rd Ed., Cold Spring Harbor Laboratory Press, New York (2001)). The choice of codons, suitable expression vectors and suitable host cells will vary depending on a number of factors, and may be easily optimized as needed. An antibody (or fragment thereof) described herein can be expressed in mammalian cells or in other expression systems including but not limited to yeast, baculovirus, and in vitro expression systems (see, e.g., Kaszubska et al. (2000) *Protein Expression and Purification* 18:213-220).

Following expression, the anti-CD161 antibodies and antigen-binding fragments thereof described herein can be isolated. An antibody or fragment thereof can be isolated or purified in a variety of ways known to those skilled in the art depending on what other components are present in the sample. Standard purification methods include electrophoretic, molecular, immunological, and chromatographic techniques, including ion exchange, hydrophobic, affinity, and reverse-phase HPLC chromatography. For example, an antibody can be purified using a standard anti-antibody column (e.g., a protein-A or protein-G column). Ultrafiltration and diafiltration techniques, in conjunction with protein concentration, are also useful. See, e.g., Scopes (1994) "Protein Purification, $3^{rd}$ edition," Springer-Verlag, New York City, N.Y. The degree of purification necessary will vary depending on the desired use. In some instances, no purification of the expressed antibody or fragments thereof will be necessary.

Methods for determining the yield or purity of a purified anti-CD161 antibody or antigen-binding fragment thereof described herein are known in the art and include, e.g., Bradford assay, UV spectroscopy, Biuret protein assay, Lowry protein assay, amido black protein assay, high pressure liquid chromatography (HPLC), mass spectrometry (MS), and gel electrophoretic methods (e.g., using a protein stain such as Coomassie Blue or colloidal silver stain).

Modification of the Antibodies or Antigen-Binding Portions Thereof

The anti-CD161 antibodies or antigen-binding fragments thereof described herein can be modified following their expression and purification. The modifications can be covalent or non-covalent modifications. Such modifications can be introduced into the antibodies or fragments by, e.g., reacting targeted amino acid residues of the polypeptide with an organic derivatizing agent that is capable of reacting with selected side chains or terminal residues. Suitable sites for modification can be chosen using any of a variety of criteria including, e.g., structural analysis or amino acid sequence analysis of the antibodies or fragments.

In some embodiments, the anti-CD161 antibodies or antigen-binding fragments thereof described herein can be conjugated to a heterologous moiety. The heterologous moiety can be, e.g., a heterologous polypeptide, a therapeutic agent (e.g., a toxin or a drug), or a detectable label such as, but not limited to, a radioactive label, an enzymatic label, a fluorescent label, a heavy metal label, a luminescent label, or an affinity tag such as biotin or streptavidin. Suitable heterologous polypeptides include, e.g., an antigenic tag (e.g., FLAG (DYKDDDDK; SEQ ID NO: 332), polyhistidine (6-His; HHHHHH; SEQ ID NO: 333), hemagglutinin (HA; YPYDVPDYA; SEQ ID NO: 334), glutathione-S-transferase (GST), or maltose-binding protein (MBP)) for use in purifying the antibodies or fragments. Heterologous polypeptides also include polypeptides (e.g., enzymes) that are useful as diagnostic or detectable markers, for example, luciferase, a fluorescent protein (e.g., green fluorescent protein (GFP)), or chloramphenicol acetyl transferase (CAT). Suitable radioactive labels include, e.g., $^{32}$P, $^{33}$P, $^{14}$C, $^{125}$I, $^{131}$I, $^{35}$S, and $^{3}$H. Suitable fluorescent labels include, without limitation, fluorescein, fluorescein isothiocyanate (FITC), green fluorescent protein (GFP), DyLight™ 488, phycoerythrin (PE), propidium iodide (PI), PerCP, PE-Alexa Fluor® 700, Cy5, allophycocyanin, and Cy7. Luminescent labels include, e.g., any of a variety of luminescent lanthanide (e.g., europium or terbium) chelates. For example, suitable europium chelates include the europium chelate of diethylene triamine pentaacetic acid (DTPA) or tetraazacyclododecane-1,4,7,10-tetraacetic acid (DOTA). Enzymatic labels include, e.g., alkaline phosphatase, CAT, luciferase, and horseradish peroxidase.

Two proteins (e.g., an antibody and a heterologous moiety) can be cross-linked using any of a number of known chemical cross linkers. Examples of such cross linkers are those which link two amino acid residues via a linkage that includes a "hindered" disulfide bond. In these linkages, a disulfide bond within the cross-linking unit is protected (by hindering groups on either side of the disulfide bond) from reduction by the action, for example, of reduced glutathione or the enzyme disulfide reductase. One suitable reagent, 4-succinimidyloxycarbonyl-α-methyl-α(2-pyridyldithio) toluene (SMPT), forms such a linkage between two proteins utilizing a terminal lysine on one of the proteins and a terminal cysteine on the other. Heterobifunctional reagents that cross-link by a different coupling moiety on each protein can also be used. Other useful cross-linkers include, without limitation, reagents which link two amino groups (e.g., N-5-azido-2-nitrobenzoyloxysuccinimide), two sulfhydryl groups (e.g., 1,4-bis-maleimidobutane), an amino group and a sulfhydryl group (e.g., m-maleimidobenzoyl-N-hydroxysuccinimide ester), an amino group and a carboxyl group (e.g., 4-[p-azidosalicylamido]butylamine), and an amino group and a guanidinium group that is present in the side chain of arginine (e.g., p-azidophenyl glyoxal monohydrate).

In some embodiments, a radioactive label can be directly conjugated to the amino acid backbone of the antibody. Alternatively, the radioactive label can be included as part of a larger molecule (e.g., $^{125}$I in meta-[$^{125}$I]iodophenyl-N-hydroxysuccinimide ([$^{125}$I]mIPNHS) which binds to free amino groups to form meta-iodophenyl (mIP) derivatives of relevant proteins (see, e.g., Rogers et al. (1997) *J Nucl Med* 38:1221-1229) or chelate (e.g., to DOTA or DTPA) which is in turn bound to the protein backbone. Methods of conjugating the radioactive labels or larger molecules/chelates containing them to the antibodies or antigen-binding fragments described herein are known in the art. Such methods involve incubating the proteins with the radioactive label under conditions (e.g., pH, salt concentration, and/or temperature) that facilitate binding of the radioactive label or chelate to the protein (see, e.g., U.S. Pat. No. 6,001,329).

Methods for conjugating a fluorescent label (sometimes referred to as a "fluorophore") to a protein (e.g., an antibody) are known in the art of protein chemistry. For example, fluorophores can be conjugated to free amino groups (e.g., of lysines) or sulfhydryl groups (e.g., cysteines) of proteins using succinimidyl (NHS) ester or tetrafluorophenyl (TFP) ester moieties attached to the fluorophores. In some embodiments, the fluorophores can be conjugated to a heterobifunctional cross-linker moiety such as sulfo-SMCC. Suitable conjugation methods involve incubating an antibody protein, or fragment thereof, with the fluorophore under conditions that facilitate binding of the fluorophore to the protein. See, e.g., Welch and Redvanly (2003) "Handbook of Radiopharmaceuticals: Radiochemistry and Applications," John Wiley and Sons (ISBN 0471495603).

In some embodiments, the anti-CD161 antibodies or antigen binding fragments described herein can be modified, e.g., with a moiety that improves the stabilization and/or retention of the antibodies in circulation, e.g., in blood, serum, or other tissues. For example, the antibody or fragment can be PEGylated as described in, e.g., Lee et al. (1999) *Bioconjug Chem* 10(6): 973-8; Kinstler et al. (2002) *Advanced Drug Deliveries Reviews* 54:477-485; and Roberts et al. (2002) *Advanced Drug Delivery Reviews* 54:459-476 or HESylated (Fresenius Kabi, Germany; see, e.g., Pavisić et al. (2010) *Int J Pharm* 387(1-2):110-119). The stabilization moiety can improve the stability, or retention of, the antibody (or fragment) by at least 1.5 (e.g., at least 2, 5, 10, 15, 20, 25, 30, 40, or 50 or more) fold.

In some embodiments, the antibodies or antigen-binding fragments thereof described herein can be glycosylated. In some embodiments, the anti-CD161 antibodies or antigen binding fragments described herein can be subjected to enzymatic or chemical treatment, or produced from a cell, such that the antibody or fragment has reduced or absent glycosylation. Methods for producing antibodies with reduced glycosylation are known in the art and described in, e.g., U.S. Pat. No. 6,933,368; Wright et al. (1991) *EMBO J* 10(10):2717-2723; and Co et al. (1993) *Mol Immunol* 30:1361.

Pharmaceutical Compositions and Formulations

In certain embodiments, the invention provides for a pharmaceutical composition comprising an anti-CD161 antibody or antigen-binding portion thereof with a pharmaceutically acceptable diluent, carrier, solubilizer, emulsifier, preservative and/or adjuvant.

In certain embodiments, acceptable formulation materials preferably are nontoxic to recipients at the dosages and concentrations employed. In certain embodiments, the formulation material(s) are for s.c. and/or I. V. administration. In certain embodiments, the pharmaceutical composition can contain formulation materials for modifying, maintaining or preserving, for example, the pH, osmolality, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (Remington's Pharmaceutical Sciences, 18th Edition, A. R. Gennaro, ed., Mack Publishing Company (1995). In certain embodiments, the formulation comprises PBS; 20 mM NAOAC, pH 5.2, 50 mM NaCl; and/or 10 mM NAOAC, pH 5.2, 9% Sucrose. In certain embodiments, the optimal pharmaceutical composition will be determined by one skilled in the art depending upon, for example, the intended route of administration, delivery format and desired dosage. See, for example, Remington's Pharmaceutical Sciences, supra. In certain embodiments, such compositions may influence the physical state, stability, rate of in vivo release and/or rate of in vivo clearance of the anti-CD161 antibody.

In certain embodiments, the primary vehicle or carrier in a pharmaceutical composition can be either aqueous or non-aqueous in nature. For example, in certain embodiments, a suitable vehicle or carrier can be water for injection, physiological saline solution or artificial cerebrospinal fluid, possibly supplemented with other materials common in compositions for parenteral administration. In certain embodiments, the saline comprises isotonic phosphate-buffered saline. In certain embodiments, neutral buffered saline or saline mixed with serum albumin are further exemplary vehicles. In certain embodiments, pharmaceutical compositions comprise Tris buffer of about pH 7.0-8.5, or acetate buffer of about pH 4.0-5.5, which can further include sorbitol or a suitable substitute therefore. In certain embodiments, a composition comprising an anti-CD161 antibody can be prepared for storage by mixing the selected composition having the desired degree of purity with optional formulation agents (Remington's Pharmaceutical Sciences, supra) in the form of a lyophilized cake or an aqueous solution. Further, in certain embodiments, a composition comprising an anti-CD161 antibody can be formulated as a lyophilizate using appropriate excipients such as sucrose.

In certain embodiments, the pharmaceutical composition can be selected for parenteral delivery. In certain embodiments, the compositions can be selected for inhalation or for delivery through the digestive tract, such as orally. The preparation of such pharmaceutically acceptable compositions is within the ability of one skilled in the art.

In certain embodiments, the formulation components are present in concentrations that are acceptable to the site of administration. In certain embodiments, buffers are used to maintain the composition at physiological pH or at a slightly lower pH, typically within a pH range of from about 5 to about 8.

In certain embodiments, when parenteral administration is contemplated, a therapeutic composition can be in the form of a pyrogen-free, parenterally acceptable aqueous solution comprising an anti-CD161 antibody, in a pharmaceutically acceptable vehicle. In certain embodiments, a vehicle for parenteral injection is sterile distilled water in which an anti-CD161 antibody is formulated as a sterile, isotonic solution, and properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that can provide for the controlled or sustained release of the product which can then be delivered via a depot injection. In certain embodiments, hyaluronic acid can also be used, and can have the effect of promoting sustained duration in the circulation. In certain embodiments, implantable drug delivery devices can be used to introduce the desired molecule.

In certain embodiments, a pharmaceutical composition can be formulated for inhalation. In certain embodiments, an anti-CD161 antibody can be formulated as a dry powder for inhalation. In certain embodiments, an inhalation solution comprising an anti-CD161 antibody can be formulated with a propellant for aerosol delivery. In certain embodiments, solutions can be nebulized. Pulmonary administration is further described in PCT application No. PCT/US94/001875, which describes pulmonary delivery of chemically modified proteins.

In certain embodiments, it is contemplated that formulations can be administered orally. In certain embodiments, an anti-CD161 antibody that is administered in this fashion can be formulated with or without those carriers customarily used in the compounding of solid dosage forms such as tablets and capsules. In certain embodiments, a capsule can be designed to release the active portion of the formulation at the point in the gastrointestinal tract when bioavailability is maximized and pre-systemic degradation is minimized In certain embodiments, at least one additional agent can be included to facilitate absorption of an anti-CD161 antibody. In certain embodiments, diluents, flavorings, low melting point waxes, vegetable oils, lubricants, suspending agents, tablet disintegrating agents, and binders can also be employed.

In certain embodiments, a pharmaceutical composition can involve an effective quantity of an anti-CD161 antibody in a mixture with non-toxic excipients which are suitable for the manufacture of tablets. In certain embodiments, by dissolving the tablets in sterile water, or another appropriate vehicle, solutions can be prepared in unit-dose form. In certain embodiments, suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving an anti-CD161 antibody in sustained- or controlled-delivery formulations. In certain embodiments, techniques for formulating a variety of other sustained- or controlled-delivery means, such as liposome carriers, bio-erodible microparticles or porous beads and depot injections, are also known to those skilled in the art. See for example, PCT Application No. PCT/US93/00829 which describes the controlled release of porous polymeric microparticles for the delivery of pharmaceutical compositions. In certain embodiments, sustained-release preparations can include semipermeable polymer matrices in the form of shaped articles, e.g. films, or microcapsules. Sustained release matrices can include polyesters, hydrogels, polylactides (U.S. Pat. No. 3,773,919 and EP 058,481), copolymers of L-glutamic acid and gamma ethyl-L-glutamate (Sidman et al., Biopolymers, 22:547-556 (1983)), poly (2-hydroxyethyl-methacrylate) (Langer et al., J. Biomed. Mater. Res., 15: 167-277 (1981) and Langer, Chem. Tech., 12:98-105 (1982)), ethylene vinyl acetate (Langer et al., supra) or poly-D(−)-3-hydroxybutyric acid (EP 133,988). In certain embodiments, sustained release compositions can also include liposomes, which can be prepared by any of several methods known in the art. See, e.g., Eppstein et al, Proc. Natl. Acad. Sci. USA, 82:3688-3692 (1985); EP 036,676; EP 088,046 and EP 143,949.

The pharmaceutical composition to be used for in vivo administration typically is sterile. In certain embodiments, this can be accomplished by filtration through sterile filtration membranes. In certain embodiments, where the composition is lyophilized, sterilization using this method can be conducted either prior to or following lyophilization and reconstitution. In certain embodiments, the composition for parenteral administration can be stored in lyophilized form or in a solution. In certain embodiments, parenteral compositions generally are placed into a container having a sterile access port, for example, an intravenous solution bag or vial having a stopper pierceable by a hypodermic injection needle.

In certain embodiments, once the pharmaceutical composition has been formulated, it can be stored in sterile vials as a solution, suspension, gel, emulsion, solid, or as a dehydrated or lyophilized powder. In certain embodiments, such formulations can be stored either in a ready-to-use form or in a form (e.g., lyophilized) that is reconstituted prior to administration.

In certain embodiments, kits are provided for producing a single-dose administration unit. In certain embodiments, the kit can contain both a first container having a dried protein and a second container having an aqueous formulation. In certain embodiments, kits containing single and multi-chambered pre-filled syringes (e.g., liquid syringes and lyosyringes) are included.

In certain embodiments, the effective amount of a pharmaceutical composition comprising an anti-CD161 antibody to be employed therapeutically will depend, for example, upon the therapeutic context and objectives. One skilled in the art will appreciate that the appropriate dosage levels for treatment, according to certain embodiments, will thus vary depending, in part, upon the molecule delivered, the indication for which an anti-CD161 antibody is being used, the route of administration, and the size (body weight, body surface or organ size) and/or condition (the age and general health) of the patient. In certain embodiments, the clinician can titer the dosage and modify the route of administration to obtain the optimal therapeutic effect.

In certain embodiments, the frequency of dosing will take into account the pharmacokinetic parameters of an anti-CD161 antibody in the formulation used. In certain embodiments, a clinician will administer the composition until a dosage is reached that achieves the desired effect. In certain embodiments, the composition can therefore be administered as a single dose or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. In certain embodiments, appropriate dosages can be ascertained through use of appropriate dose-response data.

In certain embodiments, the route of administration of the pharmaceutical composition is in accord with known methods, e.g. orally, through injection by intravenous, intraperitoneal, intracerebral (intra-parenchymal), intracerebroventricular, intramuscular, subcutaneously, intra-ocular, intraarterial, intraportal, or intralesional routes; by sustained release systems or by implantation devices. In certain embodiments, the compositions can be administered by bolus injection or continuously by infusion, or by implantation device. In certain embodiments, individual elements of the combination therapy may be administered by different routes.

In certain embodiments, the composition can be administered locally via implantation of a membrane, sponge or another appropriate material onto which the desired molecule has been absorbed or encapsulated. In certain embodiments, where an implantation device is used, the device can be implanted into any suitable tissue or organ, and delivery of the desired molecule can be via diffusion, timed-release bolus, or continuous administration. In certain embodiments, it can be desirable to use a pharmaceutical composition comprising an anti-CD161 antibody in an ex vivo manner In such instances, cells, tissues and/or organs that have been removed from the patient are exposed to a pharmaceutical composition comprising an anti-CD161 antibody after which the cells, tissues and/or organs are subsequently implanted back into the patient.

In certain embodiments, an anti-CD161 antibody can be delivered by implanting certain cells that have been genetically engineered, using methods such as those described herein, to express and secrete the polypeptides. In certain embodiments, such cells can be animal or human cells, and can be autologous, heterologous, or xenogeneic. In certain embodiments, the cells can be immortalized. In certain embodiments, in order to decrease the chance of an immunological response, the cells can be encapsulated to avoid infiltration of surrounding tissues. In certain embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

Kits

In some embodiments, the disclosure provides a kit comprising an anti-CD161 antibody described herein. In some embodiments, a kit includes an anti-CD161 antibody as disclosed herein, and instructions for use. The kits may comprise, in a suitable container, an anti-CD161 antibody, one or more controls, and various buffers, reagents, enzymes and other standard ingredients well known in the art.

The container can include at least one vial, well, test tube, flask, bottle, syringe, or other container means, into which an anti-CD161 antibody may be placed, and in some instances, suitably aliquoted. Where an additional component is provided, the kit can contain additional containers into which this component may be placed. The kits can also include a means for containing an anti-CD161 antibody and any other reagent containers in close confinement for commercial sale. Such containers may include injection or blow-molded plastic containers into which the desired vials are retained. Containers and/or kits can include labeling with instructions for use and/or warnings.

In some embodiments, a kit comprises a containing comprising an anti-CD161 antibody and a pharmaceutically acceptable carrier, or a pharmaceutical composition comprising the anti-CD161 antibody, and instructions for treating or delaying progression of cancer or reducing or inhibiting tumor growth in a subject in need thereof. In some embodiments, a kit comprises a containing comprising an anti-CD161 antibody and a pharmaceutically acceptable carrier, or a pharmaceutical composition comprising the anti-CD161 antibody, and instructions for administering the anti-CD161 antibody to a subject in need thereof, alone or in combination with another agent, for treating or delaying progression of cancer or reducing or inhibiting tumor growth in the subject.

Methods of Use

The compositions of the present invention have numerous in vitro and in vivo utilities involving the detection and/or quantification of CD161 and/or inhibition of function resulting from the interaction between CD161 and CLEC2D.

The above-described compositions are useful in, inter alia, methods for treating or preventing a variety of cancers in a subject. The compositions can be administered to a subject, e.g., a human subject, using a variety of methods that depend, in part, on the route of administration. The route can be, e.g., intravenous injection or infusion (IV), subcutaneous injection (SC), intraperitoneal (IP) injection, intramuscular injection (IM), or intrathecal injection (IT). The injection can be in a bolus or a continuous infusion.

Administration can be achieved by, e.g., local infusion, injection, or by means of an implant. The implant can be of a porous, non-porous, or gelatinous material, including membranes, such as silastic membranes, or fibers. The implant can be configured for sustained or periodic release of the composition to the subject. See, e.g., U.S. Patent Application Publication No. 20080241223; U.S. Pat. Nos. 5,501,856; 4,863,457; and 3,710,795; EP488401; and EP 430539, the disclosures of each of which are incorporated herein by reference in their entirety. The composition can be delivered to the subject by way of an implantable device based on, e.g., diffusive, erodible, or convective systems, e.g., osmotic pumps, biodegradable implants, electrodiffusion systems, electroosmosis systems, vapor pressure pumps, electrolytic pumps, effervescent pumps, piezoelectric pumps, erosion-based systems, or electromechanical systems.

In some embodiments, an anti-CD161 antibody or antigen-binding fragment thereof described herein is therapeutically delivered to a subject by way of local administration.

A suitable dose of an anti-CD161 antibody or antigen-binding fragment thereof described herein, which dose is capable of treating or preventing cancer in a subject, can depend on a variety of factors including, e.g., the age, sex, and weight of a subject to be treated and the particular inhibitor compound used. For example, a different dose of a whole anti-CD161 antibody may be required to treat a subject with cancer as compared to the dose of a CD161-binding Fab' antibody fragment required to treat the same subject. Other factors affecting the dose administered to the subject include, e.g., the type or severity of the cancer. For example, a subject having metastatic melanoma may require administration of a different dosage of an anti-CD161 antibody than a subject with glioblastoma. Other factors can include, e.g., other medical disorders concurrently or previously affecting the subject, the general health of the subject, the genetic disposition of the subject, diet, time of administration, rate of excretion, drug combination, and any other additional therapeutics that are administered to the subject.

It should also be understood that a specific dosage and treatment regimen for any particular subject will also depend upon the judgment of the treating medical practitioner (e.g., doctor or nurse). Suitable dosages are described herein. In some embodiments, the anti-CD161 antibody or antigen-binding fragment thereof described herein are effective at both high and low doses.

A pharmaceutical composition can include a therapeutically effective amount of an anti-CD161 antibody or antigen-binding fragment thereof described herein. Such effective amounts can be readily determined by one of ordinary skill in the art based, in part, on the effect of the administered antibody, or the combinatorial effect of the antibody and one or more additional active agents, if more than one agent is used. A therapeutically effective amount of an antibody or fragment thereof described herein can also vary according to factors such as the disease state, age, sex, and weight of the individual, and the ability of the antibody (and one or more additional active agents) to elicit a desired response in the individual, e.g., reduction in tumor growth. For example, a therapeutically effective amount of an anti-CD161 antibody can inhibit (lessen the severity of or eliminate the occurrence of) and/or prevent a particular disorder, and/or any one of the symptoms of the particular disorder known in the art or described herein. A therapeutically effective amount is also one in which any toxic or detrimental effects of the composition are outweighed by the therapeutically beneficial effects.

Suitable human doses of any of an anti-CD161 antibody or antigen-binding fragment thereof described herein can further be evaluated in, e.g., Phase I dose escalation studies. See, e.g., van Gurp et al. (2008) *Am J Transplantation* 8(8):1711-1718; Hanouska et al. (2007) *Clin Cancer Res* 13(2, part 1):523-531; and Hetherington et al. (2006) *Antimicrobial Agents and Chemotherapy* 50(10): 3499-3500.

In some embodiments, the composition contains any of the anti-CD161 antibody or antigen-binding fragment thereof described herein and one or more (e.g., two, three, four, five, six, seven, eight, nine, 10, or 11 or more) additional therapeutic agents such that the composition as a whole is therapeutically effective. For example, a composition can contain an anti-CD161 antibody described herein and an alkylating agent, wherein the antibody and agent are each at a concentration that when combined are therapeutically effective for treating or preventing a cancer (e.g., melanoma e.g., glioblastoma) in a subject.

Toxicity and therapeutic efficacy of such compositions can be determined by known pharmaceutical procedures in cell cultures or experimental animals (e.g., animal models of any of the cancers described herein). These procedures can be used, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. An anti-CD161 antibody or antigen-binding fragment thereof described herein that exhibits a high therapeutic index is preferred. While compositions that exhibit toxic side effects may be used, care should be taken to design a delivery system that targets such compounds to the site of affected tissue and to minimize potential damage to normal cells and, thereby, reduce side effects.

The data obtained from the cell culture assays and animal studies can be used in formulating a range of dosage for use in humans. The dosage of such anti-CD161 antibodies or antigen-binding fragments thereof lies generally within a range of circulating concentrations of the antibodies or fragments that include the $ED_{50}$ with little or no toxicity. The dosage may vary within this range depending upon the dosage form employed and the route of administration utilized. For an anti-CD161 antibody described herein, the therapeutically effective dose can be estimated initially from cell culture assays. A dose can be formulated in animal models to achieve a circulating plasma concentration range that includes the $EC_{50}$ (i.e., the concentration of the antibody which achieves a half-maximal inhibition of symptoms) as determined in cell culture. Such information can be used to more accurately determine useful doses in humans. Levels in plasma may be measured, for example, by high performance liquid chromatography. In some embodiments, e.g., where local administration (e.g., to the eye or a joint) is desired, cell culture or animal modeling can be used to determine a dose required to achieve a therapeutically effective concentration within the local site.

In some embodiments, the methods can be performed in conjunction with other therapies for cancer. For example, the composition can be administered to a subject at the same time, prior to, or after, radiation, surgery, targeted or cytotoxic chemotherapy, chemoradiotherapy, hormone therapy, immunotherapy, gene therapy, cell transplant therapy, precision medicine, genome editing therapy, or other pharmacotherapy.

As described above, the compositions described herein (e.g., anti-CD161 compositions) can be used to treat a variety of cancers such as but not limited to: Kaposi's sarcoma, leukemia, acute lymphocytic leukemia, acute myelocytic leukemia, myeloblasts promyelocyte myelomonocytic monocytic erythroleukemia, chronic leukemia, chronic myelocytic (granulocytic) leukemia, chronic lymphocytic leukemia, mantle cell lymphoma, primary central nervous system lymphoma, Burkitt's lymphoma and marginal zone B cell lymphoma, Polycythemia vera Lymphoma, Hodgkin's disease, non-Hodgkin's disease, multiple myeloma, Waldenstrom's macroglobulinemia, heavy chain disease, solid tumors, sarcomas, and carcinomas, fibrosarcoma, myxosarcoma, liposarcoma, chondrosarcoma, osteogenic sarcoma, osteosarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon sarcoma, colorectal carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular tumor, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, retinoblastoma, nasopharyngeal carcinoma, esophageal carcinoma, basal cell carcinoma, biliary tract cancer, bladder cancer, bone cancer, brain and central nervous system (CNS) cancer, cervical cancer, choriocarcinoma, colorectal cancers, connective tissue cancer, cancer of the digestive system, endometrial cancer, esophageal cancer, eye cancer, head and neck cancer, gastric cancer, intraepithelial neoplasm, kidney cancer, larynx cancer, liver cancer, lung cancer (small cell, large cell), melanoma, neuroblastoma; oral cavity cancer (for example lip, tongue, mouth and pharynx), ovarian cancer, pancreatic cancer, retinoblastoma, rhabdomyosarcoma, rectal cancer; cancer of the respiratory system, sarcoma, skin cancer, stomach cancer, testicular cancer, thyroid cancer, uterine cancer, and cancer of the urinary system.

Monitoring a subject (e.g., a human patient) for an improvement in a cancer, as defined herein, means evaluating the subject for a change in a disease parameter, e.g., a reduction in tumor growth. In some embodiments, the evaluation is performed at least one (1) hour, e.g., at least 2, 4, 6, 8, 12, 24, or 48 hours, or at least 1 day, 2 days, 4 days, 10 days, 13 days, 20 days or more, or at least 1 week, 2 weeks, 4 weeks, 10 weeks, 13 weeks, 20 weeks or more, after an administration. The subject can be evaluated in one or more of the following periods: prior to beginning of treatment; during the treatment; or after one or more elements of the treatment have been administered. Evaluation can include evaluating the need for further treatment, e.g., evaluating whether a dosage, frequency of administration, or duration of treatment should be altered. It can also include evaluating the need to add or drop a selected therapeutic modality, e.g., adding or dropping any of the treatments for a cancer described herein.

In some embodiments, an anti-CD161 antibody or an antigen-binding fragment thereof described herein is administered to modulate an immune cell response in a patient, for example, by increasing immune cell cytokine production, increasing T-cell activation, and/or preventing or reducing T cell exhaustion. Inhibition of CLEC2D binding to CD161 on T cells strongly enhances T cell cytokine production, T cell cytolytic activity, and decreases or prevents T cell exhaustion. Moreover, inhibition of CLEC2D binding to CD161 on NK cells strongly enhances NK cytokine production and NK cytolytic activity. Accordingly, in some embodiments, an anti-CD161 antibody, or an antigen-binding fragment thereof, of the present disclosure is administered to a patent in need thereof to induce or increase T-cell activation, induce or increase NK cell activation, induce the production and/or secretion of inflammatory cytokines (e.g., IL-2, IFNγ, TNFα) by T cells and/or NK cells, induce a cytolytic T cell response, induce a cytolytic NK cell response, prevent or reduce T cell exhaustion, or any combination thereof.

In some embodiments, the anti-CD161 antibodies described herein induce a protective anti-tumor memory immune response. Memory T cells are a subset of antigen-specific T cells that persist long-term after having encountered and responded to their cognate antigen. Such cells quickly expand to large numbers of effector cells upon re-exposure to their cognate antigen. Accordingly, in some embodiments the anti-CD161 antibodies described herein stimulate the production of memory T cells to a cancer antigen. In some embodiments, a subject that has received an anti-CD161 antibody described herein to treat or cure a cancer, develops memory T cells specific to the cancer. In some embodiments, a subject that has received an anti-CD161 antibody described herein to treat or cure a cancer, develops an anti-tumor memory immune response upon re-exposure to the cancer. In some embodiments, the anti-tumor memory immune response comprises stimulating memory T cells to become effector cells. In some embodiments, a subject that has received an anti-CD161 antibody described herein to treat or cure a cancer, develops an anti-tumor memory immune response to a cancer antigen.

In some embodiments, the anti-CD161 antibodies protect T cells from T cell exhaustion in a tumor microenvironment. In some embodiments, the anti-CD161 antibodies reverse T cell exhaustion in a tumor microenvironment. In some embodiments, T cell exhaustion in a tumor microenvironment is reduced in the presence of an anti-CD161 antibody described herein, relative to a tumor microenvironment in the absence of the anti-CD161 antibody. In some embodiments, T cell exhaustion is determined by analyzing CD8+ T cells or CD4+ T cells for expression of co-inhibitory receptors (e.g., PD-1, TIGIT or LAG-3). In some embodiments, T cell exhaustion is detected by expression of PD-1 and TIGIT on CD4+ or CD8+ T cells isolated from a tumor microenvironment.

Combination Therapy

In some embodiments, an anti-CD161 antibody or an antigen-binding fragment thereof described herein can be administered to a subject as a monotherapy. In some embodiments, the anti-CD161 antibodies of the disclosure are used in combination with one or more additional therapies. As used herein, "combination therapy" embraces administration of each agent or therapy in a sequential manner in a regiment that will provide beneficial effects of the combination, and co-administration of these agents or therapies in a substantially simultaneous manner, such as in a single capsule or infusion having a fixed ratio of these active agents or in multiple, separate capsules or infusions for each agent. Combination therapy also includes combinations wherein individual agents may be administered at different times and/or by different routes but which act in combination to provide a beneficial effect by co-action or pharmacokinetic or pharmacodynamic effects of each agent or tumor treatment approaches of the combination therapy. For example, in some embodiments, an anti-CD161 antibody is used in combination with another immunotherapy. Exemplary immunotherapies include, but are not limited to, tumor-associated antigen targeting antibodies and immune checkpoint inhibitors. In some embodiments, an anti-CD161 antibody is used in combination with one or more chemotherapies.

Tumor-Associated Antigen Targeting Antibodies

In some embodiments, the disclosure provides anti-CD161 antibodies to be used or administered in conjunction with antibodies that target tumor antigens, referred to herein as "tumor-targeting antibodies" or "tumor-associated antigen targeting antibodies". Therapeutic monoclonal antibodies have been conceived as a class of pharmaceutically active agents which should allow tumor selective treatment by targeting tumor selective antigens or epitopes. Therapeutic antibodies that can be used in the methods of the present disclosure include, but are not limited to, any of the art-recognized anti-cancer antibodies that are approved for use, in clinical trials, or in development for clinical use. In certain embodiments, more than one anti-cancer antibody can be included in the combination therapy of the present disclosure.

In some embodiments, the disclosure provides anti-CD161 antibodies to be used or administered in conjunction with antibodies that target tumor antigens and induce antibody-dependent cell-mediated cytotoxicity (ADCC). ADCC is the process whereby an immune system effector cell lyse a target cell after binding of specific antibodies to membrane-surface antigens present on the target cell. ADCC requires that the target cell express target antigens, that the antibody bind to the target antigen, and the immune effector cells express Fc-gamma receptors (FcγR) that engage the antigen-bound antibody. In some embodiments, the antibody targets antigens highly expressed on tumor cells. In some embodiments, the antibody is a monoclonal antibody of the IgG1 or IgG3 class that bind to activating FcγRs. Natural killer cells are key effectors of ADCC in humans as they express only activating FcγRs (e.g., FcγR IIIa, e.g., FcγR IIc). Tumor-targeting antibodies that function through ADCC mediated by NK cells are reviewed in Nigro, et al. (2019) *Ann Transl Med* 7:105 and Wang et al (2015) *Frontiers Immunol* 6:368. Non-limiting examples of anti-cancer antibodies that function through ADCC include rituximab (RITUXAN™ by Genentech) which is used to treat non-Hodgkin's lymphoma or chronic lymphocytic leukemia, obinutuzumab (GAZYVA® by Roche) which is used to treat chronic lymphocytic leukemia and follicular lymphoma; dinituximab (UNITUXIN® by United Therapeutics) which is used to treat children with high-risk neuroblastoma; trastuzumab (HERCEPTIN™ by Genentech, South San Francisco, Calif.) which is used to treat HER-2/neu positive breast cancer or metastatic breast cancer; cetuximab (ERBITUX™ by ImClone Systems Incorporated, New York, N.Y.) which can be used to treat colorectal cancer, metastatic colorectal cancer, lung cancer, head and neck cancer, colon cancer, breast cancer, prostate cancer, gastric cancer, ovarian cancer, brain cancer, pancreatic cancer, esophageal cancer, renal cell cancer, prostate cancer, cervical cancer, or bladder cancer; daratumumab (DARZALEX™ by Genmab, Copenhagen, Denmark) which is used to treat multiple myeloma, diffuse large B cell lymphoma, follicular lymphoma, and mantle cell lymphoma; Hu14.18K322A (anti-GD2), which is currently in clinical trials for treatment of children with advanced stage neuroblastoma (see e.g., clinicaltrials.gov identifier NCT01857934); and Hu3F8 (anti-GD2) currently in clinical trials for treatment of neuroblastoma and GD2-positive solid tumors (see e.g., clinicaltrials.gov identifier: NCT01662804).

Additional non-limiting examples of anti-cancer antibodies include the following, without limitation: bevacizumab (AVASTIN™ by Genentech), which are used to treat colorectal cancer, metastatic colorectal cancer, breast cancer, metastatic breast cancer, non-small cell lung cancer, or renal cell carcinoma; pertuzumab (OMNITARG™ by Genentech), which is used to treat breast cancer, prostate cancer, non-small cell lung cancer, or ovarian cancer; IMC-1C11 (ImClone Systems Incorporated), which is used to treat colorectal cancer, head and neck cancer, as well as other potential cancer targets; tositumomab and tositumomab and iodine I 131 (BEXXAR XM by Corixa Corporation, Seattle, Wash.), which is used to treat non-Hodgkin's lymphoma, which can be CD20 positive, follicular, non-Hodgkin's lymphoma, with and without transformation, whose disease is refractory to Rituximab and has relapsed following chemotherapy; $In^{111}$ ibirtumomab tiuxetan; $Y^{90}$ ibirtumomab tiuxetan; $In^{111}$ ibirtumomab tiuxetan and $Y^{90}$ ibirtumomab tiuxetan (ZEVALIN™ by Biogen Idee, Cambridge, Mass.), which is used to treat lymphoma or non-Hodgkin's lymphoma, which can include relapsed follicular lymphoma; relapsed or refractory, low grade or follicular non-Hodgkin's lymphoma; or transformed B-cell non-Hodgkin's lymphoma; EMD 7200 (EMD Pharmaceuticals, Durham, N.C.), which is used for treating non-small cell lung cancer or cervical cancer; SGN-30 (a genetically engineered monoclonal antibody targeted to CD30 antigen by Seattle Genetics, Bothell, Wash.), which is used for treating Hodgkin's lymphoma or non-Hodgkin's lymphoma; SGN-15 (a genetically engineered monoclonal antibody targeted to a Lewisy-related antigen that is conjugated to doxorubicin by Seattle Genetics), which is used for treating non-small cell lung cancer; SGN-33 (a humanized antibody targeted to CD33 antigen by Seattle Genetics), which is used for treating acute myeloid leukemia (AML) and myelodysplasia syndromes (MDS); SGN-40 (a humanized monoclonal antibody targeted to CD40 antigen by Seattle Genetics), which is used for treating multiple myeloma or non-Hodgkin's lymphoma; SGN-35 (a genetically engineered monoclonal antibody targeted to a CD30 antigen that is conjugated to auristatin E by Seattle Genetics), which is used for treating non-Hodgkin's lymphoma; SGN-70 (a humanized antibody targeted to CD70 antigen by Seattle Genetics), which is used for treating renal cancer and nasopharyngeal carcinoma; SGN-75 (a conjugate comprised of the SGN70 antibody and an Auristatin derivative by Seattle Genetics); and SGN-17/19 (a fusion protein containing antibody and enzyme conjugated to melphalan prodrug by Seattle Genetics), which is used for treating melanoma or metastatic melanoma.

It should be understood that the therapeutic antibodies to be used in the methods of the present disclosure are not limited to those described supra. For example, the following approved therapeutic antibodies can also be used in the methods of the disclosure: brentuximab vedotin (ADCETRIS™) for anaplastic large cell lymphoma and Hodgkin lymphoma, ipilimumab (MDX-101; YERVOY™) for melanoma, ofatumumab (ARZERRA™) for chronic lymphocytic leukemia, panitumumab (VECTIBIX™) for colorectal cancer, alemtuzumab (CAMPATH™) for chronic lymphocytic leukemia, ofatumumab (ARZERRA™) for chronic lymphocytic leukemia, gemtuzumab ozogamicin (MYLOTARG™) for acute myelogenous leukemia.

Immune Checkpoint Blockade

In some aspects, the disclosure provides anti-CD161 antibodies to be used or administered in conjunction with immune checkpoint inhibitors or immune checkpoint blockers. T cell activation and effector functions are balanced by co-stimulatory and inhibitory signals, referred to as "immune checkpoints." Inhibitory ligands and receptors that regulate T cell effector functions are overexpressed on tumor cells. Subsequently, agonists of co-stimulatory receptors or antagonists of inhibitory signals, result in the amplification of antigen-specific T cell responses. In contrast to therapeutic antibodies which target tumor cells directly, an immune checkpoint inhibitor enhances endogenous anti-tumor activity. In certain embodiments, the immune checkpoint inhibitor suitable for use in the methods disclosed herein, is an antagonist of inhibitory signals, e.g., an antibody which targets, for example, PD-1, PD-L1, CTLA-4, LAG3, B7-H3, B7-H4, or TIM3. These ligands and receptors are reviewed in Pardoll, D., *Nature* (2012), 12:252-264, 2012 and Wei, S. et. Al. *Cancer Discovery* (2018) 8:1069.

In certain embodiments, the immune checkpoint inhibitor targets a component of the PD-1 signaling pathway. In some embodiments, the immune checkpoint inhibitor is an antibody or an antigen-binding portion thereof that disrupts the interaction between the PD-1 receptor and its ligand, PD-L1. Antibodies known in the art which bind to PD-1 or to its ligand PD-L1 and disrupt the interaction between PD-1 and PD-L1, and thereby stimulate an anti-tumor immune response, are suitable for use in the methods disclosed herein. Non-limiting examples of antibodies which bind to PD-1 or to PD-L1 include: nivolumab (OPDIVO® by Bristol-Myers Squibb); pembrolizumab (KEYTRUDA® by Merck), cemiplimab (LIBTAYO® by Sanofi and Regeneron Pharmaceuticals, Inc), avelumab (BAVENCIO® by Merck KGaA and Pfizer), durvalumab (IMFINZI® by AstraZeneca), atezolizumab (TECENTRIQ® by Genentech, Inc.), REGN2810 (in clinical trials, see e.g., clinicaltrials.gov identifiers NCT03409614, NCT03088540), BMS-936559 (Bristol-Myers Squibb, in clinical trials, see e.g., clinicaltrials.gov identifiers NCT01721746 and NCT01721772), SHR1210 (Alphamab and 3D Medicines, Incyte Biosciences and Jiangsu Hengrui medicine Corporation, in clinical trials, see e.g., clinicaltrials.gov identifiers NCT03134872 and NCT03427827), KN035 (in clinical trials, see e.g., clinicaltrials.gov identifier NCT02827968), IB1308 (Innovent Biologics Co, Ltd, in clinical trials, see e.g., clinicaltrials.gov identifier NCT03150875), PDR001 (Novartis Pharmaceuticals, in clinical trials, see e.g., clinicaltrials.gov identifier NCT02967692), BGB-A317 (BeiGene, in clinical trials, see e.g., clinicaltrials.gov identifiers NCT03358875, NCT03430843, NCT03412773), BCD-100 (Biocad, in clinical trials, see e.g., clinicaltrials.gov identifier NCT03288870), and JS001 (Shanghai Junshi Bioscience Co, Ltd., in clinical trials, see e.g., clinicaltrials.gov identifier NCT03430297). Additional examples include anti-PD-1 antibodies disclosed in U.S. Pat. No. 8,008,449, herein incorporated by reference and anti-PD-L1 antibodies disclosed in U.S. Pat. No. 7,943,743, herein incorporated by reference. It will be understood by one of ordinary skill that any antibody which binds to PD-1 or PD-L1, disrupts the PD-1/PD-L1 interaction, and stimulates an anti-tumor immune response, is suitable for use in the methods disclosed herein.

In certain embodiments, the immune checkpoint inhibitor targets a component of the CTLA-4 signaling pathway. In some embodiments, the immune checkpoint inhibitor is an antibody or an antigen-binding portion thereof that targets CTLA-4 and disrupts its interaction with CD80 and CD86. Exemplary antibodies that target CTLA-4 include ipilimumab (YERVOY® by Bristol-Myers Squibb) and tremelimumab (formerly ticilimumab, CP-675,206 in development by MedImmune and AstraZeneca). Other suitable antibodies that target CTLA-4 are disclosed in WO 2012/120125, U.S. Pat. Nos. 6,984,720, 6,682,7368, and U.S. Patent Applications 2002/0039581, 2002/0086014, and 2005/0201994, herein incorporated by reference. It will be understood by one of ordinary skill that any antibody which binds to CTLA-4, disrupts its interaction with CD80 and CD86, and stimulates an anti-tumor immune response, is suitable for use in the methods disclosed herein.

In certain embodiments, the immune checkpoint inhibitor targets a component of the LAG3 (lymphocyte activation gene 3) signaling pathway. In some embodiments, the immune checkpoint inhibitor is an antibody or an antigen-binding portion thereof that targets LAG3 and disrupts its interaction with MHC class II molecules. An exemplary antibody that targets LAG3 is LAG525 (Novartis Pharmaceuticals, in clinical trials, see e.g., clinicaltrials.gov identifier NCT03499899) and IMP321 (Immutep, in clinical trials, see e.g., clinicaltrials.gov identifier NCT03252938). Other suitable antibodies that target LAG3 are disclosed in U.S. Patent Application 2011/0150892, herein incorporated by reference. It will be understood by one of ordinary skill that any antibody which binds to LAG3, disrupts its interaction with MHC class II molecules, and stimulates an anti-tumor immune response, is suitable for use in the methods disclosed herein.

It should be understood that antibodies targeting immune checkpoints suitable for use in the methods disclosed herein are not limited to those described supra. Moreover, it will be understood by one of ordinary skill in the art that other immune checkpoint targets (e.g., ligands and receptors reviewed in Pardoll, D., *Nature.* 12: 252-264, 2012 and Wei, S. et. Al. *Cancer Discovery* (2018) 8:1069) can also be targeted by antagonists or antibodies, provided that the targeting results in the stimulation of an anti-tumor immune response as reflected in, e.g., an increase in T cell proliferation, enhanced T cell activation, and/or increased cytokine production (e.g., IFN-γ, IL-2).

Chemotherapy

In some embodiments, the disclosure provides anti-CD161 antibodies to be used or administered in combination with a chemotherapeutic agent. Chemotherapeutic agents suitable for co-administration with compositions of the present invention include, for example: taxol, cytochalasin B, gramicidin D, ethidium bromide, emetine, mitomycin, etoposide, tenoposide, vincristine, vinblastine, colchicin, doxorubicin, daunorubicin, dihydroxyanthrancindione, mitoxantrone, mithramycin, actinomycin D, 1-dehydrotestosterone, glucocorticoids, procaine, tetracaine, lidocaine, propranolol, and puromycin and analogs or homologs thereof. Further agents include, for example, antimetabolites (e.g., methotrexate, 6-mercaptopurine, 6-thioguanine, cytarabine, 5-fluorouracil decarbazine), alkylating agents (e.g. mechlorethamine, thioTEPA, chlorambucil, melphalan, carmustine (BSNU), lomustine (CCNU), cyclophosphamide, busulfan, dibromomannitol, streptozotocin, mitomycin C, cis-dichlordiamine platinum (II)(DDP), procarbazine, altretamine, cisplatin, carboplatin, oxaliplatin, nedaplatin, satraplatin, or triplatin tetranitrate), anthracycline (e.g. daunorubicin (formerly daunomycin) and doxorubicin), antibiotics (e.g. dactinomcin (formerly actinomycin), bleomycin, mithramycin, and anthramycin (AMC)), and antimitotic agents (e.g. vincristine and vinblastine) and temozolomide.

In some embodiments, an anti-CD161 antibody and the one or more additional active agents are administered at the same time. In other embodiments, the anti-CD161 antibody is administered first in time and the one or more additional active agents are administered second in time. In some embodiments, the one or more additional active agents are administered first in time and the anti-CD161 antibody is administered second in time.

An anti-CD161 antibody or an antigen-binding fragment thereof described herein can replace or augment a previously or currently administered therapy. For example, upon treating with an anti-CD161 antibody or antigen-binding fragment thereof, administration of the one or more additional active agents can cease or diminish, e.g., be administered at lower levels or dosages. In some embodiments, administration of the previous therapy can be maintained. In some embodiments, a previous therapy will be maintained until the level of the anti-CD161 antibody reaches a level sufficient to provide a therapeutic effect. The two therapies can be administered in combination.

Diagnostic Applications

In some embodiments, the compositions described herein are used in diagnostic applications. For example, detectably-labeled antigen-binding molecules can be used in assays to detect the presence or amount of the target antigen (e.g., CD161) in a sample (e.g., a biological sample). The compositions can be used in in vitro assays for studying inhibition of target antigen function (e.g. CD161-mediated cellular signaling or response, e.g., cellular signaling or response mediated by the CD161-CLEC2D interaction). In some embodiments, e.g., in which the compositions bind to and block ligand binding to a target antigen (e.g. CLEC2D binding to CD161), the compositions can be used as positive controls in assays designed to identify additional novel compounds that also bind to and block ligand binding to a target antigen (e.g., CLEC2D binding to CD161) and/or are otherwise are useful for treating a disorder associated with ligand binding to the target antigen (e.g., CLEC2D binding to CD161). For example, in some embodiments, a composition that inhibits the interaction of CD161 with CLEC2D can be used as a positive control in an assay to identify additional compounds (e.g., small molecules, aptamers, or antibodies) that inhibits or blocks binding of CLEC2D to CD161.

In some embodiments, an anti-CD161 antibody, or an antigen-binding fragment thereof, described herein, can be employed in methods of detection and/or quantification of human CD161 in a biological sample. Accordingly, an anti-CD161 antibodies, or an antigen-binding fragment thereof, as described herein, is used to diagnose, prognose, and/or determine progression of disease (e.g., cancer) in a patient.

DEFINITIONS

Terms used in the claims and specification are defined as set forth below unless otherwise specified.

It must be noted that, as used in the specification and the appended claims, the singular forms "a," "an" and "the" include plural referents unless the context clearly dictates otherwise. Further, unless otherwise required by context, singular terms shall include pluralities and plural terms shall include the singular.

As used herein, "about" will be understood by persons of ordinary skill and will vary to some extent depending on the context in which it is used. If there are uses of the term which are not clear to persons of ordinary skill given the context in which it is used, "about" will mean up to plus or minus 10% of the particular value.

As used herein, the term "alanine scanning" refers to a technique used to determine the contribution of a specific wild-type residue to the stability or function(s) (e.g., binding affinity) of a given protein or polypeptide. The technique involves the substitution of an alanine residue for a wild-type residue in a polypeptide, followed by an assessment of the stability or function(s) (e.g., binding affinity) of the alanine-substituted derivative or mutant polypeptide and comparison to the wild-type polypeptide. Techniques to substitute alanine for a wild-type residue in a polypeptide are known in the art.

As used herein, the term "ameliorating" refers to any therapeutically beneficial result in the treatment of a disease state, e.g., cancer, including prophylaxis, lessening in the severity or progression, remission, or cure thereof.

As used herein, the term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine Amino acid analogs refers to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid Amino acid mimetics refers to chemical compounds that have a structure that is different from the general chemical structure of an amino acid, but that function in a manner similar to a naturally occurring amino acid.

Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes. As used here, a "polar amino acid" refers to an amino acid comprising a side chain that prefers to reside in an aqueous environment. In some embodiments, a polar amino acid is selected from the group consisting of: arginine, asparagine, aspartic acid, glutamic acid, glutamine, histidine, lysine, serine, theronine and tyrosine. Polar amino acids can be positive, negatively or neutrally charged. As used herein, a "non-polar amino acid" refers to an amino acid selected from the group consisting of: alanine, cysteine, glycine, isoleucine, leucine, methionine, phenylalanine, proline, tryptophan and valine.

As used herein, an "amino acid substitution" refers to the replacement of at least one existing amino acid residue in a predetermined amino acid sequence (an amino acid sequence of a starting polypeptide) with a second, different "replacement" amino acid residue. An "amino acid insertion" refers to the incorporation of at least one additional amino acid into a predetermined amino acid sequence. While the insertion will usually consist of the insertion of one or two amino acid residues, larger "peptide insertions," can also be made, e.g. insertion of about three to about five or even up to about ten, fifteen, or twenty amino acid residues. The inserted residue(s) may be naturally occurring or non-naturally occurring as disclosed above. An "amino acid deletion" refers to the removal of at least one amino acid residue from a predetermined amino acid sequence.

As used herein, the term "amount" or "level" refers to a detectable quantity, level or abundance of a substance (e.g., a protein). When referring to a polypeptide, such as those described herein, the terms "level of expression" or "expression level" in general are used interchangeably and generally refer to a detectable amount of a polypeptide in a biological sample (e.g., on the surface of a cell).

As used herein, the term "antibody" refers to a whole antibody comprising two light chain polypeptides and two heavy chain polypeptides. Whole antibodies include different antibody isotypes including IgM, IgG, IgA, IgD, and IgE antibodies. The term "antibody" includes a polyclonal antibody, a monoclonal antibody, a chimerized or chimeric antibody, a humanized antibody, a primatized antibody, a deimmunized antibody, and a fully human antibody. The antibody can be made in or derived from any of a variety of species, e.g., mammals such as humans, non-human primates (e.g., orangutan, baboons, or chimpanzees), horses, cattle, pigs, sheep, goats, dogs, cats, rabbits, guinea pigs, gerbils, hamsters, rats, and mice. The antibody can be a purified or a recombinant antibody.

As used herein, the terms "antibody fragment," "antigen-binding fragment," "antigen binding portion" or similar terms refer to a fragment of an antibody that retains the ability to bind to a target antigen (e.g., CD161, e.g., human CD161) and inhibit the activity of the target antigen. Such fragments include, e.g., a single chain antibody, a single chain Fv fragment (scFv), an Fd fragment, a Fab fragment, a Fab' fragment, or an F(ab')$_2$ fragment. An scFv fragment is a single polypeptide chain that includes both the heavy and light chain variable regions of the antibody from which the scFv is derived. In addition, intrabodies, minibodies, triabodies, and diabodies are also included in the definition of antibody and are compatible for use in the methods described herein. See, e.g., Todorovska et al., (2001) *J. Immunol. Methods* 248(1):47-66; Hudson and Kortt, (1999) *J. Immunol. Methods* 231(1):177-189; Poljak, (1994) *Structure* 2(12):1121-1123; Rondon and Marasco, (1997) *Annu.*

*Rev. Microbiol.* 51:257-283, the disclosures of each of which are incorporated herein by reference in their entirety.

As used herein, the term "antibody fragment" also includes, e.g., single domain antibodies such as camelized single domain antibodies. See, e.g., Muyldermans et al., (2001) *Trends Biochem. Sci.* 26:230-235; Nuttall et al., (2000) *Curr. Pharm. Biotech.* 1:253-263; Reichmann et al., (1999) *J. Immunol. Meth.* 231:25-38; PCT application publication nos. WO 94/04678 and WO 94/25591; and U.S. Pat. No. 6,005,079, all of which are incorporated herein by reference in their entireties. In some embodiments, the disclosure provides single domain antibodies comprising two VH domains with modifications such that single domain antibodies are formed.

In some embodiment, an antigen-binding fragment includes the variable region of a heavy chain polypeptide and the variable region of a light chain polypeptide. In some embodiments, an antigen-binding fragment described herein comprises the CDRs of the light chain and heavy chain polypeptide of an antibody.

The term "antigen presenting cell" or "APC" is a cell that displays foreign antigen complexed with MHC on its surface. T cells recognize this complex using T cell receptor (TCR). Examples of APCs include, but are not limited to, dendritic cells (DCs), peripheral blood mononuclear cells (PBMC), monocytes (such as THP-1), B lymphoblastoid cells (such as C1R.A2, 1518 B-LCL) and monocyte-derived dendritic cells (DCs). Some APCs internalize antigens either by phagocytosis or by receptor-mediated endocytosis.

The term "antigen presentation" refers to the process by which APCs capture antigens and enables their recognition by T cells, e.g., as a component of an MHC-I and/or MHC-II conjugate.

As used herein, the term "binds to immobilized CD161," refers to the ability of an anti-CD161 antibody of the disclosure to bind to a CD161 polypeptide (e.g., human CD161 polypeptide), for example, expressed on the surface of a cell or which is attached to a solid support (e.g., a bead).

As used herein, "cancer antigen" refers to (i) tumor-specific antigens, (ii) tumor-associated antigens, (iii) cells that express tumor-specific antigens, (iv) cells that express tumor-associated antigens, (v) embryonic antigens on tumors, (vi) autologous tumor cells, (vii) tumor-specific membrane antigens, (viii) tumor-associated membrane antigens, (ix) growth factor receptors, (x) growth factor ligands, and (xi) any other type of antigen or antigen-presenting cell or material that is associated with a cancer.

As used herein, the term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. The anti-CD161 antibodies described herein can be used to treat patients who have, who are suspected of having, or who may be at high risk for developing any type of cancer, including renal carcinoma or melanoma. Exemplary carcinomas include those forming from tissue of the cervix, lung, prostate, breast, head and neck, colon and ovary. The term also includes carcinosarcomas, which include malignant tumors composed of carcinomatous and sarcomatous tissues. An "adenocarcinoma" refers to a carcinoma derived from glandular tissue or in which the tumor cells form recognizable glandular structures.

As used herein the term "compete", when used in the context of antigen-binding proteins (e.g., immunoglobulins, antibodies, or antigen-binding fragments thereof) that compete for binding to the same epitope, refers to a interaction between antigen-binding proteins as determined by an assay (e.g., a competitive binding assay; a cross-blocking assay), wherein a test antigen-binding protein (e.g., a test antibody) inhibits (e.g., reduces or blocks) specific binding of a reference antigen-binding protein (e.g., a reference antibody, such as KW1, KW7, KW9, KW17, KM12, or HP-3G10) to a common antigen (e.g., CD161 or a fragment thereof).

As used herein, the term "contacting" means establishing a physical connection between two or more entities. For example, contacting a cell with an anti-CD161 antibody or a composition thereof disclosed herein means that the cell and antibody or composition are made to share a physical connection. Methods of contacting cells with external entities both in vivo, in vitro, and ex vivo are well known in the biological arts. In exemplary embodiments of the disclosure, the step of contacting a mammalian cell with a composition (e.g., an isolated monoclonal anti-CD161 antibody or pharmaceutical composition of the disclosure) is performed in vivo. For example, contacting an anti-CD161 antibody composition and a cell (for example, a mammalian cell) which may be disposed within an organism (e.g., a mammal) may be performed by any suitable administration route (e.g., parenteral administration to the organism, including intravenous, intramuscular, intradermal, and subcutaneous administration). For a cell present in vitro, a composition (e.g., comprising an isolated monoclonal anti-CD161 antibody) and a cell may be contacted, for example, by adding the composition to the culture medium of the cell and may involve or result in a functional cellular effect. Moreover, more than one cell may be contacted by an isolated monoclonal anti-CD161 antibody disclosed herein.

A polypeptide or amino acid sequence "derived from" a designated polypeptide or protein refers to the origin of the polypeptide. Preferably, the polypeptide or amino acid sequence which is derived from a particular sequence has an amino acid sequence that is essentially identical to that sequence or a portion thereof, wherein the portion consists of at least 10-20 amino acids, preferably at least 20-30 amino acids, more preferably at least 30-50 amino acids, or which is otherwise identifiable to one of ordinary skill in the art as having its origin in the sequence. Polypeptides derived from another peptide may have one or more mutations relative to the starting polypeptide, e.g., one or more amino acid residues which have been substituted with another amino acid residue or which has one or more amino acid residue insertions or deletions.

A polypeptide can comprise an amino acid sequence which is not naturally occurring. Such variants necessarily have less than 100% sequence identity or similarity with the starting molecule. In certain embodiments, the variant will have an amino acid sequence from about 75% to less than 100% amino acid sequence identity or similarity with the amino acid sequence of the starting polypeptide, more preferably from about 80% to less than 100%, more preferably from about 85% to less than 100%, more preferably from about 90% to less than 100% (e.g., 91%, 92%, 93%, 94%, 95%, 96%, 97%, 98%, 99%) and most preferably from about 95% to less than 100%, e.g., over the length of the variant molecule.

It will also be understood by one of ordinary skill in the art that the antibodies suitable for use in the methods disclosed herein may be altered such that they vary in sequence from the naturally occurring or native sequences from which they were derived, while retaining the desirable activity of the native sequences. For example, nucleotide or amino acid substitutions leading to conservative substitutions or changes at "non-essential" amino acid residues may be made. Mutations may be introduced by standard techniques, such as site-directed mutagenesis and PCR-mediated mutagenesis.

The antibodies suitable for use in the methods disclosed herein may comprise conservative amino acid substitutions at one or more amino acid residues, e.g., at essential or non-essential amino acid residues. A "conservative amino acid substitution" is one in which the amino acid residue is replaced with an amino acid residue having a similar side chain Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in a binding polypeptide is preferably replaced with another amino acid residue from the same side chain family. In certain embodiments, a string of amino acids can be replaced with a structurally similar string that differs in order and/or composition of side chain family members. Alternatively, in certain embodiments, mutations may be introduced randomly along all or part of a coding sequence, such as by saturation mutagenesis, and the resultant mutants can be incorporated into binding polypeptides of the invention and screened for their ability to bind to the desired target.

As used herein, the term "cross-reacts" refers to the ability of an anti-CD161 antibody of the disclosure to bind to CD161 from a different species (e.g., non-human CD161 e.g., cynomolgus CD161) and/or to bind to a human protein with sequence and/or structural homology to human CD161 (e.g., a protein selected from the C-type lectin receptor family, e.g., an NK cell receptor, e.g., a protein comprising a CTLD). For example, an antibody of the present disclosure which binds human CD161 may also bind CD161 from a different species (e.g., non-human CD161 e.g., cynomolgus CD161) such that the antibody cross-reacts with CD161 from a different species. In another example, an antibody of the present disclosure does not bind to a human protein with sequence or structural homology to human CD161 (e.g., a protein selected from the C-type lectin receptor family, e.g., an NK cell receptor, e.g., a protein comprising a CTLD) such that the antibody does not significantly cross-react with a human protein with sequence or structural homology to human CD161.

In some embodiments, cross-reactivity of an anti-CD161 antibody disclosed herein to an antigen (e.g., cynomolgus CD161, e.g., protein comprising structural and/or sequence homology with human CD161) is measured by detecting a specific reactivity with purified antigen in binding assays. Methods for determining cross-reactivity to purified antigen include standard binding assays as described herein, for example, by ELISA, by surface plasmon resonance (SPR) analysis (e.g., using Biacore, GE Healthcare), by bio-layer interferometry analysis (e.g., using Octet, ForteBio) or flow cytometric techniques.

As used herein, the term "cytotoxic T lymphocyte (CTL) response" refers to an immune response induced by cytotoxic T cells. CTL responses are mediated primarily by $CD8^+$ T cells.

As used herein, the term "$EC_{50}$" refers to the concentration of an antibody or an antigen-binding portion thereof, which induces a response, either in an in vitro or an in vivo assay, which is 50% of the maximal response, i.e., halfway between the maximal response and the baseline.

As used herein, the term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. Amounts effective for this use will depend upon the severity of the disorder being treated and the general state of the patient's own immune system.

As used herein, the term "epitope" or "antigenic determinant" refers to a determinant or site on an antigen (e.g., CD161, e.g., human CD161) to which an antigen-binding protein (e.g., an anti-CD161 immunoglobulin, antibody, or antigen-binding fragment disclosed herein) specifically binds. The epitopes of protein antigens can be demarcated into "linear epitopes" and "conformational epitopes". As used herein, the term "linear epitope" refers to an epitope formed from a contiguous, linear sequence of linked amino acids. Linear epitopes of protein antigens are typically retained upon exposure to chemical denaturants (e.g., acids, bases, solvents, cross-linking reagents, chaotropic agents, disulfide bond reducing agents) or physical denaturants (e.g. thermal heat, radioactivity, or mechanical shear or stress). In some embodiments, an epitope is non-linear, also referred to as an interrupted epitope. As used herein, the term "conformational epitope" or "non-linear epitope" refers to an epitope formed from noncontiguous amino acids juxtaposed by tertiary folding of a polypeptide. Conformational epitopes are typically lost upon treatment with denaturants. An epitope typically includes at least 3, 4, 5, 6, 7, 8, 9, 10, 11, 12, 13, 14 or 15 amino acids in a unique spatial conformation. In some embodiments, an epitope includes fewer than 25, 24, 23, 22, 21, 20, 19, 18, 17, 16, 15, 14, 13, 12, 11, 10, 9, 8, 7, 6 or 5 amino acids in a unique spatial conformation. Generally, an antibody, or antigen-binding fragment thereof, specific for a particular target molecule will preferentially recognize and bind to a specific epitope on the target molecule within a complex mixture of proteins and/or macromolecules. In some embodiments, an epitope does not include all amino acids of the extracellular domain of CD161 (e.g., human CD161).

Also encompassed by the present disclosure are antibodies that bind to an epitope on CD161 (e.g., human CD161) which comprises all or a portion of an epitope recognized by the particular antibodies described herein (e.g., the same or an overlapping region or a region between or spanning the region).

As used herein, the term "epitope mapping" refers to a process or method of identifying the binding site, or epitope, of an antibody, or antigen binding fragment thereof, on its target protein antigen. Epitope mapping methods and techniques are provided herein.

As used herein, the terms "Fc-mediated effector functions" or "Fc effector functions" refer to the biological activities of an antibody other than the antibody's primary function and purpose. For example, the effector functions of a therapeutic agnostic antibody are the biological activities other than the activation of the target protein or pathway. Examples of antibody effect functions include C1q binding and complement dependent cytotoxicity; Fc receptor binding; antibody-dependent cell-mediated cytotoxicity (ADCC); phagocytosis; down regulation of cell surface receptors (e.g., B cell receptor); lack of activation of platelets that express Fc receptor; and B cell activation. Many effector functions begin with Fc binding to an Fcγ receptor.

As used herein, the term "Fc receptor" refers to a polypeptide found on the surface of immune effector cells, which is bound by the Fc region of an antibody. In some embodiments, the Fc receptor is an Fcγ receptor. There are three subclasses of Fcγ receptors, FcγRI (CD64), FcγRII (CD32) and FγcRIII (CD16). All four IgG isotypes (IgG1, IgG2, IgG3 and IgG4) bind and activate Fc receptors FcγRI, FcγRIIA and FcγRIIIA. FcγRIIB is an inhibitory receptor, and therefore antibody binding to this receptor does not activate complement and cellular responses. FcγRI is a high affinity receptor that binds to IgG in monomeric form, whereas FcγRIIA and FcγRIIA are low affinity receptors that bind IgG only in multimeric form and have slightly lower affinity. The binding of an antibody to an Fc receptor and/or C1q is governed by specific residues or domains within the Fc regions. Binding also depends on residues located within the hinge region and within the CH2 portion of the antibody. In some embodiments, the agonistic and/or therapeutic activity of the antibodies described herein is dependent on binding of the Fc region to the Fc receptor (e.g., FcγR). In some embodiments, the agonistic and/or therapeutic activity of the antibodies described herein is enhanced by binding of the Fc region to the Fc receptor (e.g., FcγR).

As used herein, the term "glycosylation pattern" is defined as the pattern of carbohydrate units that are covalently attached to a protein, more specifically to an immunoglobulin protein. A glycosylation pattern of a heterologous antibody can be characterized as being substantially similar to glycosylation patterns which occur naturally on antibodies produced by the species of the nonhuman transgenic animal, when one of ordinary skill in the art would recognize the glycosylation pattern of the heterologous antibody as being more similar to said pattern of glycosylation in the species of the nonhuman transgenic animal than to the species from which the CH genes of the transgene were derived.

As used herein, the term "human antibody" includes antibodies having variable and constant regions (if present) of human germline immunoglobulin sequences. Human antibodies of the disclosure can include amino acid residues not encoded by human germline immunoglobulin sequences (e.g., mutations introduced by random or site-specific mutagenesis in vitro or by somatic mutation in vivo) (See, e.g., Lonberg et al., (1994) Nature 368(6474): 856-859); Lonberg, (1994) Handbook of Experimental Pharmacology 113: 49-101; Lonberg & Huszar, (1995) Intern. Rev. Immunol. 13:65-93, and Harding & Lonberg, (1995) Ann. N.Y. Acad. Sci. 764:536-546). However, the term "human antibody" does not include antibodies in which CDR sequences derived from the germline of another mammalian species, such as a mouse, have been grafted onto human framework sequences (i.e. humanized antibodies).

As used herein, the term "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

As used herein, the terms "inducing an immune response" and "enhancing an immune response" are used interchangeably and refer to the stimulation of an immune response (i.e., either passive or adaptive) to a particular antigen. The term "induce" as used with respect to inducing CDC or ADCC refer to the stimulation of particular direct cell killing mechanisms.

As used herein, a subject "in need of prevention," "in need of treatment," or "in need thereof," refers to one, who by the judgment of an appropriate medical practitioner (e.g., a doctor, a nurse, or a nurse practitioner in the case of humans; a veterinarian in the case of non-human mammals), would reasonably benefit from a given treatment (such as treatment with a composition comprising an anti-CD161 antibody).

The term "in vivo" refers to processes that occur in a living organism.

As used herein, the term "isolated antibody" is intended to refer to an antibody which is substantially free of other antibodies having different antigenic specificities (e.g., an isolated antibody that specifically binds to human CD161 is substantially free of antibodies that specifically bind antigens other than human CD161). An isolated antibody that specifically binds to an epitope may, however, have cross-reactivity to CD161 proteins from different species (e.g., cynomolgus CD161). However, the antibody continues to display specific binding to human CD161 in a specific binding assay as described herein. In addition, an isolated antibody is typically substantially free of other cellular material and/or chemicals. In some embodiments, a combination of "isolated" antibodies having different CD161 specificities is combined in a well-defined composition.

As used herein, the term "isolated nucleic acid molecule" refers to nucleic acids encoding antibodies or antibody portions (e.g., $V_H$, $V_L$, CDR3) that bind to CD161 (e.g., human CD161), is intended to refer to a nucleic acid molecule in which the nucleotide sequences encoding the antibody or antibody portion are free of other nucleotide sequences encoding antibodies or antibody portions that bind antigens other than CD161 (e.g., human CD161), which other sequences may naturally flank the nucleic acid in human genomic DNA.

As used herein, "isotype" refers to the antibody class (e.g., IgM or IgG1) that is encoded by heavy chain constant region genes. In some embodiments, a human monoclonal antibody of the disclosure is of the IgG1 isotype. In some embodiments, a human monoclonal antibody of the disclosure is of the IgG1 isotype and comprises a mutation of one or more amino acid residues. In some embodiments, the mutation is a substitution at Leu234, Leu235 and Pro329. In some embodiments, the mutation is a substitution of Leu234 to alanine, a substitution of Leu235 to alanine, and a substitution of Pro329 to glycine. In some embodiments, a human monoclonal antibody of the disclosure is of the IgG2 isotype. In some embodiments, a human monoclonal antibody of the disclosure is of the IgG3 isotype. In some embodiments, a human monoclonal antibody of the disclosure is of the IgG4 isotype.

As used herein, the term "isotype switching" refers to the phenomenon by which the class, or isotype, of an antibody changes from one Ig class to one of the other Ig classes.

As used herein, the terms "linked," "fused", or "fusion", are used interchangeably. These terms refer to the joining together of two more elements or components or domains, by whatever means including chemical conjugation or recombinant means. Methods of chemical conjugation (e.g., using heterobifunctional crosslinking agents) are known in the art.

As used herein, "local administration" or "local delivery," refers to delivery that does not rely upon transport of the composition or agent to its intended target tissue or site via the vascular system. For example, the composition may be delivered by injection or implantation of the composition or agent or by injection or implantation of a device containing the composition or agent. Following local administration in the vicinity of a target tissue or site, the composition or agent, or one or more components thereof, may diffuse to the intended target tissue or site.

As used herein, "MHC molecules" refers to two types of molecules, MHC class I and MHC class II. MHC class I molecules present antigen to specific CD8+ T cells and MHC class II molecules present antigen to specific CD4+ T cells. Antigens delivered exogenously to APCs are processed primarily for association with MHC class II. In contrast, antigens delivered endogenously to APCs are processed primarily for association with MHC class I.

As used herein, the term "monoclonal antibody" refers to an antibody which displays a single binding specificity and affinity for a particular epitope. Accordingly, the term "human monoclonal antibody" refers to an antibody which displays a single binding specificity and which has variable and optional constant regions derived from human germline immunoglobulin sequences. In some embodiments, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

As used herein, the term "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

As used herein, the term "nonswitched isotype" refers to the isotypic class of heavy chain that is produced when no isotype switching has taken place; the CH gene encoding the nonswitched isotype is typically the first CH gene immediately downstream from the functionally rearranged VDJ gene. Isotype switching has been classified as classical or non-classical isotype switching. Classical isotype switching occurs by recombination events which involve at least one switch sequence region in the transgene. Non-classical isotype switching may occur by, for example, homologous recombination between human $\sigma_\mu$ and human $\Sigma_\mu$ (δ-associated deletion). Alternative non-classical switching mechanisms, such as intertransgene and/or interchromosomal recombination, among others, may occur and effectuate isotype switching.

As used herein, the term "nucleic acid" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed-base and/or deoxyinosine residues (Batzer et al., Nucleic Acid Res. 19:5081, 1991; Ohtsuka et al., Biol. Chem. 260:2605-2608, 1985; and Cassol et al, 1992; Rossolini et al, Mol. Cell. Probes 8:91-98, 1994). For arginine and leucine, modifications at the second base can also be conservative. The term nucleic acid is used interchangeably with gene, cDNA, and mRNA encoded by a gene.

Polynucleotides used herein can be composed of any polyribonucleotide or polydeoxyribonucleotide, which can be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, the polynucleotide can be composed of triple-stranded regions comprising RNA or DNA or both RNA and DNA. A polynucleotide can also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

As used herein, the term "paratope", also "antigen-binding site" refers to a portion of an antibody, or antigen-binding fragment thereof, which recognizes and binds to an epitope on an antigen, comprising the set of complementarity determining regions (CDRs) located within variable heavy and light chains.

As used herein, "parenteral administration," "administered parenterally," and other grammatically equivalent phrases, refer to modes of administration other than enteral and topical administration, usually by injection, and include, without limitation, intravenous, intranasal, intraocular, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural, intracerebral, intracranial, intracarotid and intrasternal injection and infusion.

As used herein, the term "patient" includes human and other mammalian subjects that receive either prophylactic or therapeutic treatment.

As used herein, the term "percent identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the "percent identity" can exist over a region of the sequence being compared, e.g., over a functional domain, or, alternatively, exist over the full length of the two sequences to be compared. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information website.

As generally used herein, "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

As used herein, a "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt (see, e.g., Berge et al. (1977) *J Pharm Sci* 66:1-19).

As used herein, the terms "polypeptide," "peptide", and "protein" are used interchangeably to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

As used herein, the term "preventing" when used in relation to a condition, refers to administration of a composition which reduces the frequency of, or delays the onset of, symptoms of a medical condition in a subject relative to a subject which does not receive the composition.

As used herein, the term "purified" or "isolated" as applied to any of the proteins (antibodies or fragments) described herein refers to a polypeptide that has been separated or purified from components (e.g., proteins or other naturally-occurring biological or organic molecules) which naturally accompany it, e.g., other proteins, lipids, and nucleic acid in a prokaryote expressing the proteins. Typically, a polypeptide is purified when it constitutes at least 60 (e.g., at least 65, 70, 75, 80, 85, 90, 92, 95, 97, or 99) %, by weight, of the total protein in a sample.

As used herein, the term "rearranged" refers to a configuration of a heavy chain or light chain immunoglobulin locus wherein a V segment is positioned immediately adjacent to a D-J or J segment in a conformation encoding essentially a complete $V_H$ or $V_L$ domain, respectively. A rearranged immunoglobulin gene locus can be identified by comparison to germline DNA; a rearranged locus will have at least one recombined heptamer/nonamer homology element.

As used herein, the term "recombinant host cell" (or simply "host cell") is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

As used herein, the term "recombinant human antibody" includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies comprise variable and constant regions that utilize particular human germline immunoglobulin sequences are encoded by the germline genes, but include subsequent rearrangements and mutations which occur, for example, during antibody maturation. As known in the art (see, e.g., Lonberg (2005) Nature Biotech. 23(9):1117-1125), the variable region contains the antigen binding domain, which is encoded by various genes that rearrange to form an antibody specific for a foreign antigen. In addition to rearrangement, the variable region can be further modified by multiple single amino acid changes (referred to as somatic mutation or hypermutation) to increase the affinity of the antibody to the foreign antigen. The constant region will change in further response to an antigen (i.e., isotype switch). Therefore, the rearranged and somatically mutated nucleic acid molecules that encode the light chain and heavy chain immunoglobulin polypeptides in response to an antigen may not have sequence identity with the original nucleic acid molecules, but instead will be substantially identical or similar (i.e., have at least 80% identity).

As used herein, the term "reference antibody" (used interchangeably with "reference mAb") or "reference antigen-binding protein" refers to an antibody, or an antigen-binding fragment thereof, that binds to a specific epitope on CD161 (e.g., human CD161) and is used to establish a relationship between itself and one or more distinct antibodies. In some embodiments, the relationship is the binding of the reference antibody and the one or more distinct antibodies to the same epitope on CD161 (e.g., human CD161). As used herein, the term connotes an anti-CD161 antibody that is useful in a test or assay, such as those described herein, (e.g., a competitive binding assay), as a competitor, wherein the assay is useful for the discovery, identification or development, of one or more distinct antibodies that bind to the same epitope. In some embodiments, the term reference antibody connotes an anti-CD161 antibody that is useful in a test or assay, as a comparator, wherein the assay is useful for distinguishing characteristics of the antibodies (e.g., toxicity, anti-tumor efficacy). In some embodiments, the reference antibodies described herein include KW1, KW7, KW9, KW17, KM12, or HP-3G10. In some embodiments, the reference antibodies described herein are commercially available anti-CD161 antibodies that include HP-3G10; DX12 (Lanier, et al (1994) *J Immunol* 153:2417-2428); B199.2 (see e.g., Biolegend catalog #MCA1855T); mAB7448 (see e.g., R&D Systems Catalog #MAB7448-SP); 14F1F11 (see e.g., Novus Biologicals Catalog #NBP2-14845); EP7169 (see e.g., Abcam Catalog #ab137059); and 4C6A11 (see, e.g., Abcam Catalog #ab233785).

As used herein, the term "anti-CD161 KW1" (used interchangeably with "KW1") refers to an exemplary anti-CD161 antibody comprising a variable heavy chain ($V_H$) and a variable light chain ($V_L$) comprising the amino acid sequences set forth by SEQ ID NOs: 1 and 152 respectively.

As used herein, the term "anti-CD161 KW7" (used interchangeably with "KW7") refers to an exemplary anti-CD161 antibody comprising a variable heavy chain ($V_H$) and a variable light chain ($V_L$) comprising the amino acid sequences set forth by SEQ ID NOs: 22 and 152 respectively.

As used herein, the term "anti-CD161 KW9" (used interchangeably with "KW9") refers to an exemplary anti-CD161 antibody comprising a variable heavy chain ($V_H$) and a variable light chain ($V_L$) comprising the amino acid sequences set forth by SEQ ID NOs: 43 and 152 respectively.

As used herein, the term "anti-CD161 KW17" (used interchangeably with "KW17") refers to an exemplary anti-CD161 antibody comprising a variable heavy chain ($V_H$) and a variable light chain ($V_L$) comprising the amino acid sequences set forth by SEQ ID NOs: 61 and 245 respectively.

As used herein, the term "anti-CD161 KM12" (used interchangeably with "KM12") refers to an exemplary anti-CD161 antibody comprising a variable heavy chain ($V_H$) and a variable light chain ($V_L$) comprising the amino acid sequences set forth by SEQ ID NOs: 88 and 152 respectively.

As used herein, the term "anti-CD161 HP-3G10" (used interchangeably with "HP-3G10") refers to an exemplary murine-derived anti-human CD161 monoclonal antibody (see, e.g., Marquez et al (1998) *Blood* 91:2760-2771).

As used herein, the terms "specific binding," "selective binding," "selectively binds," and "specifically binds," refer to antibody binding to an epitope on a predetermined antigen. Typically, the antibody binds with an equilibrium dissociation constant ($K_D$) of approximately less than $10^{-6}$ M, such as approximately less than $10^{-7}$, $10^{-8}$M, $10^{-9}$ M or $10^{-10}$ M or even lower when determined by a binding assay described herein (e.g., a flow cytometry based assay measuring binding of an anti-CD161 antibody to human CD161 expressed on a cell surface). The antibody further binds with a binding affinity ($K_D$) that is at least 2-fold, at least 3-fold, at least 4-fold, at least 5-fold, at least 6-fold, at least 7-fold, at least 8-fold, at least 9-fold, or at least 10-fold lower than its binding affinity ($K_D$) to a non-specific antigen other than the predetermined antigen or a closely-related antigen. The phrases "an antibody recognizing an antigen" and "an antibody specific for an antigen" are used interchangeably herein with the term "an antibody which binds specifically to an antigen."

As used herein, the term "switch sequence" refers to those DNA sequences responsible for switch recombination. A "switch donor" sequence, typically a µ switch region, will be 5' (i.e., upstream) of the construct region to be deleted during the switch recombination. The "switch acceptor" region will be between the construct region to be deleted and the replacement constant region (e.g., 7, e, etc.). As there is no specific site where recombination always occurs, the final gene sequence will typically not be predictable from the construct.

As used herein, the term "subject" includes any human or non-human animal. For example, the methods and compositions of the present invention can be used to treat a subject with an immune disorder. The term "non-human animal" includes all vertebrates, e.g., mammals and non-mammals, such as non-human primates, sheep, dog, cow, chickens, amphibians, reptiles, etc.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

The percent identity between two sequences is a function of the number of identical positions shared by the sequences (i.e., % homology=#of identical positions/total #of positions x 100), taking into account the number of gaps, and the length of each gap, which need to be introduced for optimal alignment of the two sequences. The comparison of sequences and determination of percent identity between two sequences can be accomplished using a mathematical algorithm known in the art.

The percent identity between two nucleotide sequences can be determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present disclosure can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See http://www.ncbi.nlm.nih.gov.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

The nucleic acid compositions of the present disclosure, while often in a native sequence (except for modified restriction sites and the like), from either cDNA, genomic or mixtures thereof may be mutated, in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

As used herein, the term "tumor microenvironment" (alternatively "cancer microenvironment"; abbreviated TME) refers to the cellular environment or milieu in which the tumor or neoplasm exists, including surrounding blood vessels as well as non-cancerous cells including, but not limited to, immune cells, fibroblasts, bone marrow-derived inflammatory cells, and lymphocytes. Signaling molecules and the extracellular matrix also comprise the TME. The tumor and the surrounding microenvironment are closely related and interact constantly. Tumors can influence the microenvironment by releasing extracellular signals, promoting tumor angiogenesis and inducing peripheral immune tolerance, while the immune cells in the microenvironment can affect the growth and evolution of tumor cells.

As used herein, the term "T cell" refers to a type of white blood cell that can be distinguished from other white blood cells by the presence of a T cell receptor on the cell surface. There are several subsets of T cells, including, but not limited to, T helper cells (a.k.a. $T_H$ cells or CD4$^+$ T cells) and subtypes, including $T_H1$, $T_H2$, $T_H3$, $T_H17$, $T_H9$, and $T_{FH}$ cells, cytotoxic T cells (i.e., Tc cells, CD8$^+$ T cells, cytotoxic T lymphocytes, T-killer cells, killer T cells), memory T cells and subtypes, including central memory T cells ($T_{CM}$ cells), effector memory T cells ($T_{EM}$ and $T_{EMRA}$ cells), and resident memory T cells ($T_{RM}$ cells), regulatory T cells (a.k.a. $T_{reg}$ cells or suppressor T cells) and subtypes, including CD4$^+$ FOXP3$^+$ $T_{reg}$ cells, CD4$^+$FOXP3$^-$ $T_{reg}$ cells, Tr1 cells, Th3 cells, and $T_{reg}17$ cells, natural killer T cells (a.k.a. NKT cells), mucosal associated invariant T cells (MAITs), and gamma delta T cells (γδ T cells), including Vγ9/Vδ2 T cells. Any one or more of the aforementioned or unmentioned T cells may be the target cell type for a method of use of the invention.

As used herein, the term "T cell activation" or "activation of T cells" refers to a cellular process in which mature T cells, which express antigen-specific T cell receptors on their surfaces, recognize their cognate antigens and respond by entering the cell cycle, secreting cytokines or lytic enzymes, and initiating or becoming competent to perform cell-based effector functions. T cell activation requires at least two signals to become fully activated. The first occurs after engagement of the T cell antigen-specific receptor (TCR) by the antigen-major histocompatibility complex (MHC), and the second by subsequent engagement of co-stimulatory molecules (e.g., CD28). These signals are transmitted to the nucleus and result in clonal expansion of T cells, upregulation of activation markers on the cell surface, differentiation into effector cells, induction of cytotoxicity or cytokine secretion, induction of apoptosis, or a combination thereof. Methods of inducing activation of isolated T cells (e.g., human T cells isolated from peripheral blood mononuclear cells) are known in the art and further described in the Examples, and include activation by immobilized anti-CD3 and anti-CD28 antibodies (e.g., bead-immobilized anti-CD3 and/or anti-CD28 antibodies), wherein the anti-CD3 antibody provides engagement of the TCR and the anti-CD28 antibody provides engagement of the co-stimulatory receptor CD28.

As used herein, the term "T cell-mediated response" refers to any response mediated by T cells, including, but not limited to, effector T cells (e.g., CD8$^+$ cells) and helper T cells (e.g., CD4$^+$ cells). T cell mediated responses include, for example, T cell cytotoxicity and proliferation.

As used herein, the terms "therapeutically effective amount" or "therapeutically effective dose," or similar terms used herein are intended to mean an amount of an agent (e.g., an anti-CD161 antibody or an antigen-binding fragment thereof) that will elicit the desired biological or medical response (e.g., an improvement in one or more symptoms of a cancer).

As used herein, the terms "treat," "treating," and "treatment," as used herein, refer to therapeutic or preventative measures described herein. The methods of "treatment" employ administration to a subject, in need of such treatment, a human antibody of the present disclosure, for example, a subject in need of an enhanced immune response against a particular antigen or a subject who ultimately may acquire such a disorder, in order to prevent, cure, delay, reduce the severity of, or ameliorate one or more symptoms of the disorder or recurring disorder, or in order to prolong the survival of a subject beyond that expected in the absence of such treatment.

As used herein, the term "unrearranged" or "germline configuration" refers to the configuration wherein the V segment is not recombined so as to be immediately adjacent to a D or J segment.

As used herein, the term "vector" is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

Unless otherwise defined, all technical and scientific terms used herein have the same meaning as commonly understood by one of ordinary skill in the art to which this disclosure pertains. Preferred methods and materials are described below, although methods and materials similar or equivalent to those described herein can also be used in the practice or testing of the presently disclosed methods and compositions. All publications, patent applications, patents, and other references mentioned herein are incorporated by reference in their entirety.

EXAMPLES

Example 1: Single-Cell RNA Sequencing (scRNA-Seq) for Measuring Transcriptional Signatures of Clonally-Expanded Infiltrating T Cells in Human Glioblastoma Tumors Diffuse gliomas are the most common type of primary human brain tumor. In adults, diffuse gliomas are subdivided into three main entities defined by mutational spectrum, histopathology, and copy-number aberrations: (I) glioblastoma, isocitrate dehydrogenase (IDH) wildtype (IDHwt-GBM) or (IIa) astrocytoma, IDH-mutant and (IIb) oligodendroglioma, IDH-mutant, 1p/19q co-deleted (collectively IIa-b: IDHmut glioma). Current therapeutic approaches (e.g., surgery, radiation, and/or chemotherapy) largely fail to prevent relapse in all classes of diffuse gliomas, likely due to the genetic and cellular heterogeneity of malignant cells (Neftel, et al (2019) *Cell* 178:835-849; Patel, et al (2014) *Science* 344:1396-1401; Venteicher et al. (2017) *Science* 355: eaai8478). Endogenous or therapy-induced T cell responses have the potential to target a diverse set of tumor antigens, offering the possibility of treating highly heterogenous tumors like diffuse gliomas through T cell-mediated immunity. However, cancer cells evade immune detection by modulating the function of T cells, often through the expression of cell surface proteins that inhibit T cell recognition and/or activation. For example, infiltrating T cells in diffuse gliomas have been shown to express several inhibitory receptors, including PD-1, CTLA-4, and LAG-3 (Woroniecka et al. (2018) *Clin Cancer Res* 24:4175-4186), that likely contribute to immunosuppression of infiltrating T cells in these tumors.

To better understand mechanisms of T cell suppression, single-cell RNA-sequencing (scRNA-seq) was used to evaluate the expression profiles of CD3$^+$ T cells isolated from surgically resected glioblastoma tumors obtained from 26 patients (11 IDHwt-GBM and 15 IDHmut-glioma patients). Analysis of gene expression profiles by scRNA-seq in tumor infiltrating T cells isolated from human glioma tissues samples is further described in WO/2019/094983, the entire contents of which are expressly incorporated herein by reference.

To obtain T cells, resected glioma specimens were processed into single cell suspensions using an enzymatic brain dissociation kit (Miltenyi Biotec, Bergisch Gladbach, Germany) following the manufacturer's protocol. Fc receptor blocking was performed on the total cell suspension using Human TruStain FcX reagent (Biolegend, San Diego, Calif.). Cell suspensions were stained for flow cytometry using antibodies specific for CD44 [HI30]-BV605, CD3 [HIT3a]-BV510, PD-1 (CD279) [MIH4]-PE, CD161 [DX12]-BV421, CD45 [REA747]-VioBlue, and CD3 [BW264/56]-PE. Exclusion labeling was also performed using APC-labeled antibodies to CD14 [63D3], CD64 [10.1], CD163 [GHI/61], CD15 [H198], and CD66b [G10F5]. The cells were labeled with calcein AM as a live/dead marker. Live, single T cells (gating: calcein AM positive, exclusion negative, CD45 positive, CD3 positive) were sorted into individual wells of a 96-well twin.tec PCR plate (Eppendorf; Hamburg, Germany) that contained RLT buffer (Qiagen, Venlo, Netherlands) using a BD Biosciences Aria III sorter. Plates were centrifuged and frozen. Subsequently, the cells were profiled by full-length scRNA-Seq.

Single cell cDNA and sequencing libraries were prepared for scRNA-seq analysis using previously established methods (see, e.g., the SMART-seq2 method described by Picelli, et al (2014) *Nat. Protoc.* 9:171-181). Libraries were tagmented and enriched with dual indexes using Illumina Nextera XT Library Prep kits. Libraries from 384 or 786 cells with unique indexes were pooled together and sequenced at 2 pM on an Illumina Nextseq 500 sequencer, yielding paired-end 38 base pair reads.

The sequencing data from raw reads was processed to provide gene expression matrices using established methods (see, e.g., Tirosh, et al. (2016) *Nature* 539:309-313). Bcl2fastq conversion software (Illumina, San Diego, Calif.) was used to demultiplex sequencing data and generate FASTQ files for data analysis. The files comprising paired-end scRNA-seq reads were aligned to the human transcriptome using Bowtie (v0.12.7) (see, e.g., Langmead, et al (2009) *Genome Biol* 10:R25). The gene expression levels from these alignments were obtained using RSEM (v1.2.19) software in paired-end mode and quantified using transcripts-per-million (TPM) values. The total transcripts per cell was normalized to one-hundred thousand (TP100K), as this is the estimated complexity of single-cell libraries prepared by SMART-Seq2, then log-transformed to report gene expression as $E=\ln(TP100K+1)$. For each cell, a gene was considered as detected if TP100K>0. All cells with <500 or >7,500 unique genes detected were excluded. In addition, cells with fewer than 20 housekeeping genes detected were excluded, using a curated gene set previously described (see, e.g., Tirosh et al (2016) *Nature* 539:309-313). Graph-based clustering was used to identify cell types and states and a small percentage of cells (8%) were removed, including B cells, NK cells, myeloid cells, astrocytes, and cell doublets that had been flow-sorted with the T cells. Within the remaining T cells, a small percentage (2%) were excluded that did not follow regular T cell classification: either cycling T cells that expressed CD4 and CD8, or expressed neither, or Tregs that expressed CD8. Positive gene expression was defined as $\ln(TP100K+1)>1$ and negative gene expression was defined as $\ln(TP100K+1)<1$. After quality control filtering, 8,252 T cells from 27 glioma samples, with a total of 22,448 genes detected in at least one cell, were retained for subsequent analyses.

To identify novel genes and programs that contribute to T cell function, scRNA-seq transcripts were used to reconstruct T cell receptor (TCR) sequences and identify clonally expanded T cell populations which may have proliferated in response to tumor antigen recognition. The TCR $\alpha$ and $\beta$ chain sequences from the single cell RNA-seq data were computationally reconstructed for each T cell using reconstruction of TCR sequences from scRNA-seq data (TraCeR) software (v0.6.0) (see, e.g., Stubbington, et al (2016) *Nat Methods* 13:329-332). The software comprises computational methods that allow reconstruction of sequences of rearranged and expressed TCR genes from scRNA-seq data. The TCR sequences are then used to identify cells that have the same receptor sequences and are thus derived from the same original clonally-expanded T cell. A T cell was classified as having a reconstructed TCR if it was possible to reconstruct productive sequences for $\alpha$ and/or $\beta$ chains and clonotypes could be defined based upon grouping T cells that shared an identical $\alpha$ and/or $\beta$ chains.

Based upon these criteria, full-length, productive TCR sequences (α and/or β chains) were detected for 4,630 of 8,252 T cells. A substantial number of distinct clonotypes (≥2 sequenced T cells with the same TCR sequences) were identified in most patient samples (ranging between approximately 2 and 33 clonotypes per tumor) and positively correlated to the overall proportion of cells with reconstructed TCRs (FIG. 1A). Additionally, a substantial fraction of T cells belonged to detectable clones, ranging from 4% to greater than 60% of T cells with a reconstructed TCR in a given tumor.

Example 2: KLRB1 is Highly Expressed in Clonally Expanded CD8 T Cells in Primary Human Glioblastoma as Determined by scRNA-Seq Analysis Analyzing the expression patterns of clonal T cells as described in Example 1 allowed identification of four major clusters: CD8 T cells, CD4 conventional T cells (CD4 $T_{conv}$), CD4 regulatory T cells ($T_{reg}$), and cycling T cells that did not vary between IDHwt-GBM and IDHmut-gliomas based on expression of cluster-related marker genes (data not shown). However, distinct expression features were identified between non-clonal cells (defined as singleton cells with detectable TCR) and clonal T cells. Specifically, for each gene, the mean or variance in gene expression was compared between clonal and non-clonal CD8 T cells or CD4 $T_{conv}$ cells for IDHwt-GBM and IDHmut-gliomas.

Quantification of Gene Expression and Variability from scRNA-Seq

To quantify gene expression, the mean expression value of each gene was evaluated for all T cells from all clonotypes in each tumor sample. In parallel, for each clonotype in a given patient tumor sample, the gene expression values were measured from random sets of non-clonal cells. These sets came from the same tumor as the corresponding clonotypes, had the same number of cells as the corresponding clonotypes, and each cell in the set had a reconstructed (singleton) TCR. For each clonotype in each tumor, 10 random sets of non-clonal cells were selected. For each gene, the mean of its expression values across all random sets of non-clonal cells from all tumors was determined. Finally, for each gene, the mean expression in non-clonal cells was subtracted from mean expression in clonal cells.

Expression variability was determined in a conceptually similar manner. To quantify variability of each gene, the $L_1$ distance was used, which is defined as the absolute difference in expression of a gene in clone x relative to it expression in clone y. For each gene, the mean of all $L_1$ distances between all pairs of clones x and y from the same clonotype, using clonotypes collected from all patient tumors, was determined. The resulting variability was divided by the gene mean expression to get a coefficient of variation (CV). The difference in CV values between clonal and non-clonal cells was obtained, with non-clonal cells defined as described above. Genes were excluded with low mean expression in both the clonal and non-clonal cells (ln(TP100K+1)<0.1) as these genes would inflate CV values and not be reliably quantified.

For each gene, to test whether the differences in mean expression or CV were significantly different between clonal and non-clonal cells, a background distribution was simulated. The expression values between clonal and non-clonal cells were shuffled for each gene, and the differences in mean expression and CV were calculated for the shuffled expression data. This randomization was repeated 100 times for each gene, and a z-score was calculated of the observed differences relative to the simulated, background distribution. If the magnitude of the z-score was greater than 3, the observed difference in the actual data was deemed more extreme than any of the values in the simulated, background distribution.

Figure 1C:
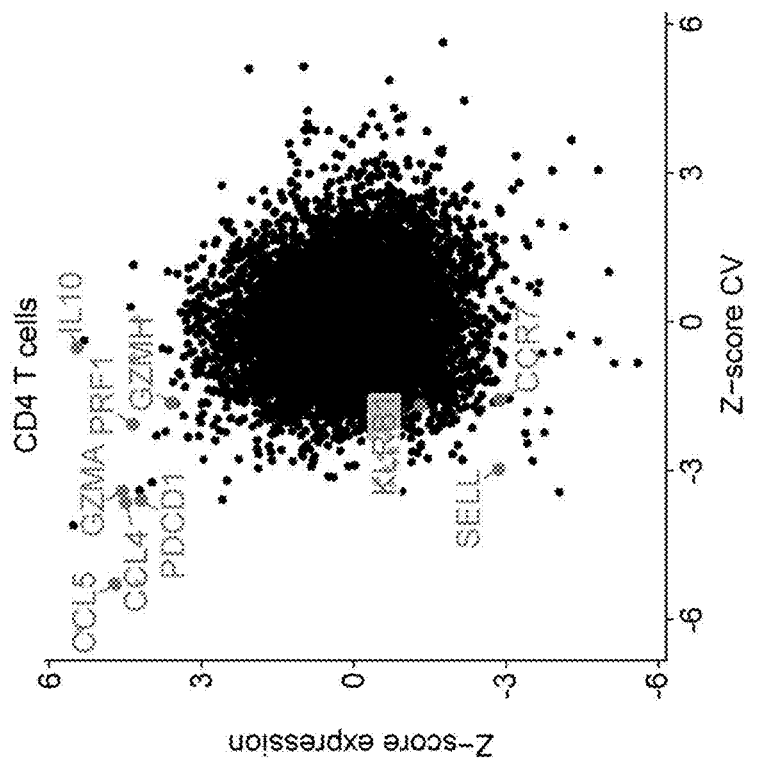
FIGS. 1B-1C provide graphs showing mean expression (Z-score of expression) versus variance of expression (Z-score of coefficient of variation (CV) of expression) between clonally-expanded and non-clonal T cells for genes measured by single-cell RNA sequencing (scRNA-seq) in CD8 T cells (FIG. 1B) or CD4 T cells (FIG. 1C) that were isolated from IDHwt-GBM tumors.
Figure 1B:
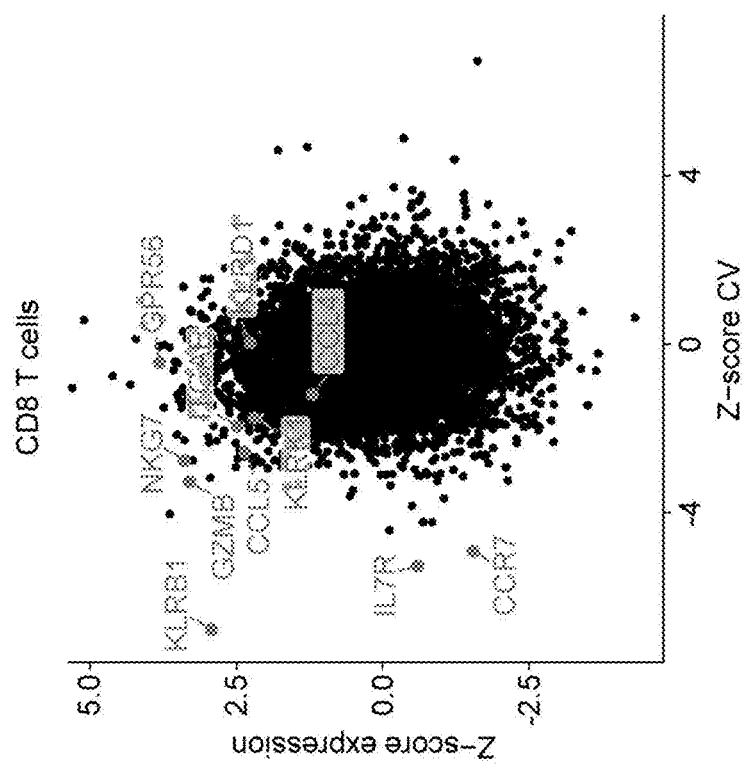

Shown in FIGS. 1B-1C is a comparison of expression for each gene in clonal versus non-clonal CD8 T cells (FIG. 1B) and $CD4_{conv}$ T cells (FIG. 1C) from IDHwt-GBM tumors. Z-score of expression (y-axis) and Z-score for CV of expression (x-axis) is shown for each gene. Clonal CD8 T cells had higher expression of cytotoxicity genes (GZMB, NKG7) and NK receptors (KLRB1, KLRD1) than non-clonal cells in IDHwt-GBM (FIG. 1B). In particular, KLRB1 expression was both higher and less variable in clonal T cells compared to non-clonal T cells in IDHwt-GBM. It was also less variable in clonal CD8 T cells compared to non-clonal cells in IDHmut-gliomas (data not shown). KLRB1 encodes the CD161 protein that was previously shown to inhibit NK cell-mediated cytotoxicity following binding to CLEC2D (Aldemir, et al (2005) *J Immunol* 175:7791-7795; Rosen, et al (2005) *J Immunol* 175:7796-7799). Clonal CD4 T cells more highly expressed several cytotoxicity genes (PRF1, GZMA, GZMH) and chemokine genes (CCL4 and CCL5) (FIG. 1C).

Example 3: Expression of CD161 Receptor by T Cells and CLEC2D Ligand by Malignant and Myeloid Cells in Diffuse Gliomas The expression of certain NK cell receptors by IDHwt-GBM-infiltrating T cells was measured by flow cytometry. Specifically, human IDHwt-GBM tissue was dissociated into a single cell suspension and Fc blocked prior to antibody staining as described in Example 1. Cells were stained with antibodies against the following targets:

| CD45 [HI30]-PacificBlue | TIGIT [A15153G]-PE/Cy7 | NKG2c [REA205]-PE |
|---|---|---|
| CD8α [HIT8a]-AlexaFluor488 | CD279 (PD-1) [EH12.2H7]-APC | NKp80 [239127]-AlexaFluor750 |
| CD4 [OKT4]-AlexaFluor700 | CD3 [HIT3a]-BV510 | Zombie NIR |
| CD16 [3G8]-BV750 | CD161 {DX12]-BV421 | |
| CD25 [BC96]-BV605 | CD56 [CMSSB]-PerCP/eFluor710 | |

Figure 2B:
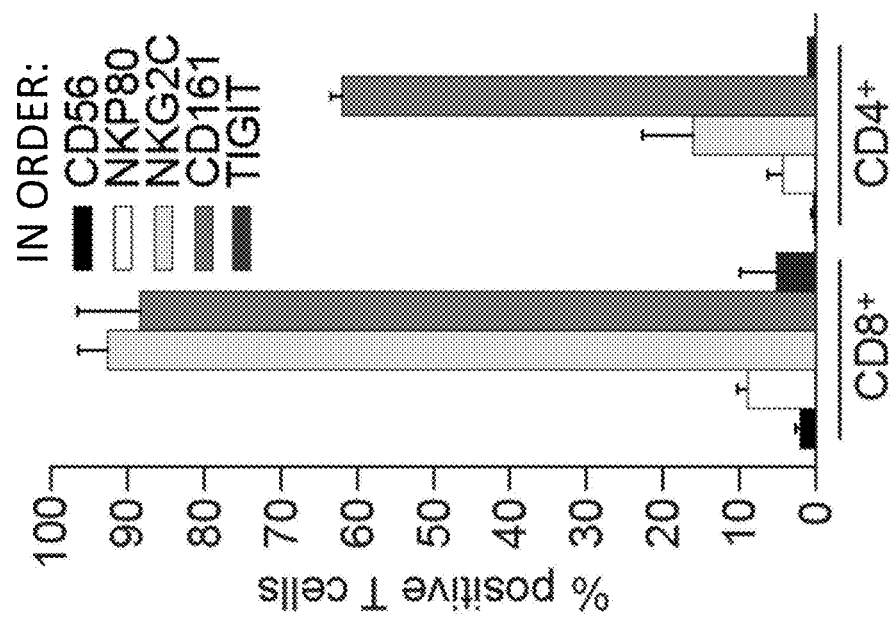
FIG. 2B provides a bar graph quantifying expression of NK cell receptors in tumor-infiltrating CD8 and CD4 T cells from two IDHwt-GBM patients as measured by flow cytometry.
Figure 2A:
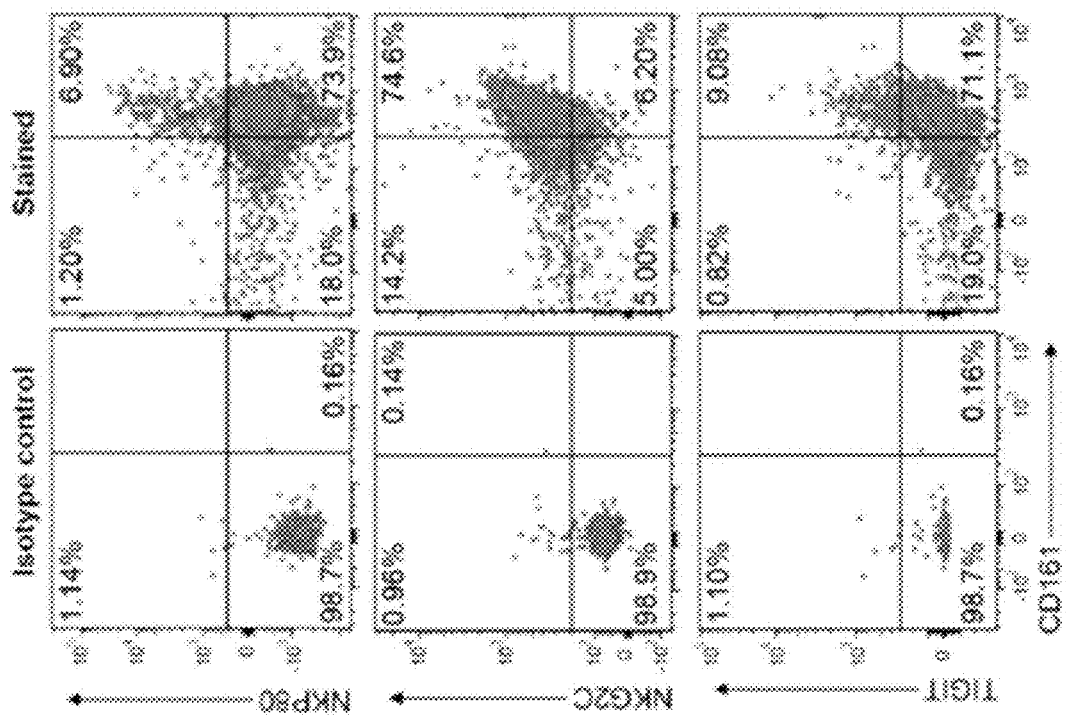
FIG. 2A provides plots depicting flow cytometry analysis of NK cell receptors in IDHwt-GBM infiltrating CD8 T cells from one patient, with CD161 (i.e., KLRB1 gene product) expression level (x-axis) shown relative to NKP80 (top), NKG2C (middle) and TIGIT (bottom) expression levels (y-axis). Shown are cells stained with antibodies against the NK cell receptors (right column) and cells stained with antibody isotype controls to measure background staining (left column).

Samples were analyzed on a Sony SP6800 spectral analyzer using a 32-channel photomultiplier tube (fluorescence emission 500-800 nm). The signals from each fluorophore were unmixed mathematically by spectral shape using an algorithm based upon the least squares method. Cells were gated on live (ZombieNIR negative), CD45 positive, CD3 positive, and CD8 or CD4 positive populations Cells were further analyzed for labeling by antibodies against CD161, as well as PD-1, TIGIT, CD56, NKG2C, NKG2C, and NKp80 receptors. Shown in FIG. 2A is flow cytometric analysis of IDHwt-GBM-infiltrating CD8 T cells from one patient for protein levels of CD161 (x-axis), NKp80, NKG2C, and TIGIT (y-axis, top, middle and bottom respectively). A summary of protein expression of NK receptors for both CD8 and CD4 T cells isolated from two human IDHwt-GBM tumors is shown in FIG. 2B. Both CD8 and CD4 T cells were mostly negative for the CD56 NK cell marker. However, the inhibitory CD161 receptor (encoded by KLRB1) and the activating NKG2C/CD94 receptor (encoded by KLRC2 and KLRD1) were expressed by a substantial population of CD8 T cells, while the activating NKp80 (encoded by KLRF1) and inhibitory TIGIT (encoded by TIGIT) receptors were detected on a smaller subset of cells. The inhibitory CD161 receptor was also expressed by a majority of CD4 T cells (FIG. 2B).

Figure 2D:
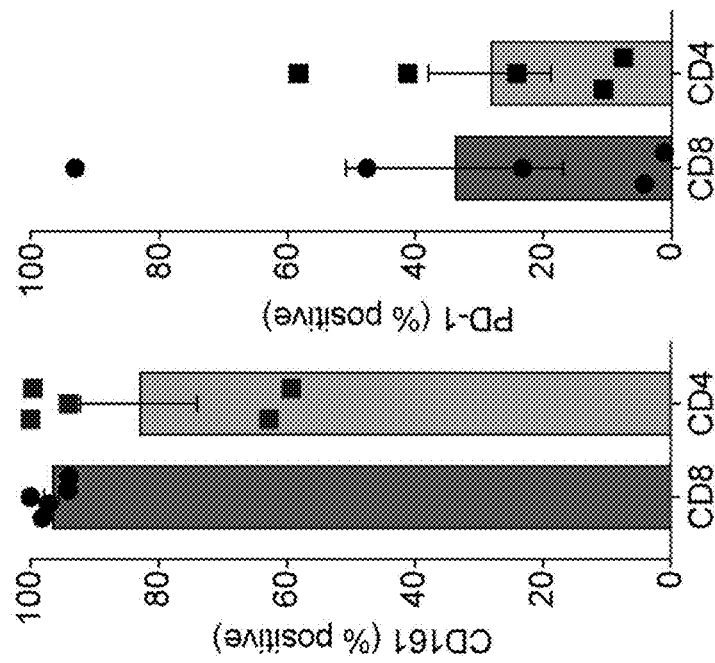
FIG. 2D provides bar graphs quantifying CD161 and PD-1 positive CD8 and CD4 T cells from five IDHwt-GBM tumors. Error bars denote SEM.
Figure 2C:
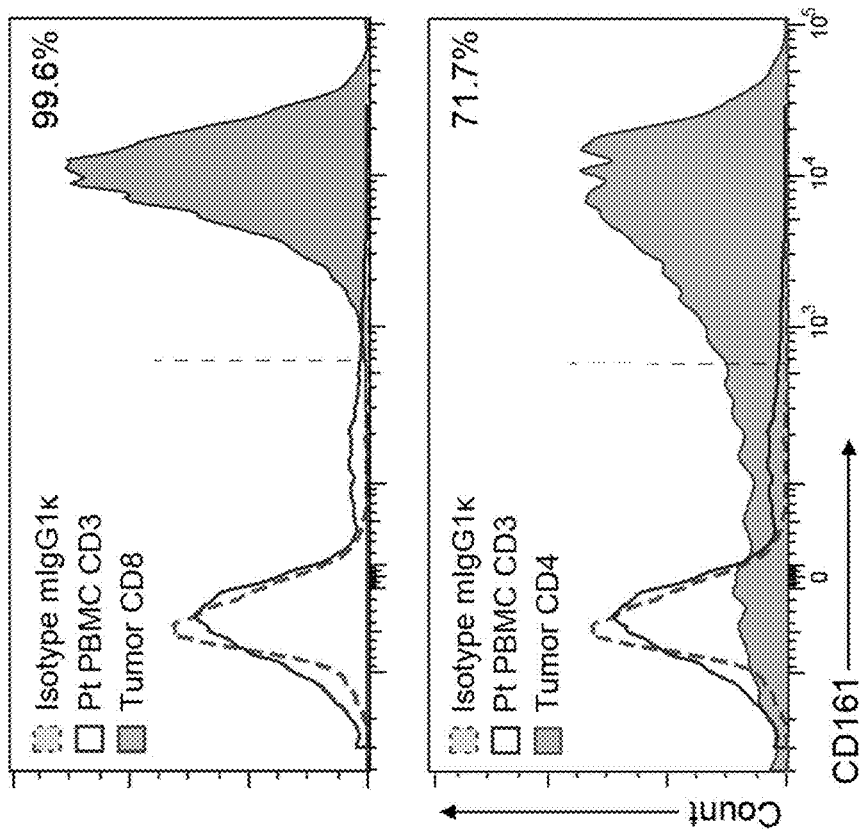
FIG. 2C provides histograms quantifying expression of CD161 protein expression in CD8 T cells (top) and CD4 T cells (bottom) in IDHwt-GBM tumor (filled line) relative to blood from the same patient (solid line) as measured by flow cytometry. Dotted line shows background staining determined by staining with isotype control antibody.

Additionally, flow cytometry showed that a large fraction of CD8 T cells and the majority of CD4 T cells were CD161 positive, while CD161 was detected in only a small subset of blood T cells from the same patients (FIG. 2C). The proportion of CD161 positive T cells was substantially larger (P<0.005, Mann-Whitney U test) and less variable (P<0.001, F-test) than that of PD-1 positive T cells when quantified across five IDHwt-GBM tumors (FIG. 2D).

Glioma cells express CLEC2D mRNA and protein (Roth et al (2007) *Cancer Res* 67:3540-3544). Therefore, it was hypothesized that the CD161 receptor inhibits activation of T cell populations in diffuse gliomas following engagement of CLEC2D ligand. To validate this hypothesis, CLEC2D mRNA transcript levels were quantified in malignant cells, myeloid cells and oligodendrocytes from published scRNA-seq datasets prepared from cohorts of IDHmut-astrocytoma, IDHmut-oligodendroglioma, and IDHwt-GBM (Neftel, et al (2019) *Cell* 178:835-849; Tirosh et al (2016) *Nature* 539: 309-313; Venteicher et al (2017) *Science* 355:eaai8478). CLEC2D mRNA was found to be expressed in both malignant cells and microglia/macrophage, but not oligodendrocytes, across glioma subsets (data not shown).

Expression of KLRB1 by T cells and CLEC2D by tumors cells was further assessed using in situ hybridization. Paraffin-embedded tissue sections from human tumors (two IDHwt-GBM and two IDHmut-glioma tumors) mounted on glass slides were stained using the RNAscope 2.5 HD Duplex Detection Kit (Advanced Cell Diagnostics, Cat. No. 322430). Slides were baked for 1 hour at 60° C., deparaffinized and dehydrated with xylene and ethanol. The tissues were pretreated with RNAscope hydrogen peroxide (Advanced Cell Diagnostics, Cat. No. 322335) for 10 minutes at room temperature and RNAscope Target retrieval reagent (Advanced Cell Diagnostics, Cat. No. 322000) for 15 minutes at 98° C. RNAscope Protease Plus (Advanced Cell Diagnostics, Cat. No. 322331) was then applied to the tissue for 30 minutes at 40° C. Hybridization probes were prepared by diluting the C2 probe (red) at 1:40 into the C1 probe (green). Advanced Cell Technologies RNAscope Target Probes used included Hs-CD3E (Cat. No. 553971-C2); Hs-KLRB1 (Cat. No. 509031), Hs-Hs-PTPRC (Cat. No. 601991-C2), Hs-NPM1-X-CLEC2D (Cat. No. 419751). Probes were added to the tissue and hybridized for 2 hours at 40° C. A series of 10 amplification steps were performed according to the manufacturer's protocol. Tissue was counterstained with Gill's hematoxylin for 25 seconds at room temperature followed by mounting with VectaMount media (Vector Laboratories). The in situ hybridization confirmed KLRB1 was expressed in populations of CD3E positive T cells and that CLEC2D mRNA was expressed primarily in cells with cytonuclear atypia that represent malignant cells, but also in CD45 positive immune cells (data not shown).

Example 4: Inactivation of KLRB1 Gene Expression Enhances Cytokine Production by Human T Cells and Improves Survival in a Humanized Glioma Mouse Model To evaluate if CLEC2D-expressing tumor cells can inhibit T cells expressing CD161, a co-culture system was established. The co-culture comprised primary human T cells that were gene-edited using CRISPR/Cas9 methods to inactivate KLRB1 expression and further transfected with a NY-ESO-1 specific TCR. The response of KLRB1-inactivated T cells to glioblastoma target cells was evaluated relative to equivalent T cells with endogenous expression of KLRB1.

CD161-expressing T cells (negative for Vα7.2, a marker for mucosal associated invariant T cells or MAIT cells) were isolated from peripheral blood samples of healthy donors. Specifically, primary human T cells were isolated from fresh leukophoresis blood collars. PBMCs were isolated by density gradient centrifugation. T cells were then isolated using the Human T cell isolation kit (EasySep #17951) per the manufacturer's protocol. Human T cells were maintained in vitro in RPMI-1640 medium supplemented with 9% fetal bovine serum, 1% human serum, 50 U/mL penicillin/streptomycin, 5 mM HEPES, 2 mM Glutamax, 5 mM non-essential amino acids, 5 mM sodium pyruvate, 50 μM β-mercaptoethanol, and 30 U/mL of recombinant human IL-2 (Peptrotech, Rocky Hill, N.J.). CD161+Vα7.2-T cells were isolated by FACS using an Aria III (BD Biosciences) after blocking Fc receptors and staining with antibodies specific for CD3 [HIT3a]-APC, CD161 [HP-3G10]-PerCP-Cy5.5, Vα7.2 [3C10]-BV786. Following sorting, T cells were expanded for three days using αCD3/αCD28 coated human Dynabeads (ThermoFisher Scientific, Waltham, Mass.) at a bead to cell ratio of 1:1 in the presence of IL-2 (30 U/mL).

Figure 3A:
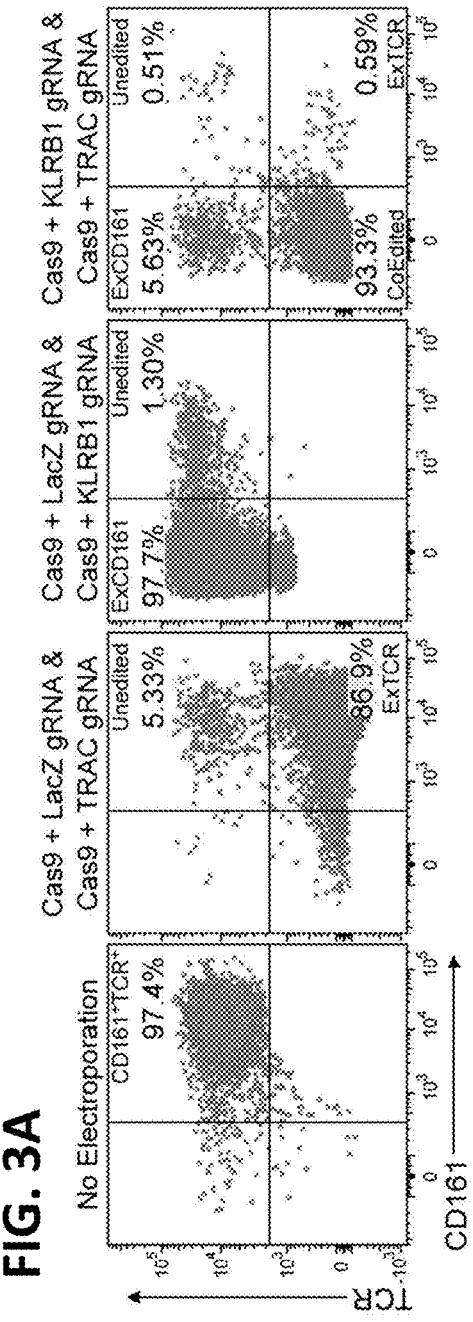
FIG. 3A provides dot plots quantifying CD161 expression (x-axis) relative to expression of endogenous TCR (y-axis) in FACS-purified CD161-positive human T cells that were either unedited (no electroporation; left panel) or gene-edited by electroporation with Cas9 protein and bound gRNAs, using gRNAs targeting LacZ (editing control) and TRAC (panel second from left), gRNAs targeting LacZ and KLRB1 (panel second from right), or gRNAs targeting KLRB1 and TRAC (right panel) as measured by flow cytometry at three days post-editing.

To inactivate KLRB1 gene expression, T cells were electroporated with ribonucleoproteins (RNPs) comprising Cas9 and gRNA targeting the TRAC and either KLRB1 or the control gene LacZ. Sequences of gRNAs are depicted in Table 2. The gRNAs comprised a crisprRNA (crRNA) targeting TRAC, KLRB1, or LacZ and a tracrRNA and were prepared by incubating the crRNA and tracrRNA at equimolar concentrations at 95° C. for 5 minutes, then cooled to room temperature. The RNPs were prepared by incubating gRNA at a final concentration of 60 μM with Cas9 protein at a final concentration of 20 μM for 15 minutes at 37° C. The Cas9 protein comprised two nuclear localization signals (Cas9-NLS, QB3 Macrolab). As shown in FIG. 3A, gene-editing resulted in inactivation of KLRB1 and inactivation of endogenous TCR (TRAC) expression with >90% efficiency compared to unedited T cells.

TABLE 2

| gRNAs used for gene-disruption in human T cells | | |
|---|---|---|
| Name/ Description | Sequence (PAM of target gene sequence underlined) | SEQ ID NO |
| TRAC gRNA spacer | UCAGGGUUCUGGAUAUCUGU | 350 |
| TRAC target gene | TCAGGGTTCTGGATATCTGT<u>GGG</u> | 351 |
| KLRB1 gRNA spacer | AAUUAAAGCCACUUACCCCG | 352 |
| KLRB1 target gene | AATTAAAGCCACTTACCCCG<u>AGG</u> | 353 |
| LacZ gRNA spacer | GCUGAGCGCUCGGAGCGCCU | 354 |
| LacZ target gene | GCTGAGCGCTCGGAGCGCCT | 355 |

Following electroporation, cells were expanded using fresh Dynabeads and IL-2 for an additional three days. The cells were then transfected to induce expression of a NY-ESO-1 TCR that is specific to the 1G4 epitope (nucleotide sequence set forth in SEQ ID NO: 369; amino acid sequence set forth in SEQ ID NO: 392) when presented by HLA-A2.1. Plasmid sequence of the NY-ESO-1 TCR is depicted in Table 3. To induce NY-ESO-1 [1G4] TCR expression in harvested primary human T cells, HA and PC epitope tags were placed at the N-terminus of the mature TCR α and β chains, respectively, of the NY-ESO-1 [1G4] TCR cDNA (see, e.g., Robbins, et al (2008) *J. Immunol.* 180:6116-6131). SEQ ID NOs of components of the NY-ESO-1 TCR plasmid are provided in Table 3. cDNA was gel purified and inserted into a pHAGE-MCS lentiviral vector backbone under control of an EF-1α promoter using NheI and ClaI restriction enzymes. T cells were then transfected with NY-ESO-1 TCR [1G4] lentivirus. Labeling of transduced, unsorted T cells with antibodies against the PC and HA epitope tags enabled verification of expression of both 1G4 TCRα and β chains respectively (data not shown).

TABLE 3

Plasmid sequences and sequence components of NY-ESO-1 TCR and NY-ESO-1 peptide constructs

| Name | Nucleic acid SEQ ID NO |
|---|---|
| Full-length NY-ESO-1 TCR construct | 356 |
| Kozak sequence | 357 |
| NY-ESO-1 TCR alpha chain signal peptide | 358 |
| HA tag | 359 |
| NY-ESO-1 TCR alpha chain variable region | 360 |
| NY-ESO-1 TCR alpha chain constant region | 361 |
| T2A skip peptide | 362 |
| NY-ESO-1 TCR beta chain signal peptide | 363 |
| PC tag | 364 |
| NY-ESO-1 TCR beta chain variable region | 365 |
| NY-ESO-1 TCR beta chain constant region | 366 |
| Full-length NY-ESO-1 peptide construct | 367 |
| NY-ESO-1 peptide | 368 |
| NY-ESO-1 1G4 epitope | 369 |
| T2A skip peptide | 362 |
| Luciferase | 370 |
| IRES | 371 |
| NGFR signal peptide | 372 |
| NGFR extracellular domain | 373 |
| NGFR transmembrane domain | 374 |
| NGFR truncated cytoplasmic tail | 375 |

Transduced T cells were labeled using anti-HA [3F10] primary antibody and a secondary anti-rat FITC antibody to enable isolation of NY-ESO-1 TCR positive T cells (e.g., HA positive) at >90% purity using an Aria III FACS instrument. The HA-sorted cells were further expanded with Dynabeads and IL-2 (30 U/mL) for five days. Sorted T cells (e.g., NY-ESO-1 positive) edited with KLRB1 and TRAC RNPs were shown to have high levels of KLRB1 inactivation, with <5% of cells expressing CD161 at the cell surface (data not shown). Furthermore, sorted T cells (NY-ESO-1 positive) reanalyzed 10 days following purification retained >90% surface TCR expression (data not shown).

To generate tumor target cells, cells of the HLA-A2.1 positive U87MG glioblastoma tumor cell line were transfected with NY-ESO-1 cDNA (Accession number: NM_139250.2). The cDNA encoding NY-ESO-1 was linked to luciferase through a 2A ribosomal skip sequence and was cloned into the pHAGE-MCS lentiviral vector under control of the EF-1α promoter to generate a lentiviral construct. Plasmid sequence identifier of the NY-ESO-1 TCR and SEQ ID NOs of the plasmid components are provided in Table 3. The T2A skip peptide was used for co-expression of luciferase. The construct further comprised an IRES that was used for expression of the nonfunctional, extracellular domain of human nerve growth factor (NGFR) as a marker for transduced cells. Lentivirus was applied to U-87 MG cells in a serial dilution from 1:1 to 1:2048. U-87MG cells were isolated by FACS to >99% purity based upon staining for the human NGFR antigen (positive cells indicated as U87-NYEP cells)

Figure 3B:
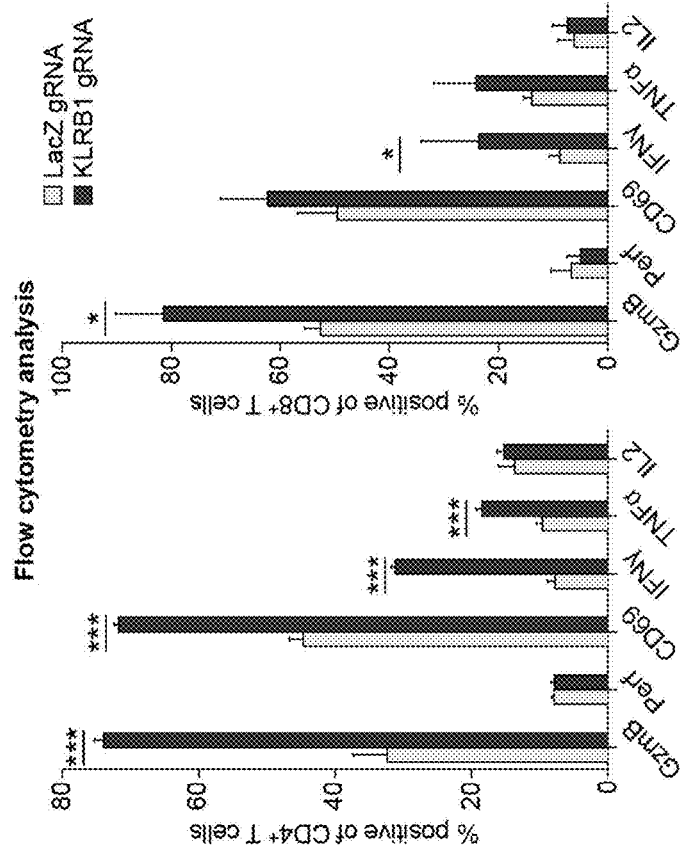
FIG. 3B provides bar graphs depicting expression of surface and intracellular markers in KLRB1 or control (LacZ gRNA)-edited primary T cells that expressed a NY-ESO-1 specific TCR following a 48 hour co-culture with U87MG tumor cells expressing NY-ESO-1 protein antigen, as measured by flow cytometry. Shown is expression for edited CD4 T cells (left) and CD8 T cells (right). *$P<0.05$, ***$P<0.001$, error bars denote SEM.

The response of KLRB1-inactivated T cells expressing the NY-ESO-1 [1G4] TCR to U87MG cells expressing NY-ESO-1 antigen was evaluated. Specifically, U87-NYEP positive tumor cells were seeded into 96-well plates at 30,000 cells per well and allowed to attach for 8 hours. NY-ESO-1 TCR positive T cells, edited with KLRB1 or LacZ-targeting gRNAs and TRAC gRNA, were seeded in triplicate at various ratios of T cells to tumor cells and cultured for 48 or 72 hours. Cells were co-cultured in the presence of protein transport inhibitor cocktail for the final six hours, stained for extracellular epitopes, fixed, and permeabilized for intracellular epitope detection. The cells were stained with antibodies targeting CD3 [HIT3a]-BV510, CD8 [RPA-T8]-BV650, CD4 [OKT4]-APC/Cy7, CD69 [FN50]-BV421, CD161 [HP-3G10]-PerCP/Cy5.5, perforin [B-D48]-PE, GranzymeB [GB11]-AlexaFluor647, IL-2 [MQ1-17H12]-FITC, IFNγ [4S.B3]-BV711, and TNFα [Mab11]-PE/Cy7. Flow cytometry using a LSR Fortessa X-20 analyzer was used to assess antibody labeling. KLRB1-inactivated CD4 and CD8 T cells expressed significantly higher levels of granzyme B and IFNγ compared to their control counterparts at 24 hours (data not shown) and 48 hours (FIG. 3B) at a T cell to target cell ratio of 0.25 to 1.

Figure 3C:
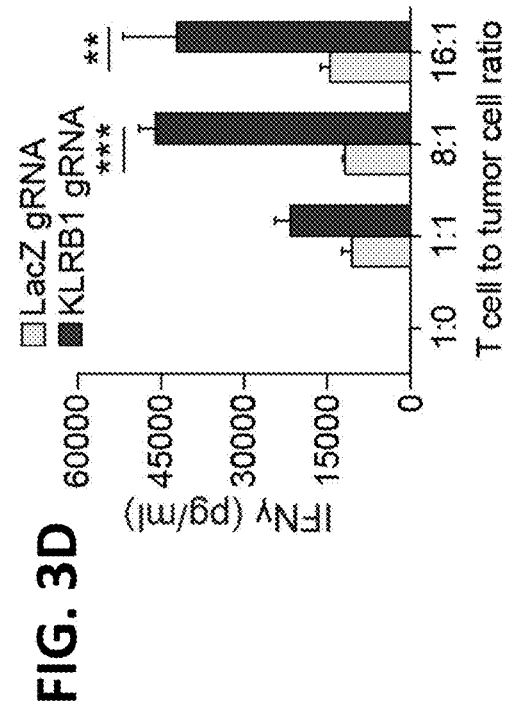
FIGS. 3C-3D provide bar graphs quantifying IL-2 (FIG. 3C) and IFNγ (FIG. 3D) in supernatant of co-culture of NY-ESO-1-expressing U87MG tumor cells and NY-ESO-1 TCR-expressing T cells edited as in FIG. 3B and incubated for 72 hours at indicated T cell to tumor cell ratios. *$P<0.05$, $P<0.01$, *$P<0.001$, ****$P<0.0001$, error bars denote SEM.
Figure 3D:
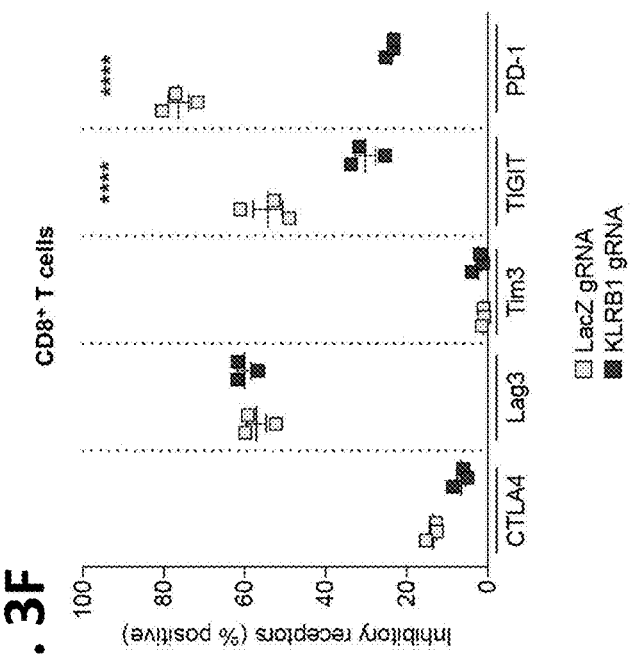

Furthermore, quantities of cytokines IL-2 and IFNγ in co-culture supernatants was measured by ELISA. Higher quantities of both IL-2 (FIG. 3C) and IFNγ (FIG. 3D) were detected in supernatants from KLRB1-inactivated T cell co-cultures compared to control (LacZ targeted) T cell co-cultures at both 48 hours (data not shown) and 72 hours (FIGS. 3C-3D), with the co-culture T cell to tumor cell ratios evaluated as indicated.

Figure 3E:
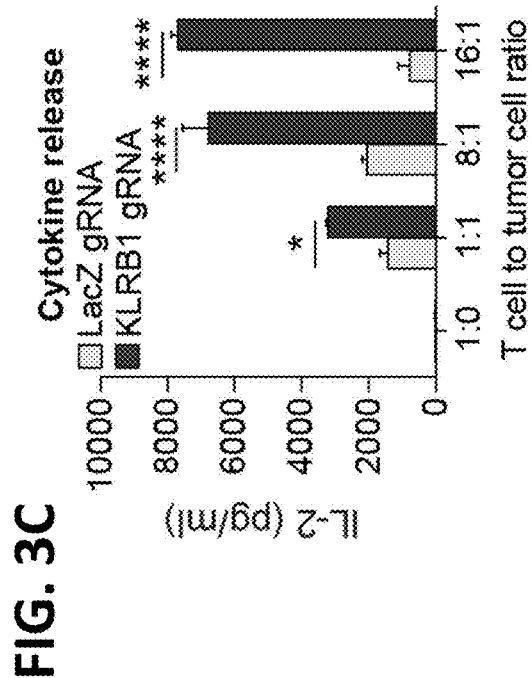
FIGS. 3E-3F provide dot plots quantifying surface levels of PD-1 (FIG. 3E) or other inhibitor receptors (FIG. 3F) on CD8 T cells edited with LacZ (control) or KLRB1 gRNAs following 72 hour co-culture with NY-ESO-1-expressing U87MG tumor cells as measured by flow cytometry. ****$P<0.0001$, error bars denote SEM.
Figure 3F:
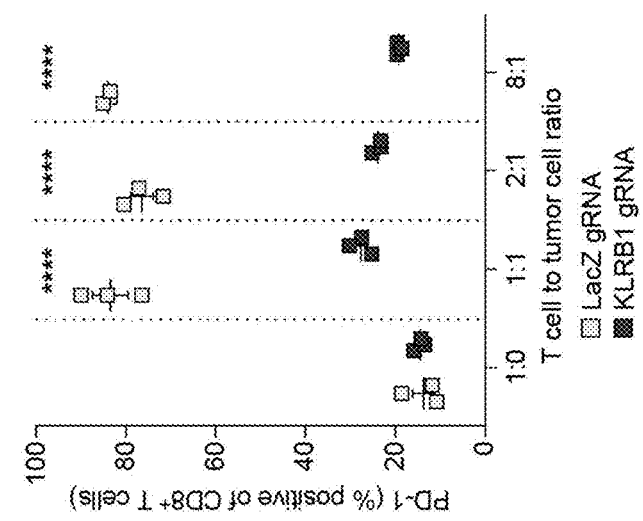

Activation of T cells is known to result in expression of the PD-1 inhibitor receptor. Interestingly, a substantially smaller fraction of KLRB1-inactivated T cells versus control CD8 T cells (LacZ targeted) became positive for PD-1 protein or TIGIT inhibitory receptor following 48 hour (data not shown) and 72 hour incubation (FIGS. 3E-3F) at indicated T cell to tumor cell ratios. However, expression of CTLA-4 and LAG-3 receptors were not affected by KLRB1 inactivation when evaluated for CD8 T cells edited with LacZ or KLRB1 gRNAs and incubated in a 72 hour co-culture at 2:1 T cells:tumor cells (FIG. 3F). Diminished expression of PD-1 upon KLRB1 inactivation was also observed for CD4 T cells, albeit to a lesser extent than for CD8 T cells (data not shown).

Figure 3H:
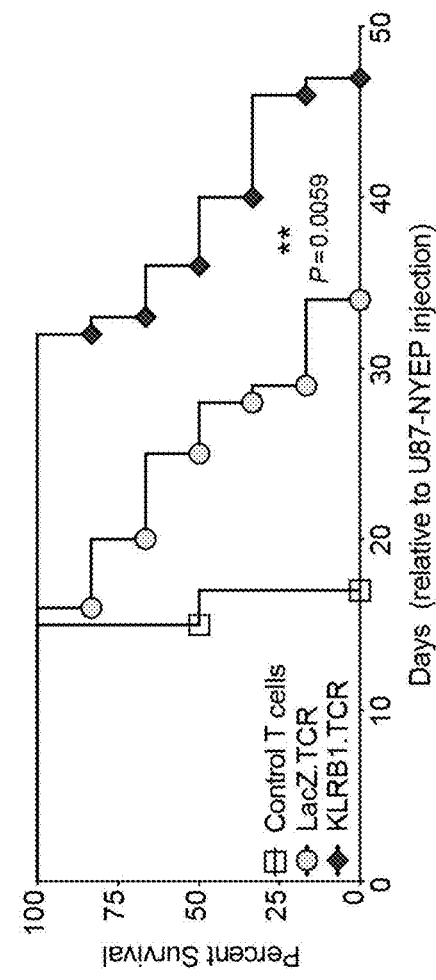
FIGS. 3G-3H provides graphs showing the effect of administration of unedited or edited T cells in a humanized glioma mouse model. Mice received either control T cells (non-engineered; open squares) or NY-ESO-1 TCR transduced T cells edited with either LacZ gRNA (LacZ.TCR, circles) or KLRB1 gRNA (KLRB1.TCR, diamonds).
Figure 3G:
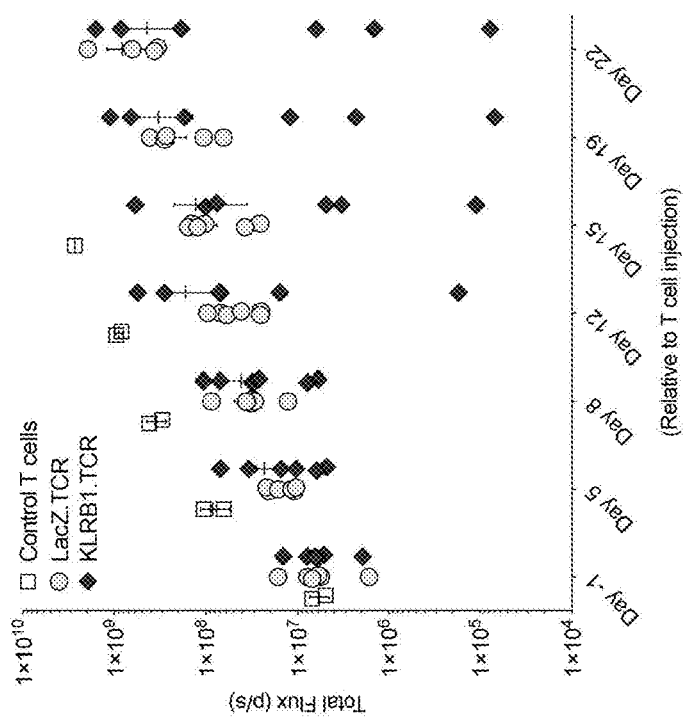

The function of KLRB1-inactivated T cells was next tested in vivo using a humanized mouse model of GBM. U87-NYEP tumor cells ($1.5 \times 10^4$) were implanted into the central nervous system (CNS) of the immunodeficient mouse brain via stereotactic injection into the left striatum, followed by the administration of T cells into the cerebrospinal fluid (CSF) via the contralateral ventricle, 7 days later. Mice received either (1) control T cells (non-transduced T cells that expressed endogenous TCRs), or NY-ESO-1 TCR transduced T cells (with an edited TRAC gene to inactivate the endogenous TCRα chain) that were electroporated with (2) control (LacZ) or (3) KLRB1 gRNAs bound to Cas9 protein. Mice received $0.4 \times 10^6$ T cells and were examined twice weekly by bioluminescence imaging (BLI). All tumors increased in size for the first five days following T cell transfer; by day 12 tumor bioluminescence decreased in 50% of the mice that received T cells with inactivated KLRB1, compared to mice that received control T cells (FIG. 3G). Further, mice that received KLRB1-deficient T cells showed significantly improved survival (FIG. 3H).

Figure 4:
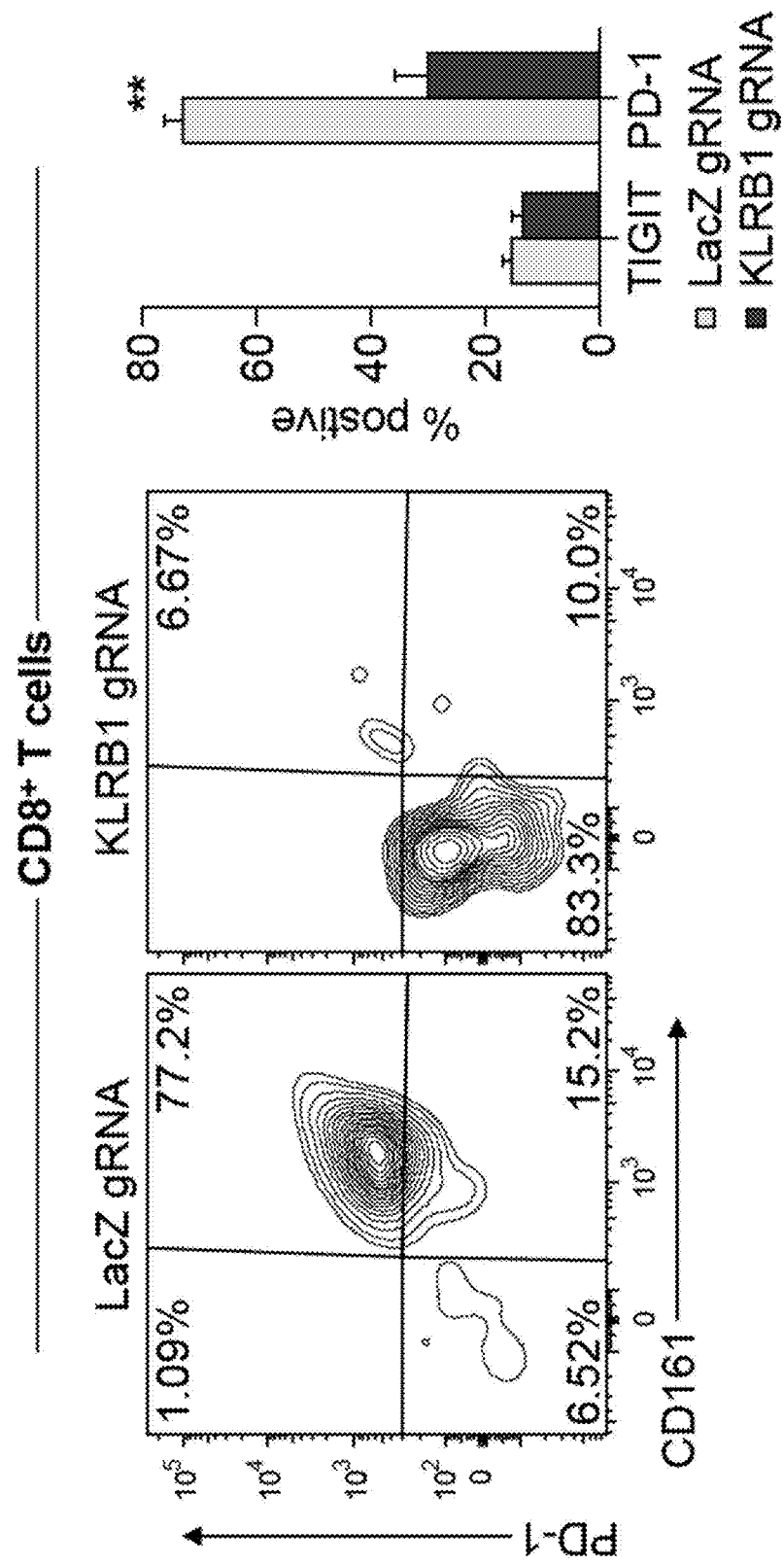
FIG. 4 provides quantification of T cells following administration as in FIGS. 3G-3H. Tumors were harvested from mice at 8 days following administration of unedited or edited T cells, and tumor-infiltrating T cells were examined by flow cytometry. Representative flow plots of CD161 (x-axis) versus PD-1 (y-axis) expression on CD8 T cells in mice that received T cells edited with LacZ (left) or KLRB1 (right) gRNAs Summary graphs for 6 mice per group are shown for expression of TIGIT and PD-1. **$P<0.01$, error bars denote SEM.

Ex vivo analysis of tumor-infiltrating T cells was performed. Mice received $2 \times 10^6$ T cells per mouse. Tumors were harvested at 8 days following administration of T cells and tumor-infiltrating T cells were assessed and quantified by flow cytometry as described in Example 3. The expression of PD-1 was assessed in CD8 and CD4 T cells and compared for the three experimental groups. The PD-1 expression was lower in KLRB1-edited CD8 (FIG. 4) and CD4 T cells (data not shown), compared to mice that received control T cells, consistent with the in vitro findings.

Together, these data demonstrate that CD161 inhibits the function of both CD4 and CD8 T cells, and that CD161 signaling contribute to PD-1 expression.

Example 5: KLRB1 Expression is Present in Tumor-Infiltrating T Cells Across Human Cancer Types Whether KLRB1 is associated with transcriptional programs of T cells infiltrating other human tumor types was assessed. Specifically, published scRNA-seq T cell datasets were evaluated from four other human cancers: melanoma, non-small cell lung cancer (NSCLC), hepatocellular carcinoma, and colorectal cancer (see, e.g., Guo et al (2018) Nat Med 24:978-985; Jerby-Arnon, et al (2018) Cell 175:984-997; Zhang, et al (2018) Nature 564:268-272; Zheng, et al (2017) Cell 169:1342-1356). Published sample and cell-type annotations were used to select T cells from the malignant tissue samples. t-distributed stochastic neighbor embedding (t-SNE) visualization showing expression of key genes in T cells were prepared.

Using this approach, KLRB1 was found to be expressed by a subset of tumor-infiltrating CD4 and CD8 T cells in each of these cancers. Expression was particularly prominent in lung cancer (KLRB1 detected in 40% of CD4 T cells and 25% of CD8 T cells) and in melanoma (KLRB1 detected in 20% of CD4 T cells and 9% of CD8 T cells). The expression of KLRB1 was similarly detected in tumor-infiltrating T cells from liver cancer and colorectal cancer (data not shown). KLRB1 and PDCD1 (encoding the PD-1 receptor) mRNA were expressed with distinct patterns by tumor infiltrating T cell populations (data not shown). Additionally, KLRB1 expression was low in FOXP3 positive regulator T cells, suggesting a primary function for inhibition of CD8 and CD4 effector T cells (data not shown).

Example 6: Human Monoclonal Antibodies Produced in Yeast Exhibit Binding to Human CD161

Purified CD161 linked to an Fc domain (CD161-Fc) was biotinylated. To prepare the recombinant CD161 human IgG1 Fc fusion protein, a plasmid was designed with a signal peptide preceding a copy of CD161 (KLRB1) connected to the hinge and Fc domain of human IgG1 by a flexible linker. Protein expression was driven by a gpCMV promoter. The protein (referred to as CD161-Fc, SEQ ID NO: 376) was isolated by affinity and gel filtration chromatography and was further biotinylated using a biotin succinimidyl ester. Additionally, a variant of the CD161-Fc fusion protein was prepared wherein a free cysteine residue of CD161 was substituted with serine (C29S, referred to as variant-CD161-Fc, SEQ ID NO: 380). Nucleotide sequences of the CD161-Fc and variant-CD161-Fc fusion proteins and components thereof are identified in Table 4.

TABLE 4

| CD161-Fc fusion protein nucleotide sequences | |
|---|---|
| Name | Nucleotide SEQ ID NO |
| Monovalent CD161-Fc Fusion | |
| Full-length | 376 |
| Kozak | 357 |
| Signal peptide | 358 |
| CD161 (KLRB1) extracellular domain | 377 |
| Flexible linker | 378 |
| Wild-type human IgG1 hinge + Fc | 379 |
| Monovalent variant CD161-Fc Fusion | |
| Full-length | 380 |
| Kozak | 357 |
| Signal peptide | 358 |
| CD161 (KLRB1) extracellular domain variant | 381 |
| Flexible linker | 378 |
| Wild-type human IgG1 hinge + Fc | 379 |

Synthetic naïve antibody libraries were designed, generated, and propagated as described previously (see, e.g., WO2009036379, Xu et al (2013) Protein Eng Des Sel (2013) 26:663-670; Kelly, et al (2018) J Mol Biol 430:119-130). Specifically, a synthetic scFv library was prepared to minimize cross-interaction prone motifs as previously described (Kelly, et al (2018) J Mol Biol 430:119-130). The library comprised five VH segments (VH1-69, VH3-15, VH3-23, VH4-39, VH5-51) and three VL segments (VK1-39, VK3-20, Vλ1-40). Junctional diversity in the VL segments was limited to the most common residue for the given segment. All VH segments were equally represented in the final design, while the VL segments were designed to be at a 2:2:1 ratio, with the two kappa segments twice as likely to appear as the lambda segment. Diversity in the H3 region was created via trinucleotide synthesis using defined ratios of amino acids based on natural repertoire frequencies with the exception that Trp residues were eliminated and frequency of Arg and Val residues was reduced (Kelly, et al (2018) J Mol Biol 430:119-130). The H3 loop length was varied from 6-17 as defined by Kabat numbering. The segments were assembled in a VL-VH scFv format and transformed into a one billion member library in yeast display format. All yeast experiments were conducted in the RJY100 strain.

Selection Strategy with Fc Antigen

Parallel selections were conducted using previously described yeast display techniques (see, e.g., Ossipow, et al (2014) Humana Press p151-181; Chao, et al (2006) Nat Protoc 1:755-768; Feldhaus et al (2004) J Immunol Methods, 286:141-153). Briefly, the human scFv yeast library was cultured and approximately 10 billion cells were pelleted and induced for scFv expression. The library was enriched using negative selections to remove non-specific binders, with sorting performed using magnetic bead selection techniques as described by Feldhaus et al (2004) J Immunol Methods, 286:141-153. Specifically, the library was exposed to streptavidin MACS microbeads alone to remove non-specific binders to streptavidin and to biotinylated Fc with use of streptavidin microbeads to remove non-specific binders to Fc. Subsequently, the library was separately enriched using positive selections for binders to biotinylated CD161-Fc (bCD161-Fc) or biotinylated variant-CD161-Fc (b-variant-CD161-Fc). Three rounds of negative and positive selection were performed using magnetic beads selection techniques. The positive selections were performed in the presence of non-biotinylated Fc at a concentration 10-fold higher than the concentration of bCD161-Fc or b-variant-CD161-Fc (10 µM non-biotinylated Fc and 1 µM bCD161-Fc or b-variant-CD161-Fc).

Candidate CD161 binders were then further enriched from the scFv yeast library using flow cytometry. The cells were labeled with bCD161-Fc or b-variant-CD161-Fc antigen in the presence of non-biotinylated Fc and with secondary reagents to label scFv epitope tags and antigen. CD161-binding cells were sorted using FACS. The enriched population was propagated and exposed to three more rounds of FACS-based sorting to further enrich for CD161-binding clones.

Figure 5A:
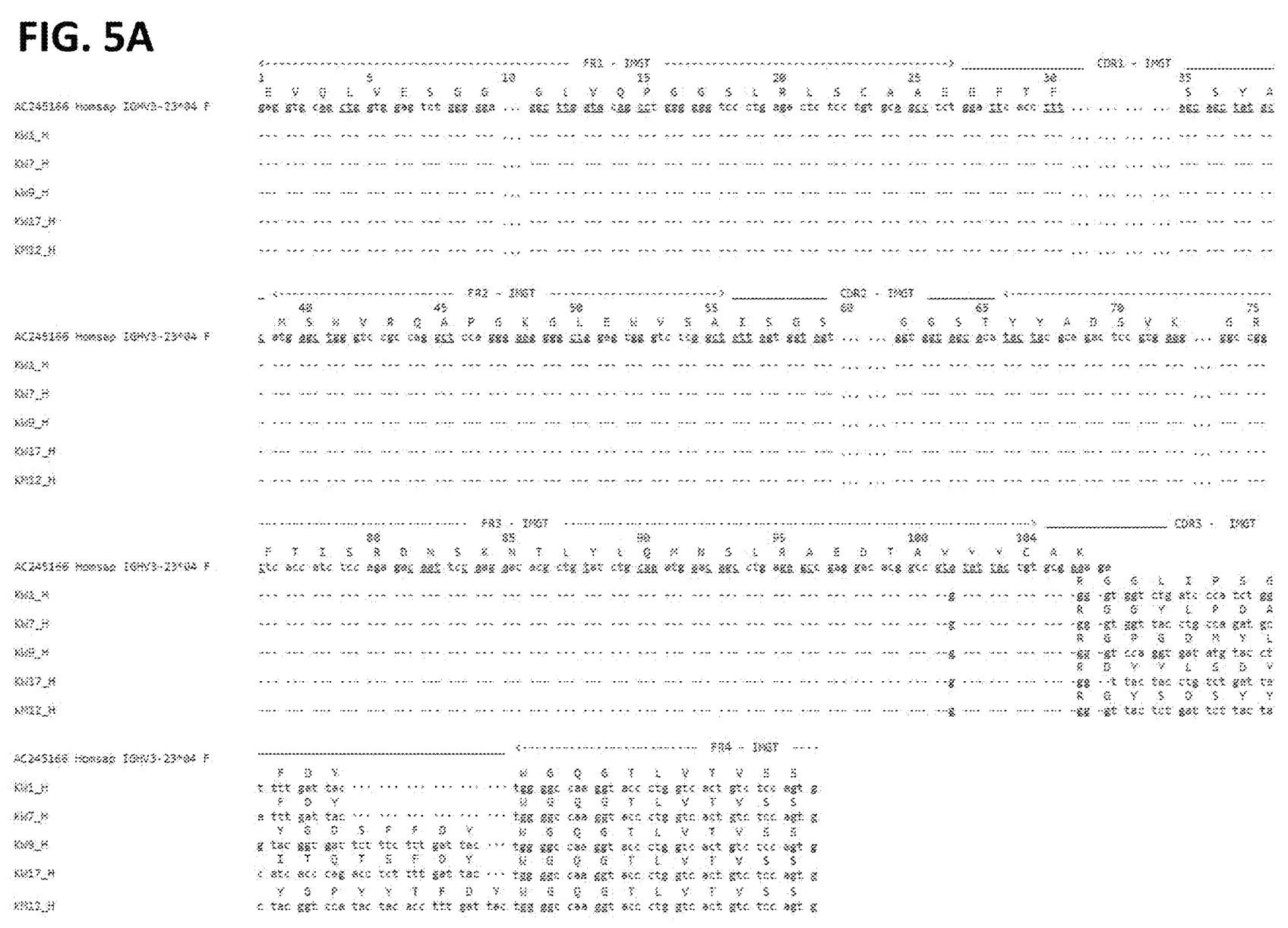
Figure 5B:
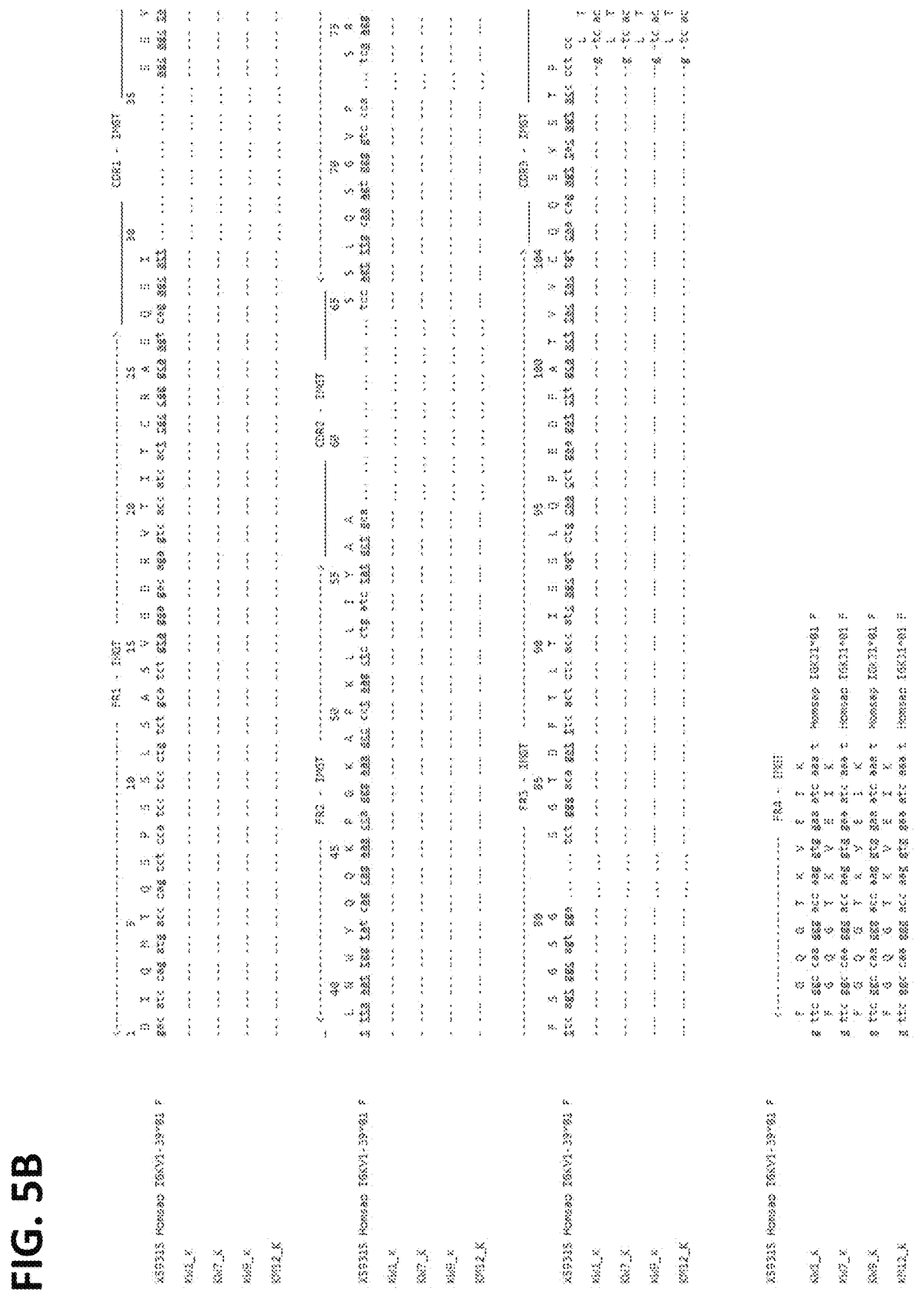
Figure 5C:
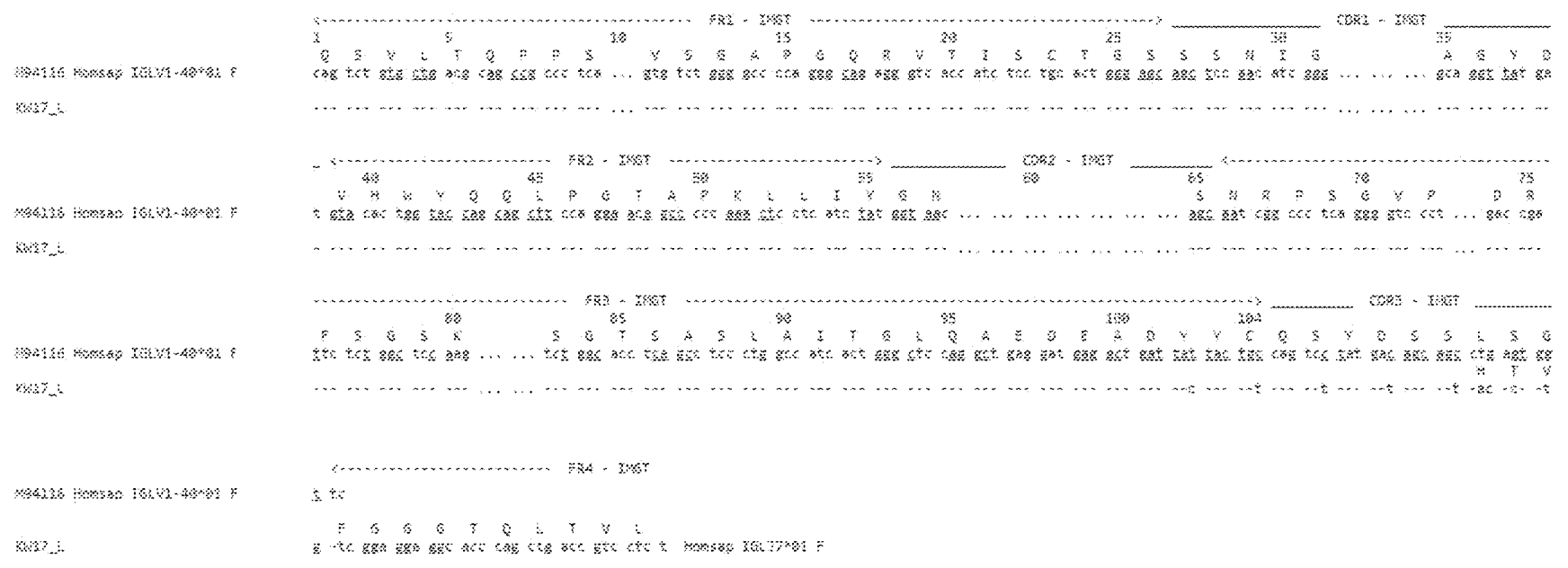

The output of these rounds included four clones (KW#: KW1, KW7, KW9, and KW17) from populations enriched with bCD161-Fc and one clone (KM12) from those enriched with b-variant-CD161-Fc that were plated and isolates were picked for sequencing and characterization. The sequence of the VH and VL domains of the antibody clones are identified in Table 5 and Table 6 respectively. Sequence alignment and numbering of the heavy chains are shown in FIG. 5A. Four clones comprised a kappa light chain, with sequence alignment and numbering as shown in FIG. 5B (clones KW1, KW7, KW9 and KM12). Clone KW17 comprised a lambda light chain as shown in FIG. 5C. Antibody numbering is defined according to IMGT unique numbering (see, e.g., Lefranc (2005) *Nucl Acids Res* 33:D593-D597). The heavy chains were identical in sequence except for the CDR H3 region, with the CDR H3 sequences as shown in Table 7. The clones comprising a kappa light chain were also identical in each sequence, with sequences of the kappa and lambda light chain CDRs shown in Table 8.

TABLE 5

Sequence identification for $V_H$ Domain of human anti-CD161 clones identified by yeast display

| Antibody clone | $V_H$ Domain Name | V-Gene and allele | J-Gene and allele | D-Gene and allele | $V_H$ Domain SEQ ID NO |
|---|---|---|---|---|---|
| KW1 | KW1_H | IGHV3-23*04 F | IGHJ4*01 F or IGHJ4*03 F | IGHD3-10*01 F | 1 |
| KW7 | KW7_H | IGHV3-23*04 F | IGHJ4*01 F | IGHD3-3*01 F | 22 |
| KW9 | KW9_H | IGHV3-23*04 F | IGHJ4*01 F or IGHJ4*03 F | IGHD2-2*01 F | 43 |
| KW17 | KW17_H | IGHV3-23*04 F | IGHJ4*01 F or IGHJ4*03 F | IGHD3-22*01 F | 61 |
| KM12 | KM12_H | IGHV3-23*04 F | IGHJ4*01 F | IGHD3-22*01 F | 88 |

TABLE 6

Sequence identification for $V_L$ Domain of human anti-CD161 clones identified by yeast display

| Antibody | $V_L$ Domain Name | V-Gene and allele | J-Gene and allele | $V_L$ Domain SEQ ID NO |
|---|---|---|---|---|
| KW1 | KW1_K | IGKV1-39*01 F or IGKV1D-39*01 F | IGKJ1*01 F or IGKJ4*02 F | 152 |
| KW7 | KW7_K | IGKV1-39*01 F or IGKV1D-39*01 F | IGKJ1*01 F or IGKJ4*02 F | 152 |
| KW9 | KW9_K | IGKV1-39*01 F or IGKV1D-39*01 F | IGKJ1*01 F or IGKJ4*02 F | 152 |
| KW17 | KW17_L | IGLV1-40*01 F | IGLJ7*01 F | 245 |
| KM12 | KM12_K | IGKV1-39*01 F or IGKV1D-39*01 F | IGKJ1*01 F or IGKJ4*02 F | 152 |

TABLE 7

Sequence of $V_H$ CDRs of human anti-CD161 clones identified by yeast display

| Antibody | $V_H$ CDR1 | SEQ ID NO | $V_H$ CDR2 | SEQ ID NO | $V_H$ CDR3 | SEQ ID NO |
|---|---|---|---|---|---|---|
| KW1 | GFTFSSYA | 127 | ISGSGGST | 132 | ARGGLIPSGFDY | 141 |
| KW7 | GFTFSSYA | 127 | ISGSGGST | 132 | ARGGYLPDAFDY | 143 |
| KW9 | GFTFSSYA | 127 | ISGSGGST | 132 | ARGPGDMYLYGDSFFDY | 144 |
| KW17 | GFTFSSYA | 127 | ISGSGGST | 132 | ARDYYLSDYITQTSFDY | 147 |
| KM12 | GFTFSSYA | 127 | ISGSGGST | 132 | ARGYSDSYYYGPYYTFDY | 150 |

TABLE 8

Sequence of $V_L$ CDRs of human anti-CD161 clones identified by yeast display

| Antibody | $V_L$ CDR1 | SEQ ID NO | $V_L$ CDR2 | SEQ ID NO | $V_L$ CDR3 | SEQ ID NO |
|---|---|---|---|---|---|---|
| KW1 | QSISSY | 273 | AAS | 279 | QQSYSTPLT | 281 |
| KW7 | QSISSY | 273 | AAS | 279 | QQSYSTPLT | 281 |
| KW9 | QSISSY | 273 | AAS | 279 | QQSYSTPLT | 281 |
| KW17 | SSNIGAGYD | 277 | GNS | 280 | QSYDSSHTV | 289 |
| KM12 | QSISSY | 273 | AAS | 279 | QQSYSTPLT | 281 |

Affinity Maturation of Clones Identified in Naïve Selections

The five parental clones identified from the scFv yeast library (KW1, KW7, KW9, KW17, and KM12) were further engineered for increased affinity to CD161 using previously described techniques (see, e.g., Chao, et al (2006) *Nat Protoc* 1:755-768). Briefly, each plasmid DNA of the parental clones was mutagenized by error-prone PCR to create five initial yeast libraries. The five initial yeast libraries were subjected to three rounds of parallel flow-based positive selection against bCD161-Fc in the presence of 10 µM unbiotinylated Fc. Subsequent libraries were generated with plasmid DNA isolated from the library of enriched CD161-binding scFvs by error-prone PCR. The mutagenized PCR product was separated from template DNA using gel-purification and amplified. The PCR product was inserted into pCTCON2 plasmid and transformed into yeast using previously described electroporation techniques (see, e.g., Chao, et al (2006) *Nat Protoc* 1:755-768; Meilhoc et al (1990) *Bio/Technology* 8:223-227).

Selection of CD161-binders with increased affinity was performed using FACS-based sorting. In the first two rounds, CD161-binders were screened based upon their equilibrium dissociation constants ($K_D$). The mutagenized scFv yeast library was incubated with b-CD161-Fc at a concentration of 5-10-fold higher than the $K_D$ determined for the parental clones, and binding was allowed to reach equilibrium (approximately 3 hours). In the third round, the library was further enriched using kinetic competition, where the library was incubated with saturating concentration of b-CD161-Fc, washed, and then incubated with 10-fold excess of non-biotinylated b-CD161-Fc. By preventing re-binding of labeled antigen, the library was enriched for CD161-binders with reduced dissociation rate constants ($k_{off}$).

Figure 5D:
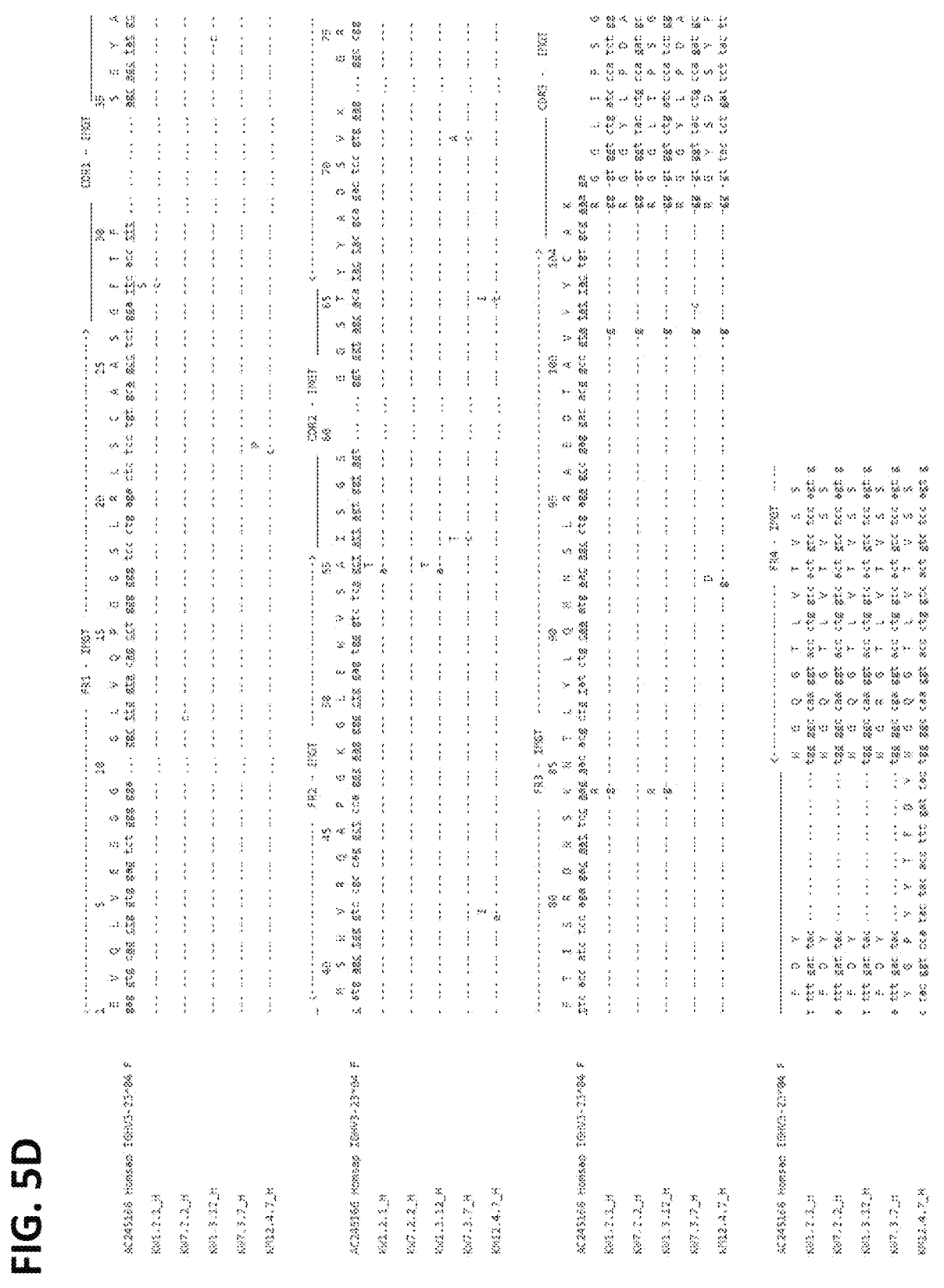
Figure 5E:
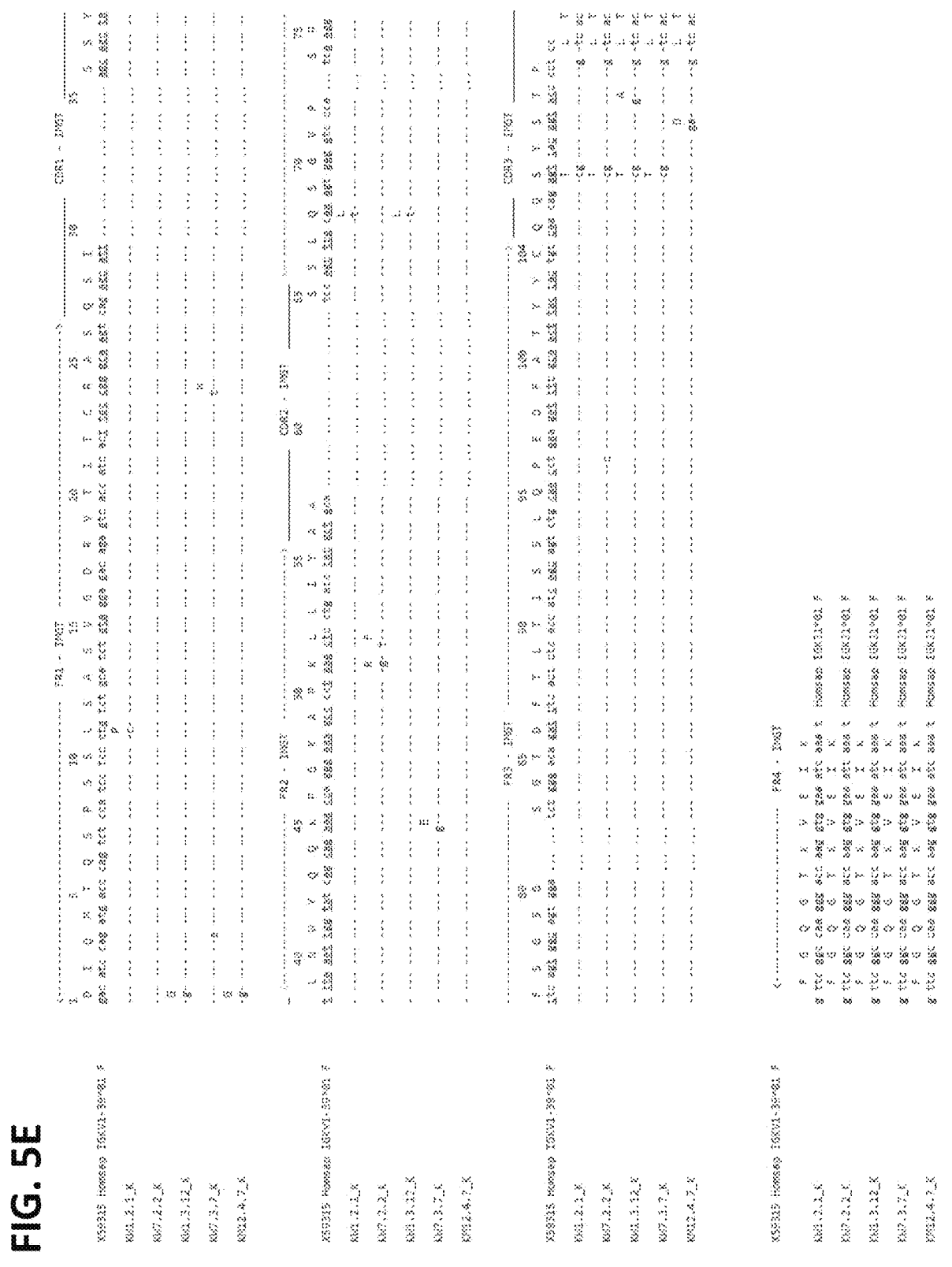

The output of these selection rounds were plated and isolates were picked for sequencing and characterization. Sequence alignment and numbering of representative heavy chains of affinity matured CD161-binding scFvs is shown in FIG. 5D (IMGT numbering). Additionally, alignment of representative affinity matured clones comprising a kappa light chain is shown in FIG. 5E. The kappa light chain identified for clones KW1.3.12 and clone KM12.4.7 as shown in FIG. 5E included a glycine in position 1 of the sequence (KW1.3.12 VL amino acid and nucleotide sequences set forth in SEQ ID NOs: 393 and 394; KM12.4.7 VL amino acid and nucleotide sequences set forth in SEQ ID NOs: 395 and 396). In expressing the antibody clones, the glycine in position 1 of the sequence was reverted to aspartate (KW1.3.12 VL amino acid and nucleotide sequences set forth in SEQ ID NOs: 167 and 168; KM12.4.7 VL amino acid and nucleotide sequences set forth in SEQ ID NOs: 235 and 236).

IgG Production and Purification

The antibody scFvs were prepared as scFv fusions to an Fc domain Specifically, the $V_H$ and $V_L$ domains of each clone were expressed in an IgG1 Fc framework. The IgG1 Fc comprised a LALA-PG sequence variation that abolishes FcγR interactions, but maintains FcRn interactions that are important for Fc stability (Human IgG1 Fc with LALA-PG variation: amino acid and nucleotide sequence identified by SEQ ID NO: 326 and SEQ ID NO: 331 respectively). The cDNA of each antibody was synthesized and cloned into the gWiz vector (Genlantis). The antibodies were expressed in HEK 293F cells and further purified using rProtein A resin (GE Life Sciences).

Example 7: Evolved CD161-Targeting Antibodies Bind CD161 and Block Interactions with its Ligand CLEC2D Antibodies identified and isolated as described in Example 6 were further evaluated for binding to cells expressing KLRB1 (CD161). Specifically, Jurkat cells were transduced to express KLRB1 (CD161). cDNA encoding KLRB1 was cloned into the pHAGE-MCS lentiviral vector under control of the EF-1α promoter. The nucleotide sequence of full-length KLRB1 is identified by SEQ ID NO: 382 (the KLRB1 cytoplasmic domain is identified by SEQ ID NO: 383; the transmembrane region by SEQ ID NO: 384; and the extracellular domain by SEQ ID NO: 385). The plasmid was transfected with packaging plasmids pCMV-dR8.91 and pCMV-VSV-G (Addgene #8454) into HEK293FT cells. Transfection was performed using TransIT-293 (Minis, MIR2700) following the manufacturer's protocol, and viral supernatant was harvested. Lentivirus was applied on wild-type (WT) Jurkat [E6-1] cells (ATCC). A non-tissue culture treated 24-well plate was coated with retronectin (Takara; Kusatsu, Japan) at a final concentration of 15 μg/mL at 4° C. overnight. The plate was blocked with 2% bovine serum albumin. Virus was applied in a serial dilution, allowed to attach at 32° C. with centrifugation, and plates were decanted and washed. WT Jurkat [E6-1] cells were transferred in the presence of protamine sulfate (10 μg/mL). The cells were cultured for 3 days and subsequently sorted by FACS following staining with an anti-CD161 [HP-3G10] antibody.

Figure 6A:
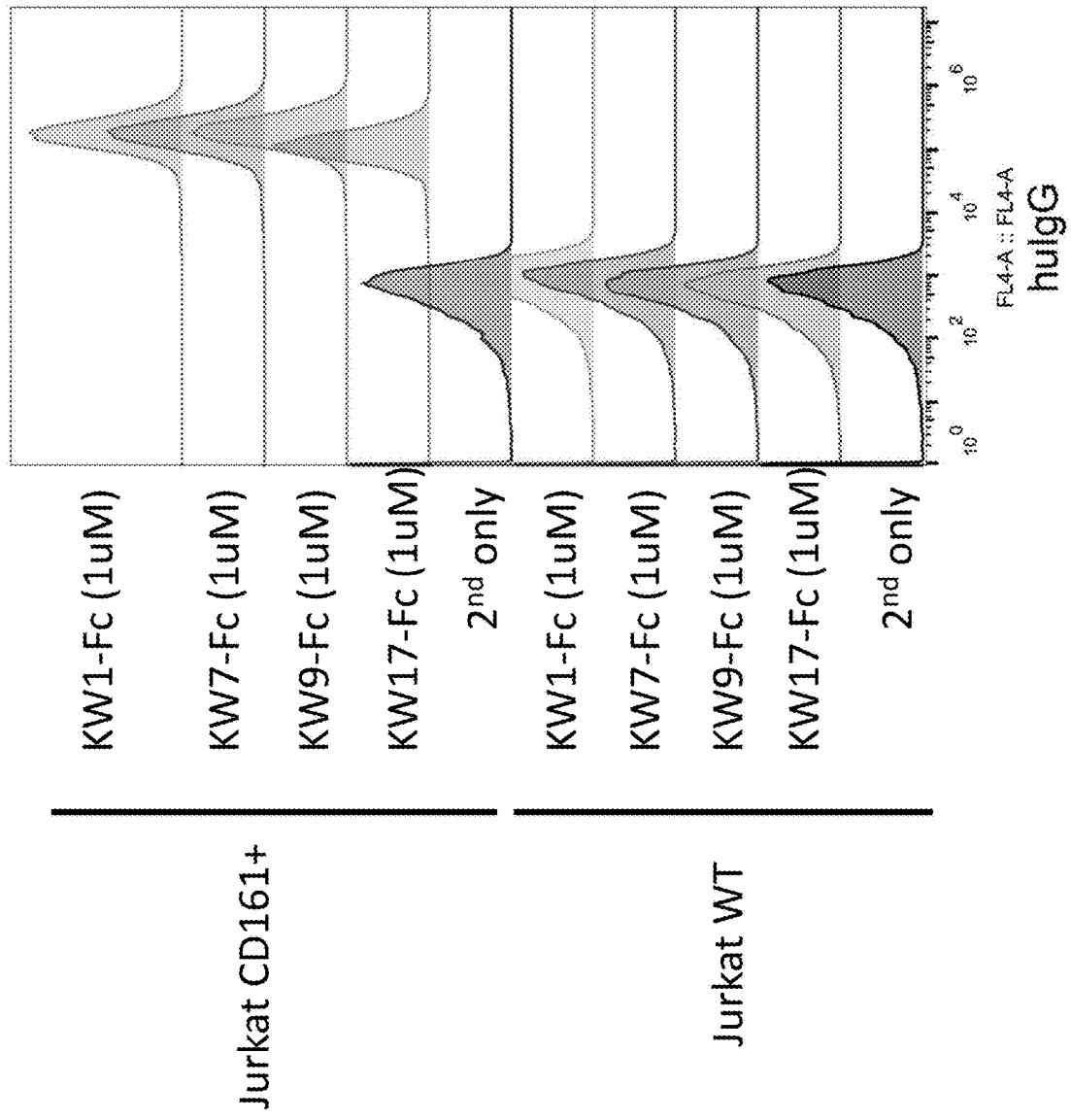
FIG. 6A provides histograms depicting degree of binding of parental human anti-CD161 antibodies identified by yeast display to Jurkat cells expressing human KLRB1/CD161 or wild-type Jurkat cells as measured by flow cytometry. Background staining determined using staining with secondary detection reagent only.

To assess binding to CD161, antibodies (KW1, KW7, KW9, and KW17 scFvs fused to an Fc domain as described in Example 6) were incubated at a concentration of 1 μM with either wild type Jurkat cells or Jurkat cells transduced to express CD161 for up to 4 hours on ice. Cells were then washed and labeled with a goat-anti-human-IgG-Alexa-Flour-647 secondary antibody (Invitrogen) to detect binding. Negative control cells were labeled with the secondary antibody only. Labeling was evaluated by flow cytometry. As shown in FIG. 6A, none of the CD161-binding antibodies evaluated bound to wild type Jurkat cells. However, all of the anti-CD161 antibodies bound to Jurkat cells expressing CD161.

Figure 6B:
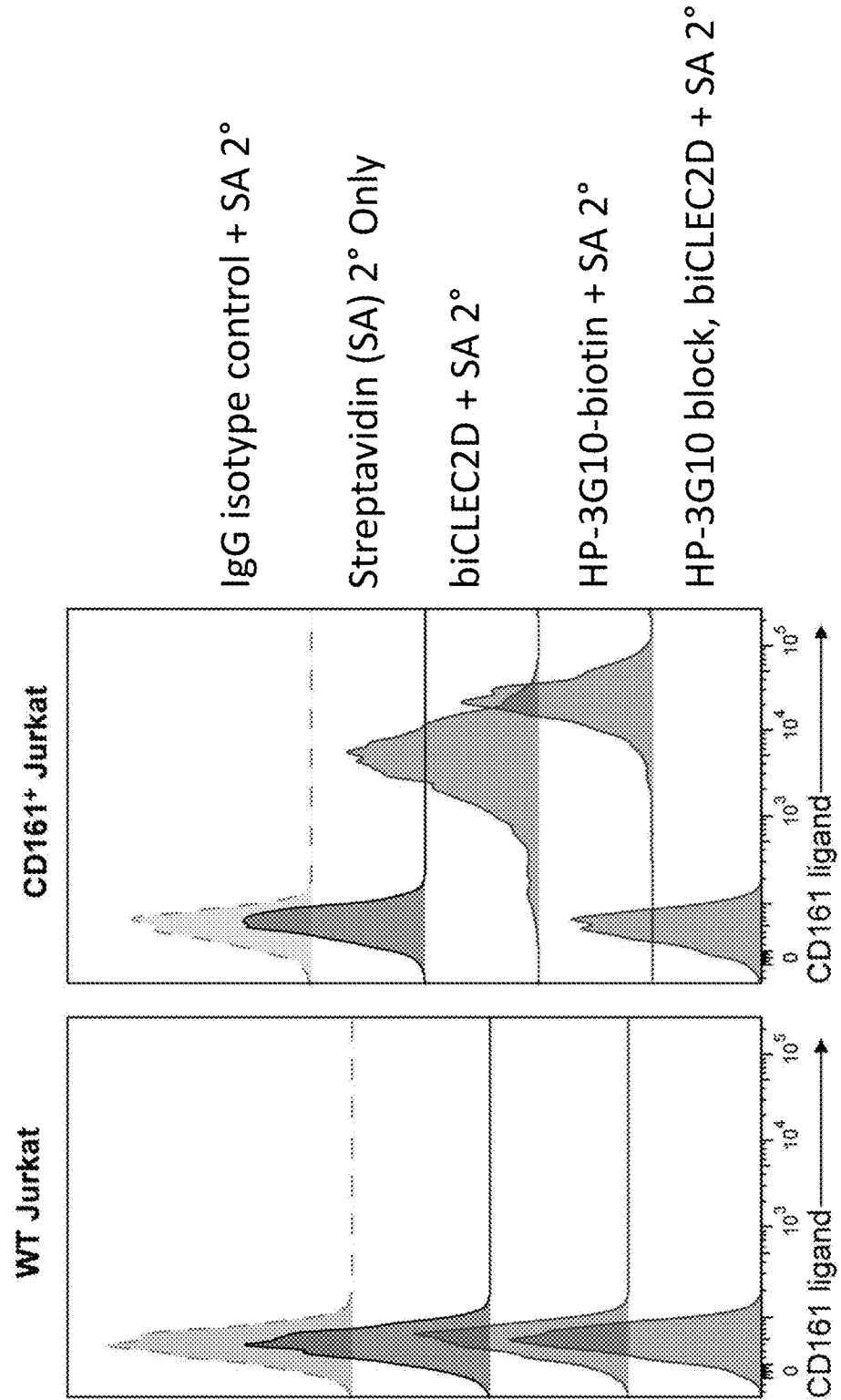
FIG. 6B provides histograms depicting the detection of CD161 on the surface of wild-type Jurkat cells (left) or Jurkat cells expressing human CD161 (right) with biotinylated bivalent CLEC2D Fc fusion protein (biCLEC2D) alone or following incubation of cells in the presence of mouse anti-human CD161 (KLRB1) antibody (HP-3G10). Also shown is detection of bound HP-3G10 following incubation with biotinylated antibody alone.

The ability of the antibodies to block binding of CLEC2D to CD161 was further evaluated. A bivalent CLEC2D-IgG fusion protein was generated with a mutated Fc-region of IgG1 which showed specific binding to CD161$^+$ but not CD161 (WT) Jurkat cells. The protein was designed to be bivalent due to the close proximity of the N- and C-termini in the CLEC2D crystal structure. To generate the fusion protein, cDNA of CLEC2D (Accession number: NM_013269.6) was synthesized as a gBlock. Two copies of the gene were connected by a flexible linker followed by mutated human IgG1 Fc region (to prevent binding to activated Fc receptors) and cloned into the UCOE Hu-P vector (EMD Millipore, Burlington, Mass.). The two copies differed in nucleotide sequence, but encode the same CLEC2D polypeptide. The nucleotide sequence of the bivalent CLEC2D-Fc construct and of the construct components are identified in Table 9. The vector was transfected into Expi293F cells and expressed bivalent fusion protein (biCLEC2D) was isolated by affinity and gel filtration chromatography. The bivalent fusion protein was further biotinylated for subsequent use in labeling experiments. To evaluate labeling, Jurkat cells expressing human KLRB1 were treated with biotinylated biCLEC2D. Bound protein was detected using streptavidin-PE and labeling was assessed by flow cytometry. As shown in FIG. 6B, biCLEC2D effectively binds to Jurkat cells expressing KLRB1 (CD161 positive Jurkat cells), but not WT Jurkat cells. Additionally, blocking of biCLEC2D binding using a commercial mouse anti-human CD161 antibody (HP-3G10) at 20 μg/mL resulted in full blocking of biCLEC2D binding (FIG. 6B).

TABLE 9

Nucleotide sequences of bivalent CLEC2D-Fc fusion protein

| Name | Nucleotide SEQ ID NO |
|---|---|
| Bivalent human CLEC2D-Fc Fusion | |
| Full-length | 386 |
| Kozak | 357 |
| Signal peptide | 358 |
| Human CLEC2D extracellular domain copy 1 | 387 |
| Flexible GSG linker | 388 |
| Human CLEC2D extracellular domain copy 2 | 389 |
| Human IgG1 Fc domain variant (LALA-PG sequence variation) | 391 |

Figure 6C:
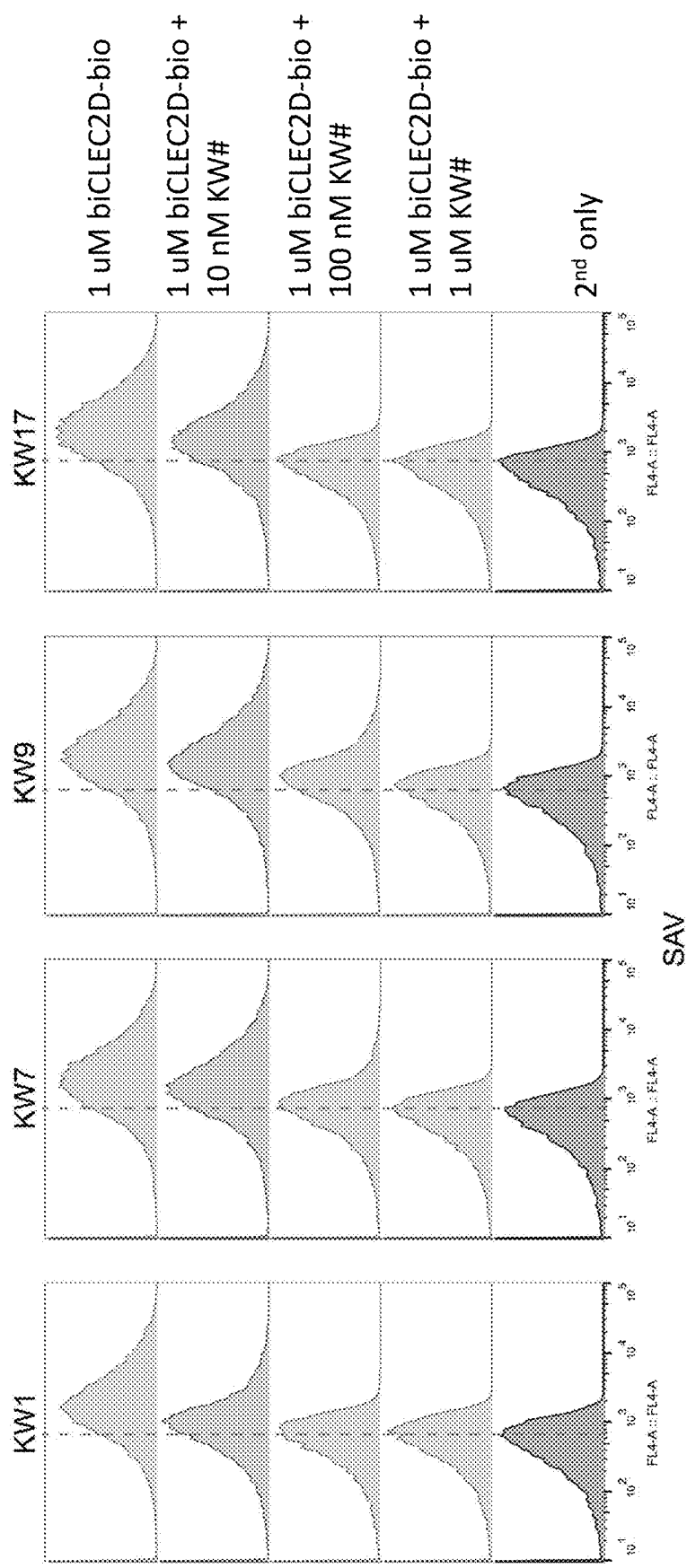

Jurkat cells expressing human KLRB1 were incubated with 1 µM biotinylated biCLEC2D alone or in combination with 10 nM, 100 nM or 1 µM anti-CD161 antibody. CD161-binding antibody clones described in Example 6 were evaluated (KW1, KW7, KW9, KM12, and KW17), as well as a commercial mouse anti-human-CD161 antibody clone [HP-3G10]. Following incubation on ice for 1 hour, the cells were washed and labeled with a streptavidin-Alexa-Fluor-647. Detection of CD161 was assessed by flow cytometry. As shown in FIGS. 6C-6D, biCLEC2D alone demonstrated good binding to CD161-expressing Jurkat cells. However, binding was reduced in the presence of each of the anti-CD161 antibodies (KW1, KW7, KW9 and KW17 as shown in FIG. 6C and KM12 and HP-3G10 as shown in FIG. 6D). Indeed, incubation with 1 µM of anti-CD161 antibody reduced biCLEC2D binding to background levels. Additionally, biCLEC2D binding was reduced to a similar extent for fully-human anti-CD161 antibodies generated by yeast display and the commercial anti-CD161 (KLRB1) antibody [HP-3G10] (FIG. 6D).

Figure 6E:
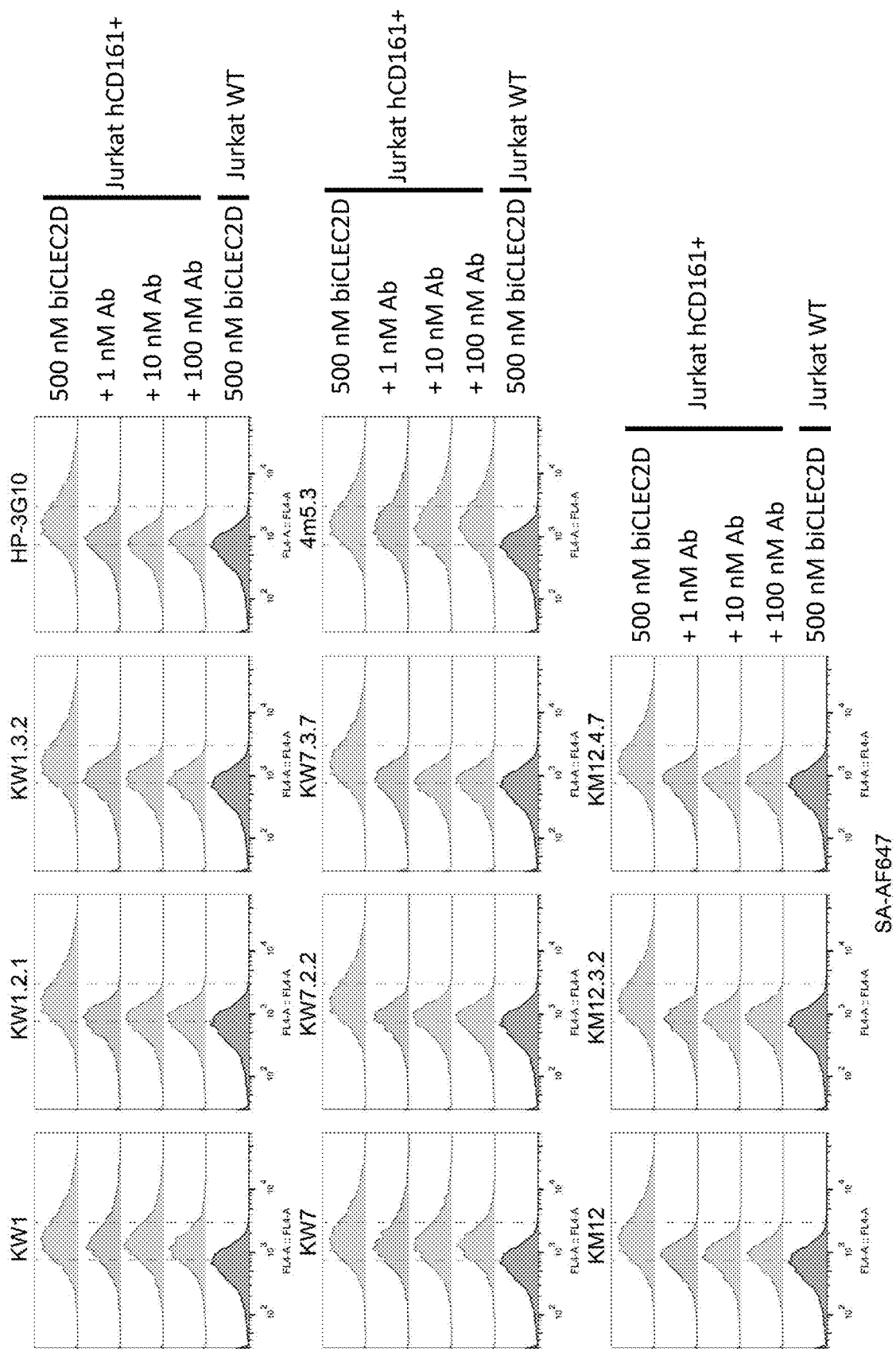
FIG. 6E provides histograms depicting binding of biCLEC2D-bio to Jurkat cells expressing human CD161 in the presence of increasing concentrations of affinity matured human anti-CD161 antibodies identified by yeast display as measured by flow cytometry.

Affinity-matured anti-CD161 antibodies prepared as described in Example 6 were also evaluated for blocking biCLEC2D binding to CD161. In this case CD161-positive Jurkat cells were treated with 500 nM biCLEC2D alone or in combination with 1 nM, 10 nM, or 100 nM antibody. As a negative control, binding of biCLEC2D to wild type Jurkat cells was evaluated. As shown in FIG. 6E, blocking of biCLEC2D binding to CD161 using the parental anti-CD161 antibodies is shown in the leftmost panel, and blocking induced by affinity-matured anti-CD161 antibodies are shown in panels to the right. FITC-specific antibody [4m5.3] was used as a control and no blocking of biCLEC2D binding to CD161 was observed in the presence of this antibody. In most cases treatment with affinity-matured anti-CD161 antibodies eliminated biCLEC2D binding at concentrations of antibody as low as 1 nM.

Thus, the human anti-CD161 antibodies generated as described in Example 6 bind to cells expressing CD161 (KLRB1) and further inhibits binding of CD161-expressing cells to biCLEC2D.

Figure 7A:
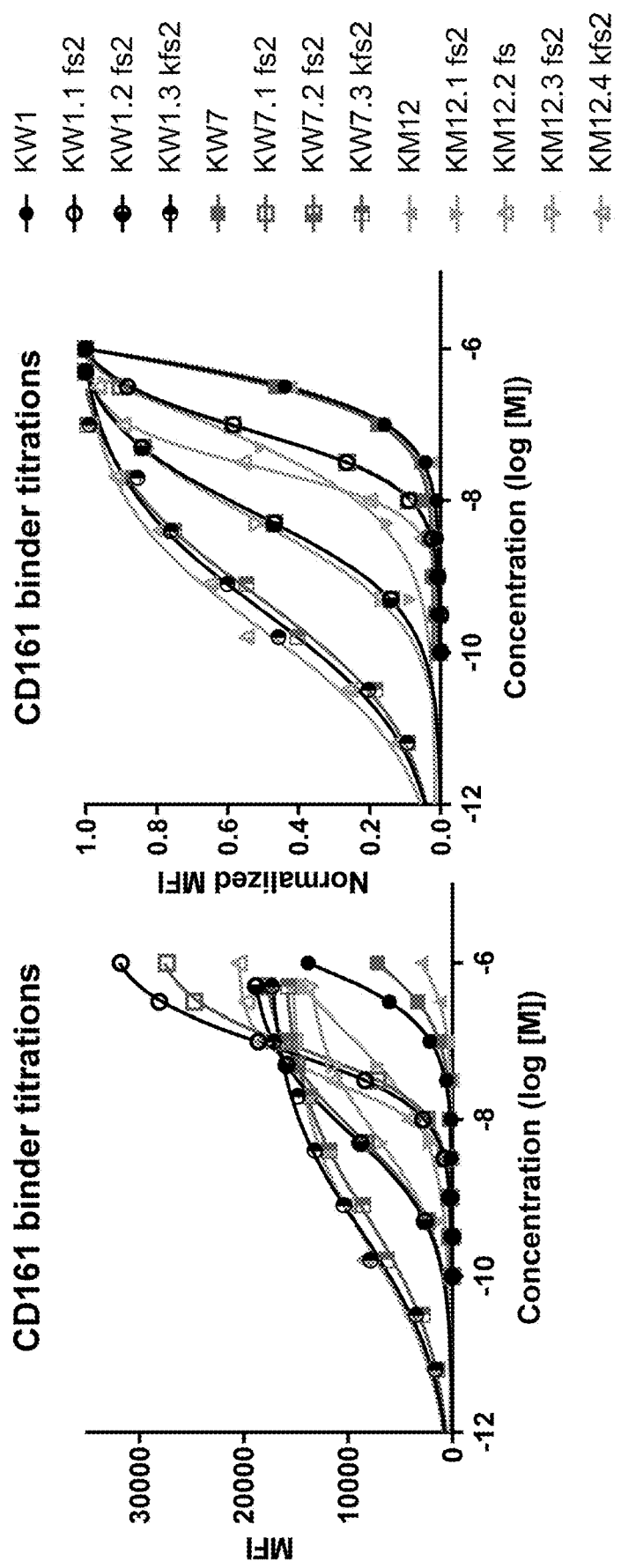
FIG. 7A provides line graphs depicting binding of CD161-Fc fusion protein to yeast expressing parental anti-CD161 scFvs or flow enriched yeast populations as a function of CD161-Fc concentration as measured by flow cytometry The degree of binding is represented by raw mean fluorescence intensity (MFI) values (left) or MFI values normalized to the highest value in each dataset (right).

Example 8: Distribution of Binding Affinities for Parental and Affinity-Matured CD161-Targeting Antibodies Binding affinity of CD161-targeting scFvs was evaluated for both parental clones and affinity matured populations. The yeast populations displaying scFvs were incubated with bCD161-Fc at various concentrations at room temperature for up to 16 hours. At low concentrations, incubation volumes were sufficiently large such that ligand was depleted less than 10% due to association with yeast-displayed scFvs. The cells were washed and labeled with chicken anti-cmyc antibody, then with goat-anti-chicken-Alexa-Fluor-488 antibody and streptavidin-Alexa-Fluor-647. Labeling was assessed using flow cytometry to measure the mean fluorescence intensity (MFI). The MFI as a function of bCD161-Fc concentration is shown in FIG. 7A (left panel). Also shown is the MFI normalized to the maximum fluorescence intensity identified in each data set (FIG. 7A, right panel). Non-linear regression analysis of binding versus concentration was used to yield the equilibrium binding constant ($K_D$) as shown in FIG. 7A, thus providing a measure of binding affinity. The measured binding affinity for each enriched population is shown in Table 10. Values are shown for the yeast population comprising the parental clone and yeast populations generated from the parental clone that were further enriched by flow sorting as described in Example 6. Provided in Table 10 are the binding affinity measured for the following yeast populations:

(1) a yeast population expressing the KW1 parental clone (KW1) and yeast populations affinity matured from the KW1 parental clone by a first round of flow sorting (KW1.1 fs2), a second round of flow sorting (KW1.2 fs2), and a third round of kinetic-based flow sorting (KW1.3 kfs2);

(2) a yeast population expressing the KW7 parental clone (KW7) and yeast populations affinity matured from the KW7 parental clone by a first round of flow sorting (KW7.1 fs2), a second round of flow sorting (KW7.2 fs2), and a third round of kinetic-based flow sorting (KW7.3 kfs2); and (3) a yeast population expressing the KM12 parental clone (KM12) and the yeast populations affinity matured from the KM12 parental clone following a first round of flow sorting (KM12.1 fs2), a second round of flow sorting (KM12.2 fs2), a third round of flow sorting (KM12.3 fs2), and a fourth round of kinetic-based flow sorting (KM12.4 kfs2). Each round of selection resulted in increased binding affinity for CD161.

TABLE 10

Binding affinity of yeast displaying anti-CD161 scFV to human CD161

| Flow-enriched yeast populations | $K_D$ (nM) |
|---|---|
| KW1 | 1114 |
| KW1.1 fs2 | 82.37 |
| KW1.2 fs2 | 6.73 |
| KW1.3 kfs2 | 0.3671 |
| KW7 | 926.3 |
| KW7.1 fs2 | 81.13 |
| KW7.2 fs2 | 6.767 |
| KW7.3 kfs2 | 0.5698 |
| KM12 | 1979 |
| KM12.1 fs2 | 151.4 |
| KM12.2 fs | 26.56 |
| KM12.3 fs2 | 5.494 |
| KM12.4 kfs2 | 0.1953 |

Figure 7C:
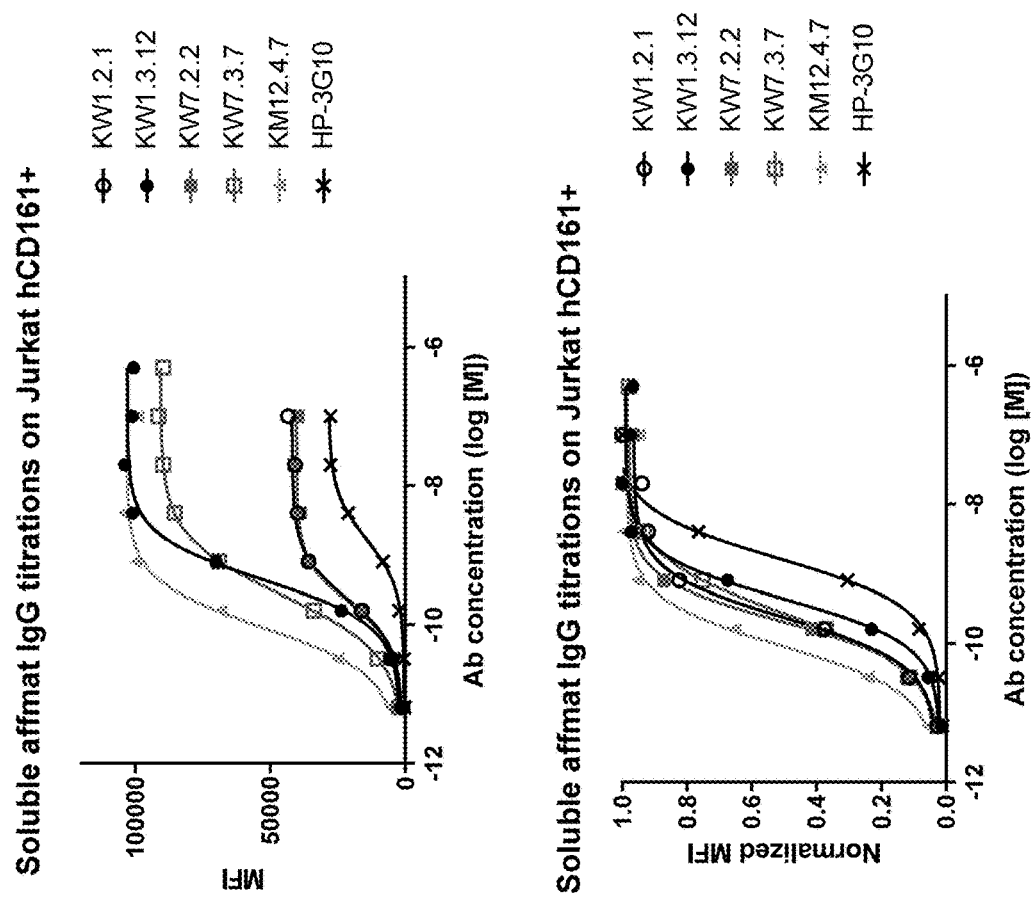
FIGS. 7C-7D provide line graphs depicting binding of affinity matured human anti-CD161 antibodies or mouse anti-human CD161 (HP-3G10) to Jurkat cells expressing human CD161 (FIG. 7C) or cynomolgus CD161 (FIG. 7D) as a function of antibody concentration as measured by flow cytometry. The degree of binding is represented by raw MFI values (top) or MFI values normalized to the highest value in each dataset (bottom).
Figure 7B:
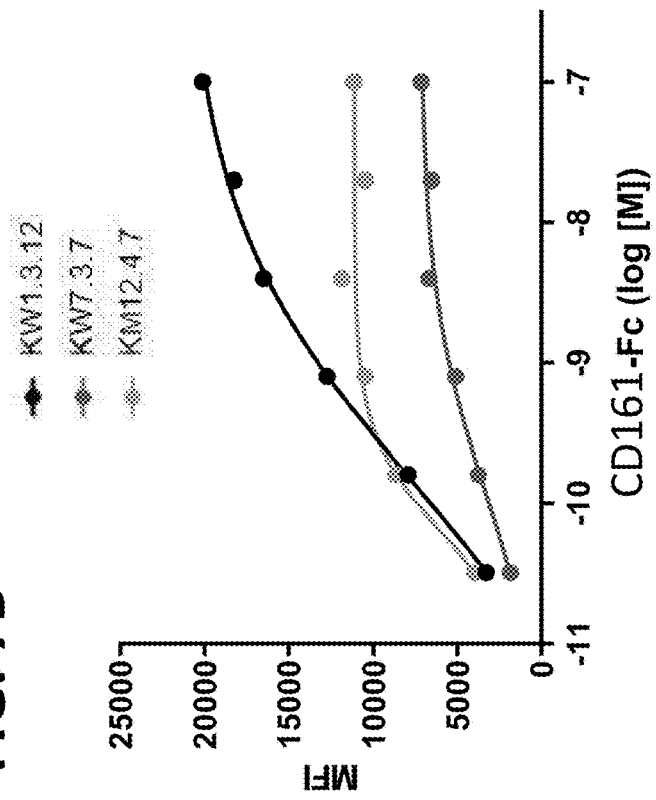
FIG. 7B provides line graphs depicting binding of CD161-Fc fusion protein to yeast expressing anti-CD161 scFvs as a function of CD161-Fc concentration as measured by flow cytometry.

Single clones isolated from enriched populations were individually evaluated by measuring binding of yeast displaying the anti-CD161 scFvs to CD161 antigen as above. Measurements made with yeast displaying high-affinity scFvs are shown in FIG. 7B, and $K_D$ values based on these measurements are shown in Table 11.

TABLE 11

Binding affinity of yeast displaying anti-CD161 scFv to CD161

| Antibody | $V_H$ domain (SEQ ID NO) | $V_L$ domain (SEQ ID NO) | $K_D$ (pM) |
|---|---|---|---|
| KW1.3.12 | 8 | 167 | 136.9 |
| KW7.3.7 | 41 | 190 | 118.8 |
| KM12.4.7 | 117 | 235 | 64.87 |

Figure 7D:
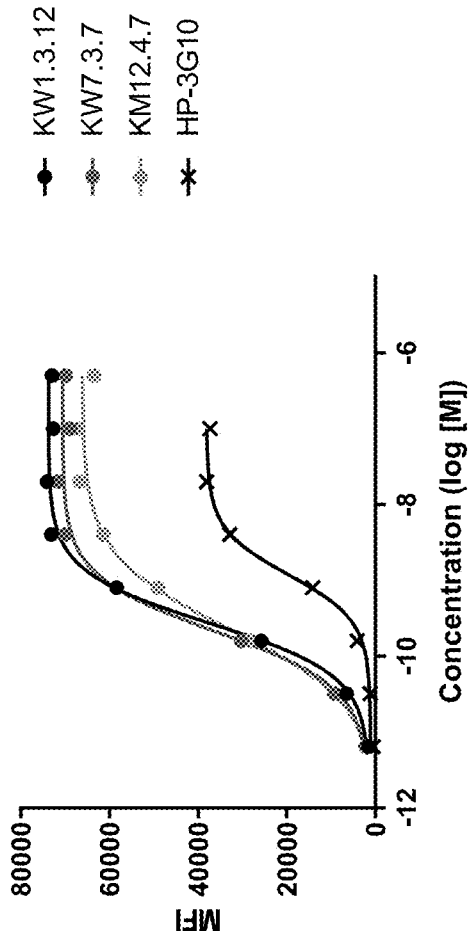
Figure 7D:
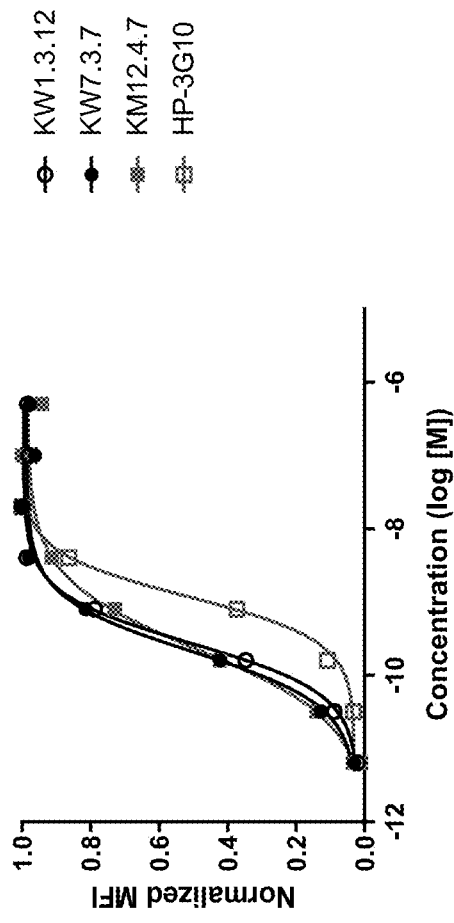

Additionally, binding affinity of affinity-matured CD161-targeting antibodies was evaluated against both human CD161 (hCD161) and cynomolgus CD161 (cynoCD161) and compared to binding of commercial mouse anti-human CD161 (HP-3G10). To measure binding, Jurkat cells expressing hCD161 or cynoCD161 were incubated with 0.01 nM to either 0.1 µM or 0.3 µM anti-CD161 antibodies as listed in Table 12. Jurkat cells expressing cynoCD161 were prepared using the methods described in Example 7. Volumes were sufficiently large such that ligand was depleted less than 10%. Following a three-hour incubation on ice, cells were washed and stained with fluorescent anti-human secondary antibody. The cells were washed, and labeling of antibody binding was assessed by flow cytometry to determine the MFI as a function of anti-CD161 antibody concentration. Raw MFI (top panel) and MFI normalized to the maximum value in each dataset (bottom panel) are shown for binding to hCD161 (FIG. 7C) and to cynoCD161 (FIG. 7D). Binding to both hCD161 and cynoCD161 was approximately 10-fold higher for the affinity matured antibodies relative to the commercial anti-CD161 antibody (HP-3G10). Additionally, several of the clones had similar binding affinity to hCD161 and cynoCD161 (KW1.2.1, KW1.3.12, KW7.2.2, and KW7.3.7). While one clone showed weaker binding affinity to cynoCD161 compared to hCD161 (KM12.4.7), demonstrating reduced cross-species reactivity.

TABLE 12

Binding affinity of anti-CD161 antibodies to human and cynomolgus CD161

| Antibody | $V_H$ domain (SEQ ID NO) | $V_L$ domain (SEQ ID NO) | $K_D$ (pM) to hCD161 | $K_D$ (pM) to cynoCD161 |
|---|---|---|---|---|
| KW1.2.1 | 15 | 165 | 232.6 | 247.3 |
| KW1.3.12 | 8 | 167 | 248.6 | 274.3 |
| KW7.2.2 | 22 | 185 | 207.1 | 240.0 |
| KW7.3.7 | 41 | 190 | 267.2 | 211.8 |
| KM12.4.7 | 117 | 235 | 92.47 | 225 |
| HP-3G10 | — | — | 1672 | 1183 |

Example 9: Identification of Shared Epitopes of CD161-Targeting Antibodies by Competition Analysis The CD161 epitopes recognized by the human anti-CD161 antibodies was assessed using a competition-based binding assay. Parental anti-CD161 scFvs identified as described in Example 6 (KW1, KW7, KW9, and KW17) were expressed as an scFv fused to a IgG1 Fc domain (with LALA-PG sequence variation; amino acid sequence set forth by SEQ ID NO: 326) and purified with rProtein A resin (GE Life Sciences). The resulting fusion proteins were fluorescently labeled with AlexaFluor647 succinimidyl ester and purified using Amicon centrifugal filters.

Figure 8A:
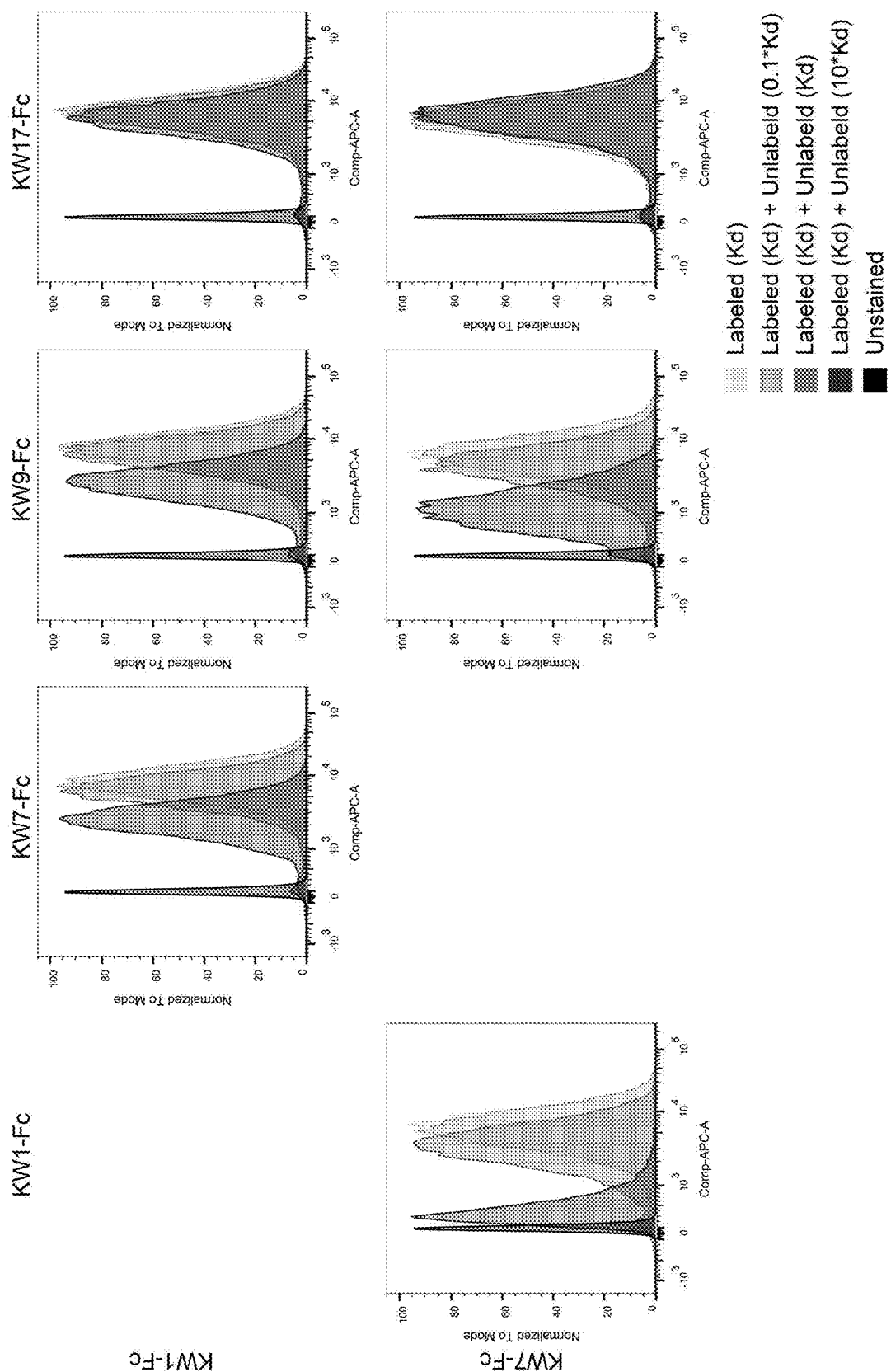
FIGS. 8A-8B provides histograms depicting binding of a labeled human anti-CD161 antibody (top to bottom=KW1, KW7 in FIG. 8A; top to bottom=KW9 and KW17 in FIG. 8B) to human CD161-expressing Jurkat cells measured by flow cytometry following labeling either alone or in the presence of increasing concentrations of an unlabeled human anti-CD161 antibody (left to right=KW1, KW7, KW9 and KW17), as compared to unstained cells as a negative control.
Figure 8B:
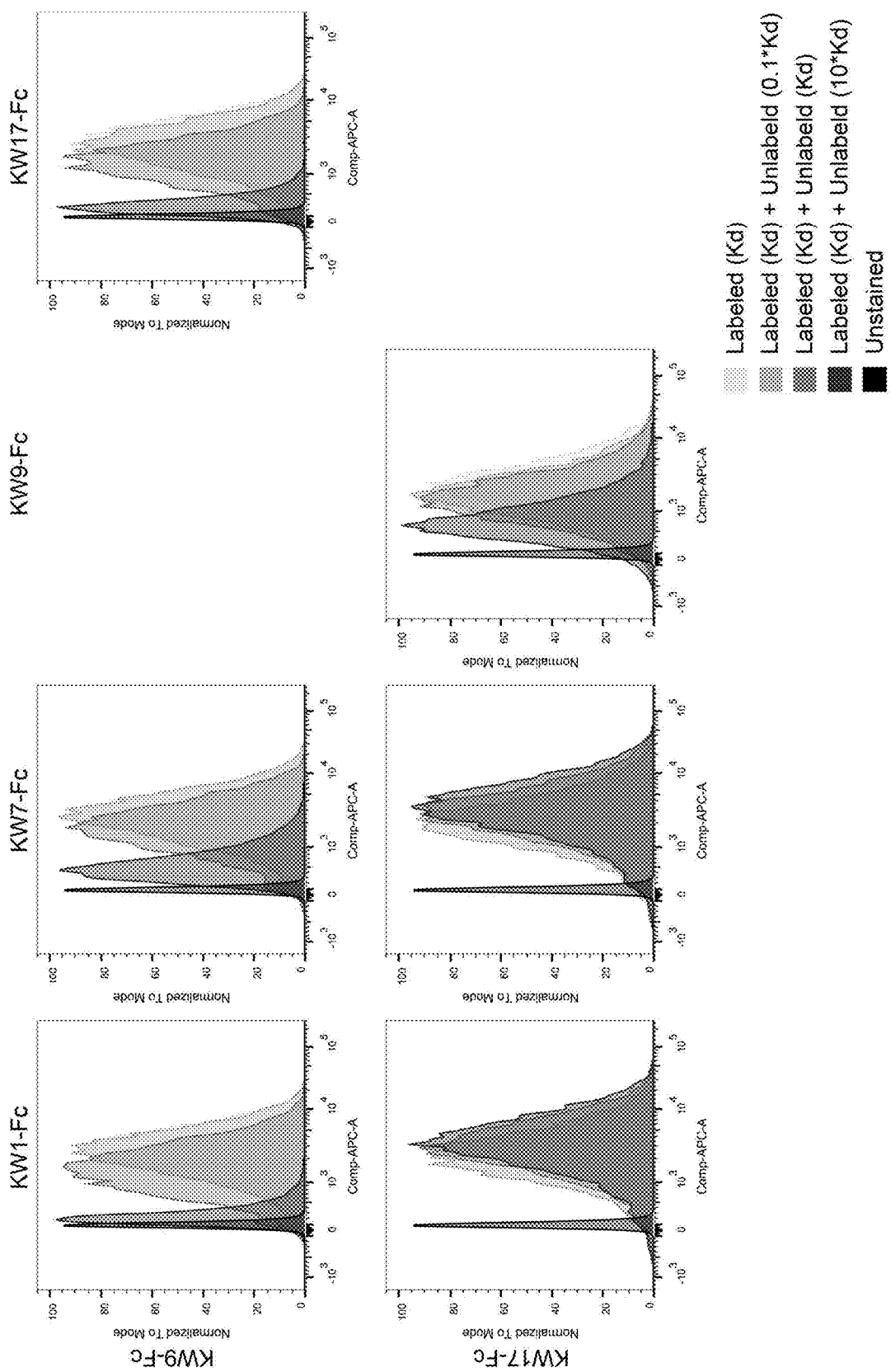

To evaluate competitive binding, hCD161-expressing Jurkat cells were incubated with labeled anti-CD161 fusion protein and an anti-CD161 fusion protein derived from a different clone that was unlabeled. The cells were treated with labeled anti-CD161 at a concentration equivalent to the $K_D$ for that clone and with unlabeled anti-CD161 at a concentration equivalent to the $K_D$ for that clone, 10-fold lower than the $K_D$ or 10-fold higher than the $K_D$. Cells were incubated with antibody for 1 hour, washed, and subsequently assessed for labeling by flow cytometry as shown in FIGS. 8A-8B. If labeling with a fluorescent anti-CD161 clone was reduced upon treatment with increasing concentrations of unlabeled anti-CD161 clone, the anti-CD161 scFvs were concluded to have competitive binding. Based upon analysis of labeling as shown in FIGS. 8A-8B, competitive binding interactions were defined for the scFvs as shown in Table 13. Without being bound by theory, competitive binding is potentially indicative of a common epitope shared by the anti-CD161 scFvs.

Figure 8D:
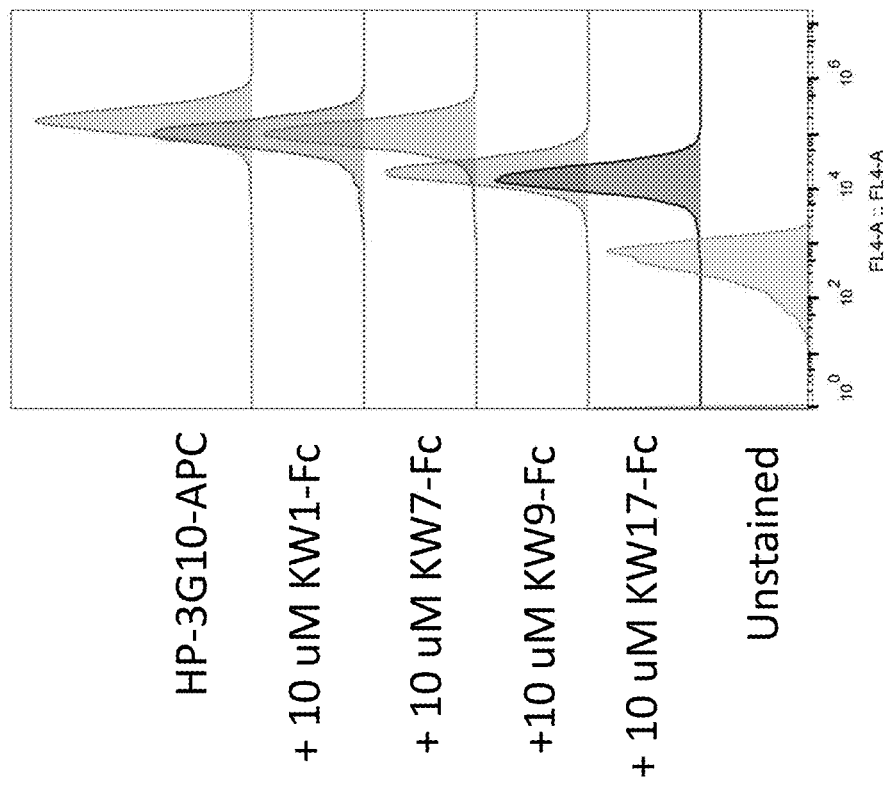
FIG. 8D provides histograms depicting binding of labeled mouse anti-human CD161 antibody (HP-3G10) to human CD161-expressing Jurkat cells measured by flow cytometry following labeling alone or in the presence of an unlabeled human anti-CD161 antibody (KW1, KW7, KW9, KW17), with unstained cells used as a negative control.
Figure 8C:
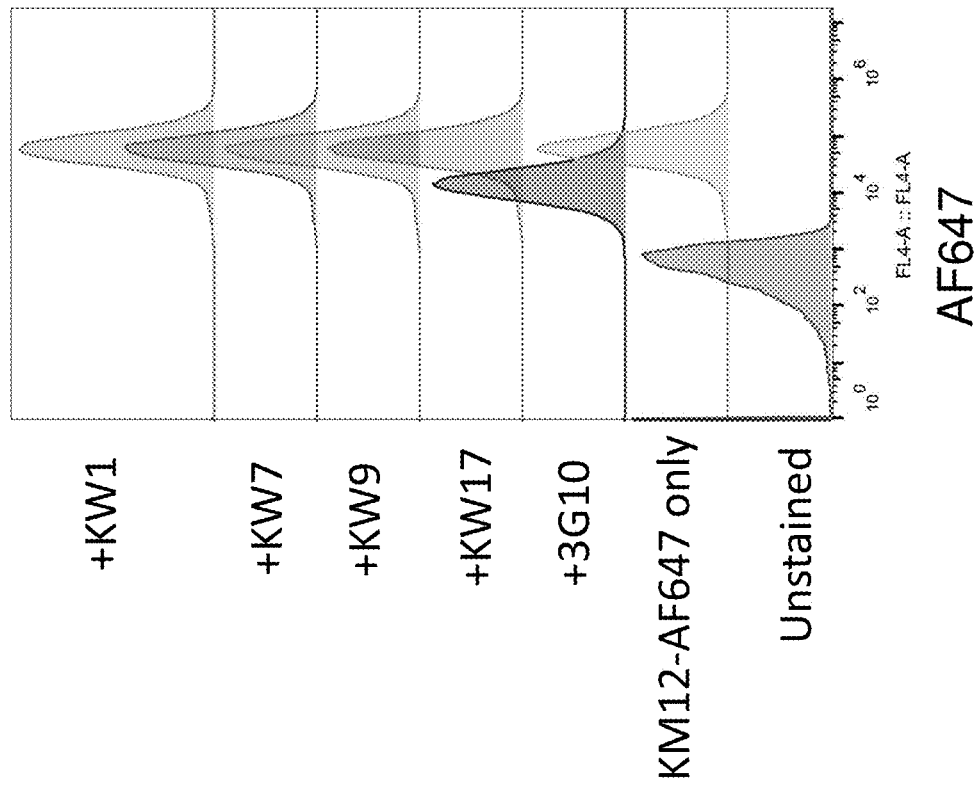
FIG. 8C provides histograms depicting binding of labeled human anti-CD161 antibody (KM12) to human CD161-expressing Jurkat cells measured by flow cytometry following labeling alone or in the presence of an unlabeled human anti-CD161 antibody (KW1, KW7, KW9, KW17) or mouse anti-human CD161 antibody (HP-3G10), as compared to unstained cells as a negative control.

Using the same approach, competitive binding was assessed for labeled KM12-Fc to other anti-CD161 scFv clones or commercial mouse anti-hCD161 (HP-3G10) as shown in FIG. 8C. hCD161-expressing Jurkat cells were treated with AF647-labeled KM12-Fc at a concentration equivalent to its $K_D$, while cells were treated with unlabeled antibody (KW1-Fc, KW7-Fc, KW9-Fc, KW17-Fc, or HP-3G10) at a concentration equivalent to 10 fold higher than the $K_D$ of each. Following incubation for 1 hour, the cells were washed and assessed for binding of KM12-Fc by flow cytometry. As shown in FIG. 8C, only co-incubation with HP-3G10 reduced binding of KM12-Fc to hCD161.

Furthermore, completive binding was assessed for Alexa-Fluor-647-labeled HP-3G10 to anti-CD161 scFv clones (KW1-Fc, KW7-Fc, KW9-Fc, and KW17-Fc) as shown in FIG. 8D. hCD161-expressing Jurkat cells were treated with 1 µM APC-labeled HP-3G10 and 10 µM unlabeled scFV-Fc. Following incubation for 1 hour, the cells were washed and assessed for binding of HP-3G10 by flow cytometry. As shown in FIG. 8C, co-incubation with KW9 and KW17 reduced binding of HP-3G10 to hCD161.

A summary of competitive binding interactions determined as shown in FIGS. 8A-8D is provided in Table 13.

TABLE 13

Summary of competitive binding analysis

| Anti-CD161 scFv | KW1 | KW7 | KW9 | KW17 | KM12 | HP-3G10 |
|---|---|---|---|---|---|---|
| KW1 | − | + | + | ND | ND | ND |
| KW7 | + | − | + | ND | ND | ND |
| KW9 | + | + | − | + | ND | + |
| KW17 | ND | ND | + | − | ND | + |
| KM12 | ND | ND | ND | ND | − | + |
| HP-3G10 | ND | ND | + | + | + | − |

+ indicates competitive binding to hCD161
ND indicates competitive binding not detected Example 10: Identification of Epitopes Using Alanine Scanning Mutagenesis of CD161

The CD161 epitopes recognized by parental CD161-binding scFv clones identified as described in Example 6 were evaluated. Specifically, a cell-based system was developed to express mutant forms of human CD161 where certain residues were mutagenized to alanine. The effect on antibody binding could then be assessed, with the assumption that reduced binding to a mutant CD161 was indicative of the mutagenized residue being important for antibody binding.

The system developed comprised transient expression of mutant hCD161 in HEK cells. Briefly, wild-type hCD161 or hCD161 comprising a residue mutated to alanine were inserted into a pIRES2 vector encoding GFP. Following transfection in HEK cells, GFP expression is localized to the cytoplasm to allow detection of transfected cells, and hCD161 is expressed on the cell membrane. hCD161 mutants included substitution of alanine for residues that were identified as being surface-exposed based upon analysis of the published hCD161 crystal structure (PDB 5mgt) and/or residues that were charged.

Figure 9:
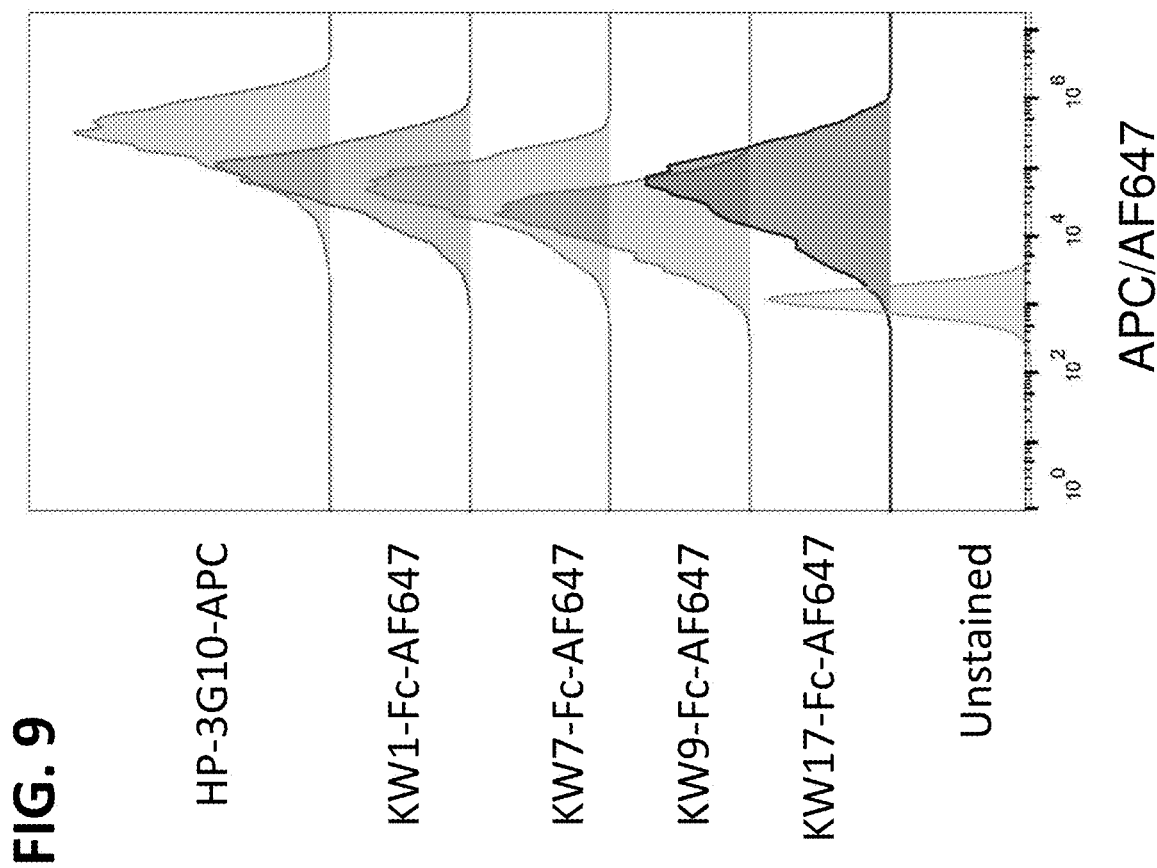
FIG. 9 provides histograms depicting binding of labeled human anti-CD161 antibodies (KW1, KW7, KW9, KW17) or labeled mouse anti-human CD161 antibody (HP-3G10) to HEK cells transiently expressing CD161 as measured by flow cytometry.

Binding to HEK cells expressing wild-type hCD161 or mutant hCD161 was evaluated for anti-CD161 scFvs fused to an Fc domain and fluorescently labeled with Alexa Fluor 647 as described in Example 9 (KW1, KW7, KW9, KW17, or KM12 scFVs). Binding was also evaluated for mouse anti-CD161 antibody (HP-3G10) labeled with APC. To evaluate binding, HEK cells were incubated with anti-CD161 protein for 1 hour at a concentration of 10-100 nM. The cells were then washed and assessed for labeling by flow cytometry. A high degree of labeling was observed for scFv-Fc fusion or HP-3G10 to HEK cells expressing wild-type hCD161 as shown in FIG. 9. Binding to mutant hCD161 was then compared to binding to wild-type hCD161. The outcome of these measurements are detailed in Table 14.

TABLE 14

CD161 residues important for binding of anti-CD161 antibodies

| CD161 substitution | KW1 | KW7 | KW9 | KW17 | KM12 | HP-3G10 |
|---|---|---|---|---|---|---|
| I96A | − | +++ | − | − | ++ | − |
| R102A | − | − | − | − | + | − |
| E103A | − | − | − | − | + | + |
| H110A | − | − | − | − | − | − |
| T111A | − | − | − | − | − | − |
| V112A | − | − | − | − | − | − |
| N113A | − | − | − | − | − | − |
| P114A | − | − | − | − | − | − |
| N116A | − | − | − | − | − | − |
| L119A | − | − | − | − | − | − |
| D121A | ++ | ++ | − | − | + | − |
| S123A | − | − | − | − | − | − |
| T124A | − | − | − | − | − | − |
| K125A | − | +++ | + | + | +++ | + |
| E126A | − | +++ | − | − | − | − |
| R133A | − | − | − | − | + | − |
| K135A | − | − | − | − | + | − |
| D136A | − | − | − | − | − | − |
| R146A | − | − | +++ | − | + | − |
| D147A | − | − | − | − | − | − |
| K148A | − | + | − | − | + | + |
| K163A | − | − | − | − | − | − |
| L151A | − | − | − | +++ | − | − |
| N157A | − | − | − | − | − | − |
| E162A | − | − | − | − | − | − |
| K163A | − | − | − | − | + | − |
| K166A | − | − | − | − | − | − |
| D177A | − | − | − | − | − | − |
| E179A | − | − | − | − | − | − |
| R181A | − | − | − | − | − | − |
| D183A | − | − | − | − | − | − |
| K185A | − | − | − | − | − | − |
| E186A | − | − | − | − | − | − |
| Y198A | − | − | − | +++ | − | − |
| S199A | − | − | − | − | − | − |
| E200A | − | − | − | +++ | − | ++ |
| Y201A | − | − | − | − | − | − |

TABLE 14-continued

CD161 residues important for binding of anti-CD161 antibodies

| CD161 substitution | KW1 | KW7 | KW9 | KW17 | KM12 | HP-3G10 |
|---|---|---|---|---|---|---|
| S203A | − | − | − | − | − | − |
| T204A | − | − | − | − | − | − |
| E205A | − | − | − | +++ | − | − |
| K212A | − | − | − | − | − | − |
| E213A | − | − | − | − | − | − |

Reduction in binding for mutant hCD161 relative to wild-type hCD161:
− indicates binding 61-100% of wild-type hCD161
+ indicates binding 41-60% of wild-type hCD161
++ indicated binding 21-40% of wild-type hCD161
+++ indicated binding 0-20% of wild-type hCD161

Example 11: Increased T Cell Activation in Presence of CD161-Targeting Antibodies The effect of human anti-CD161 antibodies generated in Example 6 on CD161-expressing human T cells was evaluated. Human T cells were isolated and prepared according to the methods described in Example 4. Briefly, CD161-expressing T cells were sorted from PBMCs isolated from human blood of healthy donors. The T cells were expanded in culture, then electroporated with Cas9 and gRNA targeting the TRAC gene locus to knockout endogenous TCR expression. The edited T cells were further expanded and induced to express a NY-ESO-1 [1G4] TCR using lentiviral transfection as described in Example 4. T cells were sorted for cells positive for NY-ESO-1 [1G4] TCR expression.

The response of edited T cells to U87-NYEP positive tumor cells prepared as described in Example 4 was evaluated alone or in the presence of anti-CD161 scFvs identified from the yeast display library and expressed as IgG1 antibodies. The CD161-targeting antibodies evaluated included KW1.2.1, KW7.2.2, and KM12.3.2, with sequences of the $V_H$ and $V_L$ domains identified in Table 15. Response was compared to a human IgG1 isotype control. Specifically, U87-NYEP positive tumor cells were seeded into 96-well plates at 30,000 cells per well and allowed to attach for 8 hours. Edited NY-ESO-1 TCR positive T cells were added at a density of 2.5:1 T cells to target cells. The cells were co-cultured for 72 hours in the presence of anti-CD161 antibody added at a concentration of 20 μg/μl.

TABLE 15

Antigen-targeting domain of CD161-targeting antibodies

| CD161-targeting antibody | VH SEQ ID NO | VL SEQ ID NO |
|---|---|---|
| KW1.2.1 | 15 | 165 |
| KW7.2.2 | 22 | 185 |
| KM12.3.2 | 113 | 212 |

Figure 10A:
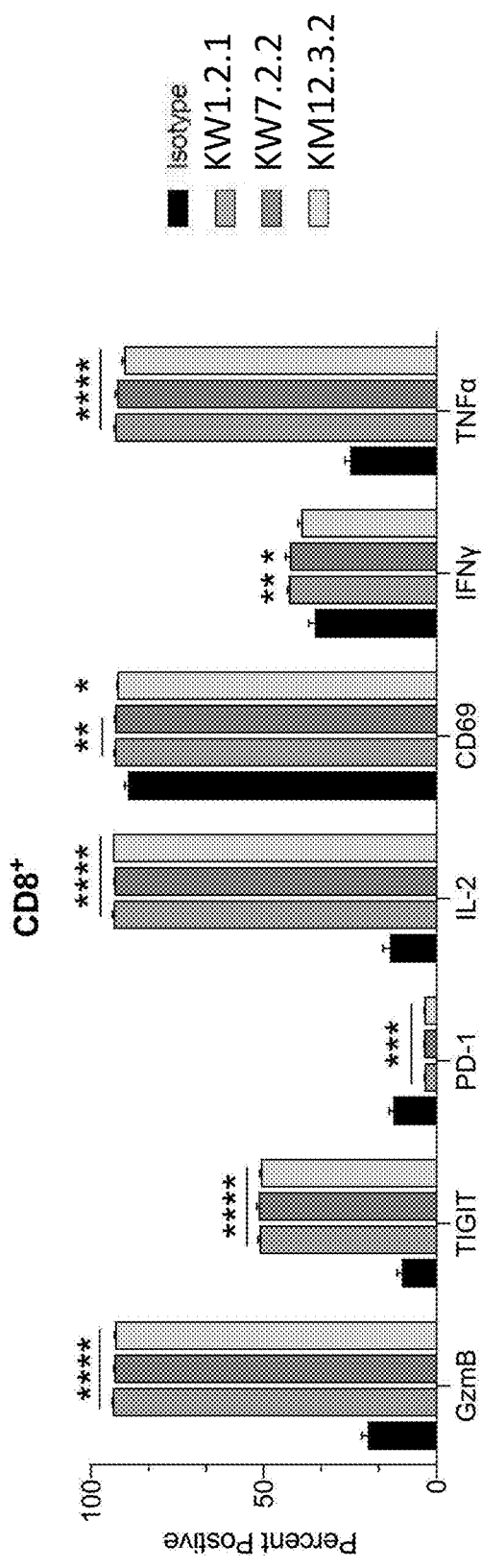
FIGS. 10A-10B provide bar graphs depicting expression of surface and intracellular markers of edited primary T cells that express a NY-ESO-1 specific TCR following co-culture with NY-ESO-1 protein antigen-expressing U87MG tumor cells in the presence of affinity-matured human anti-CD161 antibodies or a non-CD161 binding antibody isotype control as measured by flow cytometry. Shown are percentage of T cells positive for the indicated markers that are CD8 T cells (FIG. 10A) or CD4 T cells (FIG. 10B).
Figure 10B:
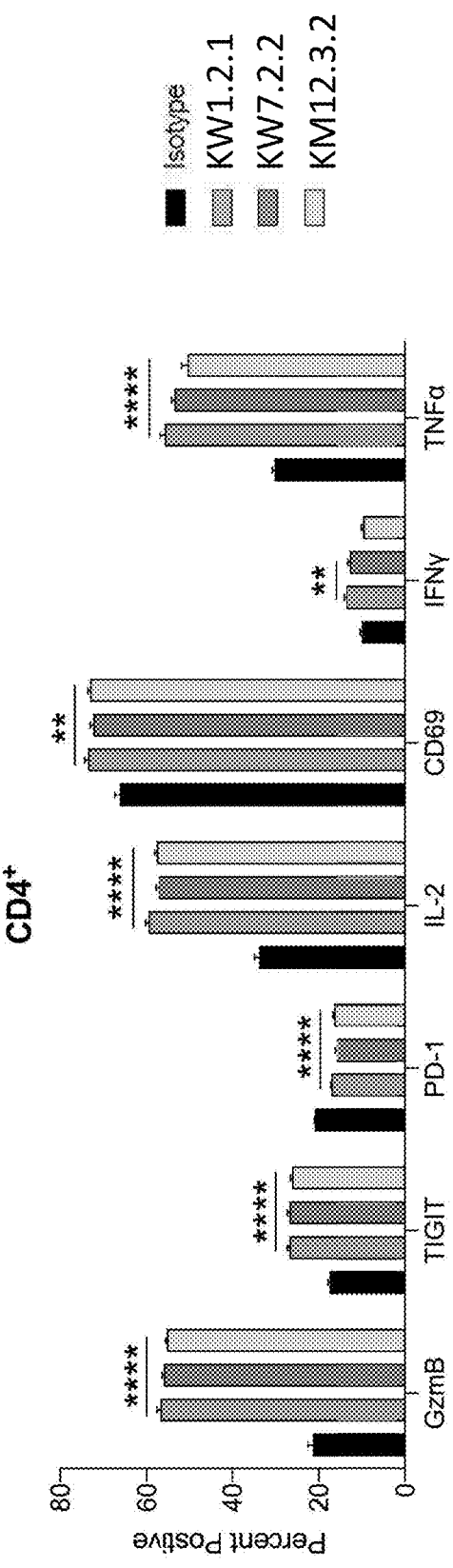

Following co-culture, the phenotype of the CD161-expressing CD4 or CD8 T cells was evaluated by flow cytometry as described in Example 4. Treatment with each of the antibody clones altered the phenotype of both CD8 and CD4 T cells substantially over treatment with an antibody isotype control as shown in FIG. 10A and FIG. 10B respectively. Treatment with human anti-CD161 antibodies resulted in a larger proportion of cells expressing intracellular cytokines (IL-2, IFNγ, and TNFα) and granzyme B (GzmB). Additionally, PD-1 expression was reduced in both CD8 and CD4 T cells treated with human anti-CD161 antibodies relative to an isotype control (FIGS. 10A-10B). The phenotype of the T cells was similar to that seen upon knockout of the KLRB1 gene as described in Example 4, indicating that the anti-CD161 antibodies identified by yeast display are sufficient for blocking function of the CD161 receptor in CD161-expressing T cells.

Example 12: CD161-Targeting Antibodies Induce In Vitro T Cell Response to Human Lymphoma Cells The effect of human anti-CD161 antibodies generated in Example 6 on response of T cells to CLEC2D-expressing lymphoma cells was evaluated using an in vitro co-culture assay. Specifically, the co-culture assay used CD161-expressing T cells transfected with a NY-ESO-1 specific TCR as described in Example 4 and CLEC2D-expressing tumor cells further expressing HLA-A*02:01 for presentation of the NY-ESO-1 peptide.

Figure 11:
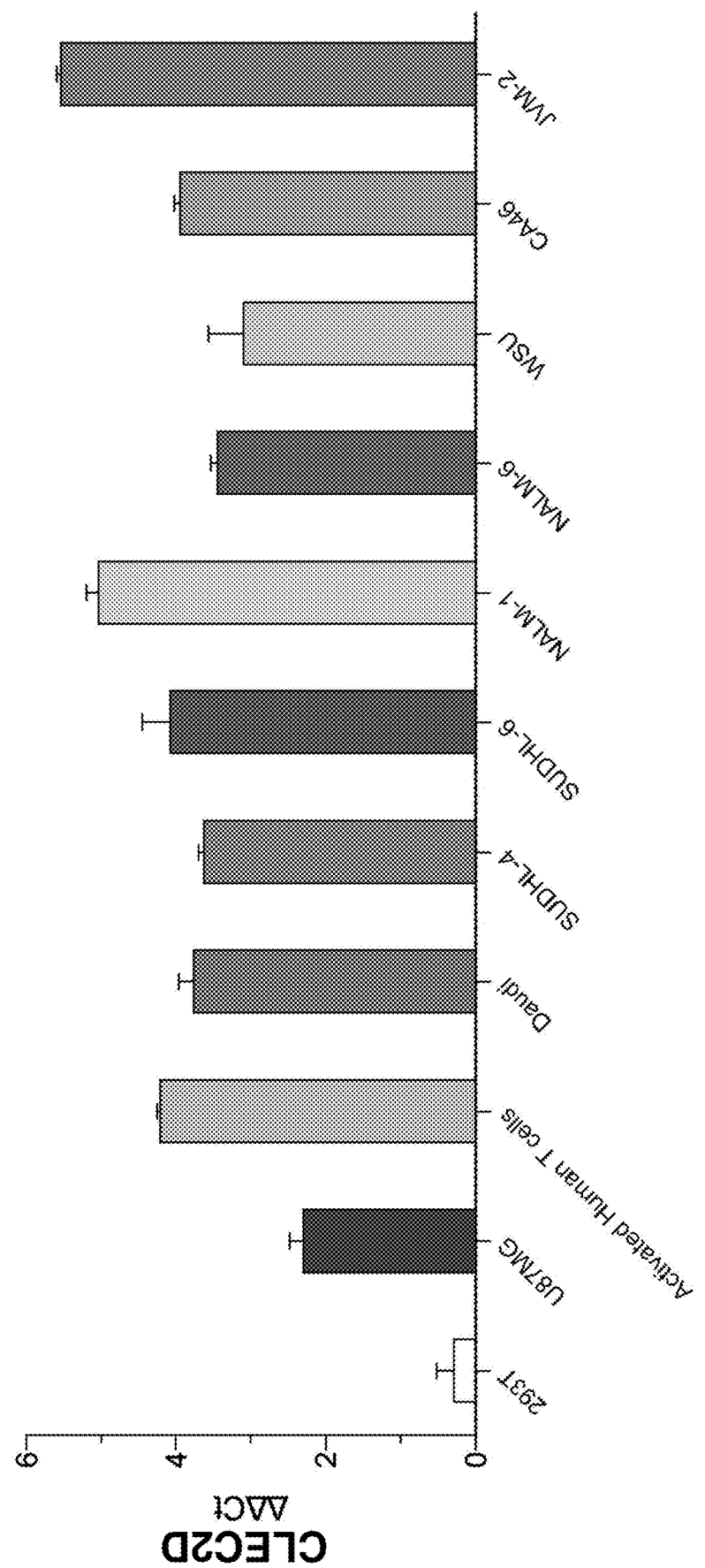
FIG. 11 provides a bar graph quantifying fold change in expression of CLEC2D mRNA by the indicated cell lines as measured by qPCR.

Briefly, expression of CLEC2D and HLA-A*02:01 was assessed in multiple human leukemia or lymphoma tumor cell lines, including Daudi, SUDHL-4, SUDHL-6, NALM-1, NALM-6, WSU, CA46, and JVM-2 by quantitative PCR (qPCR). The tumor cells were harvested from culture, and RNA was extracted using (RNeasy Mini; Qiagen). U87MG cells and isolated human T cells activated as described in Example 4 were used as positive controls as they each express CLEC2D, and HEK-293T cells were used as a negative control. The qPCR assay was performed using PowerUp SYBR Green Master Mix (ThermoFisher) according to the manufacture's protocol. PCR amplification was performed using forward and reverse primers targeting CLEC2D, and forward and reverse primers targeting housekeeping gene GAPDH. Quantification of CLEC2D RNA transcripts was performed using the ΔΔCt method. As shown in FIG. 11, CLEC2D transcripts were abundantly expressed by each of the tumor cell lines evaluated as compared to the positive controls. Additionally, each tumor cell line was confirmed for HLA-A2 expression by PCR amplification of genomic DNA and Sanger sequencing for the HLA-A*02:01 locus.

Subsequently, NALM-6 human lymphoma cells were selected for co-culture with human T cells engineered to express a NY-ESO-1 [1G4] TCR, prepared as described in Example 4. Following transfection with NY-ESO-1 TCR, the T cells were rested in culture supplemented with IL-2 (i.e., absence of anti-CD3 or anti-CD28 stimulation) for three days prior to the co-culture assay. Thereafter, NALM-6 tumor cells were seeded into 96-well plates at 75,000 cells per well, and were pulsed for 2.5 hours with the 1G4 NY-ESO-1 peptide (SLLMWITQC; SEQ ID NO: 392) at a concentration of 10 nM or 100 nM. The HLA-A*02:01 positive NALM-6 cells were expected to present NY-ESO-1 1G4 peptide epitope for activation of T cells expressing the NY-ESO-1 TCR. T cells were seeded in triplicate at a ratio of 0.25:1 or 1:1 T cell to tumor cell. Cells were co-cultured alone or in the presence of the anti-CD161 antibody KW1.3.12 which was prepared as a full human IgG1 with LALA-PG mutation as described in Example 6 (VH domain set forth in SEQ ID NO: 8; VL domain set forth in SEQ ID NO: 167; IgG1 heavy chain constant region set forth in SEQ ID NO: 326) or the mouse anti-CD161 HP-3G10 antibody. Non-CD161 specific human antibody and mouse antibody were used as corresponding isotype controls. The co-culture was incubated for 48 hours.

Figure 12A:
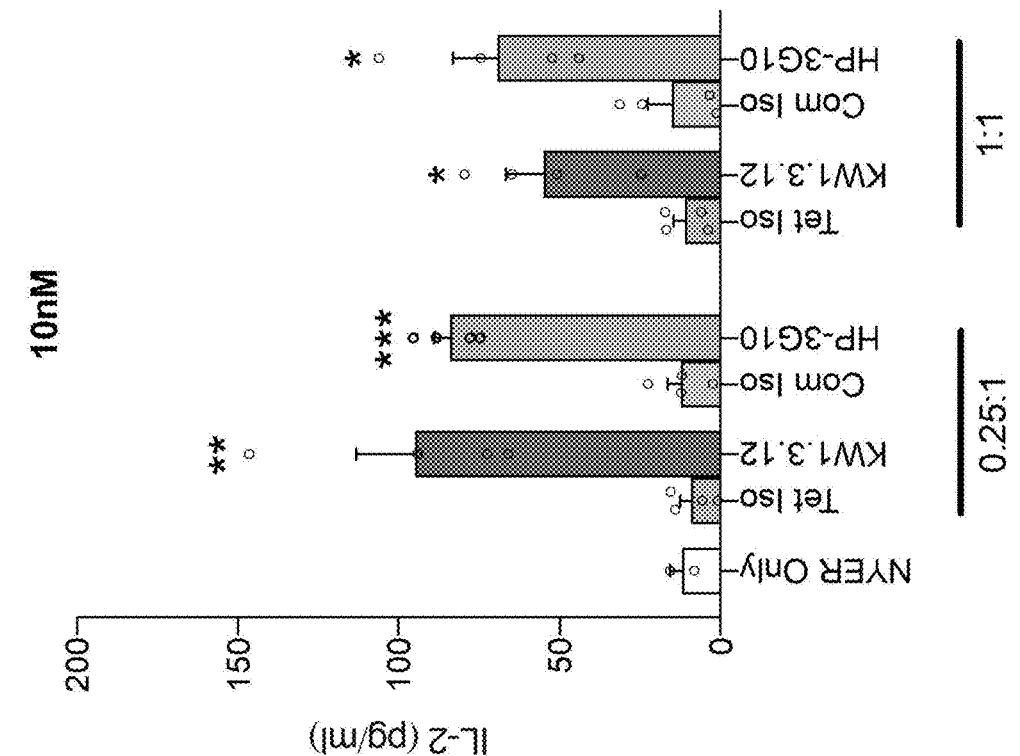
FIGS. 12A-12B provide bar graphs quantifying IL-2 in supernatant of NALM-6 human lymphoma cells pulsed with NY-ESO-1 1G4 peptide epitope at a concentration of 100 nM (FIG. 12A) or 10 nM (FIG. 12B) and co-cultured with NY-ESO-1 TCR-expressing T cells at the indicated T cell to tumor cell ratios, either co-cultured alone or in the presence of human anti-CD161 antibody KW1.3.12, mouse anti-CD161 antibody HP-3G10 or corresponding isotype controls (Tet Iso or Com Iso respectively). *$P<0.05$, $P<0.01$, *$P<0.001$, error bars denote SEM.
Figure 12B:
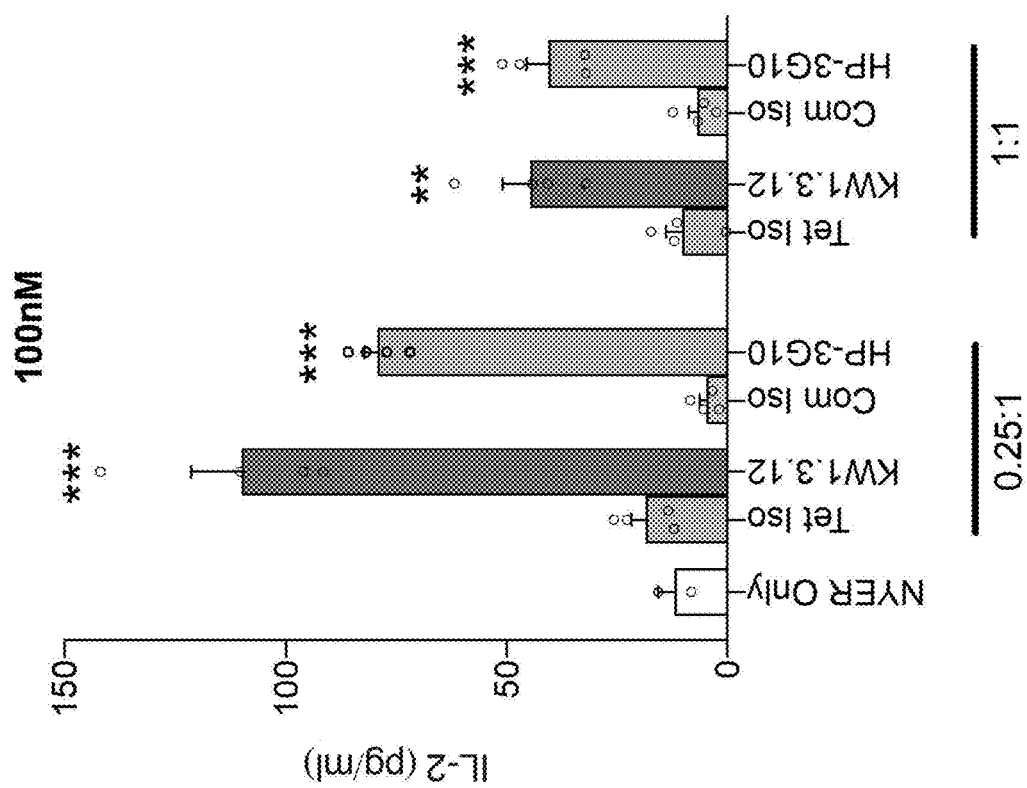
Figure 13B:
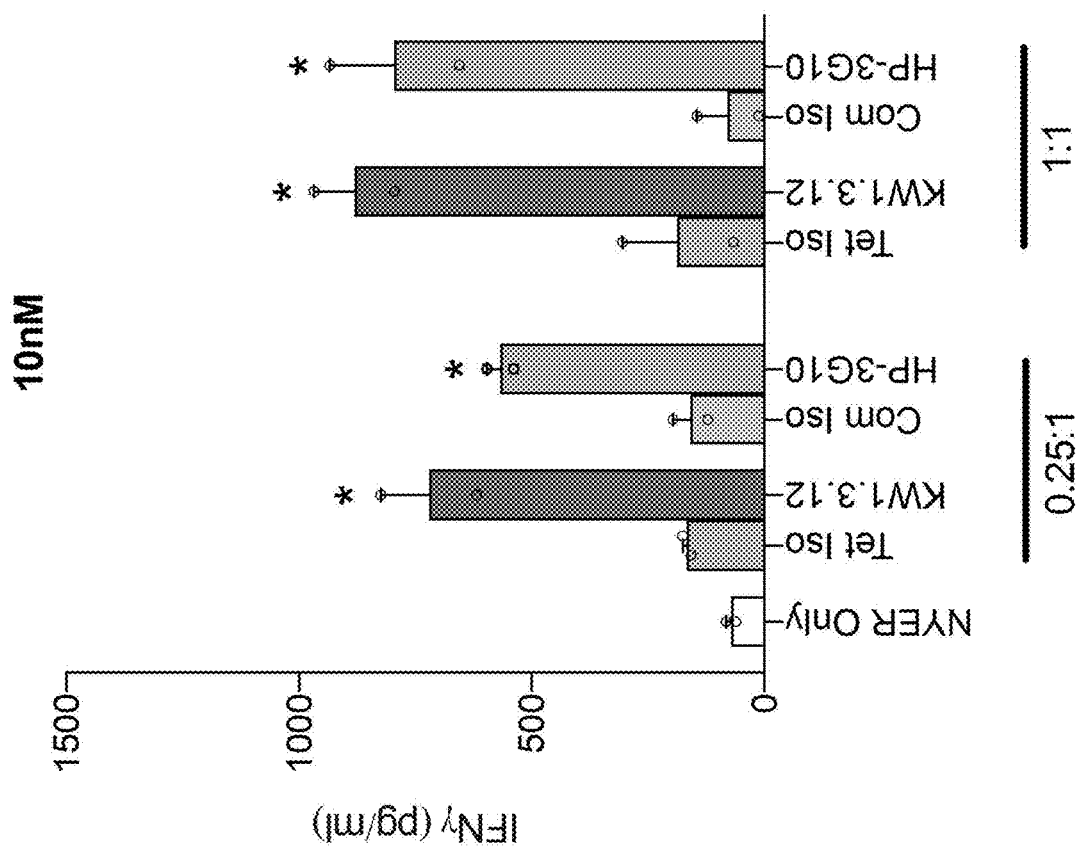
FIGS. 13A-13B provide bar graphs quantifying IFNγ in supernatant of NALM-6 human lymphoma cells pulsed with NY-ESO-1 1G4 peptide epitope at a concentration of 100 nM (FIG. 13A) or 10 nM (FIG. 13B) and co-cultured with NY-ESO-1 TCR-expressing T cells at the indicated T cell to tumor cell ratios, either co-cultured alone or in the presence of human anti-CD161 antibody KW1.3.12, mouse anti-CD161 antibody HP-3G10 or corresponding isotype controls (Tet Iso or Com Iso respectively). *$P<0.05$, **$P<0.01$, error bars denote SEM.
Figure 13A:
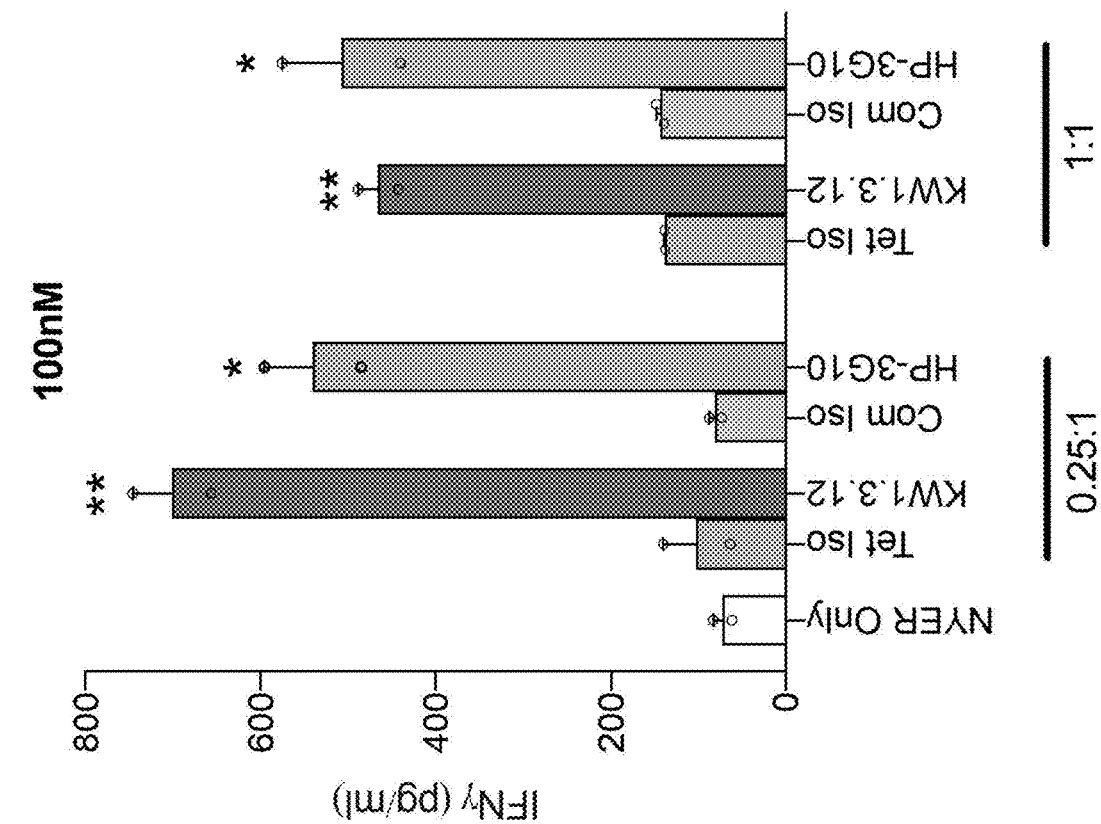

Subsequently, quantities of IL-2 and IFNγ in co-culture supernatants was measured by ELISA (ELISA MAX Deluxe; Biolegend) in order to measure T cell response to CLEC2D-expressing NALM-6 cells. Higher quantities of both IL-2 (FIGS. 12A-12B) and IFNγ (FIGS. 13A-13B) were detected in supernatants from co-culture incubated with either anti-CD161 antibody, at either high (FIGS. 12A and 13A) or low (FIGS. 12B and 13B) 1G4 peptide epitope concentration. Moreover, the KW1.3.12 antibody resulted in the highest levels of T cell cytokine production, indicating effective CD161 blockade.

Example 13: CD161-Targeting Antibodies have Low Reactivity to Homologous Human Proteins The reactivity of anti-CD161 antibodies to protein targets sharing structural homology with hCD161 was evaluated. Protein targets that were selected included proteins with a C-type lectin fold, as this is a key structural feature of CD161. These included other members within the killer cell lectin-like receptor subfamily. Additionally, the anti-CD161 antibodies were evaluated for binding to cynoCD161.

Binding was evaluated against Jurkat cells expressing either hCD161 or an alternate protein target. Jurkat cells expressing the desired protein target were prepared according to the methods described in Example 7.

To assess binding, anti-CD161 antibodies were incubated with either wild type Jurkat cells or Jurkat cells expressing target protein. The anti-CD161 antibodies that were evaluated are listed in Table 16 and included both parental and affinity-matured clones identified as described in Example 6. Cross-reactivity was compared to commercial mouse-anti-CD161 antibody (HP-3G10).

TABLE 16

| Anti-CD161 antibodies evaluated for cross-reactivity | | |
|---|---|---|
| Antibody | $V_H$ domain SEQ ID NO | $V_L$ domain SEQ ID NO |
| KW1 | 1 | 152 |
| KW7 | 22 | 152 |
| KW9 | 43 | 152 |
| KW17 | 61 | 245 |
| KW12 | 88 | 152 |
| KW1.2.1 | 15 | 165 |
| KW1.3.12 | 8 | 167 |
| KW7.2.2 | 22 | 185 |
| KW7.3.7 | 41 | 190 |
| KW9.3.3 | 56 | 206 |
| KW17.3.4 | 78 | 267 |
| KM12.2.3 | 105 | 223 |
| KM12.4.7 | 117 | 235 |
| HP-3G10 | — | — |

The cells were treated with antibody at a concentration of 100 nM for 1 hour on ice. Cells were then washed and labeled with a fluorescent anti-human secondary reagent to detect binding of the anti-CD161 antibody. Labeling was evaluated by flow cytometry. The MFI values normalized to WT indicating the degree of labeling for each antibody tested are shown for the parental clones in Table 17A and for the affinity-matured clones in Table 17B. No labeling was detected in the presence of the secondary reagent only for any of the target-expressing cells or for a non-anti-CD161 binding antibody (e.g., 4m5.3). No binding above background levels was detected to protein targets sharing structural homology with hCD161 for the anti-CD161 antibodies identified from the yeast-display library. These results indicate that the identified clones are specific for epitopes unique to hCD161.

TABLE 17A

Binding of anti-CD161 antibody parental clones to protein targets sharing sequence or structural homology with human CD161

|  | KW1 | KW7 | KW9 | KW17 | KM12 | HP-3G10 |
|---|---|---|---|---|---|---|
| Jurkat WT | 1.00 | 1.00 | 1.00 | 1.00 | 1.00 | 1.00 |
| hCD161 | 19.13 | 30.80 | 16.49 | 53.86 | 156.84 | 75.20 |
| cynoCD161 | 18.70 | 22.31 | 1.12 | 0.98 | 5.70 | 46.69 |
| hKLRF1 | 1.03 | 1.00 | 1.01 | 0.89 | 0.97 | 0.94 |
| hCD94 | 1.10 | 1.07 | 1.15 | 0.95 | 0.99 | 1.00 |
| hKLRF2 | 1.18 | 1.13 | 1.16 | 1.01 | 1.05 | 1.07 |
| hClec12B | 1.22 | 1.16 | 1.21 | 1.04 | 1.08 | 1.10 |
| hClec7A | 1.30 | 1.23 | 1.29 | 1.13 | 1.16 | 1.16 |
| hKLRG1 | 1.20 | 1.16 | 1.22 | 1.05 | 1.08 | 1.07 |
| hOLR1 | 1.13 | 1.09 | 1.13 | 0.98 | 1.01 | 1.01 |
| hClec5A | 1.21 | 1.14 | 1.17 | 1.04 | 1.07 | 1.08 |
| hClec9A | 1.21 | 1.15 | 1.20 | 1.07 | 1.08 | 1.09 |
| hCD209 | 1.05 | 1.01 | 1.06 | 0.92 | 0.98 | 1.01 |
| hClec4E | 1.07 | 1.07 | 1.08 | 0.94 | 0.97 | 1.00 |
| hClec10A | 1.10 | 1.12 | 1.10 | 0.96 | 0.99 | 1.00 |

TABLE 17B

Binding of anti-CD161 antibody affinity-matured clones to protein targets sharing sequence or structural homology with human CD161

|  | KW 1.2.1 | KW 1.3.12 | KW 7.2.2 | KW 7.3.7 | KW 9.3.3 | KM 17.3.4 | KM 12.2.3 | KM 12.4.7 |
|---|---|---|---|---|---|---|---|---|
| Jurkat WT | 1.00 | 1.00 | 1.00 | 1.00 | 1.00 | 1.00 | 1.00 | 1.00 |
| hCD161 | 172.03 | 163.31 | 144.70 | 137.17 | 149.85 | 142.64 | 122.43 | 166.44 |
| cynoCD161 | 102.59 | 117.26 | 107.98 | 107.77 | 0.89 | 1.03 | 11.92 | 115.72 |
| hKLRF1 | 1.14 | 1.02 | 1.18 | 1.19 | 0.80 | 0.91 | 1.18 | 1.14 |
| hCD94 | 1.13 | 1.07 | 1.29 | 1.01 | 0.84 | 0.97 | 1.36 | 1.20 |
| hKLRF2 | 1.05 | 1.08 | 1.12 | 1.03 | 0.90 | 1.03 | 1.37 | 1.13 |
| hClec12B | 1.11 | 1.10 | 1.37 | 1.05 | 0.94 | 1.09 | 1.33 | 1.12 |
| hClec7A | 1.25 | 1.38 | 1.46 | 1.18 | 1.03 | 1.16 | 1.11 | 1.36 |
| hKLRG1 | 1.24 | 1.25 | 1.30 | 1.06 | 0.93 | 1.08 | 1.42 | 1.25 |
| hOLR1 | 1.28 | 1.24 | 1.42 | 1.15 | 0.90 | 1.03 | 1.33 | 1.30 |
| hClec5A | 1.13 | 1.19 | 1.24 | 1.08 | 0.93 | 1.12 | 1.41 | 1.31 |
| hClec9A | 1.24 | 1.11 | 1.42 | 1.01 | 0.94 | 1.13 | 1.42 | 1.17 |
| hCD209 | 0.96 | 0.91 | 1.00 | 0.85 | 0.81 | 0.94 | 1.48 | 0.97 |
| hClec4E | 0.99 | 1.17 | 1.10 | 0.88 | 0.85 | 0.97 | 1.68 | 1.01 |
| hClec10A | 0.94 | 0.90 | 0.90 | 0.89 | 0.86 | 0.98 | 1.44 | 1.01 |

The degree of binding to cynoCD161 varied among the anti-CD161 clones. The parental KW1 and KW7 parental clones, as well as affinity matured variants derived from these clones, showed a similar degree of binding to hCD161 and cynoCD161. Additionally, the affinity matured clone KM12.4.7 showed comparable binding to hCD161 and cynoCD161. However, KW9, KW17, and KM12 parental clones and KW9 and KW17 affinity matured clones showed reduced binding to cynoCD161 relative to hCD161. Indeed, the KW9 and KW17 clones showed no binding to cynoCD161 over background. Thus, the minor sequence variation present in cynoCD161 relative to hCD161 is sufficient to eliminate binding of these antibodies.

Anti-CD161 Antibody VH and VL Sequences and Combination

TABLE 18

Anti-CD161 VH Domain

| Name | Sequence type | Sequence (IMGT Numbering) | SEQ ID NO |
|---|---|---|---|
| $V_H1$ | amino acid | EVQLVESGGGLVQPGGSLRLSCAASGFTFSSYAMSWVRQAPGK GLEWVSAISGSGGSTYYADSVKGRFTISRDNSKNTLYLQMNSL RAEDTAVYYCARGGLIPSGFDYWGQGTLVTVSS | 1 |
| $V_H1.0$ | Nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGGTCCGCCAGGCTCCAGGGAAG GGGCTGGAGTGGGTCTCAGCTATTAGTGGTAGTGGTGGTAGCA CATACTACGCAGACTCCGTGAAGGGCCGGTTCACCATCTCCAG AGACAATTCCAAGAACACGCTGTATCTGCAAATGAACAGCCTG | 2 |

TABLE 18-continued

Anti-CD161 VH Domain

| Name | Sequence type | Sequence (IMGT Numbering) | SEQ ID NO |
|---|---|---|---|
| | | AGAGCCGAGGACACGGCCGTGTATTACTGTGCGAGGGGTGGTC TGATCCCATCTGGTTTTGATTACTGGGGCCAAGGTACCCTGGT CACTGTCTCCAGT | |
| V$_H$1.1 | Nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGGTCCGCCAGGCTCCAGGGAAG GGGCTGGAGTGGGTCTCAGCTATTAGTGGTAGTGGTGGTAGCA CATACTACGCAGACTCCGTGAAGGGCCGGTTCACCATCTCCAG AGACAATTCCAAGAACACGCTGTATCTGCAAATGAACAGCCTG AGAGCCGAGGACACGGCCGTGTATTACTGTGCGAGAGGTGGTC TGATCCCATCTGGTTTTGATTACTGGGGCCAAGGTACCCTGGT CACTGTCTCCAGT | 3 |
| V$_H$2 | amino acid | EVQLVESGGGLVQPGGSLRLSCAASGFTFSSYAMSWVRQAPGK GLEWVSAISGSGGSTYYADSVKGRFTISRDNSKNALYLQMNSL RAEDTAVYYCARGGLIPSGFGYWGQGTLVTVSS | 4 |
| V$_H$2.0 | Nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGGTCCGCCAGGCTCCAGGGAAG GGGCTGGAGTGGGTCTCAGCTATTAGTGGTAGTGGTGGTAGCA CATACTACGCAGACTCCGTGAAGGGCCGGTTCACCATCTCCAG AGACAATTCCAAGAACGCGCTGTATCTGCAAATGAACAGCCTG AGAGCCGAGGACACGGCCGTGTATTACTGTGCGAGGGGTGGTC TGATCCCATCTGGTTTTGGTTACTGGGGCCAAGGTACCCTGGT CACTGTCTCCAGT | 5 |
| V$_H$3 | amino acid | EVQLVESGGGLVQPGGSLRLSCAASGFTFSSYAMSWVSQAPGK GLEWVSAISGSGGSTYYADSVKGRFTISRDNSKNTLYLQMNSL RAEDTAVYYCARGGLIPSGFDYWGQGTLVTVSS | 6 |
| V$_H$3.0 | Nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGGTCAGCCAGGCTCCAGGGAAG GGGCTGGAGTGGGTCTCAGCTATTAGTGGTAGTGGTGGTAGCA CATACTACGCAGACTCCGTGAAGGGCCGGTTCACCATCTCCAG AGACAATTCCAAGAACACGCTGTATCTGCAAATGAACAGCCTG AGAGCCGAGGACACGGCCGTGTATTACTGTGCGAGGGGTGGTC TGATCCCATCTGGTTTTGATTACTGGGGCCAAGGTACCCTGGT CACTGTCTCCAGT | 7 |
| V$_H$4 | amino acid | EVQLVESGGGLVQPGGSLRLSCAASGFTFSSYAMSWVRQAPGK GLEWVSTISGSGGSTYYADSVKGRFTISRDNSRNTLYLQMNSL RAEDTAVYYCARGGLIPSGFDYWGQGTLVTVSS | 8 |
| V$_H$4.0 | Nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTACGCCATGAGCTGGGTCCGCCAGGCTCCAGGGAAG GGGCTGGAGTGGGTCTCAACTATTAGTGGTAGTGGTGGTAGCA CATACTACGCAGACTCCGTGAAGGGCCGGTTCACCATCTCCAG AGACAATTCCAGGAACACGCTGTATCTGCAAATGAACAGCCTG AGAGCCGAGGACACGGCCGTGTATTACTGTGCGAGGGGTGGTC TGATCCCATCTGGTTTTGATTACTGGGGCCAAGGTACCCTGGT CACTGTCTCCAGT | 9 |
| V$_H$4.1 | Nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGGTCCGCCAGGCTCCAGGGAAG GGGCTGGAGTGGGTCTCAACTATTAGTGGTAGTGGTGGTAGCA CATACTACGCAGACTCCGTGAAGGGCCGGTTCACCATCTCCAG AGACAATTCCAGGAACACGCTGTATCTGCAAATGAACAGCCTG AGAGCCGAGGACACGGCCGTGTATTACTGTGCGAGGGGTGGTC TGATCCCATCTGGTTTTGATTACTGGGGCCAAGGTACCCTGGT CACTGTCTCCAGT | 10 |
| V$_H$5 | amino acid | EVQLVESGGGLVQPGGSLRLSCAASGFPFSSYAMSWVRQAPGK GLEWVSAISGSGGSTYYADSVKGRFTISRDNSKNTLYLQMNSL RAEDTAVYYCARGGLIPSGFDYWGQGTLVTVSS | 11 |
| V$_H$5.0 | Nucleic acid | GAGGTGCAGCTGGTGGAGTCTGGGGGAGGCTTGGTACAGCCTG GGGGGTCCCTGAGACTCTCCTGTGCAGCCTCTGGATTCCCCTT TAGCAGCTATGCCATGAGCTGGGTCCGCCAGGCTCCAGGGAAG GGGCTGGAGTGGGTCTCAGCTATTAGTGGTAGTGGTGGTAGCA | 12 |

TABLE 18-continued

Anti-CD161 VH Domain

| Name | Sequence type | Sequence (IMGT Numbering) | SEQ ID NO |
|---|---|---|---|
| | | CATACTACGCAGACTCCGTGAAGGGCCGGTTCACCATCTCCAG AGACAATTCCAAGAACACGCTGTATCTGCAAATGAACAGCCTG AGAGCCGAGGACACGGCCGTGTATTACTGTGCGAGGGGTGGTC TGATCCCATCTGGTTTTGATTACTGGGGCCAAGGTACCCTGGT CACTGTCTCCAGT | |
| $V_H6$ | amino acid | EVQLVESGGGLVQPGGSLRLSCAASGFTFSSYAMSWVRQAPGK GLEWVSAISGSGGSTYYADSVKGRFTISRGNSKNTLYLQMNSL RAEDTAVYYCARGGLIPSGFDYWGQGTLVTVSS | 13 |
| $V_H6.0$ | Nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGGTCCGCCAGGCTCCAGGGAAG GGGCTGGAGTGGGTCTCAGCTATTAGTGGTAGTGGTGGTAGCA CATACTACGCAGACTCCGTGAAGGGCCGGTTCACCATCTCCAG AGGCAATTCCAAGAACACGCTGTATCTGCAAATGAACAGCCTG AGAGCCGAGGACACGGCCGTGTATTACTGTGCGAGGGGTGGTC TGATCCCATCTGGTTTTGATTACTGGGGCCAAGGTACCCTGGT CACTGTCTCCAGT | 14 |
| $V_H7$ | amino acid | EVQLVESGGGLVQPGGSLRLSCAASGSTFSSYAMSWVRQAPGK GLEWVSTISGSGGSTYYADSVKGRFTISRDNSRNTLYLQMNSL RAEDTAVYYCARGGLIPSGFDYWGQGTLVTVSS | 15 |
| $V_H7.0$ | Nucleic acid | GAGGTGCAGCTGGTGGAGTCTGGGGGAGGCTTGGTACAGCCTG GGGGGTCCCTGAGACTCTCCTGTGCAGCCTCTGGATCCACCTT TAGCAGCTATGCCATGAGCTGGGTCCGCCAGGCTCCAGGGAAG GGGCTGGAGTGGGTCTCAACTATTAGTGGTAGTGGTGGTAGCA CATACTACGCAGACTCCGTGAAGGGCCGGTTCACCATCTCCAG AGACAATTCCAGGAACACGCTGTATCTGCAAATGAACAGCCTG AGAGCCGAGGACACGGCCGTGTATTACTGTGCGAGGGGTGGTC TGATCCCATCTGGTTTTGATTACTGGGGCCAAGGTACCCTGGT CACTGTCTCCAGT | 16 |
| $V_H7.1$ | Nucleic acid | GAGGTGCAGCTGGTGGAGTCTGGGGGAGGCTTGGTACAGCCTG GGGGGTCCCTGAGACTCTCCTGTGCAGCCTCTGGATCCACCTT TAGCAGTTATGCCATGAGCTGGGTCCGCCAGGCTCCAGGGAAG GGGCTGGAGTGGGTCTCAACTATTAGTGGTAGTGGTGGTAGCA CATACTACGCAGACTCCGTGAAGGGCCGGTTCACCATCTCCAG AGACAATTCCAGGAACACGCTGTATCTGCAAATGAACAGCCTG AGAGCCGAGGACACGGCCGTGTATTACTGTGCGAGGGGTGGTC TGATCCCATCTGGTTTTGATTACTGGGGCCAAGGTACCCTGGT CACTGTCTCCAGT | 17 |
| $V_H8$ | amino acid | EVQLVESGGGLVQPGGSLRLSCAASGFTFSSYAMSWVRQAPGK GLEWVSTISGSGGSTYYADSVKGRFTISRDNPRNTLYLQMNSL RAEDTAVYYCARGGLIPSGFDYWGQGTLVTVSS | 18 |
| $V_H8.0$ | Nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGGTCCGCCAGGCTCCAGGGAAG GGGCTGGAGTGGGTCTCAACTATTAGTGGTAGTGGTGGTAGCA CATACTACGCAGACTCCGTGAAGGGCCGGTTCACCATCTCCAG AGACAATCCCAGGAACACGCTGTATCTGCAAATGAACAGCCTG AGAGCCGAGGACACGGCCGTGTATTACTGTGCGAGGGGTGGTC TGATCCCATCTGGTTTTGATTACTGGGGCCAAGGTACCCTGGT CACTGTCTCCAGT | 19 |
| $V_H9$ | amino acid | EVQLVESGGGLVQPGGSLRLSCAASGFTFSSYAMSWVRQAPGK GLEWVSTISGSGGSTYYADSVKGRFTISRANSRNTLYLQMNSL RAEDTAVYYCARGGL1PSGFDYWGQGTLVTVSS | 20 |
| $V_H9.1$ | Nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGGTCCGCCAGGCCCCAGGGAAG GGGCTGGAGTGGGTCTCAACTATTAGTGGTAGTGGTGGTAGCA CATACTACGCAGACTCCGTGAAGGGCCGGTTCACCATCTCCAG AGCCAATTCCAGGAACACGCTGTATCTGCAAATGAACAGCCTG AGAGCCGAGGACACGGCCGTGTATTACTGTGCGAGGGGTGGTC TGATCCCATCTGGTTTTGATTACTGGGGCCAAGGTACCCTGGT CACTGTCTCCAGT | 21 |

TABLE 18-continued

Anti-CD161 VH Domain

| Name | Sequence type | Sequence (IMGT Numbering) | SEQ ID NO |
|---|---|---|---|
| V<sub>H</sub>10 | amino acid | EVQLVESGGGLVQPGGSLRLSCAASGFTFSSYAMSWVRQAPGK GLEWVSAISGSGGSTYYADSVKGRFTISRDNSKNTLYLQMNSL RAEDTAVYYCARGGYLPDAFDYWGQGTLVTVSS | 22 |
| V<sub>H</sub>10.0 | Nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGGTCCGCCAGGCTCCAGGGAAG GGGCTGGAGTGGGTCTCAGCTATTAGTGGTAGTGGTGGTAGCA CATACTACGCAGACTCCGTGAAGGGCCGGTTCACCATCTCCAG AGACAATTCCAAGAACACGCTGTATCTGCAAATGAACAGCCTG AGAGCCGAGGACACGGCCGTGTATTACTGTGCGAGGGGTGGTT ACCTGCCAGATGCATTTGATTACTGGGGCCAAGGTACCCTGGT CACTGTCTCCAGT | 23 |
| V<sub>H</sub>10.1 | Nucleic acid | GAGGTGCAGCTGGTGGAGTCTGGGGGAGGCCTGGTACAGCCTG GGGGGTCCCTGAGACTCTCCTGTGCAGCCTCTGGATTCACCTT TAGCAGCTATGCCATGAGCTGGGTCCGCCAGGCTCCAGGGAAG GGGCTGGAGTGGGTCTCAGCTATTAGTGGTAGTGGTGGTAGCA CATACTACGCAGACTCCGTGAAGGGCCGGTTCACCATCTCCAG AGACAATTCCAAGAACACGCTGTATCTGCAAATGAACAGCCTG AGAGCCGAGGACACGGCCGTGTATTACTGTGCGAGGGGTGGTT ACCTGCCAGATGCATTTGATTACTGGGGCCAAGGTACCCTGGT CACTGTCTCCAGT | 24 |
| V<sub>H</sub>10.2 | Nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGGTCCGCCAGGCTCCAGGGAAG GGGCTGGAGTGGGTCTCAGCTATTAGTGGTAGTGGTGGTAGCA CATACTACGCAGACTCCGTGAAGGGCCGGTTCACCATCTCCAG AGACAATTCCAAGAACACGCTGTATCTGCAAATGAACAGCCTG AGAGCCGAGGACACGGCCGTGTACTACTGTGCGAGGGGTGGTT ACCTGCCAGATGCATTTGATTACTGGGCCAAGGTACCCTGGT CACTGTCTCCAGT | 25 |
| V<sub>H</sub>10.3 | Nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGGTCCGCCAGGCTCCAGGGAAG GGGCTGGAGTGGGTCTCAGCTATTAGTGGTAGTGGTGGTAGCA CATACTACGCAGACTCCGTGAAGGGCCGGTTCACCATCTCCAG AGACAATTCCAAGAACACGCTGTATCTGCAAATGAACAGCCTG AGAGCCGAGGACACGGCCGTGTATTACTGTGCGAGGGGTGGTT ACCTGCCAGATGCATTCGATTACTGGGGCCAAGGTACCCTGGT CACTGTCTCCAGT | 26 |
| V<sub>H</sub>10.4 | Nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGGTCCGCCAGGCTCCGGGGAAG GGGCTGGAGTGGGTCTCAGCTATTAGTGGTAGTGGTGGTAGCA CATACTACGCAGACTCCGTGAAGGGCCGGTTCACCATCTCCAG AGACAATTCCAAGAACACGCTGTATCTGCAAATGAACAGCCTG AGAGCCGAGGACACGGCCGTGTATTACTGTGCGAGGGGTGGTT ACCTGCCAGACGCATTTGATTACTGGGGCCAAGGTACCCTGGT CACTGTCTCCAGT | 27 |
| V<sub>H</sub>10.5 | Nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGGTCCGCCAGGCTCCAGGGAAG GGGCTGGAGTGGGTCTCAGCTATTAGTGGTAGTGGTGGTAGCA CATACTACGCAGACTCCGTGAAGGGCCGGTTCACCATCTCCAG AGACAATTCCAAGAACACGCTGTATCTGCAAATGAACAGCCTG AGAGCCGAAGACACGGCCGTGTATTACTGTGCGAGGGGTGGTT ACCTGCCAGATGCATTTGATTACTGGGGCCAAGGTACCCTGGT CACTGTCTCCAGT | 28 |
| V<sub>H</sub>11 | amino acid | EVQLVESGGGLVQPGGSLRLSCAASGFTFSSYAMSWVRQAPGK GLEWVSAISGSGGSTYYADSVKGRFTISRDNSKNTLYLQMSSL RAEDTAVYYCARGGYLPDAFDYWGQGTLVTVSS | 29 |
| V<sub>H</sub>11.0 | Nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGGTCCGCCAGGCTCCAGGGAAG GGGCTGGAGTGGGTCTCAGCTATTAGTGGTAGTGGTGGTAGCA CATACTACGCAGACTCCGTGAAGGGCCGGTTCACCATCTCCAG | 30 |

TABLE 18-continued

Anti-CD161 VH Domain

| Name | Sequence type | Sequence (IMGT Numbering) | SEQ ID NO |
|---|---|---|---|
| | | AGACAATTCCAAGAACACGCTGTATCTGCAAATGAGCAGCCTG AGAGCCGAGGACACGGCCGTGTATTACTGTGCGAGGGGTGGTT ACCTGCCAGATGCATTTGATTACTGGGGCCAAGGTACCCTGGT CACTGTCTCCAGT | |
| $V_H13$ | amino acid | EVQLVESGGGLVQPGGSLRLSCAASGFTFSSYAMSWVRQAPCK GLEWVSAISGSGGSTYYADPVKGRFTISRDNSKNTLYLQMNSL RAEDTAVYYCARGGYLPDAFDYWGQGTLVTVSS | 31 |
| $V_H13.0$ | Nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGGTCCGCCAGGCTCCAGGGAAG GGGCTGGAGTGGGTCTCAGCTATTAGTGGCAGTGGTGGTAGCA CATACTACGCAGACCCCGTGAAGGGCCGGTTCACCATCTCCAG AGACAATTCCAAGAACACGCTGTATCTGCAAATGAACAGCCTG AGAGCCGAGGACACGGCCGTGTATTACTGTGCGAGGGGTGGTT ACCTGCCAGATGCATTTGATTACTGGGGCCAAGGTACCCTGGT CACTGTCTCCAGT | 32 |
| $V_H14$ | amino acid | EVQLVESGGGLVQPGGSLRLSCAASGFTFSSYAMSWVRQAPGK GLEWVSAISGSGGSTYYADSVKGRFTISRDNSKNTLYLQMNSL RAEDPAVYYCARGGYLPDAFDYWGQGTLVTVSS | 33 |
| $V_H14.0$ | Nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGGTCCGCCAGGCTCCAGGGAAG GGGCTGGAGTGGGTCTCAGCTATTAGTGGTAGTGGTGGTAGCA CATACTACGCAGACTCCGTGAAGGGCCGGTTCACCATCTCCAG AGACAATTCCAAGAACACGCTGTATCTGCAAATGAACAGCCTG AGAGCCGAGGACCCGGCCGTGTATTACTGTGCGAGGGGTGGTT ACCTGCCAGATGCATTTGATTACTGGGGCCAAGGTACCCTGGT CACTGTCTCCAGT | 34 |
| $V_H15$ | amino acid | EVQLVESGGGLVQPGGSLRLSCAASGFTFSSYAMSWVRQAPGK GLEWVSAISGSGGSTYYADSAKGRFTISRDNSKNTLYLQMNSL RAEDTAVYYCARGGYLPDAFDYWGQGTLVTVSS | 35 |
| $V_H15.0$ | Nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGGTCCGCCAGGCTCCAGGGAAG GGGCTGGAGTGGGTCTCAGCTATTAGTGGTAGTGGTGGTAGCA CATACTACGCAGACTCCGCGAAGGGCCGGTTCACCATCTCCAG AGACAATTCCAAGAACACGCTGTATCTGCAAATGAACAGCCTG AGAGCCGAGGACACGGCCGTGTACTACTGTGCGAGGGGTGGTT ACCTGCCAGATGCATTTGACTACTGGGGCCAAGGTACCCTGGT CACTGTCTCCAGT | 36 |
| $V_H16$ | amino acid | EVQLVESGGGLVQPGGPLRLSCAASGSTFSSYAMSWVRQAPGK GLEWVSAISGSGGSTYYADSVKGRFTISRDNSKNALYLQMNSL RAEDTAVYYCARGGYLPDAFDYWGQGTLVTVSS | 37 |
| $V_H16.0$ | Nucleic acid | GAGGTGCAGCTGGTGGAGTCTGGGGGAGGCTTGGTACAGCCTG GGGGGCCCCTGAGACTCTCCTGTGCAGCCTCTGGATCCACCTT TAGCAGCTATGCCATGAGCTGGGTCCGCCAGGCTCCAGGGAAG GGGCTGGAGTGGGTCTCAGCTATTAGTGGTAGTGGTGGTAGCA CATACTACGCAGACTCCGTGAAGGGCCGGTTCACCATCTCCAG AGACAATTCCAAGAACGCGCTGTATCTGCAAATGAACAGCCTG AGAGCCGAGGACACGGCCGTGTATTACTGTGCGAGGGGTGGTT ACCTGCCAGATGCATTTGATTACTGGGGCCAAGGTACCCTGGT CACTGTCTCCAGT | 38 |
| $V_H17$ | amino acid | EVQLVESGGGLVQPGGSLRLSCAASGFTFSSYAMSWVRQAPGK GLEWVSAISGSGGSTYYADSVKGRFTISRDSSKNTLYLQMNSL RAEDTAVYYCARGGYLPDAFDYWGQGTLVTVSS | 39 |
| $V_H17.0$ | Nucleic acid | GAGGTGCAGCTGGTGGAGTCTGGGGGAGGCTTGGTACAGCCTG GGGGGTCCCTGAGACTCTCCTGTGCAGCCTCTGGATTCACTTT TAGCAGCTATGCCATGAGCTGGGTCCGCCAGGCTCCAGGGAAG GGGCTGGAGTGGGTCTCAGCTATTAGTGGTAGTGGTGGTAGCA CATACTACGCAGACTCCGTGAAGGGCCGGTTCACCATCTCCAG AGACAGTTCCAAGAACACGCTGTATCTGCAAATGAACAGCCTG AGAGCCGAGGACACGGCCGTGTATTACTGTGCGAGGGGTGGTT ACCTGCCAGATGCATTTGATTACTGGGGCCAAGGTACCCTGGT CACTGTCTCCAGT | 40 |

TABLE 18-continued

Anti-CD161 VH Domain

| Name | Sequence type | Sequence (IMGT Numbering) | SEQ ID NO |
|---|---|---|---|
| V<sub>H</sub>18 | amino acid | EVQLVESGGGLVQPGGSLRLSCAASGFTFSSYAMSWVRQAPGK GLEWVSATSGSGGSTYYADSAKGRFTISRDNSKNTLYLQMNSL RAEDTAVYYCARGGYLPDAFDYWGRGTLVTVSS | 41 |
| V<sub>H</sub>18.0 | Nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGGTCCGCCAGGCTCCAGGGAAG GGGCTGGAGTGGGTCTCAGCTACTAGTGGTAGTGGTGGTAGCA CATACTACGCAGACTCCGCGAAGGGCCGGTTCACCATCTCCAG AGACAATTCCAAGAACACGCTGTATCTGCAAATGAACAGCCTG AGAGCCGAGGACACGGCCGTGTACTACTGTGCGAGGGGTGGTT ACCTGCCAGATGCATTTGACTACTGGGGCCGAGGTACCCTGGT CACTGTCTCCAGT | 42 |
| V<sub>H</sub>19 | amino acid | EVQLVESGGGLVQPGGSLRLSCAASGFTFSSYAMSWVRQAPGK GLEWVSAISGSGGSTYYADSVKGRFTISRDNSKNTLYLQMNSL RAEDTAVYYCARGPGDMYLYGDSFFDYWGQGTLVTVSS | 43 |
| V<sub>H</sub>19.0 | Nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGGTCCGCCAGGCTCCAGGGAAG GGGCTGGAGTGGGTCTCAGCTATTAGTGGTAGTGGTGGTAGCA CATACTACGCAGACTCCGTGAAGGGCCGGTTCACCATCTCCAG AGACAATTCCAAGAACACGCTGTATCTGCAAATGAACAGCCTG AGAGCCGAGGACACGGCCGTGTATTACTGTGCGAGGGGTCCAG GTGATATGTACCTGTACGGTGATTCTTTCTTTGATTACTGGGG CCAAGGTACCCTGGTCACTGTCTCCAGT | 44 |
| V<sub>H</sub>20 | amino acid | EVQLVESGGGLVQPGGSLRLSCAASGFTFSSYAMSWVRQAPGK GLEWVSAISGSGGSTYYADSVKGRFTISRDNSKNTLYLQMNSL RAEDTTVYYCARGPGDMYLYGDSFFDYWGQGTLVTVSS | 45 |
| V<sub>H</sub>20.0 | Nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGGTCCGCCAGGCTCCAGGGAAG GGGCTGGAGTGGGTCTCAGCTATTAGTGGTAGTGGTGGTAGCA CATACTACGCAGACTCCGTGAAGGGCCGGTTCACCATCTCCAG AGACAATTCCAAGAACACGCTGTATCTGCAAATGAACAGCCTG AGAGCCGAGGACACGACCGTGTATTACTGTGCGAGGGGTCCAG GTGATATGTACCTGTACGGTGATTCTTTCTTTGATTACTGGGG CCAAGGTACCCTGGTCACTGTCTCCAGT | 46 |
| V<sub>H</sub>21 | amino acid | EVQLVESGGGLVQPGGSLRLSCAASGFTFSSYAMSWVRQAPGK GLEWVSAISGSGGSTYYADSVKGRFTISRDNSKNTLYLQMNSL RAEDTAVYYCARGPGYMYLYGDSFFDYWGQGTLVTVSS | 47 |
| V<sub>H</sub>21.0 | Nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGGTCCGCCAGGCTCCAGGGAAG GGGCTGGAGTGGGTCTCAGCTATTAGTGGTAGTGGTGGTAGCA CATACTACGCAGACTCCGTGAAGGGCCGGTTCACCATCTCCAG AGACAATTCCAAGAATACGCTGTATCTGCAAATGAACAGCCTG AGAGCCGAGGACACGGCCGTGTATTACTGTGCGAGGGGTCCAG GTTATATGTACCTGTACGGTGATTCTTTCTTTGATTACTGGGG CCAAGGTACCCTGGTCACTGTCTCCAGT | 48 |
| V<sub>H</sub>21.1 | Nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGGTCCGCCAGGCTCCAGGGAAG GGGCTGGAGTGGGTCTCAGCTATTAGTGGTAGTGGTGGTAGCA CATACTACGCAGACTCCGTGAAGGGCCGGTTCACCATCTCCAG AGACAATTCCAAGAATACGCTATATCTGCAAATGAACAGCCTG AGAGCCGAGGACACGGCCGTGTATTACTGTGCGAGGGGTCCAG GTTATATGTACCTGTACGGTGATTCTTTCTTTGATTACTGGGG CCAAGGTACCCTGGTCACTGTCTCCAGT | 49 |
| V<sub>H</sub>22 | amino acid | EVRLVESGGGLVQPGGSLRLSCAASGFTFSSYAMSWVRQAPGK GLEWVSAISGSGGSTYYADSVKGRFTISRDNSKNTLYLQMNSL RAEDTAVYYCARGPGYMYLYGDSFFDYWGQGTLVTVSS | 50 |
| V<sub>H</sub>22.0 | Nucleic acid | GAGGTGCGGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGGTCCGCCAGGCTCCAGGGAAG | 51 |

TABLE 18-continued

Anti-CD161 VH Domain

| Name | Sequence type | Sequence (IMGT Numbering) | SEQ ID NO |
|---|---|---|---|
| | | GGGCTGGAGTGGGTCTCAGCTATTAGTGGTAGTGGTGGTAGCA CATACTACGCAGACTCCGTGAAGGGCCGGTTCACCATCTCCAG AGACAACTCCAAGAACACGCTGTATCTGCAAATGAACAGCCTG AGAGCCGAGGACACGGCCGTGTATTACTGTGCGAGGGGTCCAG GTTATATGTACCTGTACGGTGATTCTTTCTTTGATTACTGGGG CCAAGGTACCCTGGTCACTGTCTCCAGT | |
| V<sub>H</sub>23 | amino acid | EVQLVESGGGLVQPGGSLRLSCAASGFTFSSYAMSWVRQAPGK GLEWVSGISGSGGSTYYADSVKGRFTISRDNSKNTLYLQMNSL RAEDTAVYYCARGPGYMYLYGDSFFDYWGQGTLVTVSS | 52 |
| V<sub>H</sub>23.0 | Nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGGTCCGCCAGGCTCCAGGGAAG GGGCTGGAGTGGGTCTCAGGTATTAGTGGTAGTGGTGGTAGCA CATACTACGCAGACTCCGTGAAGGGCCGGTTCACCATCTCCAG AGACAATTCCAAGAACACGCTGTATCTGCAAATGAACAGCCTG AGAGCCGAGGACACGGCCGTGTATTACTGTGCGAGGGGTCCAG GTTATATGTACCTGTACGGTGATTCTTTCTTTGATTACTGGGG CCAAGGTACCCTGGTCACTGTCTCCAGT | 53 |
| V<sub>H</sub>25 | amino acid | EVQLVESGGGLVQPGGSLRLSCAASGFTFSSYAMSWVRQAPGK GLEWVSAISGSGGSTYYADSVKGRFTVSRDNSKNTLYLQMNSL RAEDTAVYYCARGPGYMYLYGDSFFDYWGQGTLVTVSS | 54 |
| V<sub>H</sub>25.0 | Nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGGTCCGCCAGGCTCCAGGGAAG GGGCTGGAGTGGGTCTCAGCTATTAGTGGTAGTGGTGGTAGCA CATACTACGCAGACTCCGTGAAGGGCCGGTTCACCGTCTCCAG AGACAATTCTAAGAATACGCTGTATCTGCAAATGAACAGCCTG AGAGCCGAGGACACGGCCGTGTATTACTGTGCGAGGGGTCCAG GTTATATGTACCTGTACGGTGATTCTTTCTTTGATTACTGGGG CCAAGGTACCCTGGTCACTGTCTCCAGT | 55 |
| V<sub>H</sub>26 | amino acid | EVQLVESGGGLVQPGGSLRLSCAASGFTFSSYAMSWVRQAPGK GLEWVSAISGSGGRTYYADSVKGRFTISRDNSKNTLYLQMNSL RAEDTAMYYCARGPGYMYLYGDSFFEYWGQGTLVTVSS | 56 |
| V<sub>H</sub>26.0 | Nucleic acid | GAGGTGCAGCTGGTGGAGTCTGGGGGAGGCTTGGTACAGCCTG GGGGGTCCCTGAGACTTTCCTGTGCAGCCTCTGGATTCACCTT TAGCAGCTATGCCATGAGCTGGGTCCGCCAGGCTCCAGGGAAG GGGCTGGAGTGGGTCTCAGCTATTAGTGGTAGTGGTGGTCGCA CATACTACGCAGACTCCGTGAAGGGCCGGTTCACCATCTCCAG AGACAATTCCAAGAATACGCTGTATCTGCAAATGAACAGCCTG AGAGCCGAGGACACGGCCATGTATTACTGTGCGAGGGGTCCAG GTTATATGTACCTGTACGGTGATTCTTTCTTTGAATACTGGGG CCAAGGTACCCTGGTCACTGTCTCCAGT | 57 |
| V<sub>H</sub>26.1 | Nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGGTCCGCCAGGCTCCAGGGAAG GGGCTGGAGTGGGTCTCAGCTATTAGTGGTAGTGGTGGTCGCA CATACTACGCAGACTCCGTGAAGGGCCGGTTCACCATCTCCAG AGACAATTCCAAGAATACGCTGTATCTGCAAATGAACAGCCTG AGAGCCGAGGACACGGCCATGTATTACTGTGCGAGGGGTCCAG GTTATATGTACCTGTACGGTGATTCTTTCTTTGAATACTGGGG CCAAGGTACCCTGGTCACTGTCTCCAGT | 58 |
| V<sub>H</sub>27 | amino acid | EVQLVESGGGLVRPGGSLRLSCAASGFTFSSYAMSWVRQAPGK GLEWVSGISGSGGSTYYADSVKGRFTISRDNSKNTLYLQMNSL RAEDTAVYYCARGPGYMYLYGDSFFDYWGQGTLVTVSS | 59 |
| V<sub>H</sub>27.0 | Nucleic acid | GAGGTGCAGCTGGTGGAGTCTGGGGGAGGCTTGGTACGGCCTG GGGGGTCCCTGAGACTCTCCTGTGCAGCCTCTGGATTCACCTT TAGCAGCTATGCCATGAGCTGGGTCCGCCAGGCTCCAGGGAAG GGGCTGGAGTGGGTCTCAGGTATTAGTGGTAGTGGTGGTAGCA CATACTACGCAGACTCCGTGAAGGGCCGGTTCACCATCTCCAG AGACAATTCCAAGAACACGCTGTATCTGCAAATGAACAGCCTG AGAGCCGAGGACACGGCCGTGTATTACTGTGCGAGGGGTCCAG GTTATATGTACCTGTATGGTGATTCTTTCTTTGATTACTGGGG CCAAGGTACCCTGGTCaCTGTCTCCAGT | 60 |

TABLE 18-continued

Anti-CD161 VH Domain

| Name | Sequence type | Sequence (IMGT Numbering) | SEQ ID NO |
|---|---|---|---|
| $V_H28$ | amino acid | EVQLVESGGGLVQPGGSLRLSCAASGFTFSSYAMSWVRQAPGK GLEWVSAISGSGGSTYYADSVKGRFTISRDNSKNTLYLQMNSL RAEDTAVYYCARDYYLSDYITQTSFDYWGQGTLVTVSS | 61 |
| $V_H28.0$ | Nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGGTCCGCCAGGCTCCAGGGAAG GGGCTGGAGTGGGTCTCAGCTATTAGTGGTAGTGGTGGTAGCA CATACTACGCAGACTCCGTGAAGGGCCGGTTCACCATCTCCAG AGACAATTCCAAGAACACGCTGTATCTGCAAATGAACAGCCTG AGAGCCGAGGACACGGCCGTGTATTACTGTGCGAGGGATTACT ACCTGTCTGATTACATCACCCAGACCTCTTTTGATTACTGGGG CCAAGGTACCCTGGTCACTGTCTCCAGT | 62 |
| $V_H29$ | amino acid | EVQLVESGGGLVQPGGSLRLSCAASGFTFSSYAMSWVRQAPGK GLEWVSAISGSGGSTYYADSVKGRFTISRDNSKNTLYLQMNSL RAEDTAVYYCARDYYLFDYITQTSFDYWGQGTLVTVSS | 63 |
| $V_H29.0$ | Nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGGTCCGCCAGGCTCCAGGGAAG GGGCTGGAGTGGGTCTCAGCTATTAGTGGTAGTGGTGGTAGCA CATACTACGCAGACTCCGTGAAGGGCCGGTTCACCATCTCCAG AGACAATTCCAAGAACACGCTGTACCTGCAAATGAACAGCCTG AGAGCCGAGGACACGGCCGTGTATTACTGTGCGAGGGATTACT ACCTGTTTGATTACATCACCCAGACCTCTTTTGATTACTGGGG CCAAGGTACCCTGGTCACTGTCTCCAGT | 64 |
| $V_H29.1$ | Nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGGTCCGCCAGGCTCCAGGGAAG GGGCTGGAGTGGGTCTCAGCTATTAGTGGTAGTGGTGGTAGCA CATACTACGCAGACTCCGTGAAGGGCCGGTTCACCATCTCCAG AGACAATTCCAAGAACACGCTGTATCTGCAAATGAACAGCCTG AGAGCCGAGGACACGGCCGTGTATTACTGTGCGAGGGATTACT ACCTGTTTGATTACATCACCCAGACCTCTTTTGATTACTGGGG CCAAGGTACCCTGGTCACTGTCTCCAGT | 65 |
| $V_H30$ | amino acid | EVQLVESGGGLVQPGGSLRLSCAASGFTFSSYAMSWVRQAPGK GLEWVSAISGSGGSTYYADSVKGRFTISRDNSKNTLYLQMNSL RAEDTAVYYCARDYYLYDYITQTSFDYWGQGTLVTVSS | 66 |
| $V_H30.1$ | Nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGGTCCGCCAGGCTCCAGGGAAG GGGCTGGAGTGGGTCTCAGCTATTAGTGGTAGTGGTGGTAGCA CATACTACGCAGACTCCGTGAAGGGCCGGTTCACCATCTCCAG AGACAATTCCAAGAACACGCTGTATCTGCAAATGAACAGCCTG AGAGCCGAGGACACGGCCGTGTATTACTGTGCGAGGGATTACT ACCTGTATGATTACATCACCCAGACCTCTTTTGATTACTGGGG CCAAGGTACCCTGGTCACTGTCTCCAGT | 67 |
| $V_H31$ | amino acid | EVQLVESGGGSVQPGGSLRLSCAASGFTFSSYAMSWVRQAPGK GLEWVSAISGSGGSTYYADSVKGRFTISRDNSKNTLYLQMNSL RAEDTAVYYCARDYYLFDYITQTSFDYWGQGTLVTVSS | 68 |
| $V_H31.0$ | Nucleic acid | GAGGTGCAGCTGGTGGAGTCTGGGGGAGGCTCGGTACAGCCTG GGGGGTCCCTGAGACTCTCCTGTGCAGCCTCTGGATTCACCTT TAGCAGCTATGCCATGAGCTGGGTCCGCCAGGCTCCAGGGAAG GGGCTGGAGTGGGTCTCAGCTATTAGTGGTAGTGGTGGTAGCA CATACTACGCAGACTCCGTGAAGGGCCGGTTCACCATCTCCAG AGACAATTCCAAGAACACGCTGTATCTGCAAATGAACAGCCTG AGAGCCGAGGACACGGCCGTGTATTACTGTGCGAGGGATTACT ACCTGTTTGATTACATCACCCAGACCTCTTTTGATTACTGGGG CCAAGGTACCCTGGTCACTGTCTCCAGT | 69 |
| $V_H32$ | amino acid | EVQLVESGGGLVQPGGSLRLSCAASGFTFSSYAMSWVRQAPGK GLEWVSAISGSGGSTYYADSVKGRFTISRDNSKNTLYLQMNSL RAEDAAVYYCARDYYLYDYITQTSFDYWGQGTLVTVSS | 70 |
| $V_H32.0$ | nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGGTCCGCCAGGCTCCAGGGAAG | 71 |

TABLE 18-continued

Anti-CD161 VH Domain

| Name | Sequence type | Sequence (IMGT Numbering) | SEQ ID NO |
|---|---|---|---|
| | | GGGCTGGAGTGGGTCTCAGCTATTAGTGGTAGTGGTGGTAGCA CATACTACGCAGACTCCGTGAAGGGCCGGTTCACCATCTCCAG AGACAATTCCAAGAACACGCTGTATCTGCAAATGAACAGCCTG AGAGCCGAGGACGCGGCCGTGTATTACTGTGCGAGGGATTACT ACCTGTATGATTACATCACCCAGACCTCTTTTGATTACTGGGG CCAAGGTACCCTGGTCACTGTCTCCAGT | |
| $V_H33$ | amino acid | EVQLVESGGGLVQPGGSLRLSCAASGFTFSSYAMSWVRQAPGK GLEWVSAISGSGGSAYYADSVKGRFTISRDNSKNTLYLQMNSL RAEDTAVYYCARDYYLYDYITQTSFDYWGQGTLVTVSS | 72 |
| $V_H33.0$ | Nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGGTCCGCCAGGCTCCAGGGAAG GGGCTGGAGTGGGTCTCAGCTATTAGTGGTAGTGGTGGTAGCG CATACTACGCAGACTCCGTGAAGGGCCGGTTCACCATCTCCAG AGACAATTCCAAGAACACGCTGTATCTGCAAATGAACAGCCTG AGAGCCGAGGACACGGCCGTGTATTACTGTGCGAGGGATTACT ACCTGTATGATTACATCACCCAGACCTCTTTTGATTACTGGGG CCAAGGTACCCTGGTCACTGTCTCCAGT | 73 |
| $V_H34$ | amino acid | EVQLVESGGGLVQPGGSLRLSCAASGFTFSSYAMSWVRQTPGK GLEWVSAISGSGGSTYYADSVKGRFTISRDNSKNTLYLQMNSL RAEDTAVYYCARDYYLYDYITQTSFDYWGQGTLVTVSS | 74 |
| $V_H34.0$ | Nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGGTCCGCCAGACTCCAGGGAAG GGGCTGGAGTGGGTCTCAGCTATTAGTGGTAGTGGTGGTAGCA CATACTACGCAGACTCCGTGAAGGGCCGGTTCACCATCTCCAG AGACAATTCCAAGAACACGCTGTATCTGCAAATGAACAGCCTG AGAGCCGAGGACACGGCCGTGTATTACTGTGCGAGGGATTACT ACCTGTATGATTACATCACCCAGACCTCTTTTGATTACTGGGG CCAAGGTACCCTGGTCACTGTCTCCAGT | 75 |
| $V_H35$ | amino acid | EVQLVESGGGLVQPGGSLRLSCAASGFAFISYAMSWVRQAPGK GLEWVSAISGSGGSTYYADSVKGRFTISRDNSKNALYLQMNSL RAEDTAVYYCARDYYLYDYITQTSFDYWGQGTLVTVSS | 76 |
| $V_H35.0$ | amino acid | GAGGTGCAGCTGGTGGAGTCTGGGGGAGGCTTGGTACAGCCTG GGGGGTCCCTGAGACTCTCCTGTGCAGCCTCTGGATTCGCCTT TATCAGCTATGCCATGAGCTGGGTCCGCCAGGCTCCAGGGAAG GGGCTGGAGTGGGTCTCAGCTATTAGTGGTAGTGGTGGTAGCA CATACTACGCAGACTCCGTGAAGGGCCGGTTCACCATCTCCAG AGACAATTCCAAGAACGCGCTGTATCTGCAAATGAACAGCCTG AGAGCCGAGGACACGGCCGTGTATTACTGTGCGAGGGATTACT ACCTGTATGATTACATCACCCAGACCTCTTTTGATTACTGGGG CCAAGGTACCCTGGTCACTGTCTCCAGT | 77 |
| $V_H36$ | amino acid | EVQLVESGGGLVQPGGSLRLSCAASGFTFSSYAMSWVRQAPGK GLEWVSAISGSGRSTYYADSVKGRFTISRDNSKNTLYLQMNSL RAEDTAVYYCARDYYLYDYITQTSFDYWGQGTLVTVSS | 78 |
| $V_H36.0$ | Nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGGTCCGCCAGGCTCCAGGGAAG GGGCTGGAGTGGGTCTCAGCTATTAGTGGTAGTGGTCGTAGCA CATACTACGCAGACTCCGTGAAGGGCCGGTTCACCATCTCCAG AGACAATTCCAAGAACACGCTGTATCTGCAAATGAACAGCCTG AGAGCCGAGGACACGGCCGTGTATTACTGTGCGAGGGATTACT ACCTGTATGATTACATCACCCAGACCTCTTTTGATTACTGGGG CCAAGGTACCCTGGTCACTGTCTCCAGT | 79 |
| $V_H37$ | amino acid | EVQLVESGGGLAQPGGSLRLSCAASGFTFSSYAMSWVRQAPGK GLEWVSAISGSGRSTYYADPVKGRFTISRDNSKNTLYLQMNSL RAGDTAVYYCARDYYLYDYITQTSFDYWGQGTLVTVSS | 80 |
| $V_H37.0$ | nucleic acid | GAGGTGCAGCTGGTGGAGTCTGGGGGAGGCTTGGCACAGCCTG GGGGGTCCCTGAGACTCTCCTGTGCAGCCTCTGGATTCACCTT TAGCAGCTATGCCATGAGCTGGGTCCGCCAGGCTCCAGGGAAG GGGCTGGAGTGGGTCTCAGCTATTAGTGGTAGTGGTCGTAGCA CATACTACGCAGACCCCGTGAAGGGCCGGTTCACCATCTCCAG | 81 |

TABLE 18-continued

Anti-CD161 VH Domain

| Name | Sequence type | Sequence (IMGT Numbering) | SEQ ID NO |
|---|---|---|---|
| | | AGACAATTCCAAGAACACGCTGTACCTGCAAATGAACAGCCTG AGAGCCGGGGACACGGCCGTGTATTACTGTGCGAGGGATTACT ACCTGTATGATTACATCACCCAGACCTCTTTTGATTACTGGGG CCAAGGTACCCTGGTCACTGTCTCCAGT | |
| $V_H38$ | amino acid | EVQLVESGGGLAQPGGSLRLSCAASGFTFSSYAMSWVRQAPGK GLEWVSAISGSGRSTYYADSVKGRFTISRDNSKNTLYLQMNSL RAEDAAVYYCARDYYLYDYITQTSFDYWGQGTLVTVSS | 82 |
| $V_H38.0$ | nucleic acid | GAGGTGCAGCTGGTGGAGTCTGGGGGAGGCTTGGCACAGCCTG GGGGGTCCCTGAGACTCTCCTGTGCAGCCTCTGGATTCACCTT TAGCAGCTATGCCATGAGCTGGGTCCGCCAGGCTCCAGGGAAG GGGCTGGAGTGGGTCTCAGCTATTAGTGGTAGTGGTCGTAGCA CATACTACGCAGACTCCGTGAAGGGCCGGTTCACCATCTCCAG AGACAATTCCAAGAACACGCTGTATCTGCAAATGAACAGCCTG AGAGCCGAGGACGCGGCCGTGTATTACTGTGCGAGGGATTACT ACCTGTATGATTACATCACCCAGACCTCTTTTGATTACTGGGG CCAAGGTACCCTGGTCACTGTCTCCAGT | 83 |
| $V_H39$ | amino acid | EVQLVESGGGLVQPGGSLRLSCAASGFTFSSYAMSWVRQAPGK GLEWVSAISGSGRSTYYAGSVKGRFTISRDNSKNTLYLQMNSL RAEDTAVYYCARDYYLYDYITQTSFDYWGQGTLVTVSS | 84 |
| $V_H39.0$ | nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGGTCCGCCAGGCTCCAGGGAAG GGGCTGGAGTGGGTCTCAGCTATTAGTGGTAGTGGTCGTAGCA CATACTACGCAGGCTCCGTGAAGGGCCGGTTCACCATCTCCAG AGACAATTCCAAGAACACGCTGTATCTGCAAATGAACAGCCTG AGAGCCGAGGACACGGCCGTGTATTACTGTGCGAGGGATTACT ACCTGTATGATTACATCACCCAGACCTCTTTTGATTACTGGGG CCAAGGTACCCTGGTCACTGTCTCCAGT | 85 |
| $V_H40$ | amino acid | EVQLVESGGGLVQPGGSLRLSCAASGFTFSSYAMSWVRQAPGK GLEWVSAISGSGRSTYYADSVKGRFTISRDNSKNTLYLQMNSL RAEDAAVYYCARDYYLYDYITQTSFDYWGQGTLVTVSS | 86 |
| $V_H40.0$ | nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGGTCCGCCAGGCTCCAGGGAAG GGGCTGGAGTGGGTCTCAGCTATTAGTGGTAGTGGTCGTAGCA CATACTACGCAGACTCCGTGAAGGGCCGGTTCACCATCTCCAG AGACAATTCCAAGAACACGCTGTATCTGCAAATGAACAGCCTG AGAGCCGAGGACGCGGCCGTGTATTACTGTGCGAGGGATTACT ACCTGTATGATTACATCACCCAGACCTCTTTTGATTACTGGGG CCAAGGTACCCTGGTCACTGTCTCCAGT | 87 |
| $V_H41$ | amino acid | EVQLVESGGGLVQPGGSLRLSCAASGFTFSSYAMSWVRQAPGK GLEWVSAISGSGGSTYYADSVKGRFTISRDNSKNTLYLQMNSL RAEDTAVYYCARGYSDSYYYGPYYTFDYWGQGTLVTVSS | 88 |
| $V_H41.0$ | Nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGGTCCGCCAGGCTCCAGGGAAG GGGCTGGAGTGGGTCTCAGCTATTAGTGGTAGTGGTGGTAGCA CATACTACGCAGACTCCGTGAAGGGCCGGTTCACCATCTCCAG AGACAATTCCAAGAACACGCTGTATCTGCAAATGAACGGCCTG AGAGCCGAGGACACGGCCGTGTATTACTGTGCGAGGGGTTACT CTGATTCTTACTACTACGGTCCATACTACACCTTTGATTACTG GGGCCAAGGTACCCTGGTCACTGTCTCCAGT | 89 |
| $V_H42$ | amino acid | EVQLVESGGGLVQPGGSLRLSCAASGFTFSSYAMSWVRQAPGK GLEWVSAISGSGGITYYADSVKGRFTISRDNSKNTLYLQMNSL RAEDTAVYYCARGYSDSYYYGPYYTFDYWGQGTLVTVSS | 90 |
| $V_H42$ | Nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGGTCCGCCAGGCTCCAGGGAAG GGGCTGGAGTGGGTCTCAGCTATTAGTGGTAGTGGTGGTATCA CATACTACGCAGACTCCGTGAAGGGCCGGTTCACCATCTCCAG AGACAATTCCAAGAACACGCTGTATCTGCAAATGAACAGCCTG AGAGCCGAGGACACGGCCGTGTATTACTGTGCGAGGGGTTACT CTGATTCTTACTACTACGGTCCTTACTACACCTTTGATTACTG GGGCCAAGGTACCCTGGTCACTGTCTCCAGT | 91 |

TABLE 18-continued

Anti-CD161 VH Domain

| Name | Sequence type | Sequence (IMGT Numbering) | SEQ ID NO |
|---|---|---|---|
| $V_H43$ | amino acid | EVQLVESGGGLVQPGGSLRLSCAASGFTFSSYAMSWIRQAPGK GLEWVSAISGSGGSIYYADSVKGRFTISRDNSKNTLYLQMNSL RAEDTAVYYCARGYSDSYYYGPYYTFDYWGQGTLVTVSS | 92 |
| $V_H43$ | nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGATCCGCCAGGCTCCAGGGAAG GGGCTGGAGTGGGTCTCAGCTATTAGTGGTAGTGGTGGTAGCA TATACTACGCAGACTCCGTGAAGGGCCGGTTCACCATCTCCAG AGACAATTCCAAGAACACGCTGTATCTGCAAATGAACAGCCTG AGAGCCGAGGACACGGCCGTGTATTACTGTGCGAGGGGTTACT CTGATTCTTACTACTACGGTCCATACTACACCTTTGATTACTG GGGCCAAGGTACCCTGGTCACTGTCTCCAGT | 93 |
| $V_H44$ | amino acid | EVQLVESGGGLVQPGGSLRLSCAASGFTFSSYAMSWVRQAPGK GLEWVSAISGSGGSIYYADSVKGRFTISRDNSKNTLYLQMNSL RAEDTAVYYCARGYSDSYYYGPYYTFDYWGQGTLVTVSS | 94 |
| $V_H44.0$ | nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGGTCCGCCAGGCTCCAGGGAAG GGGCTGGAGTGGGTCTCAGCTATTAGTGGTAGTGGTGGTAGCA TATACTACGCAGACTCCGTGAAGGGCCGGTTCACCATCTCCAG AGACAATTCCAAGAACACGCTGTATCTGCAAATGAACAGCCTG AGAGCCGAGGACACGGCCGTGTATTACTGTGCGAGGGGTTACT CTGATTCTTACTACTACGGTCCATACTACACCTTTGATTACTG GGGCCAAGGTACCCTGGTCACTGTCTCCAGT | 95 |
| $V_H45$ | amino acid | EVQLVESGGGLVQPGGSLRLSCAASGFTFSSYAMSWVRQAPGK GLEWVSAISGSGGITYYADSVKGRFTISRDNSKNTLYLQMNSL RAEDTAAYYCARGYSDSYYYGPYYTFDYWGQGTLVTASS | 96 |
| $V_H45.0$ | nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGGTCCGCCAGGCTCCAGGGAAG GGGCTGGAGTGGGTCTCAGCCATTAGTGGTAGTGGTGGTATCA CATACTACGCAGACTCCGTGAAGGGCCGGTTCACCATCTCCAG AGACAATTCCAAGAACACGCTGTATCTGCAAATGAACAGCCTG AGAGCCGAGGACACGGCCGCGTATTACTGTGCGAGGGGTTACT CTGATTCTTACTACTACGGTCCATACTACACCTTTGATTACTG GGGCCAAGGTACCCTGGTCACTGCCTCCAGT | 97 |
| $V_H46$ | amino acid | EVQLVESGGGLVQPGGSLRLSCAASGFTFSSYDMSWVRQAPGK GLEWVSAISGSGGSTYYADSVKGRFTISRDNSKNTLYLQMDSL RAEDTAVYYCARGYSDSYFYGPYYTFDYWGQGTLVTVSS | 98 |
| $V_H46.0$ | nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGACATGAGCTGGGTCCGCCAGGCTCCAGGGAAG GGGCTGGAGTGGGTCTCAGCTATTAGTGGTAGTGGTGGTAGCA CATACTACGCAGACTCCGTGAAGGGCCGGTTCACCATCTCCAG AGACAATTCCAAGAACACGCTGTATCTGCAAATGGACAGCCTG AGAGCCGAGGACACGGCCGTGTATTACTGTGCGAGGGGTTACT CTGATTCTTACTTCTACGGTCCATACTACACCTTTGATTACTG GGGCCAAGGTACCCTGGTCACTGTCTCCAGT | 99 |
| $V_H46.1$ | nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGACATGAGCTGGGTCCGCCAGGCTCCAGGGAAG GGGCTGGAGTGGGTCTCAGCTATTAGTGGTAGTGGTGGTAGCA CATACTACGCAGACTCCGTGAAGGGCCGGTTCACCATCTCCAG AGACAATTCCAAGAACACGCTGTATCTGCAAATGGACAGCCTG AGAGCCGAGGACACGGCCGTGTATTACTGTGCGAGGGGTTACT CTGATTCTTACTTCTACGGTCCATACTACACCTTTGACTACTG GGGCCAAGGTACCCTGGTCACTGTCTCCAGT | 100 |
| $V_H48$ | amino acid | EVQLVESGGGLVQPGGSLRLSCAASGFXFSSYDMSWVRQAPGK GLEWVSAISGSGGGXYYADSVKGRFXISRDNSKNXLYLQMDSL RAEDTAVYYCARGYSDSYFYGPYYTFDYWGQGTLVTVSS | 101 |
| $V_H48.0$ | nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGACATGAGCTGGGTCCGCCAGGCTCCAGGGAAG GGGCTGGAGTGGGTCTCAGCTATTAGTGGTAGTGGTGGTGGCA CATACTACGCAGACTCCGTGAAGGGCCGGTTCACCATCTCCAG | 102 |

TABLE 18-continued

Anti-CD161 VH Domain

| Name | Sequence type | Sequence (IMGT Numbering) | SEQ ID NO |
|---|---|---|---|
| | | AGACAATTCCAAGAACACGCTGTATCTGCAAATGGACAGCCTG AGAGCCGAGGACACGGCCGTGTATTACTGTGCGAGGGGTTACT CTGATTCTTACTTCTACGGTCCATACTACACCTTTGATTACTG GGGCCAAGGTACCCTGGTCACTGTCTCCAGT | |
| $V_H49$ | amino acid | EVQLMESGGGLVQPGGSLRLSCAASGFTFSSYAMSWVRQAPCK GLEWVSAISSSGGSTYYADSVKGRFTISRDNSKNTLYLQMDSL GAEDTAVYYCARGYSDSYFYGPYYTFDYWGQGTLVTVSS | 103 |
| $V_H49.0$ | nucleic acid | GAGGTGCAGCTGATGGAGTCTGGGGGAGGCTTGGTACAGCCTG GGGGGTCCCTGAGACTCTCCTGTGCAGCCTCTGGATTCACCTT TAGCAGCTATGCCATGAGCTGGGTCCGCCAGGCTCCAGGGAAG GGGCTGGAGTGGGTCTCAGCTATTAGTAGTAGTGGTGGTAGCA CATACTACGCAGACTCCGTGAAGGGCCGGTTCACCATCTCCAG AGACAATTCCAAGAACACGCTGTATCTGCAAATGGACAGCCTG GGAGCCGAGGACACGGCCGXGXAXXXACXGXGCGAGGGGXXACX CTGATTCTTACTTCTACGGCCCATACTACACCTTTGATTACTG GGGCCAAGGTACCCTGGTCACTGTCTCCAGT | 104 |
| $V_H50$ | amino acid | EVQLVESGGGLVQPGGSLRLSCAASGFTFSSYAMSWIRQAPGK GLEWVSAISGSGGSIYYADSVKGRFTISRDNSKNTLYLQMNSL RAEDXAVYYCARGYSDSYFYGPYYXFDYWGQGXLVXVSS | 105 |
| $V_H50.0$ | nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGATCCGCCAGGCTCCAGGGAAG GGGCTGGAGTGGGTCTCAGCTATTAGTGGTAGTGGTGGTAGCA TATACTACGCAGACTCCGTGAAGGGCCGGTTCACCATCTCCAG AGACAATTCCAAGAACACGCTGTATCTGCAAATGAACAGCCTG AGAGCCGAGGACACGGCCGTGTATTACTGTGCGAGGGGTTACT CTGATTCTTACTTCTACGGTCCATACTACACCTTTGATTACTG GGGCCAAGGTACCCTGGTCACTGTCTCCAGT | 106 |
| $V_H51$ | amino acid | EVQLVESGGGLVQPGGSLRLSCAASGFTFSSYAMSWVRQAPGK GLEWVSAISGSGGSTYYADSVKGRFTTSRDNSKNTLYLQMDSL RAEDTAVYYCARGYSDSYFYGPYYTFDYWGQGTLVTVSS | 107 |
| $V_H51.0$ | nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGGTCCGCCAGGCTCCAGGGAAG GGGCTGGAGTGGGTCTCAGCTATTAGTGGTAGTGGTGGTAGCA CATACTACGCAGACTCCGTGAAGGGCCGGTTCACCACCTCCAG AGACAATTCCAAGAACACGCTGTATCTGCAAATGGACAGCCTG AGAGCCGAGGACACGGCCGTGTATTACTGTGCGAGGGGTTACT CTGATTCTTACTTCTACGGTCCAXACTACACCTTTGATTACTG GGGCCAAGGTACCCTGGTCACTGTCTCCAGT | 108 |
| $V_H52$ | amino acid | EVQLVESGGGLVQPGGSLRLSCAASGFTFSSYAMSWVRQAPGE GLEWVSAISSSGGSTYYADSVKGRFTISRDNSKNTLYLQMDSL RAEDTAVYYCARGYSDSYFYGPYYTFDYWGQGTLVTASS | 109 |
| $V_H52.0$ | nucleic acid | GAGGTGCAGCTGGXGGAGTCXGGGGGAGGCTTGGTACAGCCTG GGGGGXCCCXGAGACXCXCCXGXGCAGCCXCXGGAXXCACCXX TAGCAGCTATGCCATGAGCTGGGTCCGCCAGGCTCCAGGGGAG GGGCTGGAGTGGGTCTCAGCTATTAGTAGTAGTGGTGGTAGCA CGTACTATGCAGACTCCGTGAAGGGCCGGTTCACCATCTCCAG AGACAATTCCAAGAACACGCTGTATCTGCAAATGGACAGCCTG AGAGCCGAGGACACGGCCGTGTATTACTGTGCGAGGGGTTACT CTGATTCTTACTTCTACGGTCCATACTACACCTTTGATTACTG GGGCCAAGGTACCCTGGTCACTGCCTCCAGT | 110 |
| $V_H53$ | amino acid | EVQLVESGGGLVQPGGSLRLSCAASGFTFSSYDMSWVRQAPGK GLEWISAISGSGGSTYYADSVKGRFTISRDNSKNTLYLQMNSL RAEDTAVYYCARGYSDSYYYGPYYTFDYWGQGTLVTVSS | 111 |
| $V_H53.0$ | nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGACATGAGCTGGGTCCGCCAGGCTCCAGGGAAG GGGCTGGAGTGGATCTCAGCTATTAGTGGTAGTGGTGGTAGCA CATACTACGCAGACTCCGTGAAGGGCCGGTTCACCATCTCCAG AGACAATTCCAAGAACACGCTGTATCTGCAAATGAACAGCCTG AGAGCCGAGGACACGGCCGTGTATTACTGTGCGAGGGGTTACT CTGATTCTTACTACTACGGTCCATACTACACCTTTGATTACTG GGGCCAAGGTACCCTGGTCACTGTCTCCAGT | 112 |

TABLE 18-continued

Anti-CD161 VH Domain

| Name | Sequence type | Sequence (IMGT Numbering) | SEQ ID NO |
|---|---|---|---|
| $V_H54$ | amino acid | EVQLVESGGGLVQPGGSLRLSCAASGFTFSSYAMSWIRQAPGK GLEWVSAISGSGGSIYYADSVKGRFTISRDNSKNTLYLQMDSL RAEDTAVYYCARGYSDSYFYGPYYTFDYWGQGTLVTVSS | 113 |
| $V_H54.0$ | nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGATCCGCCAGGCTCCAGGGAAG GGGCTGGAGTGGGTCTCAGCTATTAGTGGTAGTGGTGGTAGCA TATACTACGCAGACTCCGTGAAGGGCCGGTTCACCATCTCCAG AGACAATTCCAAGAACACGCTGTATCTGCAAATGGACAGCCTG AGAGCCGAGGACACGGCCGTGTATTACTGTGCGAGGGGTTACT CTGATTCTTACTTCTACGGTCCATACTACACCTTTGATTACTG GGGCCAAGGTACCCTGGTCACTGTCTCCAGT | 114 |
| $V_H55$ | amino acid | EVQLVESGGGLVQPGGSLRLSCAASGFTFSSYAMSWIRQAPGK GLEWISAISGSGGSTYYADSVKGRFTISRDNSKNTLYLQMNSL RAEDTAVYYCARGYSDSYYYGPYYTFDYWGQGTLVTVSS | 115 |
| $V_H55.0$ | nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGATCCGCCAGGCTCCAGGGAAG GGGCTGGAGTGGATCTCAGCTATTAGTGGTAGTGGTGGTAGCA CATACTACGCAGACTCCGTGAAGGGCCGGTTCACCATCTCCAG AGACAATTCCAAGAACACGCTGTATCTGCAAATGAACAGCCTG AGAGCCGAGGACACGGCCGTGTATTACTGTGCGAGGGGTTACT CTGATTCTTACTACTACGGTCCATACTACACCTTTGATTACTG GGGCCAAGGTACCCTGGTCACTGTCTCCAGT | 116 |
| $V_H56$ | amino acid | EVQLVESGGGLVQPGGSLRLPCAASGFTFSSYAMSWIRQAPGK GLEWVSAISGSGGSIYYADSVKGRFTISRDNSKNTLYLQMDSL RAEDTAVYYCARGYSDSYFYGPYYTFDYWGQGTLVTVSS | 117 |
| $V_H56.0$ | Nucleic acid | GAGGTGCAGCTGGTGGAGTCTGGGGGAGGCTTGGTACAGCCTG GGGGGTCCCTGAGACTCCCCTGTGCAGCCTCTGGATTCACCTT TAGCAGCTATGCCATGAGCTGGATCCGCCAGGCTCCAGGGAAG GGGCTGGAGTGGGTCTCAGCTATTAGTGGTAGTGGTGGTAGCA TATACTACGCAGACTCCGTGAAGGGCCGGTTCACCATCTCCAG AGACAATTCCAAGAACACGCTGTATCTGCAAATGGACAGCCTG AGAGCCGAGGACACGGCCGTGTATTACTGTGCGAGGGGTTACT CTGATTCTTACTTCTACGGTCCATACTACACCTTTGATTACTG GGGCCAAGGTACCCTGGTCACTGTCTCCAGT | 118 |
| $V_H57$ | amino acid | EVQLVESGGGLVQPGGSLRLSCAASGFTFSSYAMSWVRQAPGK GLEWVSAISGSGGSIYYADSVKGRFTISRDNSKNTLYLQMDSL RAEDTAVYYCARGYSDSYFYGPYYTFDYWGQGTLVTVSS | 119 |
| $V_H57.0$ | nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGGTCCGCCAGGCTCCAGGGAAG GGGCTGGAGTGGGTCTCAGCTATTAGTGGTAGTGGTGGTAGCA TATACTACGCAGACTCCGTGAAGGGCCGGTTCACCATCTCCAG AGACAATTCCAAGAACACGCTGTATCTGCAAATGGACAGCCTG AGAGCCGAGGACACGGCCGTGTATTACTGTGCGAGGGGTTACT CTGATTCTTACTTCTACGGTCCATACTACACCTTTGACTACTG GGGCCAAGGTACCCTGGTCACTGTCTCCAGT | 120 |
| $V_H58$ | amino acid | EVQLVESGGGLVQPGGSLRLSCAASGFTFSSYAMSWIRQAPGR GLEWVSAISGSGGSIYYADSVKGRFTISRDNSKNTLYLQMNSL RAEDTAVYYCARGYSDSYFYGPYYTFDYWGQGTLVTVSS | 121 |
| $V_H58.0$ | nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGATCCGCCAGGCTCCAGGGAGG GGGCTGGAGTGGGTCTCAGCTATTAGTGGTAGTGGTGGTAGCA TATACTACGCAGACTCCGTGAAGGGCCGGTTCACCATCTCCAG AGACAATTCCAAGAACACGCTGTATCTGCAAATGAACAGCCTG AGAGCCGAGGACACGGCCGTGTATTACTGTGCGAGGGGTTACT CTGATTCTTACTTCTACGGTCCATACTACACCTTTGATTACTG GGGCCAAGGTACCCTGGTCACTGTCTCCAGT | 122 |
| $V_H59$ | amino acid | EVQLVESGGGLVQPGGSLRLSCAASGFTFSSYAMSWIRQAPGK GLEWVSAISGSGGSIYYADSVKGRFTISRDNPKNTLYLQMDSL RAEDAAVYYCARGYSDSYFYGPYYTFDYWGQGTLVTVSS | 123 |

TABLE 18-continued

Anti-CD161 VH Domain

| Name | Sequence type | Sequence (IMGT Numbering) | SEQ ID NO |
|---|---|---|---|
| $V_H$59.0 | nucleic acid | GAGGTGCAGCTGGTGGAGTCTGGGGGAGGCTTGGTACAGCCTG GGGGGTCCCTGAGACTCTCCTGTGCAGCCTCTGGATTCACCTT TAGCAGCTATGCCATGAGCTGGATCCGCCAGGCTCCAGGGAAG GGGCTGGAGTGGGTCTCAGCTATTAGTGGTAGTGGTGGTAGCA TATACTACGCAGACTCCGTGAAGGGCCGGTTCACCATCTCCAG AGACAATCCCAAGAACACGCTGTATCTGCAAATGGACAGCCTG AGAGCCGAGGACGCGGCCGTGTATTACTGTGCGAGGGGTTACT CTGATTCTTACTTCTACGGTCCATACTACACCTTTGATTACTG GGGCCAAGGTACCCTGGTCACTGTCTCCAGT | 124 |
| $V_H$60 | amino acid | EVQLVESGGGLVQPGGSLRLPCAASGFTFSSYAMSWIRQAPGK GLEWVSAISGSGGSIYYADSVKGRFTISRDNSKNTLYLQMDSL RAEDTAMYYCARGYSDSYFYGPYYTFDYWGQGTLVTVSS | 125 |
| $V_H$60.0 | nucleic acid | GAGGTGCAGCTGGTGGAGTCTGGGGGAGGCTTGGTACAGCCTG GGGGGTCCCTGAGACTCCCCTGTGCAGCCTCTGGATTCACCTT TAGCAGCTATGCCATGAGCTGGATCCGCCAGGCTCCAGGGAAG GGGCTGGAGTGGGTCTCAGCTATTAGTGGTAGTGGTGGTAGCA TATACTACGCAGACTCCGTGAAGGGCCGGTTCACCATCTCCAG AGACAATTCCAAGAACACGCTGTATCTGCAAATGGACAGCCTG AGAGCCGAGGACACGGCCATGTATTACTGTGCGAGGGGTTACT CTGATTCTTACTTCTACGGTCCATACTACACCTTTGATTACTG GGGCCAAGGTACCCTGGTCACTGTCTCCAGT | 126 |
| $V_H$ CDR1.1 | amino acid | GFTFSSYA | 127 |
| $V_H$ CDR1.2 | amino acid | GFPFSSYA | 128 |
| $V_H$ CDR1.3 | amino acid | GSTFSSYA | 129 |
| $V_H$ CDR1.5 | amino acid | GFAFISYA | 130 |
| $V_H$ CDR1.6 | amino acid | GFTFSSYD | 131 |
| $V_H$ CDR2.1 | amino acid | ISGSGGST | 132 |
| $V_H$ CDR2.2 | amino acid | TSGSGGST | 133 |
| $V_H$ CDR2.3 | amino acid | ISGSGGRT | 134 |
| $V_H$ CDR2.4 | amino acid | ISGSGGSA | 135 |
| $V_H$ CDR2.5 | amino acid | ISGSGRST | 136 |
| $V_H$ CDR2.6 | amino acid | ISGSGGIT | 137 |
| $V_H$ CDR2.7 | amino acid | ISGSGGSI | 138 |
| $V_H$ CDR2.8 | amino acid | ISGSGGGT | 139 |
| $V_H$ CDR2.9 | amino acid | ISSSGGST | 140 |
| $V_H$ CDR3.1 | amino acid | ARGGLIPSGFDY | 141 |
| $V_H$ CDR3.2 | amino acid | ARGGLIPSGFGY | 142 |
| $V_H$ CDR3.3 | amino acid | ARGGYLPDAFDY | 143 |

TABLE 18-continued

Anti-CD161 VH Domain

| Name | Sequence type | Sequence (IMGT Numbering) | SEQ ID NO |
|---|---|---|---|
| V<sub>H</sub> CDR3.4 | amino acid | ARGPGDMYLYGDSFFDY | 144 |
| V<sub>H</sub> CDR3.5 | amino acid | ARGPGYMYLYGDSFFDY | 145 |
| V<sub>H</sub> CDR3.6 | amino acid | ARGPGYMYLYGDSFFEY | 146 |
| V<sub>H</sub> CDR3.6 | amino acid | ARDYYLSDYITQTSFDY | 147 |
| V<sub>H</sub> CDR3.7 | amino acid | ARDYYLFDYITQTSFDY | 148 |
| V<sub>H</sub> CDR3.8 | amino acid | ARDYYLYDYITQTSFDY | 149 |
| V<sub>H</sub> CDR3.9 | amino acid | ARGYSDSYYYGPYYTFDY | 150 |
| V<sub>H</sub> CDR3.10 | amino acid | ARGYSDSYFYGPYYTFDY | 151 |

TABLE 19

Anti-CD161 VL Domain

| Name | Sequence type | Sequence (IMGT Numbering) | SEQ ID NO |
|---|---|---|---|
| V<sub>L</sub>1 | amino acid | DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGQGTKVEIK | 152 |
| V<sub>L</sub>1.0 | Nucleic acid | GACATCCAGATGACCCAGTCTCCATCCTCCCTGTCTGCATCTGTAGGAGACAGAGTCACCATCACTTGCCGGGCAAGTCAGAGCATTAGCAGCTATTTAAATTGGTATCAGCAGAAACCAGGGAAAGCCCCTAAGCTCCTGATCTATGCTGCATCCAGTTTGCAAAGTGGGGTCCCATCAAGGTTCAGTGGCAGTGGATCTGGGACAGATTTCACTCTCACCATCAGCAGTCTGCAACCTGAAGATTTTGCAACTTACTACTGTCAACAGAGTTACAGTACCCCGCTCACGTTCGGCCAAGGGACCAAGGTGGAAATCAAA | 153 |
| V<sub>L</sub>1.4 | Nucleic acid | GACATCCAGATGACCCAGTCTCCATCCTCCCTGTCTGCATCTGTAGGAGACAGAGTCACCATCACTTGCCGGGCAAGTCAGAGCATTAGCAGCTATTTAAATTGGTATCAGCAGAAACCAGGGAAAGCCCCTAAGCTCCTGATCTATGCTGCATCCAGTTTGCAAAGTGGGGTCCCATCAAGGTTCAGTGGCAGTGGATCTGGGACAGATTTCACTCTCACCATCAGCAGTCTGCAACCTGAAGATTTTGCAACTTACTACTGTCAGCAGAGTTACAGTACCCCGCTCACGTTCGGCCAAGGGACCAAGGTGGAAATCAAA | 154 |
| V<sub>L</sub>2 | amino acid | DIQMTQSPSSLSASVGDRVTITCRASQSISSYLNWYQQKPGKAPKLLIYAASSLQSGVPSRFSGSGSGTDFTLTISSLQPEDFATYYCQQSYGTPLTFGQGTKVEIK | 155 |
| V<sub>L</sub>2.0 | nucleic acid | GACATCCAGATGACCCAGTCTCCATCCTCCCTGTCCGCATCTGTAGGAGACAGAGTCACCATCACTTGCCGGGCAAGTCAGAGCATTAGCAGCTATTTAAATTGGTATCAGCAGAAACCAGGGAAAGCCCCTAAGCTCCTGATCTATGCTGCATCCAGTTTGCAAAGTGGGGTCCCATCAAGGTTCAGTGGCAGTGGATCTGGGACAGATTTCACTCTCACCATCAGCAGTCTGCAACCTGAAGATTTCGCAACTTACTACTGTCAACAGAGTTACGGTACCCCGCTCACGTTCGGCCAAGGGACCAAGGTGGAAATCAAA | 156 |
| V<sub>L</sub>3 | amino acid | GIQMTQSPSSLSASVGDRVTITCRASQSISSYLNWYQQKPGKAPKLLIYAASSLQSGVPSRFSGSGSGTDFTLTISSLQPEDFATYYCQQTYSTPLTFGQGTKVEIK | 157 |

TABLE 19-continued

Anti-CD161 VL Domain

| Name | Sequence type | Sequence (IMGT Numbering) | SEQ ID NO |
|---|---|---|---|
| V$_L$3.0 | nucleic acid | GGCATCCAGATGACCCAGTCTCCATCCTCCCTGTCTGCATCTG TAGGAGACAGAGTTACCATCACTTGCCGGGCAAGTCAGAGCAT TAGCAGCTATTTAAATTGGTATCAGCAGAAACCAGGGAAAGCC CCTAAGCTCCTGATCTATGCTGCATCCAGTTTGCAAAGTGGGG TCCCATCAAGGTTCAGTGGCAGTGGATCTGGGACAGATTTCAC TCTCACCATCAGCAGTCTGCAACCTGAAGATTTTGCAACTTAC TACTGTCAACAGACGTACAGTACCCCGCTCACGTTCGGCCAAG GGACCAAGGTGGAAATCAAA | 158 |
| V$_L$3.1 | nucleic acid | GGCATCCAGATGACCCAGTCTCCATCCTCCCTGTCTGCATCTG TAGGAGACAGAGTCACCATCACTTGCCGGGCAAGTCAGAGCAT TAGCAGCTATTTAAATTGGTATCAGCAGAAACCAGGGAAAGCC CCTAAGCTCCTGATCTATGCTGCATCCAGTTTGCAAAGTGGGG TCCCATCAAGGTTCAGTGGCAGTGGATCTGGGACAGATTTCAC TCTCACCATCAGCAGTCTGCAACCTGAAGATTTTGCAACTTAC TACTGTCAACAGACGTACAGTACCCCGCTCACGTTCGGCCAAG GGACCAAGGTGGAAATCAAA | 159 |
| V$_L$4 | amino acid | DIQMTQSPSSLSASVGDRVTITCRASQSISSYLNWYQQKPGKA PKLLIYAASSLQSGVPSRFSGSGSGTDFTLTISSLQPEDFATY YCQQTYSTPLTFGQGTKVEIK | 160 |
| V$_L$4.0 | nucleic acid | GACATCCAGATGACCCAGTCTCCATCCTCCCTGTCTGCATCTG TAGGAGACAGAGTCACCATCACTTGCCGGGCAAGTCAGAGCAT TAGCAGCTATTTAAATTGGTATCAGCAGAAACCAGGGAAAGCC CCTAAGCTCCTGATCTATGCTGCATCCAGTTTGCAAAGTGGGG TCCCATCAAGGTTCAGTGGCAGTGGATCTGGGACAGATTTCAC TCTCACCATCAGCAGTCTGCAACCTGAAGATTTTGCAACTTAC TACTGTCAACAGACGTACAGTACCCCGCTCACGTTCGGCCAAG GGACCAAGGTGGAAATCAAA | 161 |
| V$_L$5 | amino acid | DIQMTQSPSSLSASVGDRVTITCRASQSISSYLNWYQQKPGKA PKLLIYAASSLQSGIPSRFSGSGSGTDFTLTISSLQPEDFATY YCQQTYSTPLTFGQGTKVEIK | 162 |
| V$_L$5.0 | nucleic acid | GACATCCAGATGACCCAGTCTCCATCCTCCCTGTCTGCATCTG TAGGAGACAGAGTCACCATCACTTGCCGGGCAAGTCAGAGCAT TAGCAGCTATTTAAATTGGTATCAGCAGAAACCAGGGAAAGCC CCTAAGCTCCTGATCTATGCTGCATCCAGTTTGCAAAGTGGGA TCCCATCAAGGTTCAGTGGCAGTGGATCTGGGACAGATTTCAC TCTCACCATCAGCAGTCTGCAAGGATTTTGCAACTTAC TACTGTCAACAGACGTACAGTACCCCGCTCACGTTCGGCCAAG GGACCAAGGTGGAAATCAAA | 163 |
| V$_L$5.1 | nucleic acid | GACATCCAGATGACCCAGTCTCCATCCTCCCTGTCTGCATCTG TAGGAGACAGAGTCACCATCACTTGCCGGGCAAGCCAGAGCAT TAGCAGCTATTTAAATTGGTATCAGCAGAAACCAGGGAAAGCC CCTAAGCTCCTGATCTATGCTGCATCCAGTTTGCAAAGTGGGA TCCCATCAAGGTTCAGTGGCAGTGGATCTGGGACAGATTTCAC TCTCACCATCAGCAGTCTGCAACCTGAAGATTTTGCAACTTAC TACTGTCAACAGACGTACAGTACCCCGCTCACGTTCGGCCAAG GGACCAAGGTGGAAATCAAA | 164 |
| V$_L$6 | amino acid | DIQMTQSPSSPSASVGDRVTITCRASQSISSYLNWYQQKPGKA PKLLIYAASSLLSGVPSRFSGSGSGTDFTLTISSLQPEDFATY YCQQTYSTPLTFGQGTKVEIK | 165 |
| V$_L$6.0 | Nucleic acid | GACATCCAGATGACCCAGTCTCCATCCTCCCCGTCTGCATCTG TAGGAGACAGAGTCACCATCACTTGCCGGGCAAGTCAGAGCAT TAGCAGCTATTTAAATTGGTATCAGCAGAAACCAGGGAAAGCC CCTAAGCTCCTGATCTATGCTGCATCCAGTTTGCTAAGTGGGA TCCCATCAAGGTTCAGTGGCAGTGGATCTGGGACAGATTTCAC TCTCACCATCAGCAGTCTGCAACCTGAAGATTTTGCAACTTAC TACTGTCAACAGACGTACAGTACCCCGCTCACGTTCGGCCAAG GGACCAAGGTGGAAATCAAA | 166 |
| V$_L$7 | amino acid | DIQMTQSPSSLSASVGDRVTITCRASQSISSYLNWYQQKPGKA PKLLIYAASSLLSGVPSRFSGSGSGTDFTLTISSLQPEDFATY YCQQTYSAPLTFGQGTKVEIK | 167 |
| V$_L$7.0 | Nucleic acid | GACATCCAGATGACCCAGTCTCCATCCTCCCTGTCTGCATCTG TAGGAGACAGAGTCACCATCACTTGCCGGGCAAGTCAGAGCAT TAGCAGCTATTTAAATTGGTATCAGCAGAAACCAGGGAAAGCC | 168 |

TABLE 19-continued

Anti-CD161 VL Domain

| Name | Sequence type | Sequence (IMGT Numbering) | SEQ ID NO |
|---|---|---|---|
| | | CCTAAGCTCCTGATCTATGCTGCATCCAGTTTGCTAAGTGGGG<br>TCCCATCAAGGTTCAGTGGCAGTGGATCTGGGACAGATTTCAC<br>TCTCACCATCAGCAGTCTGCAACCTGAAGATTTTGCAACTTAC<br>TACTGTCAACAGACGTACAGTGCCCCGCTCACGTTCGGCCAAG<br>GGACCAAGGTGGAAATCAAA | |
| $V_L8$ | amino acid | GIQMTQSPSSLSASVGDRVTITCRASQSISSYLNWYQQKPGKA<br>PKLLIYAASSLLSGVPSRFSGSGSGTDFTLTISSLQPEDFATY<br>YCQQTYSTPLTFGQGTKVEIK | 169 |
| $V_L8.0$ | nucleic acid | GGCATCCAGATGACCCAGTCTCCATCCTCCCTGTCTGCATCTG<br>TAGGAGACAGAGTCACCATCACTTGCCGGGCAAGTCAGAGCAT<br>TAGCAGCTATTTAAATTGGTATCAGCAGAAACCAGGGAAAGCC<br>CCTAAGCTCCTGATCTATGCTGCATCCAGTTTGCTAAGTGGGG<br>TCCCATCAAGGTTCAGTGGCAGTGGATCTGGGACAGATTTCAC<br>TCTCACCATCAGCAGTCTGCAACCTGAAGATTTTGCAACTTAC<br>TACTGTCAACAGACGTACAGTACCCCGCTCACGTTCGGCCAAG<br>GGACCAAGGTGGAAATCAAA | 170 |
| $V_L9$ | amino acid | DIQMTQSPSSLSASVGDRVTITCRASQSISSYLNWYQQKPGKA<br>PKLLIYAASSLLSGVPSRFSGGGSGTDFTLTISSLQPEDFATY<br>YCQQTYSTPLTFGQGTKVEIK | 171 |
| $V_L9.0$ | nucleic acid | GACATCCAGATGACCCAGTCTCCATCCTCCCTGTCTGCATCTG<br>TAGGAGACAGAGTCACCATCACTTGCCGGGCAAGTCAGAGCAT<br>TAGCAGCTATTTAAATTGGTATCAGCAGAAACCAGGGAAAGCC<br>CCTAAGCTCCTGATCTATGCTGCATCCAGTTTGCTAAGTGGGG<br>TCCCATCAAGGTTCAGTGGCGGTGGATCTGGGACAGATTTCAC<br>TCTCACCATCAGCAGTCTGCAACCTGAAGATTTTGCAACTTAC<br>TACTGTCAACAGACGTACAGTACCCCGCTCACGTTCGGCCAAG<br>GGACCAAGGTGGAAATCAAA | 172 |
| $V_L10$ | amino acid | DIQMTQSPSSLSASVGDRVTITCRASQSISSYLNWYQQRPGRA<br>PKLLIYAASSLLSGVPSRFSGSGSGTDFTLTISSLQPEDFATY<br>YCQQTYSTPLTFGQGTKVEIK | 173 |
| $V_L10.0$ | nucleic acid | GACATCCAGATGACCCAGTCTCCATCCTCCCTGTCTGCATCTG<br>TAGGAGACAGAGTCACCATCACTTGCCGGGCAAGTCAGAGCAT<br>TAGCAGCTATTTAAATTGGTATCAGCAGAGACCAGGGAGAGCC<br>CCTAAGCTCCTGATCTATGCTGCATCCAGTTTGCTAAGTGGGG<br>TCCCATCAAGGTTCAGTGGCAGTGGATCTGGGACAGATTTCAC<br>TCTCACCATCAGCAGTCTGCAACCTGAAGATTTTGCAACTTAC<br>TACTGTCAACAGACGTACAGTACCCCGCTCACGTTCGGCCAAG<br>GGACCAAGGTGGAAATCAAA | 174 |
| $V_L11$ | amino acid | DIQMTQSPSSLSASVGDRVAITCRASQSISSYLNWYQQKPGKA<br>PKLLIYAASSLQSGVPSRFSGSGSGTDFTLTISSLQPEDFATY<br>YCQQSYSTPLTFGQGTKVEIK | 175 |
| $V_L11.0$ | nucleic acid | GACATCCAGATGACCCAGTCTCCATCCTCCCTGTCTGCATCTG<br>TAGGAGACAGAGTCGCCATCACTTGCCGGGCAAGTCAGAGCAT<br>TAGCAGCTATTTAAATTGGTATCAGCAGAAACCAGGGAAAGCC<br>CCTAAGCTCCTGATCTATGCTGCATCCAGTTTGCAAAGTGGGG<br>TCCCATCAAGGTTCAGTGGCAGTGGATCTGGGACAGATTTCAC<br>TCTCACCATCAGCAGTCTGCAACCTGAAGATTTTGCAACTTAC<br>TACTGTCAACAGAGTTACAGTACCCCGCTCACGTTCGGCCAAG<br>GGACCAAGGTGGAAATCAAA | 176 |
| $V_L12$ | amino acid | DIQMTQSPSSLSASVGDRVTISCRASQSISSYLNWYQQKPGKA<br>PKLLIYAASSLQSGVPSRFSGSGSGTDFTLTISSLQPEDFATY<br>YCQQTYSTPLTFGQGTKVEIK | 177 |
| $V_L12.0$ | nucleic acid | GACATCCAGATGACCCAGTCTCCATCCTCCCTGTCTGCATCTG<br>TAGGAGACAGAGTCACCATCTCTTGCCGGGCAAGTCAGAGCAT<br>TAGCAGCTATTTAAATTGGTATCAGCAGAAACCAGGGAAAGCC<br>CCTAAGCTCCTGATCTATGCTGCATCCAGTTTGCAAAGTGGGG<br>TCCCATCAAGGTTCAGTGGCAGTGGATCTGGGACAGATTTCAC<br>TCTCACCATCAGCAGTCTGCAACCTGAAGATTTTGCGACTTAC<br>TACTGTCAACAGACGTACAGTACCCCGCTCACGTTCGGCCAAG<br>GGACCAAGGTGGAAATCAAA | 178 |
| $V_L13$ | amino acid | DIQMTQSPSSLSASVGDRVTITCRASQSISSYLNWYQQKPGKA<br>PKLLIYAASSLQSGVPSRFSGSGSGTDFTLTISSLQPEDLATY<br>YCQQTYSTPLTFGQGTKVEIK | 179 |

TABLE 19-continued

Anti-CD161 VL Domain

| Name | Sequence type | Sequence (IMGT Numbering) | SEQ ID NO |
|---|---|---|---|
| V$_L$13.0 | nucleic acid | GACATCCAGATGACCCAGTCTCCATCCTCCCTGTCTGCATCTG TAGGAGACAGAGTCACCATCACTTGCCGGGCAAGTCAGAGCAT TAGCAGCTATTTAAATTGGTATCAGCAGAAACCAGGGAAAGCC CCTAAGCTCCTGATCTATGCTGCATCCAGTTTGCAAAGTGGGG TCCCATCAAGGTTCAGTGGCAGTGGATCTGGGACAGATTTCAC TCTCACCATCAGCAGTCTGCAACCTGAAGATTTAGCAACTTAC TACTGTCAACAGACGTACAGTACCCCGCTCACGTTCGGCCAAG GGACCAAGGTGGAAATCAAA | 180 |
| V$_L$14 | amino acid | EIQMTQSPSSLSASVGGRVTITCRASQSISSYLNWYQQKPGKA PKLLIYAASSLQSGVPSRFSGSGSGTDFTLTISSLQPEDFATY YCQQTYSTPLTFGQGTKVEIK | 181 |
| V$_L$14.0 | nucleic acid | GAGATCCAGATGACCCAGTCTCCATCCTCCCTGTCTGCATCTG TAGGAGGCAGAGTCACCATCACTTGCCGGGCAAGTCAGAGCAT TAGCAGCTATTTAAATTGGTATCAGCAGAAACCAGGGAAAGCC CCTAAGCTCCTGATCTATGCTGCATCCAGTTTGCAAAGTGGGG TCCCATCAAGGTTCAGTGGCAGTGGATCTGGGACAGATTTCAC TCTCACCATCAGCAGTCTGCAACCTGAAGATTTTGCAACTTAC TACTGTCAACAGACGTACAGTACCCCGCTCACGTTCGGCCAAG GGACCAAGGTGGAAATCAAA | 182 |
| V$_L$15 | amino acid | DIQMTQSPSSLSASVGDRVTITCRASQSISSYLNWYQQKPGKA PKLLIYAASSLQSGVPSRFSGSGSGTDFALTISSLQPEDFATY YCQQTYSTPLTFGQGTKVEIK | 183 |
| V$_L$15.0 | nucleic acid | GACATCCAGATGACCCAGTCTCCATCCTCCCTGTCTGCATCTG TAGGAGACAGAGTCACCATCACTTGCCGGGCAAGTCAGAGCAT TAGCAGCTATTTAAATTGGTATCAGCAGAAACCAGGGAAAGCC CCTAAGCTCCTGATCTATGCTGCATCCAGTTTGCAAAGTGGGG TCCCATCAAGGTTCAGTGGCAGTGGATCTGGGACAGATTTCGC CCTCACCATCAGCAGTCTGCAACCTGAAGATTTTGCAACTTAC TACTGTCAACAGACGTACAGTACCCCGCTCACGTTCGGCCAAG GGACCAAGGTGGAAATCAAA | 184 |
| V$_L$16 | amino acid | DIQMTQSPSSLSASVGDRVTITCRASQSISSYLNWYQQKPGKA PRFLIYAASSLQSGVPSRFSGSGSGTDFTLTISSLQPEDFATY YCQQTYSTPLTFGQGTKVEIK | 185 |
| V$_L$16.0 | Nucleic acid | GACATCCAGATGACCCAGTCTCCATCCTCCCTGTCTGCATCTG TAGGAGACAGAGTCACCATCACTTGCCGGGCAAGTCAGAGCAT TAGCAGCTATTTAAATTGGTATCAGCAGAAACCAGGGAAAGCC CCTAGGTTCCTGATCTATGCTGCATCCAGTTTGCAAAGTGGGG TCCCATCAAGGTTCAGTGGCAGTGGATCTGGGACAGATTTCAC TCTCACCATCAGCAGTCTGCAACCCGAAGATTTTGCAACTTAC TACTGTCAACAGACGTACAGTACCCCGCTCACGTTCGGCCAAG GGACCAAGGTGGAAATTAAA | 186 |
| V$_L$17 | amino acid | DIQMTQSPSSLSASVGDRVTITCRASQSISSYLNWYQQEPGKA PKLLIYAASSLQSGVPSRFSGSGSGTDFTLTISSLQPEDFATY YCQQTYSTPLTFGQGTKVEIK | 187 |
| V$_L$17.0 | nucleic acid | GACATCCAGATGACCCAGTCTCCATCCTCCCTGTCTGCATCTG TAGGAGACAGAGTCACCATCACTTGCCGGGCAAGTCAGAGCAT TAGCAGCTATTTAAATTGGTATCAGCAGGAACCAGGGAAAGCC CCTAAGCTCCTGATCTATGCCGCATCCAGTTTGCAAAGTGGGG TCCCATCAAGGTTCAGTGGCAGTGGATCTGGGACAGATTTCAC TCTCACCATCAGCAGTCTGCAACCTGAAGATTTTGCAACTTAC TACTGTCAACAGACGTACAGTACCCCGCTCACGTTCGGCCAAG GGACCAAGGTGGAAATTAAA | 188 |
| V$_L$17.1 | nucleic acid | GACATCCAAATGACCCAGTCTCCATCCTCCCTGTCTGCATCTG TAGGAGACAGAGTCACCATCACTTGCCGGGCAAGTCAGAGCAT TAGCAGCTATTTAAATTGGTATCAGCAGGAACCAGGGAAAGCC CCTAAGCTCCTGATCTATGCTGCATCCAGTTTGCAAAGTGGGG TCCCATCAAGGTTCAGTGGCAGTGGATCTGGGACAGATTTCAC TCTCACCATCAGCAGTCTGCAACCTGAAGATTTTGCAACTTAC TACTGTCAACAGACGTACAGTACCCCGCTCACGTTCGGCCAAG GGACCAAGGTGGAAATCAAA | 189 |
| V$_L$18 | amino acid | DIQMTQSPSSLSASVGDRVTITCWASQSISSYLNWYQQEPGKA PKLLIYAASSLQSGVPSRFSGSGSGTDFTLTISSLQPEDFATY YCQQTYSTPLTFGQGTKVEIK | 190 |

TABLE 19-continued

Anti-CD161 VL Domain

| Name | Sequence type | Sequence (IMGT Numbering) | SEQ ID NO |
|---|---|---|---|
| $V_L18.0$ | Nucleic acid | GACATCCAAATGACCCAGTCTCCATCCTCCCTGTCTGCATCTG TAGGAGACAGAGTCACCATCACTTGCTGGGCAAGTCAGAGCAT TAGCAGCTATTTAAATTGGTATCAGCAGGAACCAGGGAAAGCC CCTAAGCTCCTGATCTATGCTGCATCCAGTTTGCAAAGTGGGG TCCCATCAAGGTTCAGTGGCAGTGGATCTGGGACAGATTTCAC TCTCACCATCAGCAGTCTGCAACCTGAAGATTTTGCAACTTAC TACTGTCAACAGACGTACAGTACCCCGCTCACGTTCGGCCAAG GGACCAAGGTGGAAATCAAA | 191 |
| $V_L19$ | amino acid | DIQMTQSPSSLSASVGDRVTITCRASQSISSYLNWYQQKPGKA PKLLIYAASSLQSGVPSRFSGSGSGTDFTLTIGSLQPEDFATY YCQQSYSTPLTFGQGTKVEIK | 192 |
| $V_L19.0$ | nucleic acid | GACATCCAGATGACCCAGTCTCCATCCTCCCTGTCTGCATCTG TAGGAGACAGAGTCACCATCACTTGCCGGGCAAGTCAGAGCAT TAGCAGCTATTTAAACTGGTATCAGCAGAAACCAGGGAAAGCC CCTAAGCTCCTGATCTATGCTGCATCCAGTTTGCAAAGTGGGG TCCCATCAAGGTTCAGTGGCAGTGGATCTGGGACAGATTTCAC TCTCACCATCGGCAGTCTGCAACCTGAAGATTTTGCAACTTAC TACTGTCAACAGAGTTACAGTACCCCGCTCACGTTCGGCCAAG GGACCAAGGTGGAAATCAAA | 193 |
| $V_L20$ | amino acid | DIQMTQSPSSLSASVGDRVTITCRASQSISSYLNWYQQKPGKA PKLLIYAASSLQSGVPSRFSGSGSGTDFALTISSLQPEDFATY YCQQSYSTPLTFGQGTKVEIK | 194 |
| $V_L20.0$ | nucleic acid | GACATCCAGATGACCCAGTCTCCATCCTCCCTGTCCGCATCTG TAGGAGACAGAGTCACCATCACTTGCCGGGCAAGTCAGAGCAT TAGCAGCTATTTAAATTGGTATCAGCAGAAACCAGGGAAAGCC CCTAAGCTCCTGATCTATGCTGCATCCAGTTTGCAAAGTGGGG TCCCATCAAGGTTCAGTGGCAGTGGATCTGGGACAGATTTCGC TCTCACCATCAGCAGTCTGCAACCTGAAGATTTTGCAACTTAC TACTGTCAACAGAGTTACAGTACCCCGCTCACGTTCGGCCAAG GGACCAAGGTGGAAATCAAA | 195 |
| $V_L21$ | amino acid | DIQMTQSPSSLSASVGDRVTITCRASQSISSYLNWYQQKPGKA PKLLIYAASSLQSGVPSRFSGSGSGTDFTLTISSLQPEDFATY YCQQSYSIPLTFGQGTKVEIK | 196 |
| $V_L21.0$ | nucleic acid | GACATCCAGATGACCCAGTCTCCATCCTCCCTGTCTGCATCTG TAGGAGACAGAGTCACCATCACTTGCCGGGCAAGTCAGAGCAT TAGCAGCTATTTAAATTGGTATCAGCAGAAACCAGGGAAAGCC CCTAAGCTCCTGATCTATGCTGCATCCAGTTTGCAAAGTGGGG TCCCATCAAGGTTCAGTGGCAGTGGATCTGGGACAGATTTCAC TCTCACCATCAGCAGTCTGCAACCTGAAGATTTTGCAACTTAC TACTGTCAACAGAGTTACAGTATCCCGCTCACGTTCGGCCAAG GGACCAAGGTGGAGATCAAA | 197 |
| $V_L21.1$ | nucleic acid | GACATCCAGATGACCCAGTCTCCATCCTCCCTGTCTGCATCTG TAGGAGACAGAGTCACCATCACTTGCCGGGCAAGTCAGAGCAT TAGCAGCTATTTAAATTGGTATCAGCAGAAACCAGGGAAAGCC CCTAAGCTCCTGATCTATGCTGCATCCAGTTTGCAAAGTGGGG TCCCATCAAGGTTCAGTGGCAGTGGATCTGGGACAGATTTCAC TCTCACCATCAGCAGTCTGCAACCTGAAGATTTTGCAACTTAC TACTGTCAACAGAGTTACAGTATCCCGCTCACGTTCGGCCAAG GGACCAAGGTGGAAATCAAA | 198 |
| $V_L22$ | amino acid | DIQMTQSPSSLSASIGDRVTITCRASQSISSYLNWYQQKPGKA PKLLIYAASSLQSGVPSRFSGSGSGTDFTLTISSLQPEDFATY YCQQSYSTPLTFGQGTKVEIK | 199 |
| $V_L22.0$ | nucleic acid | GACATCCAGATGACCCAGTCTCCATCCTCCCTGTCTGCATCTA TAGGAGACAGAGTCACCATCACTTGCCGGGCAAGTCAGAGCAT TAGCAGCTATTTAAATTGGTATCAGCAGAAACCAGGGAAAGCC CCTAAGCTCCTGATCTATGCTGCATCCAGTTTGCAAAGTGGGG TCCCATCAAGGTTCAGTGGCAGTGGATCTGGGACAGATTTCAC TCTCACCATCAGCAGTCTGCAACCTGAAGATTTTGCAACTTAC TACTGTCAACAGAGTTACAGTACCCCGCTCACGTTCGGCCAAG GGACCAAGGTGGAAATCAAA | 200 |
| $V_L22.1$ | nucleic acid | GACATCCAGATGACCCAGTCTCCATCCTCCCTGTCTGCATCTA TAGGAGATAGAGTCACCATCACTTGCCGGGCAAGTCAGAGCAT TAGCAGCTATTTAAATTGGTATCAGCAGAAACCAGGGAAAGCC | 201 |

TABLE 19-continued

Anti-CD161 VL Domain

| Name | Sequence type | Sequence (IMGT Numbering) | SEQ ID NO |
|---|---|---|---|
| | | CCTAAGCTCCTGATCTATGCTGCATCCAGTTTGCAAAGTGGGG<br>TCCCATCAAGGTTCAGTGGCAGTGGATCTGGGACAGATTTCAC<br>TCTCACCATCAGCAGTCTGCAACCTGAAGATTTTGCGACTTAC<br>TACTGTCAACAGAGTTACAGTACCCCGCTCACGTTCGGCCAAG<br>GGACCAAGGTGGAAATCAAA | |
| $V_L23$ | amino acid | DIQMTQSPSSLSASVGDRVTITCRASQSISNYLNWYQQKPGKA<br>PKLLIYAASSLQSGVPSRFSGSGSGTDFTLTISSLQPEDFATY<br>YCQQSYSTPLTFGQGTKVEIK | 202 |
| $V_L23.0$ | nucleic acid | GACATCCAGATGACCCAGTCTCCATCCTCCCTGTCTGCATCTG<br>TAGGAGACAGAGTCACCATCACTTGCCGGGCGAGTCAGAGCAT<br>TAGCAACTATTTAAATTGGTATCAGCAGAAACCAGGGAAAGCC<br>CCTAAGCTCCTGATCTATGCTGCATCCAGTTTGCAAAGTGGGG<br>TCCCATCAAGGTTCAGTGGCAGTGGATCTGGGACAGATTTCAC<br>TCTCACCATCAGCAGTCTGCAACCTGAAGATTTTGCAACTTAC<br>TACTGTCAACAGAGTTACAGTACCCCGCTCACGTTCGGCCAAG<br>GGACCAAGGTGGAAATCAAA | 203 |
| $V_L24$ | amino acid | DIQMAQSPSSLSASVGDRVTITCRASQGISSYLNWYQQKPGKA<br>PKLLIYAASSLQSEVPSRFSGSGYGTDFTLTISSLQPEDFATY<br>YCQQSYSIPLTFGQGTKVEIK | 204 |
| $V_L24.0$ | nucleic acid | GACATCCAGATGGCCCAGTCTCCGTCCTCCCTGTCTGCATCTG<br>TAGGAGACAGAGTCACCATCACTTGCCGGGCAAGTCAGGGCAT<br>TAGCAGCTACTTAAATTGGTATCAGCAGAAACCAGGGAAAGCC<br>CCTAAGCTCCTGATCTATGCTGCATCCAGTTTGCAAAGTGAGG<br>TCCCATCAAGGTTCAGTGGCAGTGGATATGGGACAGATTTCAC<br>TCTCACCATCAGCAGTCTGCAACCTGAAGATTTTGCAACTTAC<br>TACTGTCAACAGAGTTACAGTATCCCGCTCACGTTCGGCCAAG<br>GGACCAAGGTGGAGATCAAA | 205 |
| $V_L25$ | amino acid | DIQMAQSPSSLSASVGDRVTITCRASQGISSYLNWYQQKPGKA<br>PKLLIYAASSLQSGVPSRFSGSGYGTDFTLTISSLQPEDFATY<br>YCQQSYSTPLTFGQGTKVEIK | 206 |
| $V_L25.0$ | nucleic acid | GACATCCAGATGGCCCAGTCTCCGTCCTCCCTGTCTGCATCTG<br>TAGGAGACAGAGTCACCATCACTTGCCGGGCAAGTCAGGGCAT<br>TAGCAGCTATTTAAATTGGTATCAGCAGAAACCAGGGAAAGCC<br>CCTAAGCTCCTGATCTATGCTGCATCCAGTTTGCAAAGTGGGG<br>TCCCATCAAGGTTCAGTGGCAGTGGATATGGGACAGATTTCAC<br>TCTCACCATCAGCAGTCTGCAACCTGAAGATTTTGCAACTTAC<br>TACTGTCAACAGAGTTACAGTACCCCGCTCACGTTCGGCCAAG<br>GGACCAAGGTGGAGATCAAA | 207 |
| $V_L26$ | amino acid | DIQMAQSPTSLSASVGDRVTITCRASQSISSYLNWYQQKPGKA<br>PKLLIYAASSLQSGVPSRFSGSGSGTDFTLTISSLQPEDFATY<br>YCQQSYSTPLTFGQGTKVEIK | 208 |
| $V_L26.0$ | nucleic acid | GACATCCAGATGGCCCAGTCTCCAACCTCCCTGTCTGCATCTG<br>TAGGAGACAGAGTCACCATCACTTGCCGGGCAAGTCAGAGCAT<br>TAGCAGCTATTTAAATTGGTATCAGCAGAAACCAGGGAAAGCC<br>CCTAAGCTCCTGATCTATGCTGCATCCAGTTTGCAAAGTGGGG<br>TCCCATCAAGGTTCAGTGGCAGTGGATCTGGGACAGATTTCAC<br>TCTCACCATCAGCAGTCTGCAACCTGAAGATTTTGCAACTTAC<br>TACTGTCAACAGAGTTACAGTACCCCGCTCACGTTCGGCCAAG<br>GGACCAAGGTGGAAATCAAA | 209 |
| $V_L27$ | amino acid | DIQMTQSPSSLSASVGDRVTITCRASQSISSYLNWYQQKPGKA<br>PKLLIYAASSLQSGVPSRFGGSGSGTDFTLTISSLQPEDFATY<br>YCQQSYSTPLTFGQGTKVEIK | 210 |
| $V_L27.0$ | nucleic acid | GACATCCAGATGACCCAGTCTCCATCCTCCCTGTCTGCATCTG<br>TAGGAGACAGAGTCACCATCACTTGCCGGGCAAGTCAGAGCAT<br>TAGCAGCTATTTAAATTGGTATCAGCAGAAACCAGGGAAAGCC<br>CCTAAGCTCCTGATCTATGCTGCATCCAGTTTGCAAAGTGGGG<br>TCCCATCAAGGTTCGGTGGCAGTGGATCTGGGACAGATTTCAC<br>TCTCACCATCAGCAGTCTGCAACCTGAAGATTTTGCGACTTAC<br>TACTGTCAACAGAGTTACAGTACCCCGCTCACGTTCGGCCAAG<br>GGACCAAGGTGGAAATCAAA | 211 |
| $V_L28$ | amino acid | DIQMTQSPSSLSASVGDRVTITCRASQSISSYLNWYQQKPGKA<br>PKLLIYAASSLQSGVPSRFSGSGSGTDFTLTISSLQPEDFATY<br>YCQQSYNTPLTFGQGTKVEIK | 212 |

TABLE 19-continued

Anti-CD161 VL Domain

| Name | Sequence type | Sequence (IMGT Numbering) | SEQ ID NO |
|---|---|---|---|
| V$_L$28.0 | nucleic acid | GACATCCAGATGACCCAGTCTCCATCCTCCCTGTCTGCATCTG TAGGAGACAGAGTCACCATCACTTGCCGGGCAAGTCAGAGCAT TAGCAGCTATTTAAATTGGTATCAGCAGAAACCAGGGAAAGCC CCTAAGCTCCTGATCTATGCTGCATCCAGTTTGCAAAGTGGGG TCCCATCAAGGTTCAGTGGCAGTGGATCTGGGACAGATTTCAC TCTCACCATCAGCAGTCTGCAACCTGAAGATTTTGCAACTTAC TACTGTCAACAGAGTTACAATACCCCGCTCACGTTCGGCCAAG GGACCAAGGTGGAAATCAAA | 213 |
| V$_L$28.1 | nucleic acid | GACATCCAGATGACCCAGTCTCCATCCTCCCTGTCTGCATCTG TAGGAGACAGAGTCACCATCACTTGCCGGGCAAGTCAGAGCAT TAGCAGCTATTTAAATTGGTATCAGCAGAAACCAGGGAAAGCC CCTAAGCTCCTGATCTACGCTGCATCCAGTTTGCAAAGTGGGG TCCCATCAAGGTTCAGTGGCAGTGGATCTGGGACAGATTTCAC TCTCACCATCAGCAGTCTGCAACCTGAAGATTTTGCAACTTAC TACTGTCAACAGAGTTACAATACCCCGCTCACGTTCGGCCAAG GGACCAAGGTGGAAATCAAA | 214 |
| V$_L$29 | amino acid | DIQMTQSPSSLSASVGDRVTITCRASRSISSYLNWYQQKPGKA PKLLIYAASSLQSGVPSRFSGSGSGTDFTLTISSLQPEDFATY YCQQSYSTPLTFGQGTKVEIK | 215 |
| V$_L$29.0 | nucleic acid | GACATCCAGATGACCCAGTCTCCATCCTCCCTGTCTGCATCTG TAGGAGACAGAGTCACCATCACTTGCCGGGCAAGTCGGAGCAT TAGCAGCTATTTAAATTGGTATCAGCAGAAACCAGGGAAAGCC CCTAAGCTCCTGATCTATGCTGCATCCAGTTTGCAAAGTGGGG TCCCATCAAGGTTCAGTGGCAGTGGATCTGGGACAGATTTCAC TCTCACCATCAGCAGTCTGCAACCTGAAGATTTTGCAACTTAC TACTGTCAACAGAGTTACAGTACCCCGCTCACGTTCGGCCAAG GGACCAAGGTGGAAATCAAA | 216 |
| V$_L$30 | amino acid | DIQMTQSPSSLSASAGDRVTITCRASQSISSYLNWYQQKPGKA PKLLIYAASSLQSGVPSRFSGSGSGTDFTLTISSLQPEDFATY YCQQSYSTPLTFGQGTKVEIK | 217 |
| V$_L$30.0 | nucleic acid | GACATCCAGATGACCCAGTCTCCATCCTCCCTGTCTGCATCTG CAGGAGACAGGGTCACCATCACTTGCCGGGCAAGTCAGAGCAT TAGCAGCTATTTAAATTGGTATCAGCAGAAACCAGGGAAAGCC CCTAAGCTCCTGATCTATGCTGCATCCAGTTTGCAAAGTGGGG TCCCATCAAGGTTCAGTGGCAGTGGATCTGGGACAGATTTCAC TCTCACCATCAGCAGTCTGCAACCTGAAGATTTTGCAACTTAC TACTGTCAACAGAGTTACAGTACCCCGCTCACGTTCGGCCAAG GGACCAAGGTGGAAATCAAA | 218 |
| V$_L$31 | amino acid | DIQMTQSPSSLSASVGDRVTITCRASQSISSYLNWYQQKPGTA PKLLIYAASSLQSGVPSRFSGSGSGTDFTLTISSLQPEDFATY YCQQSYNTPLTFGQGTKVEIK | 219 |
| V$_L$31.0 | nucleic acid | GACATCCAGATGACCCAGTCTCCATCCTCCCTGTCTGCATCTG TAGGAGACAGAGTCACCATCACTTGCCGGGCAAGTCAGAGCAT TAGCAGCTATTTAAATTGGTATCAGCAGAAACCAGGGACAGCC CCTAAGCTCCTGATCTATGCTGCATCCAGTTTGCAAAGTGGGG TCCCATCAAGGTTCAGTGGCAGTGGATCTGGGACAGATTTCAC TCTCACCATCAGCAGTCTGCAACCTGAAGATTTTGCAACTTAC TACTGTCAACAGAGTTACAATACCCCGCTCACGTTCGGCCAAG GGACCAAGGTGGAAATCAAA | 220 |
| V$_L$32 | amino acid | DIQMTQSSSSLSASVGDRVTITCRASQSISSYLNWYQQKPGKA PKLLIYAASSLQSGVPSRFSGSGSGTDFTLTISSLQPEDFATY YCQQSYNTPLTFGQGTKVEIK | 221 |
| V$_L$32.0 | nucleic acid | GACATCCAGATGACCCAGTCTTCATCCTCCCTGTCTGCATCTG TAGGAGACAGAGTCACCATCACTTGCCGGGCAAGTCAGAGCAT TAGCAGCTATTTAAATTGGTATCAGCAGAAACCAGGGAAAGCC CCTAAGCTCCTGATCTATGCTGCATCCAGTTTGCAAAGTGGGG TCCCATCAAGGTTCAGTGGCAGTGGATCTGGGACAGATTTCAC TCTCACCATCAGCAGTCTGCAACCTGAAGATTTTGCAACTTAC TACTGTCAACAGAGTTACAATACCCCGCTCACGTTCGGCCAAG GGACCAAGGTGGAAATCAAA | 222 |
| V$_L$33 | amino acid | DIQMTQSPSSLSASVGDRVTITCRASQGISSYLNWYQQKPGKA PKLLIYAASSLQSGVSSRFSGSGSGTDFTLTISSLQPEDFATY YCQQSYNTPLTFGQGTKVEIK | 223 |

TABLE 19-continued

Anti-CD161 VL Domain

| Name | Sequence type | Sequence (IMGT Numbering) | SEQ ID NO |
|---|---|---|---|
| V$_L$33.0 | nucleic acid | GACATCCAGATGACCCAGTCTCCATCCTCCCTGTCTGCATCTG TAGGAGACAGAGTCACCATCACCTGCCGGGCAAGTCAGGGCAT TAGCAGCTATTTAAATTGGTATCAGCAGAAACCAGGGAAAGCC CCCAAGCTCCTGATCTATGCTGCATCCAGTTTGCAAAGTGGGG TCTCATCAAGGTTCAGTGGCAGTGGATCTGGGACAGATTTCAC TCTCACCATCAGCAGTCTGCAACCTGAAGATTTTGCAACTTAC TACTGTCAACAGAGTTACAATACCCCGCTCACGTTCGGCCAAG GGACCAAGGTGGAAATCAAA | 224 |
| V$_L$34 | amino acid | GIQMTQSPSSLSASVGDRVTITCRASQSISSYLNWYQQKPGKA PKLLIYAASSLQSGVPSRFSGSGSGTDFTLTISSLQPEDFATY YCQQSYNTPLTFGQGTKVEIK | 225 |
| V$_L$34.0 | nucleic acid | GGCATCCAGATGACCCAGTCTCCATCCTCCCTGTCTGCATCTG TAGGAGACAGAGTCACCATCACTTGCCGGGCAAGTCAGAGCAT TAGCAGCTATTTAAATTGGTATCAGCAGAAACCAGGGAAAGCC CCTAAGCTCCTGATCTATGCTGCATCCAGTTTGCAAAGTGGGG TCCCATCAAGGTTCAGTGGCAGTGGATCTGGGACAGATTTCAC TCTCACCATCAGCAGTCTGCAACCTGAAGATTTTGCAACTTAC TACTGTCAACAGAGTTACAATACCCCGCTCACGTTCGGCCAAG GGACCAAGGTGGAAATCAAA | 226 |
| V$_L$34.1 | nucleic acid | GGCATCCAGATGACCCAGTCTCCATCCTCCCTGTCTGCATCTG TAGGAGACAGAGTCACCATCACTTGCCGGGCAAGTCAGAGCAT TAGCAGCTATTTAAATTGGTATCAGCAGAAACCAGGGAAAGCC CCTAAGCTCCTGATCTACGCTGCATCCAGTTTGCAAAGTGGGG TCCCATCAAGGTTCAGTGGCAGTGGATCTGGGACAGATTTCAC TCTCACCATCAGCAGTCTGCAACCTGAAGATTTTGCAACTTAC TACTGTCAACAGAGTTACAATACCCGCTCACGTTCGGCCAAG GGACCAAGGTGGAAATCAAA | 227 |
| V$_L$35 | amino acid | DIQMTQSPSSLSASVGDRVTIACRASQSISSYLNWYQQKPGKA PKLLIYAASSLQSGVPSRFSGSGSGTDFTLTISSLQPEDFATY YCQQSYNTPLTFGQGTKVEIK | 228 |
| V$_L$35 | nucleic acid | GACATCCAGATGACCCAGTCTCCATCCTCCCTGTCTGCATCTG TAGGAGACAGAGTCACCATCGCTTGCCGGGCAAGTCAGAGCAT TAGCAGCTATTTAAATTGGTATCAGCAGAAACCAGGGAAAGCC CCTAAGCTCCTGATCTATGCTGCATCCAGTTTGCAAAGTGGGG TCCCATCGAGGTTCAGTGGCAGTGGATCTGGGACAGATTTCAC TCTCACCATCAGCAGTCTGCAACCTGAAGATTTTGCAACTTAC TACTGTCAACAGAGTTACAATACCCCGCTCACGTTCGGCCAAG GGACCAAGGTGGAAATCAAA | 229 |
| V$_L$36 | amino acid | GIQMTQSPSSLSASVGDRVTITCRASQSISSYLNWYQQKPGKA PKLLIYAASSLQSGVPSRFSGSGSGTDFTLTISSLQPEDFATY YCQQSYSTPLTFGQGTKVEIK | 230 |
| V$_L$36.0 | nucleic acid | GGCATCCAGATGACCCAGTCTCCATCCTCCCTGTCTGCATCTG TAGGAGACAGAGTCACCATCACTTGCCGGGCAAGTCAGAGCAT TAGCAGCTATCTAAATTGGTATCAGCAGAAACCAGGGAAAGCC CCTAAGCTCCTGATCTATGCTGCATCCAGTTTGCAAAGTGGGG TCCCATCAAGGTTCAGTGGCAGTGGATCTGGGACAGATTTCAC TCTCACCATCAGCAGTCTGCAACCTGAAGATTTTGCAACTTAC TACTGTCAACAGAGTTACAGTACCCCGCTCACGTTCGGCCAAG GGACCAAGGTGGAAATCAAA | 231 |
| V$_L$36.1 | nucleic acid | GGCATCCAGATGACCCAGTCTCCATCCTCCCTGTCTGCATCTG TAGGAGACAGAGTCACCATCACTTGCCGGGCAAGTCAGAGCAT TAGCAGCTATTTAAATTGGTATCAGCAGAAACCAGGGAAAGCC CCTAAGCTCCTGATCTATGCTGCATCCAGTTTGCAAAGTGGGG TCCCATCAAGGTTCAGTGGCAGTGGATCTGGGACAGATTTCAC TCTCACCATCAGCAGTCTGCAACCTGAAGATTTTGCAACTTAC TACTGTCAACAGAGTTACAGTACCCCGCTCACGTTCGGCCAAG GGACCAAGGTGGAAATCAAA | 232 |
| V$_L$37 | amino acid | GIQMTQSPSSLSASVGDRVTITCRASQGISSYLNWYQQKPGKA PKLLIYAASSLQSGVSSRFSGSGSGTDFTLTISSLQPEDFATY YCQQSYNTPLTFGQGTKVEIK | 233 |
| V$_L$37.0 | Nucleic acid | GGCATCCAGATGACCCAGTCTCCATCCTCCCTGTCTGCATCTG TAGGAGACAGAGTCACCATCACCTGCCGGGCAAGTCAGGGCAT TAGCAGCTATTTAAATTGGTATCAGCAGAAACCAGGGAAAGCC CCCAAGCTCCTGATCTATGCTGCATCCAGTTTGCAAAGTGGGG | 234 |

TABLE 19-continued

Anti-CD161 VL Domain

| Name | Sequence type | Sequence (IMGT Numbering) | SEQ ID NO |
|---|---|---|---|
| | | TCTCATCAAGGTTCAGTGGCAGTGGATCTGGGACAGATTTCAC TCTCACCATCAGCAGTCTGCAACCTGAAGATTTTGCAACTTAC TACTGTCAACAGAGTTACAATACCCCGCTCACGTTCGGCCAAG GGACCAAGGTGGAAATCAAA | |
| $V_L39$ | amino acid | DIQMTQSPSSLSASVGDRVTITCRASQSISSYLNWYQQKPGKA PKLLIYAASSLQSGVPSRFSGSGSGTDFTLTISSLQPEDFATY YCQQSYDTPLTFGQGTKVEIK | 235 |
| $V_L39.0$ | Nucleic acid | GACATCCAGATGACCCAGTCTCCATCCTCCCTGTCTGCATCTG TAGGAGACAGAGTCACCATCACTTGCCGGGCAAGTCAGAGCAT TAGCAGCTATTTAAATTGGTATCAGCAGAAACCAGGGAAAGCC CCTAAGCTCCTGATCTATGCTGCATCCAGTTTGCAAAGTGGGG TCCCATCAAGGTTCAGTGGCAGTGGATCTGGGACAGATTTCAC TCTCACCATCAGCAGTCTGCAACCTGAAGATTTTGCAACTTAC TACTGTCAACAGAGTTACGATACCCCGCTCACGTTCGGCCAAG GGACCAAGGTGGAAATCAAA | 236 |
| $V_L41$ | amino acid | GIQMTQSPSSLSASVGDRVTITCRASQSISSYLNWYQQKPGKA PKLLIYAASSLQSGVSSRFSGSGSGTDFTLTISSLQPEDFATY YCQQSYNTPLTFGQGTKVEIK | 237 |
| $V_L41.0$ | nucleic acid | GGCATCCAGATGACCCAGTCTCCATCCTCCCTGTCTGCATCTG TAGGAGACAGAGTCACCATCACCTGCCGGGCAAGTCAGAGCAT TAGCAGCTATTTAAATTGGTATCAGCAGAAACCAGGGAAAGCC CCCAAGCTCCTGATCTATGCTGCATCCAGTTTGCAAAGTGGGG TCTCATCAAGGTTCAGTGGCAGTGGATCTGGGACAGATTTCAC TCTCACCATCAGCAGTCTGCAACCTGAAGATTTTGCAACTTAC TACTGTCAACAGAGTTACAATACCCCGCTCACGTTCGGCCAAG GGACCAAGGTGGAAATCAAA | 238 |
| $V_L43$ | amino acid | GIQMTQSPSSLSASVGDRVTIACRASQSISSYLNWYQQKPGKA PKLLIYAASSLQSGVPSRFSGSGSGTDFTLTISSLQPEDFATY YCQQSYNTPLTFGQGTKVEIK | 239 |
| $V_L43.0$ | Nucleic acid | GGCATCCAGATGACCCAGTCTCCATCCTCCCTGTCTGCATCTG TAGGAGACAGAGTCACCATCGCTTGCCGGGCAAGTCAGAGCAT TAGCAGCTATTTAAATTGGTATCAGCAGAAACCAGGGAAAGCC CCTAAGCTCCTGATCTACGCTGCATCCAGTTTGCAAAGTGGGG TCCCATCAAGGTTCAGTGGTAGTGGATCTGGGACAGATTTCAC TCTCACCATCAGCAGTCTGCAACCTGAAGATTTTGCAACTTAC TACTGTCAACAGAGTTACAATACCCCGCTCACGTTCGGCCAAG GGACCAAGGTGGAAATCAAA | 240 |
| $V_L44$ | amino acid | GIQMTQSPSSLSASVGDRVTITCRASQSISSYLNWYQQKPGEA PKLLIYAASSLQSGVPSRFSGSGSGTDFTLTISSLQPEDFATY YCQQSYDTPLTFGQGTKVEIK | 241 |
| $V_L44.0$ | nucleic acid | GGCATCCAGATGACCCAGTCTCCATCCTCCCTGTCTGCATCTG TAGGAGACAGAGTCACCATCACTTGCCGGGCAAGTCAGAGCAT TAGCAGCTATTTAAATTGGTATCAGCAGAAACCAGGGGAAGCC CCTAAGCTCCTGATCTATGCTGCATCCAGTTTGCAAAGTGGGG TCCCATCAAGGTTCAGTGGCAGTGGATCTGGGACAGATTTCAC CCTCACCATCAGCAGTCTGCAACCTGAAGATTTTGCAACTTAC TACTGTCAACAGAGTTACGATACCCCGCTCACGTTCGGCCAAG GGACCAAGGTGGAAATCAAA | 242 |
| $V_L45$ | amino acid | GIQMTQSPSSLSASVGDRVTITCRASQSISSYLNWYQQQPGKA PKLLIYAASSLQSGVPPRFSGSGSGTDFTLTISSLQPEDFATY YCQQSYNAPLTFGQGTKVEIK | 243 |
| $V_L45.0$ | nucleic acid | GGCATCCAGATGACCCAGTCTCCATCCTCCCTGTCTGCATCTG TAGGAGACAGAGTCACCATCACTTGCCGGGCAAGTCAGAGCAT TAGCAGCTATTTAAATTGGTATCAGCAGCAACAGGGAAAGCC CCTAAGCTCCTGATCTACGCTGCATCCAGTTTGCAAAGTGGGG TCCCACCAAGGTTCAGTGGCAGTGGATCTGGGACAGATTTCAC TCTCACCATCAGCAGTCTGCAACCTGAAGATTTTGCAACTTAC TACTGTCAACAGAGTTACAATGCCCCGCTCACGTTCGGCCAAG GGACCAAGGTGGAAATCAAA | 244 |
| $V_L46$ | amino acid | QSVLTQPPSVSGAPGQRVTISCTGSSSNIGAGYDVHWYQQLPG TAPKLLIYGNSNRPSGVPDRFSGSKSGTSASLAITGLQAEDEA DYYCQSYDSSHTVFGGGTQLTVL | 245 |

TABLE 19-continued

Anti-CD161 VL Domain

| Name | Sequence type | Sequence (IMGT Numbering) | SEQ ID NO |
|---|---|---|---|
| V<sub>L</sub>46.0 | Nucleic acid | CAGTCTGTGCTGACGCAGCCGCCCTCAGTGTCTGGGGCCCCAG GGCAGAGGGTCACCATCTCCTGCACTGGGAGCAGCTCCAACAT CGGGGCAGGTTATGATGTACACTGGTACCAGCAGCTTCCAGGA ACAGCCCCCAAACTCCTCATCTATGGTAACAGCAATCGGCCCT CAGGGGTCCCTGACCGATTCTCTGGCTCCAAGTCTGGCACCTC AGCCTCCCTGGCCATCACTGGGCTCCAGGCTGAGGATGAGGCT GATTACTACTGTCAGTCTTATGATAGCAGTCACACTGTGTTCG GAGGAGGCACCCAGCTGACCGTCCTC | 246 |
| V<sub>L</sub>46.1 | Nucleic acid | CAGTCTGTGCTGACGCAGCCGCCCTCAGTGTCTGGGGCCCCAG GGCAGAGGGTCACCATCTCCTGCACTGGGAGCAGCTCCAACAT CGGGGCAGGTTATGATGTACACTGGTACCAGCAGCTTCCAGGA ACAGCCCCCAAACTCCTCATCTATGGTAACAGCAATCGGCCCT CAGGGGTCCCTGACAGATTCTCTGGCTCCAAGTCTGGCACCTC AGCCTCCCTGGCCATCACTGGGCTCCAGGCTGAGGATGAGGCT GATTACTACTGTCAGTCTTATGATAGCAGTCACACTGTGTTCG GAGGAGGCACCCAGCTGACCGTCCTC | 247 |
| V<sub>L</sub>47 | amino acid | QSVLTQPPSVSGAPGQRVTISCTGSNSNIGAGYDVHWYQQLPG TAPKLLIYGNSNRPSGVPDRFSGSKSGTSASLAITGLQAEDEA DYYCQSYDSSHTVFGGGTQLTVL | 248 |
| V<sub>L</sub>47.0 | nucleic acid | CAGTCTGTGCTGACGCAGCCGCCCTCAGTGTCTGGGGCCCCAG GGCAGAGGGTCACCATCTCCTGCACTGGGAGCAACTCCAACAT CGGGGCAGGTTATGATGTACACTGGTACCAGCAGCTTCCAGGA ACAGCCCCCAAACTCCTCATCTATGGTAACAGCAATCGGCCCT CAGGGGTCCCTGACCGATTCTCTGGCTCCAAGTCTGGCACCTC AGCCTCCCTGGCCATCACTGGGCTCCAGGCTGAGGATGAGGCT GATTACTACTGTCAGTCTTATGATAGCAGTCACACTGTGTTCG GAGGAGGCACCCAGCTGACCGTCCTC | 249 |
| V<sub>L</sub>48 | amino acid | QSVLTQPPSVSGAPGQRVTISCTGSSSNIGAGYDVHWYQQLPG TAPKLLIYGNSNRPSGVPDRFSGSQSGTSASLAITGLQAEDEA DYYCQSYGSSHTVFGGGTQLTVL | 250 |
| V<sub>L</sub>48.0 | nucleic acid | CAGTCTGTGCTGACGCAGCCGCCCTCAGTGTCTGGGGCCCCAG GGCAGAGGGTCACCATCTCCTGCACTGGGAGCAGCTCCAACAT CGGGGCAGGTTATGATGTACACTGGTACCAGCAGCTTCCAGGA ACAGCCCCCAAACTCCTCATCTATGGTAACAGCAATCGGCCCT CAGGGGTCCCTGACCGATTCTCTGGCTCCCAGTCTGGCACCTC AGCCTCCCTGGCCATCACTGGGCTCCAGGCTGAGGATGAGGCT GATTACTACTGTCAGTCTTATGGTAGCAGTCACACTGTGTTCG GAGGAGGCACCCAGCTGACCGTCCTC | 251 |
| V<sub>L</sub>49 | amino acid | QSVLTQPPSVSGAPGQRVTISCTGSSSNIGAGYDVHWYQQLPG TAPKLLIYGNSNRPSGVPDRFSGSKSGTSASLAITGLQAEDGA DYYCQSYDSSHTVFGGGTQLTVL | 252 |
| V<sub>L</sub>49.0 | nucleic acid | CAGTCTGTGCTGACGCAGCCGCCCTCAGTGTCTGGGGCCCCAG GGCAGAGGGTCACCATCTCCTGCACTGGGAGCAGCTCCAACAT CGGGGCAGGTTATGATGTACACTGGTACCAGCAGCTTCCAGGA ACAGCCCCCAAACTCCTCATCTATGGTAACAGCAATCGGCCCT CAGGGGTCCCTGACCGATTCTCTGGCTCCAAGTCTGGCACCTC AGCCTCCCTGGCCATCACTGGGCTCCAGGCTGAGGATGGGGCT GACTACTACTGTCAGTCTTATGATAGCAGTCACACTGTGTTCG GAGGAGGCACCCAGCTGACCGTCCTC | 253 |
| V<sub>L</sub>50 | amino acid | QSVLTQPPSVSGAPGQRVTISCTGSSNIGAGYDVHWYQQLPG TAPKLLIYGNSDRPSGVPDRFSGSKSGTSASLAITGLQAEDEA DYYCQSYDSGHTVFGGGTQLTVL | 254 |
| V<sub>L</sub>50.0 | nucleic acid | CAGTCTGTGCTGACGCAGCCGCCCTCAGTGTCTGGGGCCCCAG GGCAGAGGGTCACCATCTCCTGCACTGGGGCAGCTCCAACAT CGGGGCAGGTTATGATGTACACTGGTACCAGCAGCTTCCAGGA ACAGCCCCCAAACTCCTCATCTATGGTAACAGCGATCGGCCCT CAGGGGTCCCTGACCGATTCTCTGGCTCCAAGTCTGGCACCTC AGCCTCCCTGGCCATCACTGGGCTCCAGGCTGAGGATGAGGCT GATTACTACTGTCAGTCTTATGATAGCGGTCACACTGTGTTCG GAGGAGGCACCCAGCTGACCGTCCTC | 255 |
| V<sub>L</sub>51 | amino acid | QSVLTQPPSVSGAPGQRVTISCTGSSSNIGAGYDVHWYQQLPG TAPKLLIYGNSNRPSGVPDRFSGSQSGTSASLAITGLQAEDEA DYYCQSYDSSHTVFGGGTQLTVL | 256 |

TABLE 19-continued

Anti-CD161 VL Domain

| Name | Sequence type | Sequence (IMGT Numbering) | SEQ ID NO |
|---|---|---|---|
| V$_L$51.0 | nucleic acid | CAGTCTGTGCTGACGCAGCCGCCCTCAGTGTCTGGGGCCCCAG GGCAGAGGGTCACCATCTCCTGCACTGGGAGCAGCTCCAACAT CGGGGCAGGTTATGATGTACACTGGTACCAGCAGCTTCCAGGA ACAGCCCCCAAACTCCTCATCTATGGTAACAGCAATCGGCCCT CAGGGGTCCCTGACCGATTCTCTGGCTCCAGTCTGGCACCTC AGCCTCCCTGGCCATCACTGGGCTCCAGGCTGAGGATGAGGCT GATTACTACTGTCAGTCCTATGATAGCAGTCACACTGTGTTCG GAGGAGGCACCCAGCTGACCGTCCTC | 257 |
| V$_L$52 | amino acid | QSVLTQPPSVSGAPGQRVTISCTGSSSNIGAGYDVHWYQQLPG TAPKLLIYGNSNRPSGVPDRFSGSKSGTSASLAITGLQAEDEA DYYCQSYGSSHTVFGGGTQLTVL | 258 |
| V$_L$52.0 | nucleic acid | CAGTCTGTGCTGACGCAGCCGCCCTCAGTGTCTGGGGCCCCAG GGCAGAGGGTCACCATCTCCTGCACTGGGAGCAGCTCCAACAT CGGGGCAGGTTATGATGTACACTGGTACCAGCAGCTTCCAGGA ACAGCCCCCAAACTCCTCATCTATGGTAACAGCAATCGGCCCT CAGGGGTCCCTGACCGATTCTCTGGCTCCAAGTCTGGCACCTC AGCCTCCCTGGCCATCACTGGGCTCCAGGCTGAGGATGAGGCT GATTACTACTGTCAGTCTTATGGTAGCAGTCACACTGTGTTCG GAGGAGGCACCCAGCTGACCGTCCTC | 259 |
| V$_L$53 | amino acid | QSVLTQPPSVSGAPGQRVTISCTGSSSNIGAGYDVHWYQQLPG TAPKLLIYGNSNRPSGVPDRFSGSKSGTSASLAITGLQAEDEA DYYCQSYDSGHSVFGGGTQLTVL | 260 |
| V$_L$53.0 | nucleic acid | CAGTCTGTGCTGACGCAGCCGCCCTCAGTGTCTGGGGCCCCAG GGCAGAGGGTCACCATCTCCTGCACTGGGAGCAGCTCCAACAT CGGGGCAGGTTATGATGTACACTGGTACCAGCAGCTTCCAGGA ACAGCCCCCAAACTCCTCATCTATGGTAACAGCAATCGGCCCT CAGGGGTCCCTGACCGATTCTCTGGCTCCAAGTCTGGCACCTC AGCCTCCCTGGCCATCACTGGGCTCCAGGCTGAGGATGAGGCT GATTACTACTGTCAGTCTTATGATAGCGGTCACTCTGTGTTCG GAGGAGGCACCCAGCTGACCGTCCTC | 261 |
| V$_L$54 | amino acid | QSVLTQPPSVSGAPGQRVTIPCTGSSSNIGAGYDVHWYQQLPG AAPKLLIYGNSNRPSGVPDRFSGSQSGTSASLAITGLQAEDEA DYYCQSYDSGHTVFGGGTQLTVL | 262 |
| V$_L$54.0 | nucleic acid | CAGTCTGTGCTGACGCAGCCGCCCTCAGTGTCTGGGGCCCCAG GGCAGAGGGTCACCATCCCCTGCACTGGGAGCAGCTCCAACAT CGGGGCAGGTTATGATGTACACTGGTACCAGCAGCTTCCAGGA GCAGCCCCCAAACTCCTCATCTATGGTAACAGCAATCGGCCCT CAGGGGTCCCTGACCGATTCTCTGGCTCCCAGTCTGGCACCTC AGCCTCCCTGGCCATCACTGGGCTCCAGGCTGAGGATGAGGCT GATTACTACTGTCAGTCCTATGATAGCGGTCACACTGTGTTCG GAGGAGGCACCCAGCTGACCGTCCTC | 263 |
| V$_L$55 | amino acid | QSVLTQPPSVSGAPGQRVTISCTGSSSNIGAGYDVHWYQQLPG TAPKLLIYGNSNRPSGVPDRFSGSQSGTSASLAITGLQAEDEA DYYCQSYDSGHTVFGGGTQLTVL | 264 |
| V$_L$55.0 | nucleic acid | CAGTCTGTGCTGACGCAGCCGCCCTCAGTGTCTGGGGCCCCAG GGCAGAGGGTCACCATCTCCTGCACTGGGAGCAGCTCCAACAT CGGGGCAGGTTATGATGTACACTGGTACCAGCAGCTTCCAGGA ACAGCCCCCAAACTCCTCATCTATGGTAACAGCAATCGGCCCT CAGGGGTCCCTGACCGATTCTCTGGCTCCCAGTCTGGCACCTC AGCCTCCCTGGCCATCACTGGGCTCCAGGCTGAGGATGAGGCT GATTACTACTGTCAGTCTTATGATAGCGGTCACACTGTGTTCG GAGGAGGCACCCAGCTGACCGTCCTC | 265 |
| V$_L$55.1 | nucleic acid | CAGTCTGTGCTGACGCAGCCGCCCTCAGTGTCTGGGGCCCCAG GGCAGAGGGTCACCATCTCCTGCACTGGGAGCAGCTCCAACAT CGGGGCAGGCTATGATGTACACTGGTACCAGCAGCTTCCAGGA ACAGCCCCCAAACTCCTCATCTACGGTAACAGCAATCGGCCCT CAGGGGTCCCTGACCGATTCTCTGGCTCCCAGTCTGGCACCTC AGCCTCCCTGGCCATCACTGGGCTCCAGGCTGAGGATGAGGCT GATTACTACTGTCAGTCTTATGATAGCGGTCACACTGTGTTCG GAGGAGGCACCCAGCTGACCGTCCTC | 266 |
| V$_L$56 | amino acid | QSVLTQPPSVSGAPGQRVTISCTGSSSNIGAGYDVHWYQQLPG TAPKLLIYGNSNRPSGVPDRFSGSQSGTSASLAITGLQAEDEA DYYCQSYNSGHTVFGGGTQLTVL | 267 |

TABLE 19-continued

Anti-CD161 VL Domain

| Name | Sequence type | Sequence (IMGT Numbering) | SEQ ID NO |
|---|---|---|---|
| V$_L$56.0 | nucleic acid | CAGTCTGTGCTGACGCAGCCGCCCTCAGTGTCTGGGGCCCAG GGCAGAGGGTCACCATCTCCTGCACTGGGAGCAGCTCCAACAT CGGGGCAGGTTATGATGTACACTGGTACCAGCAGCTTCCAGGA ACAGCCCCCAAACTCCTCATCTATGGTAACAGCAATCGGCCCT CAGGGGTCCCTGACCGATTCTCCGGCTCCCAGTCTGGCACCTC AGCCTCCCTGGCCATCACTGGGCTCCAGGCTGAGGATGAGGCT GATTACTACTGTCAGTCTTATAATAGCGGTCACACTGTGTTCG GAGGAGGCACCCAGCTGACCGTCCTC | 268 |
| V$_L$57 | amino acid | QSALTQPPSVSGAPGQRVTISCTGGSSNIGAGYDVHWYQQLPG TAPKLLIYGNSNRPSGVPDRFSGSKSGTSASLAITGLQAEDEA DYYCQSYDSGHSVFGGGTQLTVL | 269 |
| V$_L$57.0 | nucleic acid | CAGTCTGCGCTGACGCAGCCGCCCTCAGTGTCTGGGGCCCAG GGCAGAGGGTCACCATCTCCTGCACTGGGGGCAGCTCCAACAT CGGGGCAGGTTATGATGTACACTGGTACCAGCAGCTTCCAGGA ACAGCCCCCAAACTCCTCATCTATGGTAACAGCAATCGGCCCT CAGGGGTCCCTGACCGATTCTCTGGCTCCAAGTCTGGCACCTC AGCCTCCCTGGCCATCACTGGGCTCCAGGCTGAGGATGAGGCT GATTACTACTGTCAGTCTTATGATAGCGGTCACTCTGTGTTCG GAGGAGGCACCCAGCTGACCGTCCTC | 270 |
| V$_L$58 | amino acid | QSVLTQPPSVSGAPGQRVTISCTGSSSNIGAGYDVHWYQQLPG TAPKLLIFGNSNRPSGVPDRFSGSQSGTSASLAITGLQAEDEA DYYCQSYDSSHSVFGGGTQLTVL | 271 |
| V$_L$58.0 | nucleic acid | CAGTCTGTGCTGACGCAGCCGCCCTCAGTGTCTGGGGCCCAG GGCAGAGGGTCACCATCTCCTGCACTGGGAGCAGCTCCAACAT CGGGGCAGGCTATGATGTACACTGGTACCAGCAGCTTCCAGGA ACAGCCCCCAAACTCCTCATCTTTGGTAACAGCAATCGGCCCT CAGGGGTCCCTGACCGATTCTCTGGCTCCCAGTCTGGCACCTC AGCCTCCCTGGCCATCACTGGGCTCCAGGCTGAGGATGAGGCT GATTACTACTGTCAGTCTTATGATAGCAGTCACTCTGTGTTCG GAGGAGGCACCCAGCTGACCGTCCTC | 272 |
| V$_L$59 | Amino acid | GIQMTQSPSSLSASVGDRVTITCWASQSISSYLNWYQQKPGKA PKLLIYAASSLLSGVPSRFSGSGSGTDFTLTISSLQPEDFATY YCQQTYSAPLTFGQGTKVEIK | 295 |
| V$_L$59.0 | nucleotide acid | GGCATCCAGATGACCCAGTCTCCATCCTCCCTGTCTGCATCTG TAGGAGACAGAGTCACCATCACTTGCTGGGCAAGTCAGAGCAT TAGCAGCTATTTAAATTGGTATCAGCAGAAACCAGGGAAAGCC CCTAAGCTCCTGATCTATGCTGCATCCAGTTTGCTAAGTGGGG TCCCATCAAGGTTCAGTGGCAGTGGATCTGGGACAGATTTCAC TCTCACCATCAGCAGTCTGCAACCTGAAGATTTTGCAACTTAC TACTGTCAACAGACGTACAGTGCCCCGCTCACGTTCGGCCAAG GGACCAAGGTGGAAATCAAA | 296 |
| V$_L$60 | Amino acid | QSVLTQPPSVSGAPGQRVTISCTGSSSNIGAGYDVHWYQQLPG TAPKLLIYGNSNRPSGVPDRFSGSQSGTSPSLAITGLQDEDEA DYYCQSYGSSHTVFGGGTQLTVL | 297 |
| V$_L$60.0 | Nucleic acid | CAGTCTGTGCTGACGCAGCCGCCCTCAGTGTCTGGGGCCCAG GGCAGAGGGTCACCATCTCCTGCACTGGGAGCAGCTCCAACAT CGGGGCAGGTTATGATGTACACTGGTACCAGCAGCTTCCAGGA ACAGCCCCCAAACTCCTCATCTATGGTAACAGCAATCGGCCCT CAGGGGTCCCTGACCGATTCTCTGGCTCCCAGTCTGGCACCTC ACCCTCCCTGGCCATCACTGGGCTCCAGGATGAGGATGAGGCT GATTACTACTGTCAGTCCTATGGTAGCAGTCACACTGTGTTCG GAGGAGGCACCCAGCTGACCGTCCTC | 298 |
| V$_L$61 | amino acid | GIQMTQSPSSLSASVGDRVTITCRASQSISSYLNWYQQKPGKA PKLLIYAASSLLSGVPSRFSGSGSGTDFTLTISSLQPEDFATY YCQQTYSAPLTFGQGTKVEIK | 393 |
| V$_L$61.0 | Nucleic acid | GGCATCCAGATGACCCAGTCTCCATCCTCCCTGTCTGCATCTG TAGGAGACAGAGTCACCATCACTTGCCGGGCAAGTCAGAGCAT TAGCAGCTATTTAAATTGGTATCAGCAGAAACCAGGGAAAGCC CCTAAGCTCCTGATCTATGCTGCATCCAGTTTGCTAAGTGGGG TCCCATCAAGGTTCAGTGGCAGTGGATCTGGGACAGATTTCAC TCTCACCATCAGCAGTCTGCAACCTGAAGATTTTGCAACTTAC TACTGTCAACAGACGTACAGTGCCCCGCTCACGTTCGGCCAAG GGACCAAGGTGGAAATCAAA | 394 |

TABLE 19-continued

Anti-CD161 VL Domain

| Name | Sequence type | Sequence (IMGT Numbering) | SEQ ID NO |
|---|---|---|---|
| V$_L$62 | amino acid | GIQMTQSPSSLSASVGDRVTITCRASQSISSYLNWYQQKPGKA PKLLIYAASSLQSGVPSRFSGSGSGTDFTLTISSLQPEDFATY YCQQSYDTPLTFGQGTKVEIK | 395 |
| V$_L$62.0 | Nucleic acid | GGCATCCAGATGACCCAGTCTCCATCCTCCCTGTCTGCATCTG TAGGAGACAGAGTCACCATCACTTGCCGGGCAAGTCAGAGCAT TAGCAGCTATTTAAATTGGTATCAGCAGAAACCAGGGAAAGCC CCTAAGCTCCTGATCTATGCTGCATCCAGTTTGCAAAGTGGGG TCCCATCAAGGTTCAGTGGCAGTGGATCTGGGACAGATTTCAC TCTCACCATCAGCAGTCTGCAACCTGAAGATTTTGCAACTTAC TACTGTCAACAGAGTTACGATACCCCGCTCACGTTCGGCCAAG GGACCAAGGTGGAAATCAAA | 396 |
| V$_L$ CDR1.1 | amino acid | QSISSY | 273 |
| V$_L$ CDR1.2 | amino acid | QSISNY | 274 |
| V$_L$ CDR1.3 | amino acid | QGISSY | 275 |
| V$_L$ CDR1.4 | amino acid | RSISSY | 276 |
| V$_L$ CDR1.5 | amino acid | SSNIGAGYD | 277 |
| V$_L$ CDR1.6 | amino acid | NSNIGAGYD | 278 |
| V$_L$ CDR2.1 | amino acid | AAS | 279 |
| V$_L$ CDR2.2 | amino acid | GNS | 280 |
| V$_L$ CDR3.1 | amino acid | QQSYSTPLT | 281 |
| V$_L$ CDR3.2 | amino acid | QQSYGTPLT | 282 |
| V$_L$ CDR3.3 | amino acid | QQTYSTPLT | 283 |
| V$_L$ CDR3.4 | amino acid | QQTYSAPLT | 284 |
| V$_L$ CDR3.5 | amino acid | QQSYSIPLT | 285 |
| V$_L$ CDR3.6 | amino acid | QQSYNTPLT | 286 |
| V$_L$ CDR3.7 | amino acid | QQSYDTPLT | 287 |
| V$_L$ CDR3.8 | amino acid | QQSYNAPLT | 288 |
| V$_L$ CDR3.9 | amino acid | QSYDSSHTV | 289 |
| V$_L$ CDR3.10 | amino acid | QSYGSSHTV | 290 |
| V$_L$ CDR3.11 | amino acid | QSYDSGHTV | 291 |
| V$_L$ CDR3.12 | amino acid | QSYDSGHSV | 292 |

TABLE 19-continued

Anti-CD161 VL Domain

| Name | Sequence type | Sequence (IMGT Numbering) | SEQ ID NO |
|---|---|---|---|
| V$_L$ CDR3.13 | amino acid | QSYNSGHTV | 293 |
| V$_L$ CDR3.14 | amino acid | QSYDSSHSV | 294 |

TABLE 20

Anti-CD161 VH and VL Combination Table

| Anti-CD161 antibody Name | Full-length amino acid SEQ ID NO | | Full-length nucleotide SEQ ID NO | | V$_H$ CDR amino acid SEQ ID NO | | | V$_L$ CDR amino acid SEQ ID NO | | |
|---|---|---|---|---|---|---|---|---|---|---|
| | V$_H$ | V$_L$ | V$_H$ | V$_L$ | CDR1 | CDR2 | CDR3 | CDR1 | CDR2 | CDR3 |
| KW1 | 1 | 152 | 2 | 153 | 127 | 132 | 141 | 273 | 279 | 281 |
| KW7 | 22 | 152 | 23 | 153 | 127 | 132 | 143 | 273 | 279 | 281 |
| KW9 | 43 | 152 | 44 | 153 | 127 | 132 | 144 | 273 | 279 | 281 |
| KW17 | 61 | 245 | 62 | 246 | 127 | 132 | 147 | 277 | 280 | 289 |
| KM12 | 88 | 152 | 89 | 153 | 127 | 132 | 150 | 273 | 279 | 281 |
| KW1.1.6 | 1 | 155 | 2 | 156 | 127 | 132 | 141 | 273 | 279 | 282 |
| KW1.1.10 | 1 | 157 | 3 | 159 | 127 | 132 | 141 | 273 | 279 | 283 |
| KW1.1.1 | 4 | 152 | 5 | 153 | 127 | 132 | 142 | 273 | 279 | 281 |
| KW1.1.3 | 6 | 152 | 7 | 153 | 127 | 132 | 141 | 273 | 279 | 281 |
| KW1.1.9 | 8 | 157 | 10 | 158 | 127 | 132 | 141 | 273 | 279 | 283 |
| KW1.2.4 | 8 | 167 | 10 | 168 | 127 | 132 | 141 | 273 | 279 | 284 |
| KW1.3.12 | 8 | 167 | 9 | 168 | 127 | 132 | 141 | 273 | 279 | 284 |
| KW1.1.11 | 11 | 160 | 12 | 161 | 128 | 132 | 141 | 273 | 279 | 283 |
| KW1.1.12 | 13 | 162 | 14 | 163 | 127 | 132 | 141 | 273 | 279 | 283 |
| KW1.2.1 | 15 | 165 | 16 | 166 | 129 | 132 | 141 | 273 | 279 | 283 |
| KW1.2.6 | 15 | 171 | 17 | 172 | 129 | 132 | 141 | 273 | 279 | 283 |
| KW1.2.8 | 15 | 173 | 16 | 174 | 129 | 132 | 141 | 273 | 279 | 283 |
| KW1.2.5 | 18 | 169 | 19 | 170 | 127 | 132 | 141 | 273 | 279 | 283 |
| KW1.3.1 | 20 | 295 | 21 | 296 | 127 | 132 | 141 | 273 | 279 | 284 |
| KW7.1.14 | 22 | 160 | 23 | 161 | 127 | 132 | 143 | 273 | 279 | 283 |
| KW7.2.1 | 22 | 160 | 28 | 161 | 127 | 132 | 143 | 273 | 279 | 283 |
| KW7.1.15 | 22 | 162 | 27 | 164 | 127 | 132 | 143 | 273 | 279 | 283 |
| KW7.1.5 | 22 | 175 | 25 | 176 | 127 | 132 | 143 | 273 | 279 | 281 |
| KW7.1.11 | 22 | 179 | 23 | 180 | 127 | 132 | 143 | 273 | 279 | 283 |
| KW7.1.13 | 22 | 183 | 26 | 184 | 127 | 132 | 143 | 273 | 279 | 283 |
| KW7.2.2 | 22 | 185 | 24 | 186 | 127 | 132 | 143 | 273 | 279 | 283 |
| KW7.1.9 | 29 | 177 | 30 | 178 | 127 | 132 | 143 | 273 | 279 | 283 |
| KW7.1.12 | 31 | 181 | 32 | 182 | 127 | 132 | 143 | 273 | 279 | 283 |
| KW7.1.16 | 33 | 160 | 34 | 161 | 127 | 132 | 143 | 273 | 279 | 283 |
| KW7.2.3 | 35 | 187 | 36 | 188 | 127 | 132 | 143 | 273 | 279 | 283 |
| KW7.2.4 | 37 | 187 | 38 | 189 | 129 | 132 | 143 | 273 | 279 | 283 |
| KW7.2.5 | 39 | 160 | 40 | 161 | 127 | 132 | 143 | 273 | 279 | 283 |
| KW7.3.7 | 41 | 190 | 42 | 191 | 127 | 133 | 143 | 273 | 279 | 283 |
| KW9.1.1 | 43 | 192 | 44 | 193 | 127 | 132 | 144 | 273 | 279 | 281 |
| KW9.1.2 | 45 | 194 | 46 | 195 | 127 | 132 | 144 | 273 | 279 | 281 |
| KW9.1.3 | 47 | 152 | 48 | 153 | 127 | 132 | 145 | 273 | 279 | 281 |
| KW9.2.7 | 47 | 202 | 49 | 203 | 127 | 132 | 145 | 274 | 279 | 281 |
| KW9.2.1 | 50 | 196 | 51 | 197 | 127 | 132 | 145 | 273 | 279 | 285 |
| KW9.2.3 | 52 | 152 | 53 | 153 | 127 | 132 | 145 | 273 | 279 | 281 |
| KW9.3.5 | 52 | 208 | 53 | 209 | 127 | 132 | 145 | 273 | 279 | 281 |
| KW9.3.8 | 52 | 208 | 53 | 209 | 127 | 132 | 145 | 273 | 279 | 281 |
| KW9.2.5 | 56 | 199 | 57 | 200 | 127 | 134 | 146 | 273 | 279 | 281 |
| KW9.2.6 | 54 | 196 | 55 | 198 | 127 | 132 | 145 | 273 | 279 | 285 |
| KW9.2.8 | 56 | 199 | 57 | 200 | 127 | 134 | 146 | 273 | 279 | 281 |
| KW9.3.2 | 56 | 199 | 57 | 201 | 127 | 134 | 146 | 273 | 279 | 281 |
| KW9.3.3 | 56 | 206 | 58 | 207 | 127 | 134 | 146 | 275 | 279 | 281 |
| KW9.3.1 | 59 | 204 | 60 | 205 | 127 | 132 | 145 | 275 | 279 | 285 |
| KW17.2.6 | 66 | 258 | 67 | 259 | 127 | 132 | 149 | 277 | 280 | 290 |
| KW17.1.1 | 63 | 245 | 64 | 246 | 127 | 132 | 148 | 277 | 280 | 289 |
| KW17.2.1 | 63 | 250 | 65 | 251 | 127 | 132 | 148 | 277 | 280 | 290 |
| KW17.1.2 | 63 | 245 | 65 | 246 | 127 | 132 | 148 | 277 | 280 | 289 |
| KW17.1.6 | 66 | 248 | 67 | 249 | 127 | 132 | 149 | 278 | 280 | 289 |
| KW17.2.2 | 70 | 252 | 71 | 253 | 127 | 132 | 149 | 277 | 280 | 289 |
| KW17.1.5 | 68 | 245 | 69 | 247 | 127 | 132 | 148 | 277 | 280 | 289 |

TABLE 20-continued

Anti-CD161 VH and VL Combination Table

| Anti-CD161 antibody | Full-length amino acid SEQ ID NO | | Full-length nucleotide SEQ ID NO | | $V_H$ CDR amino acid SEQ ID NO | | | $V_L$ CDR amino acid SEQ ID NO | | |
|---|---|---|---|---|---|---|---|---|---|---|
| Name | $V_H$ | $V_L$ | $V_H$ | $V_L$ | CDR1 | CDR2 | CDR3 | CDR1 | CDR2 | CDR3 |
| KW17.2.3 | 66 | 250 | 67 | 251 | 127 | 132 | 149 | 277 | 280 | 290 |
| KW17.2.4 | 66 | 254 | 67 | 255 | 127 | 132 | 149 | 277 | 280 | 291 |
| KW17.2.5 | 72 | 256 | 73 | 257 | 127 | 135 | 149 | 277 | 280 | 289 |
| KW17.2.7 | 74 | 260 | 75 | 261 | 127 | 132 | 149 | 277 | 280 | 292 |
| KW17.2.8 | 76 | 297 | 77 | 298 | 130 | 132 | 149 | 277 | 280 | 290 |
| KW17.3.1 | 78 | 262 | 79 | 263 | 127 | 136 | 149 | 277 | 280 | 291 |
| KW17.3.4 | 78 | 267 | 79 | 268 | 127 | 136 | 149 | 277 | 280 | 293 |
| KW17.3.5 | 78 | 269 | 79 | 270 | 127 | 136 | 149 | 277 | 280 | 292 |
| KW17.3.2 | 80 | 264 | 81 | 265 | 127 | 136 | 149 | 277 | 280 | 291 |
| KW17.3.6 | 82 | 271 | 83 | 272 | 127 | 136 | 149 | 277 | 280 | 294 |
| KW17.3.7 | 84 | 264 | 85 | 266 | 127 | 136 | 149 | 277 | 280 | 291 |
| KW17.3.8 | 86 | 254 | 87 | 255 | 127 | 136 | 149 | 277 | 280 | 291 |
| KM12.1.1 | 90 | 210 | 91 | 211 | 127 | 137 | 150 | 273 | 279 | 281 |
| KM12.1.2 | 92 | 212 | 93 | 213 | 127 | 138 | 150 | 273 | 279 | 286 |
| KM12.1.3 | 94 | 215 | 95 | 216 | 127 | 138 | 150 | 276 | 279 | 281 |
| KM12.1.5 | 94 | 217 | 95 | 218 | 127 | 138 | 150 | 273 | 279 | 281 |
| KM12.1.4 | 96 | 152 | 97 | 153 | 127 | 137 | 150 | 273 | 279 | 281 |
| KM12.1.6 | 98 | 152 | 99 | 154 | 131 | 132 | 151 | 273 | 279 | 281 |
| KM12.1.8 | 98 | 152 | 99 | 154 | 131 | 132 | 151 | 273 | 279 | 281 |
| KM12.2.8 | 98 | 230 | 100 | 232 | 131 | 132 | 151 | 273 | 279 | 281 |
| KM12.2.1 | 101 | 219 | 102 | 220 | 131 | 139 | 151 | 273 | 279 | 286 |
| KM12.2.2 | 103 | 221 | 104 | 222 | 127 | 140 | 151 | 273 | 279 | 286 |
| KM12.3.5 | 105 | 225 | 106 | 226 | 127 | 138 | 151 | 273 | 279 | 286 |
| KM12.2.3 | 105 | 223 | 106 | 224 | 127 | 138 | 151 | 275 | 279 | 286 |
| KM12.2.4 | 107 | 225 | 108 | 226 | 127 | 132 | 151 | 273 | 279 | 286 |
| KM12.2.5 | 109 | 212 | 110 | 214 | 127 | 140 | 151 | 273 | 279 | 286 |
| KM12.2.6 | 111 | 230 | 112 | 231 | 131 | 132 | 150 | 273 | 279 | 281 |
| KM12.2.7 | 113 | 228 | 114 | 229 | 127 | 138 | 151 | 273 | 279 | 286 |
| KM12.3.2 | 113 | 212 | 114 | 214 | 127 | 138 | 151 | 273 | 279 | 286 |
| KM12.3.4 | 113 | 225 | 114 | 226 | 127 | 138 | 151 | 273 | 279 | 286 |
| KM12.4.2 | 113 | 239 | 114 | 240 | 127 | 138 | 151 | 273 | 279 | 286 |
| KM12.4.4 | 113 | 243 | 114 | 244 | 127 | 138 | 151 | 273 | 279 | 288 |
| KM12.3.1 | 115 | 233 | 116 | 234 | 127 | 132 | 150 | 275 | 279 | 286 |
| KM12.3.3 | 117 | 235 | 118 | 236 | 127 | 138 | 151 | 273 | 279 | 287 |
| KM12.4.7 | 117 | 235 | 118 | 236 | 127 | 138 | 151 | 273 | 279 | 287 |
| KM12.3.6 | 119 | 237 | 120 | 238 | 127 | 138 | 151 | 273 | 279 | 286 |
| KM12.3.7 | 121 | 219 | 122 | 220 | 127 | 138 | 151 | 273 | 279 | 286 |
| KM12.4.1 | 123 | 225 | 124 | 227 | 127 | 138 | 151 | 273 | 279 | 286 |
| KM12.4.3 | 125 | 241 | 126 | 242 | 127 | 138 | 151 | 273 | 279 | 287 |

CDR Consensus Sequence and Combination Table

TABLE 21 anti-CD161 antibody CDR consensus sequences

| Name | Amino Acid Sequence (IMGT Numbering) | SEQ ID NO |
|---|---|---|
| $V_H$ CDR1 C1 | GX$_1$X$_2$FX$_3$SYX$_4$<br>X$_1$ = F or S; X$_2$ = T, P or A; X$_3$ = S or I; X$_4$ = A or D | 299 |
| $V_H$ CDR1 C1a | GX$_1$X$_2$FSSYA<br>X$_1$ = any amino acid, optionally X$_2$ = F or S;<br>X$_2$ = any amino acid, optionally X$_1$ = T or P | 300 |
| $V_H$ CDR1 C1b | GFX$_1$FX$_2$SYA<br>X$_1$ = any amino acid, optionally X$_1$ = T or A;<br>X$_2$ = any amino acid, optionally X$_2$ = S or I | 301 |
| $V_H$ CDR1 C1c | GFTFSSYX$_1$<br>X$_1$ = any amino acid, optionally X$_1$ = A or D | 302 |
| $V_H$ CDR2 C2 | X$_1$SX$_2$SGX$_3$X$_4$X$_5$<br>X$_1$ = I or T; X$_2$ = G or S; X$_3$ = G or R;<br>X$_4$ = S, R, G or I; X$_5$ = T, I or A | 303 |
| $V_H$ CDR2 C2a | X$_1$SGSGGX$_2$T<br>X$_1$ = any amino acid, optionally X$_1$ = I or T;<br>X$_2$ = any amino acid, optionally X$_2$ = S or R | 304 |
| $V_H$ CDR2 C2b | ISGSGX$_1$SX$_2$<br>X$_1$ = an amino acid, optionally X$_1$ = G or R;<br>X$_2$ = any amino acid, X$_2$ = optionally T or A | 305 |
| $V_H$ CDR2 C2c | ISX$_1$SGGX$_2$X$_3$<br>X$_1$ = G or S; X$_2$ = S, I or G; X$_3$ = T or I | 306 |
| $V_H$ CDR3 C3 | ARGGX$_1$X$_2$PX$_3$X$_4$FX$_5$Y<br>X$_1$ = L or Y; X$_2$ = I or L; X$_3$ = S or D;<br>X$_4$ = G or A; X$_5$ = any amino acid, optionally X$_5$ = D or G | 307 |
| $V_H$ CDR3 C3a | ARGGLIPSGFX$_1$Y<br>X$_1$ = any amino acid, X$_1$ = optionally D or G | 308 |
| $V_H$ CDR3 C4 | ARGPGX$_1$MYLYGDSFFX$_2$Y<br>X$_1$ = any amino acid, optionally X$_1$ = D or Y;<br>X$_2$ = any amino acid, X$_2$ = optionally D or E | 309 |
| $V_H$ CDR3 C5 | ARDYYLX$_1$DYITQTSFDY<br>X$_1$ = any amino acid, optionally X$_1$ = S, F, or Y | 310 |
| $V_H$ CDR3 C6 | ARGYSDSYX$_1$YGPYYTFDY<br>X$_1$ = any amino acid, optionally X$_1$ = Y or F | 311 |
| $V_L$ CDR1 C7 | X$_1$X$_2$ISX$_3$Y<br>X$_1$ = Q or R; X$_2$ = S or G; X$_3$ = S or N | 312 |
| $V_L$ CDR1 C7a | QX$_1$ISX$_2$Y<br>X$_1$ = any amino acid, optionally X$_1$ = S or G;<br>X$_2$ = any amino acid, optionally X$_2$ = S or N | 313 |

TABLE 21-continued anti-CD161 antibody CDR consensus sequences

| Name | Amino Acid Sequence (IMGT Numbering) | SEQ ID NO |
|---|---|---|
| $V_L$ CDR1 C7b | $X_1X_2$ISSY<br>wherein $X_1$ = any amino acid, optionally $X_1$ = Q or R; $X_2$ = any amino acid, optionally $X_2$ = S or G | 314 |
| $V_L$ CDR1 C8 | $X_1$SNIGAGYD<br>$X_1$ = any amino acid, optionally $X_1$ = S or N | 315 |
| $V_L$ CDR2 C9 | $X_1X_2$S<br>$X_1$ = A or G; $X_2$ = A or N | 316 |
| $V_L$ CDR3 C10 | QQ$X_1$Y$X_2$$X_3$PLT<br>$X_1$ = S or T; $X_2$ = S, G, N or D; $X_3$ = T, A or I | 317 |
| $V_L$ CDR3 C10a | QQ$X_1$Y$X_2$$X_3$PLT<br>$X_1$ = S or T; $X_2$ = S or G; $X_3$ = T or A | 318 |
| $V_L$ CDR3 C10b | QQSYS$X_1$PLT<br>$X_1$ = any amino acid, optionally $X_1$ = T or I | 319 |
| $V_L$ CDR3 C10c | QQSY$X_1X_2$PLT<br>$X_1$ = any amino acid, optionally $X_1$ = S, N or D; $X_2$ = any amino acid, optionally $X_2$ = T or A | 320 |
| $V_L$ CDR3 C11 | QSY$X_1$S$X_2$H$X_3$V<br>$X_1$ = D, G or N; $X_2$ = S or G; $X_3$ = T or S | 321 |

TABLE 22 anti-CD161 antibody CDR consensus sequences Combination Table

| $V_H$ SEQ ID (amino acid) | | | $V_L$ SEQ ID NO (amino acid) | | |
|---|---|---|---|---|---|
| CDR1 | CDR2 | CDR3 | CDR1 | CDR2 | CDR3 |
| 299 | 303 | 307 | 312 | 316 | 317 |
| 299 | 303 | 307 | 312 | 316 | 318 |
| 300 | 304 | 307 | 312 | 316 | 317 |
| 300 | 304 | 307 | 312 | 316 | 318 |
| 300 | 304 | 308 | 312 | 316 | 317 |
| 300 | 304 | 308 | 312 | 316 | 318 |
| 299 | 303 | 309 | 312 | 316 | 317 |
| 299 | 303 | 309 | 313 | 316 | 319 |
| 300 | 304 | 309 | 312 | 316 | 317 |
| 300 | 304 | 309 | 313 | 316 | 319 |
| 299 | 303 | 310 | 315 | 316 | 321 |
| 301 | 305 | 310 | 315 | 316 | 321 |
| 299 | 303 | 311 | 312 | 316 | 317 |
| 299 | 303 | 311 | 314 | 316 | 320 |
| 302 | 306 | 311 | 312 | 316 | 317 |
| 302 | 306 | 311 | 314 | 316 | 320 |

Additional Sequences

TABLE 23

Antibody Constant Regions

| Name | Sequence type | Sequence | SEQ ID NO |
|---|---|---|---|
| Human IgG1 (UniProtKB Ref# P01857 IGHG1_HUMAN) | Amino acid | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 322 |
| Human IgG4 (UniProtKB Ref# P01861 IGHG4_HUMAN) | Amino acid | ASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPSCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK | 323 |
| Human Ig kappa constant (UniProtKB Ref #P01834 IGKC_HUMNAN) | Amino acid | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 324 |
| Human Ig lambda constant (UniProtKB Ref# P0CG04 IGLC1_HUMAN) | Amino acid | GQPKANPTVTLFPPSSEELQANKATLVCLISDFYPGAVTVAWKADGSPVKAGVETTKPSKQSNNKYAASSYLSLTPEQWKSHRSYSCQVTHEGSTVEKTVAPTECS | 325 |
| Human IgG1 Fc (LALA-PG sequence variation) Residues altered from wild type IgG1 in bold underline | Amino acid | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEA<br>AGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALGAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK* | 326 |

TABLE 23-continued

Antibody Constant Regions

| Name | Sequence type | Sequence | SEQ ID NO |
|---|---|---|---|
| Human IgG1 Fc (LALA-PG sequence variation) CH1 domain | Amino acid | ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKKV | 327 |
| Human IgG1 Fc (LALA-PG sequence variation) hinge | Amino acid | EPKSCDKTHTCP | 328 |
| Human IgG1 Fc (LALA-PG sequence variation) CH2 domain Residues altered from wild type in bold underline | Amino acid | PCPAPEAAGGPSVFLFPPKPKDTLMISRTPEVTCVVVDV SHEDPEVKFNWYVDGVEVHNAKTKPREEQYNSTYRVVSV LTVLHQDWLNGKEYKCKVSNKALGAPIEKTISKAK | 329 |
| Human IgG1 Fc (LALA-PG sequence variation) CH3 domain | Amino acid | GQPREPQVYTLPPSRDELTKNQVSLTCLVKGFYPSDIAV EWESNGQPENNYKTTPPVLDSDGSFFLYSKLTVDKSRWQ QGNVFSCSVMHEALHNHYTQKSLSLSPGK | 330 |
| hIgG1 Fc (LALA-PG sequence variation) | Nucleic acid | GCTAGCACCAAGGGCCCATCGGTCTTCCCCCTGGCACCC TCCTCCAAGAGCACCTCTGGGGGCACAGCGGCCCTGGGC TGCCTGGTCAAGGACTACTTCCCCGAACCGGTGACGGTG TCGTGGAACTCAGGCGCCCTGACCAGCGGCGTGCACACC TTCCCGGCTGTCCTACAGTCCTCAGGACTCTACTCCCTC AGCAGCGTGGTGACCGTGCCCTCCAGCAGCTTGGGCACC CAGACCTACATCTGCAACGTGAATCACAAGCCCAGCAAC ACCAAGGTGGACAAGAAAGTTGAGCCCAAATCTTGTGAC AAAACTCACACATGCCCACCGTGCCCAGCACCTGAAGCT GCGGGAGGACCGTCAGTCTTCCTCTTCCCCCCAAAACCC AAGGACACCCTCATGATCTCCCGGACCCCTGAGGTCACA TGCGTGGTGGTGGACGTGAGCCACGAAGACCCTGAGGTC AAGTTCAACTGGTACGTGGACGGCGTGGAGGTGCATAAT GCCAAGACAAAGCCGCGGGAGGAGCAGTACAACAGCACG TACCGTGTGGTCAGCGTCCTCACCGTCCTGCACCAGGAC TGGCTGAATGGCAAGGAGTACAAGTGCAAGGTCTCCAAC AAAGCCCTCGGAGCCCCCATCGAGAAAACCATCTCCAAA GCCAAAGGGCAGCCCCGAGAACCACAGGTGTACACCCTG CCCCCATCCCGGGATGAGCTGACCAAGAACCAGGTCAGC CTGACCTGCCTGGTCAAAGGCTTCTATCCCAGCGACATC GCCGTGGAGTGGGAGAGCAATGGGCAGCCGGAGAACAAC TACAAGACCACGCCTCCCGTGCTGGACTCCGACGGCTCC TTCTTCCTCTACAGCAAGCTCACCGTGGACAAGAGCAGG TGGCAGCAGGGGAACGTCTTCTCATGCTCCGTGATGCAT GAGGCTCTGCACAACCACTACACGCAGAAGAGCCTCTCC CTGTCTCCGGGTAAATGA | 331 |
| FLAG tag | Amino acid | DYKDDDDK | 332 |
| 6-His tag | Amino acid | HHHHHH | 333 |
| HA tag | Amino acid | YPYDVPDYA | 334 |

TABLE 24

Protein Target Sequences

| Name & Description | Sequence | SEQ ID NO |
|---|---|---|
| Human CD161 (UniProtKB #: Q12918) | MDQQAIYAELNLPTDSGPESSSPSSLPRDVCQGSPWHQFALKLSCAG IILLVLVVTGLSVSVTSLIQKSSIEKCSVDIQQSRNKTTERPGLLNC PIYWQQLREKCLLFSHTVNPWNNSLADCSTKESSLLLIRDKDELIHT QNLIRDKAILFWIGLNFSLSEKNWKWINGSFLNSNDLEIRGDAKENS CISISQTSVYSEYCSTEIRWICQKELTPVRNKVYPDS | 335 |
| Cynomolgus CD161 (UniProtKB #: A0A2K5WYI1) | MDQQMMYAELTLPKDSGPESSSPSSLPRDVCQGSPWHQFALKLSCAG IILLVLVVTGLSLSVASLLQKPSIGKCSVDIQQNRTKTTERPDLLNC PIYWQQVQEKCLLFSHTVNPWNNSLADCSTKESSLLLIQDKDELTRT QNLIHDKAISFWIGLNFSLSEKNWKWINGSFLSSNDLKITGDAKENS CVYISQTSVYSEYCSTEMKWICQKELTLVRNKVSPDSWL | 336 |
| Human CLEC2D (UniProtKB #: Q9UHP7) | MHDSNNVEKDITPSELPANPGCLHSKEHSIKATLIWRLFFLIMFLTI IVCGMVAALSAIRANCHQEPSVCLQAACPESWIGFQRKCFYFSDDTK NWTSSQRFCDSQDADLAQVESFQELNFLLRYKGPSDHWIGLSREQGQ PWKWINGTEWTRQFPILGAGECAYLNDKGASSARHYTERKWICSKSD IHV | 337 |
| Human CD94 (UniProtKB #: Q13241) | MAVEKTTLWRLISGTLGIICLSLMSTLGILLKNSFTKLSIEPAFTPG PNIELQKDSDCCSCQEKWVGYRCNCYFISSEQKTWNESRHLCASQKS SLLQLQNTDELDFMSSSQQFYWIGLSYSEEHTAWLWENGSALSQYLF PSFETFNTKNCIAYNPNGNALDESCEDKNRYICKQQLI | 338 |
| Human KLRF2 (UniProtKB #: D3W0D1) | MENEDGYMTLSFKNRCKSKQKSKDFSLYPQYYCLLLIFGCIVILIFI MTGIDLKFWHKKMDFSQNVNVSSLSGHNYLCPNDWLLNEGKCYWFST SFKTWKESQRDCTQLQAHLLVIQNLDELEFIQNSLKPGHFGWIGLYV TFQGNLWMWIDEHFLVPELFSVIGPTDDRSCAVITGNWVYSEDCSST FKGICQRDAILTHNGTSGV | 339 |
| Human Clec12B (UniProtKB #: D3W0D1) | MSEEVTYATLTFQDSAGARNNRDGNNLRKRGHPAPSPIWRHAALGLV TLCLMLLIGLVTLGMMFLQISNDINSDSEKLSQLQKTIQQQQDNLSQ QLGNSNNLSMEEEFLKSQISSVLKRQEQMAIKLCQELIIHTSDHRCN PCPKMWQWYQNSCYYFTTNEEKTWANSRKDCIDKNSTLVKIDSLEEK DFLMSQPLLMFSFFWLGLSWDSSGRSWFWEDGSVPSPSLFSTKELDQ INGSKGCAYFQKGNIYISRCSAEIFWICEKTAAPVKTEDLD | 340 |
| Human Clec7A (UniProtKB #: Q9BXN2) | MEYHPDLENLDEDGYTQLHFDSQSNTRIAVVSEKGSCAASPPWRLIA VILGILCLVILVIAVVLGTMAIWRSNSGSNTLENGYFLSRNKENHSQ PTQSSLEDSVTPTKAVKTTGVLSSPCPPNWIIYEKSCYLFSMSLNSW DGSKRQCWQLGSNLLKIDSSNELGFIVKQVSSQPDNSFWIGLSRPQT EVPWLWEDGSTFSSNLFQIRTTATQENPSPNCVWIHVSVIYDQLCSV PSYSICEKKFSM | 341 |
| Human KLRG1 (UniProtKB #: Q96E93) | MTDSVIYSMLELPTATQAQNDYGPQQKSSSSRPSCSCLVAIALGLLT AVLLSVLLYQWILCQGSNYSTCASCPSCPDRWMKYGNHCYYFSVEEK DWNSSLEFCLARDSHLLVITDNQEMSLLQVFLSEAFCWIGLRNNSGW RWEDGSPLNFSRISSNSFVQTCGAINKNGLQASSCEVPLHWVCKKCP FADQALF | 342 |
| Human OLR1 (UniProtKB #: P78380) | MTFDDLKIQTVKDQPDEKSNGKKAKGLQFLYSPWWCLAAATLGVLCL GLVVTIMVLGMQLSQVSDLLTQEQANLTHQKKKLEGQISARQQAEEA SQESENELKEMIETLARKLNEKSKEQMELHHQNLNLQETLKRVANCS APCPQDWIWHGENCYLFSSGSFNWEKSQEKCLSLDAKLLKINSTADL DFIQQAISYSSFPFWMGLSRRNPSYPWLWEDGSPLMPHLFRVRGAVS QTYPSGTCAYIQRGAVYAENCILAAFSICQKKANLRAQ | 343 |
| Human Clec5A (UniProtKB #: Q9NY25) | MNWHMIISGLIVVVLKVVGMTLFLLYFPQIFNKSNDGFTTTRSYGTV SQIFGSSSPSPNGFITTRSYGTVCPKDWEFYQARCFFLSTSESSWNE SRDECKGKGSTLAIVNTPEKLKFLQDITDAEKYFIGLIYHREEKRWR WINNSVFNGNVTNQNQNFNCATIGLTKTFDAASCDISYRRICEKNAK | 344 |
| Human Clec9A (UniProtKB #: Q6UXN8) | MHEEEIYTSLQWDSPAPDTYQKCLSSNKCSGACCLVMVISCVFCMGL LTASIFLGVKLLQVSTIAMQQQEKLIQQERALLNFTEWKRSCALQMK YCQAFMQNSLSSAHNSSPCPNNWIQNRESCYYVSEIWSIWHTSQENC LKEGSTLLQIESKEEMDFITGSLRKIKGSYDYWVGLSQDGHSGRWLW QDGSSPSPGLLPAERSQSANQVCGYVKSNSLLSSNCSTWKYFICEKY ALRSSV | 345 |
| Human CD209 (UniProtKB #: Q9NNX6) | MSDSKEPRLQQLGLLEEEQLRGLGFRQTRGYKSLAGCLGHGPLVLQL LSFTLLAGLLVQVSKVPSSISQEQSRQDAIYQNLTQLKAAVGELSEK SKLQEIYQELTQLKAAVGELPEKSKLQEIYQELTRLKAAVGELPEKS KLQEIYQELTWLKAAVGELPEKSKMQEIYQELTRLKAAVGELPEKSK QQEIYQELTRLKAAVGELPEKSKQQEIYQELTRLKAAVGELPEKSKQ QEIYQELTQLKAAVERLCHPCPWEWTFFQGNCYFMSNSQRNWHDSIT ACKEVGAQLVVIKSAEEQNFLQLQSSRSNRFTWMGLSDLNQEGTWQW | 346 |

TABLE 24-continued

Protein Target Sequences

| Name & Description | Sequence | SEQ ID NO |
|---|---|---|
| | VDGSPLLPSFKQYWNRGEPNNVGEEDCAEFSGNGWNDDKCNLAKFWI CKKSAASCSRDEEQFLSPAPATPNPPPA | |
| Human Clec4E (UniProtKB #: Q9ULY5) | MNSSKSSETQCTERGCFSSQMFLWTVAGIPILFLSACFITRCVVTFR IFQTCDEKKFQLPENFTELSCYNYGSGSVKNCCPLNWEYFQSSCYFF STDTISWALSLKNCSAMGAHLVVINSQEEQEFLSYKKPKMREFFIGL SDQVVEGQWQWVDGTPLTKSLSFWDVGEPNNIATLEDCATMRDSSNP RQNWNDVTCFLNYFRICEMVGINPLNKGKSL | 347 |
| Human Clec10A (UniProtKB #: Q8IUN9) | MTRTYENFQYLENKVKVQGFKNGPLPLQSLLQRLCSGPCHLLLSLGL GLLLLVIICVVGFQNSKFQRDLVTLRTDFSNFTSNTVAEIQALTSQG SSLEETIASLKAEVEGFKQERQAGVSELQEHTTQKAHLGHCPHCPSV CVPVHSEMLLRVQQLVQDLKKLTCQVATLNNNASTEGTCCPVNWVEH QDSCYWFSHSGMSWAEAEKYCQLKNAHLVVINSREEQNFVQKYLGSA YTWMGLSDPEGAWKWVDGTDYATGFQNWKPGQPDDWQGHGLGGGEDC AHFHPDGRWNDDVCQRPYHWVCEAGLGQTSQESH | 348 |
| Human KLRF1 (UniProtKB #: Q9NZS2) | MQDEERYMTLNVQSKKRSSAQTSQLTFKDYSVTLHWYKILLGISGTV NGILTLTLISLILLVSQGVLLKCQKGSCSNATQYEDTGDLKVNNGTR RNISNKDLCASRSADQTVLCQSEWLKYQGKCYWFSNEMKSWSDSYVY CLERKSHLLIIHDQLEMAFIQKNLRQLNYVWIGLNFTSLKMTWTWVD GSPIDSKIFFIKGPAKENSCAAIKESKIFSETCSSVFKWICQY | 349 |

TABLE 25

NY-ESO-1 TCR/NY-ESO-1 Antigen System

| Name | Sequence | SEQ ID NO |
|---|---|---|
| TRAC gRNA spacer | UCAGGGUUCUGGAUAUCUGU | 350 |
| TRAC target gene | TCAGGGTTCTGGATATCTGTGGG | 351 |
| KLRB1 gRNA spacer | AAUUAAAGCCACUUACCCCG | 352 |
| KLRB1 target gene | AATTAAAGCCACTTACCCCGAGG | 353 |
| LacZ gRNA spacer | GCUGAGCGCUCGGAGCGCCU | 354 |
| LacZ target gene | GCTGAGCGCTCGGAGCGCCT | 355 |
| NY-ESO-1 TCR | GCCGCCACCATGGTACCGTGCACGCTGCTCCTGCTGTTGGCGGCCGC CCTGGCTCCGACTCAGACCCGCGCGAAAAGTTATCCTTACGACGTGC CCGACTACGCCGGAAAGCAAGAAGTGACACAGATCCCTGCCGCTCTG TCTGTGCCTGAGGGCGAAAACCTGGTGCTGAACTGCAGCTTCACCGA CAGCGCCATCTACAACCTGCAGTGGTTCAGACAGGACCCCGGCAAGG GACTGACAAGCCTGCTGCTGATTCAGAGCAGCCAGAGAGAGCAGACC AGCGGCAGACTGAATGCCAGCCTGGATAAGTCCTCCGGCAGAAGCAC CCTGTATATCGCCGCTTCTCAGCCTGGCGATAGCGCCACATATCTGT GTGCCGTGCGACCTCTGTACGGCGGCAGCTACATCCCTACATTTGGC AGAGGCACCAGCCTGATCGTGCACCCCAACATTCAAAATCCTGATCC TGCCGTGTACCAGCTGAGAGACAGCAAGTCCAGCGACAAGAGCGTGT GCCTGTTCACCGACTTCGACAGCCAGACCAACGTGTCCCAGAGCAAG GACAGCGACGTGTACATCACCGACAAGACCGTGCTGGACATGCGGAG CATGGACTTCAAGAGCAACAGCGCCGTGGCCTGGTCCAACAAGAGCG ATTTCGCCTGCGCCAACGCCTTCAACAACAGCATTATCCCCGAGGAC ACATTCTTCCCAAGTCCTGAGAGCAGCTGCGACGTGAAGCTGGTGGA AAAGAGCTTCGAGACAGACACCAACCTGAACTTTCAAAACCTGAGCG TGATCGGCTTCCGGATCCTGCTGCTTAAGGTGGCCGGCTTCAACCTG CTGATGACCCTGAGACTGTGGTCCTCTGAGGGCAGAGGCAGCCTGT GACCTGCGGCGACGTGGAGGAGAACCCCGGCCCCATGGTACCGTGCA CGCTGCTCCTGCTGTTGGCGGCCGCCCTGGCTCCGACTCAGACCCGC GCGGAGGACCAGGTGGACCCCAGGCTGATCGACGGCAAGGGCAATGC TGGCGTCACCCAGACACCTAAGTTCCAGGTGCTGAAAACCGGCCAGA GCATGACCCTGCAGTGCGCCCAGGATATGAACCACGAGTACATGTCC | 356 |

TABLE 25-continued

NY-ESO-1 TCR/NY-ESO-1 Antigen System

| Name | Sequence | SEQ ID NO |
|---|---|---|
| | TGGTATCGGCAGGACCCTGGAATGGGGCTGAGACTGATCCACTACTC<br>TGTCGGAGCCGGCATCACCGATCAGGGCGAAGTGCCTAATGGCTACA<br>ATGTGTCCCGGTCCACCACCGAGGACTTCCCACTGAGACTGCTGTCT<br>GCTGCCCCTAGCCAGACCTCCGTGTACTTTTGTGCCAGCAGCTACGT<br>GGGCAACACCGGCGAGCTGTTTTTTGGCGAGGGCTCCAGACTGACCG<br>TGCTCGAGGACCTGAAGAACGTGTTCCCACCTGAGGTGGCCGTGTTC<br>GAGCCTTCTGAGGCCGAGATCAGCCACACACAGAAAGCCACACTCGT<br>GTGTCTGGCCACCGGCTTCTATCCCGATCACGTGGAACTGTCTTGGT<br>GGGTCAACGGCAAAGAGGTGCACAGCGGCGTCAGCACAGATCCTCAG<br>CCTCTGAAAGAGCAGCCCGCTCTGAACGACAGCAGATACTGCCTGAG<br>CAGCAGACTGAGAGTGTCCGCCACCTTCTGGCAAAATCCTAGAAACC<br>ACTTCAGATGCCAGGTGCAGTTCTACGGCCTGAGCGAGAACGATGAG<br>TGGACCCAGGATAGAGCCAAGCCTGTGACTCAGATCGTGTCTGCCGA<br>AGCCTGGGCAGAGCCGATTGTGGCTTTACCAGCGAGAGCTACCAGC<br>AGGGCGTTCTGTCTGCCACCATCCTGTACGAGATTCTGCTGGGCAAA<br>GCCACTCTGTACGCCGTGCTGGTGTCTGCCCTGGTTCTGATGGCCAT<br>GGTCAAGCGGAAGGACAGCAGAGGATGA | |
| Kozak sequence | GCCGCCACC | 357 |
| Signal peptide1 | ATGGTACCGTGCACGCTGCTCCTGCTGTTGGCGGCCGCCCTGGCTCC<br>GACTCAGACCCGCGCG | 358 |
| HA tag | TATCCTTACGACGTGCCCGACTACGCC | 359 |
| NY-ESO-1 TCR alpha-variable chain | AAGCAAGAAGTGACACAGATCCCTGCCGCTCTGTCTGTGCCTGAGGG<br>CGAAAACCTGGTGCTGAACTGCAGCTTCACCGACAGCGCCATCTACA<br>ACCTGCAGTGGTTCAGACAGGACCCCGGCAAGGGACTGACAAGCCTG<br>CTGCTGATTCAGAGCAGCCAGAGAGAGCAGACCAGCGGCAGACTGAA<br>TGCCAGCCTGGATAAGTCCTCCGGCAGAAGCACCCTGTATATCGCCG<br>CTTCTCAGCCTGGCGATAGCGCCACATATCTGTGTGCCGTGCGACCT<br>CTGTACGGCGGCAGCTACATCCCTACATTTGGCAGAGGCACCAGCCT<br>GATCGTGCACCCC | 360 |
| NY-ESO-1 TCR alpha-constant chain | AACATTCAAAATCCTGATCCTGCCGTGTACCAGCTGAGAGACAGCAA<br>GTCCAGCGACAAGAGCGTGTGCCTGTTCACCGACTTCGACAGCCAGA<br>CCAACGTGTCCCAGAGCAAGGACAGCGACGTGTACATCACCGACAAG<br>ACCGTGCTGGACATGCGGAGCATGGACTTCAAGAGCAACAGCGCCGT<br>GGCCTGGTCCAACAAGAGCGATTTCGCCTGCGCCAACGCCTTCAACA<br>ACAGCATTATCCCCGAGGACACATTCTTCCCAAGTCCTGAGAGCAGC<br>TGCGACGTGAAGCTGGTGGAAAAGAGCTTCGAGACAGACACCAACCT<br>GAACTTTCAAAACCTGAGCGTGATCGGCTTCCGGATCCTGCTGCTTA<br>AGGTGGCCGGCTTCAACCTGCTGATGACCCTGAGACTGTGGTCCTCT | 361 |
| T2A skip peptide | GAGGGCAGAGGCAGCCTGCTGACCTGCGGCGACGTGGAGGAGAACCC<br>CGGCCCC | 362 |
| TCR beta chain signal Peptide | ATGGTACCGTGCACGCTGCTCCTGCTGTTGGCGGCCGCCCTGGCTCC<br>GACTCAGACCCGCGCG | 363 |
| NY-ESO-1 TCR PC tag | GAGGACCAGGTGGACCCCAGGCTGATCGACGGCAAG | 364 |
| NY-ESO-1 TCR beta-variable chain | GGCAATGCTGGCGTCACCCAGACACCTAAGTTCCAGGTGCTGAAAAC<br>CGGCCAGAGCATGACCCTGCAGTGCGCCCAGGATATGAACCACGAGT<br>ACATGTCCTGGTATCGGCAGGACCCTGGAATGGGGCTGAGACTGATC<br>CACTACTCTGTCGGAGCCGGCATCACCGATCAGGGCGAAGTGCCTAA<br>TGGCTACAATGTGTCCCGGTCCACCACCGAGGACTTCCCACTGAGAC<br>TGCTGTCTGCTGCCCCTAGCCAGACCTCCGTGTACTTTTGTGCCAGC<br>AGCTACGTGGGCAACACCGGCGAGCTGTTTTTTGGCGAGGGCTCCAG<br>ACTGACCGTGCTC | 365 |
| NY-ESO-1 TCR beta-constant chain | GAGGACCTGAAGAACGTGTTCCCACCTGAGGTGGCCGTGTTCGAGCC<br>TTCTGAGGCCGAGATCAGCCACACACAGAAAGCCACACTCGTGTGTC<br>TGGCCACCGGCTTCTATCCCGATCACGTGGAACTGTCTTGGTGGGTC<br>AACGGCAAAGAGGTGCACAGCGGCGTCAGCACAGATCCTCAGCCTCT<br>GAAAGAGCAGCCCGCTCTGAACGACAGCAGATACTGCCTGAGCAGCA<br>GACTGAGAGTGTCCGCCACCTTCTGGCAAAATCCTAGAAACCACTTC<br>AGATGCCAGGTGCAGTTCTACGGCCTGAGCGAGAACGATGAGTGGAC<br>CCAGGATAGAGCCAAGCCTGTGACTCAGATCGTGTCTGCCGAAGCCT<br>GGGGCAGAGCCGATTGTGGCTTTACCAGCGAGAGCTACCAGCAGGGC | 366 |

TABLE 25-continued

NY-ESO-1 TCR/NY-ESO-1 Antigen System

| Name | Sequence | SEQ ID NO |
|---|---|---|
| | GTTCTGTCTGCCACCATCCTGTACGAGATTCTGCTGGGCAAAGCCAC<br>TCTGTACGCCGTGCTGGTGTCTGCCCTGGTTCTGATGGCCATGGTCA<br>AGCGGAAGGACAGCAGAGGA | |
| NY-ESO-1 construct | GCCGCCACCATGCAGGCCGAAGGAAGAGGTACAGGGGGTTCGACGGG<br>CGATGCTGATGGCCCAGGAGGCCCTGGCATTCCTGATGGCCCAGGGG<br>GCAATGCTGGTGGACCAGGAGAGGCGGGTGCCACGGGAGGTAGAGGT<br>CCACGGGGAGCAGGTGCAGCAAGGGCTTCGGGACCGGGAGGAGGTGC<br>CCCGCGGGGTCCGCATGGTGGAGCAGCTTCAGGGCTGAATGGATGCT<br>GCAGATGCGGGCCAGGGGGCCGGAGAGCCGCCTGCTTGAGTTCTAC<br>CTCGCCATGCCTTTCGCGACACCCATGGAAGCAGAGCTGGCCCGCAG<br>GAGCCTGGCCCAGGATGCCCCACCGCTTCCCGTGCCAGGGGTGCTTC<br>TGAAGGAGTTCACTGTGTCCGGCAACATACTGACTATCCGACTGACT<br>GCTGCAGACCACCGCCAACTGCAGCTCTCCATCAGCTCCTGTCTCCA<br>GCAGCTTTCCCTGTTGATGTGGATCACGCAGTGCTTTCTGCCCGTGT<br>TTTTGGCTCAGCCTCCCTCAGGGCAGAGGCGCGAGGGCAGAGGCAGC<br>CTGCTGACCTGCGGCGACGTGGAGGAGAACCCCGGCCCCATGGAAGA<br>TGCCAAGAACATCAAGAAAGGCCCTGCCCCCTTCTACCCCCTGGAAG<br>ATGGCACAGCCGGCGAGCAGCTGCACAAGGCCATGAAGAGATACGCC<br>CTGGTGCCCGGCACCATCGCCTTCACCGACGCCCACATCGAGGTGGA<br>CATCACCTACGCCGAGTATTTCGAGATGAGCGTGCGGCTGGCCGAGG<br>CCATGAAACGCTACGGCCTGAACACCAACCACCGGATCGTGGTGTGC<br>AGCGAGAACAGCCTGCAGTTCTTCATGCCCGTGCTGGGCGCCCTGTT<br>CATCGGCGTGGCCGTGGCCCCTGCCAACGACATCTACAACGAGCGGG<br>AGCTGCTGAACAGCATGGGCATCAGCCAGCCCACCGTGGTGTTCGTG<br>AGCAAGAAGGGCCTGCAGAAAATCCTGAACGTGCAGAAGAAGCTGCC<br>CATCATCCAGAAAATCATCATCATGGACAGCAAGACCGACTACCAGG<br>GCTTCCAGAGCATGTACACCTTCGTGACAGCCACCTGCCCCGTGGC<br>TTCAACGAGTACGACTTCGTGCCCGAGAGCTTCGACCGGGACAAGAC<br>CATCGCCCTGATCATGAACAGCAGCGGCAGCACCGGCCTGCCTAAAG<br>GCGTGGCCCTGCCTCACCGGACCGCCTGCGTGCGGTTCAGCCACGCC<br>CGGGACCCCATCTTCGGCAACCAGATCATCCCCGACACCGCCATCCT<br>GAGCGTGGTGCCCTTCCACCACGGCTTCGGCATGTTCACCACCCTGG<br>GCTACCTGATCTGCGGCTTCCGGGTGGTGCTGATGTACCGGTTCGAG<br>GAAGAGCTGTTCCTGCGGAGCCTGCAGGACTACAAGATCCAGAGCGC<br>CCTGCTGGTGCCCACCCTGTTCAGCTTTTTCGCCAAGAGCACCCTGA<br>TCGACAAGTACGACCTGAGCAACCTGCACGAGATCGCCAGCGGCGGA<br>GCCCCCCTGTCCAAAGAAGTGGGCGAAGCCGTCGCCAAGCGGTTCCA<br>CCTGCCCGGCATCCGGCAGGGCTATGGCCTGACCGAGACCACAAGCG<br>CCATTCTGATCACCCCCGAGGGCGACGACAAGCCTGGCGCCGTGGGC<br>AAGGTGGTGCCTTTCTTCGAGGCCAAGGTGGTGGACCTGGACACCGG<br>CAAGACCCTGGGCGTGAACCAGCGGGGCGAGCTGTGCGTGAGGGGCC<br>CCATGATCATGAGCGGCTACGTGAACAACCCCGAGGCCACCAACGCC<br>CTGATTGACAAGGACGGCTGGCTGCACAGCGGCGACATCGCCTACTG<br>GGACGAGGACGAGCACTTCTTCATCGTGGACCGGCTGAAGAGCCTGA<br>TCAAGTACAAGGGCTACCAGGTGGCCCCAGCCGAGCTGGAAAGCATC<br>CTGCTGCAGCACCCCAACATCTTCGATGCCGGGGTGGCCGGACTGCC<br>CGACGACGATGCCGGCGAGCTGCCTGCCGCCGTGGTGGTGCTGGAAC<br>ACGGCAAAACCATGACCGAGAAAGAAATCGTGGACTACGTGGCCAGC<br>CAGGTGACCACCGCCAAGAAACTGAGAGGCGGCGTGGTGTTTGTGGA<br>CGAGGTGCCCAAGGGCCTGACAGGCAAGCTGGACGCCCGGAAGATCC<br>GGGAGATCCTGATCAAGGCCAAGAAGGGCGGCAAGTCCAAATTGTAA<br>TCTAGAGGATCCCTCCCCCCCCCCTAACGTTACTGGCCGAAGCCGCT<br>TGGAATAAGGCCGGTGTGCGTTTGTCTATATGTTATTTTCCACCATA<br>TTGCCGTCTTTTGGCAATGTGAGGGCCCGGAAACCTGGCCCTGTCTT<br>CTTGACGAGCATTCCTAGGGGTCTTTCCCCTCTCGCCAAAGGAATGC<br>AAGGTCTGTTGAATGTCGTGAAGGAAGCAGTTCCTCTGGAAGCTTCT<br>TGAAGACAAACAACGTCTGTAGCGACCCTTTGCAGGCAGCGGAACCC<br>CCCACCTGGCGACAGGTGCCTCTGCGGCCAAAAGCCACGTGTATAAG<br>ATACACCTGCAAAGGCGGCACAACCCCAGTGCCACGTTGTGAGTTGG<br>ATAGTTGTGGAAAGAGTCAAATGGCTCTCCTCAAGCGTATTCAACAA<br>GGGGCTGAAGGATGCCCAGAAGGTACCCCATTGTATGGGATCTGATC<br>TGGGGCCTCGGTGCACATGCTTTACATGTGTTTAGTCGAGGTTAAAA<br>AAACGTCTAGGCCCCCCGAACCACGGGGACGTGGTTTTCCTTTGAAA<br>AACACGATGATAATATGGCCACACATATGGCCACAACCATGGACGGG<br>CCGCGCCTGCTGTTGCTGCTTCTGGGGGTGTCCCTTGGAGGTGC<br>CAAGGAGGCATGCCCCACAGGCCTGTACACACACAGCGGTGAGTGCT<br>GCAAAGCCTGCAACCTGGGCGAGGGTGTGGCCCAGCCTTGTGGAGCC<br>AACCAGACCGTGTGTGAGCCCTGCCTGGACAGCGTGACGTTCTCCGA<br>CGTGGTGAGCGCGACCGAGCCGTGCAAGCCGTGCACCGAGTGCGTGG<br>GGCTCCAGAGCATGTCGGCGCCGTGCGTGGAGGCCGACGACGCCGTG<br>TGCCGCTGCGCCTACGGCTACTACCAGGATGAGACGACTGGGCGCTG<br>CGAGGCGTGCCGCGTGTGCGAGGCGGGCTCGGGCCTCGTGTTCTCCT<br>GCCAGGACAAGCAGAACACCGTGTGCGAGGAGTGCCCCGACGGCACG<br>TATTCCGACGAGGCCAACCACGTGGACCCGTGCCTGCCCTGCACCGT | 367 |

TABLE 25-continued

NY-ESO-1 TCR/NY-ESO-1 Antigen System

| Name | Sequence | SEQ ID NO |
|---|---|---|
| | GTGCGAGGACACCGAGCGCCAGCTCCGCGAGTGCACACGCTGGCCG<br>ACGCCGAGTGCGAGGAGATCCCTGGCCGTTGGATTACACGGTCCACA<br>CCCCCAGAGGGCTCGGACAGCACAGCCCCCAGCACCCAGGAGCCTGA<br>GGCACCTCCAGAACAAGACCTCATAGCCAGCACGGTGGCAGGTGTGG<br>TGACCACAGTGATGGGCAGCTCCCAGCCCGTGGTGACCCGAGGCACC<br>ACCGACAACCTCATCCCTGTCTATTGCTCCATCCTGGCTGCTGTGGT<br>TGTGGGCCTTGTGGCCTACATAGCCTTCAAGAGGTGGAACAGTTGA | |
| NY-ESO-1 peptide | ATGCAGGCCGAAGGAAGAGGTACAGGGGGTTCGACGGGCGATGCTGA<br>TGGCCCAGGAGGCCCTGGCATTCCTGATGGCCCAGGGGGCAATGCTG<br>GTGGACCAGGAGAGGCGGGTGCCACGGGAGGTAGAGGTCCACGGGGA<br>GCAGGTGCAGCAAGGGCTTCGGGACCGGGAGGAGGTGCCCCGCGGGG<br>TCCGCATGGTGGAGCAGCTTCAGGGCTGAATGGATGCTGCAGATGCG<br>GGGCCAGGGGCCGGAGAGCCGCCTGCTTGAGTTCTACCTCGCCATG<br>CCTTTCGCGACACCCATGGAAGCAGAGCTGGCCCGCAGGAGCCTGGC<br>CCAGGATGCCCACCGCTTCCCGTGCCAGGGGTGCTTCTGAAGGAGT<br>TCACTGTGTCCGGCAACATACTGACTATCCGACTGACTGCTGCAGAC<br>CACCGCCAACTGCAGCTCTCCATCAGCTCCTGTCTCCAGCAGCTTTC<br>CCTGTTGATGTGGATCACGCAGTGCTTTCTGCCCGTGTTTTTGGCTC<br>AGCCTCCCTCAGGGCAGAGGCGC | 368 |
| 1G4 epitope | TCCCTGTTGATGTGGATCACGCAGTGC | 369 |
| Luciferase | ATGGAAGATGCCAAGAACATCAAGAAAGGCCCTGCCCCCTTCTACCC<br>CCTGGAAGATGGCACAGCCGGCGAGCAGCTGCACAAGGCCATGAAGA<br>GATACGCCCTGGTGCCCGGCACCATCGCCTTCACCGACGCCCACATC<br>GAGGTGGACATCACCTACGCCGAGTATTTCGAGATGAGCGTGCGGCT<br>GGCCGAGGCCATGAAACGCTACGGCCTGAACACCAACCACCGGATCG<br>TGGTGTGCAGCGAGAACAGCCTGCAGTTCTTCATGCCCGTGCTGGGC<br>GCCCTGTTCATCGGCGTGGCCGTGGCCCCTGCCAACGACATCTACAA<br>CGAGCGGGAGCTGCTGAACAGCATGGGCATCAGCCAGCCCACCGTGG<br>TGTTCGTGAGCAAGAAGGGCCTGCAGAAAATCCTGAACGTGCAGAAG<br>AAGCTGCCCATCATCCAGAAAATCATCATCATGGACAGCAAGACCGA<br>CTACCAGGGCTTCCAGAGCATGTACACCTTCGTGACCAGCCACCTGC<br>CCCCTGGCTTCAACGAGTACGACTTCGTGCCCGAGAGCTTCGACCGG<br>GACAAGACCATCGCCCTGATCATGAACAGCAGCGGCAGCACCGGCCT<br>GCCTAAAGGCGTGGCCCTGCCTCACCGGACCGCCTGCGTGCGGTTCA<br>GCCACGCCCGGGACCCCATCTTCGGCAACCAGATCATCCCCGACACC<br>GCCATCCTGAGCGTGGTGCCCTTCCACCACGGCTTCGGCATGTTCAC<br>CACCCTGGGCTACCTGATCTGCGGCTTCCGGGTGGTGCTGATGTACC<br>GGTTCGAGGAAGAGCTGTTCCTGCGGAGCCTGCAGGACTACAAGATC<br>CAGAGCGCCCTGCTGGTGCCCACCCTGTTCAGCTTTTTCGCCAAGAG<br>CACCCTGATCGACAAGTACGACCTGAGCAACCTGCACGAGATCGCCA<br>GCGGCGGAGCCCCCCTGTCCAAAGAAGTGGGCGAAGCCGTCGCCAAG<br>CGGTTCCACCTGCCCGGCATCCGGCAGGGCTATGGCCTGACCGAGAC<br>CACAAGCGCCATTCTGATCACCCCCGAGGGCGACGACAAGCCTGGCG<br>CCGTGGGCAAGGTGGTGCCTTTCTTCGAGGCCAAGGTGGTGGACCTG<br>GACACCGGCAAGACCCTGGGCGTGAACCAGCGGGGCGAGCTGTGCGT<br>GAGGGGCCCCATGATCATGAGCGGCTACGTGAACAACCCCGAGGCCA<br>CCAACGCCCTGATTGACAAGGACGGCTGGCTGCACAGCGGCGACATC<br>GCCTACTGGGACGAGGACGAGCACTTCTTCATCGTGGACCGGCTGAA<br>GAGCCTGATCAAGTACAAGGGCTACCAGGTGGCCCCAGCCGAGCTGG<br>AAAGCATCCTGCTGCAGCACCCCAACATCTTCGATGCCGGGGTGGCC<br>GGACTGCCCGACGACGATGCCGGCGAGCTGCCTGCCGCCGTGGTGGT<br>GCTGGAACACGGCAAAACCATGACCGAGAAAGAAATCGTGGACTACG<br>TGGCCAGCCAGGTGACCACCGCCAAGAAACTGAGAGGCGGCGTGGTG<br>TTTGTGGACGAGGTGCCCAAGGGCCTGACAGGCAAGCTGGACGCCCG<br>GAAGATCCGGGAGATCCTGATCAAGGCCAAGAAGGGCGGCAAGTCCA<br>AATTGTAA | 370 |
| IRES | TCCCTCCCCCCCCCTAACGTTACTGGCCGAAGCCGCTTGGAATAAG<br>GCCGGTGTGCGTTTGTCTATATGTTATTTTCCACCATATTGCCGTCT<br>TTTGGCAATGTGAGGGCCCGGAAACCTGGCCCTGTCTTCTTGACGAG<br>CATTCCTAGGGGTCTTTCCCCTCTCGCCAAAGGAATGCAAGGTCTGT<br>TGAATGTCGTGAAGGAAGCAGTTCCTCTGGAAGCTTCTTGAAGACAA<br>ACAACGTCTGTAGCGACCCTTTGCAGGCAGCGGAACCCCCCACCTGG<br>CGACAGGTGCCTCTGCGGCCAAAAGCCACGTGTATAAGATACACCTG<br>CAAAGGCGGCACAACCCCAGTGCCACGTTGTGAGTTGGATAGTTGTG<br>GAAAGAGTCAAATGGCTCTCCTCAAGCGTATTCAACAAGGGGCTGAA<br>GGATGCCCAGAAGGTACCCCATTGTATGGGATCTGATCTGGGGCCTC<br>GGTGCACATGCTTTACATGTGTTTAGTCGAGGTTAAAAAAACGTCTA<br>GGCCCCCCGAACCACGGGGACGTGGTTTTCCTTTGAAAAACACGATG<br>ATAA | 371 |

TABLE 25-continued

NY-ESO-1 TCR/NY-ESO-1 Antigen System

| Name | Sequence | SEQ ID NO |
|---|---|---|
| NY-ESO-1 construct Signal peptide | ATGGCCACAACCATGGACGGGCCGCGCCTGCTGCTGTTGCTGCTTCT GGGGGTGTCCCTTGGAGGTGCC | 372 |
| NY-ESO-1 construct NGFR extracellular | AAGGAGGCATGCCCCACAGGCCTGTACACACACAGCGGTGAGTGCTG CAAAGCCTGCAACCTGGGCGAGGGTGTGGCCCAGCCTTGTGGAGCCA ACCAGACCGTGTGTGAGCCCTGCCTGGACAGCGTGACGTTCTCCGAC GTGGTGAGCGCGACCGAGCCGTGCAAGCCGTGCACCGAGTGCGTGGG GCTCCAGAGCATGTCGGCGCCGTGCGTGGAGGCCGACGACGCCCGTGT GCCGCTGCGCCTACGGCTACTACCAGGATGAGACGACTGGGCGCTGC GAGGCGTGCCGCGTGTGCGAGGCGGGCTCGGGCCTCGTGTTCTCCTG CCAGGACAAGCAGAACACCGTGTGCGAGGAGTGCCCCGACGGCACGT ATTCCGACGAGGCCAACCACGTGGACCCCGTGCCTGCCCTGCACCGTG TGCGAGGACACCGAGCGCCAGCTCCGCGAGTGCACACGCTGGGCCGA CGCCGAGTGCGAGGAGATCCCTGGCCGTTGGATTACACGGTCCACAC CCCCAGAGGGCTCGGACAGCACAGCCCCAGCACCCAGGAGCCTGAG GCACCTCCAGAACAAGACCTCATAGCCAGCACGGTGGCAGGTGTGGT GACCACAGTGATGGGCAGCTCCCAGCCCGTGGTGACCCGAGGCACCA CCGACAAC | 373 |
| NY-ESO-1 construct NGFR transmembrane | CTCATCCCTGTCTATTGCTCCATCCTGGCTGCTGTGGTTGTGGGCCT TGTGGCCTACATAGCCTTC | 374 |
| NY-ESO-1 construct NGFR cytoplasmic tail | AAGAGGTGGAACAGT | 375 |
| NY-ESO-1 1G4 peptide epitope | SLLMWITQC | 392 |

TABLE 26

Expression of CD161 and CLEC2D

| Name | Sequence | SEQ ID NO |
|---|---|---|
| Monovalent CD161 (KLRB1)- Fc Fusion | GCCGCCACCATGGTACCGTGCACGCTGCTCCTGCTGTTGGCGGCCGCC TGGCTCCGACTCAGACCCGCGCGCAGAAATCATCAATAGAAAAATGCAG TGTGGACATTCAACAGAGCAGGAATAAAACAACAGAGAGACCGGGTCTC TTAAACTCCCCAATATATTGGCAGCAACTCCGAGAGAAATGCTTGTTAT TTTCTCACACTGTCAACCCTTGGAATAACAGTCTAGCTGATTGTTCCAC CAAAGAATCCAGCCTGCTGCTTATTCGAGATAAGGATGAATTGATACAC ACACAGAACCTGATACGTGACAAAGCAATTCTGTTTTGGATTGGATTAA ATTTTTCATTATCAGAAAAGAACTGGAAGTGGATAAACGGCTCTTTTTT AAAATTCTAATGACTTAGAAAATTAGAGGTGATGCTAAAGAAAACAGCTGT ATTTCCATCTCACAGACATCTGTGTATTCTGAGTACTGTAGTACAGAAA TCAGATGGATCTGCCAAAAAGAACTAACACCTGTGAGAAATAAAGTGTA TCCTGACTCTGGATCAGGTTGTCCACCTTGCCCAGCACCTGAACTCCTG GGGGGACCGTCAGTCTTCCTCTTCCCCCCAAAACCCAAGGACACCCTCA TGATCTCCCGGACCCCTGAGGTCACATGCGTGGTGGTGGACGTGAGCCA CGAAGACCCTGAGGTCAAGTTCAACTGGTACGTGGACGGCGTGGAGGTG CATAATGCCAAGACAAAGCCGCGGGAGGAGCAGTACAACAGCACGTACC GTGTGGTCAGCGTCCTCACCGTCCTGCACCAGGACTGGCTGAATGGCAA GGAGTACAAGTGCAAGGTCTCCAACAAAGCCCTCCCAGCCCCCATCGAG AAAACCATCTCCAAAGCCAAAGGGCAGCCCCGAGAACCACAGGTGTACA CCCTGCCCCCATCCCGGGATGAGCTGACCAAGAACCAGGTCAGCCTGAC CTGCCTGGTCAAAGGCTTCTATCCCAGCGACATCGCCGTGGAGTGGGAG AGCAATGGGCAGCCGGAGAACAACTACAAGACCACGCCTCCCGTGCTGG ACTCCGACGGCTCCTTCTTCCTCTACAGCAAGCTCACCGTGGACAAGAG CAGGTGGCAGCAGGGGAACGTCTTCTCATGCTCCGTGATGCATGAGGCT CTGCACAACCACTACACGCAGAAGAGCCTCTCCCTGTCTCCGGGTAAAT AA | 376 |

TABLE 26-continued

Expression of CD161 and CLEC2D

| Name | Sequence | SEQ ID NO |
|---|---|---|
| CD161 (KLRB1) extracellular domain | CAGAAATCATCAATAGAAAAATGCAGTGTGGACATTCAACAGAGCAGGA ATAAAACAACAGAGAGACCGGGTCTCTTAAACTGCCCAATATATTGGCA GCAACTCCGAGAGAAATGCTTGTTATTTTCTCACACTGTCAACCCTTGG AATAACAGTCTAGCTGATTGTTCCACCAAAGAATCCAGCCTGCTGCTTA TTCGAGATAAGGATGAATTGATACACACACAGAACCTGATACGTGACAA AGCAATTCTGTTTTGGATTGGATTAAATTTTTCATTATCAGAAAAGAAC TGGAAGTGGATAAACGGCTCTTTTTTAAATTCTAATGACTTAGAAATTA GAGGTGATGCTAAAGAAAACAGCTGTATTTCCATCTCACAGACATCTGT GTATTCTGAGTACTGTAGTACAGAAATCAGATGGATCTGCCAAAAAGAA CTAACACCTGTGAGAAATAAAGTGTATCCTGACTCT | 377 |
| Flexible linker | GGATCAGGT | 378 |
| Human IgG1 heavy chain hinge and Fc region | TGTCCACCTTGCCCAGCACCTGAACTCCTGGGGGGACCGTCAGTCTTCC TCTTCCCCCCAAAACCCAAGGACACCCTCATGATCTCCCGGACCCCTGA GGTCACATCGTGTGTGACGTGAGCCACGAAGACCCTGAGGTCAAG TTCAACTGTACGTGACGGCGTGAGGTCATAATCCAAGACAAAGC CGCGGGAGGAGCAGTACAACAGCACGTACCGTGTGGTCAGCGTCCTCAC CGTCCTGCACCAGGACTGGCTGAATGGCAAGGAGTACAAGTGCAAGGTC TCCAACAAAGCCCTCCCAGCCCCCATCGAGAAAACCATCTCCAAAGCCA AAGGGCAGCCCCGAGAACCACAGGTGTACACCCTGCCCCCATCCCGGGA TGAGCTGACCAAGAACCAGGTCAGCCTGACCTGCCTGGTCAAAGGCTTC TATCCCAGCGACATCGCCGTGGAGTGGGAGAGCAATGGGCAGCCGGAGA ACAACTACAAGACCACGCCTCCCGTGCTGGACTCCGACGGCTCCTTCTT CCTCTACAGCAAGCTCACCGTGGACAAGAGCAGGTGGCAGCAGGGGAAC GTCTTCTCATGCTCCGTGATGCATGAGGCTCTGCACAACCACTACACGC AGAAGAGCCTCTCCCTGTCTCCGGGTAAA | 379 |
| Monovalent CD161 (KLRB1)- Fc Fusion, substitution of free cysteine to serine (C29S, sequence variation in bold underline) | GCCGCCACCATGGTACCGTGCACGCTGCTCCTGCTGTTGGCGGCCGCCC TGGCTCCGACTCAGACCCGCGCGCAGAAATCATCAATAGAAAAATCCAG TGTGGACATTCAACAGAGCAGGAATAAAACAACAGAGAGACCGGGTCTC TTAAACTGCCCAATATATTGGCAGCAACTCCGAGAGAAATGCTTGTTAT TTTCTCACACTGTCAACCCTTGGAATAACAGTCTAGCTGATTGTTCCAC CAAAGAATCCAGCCTGCTGCTTATTCGAGATAAGGATGAATTGATACAC ACACAGAACCTGATACGTGACAAAGCAATTCTGTTTTGGATTGGATTAA ATTTTTCATTATCAGAAAAGAACTGGAAGTGGATAAACGGCTCTTTTTT AAATTCTAATGACTTAGAAATTAGAGGTGATGCTAAAGAAAACAGCTGT ATTTCCATCTCACAGACATCTGTGTATTCTGAGTACTGTAGTACAGAAA TCAGATGGATCTGCCAAAAAGAACTAACACCTGTGAGAAATAAAGTGTA TCCTGACTCTGGATCAGGTTGTCCACCTTGCCCAGCACCTGAACTCCTG GGGGGACCGTCAGTCTTCCTCTTCCCCCCAAAACCCAAGGACACCCTCA TGATCTCCCGGACCCCTGAGGTCACATGCGTGGTGGTGGACGTGAGCCA CGAAGACCCTGAGGTCAAGTTCAACTGGTACGTGGACGGCGTGGAGGTG CATAATGCCAAGACAAAGCCGCGGGAGGAGCAGTACAACAGCACGTACC GTGTGGTCAGCGTCCTCACCGTCCTGCACCAGGACTGGCTGAATGGCAA GGAGTACAAGTGCAAGGTCTCCAACAAAGCCCTCCCAGCCCCCATCGAG AAAACCATCTCCAAAGCCAAAGGGCAGCCCCGAGAACCACAGGTGTACA CCCTGCCCCCATCCCGGGATGAGCTGACCAAGAACCAGGTCAGCCTGAC CTGCCTGGTCAAAGGCTTCTATCCCAGCGACATCGCCGTGGAGTGGGAG AGCAATGGGCAGCCGGAGAACAACTACAAGACCACGCCTCCCGTGCTGG ACTCCGACGGCTCCTTCTTCCTCTACAGCAAGCTCACCGTGGACAAGAG CAGGTGGCAGCAGGGGAACGTCTTCTCATGCTCCGTGATGCATGAGGCT CTGCACAACCACTACACGCAGAAGAGCCTCTCCCTGTCTCCGGGTAAAT AA | 380 |
| Extracellular domain human CD161 (KLRB1) (C29S) | CAGAAATCATCAATAGAAAAATCCAGTGTGGACATTCAACAGAGCAGGA ATAAAACAACAGAGAGACCGGGTCTCTTAAACTGCCCAATATATTGGCA GCAACTCCGAGAGAAATGCTTGTTATTTTCTCACACTGTCAACCCTTGG AATAACAGTCTAGCTGATTGTTCCACCAAAGAATCCAGCCTGCTGCTTA TTCGAGATAAGGATGAATTGATACACACACAGAACCTGATACGTGACAA AGCAATTCTGTTTTGGATTGGATTAAATTTTTCATTATCAGAAAAGAAC TGGAAGTGGATAAACGGCTCTTTTTTAAATTCTAATGACTTAGAAATTA GAGGTGATGCTAAAGAAAACAGCTGTATTTCCATCTCACAGACATCTGT GTATTCTGAGTACTGTAGTACAGAAATCAGATGGATCTGCCAAAAAGAA CTAACACCTGTGAGAAATAAAGTGTATCCTGACTCT | 381 |
| Full-length human CD161 (KLRB1) | GCCGCCACCATGGATCAACAGGCCATTTATGCCGAACTCAATCTTCCAA CGGATTCTGGCCCGGAGAGTTCTAGCCCCTCCAGCCTGCCCGCGAGATGT ATGTCAAGGTAGCCCTTGGCATCAGTTTGCACTCAAACTTAGTTGCGCA GGAATTATACTGCTCGTCTTGTCGTAACCGGGTTGAGCGTATCAGTGA CTAGTTTGATCCAGAAATCTAGTATAGAGAAGTGTTCTGTAGACATCCA ACAAAGTAGAAATAAAACAACTGAACGGCCTGGCCTGCTTAATTGTCCG ATTTATTGGCAGCAGCTCCGCGAGAAATGCCTCCTTTTCAGTCATACCG | 382 |

TABLE 26-continued

Expression of CD161 and CLEC2D

| Name | Sequence | SEQ ID NO |
|---|---|---|
| | TTAATCCTTGGAATAACAGTCTCGCCGATTGTTCCACAAAAGAAAGCTC<br>TCTTCTGCTTATCCGCGATAAGGACGAACTGATTCACACTCAAAATCTC<br>ATCCGGGACAAGGCAATTCTCTTCTGGATTGGACTTAATTTTAGCCTGT<br>CCGAGAAGAATTCGGAAATGGATCAACGGTTCATTTCTCAACTCTAACGA<br>CCTTGAGATTCGCGGGGATGCTAAAGAAAATTCCTGCATCTCTATAAGC<br>CAGACGAGCGTGTATTCTGAGTATTGCAGCACGGAAATTCGCTGGATAT<br>GCCAAAAAGAATTGACACCAGTTCGAAATAAGGTCTACCCGGACTCCTG<br>A | |
| Human CD161<br>(KLRB1)<br>cytoplasmic<br>domain | ATGGATCAACAGGCCATTTATGCCGAACTCAATCTTCCAACGGATTCTG<br>GCCCGGAGAGTTCTAGCCCCTCCAGCCTGCCGCGAGATGTATGTCAAGG<br>TAGCCCTTGGCATCAGTTTGCACTCAAACTTAGTTGC | 383 |
| Human CD161<br>(KLRB1)<br>transmembrane<br>region | GCAGGAATTATACTGCTCGTGCTTGTCGTAACCGGGTTGAGCGTATCAG<br>TGACTAGTTTGATC | 384 |
| Human CD161<br>(KLRB1)<br>Extracellular<br>domain | CAGAAATCTAGTATAGAGAAGTGTTCTGTAGACATCCAACAAAGTAGAA<br>ATAAAACAACTGAACGGCCTGGCCTGCTTAATTGTCCGATTTATTGGCA<br>GCAGCTCCGCGAGAAATGCCTCCTTTTCAGTCATACCGTTAATCCTTGG<br>AATAACAGTCTCGCCGATTGTTCCACAAAAGAAAGCTCTCTTCTGCTTA<br>TCCGCGATAAGGACGAACTGATTCACACTCAAAATCTCATCCGGGACAA<br>GGCAATTCTCTTCTGGATTGGACTTAATTTTAGCCTGTCCGAGAAGAAT<br>TGGAAATGGATCAACGGTTCATTTCTCAACTCTAACGACCTTGAGATTC<br>GCGGGGATGCTAAAGAAAATTCCTGCATCTCTATAAGCCAGACGAGCGT<br>GTATTCTGAGTATTGCAGCACGGAAATTCGCTGGATATGCCAAAAAGAA<br>TTGACACCAGTTCGAAATAAGGTCTACCCGGACTCC | 385 |
| Bivalent human<br>CLEC2D-Fc<br>Fusion | GCCGCCACCATGGTACCGTGCACGCTGCTCCTGCTGTTGGCGGCCGCC<br>TGGCTCCGACTCAGACCCGCGCGAGAGCTAACTGCCATCAAGAGCCATC<br>AGTATGTCTTCAAGCTGCATGCCCAGAAAGCTGGATTGGTTTTCAAGA<br>AAGTGTTTCTATTTTTCTGATGACACCAAGAACTGGACATCAAGTCAGA<br>GGTTTTGTGACTCACAAGATGCTGATCTTGCTCAGGTTGAAAGCTTCCA<br>GGAACTGAATTTCCTGTTGAGATATAAAGGCCCATCTGATCACTGGATT<br>GGGCTGAGCAGAGAACAAGGCCAACCATGGAAATGGATAAATGGTACTG<br>AATGGACAAGACAGTTTCCTATCCTGGGAGCAGGAGAGTGTGCCTATTT<br>GAATGACAAAGGTGCCAGTAGTGCCAGGCACTACACAGAGAGGAAGTGG<br>ATTTGTTCCAAATCAGATATACATGTCGGATCAGGCAGCGGAAGAGCGA<br>ATTGCCATCAGGAGCCATCCGTCTGCCTTCAGGCCGCCTGCCCGGAGTC<br>CTGGATAGGGTTCCAACGCAAGTGTTTTTACTTCAGTGACGACACTAAA<br>AATTGGACATCTTCACAGAGATTTTGTGATTCACAGGACGCTGACCTGG<br>CGCAAGTCGAGTCATTTCAGGAACTTAACTTTCTCCTTCGGTACAAAGG<br>GCCTTCTGACCATTGGATTGGTCTTAGTCGCGAACAGGGGCAACCTTGG<br>AAGTGGATCAATGGAACCGAGTGGACTCGGCAGTTTCCAATACTGGGGG<br>CCGGGGAATGTGCGTATCTTAACGACAAGGGTGCCTCATCAGCCCGCCA<br>CTACACTGAGAGAAATGGATCTGCAGTAAATCCGACATCCACGTGGGG<br>AGCGGTTGCCCGCCTTGCCCGGCCCCAGAGCTGCTCGGCGGTCCGTCCG<br>TATTCCTGTTCCCACCTAAGCCTAAAGATACGTTGATGATTAGCAGAAC<br>TCCTGAAGTAACCTGTGTAGTGGTAGACGTCTCTCACGAGGACCCCGAA<br>GTAAAGTTTAACTGGTACGTAGATGGTGTCGAAGTCCACAACGCTAAGA<br>CCAAACCAAGGGAGGAGCAATATAACTCTACCTATCGAGTAGTTTCCGT<br>ATTGACGGTGCTGCATCAAGACTGGCTGAACGGAAAGGAATATAAATGC<br>AAGGTCTCCAATAAAGCGTTGCCTGCTCCGATTGAAAAGACGATATCAA<br>AAGCAAAGGGGCAGCCGAGAGAACCTCAAGTATATACTCTCCCTCCGTC<br>CCGCGATGAACTGACTAAAAATCAGGTATCACTGACATGTTTGGTCAAA<br>GGGTTCTATCCCTCCGATATTGCTGTCGAGTGGGAATCAAATGGTCAGC<br>CAGAAAAACAACTACAAGACCACTCCACCTGTCCTGGATTCAGATGGTTC<br>ATTCTTTCTGTACTCAAAATTGACCGTCGATAAGTCACGATGGCAGCAA<br>GGGAATGTATTCAGTTGCTCCGTCATGCACGAAGCACTGCACAATCATT<br>ACACCCAGAAAAGTCTTTCATTGTCACCCGGTAAATAA | 386 |
| Human<br>extracellular<br>domain CLEC2D<br>copy 1 | AGAGCTAACTGCCATCAAGAGCCATCAGTATGTCTTCAAGCTGCATGCC<br>CAGAAAGCTGGATTGGTTTTCAAAGAAAGTGTTTCTATTTTTCTGATGA<br>CACCAAGAACTGGACATCAAGTCAGAGGTTTTGTGACTCACAAGATGCT<br>GATCTTGCTCAGGTTGAAAGCTTCCAGGAACTGAATTTCCTGTTGAGAT<br>ATAAAGGCCCATCTGATCACTGGATTGGGCTGAGCAGAGAACAAGGCCA<br>ACCATGGAAATGGATAAATGGTACTGAATGGACAAGACAGTTTCCTATC<br>CTGGGAGCAGGAGAGTGTGCCTATTTGAATGACAAAGGTGCCAGTAGTG<br>CCAGGCACTACACAGAGAGGAAGTGGATTTGTTCCAAATCAGATATACA<br>TGTC | 387 |

TABLE 26-continued

Expression of CD161 and CLEC2D

| Name | Sequence | SEQ ID NO |
|---|---|---|
| Flexible GSG linker | GGATCAGGCAGCGGA | 388 |
| Human extracellular domain CLEC2D copy 2 | AGAGCGAATTGCCATCAGGAGCCATCCGTCTGCCTTCAGGCCGCCTGCCCGGAGTCCTGGATAGGGTTCCAACGCAAGTGTTTTTACTTCAGTGACGACACTAAAAATTGGACATCTTCACAGAGATTTTGTGATTCACAGGACGCTGACCTGGCGCAAGTCGAGTCATTTCAGGAACTTAACTTTCTCCTTCGGTACAAAGGGCCTTCTGACCATTGGATTGGTCTTAGTCGCGAACAGGGGCAACCTTGGAAGTGGATCAATGGAACCGAGTGGACTCGGCAGTTTCCAATACTGGGGGCCGGGGAATGTGCGTATCTTAACGACAAGGGTGCCTCATCAGCCCGCCACTACACTGAGAGAAAATGGATCTGCAGTAAATCCGACATCCACGTG | 389 |
| Flexible linker | GGGAGCGGT | 390 |
| Human IgG1 Fc (used in bivalent CLEC2D-Fc construct) | TGCCCGCCTTGCCCGGCCCCAGAGCTGCTCGGCGGTCCGTCCGTATTCCTGTTCCCACCTAAGCCTAAAGATACGTTGATGATTAGCAGAACTCCTGAAGTAACCTGTGTAGTGGTAGACGTCTCTCACGAGGACCCCGAAGTAAAGTTTAACTGGTACGTAGATGGTGTCGAAGTCCACAACGCTAAGACCAAACCAAGGGAGGAGCAATATAACTCTACCTATCGAGTAGTTTCCGTATTGACGGTGCTGCATCAAGACTGGCTGAACGGAAAGGAATATAAATGCAAGGTCTCCAATAAAGCGTTGCCTGCTCCGATTGAAAAGACGATATCAAAAGCAAAGGGGCAGCCGAGAGAACCTCAAGTATATACTCTCCCTCCGTCCCGCGATGAACTGACTAAAAATCAGGTATCACTGACATGTTTGGTCAAAGGGTTCTATCCCTCCGATATTGCTGTCGAGTGGGAATCAAATGGTCAGCCAGAAACAACTACAAGACCACTCCACCTGTCCTGGATTCAGATGGTTCATTCTTTCTGTACTCAAAATTGACCGTCGATAAGTCACGATGGCAGCAAGGGAATGTATTCAGTTGCTCCGTCATGCACGAAGCACTGCACAATCATTACACCCAGAAAAGTCTTTCATTGTCACCCGGTAAA | 391 |

What is claimed is:

1. An isolated human monoclonal antibody, or antigen-binding portion thereof, that specifically binds human CD161, comprising heavy and light chain CDRs selected from:

(a) heavy chain CDR1, CDR2, and CDR3 comprising amino acid sequences set forth in SEQ ID NOs: 127, 132, and 141 respectively, and light chain CDR1, CDR2, and CDR3 comprising amino acid sequences set forth in SEQ ID NOs: 273, 279, and 281 respectively;

(b) heavy chain CDR1, CDR2, and CDR3 comprising amino acid sequences set forth in SEQ ID NOs: 127, 132, and 141 respectively, and light chain CDR1, CDR2, and CDR3 comprising amino acid sequences set forth in SEQ ID NOs: 273, 279, and 282 respectively;

(c) heavy chain CDR1, CDR2, and CDR3 comprising amino acid sequences set forth in SEQ ID NOs: 127, 132, and 141 respectively, and light chain CDR1, CDR2, and CDR3 comprising amino acid sequences set forth in SEQ ID NOs: 273, 279, and 283 respectively;

(d) heavy chain CDR1, CDR2, and CDR3 comprising amino acid sequences set forth in SEQ ID NOs: 127, 132, and 141 respectively, and light chain CDR1, CDR2, and CDR3 comprising amino acid sequences set forth in SEQ ID NOs: 273, 279, and 284 respectively;

(e) heavy chain CDR1, CDR2, and CDR3 comprising amino acid sequences set forth in SEQ ID NOs: 127, 132, and 142 respectively, and light chain CDR1, CDR2, and CDR3 comprising amino acid sequences set forth in SEQ ID NOs: 273, 279, and 281 respectively;

(f) heavy chain CDR1, CDR2, and CDR3 comprising amino acid sequences set forth in SEQ ID NOs: 128, 132, and 141 respectively, and light chain CDR1, CDR2, and CDR3 comprising amino acid sequences set forth in SEQ ID NOs: 273, 279, and 283 respectively;

(g) heavy chain CDR1, CDR2, and CDR3 comprising amino acid sequences set forth in SEQ ID NOs: 129, 132, and 141 respectively, and light chain CDR1, CDR2, and CDR3 comprising amino acid sequences set forth in SEQ ID NOs: 273, 279, and 283 respectively;

(h) heavy chain CDR1, CDR2, and CDR3 comprising amino acid sequences set forth in SEQ ID NOs: 127, 132, and 143 respectively, and light chain CDR1, CDR2, and CDR3 comprising amino acid sequences set forth in SEQ ID NOs: 273, 279, and 281 respectively;

(i) heavy chain CDR1, CDR2, and CDR3 comprising amino acid sequences set forth in SEQ ID NOs: 127, 132, and 143 respectively, and light chain CDR1, CDR2, and CDR3 comprising amino acid sequences set forth in SEQ ID NOs: 273, 279, and 283 respectively;

(j) heavy chain CDR1, CDR2, and CDR3 comprising amino acid sequences set forth in SEQ ID NOs: 127, 133, and 143 respectively, and light chain CDR1, CDR2, and CDR3 comprising amino acid sequences set forth in SEQ ID NOs: 273, 279, and 283 respectively;

(k) heavy chain CDR1, CDR2, and CDR3 comprising amino acid sequences set forth in SEQ ID NOs: 129, 132, and 143 respectively, and light chain CDR1, CDR2, and CDR3 comprising amino acid sequences set forth in SEQ ID NOs: 273, 279, and 283 respectively;

(l) heavy chain CDR1, CDR2, and CDR3 comprising amino acid sequences set forth in SEQ ID NOs: 127, 132, and 144 respectively, and light chain CDR1, CDR2, and CDR3 comprising amino acid sequences set forth in SEQ ID NOs: 273, 279, and 281 respectively;

(m) heavy chain CDR1, CDR2, and CDR3 comprising amino acid sequences set forth in SEQ ID NOs: 127, 132, and 145 respectively, and light chain CDR1, CDR2, and CDR3 comprising amino acid sequences set forth in SEQ ID NOs: 273, 279, and 281 respectively;

(n) heavy chain CDR1, CDR2, and CDR3 comprising amino acid sequences set forth in SEQ ID NOs: 127, 132, and 145 respectively, and light chain CDR1, CDR2, and CDR3 comprising amino acid sequences set forth in SEQ ID NOs: 273, 279, and 285 respectively;

(o) heavy chain CDR1, CDR2, and CDR3 comprising amino acid sequences set forth in SEQ ID NOs: 127, 132, and 145 respectively, and light chain CDR1, CDR2, and CDR3 comprising amino acid sequences set forth in SEQ ID NOs: 274, 279, and 281 respectively;

(p) heavy chain CDR1, CDR2, and CDR3 comprising amino acid sequences set forth in SEQ ID NOs: 127, 132, and 145 respectively, and light chain CDR1, CDR2, and CDR3 comprising amino acid sequences set forth in SEQ ID NOs: 275, 279, and 285 respectively;

(q) heavy chain CDR1, CDR2, and CDR3 comprising amino acid sequences set forth in SEQ ID NOs: 127, 134, and 146 respectively, and light chain CDR1, CDR2, and CDR3 comprising amino acid sequences set forth in SEQ ID NOs: 273, 279, and 281 respectively;

(r) heavy chain CDR1, CDR2, and CDR3 comprising amino acid sequences set forth in SEQ ID NOs: 127, 134, and 146 respectively, and light chain CDR1, CDR2, and CDR3 comprising amino acid sequences set forth in SEQ ID NOs: 275, 279, and 281 respectively;

(s) heavy chain CDR1, CDR2, and CDR3 comprising amino acid sequences set forth in SEQ ID NOs: 127, 132, and 147 respectively, and light chain CDR1, CDR2, and CDR3 comprising amino acid sequences set forth in SEQ ID NOs: 277, 280, and 289 respectively;

(t) heavy chain CDR1, CDR2, and CDR3 comprising amino acid sequences set forth in SEQ ID NOs: 127, 132, and 148 respectively, and light chain CDR1, CDR2, and CDR3 comprising amino acid sequences set forth in SEQ ID NOs: 277, 280, and 289 respectively;

(u) heavy chain CDR1, CDR2, and CDR3 comprising amino acid sequences set forth in SEQ ID NOs: 127, 132, and 148 respectively, and light chain CDR1, CDR2, and CDR3 comprising amino acid sequences set forth in SEQ ID NOs: 277, 280, and 290 respectively;

(v) heavy chain CDR1, CDR2, and CDR3 comprising amino acid sequences set forth in SEQ ID NOs: 127, 132, and 149 respectively, and light chain CDR1, CDR2, and CDR3 comprising amino acid sequences set forth in SEQ ID NOs: 277, 280, and 289 respectively;

(w) heavy chain CDR1, CDR2, and CDR3 comprising amino acid sequences set forth in SEQ ID NOs: 127, 132, and 149 respectively, and light chain CDR1, CDR2, and CDR3 comprising amino acid sequences set forth in SEQ ID NOs: 277, 280, and 290 respectively;

(x) heavy chain CDR1, CDR2, and CDR3 comprising amino acid sequences set forth in SEQ ID NOs: 127, 132, and 149 respectively, and light chain CDR1, CDR2, and CDR3 comprising amino acid sequences set forth in SEQ ID NOs: 277, 280, and 291 respectively;

(y) heavy chain CDR1, CDR2, and CDR3 comprising amino acid sequences set forth in SEQ ID NOs: 127, 132, and 149 respectively, and light chain CDR1, CDR2, and CDR3 comprising amino acid sequences set forth in SEQ ID NOs: 277, 280, and 292 respectively;

(z) heavy chain CDR1, CDR2, and CDR3 comprising amino acid sequences set forth in SEQ ID NOs: 127, 132, and 149 respectively, and light chain CDR1, CDR2, and CDR3 comprising amino acid sequences set forth in SEQ ID NOs: 278, 280, and 289 respectively;

(aa) heavy chain CDR1, CDR2, and CDR3 comprising amino acid sequences set forth in SEQ ID NOs: 127, 135, and 149 respectively, and light chain CDR1, CDR2, and CDR3 comprising amino acid sequences set forth in SEQ ID NOs: 277, 280, and 289 respectively;

(bb) heavy chain CDR1, CDR2, and CDR3 comprising amino acid sequences set forth in SEQ ID NOs: 127, 136, and 149 respectively, and light chain CDR1, CDR2, and CDR3 comprising amino acid sequences set forth in SEQ ID NOs: 277, 280, and 291 respectively;

(cc) heavy chain CDR1, CDR2, and CDR3 comprising amino acid sequences set forth in SEQ ID NOs: 127, 136, and 149 respectively, and light chain CDR1, CDR2, and CDR3 comprising amino acid sequences set forth in SEQ ID NOs: 277, 280, and 292 respectively;

(dd) heavy chain CDR1, CDR2, and CDR3 comprising amino acid sequences set forth in SEQ ID NOs: 127, 136, and 149 respectively, and light chain CDR1, CDR2, and CDR3 comprising amino acid sequences set forth in SEQ ID NOs: 277, 280, and 293 respectively;

(ee) heavy chain CDR1, CDR2, and CDR3 comprising amino acid sequences set forth in SEQ ID NOs: 127, 136, and 149 respectively, and light chain CDR1, CDR2, and CDR3 comprising amino acid sequences set forth in SEQ ID NOs: 277, 280, and 294 respectively;

(ff) heavy chain CDR1, CDR2, and CDR3 comprising amino acid sequences set forth in SEQ ID NOs: 130, 132, and 149 respectively, and light chain CDR1, CDR2, and CDR3 comprising amino acid sequences set forth in SEQ ID NOs: 277, 280, and 290 respectively;

(gg) heavy chain CDR1, CDR2, and CDR3 comprising amino acid sequences set forth in SEQ ID NOs: 127, 132, and 150 respectively, and light chain CDR1, CDR2, and CDR3 comprising amino acid sequences set forth in SEQ ID NOs: 273, 279, and 281 respectively;

(hh) heavy chain CDR1, CDR2, and CDR3 comprising amino acid sequences set forth in SEQ ID NOs: 127, 132, and 150 respectively, and light chain CDR1, CDR2, and CDR3 comprising amino acid sequences set forth in SEQ ID NOs: 275, 279, and 286 respectively;

(ii) heavy chain CDR1, CDR2, and CDR3 comprising amino acid sequences set forth in SEQ ID NOs: 127, 132, and 151 respectively, and light chain CDR1, CDR2, and CDR3 comprising amino acid sequences set forth in SEQ ID NOs: 273, 279, and 286 respectively;

(jj) heavy chain CDR1, CDR2, and CDR3 comprising amino acid sequences set forth in SEQ ID NOs: 127, 137, and 150 respectively, and light chain CDR1, CDR2, and CDR3 comprising amino acid sequences set forth in SEQ ID NOs: 273, 279, and 281 respectively;

(kk) heavy chain CDR1, CDR2, and CDR3 comprising amino acid sequences set forth in SEQ ID NOs: 127, 138, and 150 respectively, and light chain CDR1, CDR2, and CDR3 comprising amino acid sequences set forth in SEQ ID NOs: 273, 279, and 281 respectively;

(ll) heavy chain CDR1, CDR2, and CDR3 comprising amino acid sequences set forth in SEQ ID NOs: 127, 138, and 150 respectively, and light chain CDR1, CDR2, and CDR3 comprising amino acid sequences set forth in SEQ ID NOs: 273, 279, and 286 respectively;

(mm) heavy chain CDR1, CDR2, and CDR3 comprising amino acid sequences set forth in SEQ ID NOs: 127, 138, and 150 respectively, and light chain CDR1, CDR2, and CDR3 comprising amino acid sequences set forth in SEQ ID NOs: 276, 279, and 281 respectively;

(nn) heavy chain CDR1, CDR2, and CDR3 comprising amino acid sequences set forth in SEQ ID NOs: 127, 138, and 151 respectively, and light chain CDR1, CDR2, and CDR3 comprising amino acid sequences set forth in SEQ ID NOs: 273, 279, and 286 respectively;

(oo) heavy chain CDR1, CDR2, and CDR3 comprising amino acid sequences set forth in SEQ ID NOs: 127, 138, and 151 respectively, and light chain CDR1, CDR2, and CDR3 comprising amino acid sequences set forth in SEQ ID NOs: 273, 279, and 287 respectively;

(pp) heavy chain CDR1, CDR2, and CDR3 comprising amino acid sequences set forth in SEQ ID NOs: 127, 138, and 151 respectively, and light chain CDR1, CDR2, and CDR3 comprising amino acid sequences set forth in SEQ ID NOs: 273, 279, and 288 respectively;

(qq) heavy chain CDR1, CDR2, and CDR3 comprising amino acid sequences set forth in SEQ ID NOs: 127, 138, and 151 respectively, and light chain CDR1, CDR2, and CDR3 comprising amino acid sequences set forth in SEQ ID NOs: 275, 279, and 286 respectively;

(rr) heavy chain CDR1, CDR2, and CDR3 comprising amino acid sequences set forth in SEQ ID NOs: 127, 140, and 151 respectively, and light chain CDR1, CDR2, and CDR3 comprising amino acid sequences set forth in SEQ ID NOs: 273, 279, and 286 respectively;

(ss) heavy chain CDR1, CDR2, and CDR3 comprising amino acid sequences set forth in SEQ ID NOs: 131, 132, and 151 respectively, and light chain CDR1, CDR2, and CDR3 comprising amino acid sequences set forth in SEQ ID NOs: 273, 279, and 281 respectively;

(tt) heavy chain CDR1, CDR2, and CDR3 comprising amino acid sequences set forth in SEQ ID NOs: 131, 132, and 150 respectively, and light chain CDR1, CDR2, and CDR3 comprising amino acid sequences set forth in SEQ ID NOs: 273, 279, and 281 respectively; and (uu) heavy chain CDR1, CDR2, and CDR3 comprising amino acid sequences set forth in SEQ ID NOs: 131, 139, and 151 respectively, and light chain CDR1, CDR2, and CDR3 comprising amino acid sequences set forth in SEQ ID NOs: 273, 279, and 286 respectively.

2. The isolated human monoclonal antibody or antigen-binding portion thereof of claim 1, comprising the amino acid sequences set forth in SEQ ID NOs: 117 and 235 respectively.

3. The isolated human monoclonal antibody or antigen-binding portion thereof of claim 1, wherein the heavy and light chain variable regions comprise the amino acid sequences set forth in SEQ ID NOs: 41 and 190 respectively.

4. The isolated human monoclonal antibody or antigen-binding portion thereof of claim 1, wherein the heavy and light chain variable regions comprise the amino acid sequences set forth in SEQ ID NOs: 8 and 167 respectively.

5. The isolated human monoclonal antibody, or antigen-binding portion thereof, of claim 1, comprising heavy and light chain variable regions, wherein the heavy and light chain variable regions comprise amino acid sequences which are at least 90% identical to the amino acid sequences selected from:

(a) SEQ ID NOs: 1 and 152, respectively;
(b) SEQ ID NOs: 1 and 155, respectively;
(c) SEQ ID NOs: 1 and 157, respectively;
(d) SEQ ID NOs: 4 and 152, respectively;
(e) SEQ ID NOs: 6 and 152, respectively;
(f) SEQ ID NOs: 8 and 157, respectively;
(g) SEQ ID NOs: 8 and 167, respectively;

(h) SEQ ID NOs: 11 and 160, respectively;
(i) SEQ ID NOs: 13 and 162, respectively;
(j) SEQ ID NOs: 15 and 165, respectively;
(k) SEQ ID NOs: 15 and 171, respectively;
(l) SEQ ID NOs: 15 and 173, respectively;
(m) SEQ ID NOs: 18 and 169, respectively;
(n) SEQ ID NOs: 20 and 295, respectively;
(o) SEQ ID NOs: 22 and 152, respectively;
(p) SEQ ID NOs: 22 and 160, respectively;
(q) SEQ ID NOs: 22 and 162, respectively;
(r) SEQ ID NOs: 22 and 175, respectively;
(s) SEQ ID NOs: 22 and 179, respectively;
(t) SEQ ID NOs: 22 and 183, respectively;
(u) SEQ ID NOs: 22 and 185, respectively;
(v) SEQ ID NOs: 29 and 177, respectively;
(w) SEQ ID NOs: 31 and 181, respectively;
(x) SEQ ID NOs: 33 and 160, respectively;
(y) SEQ ID NOs: 35 and 187, respectively;
(z) SEQ ID NOs: 37 and 187, respectively;
(aa) SEQ ID NOs: 39 and 160, respectively;
(bb) SEQ ID NOs: 41 and 190, respectively;
(cc) SEQ ID NOs: 43 and 152, respectively;
(dd) SEQ ID NOs: 43 and 192, respectively;
(ee) SEQ ID NOs: 45 and 194, respectively;
(ff) SEQ ID NOs: 47 and 152, respectively;
(gg) SEQ ID NOs: 47 and 202, respectively;
(hh) SEQ ID NOs: 50 and 196, respectively;
(ii) SEQ ID NOs: 52 and 152, respectively;
(jj) SEQ ID NOs: 52 and 208, respectively;
(kk) SEQ ID NOs: 54 and 196, respectively;
(ll) SEQ ID NOs: 56 and 199, respectively;
(mm) SEQ ID NOs: 56 and 206, respectively;
(nn) SEQ ID NOs: 59 and 204, respectively;
(oo) SEQ ID NOs: 61 and 245, respectively;
(pp) SEQ ID NOs: 66 and 258, respectively;
(qq) SEQ ID NOs: 63 and 250, respectively;
(rr) SEQ ID NOs: 63 and 245, respectively;
(ss) SEQ ID NOs: 66 and 248, respectively;
(tt) SEQ ID NOs: 70 and 252, respectively;
(uu) SEQ ID NOs: 68 and 245, respectively;
(vv) SEQ ID NOs: 66 and 250, respectively;
(ww) SEQ ID NOs: 66 and 254, respectively;
(xx) SEQ ID NOs: 72 and 256, respectively;
(yy) SEQ ID NOs: 74 and 260, respectively;
(zz) SEQ ID NOs: 76 and 297, respectively;
(aaa) SEQ ID NOs: 78 and 262, respectively;
(bbb) SEQ ID NOs: 78 and 267, respectively;
(ccc) SEQ ID NOs: 78 and 269, respectively;
(ddd) SEQ ID NOs: 80 and 264, respectively;
(eee) SEQ ID NOs: 82 and 271, respectively;
(fff) SEQ ID NOs: 84 and 264, respectively;
(ggg) SEQ ID NOs: 86 and 254, respectively;
(hhh) SEQ ID NOs: 88 and 152, respectively;
(iii) SEQ ID NOs: 90 and 210, respectively;
(jjj) SEQ ID NOs: 92 and 212, respectively;
(kkk) SEQ ID NOs: 94 and 215, respectively;
(lll) SEQ ID NOs: 94 and 217, respectively;
(mmm) SEQ ID NOs: 96 and 152, respectively;
(nnn) SEQ ID NOs: 98 and 230, respectively;
(ooo) SEQ ID NOs: 98 and 152, respectively;
(ppp) SEQ ID NOs: 101 and 219, respectively;
(qqq) SEQ ID NOs: 103 and 221, respectively;
(rrr) SEQ ID NOs: 105 and 225, respectively;
(sss) SEQ ID NOs: 105 and 223, respectively;
(ttt) SEQ ID NOs: 107 and 225, respectively;
(uuu) SEQ ID NOs: 109 and 212, respectively;
(vvv) SEQ ID NOs: 111 and 230, respectively;
(www) SEQ ID NOs: 113 and 228, respectively;
(xxx) SEQ ID NOs: 113 and 212, respectively;
(yyy) SEQ ID NOs: 113 and 225, respectively;
(zzz) SEQ ID NOs: 113 and 239, respectively;
(aaaa) SEQ ID NOs: 113 and 243, respectively;
(bbbb) SEQ ID NOs: 115 and 233, respectively;
(cccc) SEQ ID NOs: 117 and 235, respectively;
(dddd) SEQ ID NOs: 119 and 237, respectively;
(eeee) SEQ ID NOs: 121 and 219, respectively;
(ffff) SEQ ID NOs: 123 and 225, respectively; and
(gggg) SEQ ID NOs: 125 and 241, respectively.

6. The isolated human monoclonal antibody, or antigen-binding portion thereof, of claim 1, comprising heavy chain CDR1, CDR2, and CDR3 comprising amino acid sequences set forth in SEQ ID NOs: 127, 133, and 143 respectively, and light chain CDR1, CDR2, and CDR3 comprising amino acid sequences set forth in SEQ ID NOs: 273, 279, and 283 respectively.

7. The isolated human monoclonal antibody, or antigen-binding portion thereof, of claim 1, comprising heavy chain CDR1, CDR2, and CDR3 comprising amino acid sequences set forth in SEQ ID NOs: 127, 138, and 151 respectively, and light chain CDR1, CDR2, and CDR3 comprising amino acid sequences set forth in SEQ ID NOs: 273, 279, and 287 respectively.

8. The isolated human monoclonal antibody, or antigen-binding portion thereof, of claim 1, comprising heavy chain CDR1, CDR2, and CDR3 comprising amino acid sequences set forth in SEQ ID NOs: 127, 132, and 141 respectively, and light chain CDR1, CDR2, and CDR3 comprising amino acid sequences set forth in SEQ ID NOs: 273, 279, and 284 respectively.

9. The isolated human monoclonal antibody, or antigen-binding portion thereof, of claim 1, comprising heavy and light chain variable regions, wherein the heavy and light chain variable regions comprise amino acid sequences which are at least 90% identical to the amino acid sequences selected from:
(a) SEQ ID NOs: 41 and 190, respectively;
(b) SEQ ID NOs: 117 and 235, respectively; and
(c) SEQ ID NOs: 8 and 167, respectively.

10. The isolated human monoclonal antibody or antigen-binding portion thereof, of claim 1, wherein the antibody or antigen-binding portion:
(i) binds human CD161 with an affinity ($K_D$) of about 50-300 pM;
(ii) inhibits the interaction between human CD161 and CLEC2D; and/or
(iii) binds to an epitope on human CD161 comprising one or more amino acid residues selected from I96, D121, K125, E126, R146, L151, Y198, E200, and E205 of SEQ ID NO: 335.

11. The isolated human monoclonal antibody or antigen-binding portion thereof of claim 1, wherein the antibody or antigen-binding portion binds to an epitope comprising (i) D121 of SEQ ID NO: 335; (ii) D121, I96, K125, and E126 of SEQ ID NO: 335; (iii) I96 and K125 of SEQ ID NO: 335; (iv) R146 of SEQ ID NO: 335; or (v) L151, Y198, E200, and E205 of SEQ ID NO: 335.

12. The isolated human monoclonal antibody or antigen-binding portion thereof of claim 1, wherein the antibody or antigen-binding portion (i) does not significantly cross-react with other human proteins in the C-type lectin family; (ii) does not significantly cross-react with cynomolgus CD161; (iii) binds to human CD161 with about 10-50-fold higher binding affinity ($K_D$) than to cynomolgus CD161; (iii) binds to human CD161 with substantially equivalent affinity to cynomolgus CD161; or (iv) binds to human CD161 with binding affinity ($K_D$) that is at least 80% of its binding affinity to cynomolgus CD161.

13. The isolated human monoclonal antibody or antigen-binding portion thereof of claim 1, wherein the antibody comprises a human IgG1 heavy chain constant region, mutant IgG1 heavy chain constant region, a human IgG4 heavy chain constant region or a mutant IgG4 heavy chain constant region, optionally wherein the mutant IgG1 heavy chain comprises a substitution at Leu234, Leu235 and Pro329, or wherein the mutant IgG1 heavy chain comprises a substitution of Leu234 to alanine, a substitution of Leu235 to alanine, and a substitution of Pro329 to glycine.

14. The isolated human monoclonal antibody or antigen-binding portion thereof of claim 1, wherein the antibody or antigen-binding portion thereof
   (i) binds to a ligand-binding region of human CD161, wherein the antibody or antigen-binding portion thereof blocks the CLEC2D-binding region of human CD161, thereby inhibiting the interaction between human CD161 and CLEC2D;
   (ii) binds to a non-ligand binding region of human CD161, and wherein the antibody or antigen-binding portion thereof alters the conformation of the CLEC2D binding region of human CD161, thereby inhibiting the interaction between human CD161 and CLEC2D; and/or
   (iii) does not significantly cross-react with human proteins of the C-type lectin family selected from: KLRF1, CD94, KLRF2, Clec12B, Clec7A, KLRG1, OLR1, Clec5A, Clec9A, CD209, Clec4E, or Clec10A.

15. The isolated human monoclonal antibody or antigen-binding portion thereof of claim 1, wherein the antibody or antigen-binding portion exhibits at least one or more of the following properties selected from the group consisting of:
   (a) induces or increases activation of CD161-expressing human T cells in response to antigen-expressing target cells;
   (b) induces or increases cytokine production by CD161-expressing human T cells in response to antigen-expressing target cells;
   (c) induces or increases granzyme B expression by CD161-expressing human T cells in response to antigen-expressing target cells;
   (d) reduces exhaustion of CD161-expressing human T cells in response to antigen-expressing target cells;
   (e) reduces expression of the PD-1 receptor in human T cells in response to antigen-expressing target cells; and
   (f) a combination of (a)-(e).

16. A pharmaceutical composition comprising an isolated monoclonal human antibody or antigen-binding portion of claim 1, and a pharmaceutically acceptable carrier.

* * * * *

SEQUENCE LISTING

<160> NUMBER OF SEQ ID NOS: 396

<210> SEQ ID NO 1
<211> LENGTH: 119
<212> TYPE: PRT
<213> ORGANISM: Artificial Sequence
<220> FEATURE:
<223> OTHER INFORMATION: Synthetic: VH1

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Leu Ile Pro Ser Gly Phe Asp Tyr Trp Gly Gln Gly
            100                 105                 110

Thr Leu Val Thr Val Ser Ser
        115

```
<210> SEQ ID NO 2
<211> LENGTH: 357
<212> TYPE: DNA
<213> ORGANISM: Artificial Sequence
<220> FEATURE:
<223> OTHER INFORMATION: Synthetic: VH1.0

<400> SEQUENCE: 2
gaggtgcagc tggtggagtc tgggggaggc ttggtacagc ctgggggtc cctgagactc      60 tcctgtgcag cctctggatt cacctttagc agctatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtgt attactgtgc gagggggtggt    300 ctgatcccat ctggttttga ttactggggc caaggtaccc tggtcactgt ctccagt      357

<210> SEQ ID NO 3
<211> LENGTH: 357
<212> TYPE: DNA
<213> ORGANISM: Artificial Sequence
<220> FEATURE:
<223> OTHER INFORMATION: Synthetic: VH1.1

<400> SEQUENCE: 3
gaggtgcagc tggtggagtc tgggggaggc ttggtacagc ctgggggtc cctgagactc      60 tcctgtgcag cctctggatt cacctttagc agctatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtgt attactgtgc gagaggtggt    300
ctgatcccat ctggttttga ttactggggc caaggtaccc tggtcactgt ctccagt      357

<210> SEQ ID NO 4
<211> LENGTH: 119
<212> TYPE: PRT
<213> ORGANISM: Artificial Sequence
<220> FEATURE:
<223> OTHER INFORMATION: Synthetic: VH2

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Ser Thr Tyr Tyr Ala Asp Ser Val
    50                  55                  60

Lys Gly Arg Phe Thr Ile Ser Arg Asp Asn Ser Lys Asn Ala Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Leu Ile Pro Ser Gly Phe Gly Tyr Trp Gly Gln Gly
            100                 105                 110

Thr Leu Val Thr Val Ser Ser
        115

<210> SEQ ID NO 5
```

```
<211> LENGTH: 357
<212> TYPE: DNA
<213> ORGANISM: Artificial Sequence
<220> FEATURE:
<223> OTHER INFORMATION: Synthetic: VH2.0

<400> SEQUENCE: 5
gaggtgcagc tggtggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cgcgctgtat     240
ctgcaaatga acagcctgag agccgaggac acggccgtgt attactgtgc gagggtggt     300 ctgatcccat ctggttttgg ttactggggc caaggtaccc tggtcactgt ctccagt       357

<210> SEQ ID NO 6
<211> LENGTH: 119
<212> TYPE: PRT
<213> ORGANISM: Artificial Sequence
<220> FEATURE:
<223> OTHER INFORMATION: Synthetic: VH3

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Ser Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Leu Ile Pro Ser Gly Phe Asp Tyr Trp Gly Gln Gly
            100                 105                 110

Thr Leu Val Thr Val Ser Ser
        115

<210> SEQ ID NO 7
<211> LENGTH: 357
<212> TYPE: DNA
<213> ORGANISM: Artificial Sequence
<220> FEATURE:
<223> OTHER INFORMATION: Synthetic: VH3.0

<400> SEQUENCE: 7
gaggtgcagc tggtggagtc tgggggaggc ttggtacagc ctggggggtc cctgagactc      60
tcctgtgcag cctctggatt cacctttagc agctatgcca tgagctgggt cagccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtgt attactgtgc gagggtggt     300 ctgatcccat ctggttttga ttactggggc caaggtaccc tggtcactgt ctccagt       357

<210> SEQ ID NO 8
<211> LENGTH: 119
```

```
<212> TYPE: PRT
<213> ORGANISM: Artificial Sequence
<220> FEATURE:
<223> OTHER INFORMATION: Synthetic: VH4

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Gly Ser Gly Ser Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Gly Gly Leu Ile Pro Ser Gly Phe Asp Tyr Trp Gly Gln Gly
            100                 105                 110

Thr Leu Val Thr Val Ser Ser
        115

<210> SEQ ID NO 9
<211> LENGTH: 357
<212> TYPE: DNA
<213> ORGANISM: Artificial Sequence
<220> FEATURE:
<223> OTHER INFORMATION: Synthetic: VH4.0

<400> SEQUENCE: 9
gaggtgcagc tggtggagtc tgggggaggc ttggtacagc ctggggggtc cctgagactc      60
tcctgtgcag cctctggatt cacctttagc agctacgcca tgagctgggt ccgccaggct     120
ccagggaagg ggctggagtg ggtctcaact attagtggta gtggtggtag cacatactac     180
gcagactccg tgaagggccg gttcaccatc tccagagaca attccaggaa cacgctgtat     240
ctgcaaatga acagcctgag agccgaggac acggccgtgt attactgtgc gagggggtggt    300 ctgatcccat ctggttttga ttactggggc caaggtaccc tggtcactgt ctccagt       357

<210> SEQ ID NO 10
<211> LENGTH: 357
<212> TYPE: DNA
<213> ORGANISM: Artificial Sequence
<220> FEATURE:
<223> OTHER INFORMATION: Synthetic: VH4.1

<400> SEQUENCE: 10
gaggtgcagc tggtggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcaact attagtggta gtggtggtag cacatactac     180
gcagactccg tgaagggccg gttcaccatc tccagagaca attccaggaa cacgctgtat     240
ctgcaaatga acagcctgag agccgaggac acggccgtgt attactgtgc gagggggtggt    300 ctgatcccat ctggttttga ttactggggc caaggtaccc tggtcactgt ctccagt       357

<210> SEQ ID NO 11
<211> LENGTH: 119
<212> TYPE: PRT
```

```
<213> ORGANISM: Artificial Sequence
<220> FEATURE:
<223> OTHER INFORMATION: Synthetic: VH5

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Pro Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Leu Ile Pro Ser Gly Phe Asp Tyr Trp Gly Gln Gly
            100                 105                 110

Thr Leu Val Thr Val Ser Ser
        115

<210> SEQ ID NO 12
<211> LENGTH: 357
<212> TYPE: DNA
<213> ORGANISM: Artificial Sequence
<220> FEATURE:
<223> OTHER INFORMATION: Synthetic: VH5.0

<400> SEQUENCE: 12
gaggtgcagc tggtggagtc tgggggaggc ttggtacagc ctggggggtc cctgagactc      60
tcctgtgcag cctctggatt ccccttagc agctatgcca tgagctgggt ccgccaggct      120
ccagggaagg ggctggagtg ggtctcagct attagtggta gtggtggtag cacatactac      180
gcagactccg tgaagggccg gttcaccatc tccagagaca attccaagaa cacgctgtat      240
ctgcaaatga acagcctgag agccgaggac acggccgtgt attactgtgc gaggggtggt      300
ctgatcccat ctggttttga ttactggggc caaggtaccc tggtcactgt ctccagt       357

<210> SEQ ID NO 13
<211> LENGTH: 119
<212> TYPE: PRT
<213> ORGANISM: Artificial Sequence
<220> FEATURE:
<223> OTHER INFORMATION: Synthetic: VH6

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Gly Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

-continued

```
Ala Arg Gly Gly Leu Ile Pro Ser Gly Phe Asp Tyr Trp Gly Gln Gly
            100                 105                 110

Thr Leu Val Thr Val Ser Ser
        115

<210> SEQ ID NO 14
<211> LENGTH: 357
<212> TYPE: DNA
<213> ORGANISM: Artificial Sequence
<220> FEATURE:
<223> OTHER INFORMATION: Synthetic: VH6.0

<400> SEQUENCE: 14
gaggtgcagc tggtggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagaggca attccaagaa cacgctgtat     240
ctgcaaatga acagcctgag agccgaggac acggccgtgt attactgtgc gagggtggt      300 ctgatcccat ctggttttga ttactggggc caaggtaccc tggtcactgt ctccagt       357

<210> SEQ ID NO 15
<211> LENGTH: 119
<212> TYPE: PRT
<213> ORGANISM: Artificial Sequence
<220> FEATURE:
<223> OTHER INFORMATION: Synthetic: VH7

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Gly Ser Gly Gly Ser Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Leu Ile Pro Ser Gly Phe Asp Tyr Trp Gly Gln Gly
            100                 105                 110

Thr Leu Val Thr Val Ser Ser
        115

<210> SEQ ID NO 16
<211> LENGTH: 357
<212> TYPE: DNA
<213> ORGANISM: Artificial Sequence
<220> FEATURE:
<223> OTHER INFORMATION: Synthetic: VH7.0

<400> SEQUENCE: 16
gaggtgcagc tggtggagtc tgggggaggc ttggtacagc ctggggggtc cctgagactc      60
tcctgtgcag cctctggatc cacctttagc agctatgcca tgagctgggt ccgccaggct     120
ccagggaagg ggctggagtg ggtctcaact attagtggta gtggtggtag cacatactac     180
```

```
gcagactccg tgaagggccg gttcaccatc tccagagaca attccaggaa cacgctgtat    240
ctgcaaatga acagcctgag agccgaggac acggccgtgt attactgtgc gagggggtggt   300 ctgatcccat ctggttttga ttactggggc caaggtaccc tggtcactgt ctccagt       357
```

<210> SEQ ID NO 17
<211> LENGTH: 357
<212> TYPE: DNA
<213> ORGANISM: Artificial Sequence
<220> FEATURE:
<223> OTHER INFORMATION: Synthetic: VH7.1

<400> SEQUENCE: 17

```
gaggtgcagc tggtggagtc tgggggaggc ttggtacagc ctggggggtc cctgagactc    60
tcctgtgcag cctctggatc cacctttagc agttatgcca tgagctgggt ccgccaggct   120
ccagggaagg ggctggagtg ggtctcaact attagtggta gtggtggtag cacatactac   180
gcagactccg tgaagggccg gttcaccatc tccagagaca attccaggaa cacgctgtat   240
ctgcaaatga acagcctgag agccgaggac acggccgtgt attactgtgc gagggggtggt  300 ctgatcccat ctggttttga ttactggggc caaggtaccc tggtcactgt ctccagt      357
```

<210> SEQ ID NO 18
<211> LENGTH: 119
<212> TYPE: PRT
<213> ORGANISM: Artificial Sequence
<220> FEATURE:
<223> OTHER INFORMATION: Synthetic: VH8

<400> SEQUENCE: 18

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Gly Ser Gly Gly Ser Thr Tyr Tyr Ala Asp Ser Val
    50                  55                  60

Lys Gly Arg Phe Thr Ile Ser Arg Asp Asn Pro Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Leu Ile Pro Ser Gly Phe Asp Tyr Trp Gly Gln Gly
            100                 105                 110

Thr Leu Val Thr Val Ser Ser
        115
```

<210> SEQ ID NO 19
<211> LENGTH: 357
<212> TYPE: DNA
<213> ORGANISM: Artificial Sequence
<220> FEATURE:
<223> OTHER INFORMATION: Synthetic: VH8.0

<400> SEQUENCE: 19

```
gaggtgcagc tggtggagtc tgggggaggc ttggtacagc ctggggggtc cctgagactc    60
tcctgtgcag cctctggatt cacctttagc agctatgcca tgagctgggt ccgccaggct   120
ccagggaagg ggctggagtg ggtctcaact attagtggta gtggtggtag cacatactac   180
gcagactccg tgaagggccg gttcaccatc tccagagaca atccaggaa cacgctgtat    240
```

```
ctgcaaatga acagcctgag agccgaggac acggccgtgt attactgtgc gaggggtggt    300
ctgatcccat ctggttttga ttactggggc caaggtaccc tggtcactgt ctccagt       357
```

<210> SEQ ID NO 20
<211> LENGTH: 119
<212> TYPE: PRT
<213> ORGANISM: Artificial Sequence
<220> FEATURE:
<223> OTHER INFORMATION: Synthetic: VH9

<400> SEQUENCE: 20

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Gly Ser Gly Ser Thr Tyr Tyr Ala Asp Ser Val
    50                  55                  60

Lys Gly Arg Phe Thr Ile Ser Arg Ala Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Leu Ile Pro Ser Gly Phe Asp Tyr Trp Gly Gln Gly
            100                 105                 110

Thr Leu Val Thr Val Ser Ser
        115
```

<210> SEQ ID NO 21
<211> LENGTH: 357
<212> TYPE: DNA
<213> ORGANISM: Artificial Sequence
<220> FEATURE:
<223> OTHER INFORMATION: Synthetic: VH9.1

<400> SEQUENCE: 21

```
gaggtgcagc tggtggagtc tgggggaggc ttggtacagc ctggggggtc cctgagactc    60
tcctgtgcag cctctggatt cacctttagc agctatgcca tgagctgggt ccgccaggcc   120
ccagggaagg ggctggagtg ggtctcaact attagtggta gtggtggtag cacatactac   180
gcagactccg tgaagggccg gttcaccatc tccagagcca attccaggaa cacgctgtat   240
ctgcaaatga acagcctgag agccgaggac acggccgtgt attactgtgc gaggggtggt   300
ctgatcccat ctggttttga ttactggggc caaggtaccc tggtcactgt ctccagt      357
```

<210> SEQ ID NO 22
<211> LENGTH: 119
<212> TYPE: PRT
<213> ORGANISM: Artificial Sequence
<220> FEATURE:
<223> OTHER INFORMATION: Synthetic: VH10

<400> SEQUENCE: 22

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

Ser Ala Ile Ser Gly Ser Gly Gly Ser Thr Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Gly Tyr Leu Pro Asp Ala Phe Asp Tyr Trp Gly Gln Gly
            100                 105                 110

Thr Leu Val Thr Val Ser Ser
        115

<210> SEQ ID NO 23
<211> LENGTH: 357
<212> TYPE: DNA
<213> ORGANISM: Artificial Sequence
<220> FEATURE:
<223> OTHER INFORMATION: Synthetic: VH10.0

<400> SEQUENCE: 23
gaggtgcagc tggtggagtc tgggggaggc ttggtacagc ctgggggtc cctgagactc      60
tcctgtgcag cctctggatt cacctttagc agctatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtgt attactgtgc gagggggtggt    300
tacctgccag atgcatttga ttactgggc caaggtaccc tggtcactgt ctccagt        357

<210> SEQ ID NO 24
<211> LENGTH: 357
<212> TYPE: DNA
<213> ORGANISM: Artificial Sequence
<220> FEATURE:
<223> OTHER INFORMATION: Synthetic: VH10.1

<400> SEQUENCE: 24
gaggtgcagc tggtggagtc tgggggaggc ctggtacagc ctgggggtc cctgagactc      60
tcctgtgcag cctctggatt cacctttagc agctatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtgt attactgtgc gagggggtggt    300
tacctgccag atgcatttga ttactgggc caaggtaccc tggtcactgt ctccagt        357

<210> SEQ ID NO 25
<211> LENGTH: 357
<212> TYPE: DNA
<213> ORGANISM: Artificial Sequence
<220> FEATURE:
<223> OTHER INFORMATION: Synthetic: VH10.2

<400> SEQUENCE: 25
gaggtgcagc tggtggagtc tgggggaggc ttggtacagc ctgggggtc cctgagactc      60
tcctgtgcag cctctggatt cacctttagc agctatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtgt actactgtgc gagggggtggt    300 tacctgccag atgcatttga ttactggggc caaggtaccc tggtcactgt ctccagt    357

<210> SEQ ID NO 26
<211> LENGTH: 357
<212> TYPE: DNA
<213> ORGANISM: Artificial Sequence
<220> FEATURE:
<223> OTHER INFORMATION: Synthetic: VH10.3

<400> SEQUENCE: 26
gaggtgcagc tggtggagtc tgggggaggc ttggtacagc ctggggggtc cctgagactc    60
tcctgtgcag cctctggatt cacctttagc agctatgcca tgagctgggt ccgccaggct    120
ccagggaagg gctggagtg gtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtgt attactgtgc gagggggtggt    300 tacctgccag atgcattcga ttactggggc caaggtaccc tggtcactgt ctccagt    357

<210> SEQ ID NO 27
<211> LENGTH: 357
<212> TYPE: DNA
<213> ORGANISM: Artificial Sequence
<220> FEATURE:
<223> OTHER INFORMATION: Synthetic: VH10.4

<400> SEQUENCE: 27
gaggtgcagc tggtggagtc tgggggaggc ttggtacagc ctggggggtc cctgagactc    60
tcctgtgcag cctctggatt cacctttagc agctatgcca tgagctgggt ccgccaggct    120
ccggggaagg gctggagtg gtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtgt attactgtgc gagggggtggt    300 tacctgccag acgcatttga ttactggggc caaggtaccc tggtcactgt ctccagt    357

<210> SEQ ID NO 28
<211> LENGTH: 357
<212> TYPE: DNA
<213> ORGANISM: Artificial Sequence
<220> FEATURE:
<223> OTHER INFORMATION: Synthetic: VH10.5

<400> SEQUENCE: 28
gaggtgcagc tggtggagtc tgggggaggc ttggtacagc ctggggggtc cctgagactc    60
tcctgtgcag cctctggatt cacctttagc agctatgcca tgagctgggt ccgccaggct    120
ccagggaagg gctggagtg gtctcagct attagtggta gtggtggtag cacatactac    180
gcagactccg tgaagggccg gttcaccatc tccagagaca attccaagaa cacgctgtat    240
ctgcaaatga acagcctgag agccgaagac acggccgtgt attactgtgc gagggggtggt    300 tacctgccag atgcatttga ttactggggc caaggtaccc tggtcactgt ctccagt    357

<210> SEQ ID NO 29
<211> LENGTH: 119
<212> TYPE: PRT
<213> ORGANISM: Artificial Sequence
<220> FEATURE:
<223> OTHER INFORMATION: Synthetic: VH11

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Arg Gly Gly Tyr Leu Pro Asp Ala Phe Asp Tyr Trp Gly Gln Gly
            100                 105                 110

Thr Leu Val Thr Val Ser Ser
            115

<210> SEQ ID NO 30
<211> LENGTH: 357
<212> TYPE: DNA
<213> ORGANISM: Artificial Sequence
<220> FEATURE:
<223> OTHER INFORMATION: Synthetic: VH11.0

<400> SEQUENCE: 30
gaggtgcagc tggtggagtc tgggggaggc ttggtacagc ctggggggtc cctgagactc       60
tcctgtgcag cctctggatt cacctttagc agctatgcca tgagctgggt ccgccaggct      120
ccagggaagg ggctggagtg ggtctcagct attagtggta gtggtggtag cacatactac      180
gcagactccg tgaagggccg gttcaccatc tccagagaca attccaagaa cacgctgtat      240
ctgcaaatga gcagcctgag agccgaggac acggccgtgt attactgtgc gagggtggt       300 tacctgccag atgcatttga ttactggggc caaggtaccc tggtcactgt ctccagt        357

<210> SEQ ID NO 31
<211> LENGTH: 119
<212> TYPE: PRT
<213> ORGANISM: Artificial Sequence
<220> FEATURE:
<223> OTHER INFORMATION: Synthetic: VH13

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Pro Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Tyr Leu Pro Asp Ala Phe Asp Tyr Trp Gly Gln Gly
            100                 105                 110

Thr Leu Val Thr Val Ser Ser
            115

<210> SEQ ID NO 32
<211> LENGTH: 357
<212> TYPE: DNA
<213> ORGANISM: Artificial Sequence
<220> FEATURE:
<223> OTHER INFORMATION: Synthetic: VH13.0

<400> SEQUENCE: 32

```
gaggtgcagc tggtggagtc tgggggaggc ttggtacagc ctgggggtc cctgagactc      60
tcctgtgcag cctctggatt caccttagc agctatgcca tgagctgggt ccgccaggct     120
ccagggaagg ggctggagtg gtctcagct attagtggca gtggtggtag cacatactac     180
gcagaccccg tgaagggccg gttcaccatc tccagagaca attccaagaa cacgctgtat    240
ctgcaaatga acagcctgag agccgaggac acggccgtgt attactgtgc gaggggtggt    300
tacctgccag atgcatttga ttactggggc caaggtaccc tggtcactgt ctccagt       357
```

<210> SEQ ID NO 33
<211> LENGTH: 119
<212> TYPE: PRT
<213> ORGANISM: Artificial Sequence
<220> FEATURE:
<223> OTHER INFORMATION: Synthetic: VH14

<400> SEQUENCE: 33

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ala Ile Ser Gly Ser Gly Gly Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Pro Ala Val Tyr Tyr Cys
                85                  90                  95
Ala Arg Gly Gly Tyr Leu Pro Asp Ala Phe Asp Tyr Trp Gly Gln Gly
            100                 105                 110
Thr Leu Val Thr Val Ser Ser
        115

<210> SEQ ID NO 34
<211> LENGTH: 357
<212> TYPE: DNA
<213> ORGANISM: Artificial Sequence
<220> FEATURE:
<223> OTHER INFORMATION: Synthetic: VH14.0

<400> SEQUENCE: 34

```
gaggtgcagc tggtggagtc tgggggaggc ttggtacagc ctgggggtc cctgagactc      60
tcctgtgcag cctctggatt caccttagc agctatgcca tgagctgggt ccgccaggct     120
ccagggaagg ggctggagtg gtctcagct attagtggta gtggtggtag cacatactac     180
gcagactccg tgaagggccg gttcaccatc tccagagaca attccaagaa cacgctgtat    240
ctgcaaatga acagcctgag agccgaggac ccggccgtgt attactgtgc gaggggtggt    300
tacctgccag atgcatttga ttactggggc caaggtaccc tggtcactgt ctccagt       357
```

<210> SEQ ID NO 35
<211> LENGTH: 119
<212> TYPE: PRT
<213> ORGANISM: Artificial Sequence
<220> FEATURE:
<223> OTHER INFORMATION: Synthetic: VH15

<400> SEQUENCE: 35

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Tyr Leu Pro Asp Ala Phe Asp Tyr Trp Gly Gln Gly
            100                 105                 110

Thr Leu Val Thr Val Ser Ser
        115
```

<210> SEQ ID NO 36
<211> LENGTH: 357
<212> TYPE: DNA
<213> ORGANISM: Artificial Sequence
<220> FEATURE:
<223> OTHER INFORMATION: Synthetic: VH15.0

<400> SEQUENCE: 36

```
gaggtgcagc tggtggagtc tgggggaggc ttggtacagc ctggggggtc cctgagactc    60
tcctgtgcag cctctggatt cacctttagc agctatgcca tgagctgggt ccgccaggct   120
ccagggaagg gctggagtg gtctcagct attagtggta gtggtggtag cacatactac    180
gcagactccg cgaagggccg gttcaccatc tccagagaca attccaagaa cacgctgtat   240
ctgcaaatga acagcctgag agccgaggac acggccgtgt actactgtgc gaggggtggt   300
tacctgccag atgcatttga ctactgggc caaggtaccc tggtcactgt ctccagt      357
```

<210> SEQ ID NO 37
<211> LENGTH: 119
<212> TYPE: PRT
<213> ORGANISM: Artificial Sequence
<220> FEATURE:
<223> OTHER INFORMATION: Synthetic: VH16

<400> SEQUENCE: 37

```
Glu Val Gln Leu Val Glu Ser Gly Gly Gly Leu Val Gln Pro Gly Gly
1               5                   10                  15

Pro Leu Arg Leu Ser Cys Ala Ala Ser Gly Ser Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Ala Leu Tyr
```

```
                65                  70                  75                  80
Leu Gln Met Asn Ser Leu Arg Ala Glu Asp Thr Ala Val Tyr Tyr Cys
                    85                  90                  95

Ala Arg Gly Gly Tyr Leu Pro Asp Ala Phe Asp Tyr Trp Gly Gln Gly
                100                 105                 110

Thr Leu Val Thr Val Ser Ser
        115
```

```
<210> SEQ ID NO 38
<211> LENGTH: 357
<212> TYPE: DNA
<213> ORGANISM: Artificial Sequence
<220> FEATURE:
<223> OTHER INFORMATION: Synthetic: VH16.0

<400> SEQUENCE: 38
gaggtgcagc tggtggagtc tgggggaggc ttggtacagc ctggggggcc cctgagactc      60
tcctgtgcag cctctggatc cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cgcgctgtat     240
ctgcaaatga acagcctgag agccgaggac acggccgtgt attactgtgc gagggtggt      300 tacctgccag atgcatttga ttactggggc caaggtaccc tggtcactgt ctccagt        357
```

```
<210> SEQ ID NO 39
<211> LENGTH: 119
<212> TYPE: PRT
<213> ORGANISM: Artificial Sequence
<220> FEATURE:
<223> OTHER INFORMATION: Synthetic: VH17

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Ser Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Tyr Leu Pro Asp Ala Phe Asp Tyr Trp Gly Gln Gly
            100                 105                 110

Thr Leu Val Thr Val Ser Ser
        115
```

```
<210> SEQ ID NO 40
<211> LENGTH: 357
<212> TYPE: DNA
<213> ORGANISM: Artificial Sequence
<220> FEATURE:
<223> OTHER INFORMATION: Synthetic: VH17.0

<400> SEQUENCE: 40
gaggtgcagc tggtggagtc tgggggaggc ttggtacagc ctgggggggtc cctgagactc     60
```

```
tcctgtgcag cctctggatt cacttttagc agctatgcca tgagctgggt ccgccaggct    120
ccagggaagg ggctggagtg ggtctcagct attagtggta gtggtggtag cacatactac    180
gcagactccg tgaagggccg gttcaccatc tccagagaca gttccaagaa cacgctgtat    240
ctgcaaatga acagcctgag agccgaggac acggccgtgt attactgtgc gagggtggt    300 tacctgccag atgcatttga ttactggggc caaggtaccc tggtcactgt ctccagt      357
```

<210> SEQ ID NO 41
<211> LENGTH: 119
<212> TYPE: PRT
<213> ORGANISM: Artificial Sequence
<220> FEATURE:
<223> OTHER INFORMATION: Synthetic: VH18

<400> SEQUENCE: 41

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Thr Ser Gly Ser Gly Gly Ser Thr Tyr Tyr Ala Asp Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Tyr Leu Pro Asp Ala Phe Asp Tyr Trp Gly Arg Gly
            100                 105                 110

Thr Leu Val Thr Val Ser Ser
            115
```

<210> SEQ ID NO 42
<211> LENGTH: 357
<212> TYPE: DNA
<213> ORGANISM: Artificial Sequence
<220> FEATURE:
<223> OTHER INFORMATION: Synthetic: VH18.0

<400> SEQUENCE: 42

```
gaggtgcagc tggtggagtc tgggggaggc ttggtacagc ctggggggtc cctgagactc    60
tcctgtgcag cctctggatt caccttttagc agctatgcca tgagctgggt ccgccaggct   120
ccagggaagg ggctggagtg ggtctcagct actagtggta gtggtggtag cacatactac    180
gcagactccg tgaagggccg gttcaccatc tccagagaca attccaagaa cacgctgtat    240
ctgcaaatga acagcctgag agccgaggac acggccgtgt actactgtgc gagggtggt    300 tacctgccag atgcatttga ctactggggc cgaggtaccc tggtcactgt ctccagt      357
```

<210> SEQ ID NO 43
<211> LENGTH: 124
<212> TYPE: PRT
<213> ORGANISM: Artificial Sequence
<220> FEATURE:
<223> OTHER INFORMATION: Synthetic: VH19

<400> SEQUENCE: 43

```
Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Pro Gly Asp Met Tyr Leu Tyr Gly Asp Ser Phe Phe Asp
            100                 105                 110

Tyr Trp Gly Gln Gly Thr Leu Val Thr Val Ser Ser
        115                 120
```

<210> SEQ ID NO 44
<211> LENGTH: 372
<212> TYPE: DNA
<213> ORGANISM: Artificial Sequence
<220> FEATURE:
<223> OTHER INFORMATION: Synthetic: VH19.0

<400> SEQUENCE: 44

```
gaggtgcagc tggtggagtc tgggggaggc ttggtacagc ctgggggctc cctgagactc     60
tcctgtgcag cctctggatt cacctttagc agctatgcca tgagctgggt ccgccaggct    120
ccagggaagg gctggagtg gtctcagct attagtggta gtggtggtag cacatactac      180
gcagactccg tgaagggccg gttcaccatc tccagagaca attccaagaa cacgctgtat    240
ctgcaaatga acagcctgag agccgaggac acggccgtgt attactgtgc gaggggtcca    300
ggtgatatgt acctgtacgg tgattctttc tttgattact ggggccaagg taccctggtc    360
actgtctcca gt                                                         372
```

<210> SEQ ID NO 45
<211> LENGTH: 124
<212> TYPE: PRT
<213> ORGANISM: Artificial Sequence
<220> FEATURE:
<223> OTHER INFORMATION: Synthetic: VH20

<400> SEQUENCE: 45

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Thr Val Tyr Tyr Cys
                85                  90                  95

Ala Arg Gly Pro Gly Asp Met Tyr Leu Tyr Gly Asp Ser Phe Phe Asp
            100                 105                 110

Tyr Trp Gly Gln Gly Thr Leu Val Thr Val Ser Ser
        115                 120
```

<210> SEQ ID NO 46
<211> LENGTH: 372
<212> TYPE: DNA
<213> ORGANISM: Artificial Sequence
<220> FEATURE:
<223> OTHER INFORMATION: Synthetic: VH20.0

<400> SEQUENCE: 46

```
gaggtgcagc tggtggagtc tggggggaggc ttggtacagc ctgggggtc cctgagactc      60
tcctgtgcag cctctggatt cacctttagc agctatgcca tgagctgggt ccgccaggct     120
ccagggaagg gctggagtg gtctcagct attagtggta gtggtggtag cacatactac      180
gcagactccg tgaagggccg gttcaccatc tccagagaca attccaagaa cacgctgtat    240
ctgcaaatga acagcctgag agccgaggac acgaccgtgt attactgtgc gaggggtcca   300
ggtgatatgt acctgtacgg tgattctttc tttgattact ggggccaagg taccctggtc   360
actgtctcca gt                                                         372
```

<210> SEQ ID NO 47
<211> LENGTH: 124
<212> TYPE: PRT
<213> ORGANISM: Artificial Sequence
<220> FEATURE:
<223> OTHER INFORMATION: Synthetic: VH21

<400> SEQUENCE: 47

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ala Ile Ser Gly Ser Gly Gly Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Gly Pro Gly Tyr Met Tyr Leu Tyr Gly Asp Ser Phe Phe Asp
            100                 105                 110
Tyr Trp Gly Gln Gly Thr Leu Val Thr Val Ser Ser
        115                 120
```

<210> SEQ ID NO 48
<211> LENGTH: 372
<212> TYPE: DNA
<213> ORGANISM: Artificial Sequence
<220> FEATURE:
<223> OTHER INFORMATION: Synthetic: VH21.0

<400> SEQUENCE: 48

```
gaggtgcagc tggtggagtc tggggggaggc ttggtacagc ctgggggtc cctgagactc      60
tcctgtgcag cctctggatt cacctttagc agctatgcca tgagctgggt ccgccaggct     120
ccagggaagg gctggagtg gtctcagct attagtggta gtggtggtag cacatactac      180
gcagactccg tgaagggccg gttcaccatc tccagagaca attccaagaa tacgctgtat    240
ctgcaaatga acagcctgag agccgaggac acggccgtgt attactgtgc gaggggtcca   300
ggttatatgt acctgtacgg tgattctttc tttgattact ggggccaagg taccctggtc   360
```

```
actgtctcca gt                                                        372

<210> SEQ ID NO 49
<211> LENGTH: 372
<212> TYPE: DNA
<213> ORGANISM: Artificial Sequence
<220> FEATURE:
<223> OTHER INFORMATION: Synthetic: VH21.1

<400> SEQUENCE: 49
gaggtgcagc tggtggagtc tgggggaggc ttggtacagc ctgggggtc cctgagactc      60 tcctgtgcag cctctggatt cacctttagc agctatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa tacgctatat    240
ctgcaaatga acagcctgag agccgaggac acggccgtgt attactgtgc gagggggtcca   300 ggttatatgt acctgtacgg tgattctttc tttgattact ggggccaagg taccctggtc    360
actgtctcca gt                                                        372

<210> SEQ ID NO 50
<211> LENGTH: 124
<212> TYPE: PRT
<213> ORGANISM: Artificial Sequence
<220> FEATURE:
<223> OTHER INFORMATION: Synthetic: VH22

<400> SEQUENCE: 50

Glu Val Arg Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Pro Gly Tyr Met Tyr Leu Tyr Gly Asp Ser Phe Phe Asp
            100                 105                 110

Tyr Trp Gly Gln Gly Thr Leu Val Thr Val Ser Ser
        115                 120

<210> SEQ ID NO 51
<211> LENGTH: 372
<212> TYPE: DNA
<213> ORGANISM: Artificial Sequence
<220> FEATURE:
<223> OTHER INFORMATION: Synthetic: VH22.0

<400> SEQUENCE: 51
gaggtgcggc tggtggagtc tgggggaggc ttggtacagc ctgggggtc cctgagactc      60 tcctgtgcag cctctggatt cacctttagc agctatgcca tgagctgggt ccgccaggct    120
ccagggaagg ggctggagtg ggtctcagct attagtggta gtggtggtag cacatactac    180
gcagactccg tgaagggccg gttcaccatc tccagagaca actccaagaa cacgctgtat    240
```

```
ctgcaaatga acagcctgag agccgaggac acggccgtgt attactgtgc gagggggtcca    300 ggttatatgt acctgtacgg tgattctttc tttgattact ggggccaagg taccctggtc    360
actgtctcca gt                                                        372
```

<210> SEQ ID NO 52
<211> LENGTH: 124
<212> TYPE: PRT
<213> ORGANISM: Artificial Sequence
<220> FEATURE:
<223> OTHER INFORMATION: Synthetic: VH23

<400> SEQUENCE: 52

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Pro Gly Tyr Met Tyr Leu Tyr Gly Asp Ser Phe Phe Asp
            100                 105                 110

Tyr Trp Gly Gln Gly Thr Leu Val Thr Val Ser Ser
        115                 120
```

<210> SEQ ID NO 53
<211> LENGTH: 372
<212> TYPE: DNA
<213> ORGANISM: Artificial Sequence
<220> FEATURE:
<223> OTHER INFORMATION: Synthetic: VH23.0

<400> SEQUENCE: 53

```
gaggtgcagc tggtggagtc tgggggaggc ttggtacagc ctggggggtc cctgagactc    60
tcctgtgcag cctctggatt cacctttagc agctatgcca tgagctgggt ccgccaggct   120
ccagggaagg ggctggagtg ggtctcaggt attagtggta gtggtggtag cacatactac   180
gcagactccg tgaagggccg gttcaccatc tccagagaca attccaagaa cacgctgtat   240
ctgcaaatga acagcctgag agccgaggac acggccgtgt attactgtgc gagggggtcca   300 ggttatatgt acctgtacgg tgattctttc tttgattact ggggccaagg taccctggtc   360
actgtctcca gt                                                       372
```

<210> SEQ ID NO 54
<211> LENGTH: 124
<212> TYPE: PRT
<213> ORGANISM: Artificial Sequence
<220> FEATURE:
<223> OTHER INFORMATION: Synthetic: VH25

<400> SEQUENCE: 54

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

Ala Met Ser Trp Val Arg Gln Ala Pro Gly Lys Gly Leu Glu Trp Val
          35                  40                  45

Ser Ala Ile Ser Gly Ser Gly Gly Ser Thr Tyr Tyr Ala Asp Ser Val
 50                  55                  60

Lys Gly Arg Phe Thr Val Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
              85                  90                  95

Ala Arg Gly Pro Gly Tyr Met Tyr Leu Tyr Gly Asp Ser Phe Phe Asp
             100                 105                 110

Tyr Trp Gly Gln Gly Thr Leu Val Thr Val Ser Ser
         115                 120

<210> SEQ ID NO 55
<211> LENGTH: 372
<212> TYPE: DNA
<213> ORGANISM: Artificial Sequence
<220> FEATURE:
<223> OTHER INFORMATION: Synthetic: VH25.0

<400> SEQUENCE: 55

```
gaggtgcagc tggtggagtc tgggggaggc ttggtacagc ctggggggtc cctgagactc      60
tcctgtgcag cctctggatt caccttagc agctatgcca tgagctgggt ccgccaggct     120
ccagggaagg ggctggagtg ggtctcagct attagtggta gtggtggtag cacatactac     180
gcagactccg tgaagggccg gttcaccgtc tccagagaca attctaagaa tacgctgtat     240
ctgcaaatga acagcctgag agccgaggac acggccgtgt attactgtgc gagggggtcca     300
ggttatatgt acctgtacgg tgattctttc tttgattact ggggccaagg taccctggtc     360
actgtctcca gt                                                         372
```

<210> SEQ ID NO 56
<211> LENGTH: 124
<212> TYPE: PRT
<213> ORGANISM: Artificial Sequence
<220> FEATURE:
<223> OTHER INFORMATION: Synthetic: VH26

<400> SEQUENCE: 56

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
          35                  40                  45

Ser Ala Ile Ser Gly Ser Gly Arg Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Met Tyr Tyr Cys
              85                  90                  95

Ala Arg Gly Pro Gly Tyr Met Tyr Leu Tyr Gly Asp Ser Phe Phe Glu
             100                 105                 110

Tyr Trp Gly Gln Gly Thr Leu Val Thr Val Ser Ser
         115                 120

<210> SEQ ID NO 57

-continued

```
<211> LENGTH: 372
<212> TYPE: DNA
<213> ORGANISM: Artificial Sequence
<220> FEATURE:
<223> OTHER INFORMATION: Synthetic: VH26.0

<400> SEQUENCE: 57
gaggtgcagc tggtggagtc tgggggaggc ttggtacagc ctggggggtc cctgagactt      60
tcctgtgcag cctctggatt cacctttagc agctatgcca tgagctgggt ccgccaggct     120
ccagggaagg ggctggagtg ggtctcagct attagtggta gtggtggtcg cacatactac     180
gcagactccg tgaagggccg gttcaccatc tccagagaca attccaagaa tacgctgtat     240
ctgcaaatga acagcctgag agccgaggac acggccatgt attactgtgc gagggggtcca    300
ggttatatgt acctgtacgg tgattctttc tttgaatact ggggccaagg taccctggtc     360
actgtctcca gt                                                         372

<210> SEQ ID NO 58
<211> LENGTH: 372
<212> TYPE: DNA
<213> ORGANISM: Artificial Sequence
<220> FEATURE:
<223> OTHER INFORMATION: Synthetic: VH26.1

<400> SEQUENCE: 58
gaggtgcagc tggtggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtcg cacatactac     180
gcagactccg tgaagggccg gttcaccatc tccagagaca attccaagaa tacgctgtat     240
ctgcaaatga acagcctgag agccgaggac acggccatgt attactgtgc gagggggtcca    300
ggttatatgt acctgtacgg tgattctttc tttgaatact ggggccaagg taccctggtc     360
actgtctcca gt                                                         372

<210> SEQ ID NO 59
<211> LENGTH: 124
<212> TYPE: PRT
<213> ORGANISM: Artificial Sequence
<220> FEATURE:
<223> OTHER INFORMATION: Synthetic: VH27

<400> SEQUENCE: 59

Glu Val Gln Leu Val Glu Ser Gly Gly Gly Leu Val Arg Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Gly Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Pro Gly Tyr Met Tyr Leu Tyr Gly Asp Ser Phe Phe Asp
            100                 105                 110

Tyr Trp Gly Gln Gly Thr Leu Val Thr Val Ser Ser
        115                 120
```

<210> SEQ ID NO 60
<211> LENGTH: 372
<212> TYPE: DNA
<213> ORGANISM: Artificial Sequence
<220> FEATURE:
<223> OTHER INFORMATION: Synthetic: VH27.0

<400> SEQUENCE: 60

```
gaggtgcagc tggtggagtc tgggggaggc ttggtacggc ctgggggtc cctgagactc      60
tcctgtgcag cctctggatt cacctttagc agctatgcca tgagctgggt ccgccaggct    120
ccagggaagg gctggagtg gtctcaggt attagtggta gtggtggtag cacatactac      180
gcagactccg tgaagggccg gttcaccatc tccagagaca attccaagaa cacgctgtat    240
ctgcaaatga acagcctgag agccgaggac acggccgtgt attactgtgc gaggggtcca    300
ggttatatgt acctgtatgg tgattctttc tttgattact ggggccaagg taccctggtc    360
actgtctcca gt                                                        372
```

<210> SEQ ID NO 61
<211> LENGTH: 124
<212> TYPE: PRT
<213> ORGANISM: Artificial Sequence
<220> FEATURE:
<223> OTHER INFORMATION: Synthetic: VH28

<400> SEQUENCE: 61

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ala Ile Ser Gly Ser Gly Gly Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Asp Tyr Tyr Leu Ser Asp Tyr Ile Thr Gln Thr Ser Phe Asp
            100                 105                 110
Tyr Trp Gly Gln Gly Thr Leu Val Thr Val Ser Ser
        115                 120
```

<210> SEQ ID NO 62
<211> LENGTH: 372
<212> TYPE: DNA
<213> ORGANISM: Artificial Sequence
<220> FEATURE:
<223> OTHER INFORMATION: Synthetic: VH28.0

<400> SEQUENCE: 62

```
gaggtgcagc tggtggagtc tgggggaggc ttggtacagc ctgggggtc cctgagactc      60
tcctgtgcag cctctggatt cacctttagc agctatgcca tgagctgggt ccgccaggct    120
ccagggaagg gctggagtg gtctcagct attagtggta gtggtggtag cacatactac      180
gcagactccg tgaagggccg gttcaccatc tccagagaca attccaagaa cacgctgtat    240
ctgcaaatga acagcctgag agccgaggac acggccgtgt attactgtgc gagggattac    300
```

```
tacctgtctg attacatcac ccagacctct tttgattact ggggccaagg taccctggtc    360
actgtctcca gt                                                        372
```

<210> SEQ ID NO 63
<211> LENGTH: 124
<212> TYPE: PRT
<213> ORGANISM: Artificial Sequence
<220> FEATURE:
<223> OTHER INFORMATION: Synthetic: VH29

<400> SEQUENCE: 63

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Tyr Leu Phe Tyr Ile Thr Gln Thr Ser Phe Asp
            100                 105                 110

Tyr Trp Gly Gln Gly Thr Leu Val Thr Val Ser Ser
        115                 120
```

<210> SEQ ID NO 64
<211> LENGTH: 372
<212> TYPE: DNA
<213> ORGANISM: Artificial Sequence
<220> FEATURE:
<223> OTHER INFORMATION: Synthetic: VH29.0

<400> SEQUENCE: 64

```
gaggtgcagc tggtggagtc tgggggaggc ttggtacagc ctggggggtc cctgagactc    60
tcctgtgcag cctctggatt cacctttagc agctatgcca tgagctgggt ccgccaggct   120
ccagggaagg gctggagtg gtctcagct attagtggta gtggtggtag cacatactac    180
gcagactccg tgaagggccg gttcaccatc tccagagaca attccaagaa cacgctgtac   240
ctgcaaatga acagcctgag agccgaggac acggccgtgt attactgtgc gagggattac   300
tacctgtttg attacatcac ccagacctct tttgattact ggggccaagg taccctggtc   360
actgtctcca gt                                                        372
```

<210> SEQ ID NO 65
<211> LENGTH: 372
<212> TYPE: DNA
<213> ORGANISM: Artificial Sequence
<220> FEATURE:
<223> OTHER INFORMATION: Synthetic: VH29.1

<400> SEQUENCE: 65

```
gaggtgcagc tggtggagtc tgggggaggc ttggtacagc ctggggggtc cctgagactc    60
tcctgtgcag cctctggatt cacctttagc agctatgcca tgagctgggt ccgccaggct   120
ccagggaagg gctggagtg gtctcagct attagtggta gtggtggtag cacatactac    180
gcagactccg tgaagggccg gttcaccatc tccagagaca attccaagaa cacgctgtat   240
```

```
ctgcaaatga acagcctgag agccgaggac acggccgtgt attactgtgc gagggattac    300
tacctgtttg attacatcac ccagacctct tttgattact ggggccaagg tacccctggtc    360 actgtctcca gt                                                         372
```

<210> SEQ ID NO 66
<211> LENGTH: 124
<212> TYPE: PRT
<213> ORGANISM: Artificial Sequence
<220> FEATURE:
<223> OTHER INFORMATION: Synthetic: VH30

<400> SEQUENCE: 66

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Tyr Leu Tyr Asp Tyr Ile Thr Gln Thr Ser Phe Asp
            100                 105                 110

Tyr Trp Gly Gln Gly Thr Leu Val Thr Val Ser Ser
        115                 120
```

<210> SEQ ID NO 67
<211> LENGTH: 372
<212> TYPE: DNA
<213> ORGANISM: Artificial Sequence
<220> FEATURE:
<223> OTHER INFORMATION: Synthetic: VH30.1

<400> SEQUENCE: 67

```
gaggtgcagc tggtggagtc tgggggaggc ttggtacagc ctggggggtc cctgagactc    60
tcctgtgcag cctctggatt cacctttagc agctatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtgt attactgtgc gagggattac    300
tacctgtatg attacatcac ccagacctct tttgattact ggggccaagg tacccctggtc    360 actgtctcca gt                                                         372
```

<210> SEQ ID NO 68
<211> LENGTH: 124
<212> TYPE: PRT
<213> ORGANISM: Artificial Sequence
<220> FEATURE:
<223> OTHER INFORMATION: Synthetic: VH31

<400> SEQUENCE: 68

```
Glu Val Gln Leu Val Glu Ser Gly Gly Gly Ser Val Gln Pro Gly Gly
1               5                   10                  15

Ser Leu Arg Leu Ser Cys Ala Ala Ser Gly Phe Thr Phe Ser Ser Tyr
```

```
              20                  25                  30
Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Asp Tyr Tyr Leu Phe Asp Tyr Ile Thr Gln Thr Ser Phe Asp
            100                 105                 110

Tyr Trp Gly Gln Gly Thr Leu Val Thr Val Ser Ser
            115                 120

<210> SEQ ID NO 69
<211> LENGTH: 372
<212> TYPE: DNA
<213> ORGANISM: Artificial Sequence
<220> FEATURE:
<223> OTHER INFORMATION: Synthetic: VH31.0

<400> SEQUENCE: 69
gaggtgcagc tggtggagtc tgggggaggc tcggtacagc ctgggggggtc cctgagactc     60 tcctgtgcag cctctggatt caccttttagc agctatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtgt attactgtgc gagggattac    300
tacctgtttg attacatcac ccagacctct tttgattact ggggccaagg taccctggtc    360
actgtctcca gt                                                        372

<210> SEQ ID NO 70
<211> LENGTH: 124
<212> TYPE: PRT
<213> ORGANISM: Artificial Sequence
<220> FEATURE:
<223> OTHER INFORMATION: Synthetic: VH32

<400> SEQUENCE: 70

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Ala Ala Val Tyr Tyr Cys
                85                  90                  95

Ala Arg Asp Tyr Tyr Leu Tyr Asp Tyr Ile Thr Gln Thr Ser Phe Asp
            100                 105                 110

Tyr Trp Gly Gln Gly Thr Leu Val Thr Val Ser Ser
            115                 120
```

-continued

<210> SEQ ID NO 71
<211> LENGTH: 372
<212> TYPE: DNA
<213> ORGANISM: Artificial Sequence
<220> FEATURE:
<223> OTHER INFORMATION: Synthetic: VH32.0

<400> SEQUENCE: 71

```
gaggtgcagc tggtggagtc tgggggaggc ttggtacagc ctgggggtc cctgagactc      60
tcctgtgcag cctctggatt cacctttagc agctatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac gcggccgtgt attactgtgc gagggattac    300
tacctgtatg attacatcac ccagacctct tttgattact ggggccaagg taccctggtc    360
actgtctcca gt                                                         372
```

<210> SEQ ID NO 72
<211> LENGTH: 124
<212> TYPE: PRT
<213> ORGANISM: Artificial Sequence
<220> FEATURE:
<223> OTHER INFORMATION: Synthetic: VH33

<400> SEQUENCE: 72

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ala Ile Ser Gly Ser Gly Gly Ser Ala Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Asp Tyr Tyr Leu Tyr Asp Tyr Ile Thr Gln Thr Ser Phe Asp
            100                 105                 110
Tyr Trp Gly Gln Gly Thr Leu Val Thr Val Ser Ser
        115                 120
```

<210> SEQ ID NO 73
<211> LENGTH: 372
<212> TYPE: DNA
<213> ORGANISM: Artificial Sequence
<220> FEATURE:
<223> OTHER INFORMATION: Synthetic: VH33.0

<400> SEQUENCE: 73

```
gaggtgcagc tggtggagtc tgggggaggc ttggtacagc ctgggggtc cctgagactc      60
tcctgtgcag cctctggatt cacctttagc agctatgcca tgagctgggt ccgccaggct    120
ccagggaagg ggctggagtg ggtctcagct attagtggta gtggtggtag cgcatactac    180
gcagactccg tgaagggccg gttcaccatc tccagagaca attccaagaa cacgctgtat    240
ctgcaaatga acagcctgag agccgaggac acggccgtgt attactgtgc gagggattac    300
tacctgtatg attacatcac ccagacctct tttgattact ggggccaagg taccctggtc    360
```

```
actgtctcca gt                                                            372

<210> SEQ ID NO 74
<211> LENGTH: 124
<212> TYPE: PRT
<213> ORGANISM: Artificial Sequence
<220> FEATURE:
<223> OTHER INFORMATION: Synthetic: VH34

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Thr Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Tyr Leu Tyr Asp Tyr Ile Thr Gln Thr Ser Phe Asp
            100                 105                 110

Tyr Trp Gly Gln Gly Thr Leu Val Thr Val Ser Ser
        115                 120

<210> SEQ ID NO 75
<211> LENGTH: 372
<212> TYPE: DNA
<213> ORGANISM: Artificial Sequence
<220> FEATURE:
<223> OTHER INFORMATION: Synthetic: VH34.0

<400> SEQUENCE: 75
gaggtgcagc tggtggagtc tgggggaggc ttggtacagc ctggggggtc cctgagactc       60
tcctgtgcag cctctggatt cacctttagc agctatgcca tgagctgggt ccgccagact      120
ccagggaagg ggctggagtg ggtctcagct attagtggta gtggtggtag cacatactac      180
gcagactccg tgaagggccg gttcaccatc tccagagaca attccaagaa cacgctgtat      240
ctgcaaatga acagcctgag agccgaggac acggccgtgt attactgtgc gagggattac      300
tacctgtatg attacatcac ccagacctct tttgattact ggggccaagg taccctggtc      360
actgtctcca gt                                                          372

<210> SEQ ID NO 76
<211> LENGTH: 124
<212> TYPE: PRT
<213> ORGANISM: Artificial Sequence
<220> FEATURE:
<223> OTHER INFORMATION: Synthetic: VH35

<400> SEQUENCE: 76

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ile Ser Tyr
            20                  25                  30

Ala Met Ser Trp Val Arg Gln Ala Pro Gly Lys Gly Leu Glu Trp Val
        35                  40                  45
```

```
Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Ala Leu Tyr
 65                  70                  75                  80

Leu Gln Met Asn Ser Leu Arg Ala Glu Asp Thr Ala Val Tyr Tyr Cys
                 85                  90                  95

Ala Arg Asp Tyr Tyr Leu Tyr Asp Tyr Ile Thr Gln Thr Ser Phe Asp
             100                 105                 110

Tyr Trp Gly Gln Gly Thr Leu Val Thr Val Ser Ser
         115                 120
```

<210> SEQ ID NO 77
<211> LENGTH: 372
<212> TYPE: DNA
<213> ORGANISM: Artificial Sequence
<220> FEATURE:
<223> OTHER INFORMATION: Synthetic: VH35.0

<400> SEQUENCE: 77

```
gaggtgcagc tggtggagtc tgggggaggc ttggtacagc ctggggggtc cctgagactc      60
tcctgtgcag cctctggatt cgcctttatc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cgcgctgtat     240
ctgcaaatga acagcctgag agccgaggac acggccgtgt attactgtgc gagggattac     300
tacctgtatg attacatcac ccagacctct tttgattact ggggccaagg taccctggtc     360
actgtctcca gt                                                         372
```

<210> SEQ ID NO 78
<211> LENGTH: 124
<212> TYPE: PRT
<213> ORGANISM: Artificial Sequence
<220> FEATURE:
<223> OTHER INFORMATION: Synthetic: VH36

<400> SEQUENCE: 78

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Arg Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Tyr Tyr Leu Tyr Asp Tyr Ile Thr Gln Thr Ser Phe Asp
             100                 105                 110

Tyr Trp Gly Gln Gly Thr Leu Val Thr Val Ser Ser
         115                 120
```

<210> SEQ ID NO 79
<211> LENGTH: 372
<212> TYPE: DNA
<213> ORGANISM: Artificial Sequence
<220> FEATURE:

<223> OTHER INFORMATION: Synthetic: VH36.0

<400> SEQUENCE: 79

```
gaggtgcagc tggtggagtc tgggggaggc ttggtacagc ctggggggtc cctgagactc    60
tcctgtgcag cctctggatt cacctttagc agctatgcca tgagctgggt ccgccaggct   120
ccagggaagg ggctggagtg ggtctcagct attagtggta gtggtcgtag cacatactac   180
gcagactccg tgaagggccg gttcaccatc tccagagaca attccaagaa cacgctgtat   240
ctgcaaatga acagcctgag agccgaggac acggccgtgt attactgtgc gagggattac   300
tacctgtatg attacatcac ccagacctct tttgattact ggggccaagg tacccctggtc   360
actgtctcca gt                                                      372
```

<210> SEQ ID NO 80
<211> LENGTH: 124
<212> TYPE: PRT
<213> ORGANISM: Artificial Sequence
<220> FEATURE:
<223> OTHER INFORMATION: Synthetic: VH37

<400> SEQUENCE: 80

```
Glu Val Gln Leu Val Glu Ser Gly Gly Gly Leu Ala Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ala Ile Ser Gly Ser Gly Arg Ser Thr Tyr Tyr Ala Asp Pro Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Gly Asp Thr Ala Val Tyr Tyr Cys
                85                  90                  95
Ala Arg Asp Tyr Tyr Leu Tyr Asp Tyr Ile Thr Gln Thr Ser Phe Asp
            100                 105                 110
Tyr Trp Gly Gln Gly Thr Leu Val Thr Val Ser Ser
        115                 120
```

<210> SEQ ID NO 81
<211> LENGTH: 372
<212> TYPE: DNA
<213> ORGANISM: Artificial Sequence
<220> FEATURE:
<223> OTHER INFORMATION: Synthetic: VH37.0

<400> SEQUENCE: 81

```
gaggtgcagc tggtggagtc tgggggaggc ttggcacagc ctggggggtc cctgagactc    60
tcctgtgcag cctctggatt cacctttagc agctatgcca tgagctgggt ccgccaggct   120
ccagggaagg ggctggagtg ggtctcagct attagtggta gtggtcgtag cacatactac   180
gcagacccccg tgaagggccg gttcaccatc tccagagaca attccaagaa cacgctgtac   240
ctgcaaatga acagcctgag agccggggac acggccgtgt attactgtgc gagggattac   300
tacctgtatg attacatcac ccagacctct tttgattact ggggccaagg tacccctggtc   360
actgtctcca gt                                                      372
```

<210> SEQ ID NO 82
<211> LENGTH: 124

```
<212> TYPE: PRT
<213> ORGANISM: Artificial Sequence
<220> FEATURE:
<223> OTHER INFORMATION: Synthetic: VH38

<400> SEQUENCE: 82
```

Glu Val Gln Leu Val Glu Ser Gly Gly Gly Leu Ala Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Arg Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
                85                  90                  95

Ala Arg Asp Tyr Tyr Leu Tyr Asp Tyr Ile Thr Gln Thr Ser Phe Asp
            100                 105                 110

Tyr Trp Gly Gln Gly Thr Leu Val Thr Val Ser Ser
        115                 120

```
<210> SEQ ID NO 83
<211> LENGTH: 372
<212> TYPE: DNA
<213> ORGANISM: Artificial Sequence
<220> FEATURE:
<223> OTHER INFORMATION: Synthetic: VH38.0

<400> SEQUENCE: 83
```

| | | | | | |
|---|---|---|---|---|---|
| gaggtgcagc | tggtggagtc | tgggggaggc | ttggcacagc | ctgggggtc | cctgagactc | 60 |
| tcctgtgcag | cctctggatt | cacctttagc | agctatgcca | tgagctgggt | ccgccaggct | 120 |
| ccagggaagg | ggctggagtg | ggtctcagct | attagtggta | gtggtcgtag | cacatactac | 180 |
| gcagactccg | tgaagggccg | gttcaccatc | tccagagaca | attccaagaa | cacgctgtat | 240 |
| ctgcaaatga | acagcctgag | agccgaggac | gcggccgtgt | attactgtgc | gagggattac | 300 |
| tacctgtatg | attacatcac | ccagacctct | tttgattact | ggggccaagg | taccctggtc | 360 |
| actgtctcca | gt | | | | | 372 |

```
<210> SEQ ID NO 84
<211> LENGTH: 124
<212> TYPE: PRT
<213> ORGANISM: Artificial Sequence
<220> FEATURE:
<223> OTHER INFORMATION: Synthetic: VH39

<400> SEQUENCE: 84
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Arg Ser Thr Tyr Tyr Ala Gly Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Tyr Leu Tyr Asp Tyr Ile Thr Gln Thr Ser Phe Asp
            100                 105                 110

Tyr Trp Gly Gln Gly Thr Leu Val Thr Val Ser Ser
        115                 120

<210> SEQ ID NO 85
<211> LENGTH: 372
<212> TYPE: DNA
<213> ORGANISM: Artificial Sequence
<220> FEATURE:
<223> OTHER INFORMATION: Synthetic: VH39.0

<400> SEQUENCE: 85
gaggtgcagc tggtggagtc tgggggaggc ttggtacagc ctgggggtc cctgagactc      60 tcctgtgcag cctctggatt cacctttagc agctatgcca tgagctgggt ccgccaggct    120
ccagggaagg ggctggagtg ggtctcagct attagtggta gtggtcgtag cacatactac    180
gcaggctccg tgaagggccg gttcaccatc tccagagaca attccaagaa cacgctgtat    240
ctgcaaatga acagcctgag agccgaggac acggccgtgt attactgtgc gagggattac    300
tacctgtatg attacatcac ccagacctct tttgattact ggggccaagg taccctggtc    360
actgtctcca gt                                                        372

<210> SEQ ID NO 86
<211> LENGTH: 124
<212> TYPE: PRT
<213> ORGANISM: Artificial Sequence
<220> FEATURE:
<223> OTHER INFORMATION: Synthetic: VH40

<400> SEQUENCE: 86

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Arg Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
                85                  90                  95

Ala Arg Asp Tyr Tyr Leu Tyr Asp Tyr Ile Thr Gln Thr Ser Phe Asp
            100                 105                 110

Tyr Trp Gly Gln Gly Thr Leu Val Thr Val Ser Ser
        115                 120

<210> SEQ ID NO 87
<211> LENGTH: 372
<212> TYPE: DNA
<213> ORGANISM: Artificial Sequence
<220> FEATURE:
<223> OTHER INFORMATION: Synthetic: VH40.0

<400> SEQUENCE: 87
gaggtgcagc tggtggagtc tgggggaggc ttggtacagc ctgggggtc cctgagactc      60

```
tcctgtgcag cctctggatt cacctttagc agctatgcca tgagctgggt ccgccaggct    120
ccagggaagg ggctggagtg ggtctcagct attagtggta gtggtcgtag cacatactac    180
gcagactccg tgaagggccg gttcaccatc tccagagaca attccaagaa cacgctgtat    240
ctgcaaatga acagcctgag agccgaggac gcggccgtgt attactgtgc gagggattac    300
tacctgtatg attacatcac ccagacctct tttgattact ggggccaagg taccctggtc    360
actgtctcca gt                                                         372
```

<210> SEQ ID NO 88
<211> LENGTH: 125
<212> TYPE: PRT
<213> ORGANISM: Artificial Sequence
<220> FEATURE:
<223> OTHER INFORMATION: Synthetic: VH41

<400> SEQUENCE: 88

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Ser Asp Ser Tyr Tyr Tyr Gly Pro Tyr Tyr Thr Phe
            100                 105                 110

Asp Tyr Trp Gly Gln Gly Thr Leu Val Thr Val Ser Ser
        115                 120                 125
```

<210> SEQ ID NO 89
<211> LENGTH: 375
<212> TYPE: DNA
<213> ORGANISM: Artificial Sequence
<220> FEATURE:
<223> OTHER INFORMATION: Synthetic: VH41.0

<400> SEQUENCE: 89

```
gaggtgcagc tggtggagtc tgggggaggc ttggtacagc ctggggggtc cctgagactc     60
tcctgtgcag cctctggatt cacctttagc agctatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtgt attactgtgc gaggggttac    300
tctgattctt actactacgg tccatactac acctttgatt actggggcca aggtaccctg    360
gtcactgtct ccagt                                                     375
```

<210> SEQ ID NO 90
<211> LENGTH: 125
<212> TYPE: PRT
<213> ORGANISM: Artificial Sequence
<220> FEATURE:
<223> OTHER INFORMATION: Synthetic: VH42

<400> SEQUENCE: 90

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Ser Asp Ser Tyr Tyr Tyr Gly Pro Tyr Tyr Thr Phe
            100                 105                 110

Asp Tyr Trp Gly Gln Gly Thr Leu Val Thr Val Ser Ser
            115                 120                 125

<210> SEQ ID NO 91
<211> LENGTH: 375
<212> TYPE: DNA
<213> ORGANISM: Artificial Sequence
<220> FEATURE:
<223> OTHER INFORMATION: Synthetic: VH42

<400> SEQUENCE: 91
gaggtgcagc tggtggagtc tgggggaggc ttggtacagc ctggggggtc cctgagactc      60
tcctgtgcag cctctggatt cacctttagc agctatgcca tgagctgggt ccgccaggct     120
ccagggaagg gctggagtg gtctcagct attagtggta gtggtggtat cacatactac      180
gcagactccg tgaagggccg gttcaccatc tccagagaca attccaagaa cacgctgtat     240
ctgcaaatga acagcctgag agccgaggac acggccgtgt attactgtgc gaggggttac     300
tctgattctt actactacgg tccttactac acctttgatt actggggcca aggtaccctg     360
gtcactgtct ccagt                                                      375

<210> SEQ ID NO 92
<211> LENGTH: 125
<212> TYPE: PRT
<213> ORGANISM: Artificial Sequence
<220> FEATURE:
<223> OTHER INFORMATION: Synthetic: VH43

<400> SEQUENCE: 92

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Ile Arg Gln Ala Pro Gly Lys Gly Leu Glu Trp Val
        35                  40                  45

Ser Ala Ile Ser Gly Ser Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Ser Asp Ser Tyr Tyr Tyr Gly Pro Tyr Tyr Thr Phe

```
                          100                 105                 110
Asp Tyr Trp Gly Gln Gly Thr Leu Val Thr Val Ser Ser
            115                 120                 125

<210> SEQ ID NO 93
<211> LENGTH: 375
<212> TYPE: DNA
<213> ORGANISM: Artificial Sequence
<220> FEATURE:
<223> OTHER INFORMATION: Synthetic: VH43

<400> SEQUENCE: 93
gaggtgcagc tggtggagtc tgggggaggc ttggtacagc ctgggggtc cctgagactc      60 tcctgtgcag cctctggatt cacctttagc agctatgcca tgagctggat ccgccaggct    120
ccagggaagg ggctggagtg gtctcagct attagtggta gtggtggtag catatactac     180
gcagactccg tgaagggccg gttcaccatc tccagagaca attccaagaa cacgctgtat    240
ctgcaaatga acagcctgag agccgaggac acggccgtgt attactgtgc gaggggttac    300
tctgattctt actactacgg tccatactac acctttgatt actggggcca aggtaccctg    360
gtcactgtct ccagt                                                     375

<210> SEQ ID NO 94
<211> LENGTH: 125
<212> TYPE: PRT
<213> ORGANISM: Artificial Sequence
<220> FEATURE:
<223> OTHER INFORMATION: Synthetic: VH44

<400> SEQUENCE: 94

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Ser Asp Ser Tyr Tyr Tyr Gly Pro Tyr Tyr Thr Phe
            100                 105                 110

Asp Tyr Trp Gly Gln Gly Thr Leu Val Thr Val Ser Ser
            115                 120                 125

<210> SEQ ID NO 95
<211> LENGTH: 375
<212> TYPE: DNA
<213> ORGANISM: Artificial Sequence
<220> FEATURE:
<223> OTHER INFORMATION: Synthetic: VH44.0

<400> SEQUENCE: 95
gaggtgcagc tggtggagtc tgggggaggc ttggtacagc ctgggggtc cctgagactc      60 tcctgtgcag cctctggatt cacctttagc agctatgcca tgagctgggt ccgccaggct    120
ccagggaagg ggctggagtg gtctcagct attagtggta gtggtggtag catatactac     180
```

```
gcagactccg tgaagggccg gttcaccatc tccagagaca attccaagaa cacgctgtat    240
ctgcaaatga acagcctgag agccgaggac acggccgtgt attactgtgc gagggggttac    300 tctgattctt actactacgg tccatactac acctttgatt actggggcca aggtaccctg    360
gtcactgtct ccagt                                                      375
```

```
<210> SEQ ID NO 96
<211> LENGTH: 125
<212> TYPE: PRT
<213> ORGANISM: Artificial Sequence
<220> FEATURE:
<223> OTHER INFORMATION: Synthetic: VH45

<400> SEQUENCE: 96
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ala Tyr Tyr Cys
                85                  90                  95

Ala Arg Gly Tyr Ser Asp Ser Tyr Tyr Tyr Gly Pro Tyr Tyr Thr Phe
            100                 105                 110

Asp Tyr Trp Gly Gln Gly Thr Leu Val Thr Ala Ser Ser
        115                 120                 125

```
<210> SEQ ID NO 97
<211> LENGTH: 375
<212> TYPE: DNA
<213> ORGANISM: Artificial Sequence
<220> FEATURE:
<223> OTHER INFORMATION: Synthetic: VH45.0

<400> SEQUENCE: 97
```

```
gaggtgcagc tggtggagtc tgggggaggc ttggtacagc ctggggggtc cctgagactc    60
tcctgtgcag cctctggatt cacctttagc agctatgcca tgagctgggt ccgccaggct    120
ccagggaagg ggctggagtg ggtctcagcc attagtggta gtggtggtat cacatactac    180
gcagactccg tgaagggccg gttcaccatc tccagagaca attccaagaa cacgctgtat    240
ctgcaaatga acagcctgag agccgaggac acggccgcgt attactgtgc gagggggttac    300 tctgattctt actactacgg tccatactac acctttgatt actggggcca aggtaccctg    360
gtcactgcct ccagt                                                      375
```

```
<210> SEQ ID NO 98
<211> LENGTH: 125
<212> TYPE: PRT
<213> ORGANISM: Artificial Sequence
<220> FEATURE:
<223> OTHER INFORMATION: Synthetic: VH46

<400> SEQUENCE: 98
```

Glu Val Gln Leu Val Glu Ser Gly Gly Gly Leu Val Gln Pro Gly Gly
1               5                   10                  15

```
Ser Leu Arg Leu Ser Cys Ala Ala Ser Gly Phe Thr Phe Ser Ser Tyr
         20                  25                  30

Asp Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
         50                  55                  60

Lys Gly Arg Phe Thr Ile Ser Arg Asp Asn Ser Lys Asn Thr Leu Tyr
 65              70                  75                  80

Leu Gln Met Asp Ser Leu Arg Ala Glu Asp Thr Ala Val Tyr Tyr Cys
                 85                  90                  95

Ala Arg Gly Tyr Ser Asp Ser Tyr Phe Tyr Gly Pro Tyr Tyr Thr Phe
             100                 105                 110

Asp Tyr Trp Gly Gln Gly Thr Leu Val Thr Val Ser Ser
         115                 120                 125
```

<210> SEQ ID NO 99
<211> LENGTH: 375
<212> TYPE: DNA
<213> ORGANISM: Artificial Sequence
<220> FEATURE:
<223> OTHER INFORMATION: Synthetic: VH46.0

<400> SEQUENCE: 99

```
gaggtgcagc tggtggagtc tggggggaggc ttggtacagc ctggggggtc cctgagactc      60
tcctgtgcag cctctggatt cacctttagc agctatgaca tgagctgggt ccgccaggct     120
ccagggaagg gctggagtg gtctcagct attagtggta gtggtggtag cacatactac     180
gcagactccg tgaagggccg gttcaccatc tccagagaca attccaagaa cacgctgtat     240
ctgcaaatgg acagcctgag agccgaggac acggccgtgt attactgtgc gagggggttac     300
tctgattctt acttctacgg tccatactac acctttgatt actggggcca aggtaccctg     360
gtcactgtct ccagt                                                       375
```

<210> SEQ ID NO 100
<211> LENGTH: 375
<212> TYPE: DNA
<213> ORGANISM: Artificial Sequence
<220> FEATURE:
<223> OTHER INFORMATION: Synthetic: VH46.1

<400> SEQUENCE: 100

```
gaggtgcagc tggtggagtc tggggggaggc ttggtacagc ctggggggtc cctgagactc      60
tcctgtgcag cctctggatt cacctttagc agctatgaca tgagctgggt ccgccaggct     120
ccagggaagg gctggagtg gtctcagct attagtggta gtggtggtag cacatactac     180
gcagactccg tgaagggccg gttcaccatc tccagagaca attccaagaa cacgctgtat     240
ctgcaaatgg acagcctgag agccgaggac acggccgtgt attactgtgc gagggggttac     300
tctgattctt acttctacgg tccatactac acctttgact actggggcca aggtaccctg     360
gtcactgtct ccagt                                                       375
```

<210> SEQ ID NO 101
<211> LENGTH: 125
<212> TYPE: PRT
<213> ORGANISM: Artificial Sequence
<220> FEATURE:
<223> OTHER INFORMATION: Synthetic: VH48

<400> SEQUENCE: 101

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Gly Ser Gly Gly Thr Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asp Ser Leu Arg Ala Glu Asp Thr Ala Val Tyr Tyr Cys
                85                  90                  95

Ala Arg Gly Tyr Ser Asp Ser Tyr Phe Tyr Gly Pro Tyr Tyr Thr Phe
            100                 105                 110

Asp Tyr Trp Gly Gln Gly Thr Leu Val Thr Val Ser Ser
        115                 120                 125
```

<210> SEQ ID NO 102
<211> LENGTH: 375
<212> TYPE: DNA
<213> ORGANISM: Artificial Sequence
<220> FEATURE:
<223> OTHER INFORMATION: Synthetic: VH48.0

<400> SEQUENCE: 102

```
gaggtgcagc tggtggagtc tgggggaggc ttggtacagc ctggggggtc cctgagactc      60
tcctgtgcag cctctggatt cacctttagc agctatgaca tgagctgggt ccgccaggct     120
ccagggaagg gctggagtg gtctcagct attagtggta gtggtggtgg cacatactac      180
gcagactccg tgaagggccg gttcaccatc tccagagaca attccaagaa cacgctgtat     240
ctgcaaatgg acagcctgag agccgaggac acggccgtgt attactgtgc gaggggttac     300
tctgattctt acttctacgg tccatactac acctttgatt actggggcca aggtaccctg     360
gtcactgtct ccagt                                                      375
```

<210> SEQ ID NO 103
<211> LENGTH: 125
<212> TYPE: PRT
<213> ORGANISM: Artificial Sequence
<220> FEATURE:
<223> OTHER INFORMATION: Synthetic: VH49

<400> SEQUENCE: 103

```
Glu Val Gln Leu Met Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Ser Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Gly Ala Glu Asp Thr Ala Val Tyr Tyr Cys
                85                  90                  95

Ala Arg Gly Tyr Ser Asp Ser Tyr Phe Tyr Gly Pro Tyr Tyr Thr Phe
            100                 105                 110
```

```
Asp Tyr Trp Gly Gln Gly Thr Leu Val Thr Val Ser Ser
        115                 120                 125
```

<210> SEQ ID NO 104
<211> LENGTH: 375
<212> TYPE: DNA
<213> ORGANISM: Artificial Sequence
<220> FEATURE:
<223> OTHER INFORMATION: Synthetic: VH49.0

<400> SEQUENCE: 104

```
gaggtgcagc tgatggagtc tggggggaggc ttggtacagc ctggggggtc cctgagactc    60
tcctgtgcag cctctggatt caccttttagc agctatgcca tgagctgggt ccgccaggct   120
ccagggaagg ggctggagtg ggtctcagct attagtagta gtggtggtag cacatactac   180
gcagactccg tgaagggccg gttcaccatc tccagagaca attccaagaa cacgctgtat   240
ctgcaaatgg acagcctggg agccgaggac acggccgtgt attactgtgc gagggggttac   300 tctgattctt acttctacgg cccatactac acctttgatt actggggcca aggtaccctg   360
gtcactgtct ccagt                                                   375
```

<210> SEQ ID NO 105
<211> LENGTH: 125
<212> TYPE: PRT
<213> ORGANISM: Artificial Sequence
<220> FEATURE:
<223> OTHER INFORMATION: Synthetic: VH50

<400> SEQUENCE: 105

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Ile Arg Gln Ala Pro Gly Lys Gly Leu Glu Trp Val
        35                  40                  45

Ser Ala Ile Ser Gly Ser Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Ser Asp Ser Tyr Phe Tyr Gly Pro Tyr Tyr Thr Phe
            100                 105                 110

Asp Tyr Trp Gly Gln Gly Thr Leu Val Thr Val Ser Ser
        115                 120                 125
```

<210> SEQ ID NO 106
<211> LENGTH: 375
<212> TYPE: DNA
<213> ORGANISM: Artificial Sequence
<220> FEATURE:
<223> OTHER INFORMATION: Synthetic: VH50.0

<400> SEQUENCE: 106

```
gaggtgcagc tggtggagtc tggggggaggc ttggtacagc ctggggggtc cctgagactc    60
tcctgtgcag cctctggatt caccttttagc agctatgcca tgagctggat ccgccaggct   120
ccagggaagg ggctggagtg ggtctcagct attagtggta gtggtggtag catatactac   180
gcagactccg tgaagggccg gttcaccatc tccagagaca attccaagaa cacgctgtat   240
```

```
ctgcaaatga acagcctgag agccgaggac acggccgtgt attactgtgc gaggggttac    300
tctgattctt acttctacgg tccatactac acctttgatt actggggcca aggtaccctg    360
gtcactgtct ccagt                                                     375
```

<210> SEQ ID NO 107
<211> LENGTH: 125
<212> TYPE: PRT
<213> ORGANISM: Artificial Sequence
<220> FEATURE:
<223> OTHER INFORMATION: Synthetic: VH51

<400> SEQUENCE: 107

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Thr Ser Arg Asp Asn Ser Lys Asn Thr Leu Tyr
65                  70                  75                  80

Leu Gln Met Asp Ser Leu Arg Ala Glu Asp Thr Ala Val Tyr Tyr Cys
                85                  90                  95

Ala Arg Gly Tyr Ser Asp Ser Tyr Phe Tyr Gly Pro Tyr Tyr Thr Phe
            100                 105                 110

Asp Tyr Trp Gly Gln Gly Thr Leu Val Thr Val Ser Ser
        115                 120                 125
```

<210> SEQ ID NO 108
<211> LENGTH: 375
<212> TYPE: DNA
<213> ORGANISM: Artificial Sequence
<220> FEATURE:
<223> OTHER INFORMATION: Synthetic: VH51.0

<400> SEQUENCE: 108

```
gaggtgcagc tggtggagtc tgggggaggc ttggtacagc ctggggggtc cctgagactc    60
tcctgtgcag cctctggatt cacctttagc agctatgcca tgagctgggt ccgccaggct    120
ccagggaagg ggctggagtg ggtctcagct attagtggta gtggtggtag cacatactac    180
gcagactccg tgaagggccg gttcaccacc tccagagaca attccaagaa cacgctgtat    240
ctgcaaatgg acagcctgag agccgaggac acggccgtgt attactgtgc gaggggttac    300
tctgattctt acttctacgg tccatactac acctttgatt actggggcca aggtaccctg    360
gtcactgtct ccagt                                                     375
```

<210> SEQ ID NO 109
<211> LENGTH: 125
<212> TYPE: PRT
<213> ORGANISM: Artificial Sequence
<220> FEATURE:
<223> OTHER INFORMATION: Synthetic: VH52

<400> SEQUENCE: 109

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

Ala Met Ser Trp Val Arg Gln Ala Pro Gly Glu Gly Leu Glu Trp Val
            35                  40                  45

Ser Ala Ile Ser Ser Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asp Ser Leu Arg Ala Glu Asp Thr Ala Val Tyr Tyr Cys
                85                  90                  95

Ala Arg Gly Tyr Ser Asp Ser Tyr Phe Tyr Gly Pro Tyr Tyr Thr Phe
            100                 105                 110

Asp Tyr Trp Gly Gln Gly Thr Leu Val Thr Ala Ser Ser
        115                 120                 125

<210> SEQ ID NO 110
<211> LENGTH: 375
<212> TYPE: DNA
<213> ORGANISM: Artificial Sequence
<220> FEATURE:
<223> OTHER INFORMATION: Synthetic: VH52.0

<400> SEQUENCE: 110
gaggtgcagc tggtggagtc tgggggaggc ttggtacagc ctggggggtc cctgagactc      60
tcctgtgcag cctctggatt cacctttagc agctatgcca tgagctgggt ccgccaggct     120
ccaggggagg ggctggagtg ggtctcagct attagtagta gtggtggtag cacgtactat     180
gcagactccg tgaagggccg gttcaccatc tccagagaca attccaagaa cacgctgtat     240
ctgcaaatgg acagcctgag agccgaggac acggccgtgt attactgtgc gagggggttac     300 tctgattctt acttctacgg tccatactac acctttgatt actggggcca aggtaccctg     360
gtcactgcct ccagt                                                      375

<210> SEQ ID NO 111
<211> LENGTH: 125
<212> TYPE: PRT
<213> ORGANISM: Artificial Sequence
<220> FEATURE:
<223> OTHER INFORMATION: Synthetic: VH53

<400> SEQUENCE: 111

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Ile
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Gly Tyr Ser Asp Ser Tyr Tyr Gly Pro Tyr Tyr Thr Phe
            100                 105                 110

Asp Tyr Trp Gly Gln Gly Thr Leu Val Thr Val Ser Ser
        115                 120                 125

<210> SEQ ID NO 112

<211> LENGTH: 375
<212> TYPE: DNA
<213> ORGANISM: Artificial Sequence
<220> FEATURE:
<223> OTHER INFORMATION: Synthetic: VH53.0

<400> SEQUENCE: 112

| | |
|---|---|
| gaggtgcagc tggtggagtc tgggggaggc ttggtacagc ctggggggtc cctgagactc | 60 |
| tcctgtgcag cctctggatt cacctttagc agctatgaca tgagctgggt ccgccaggct | 120 |
| ccagggaagg ggctggagtg gatctcagct attagtggta gtggtggtag cacatactac | 180 |
| gcagactccg tgaagggccg gttcaccatc tccagagaca attccaagaa cacgctgtat | 240 |
| ctgcaaatga acagcctgag agccgaggac acggccgtgt attactgtgc gagggggttac | 300 |
| tctgattctt actactacgg tccatactac acctttgatt actggggcca aggtaccctg | 360 |
| gtcactgtct ccagt | 375 |

<210> SEQ ID NO 113
<211> LENGTH: 125
<212> TYPE: PRT
<213> ORGANISM: Artificial Sequence
<220> FEATURE:
<223> OTHER INFORMATION: Synthetic: VH54

<400> SEQUENCE: 113

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Ile Arg Gln Ala Pro Gly Lys Gly Leu Glu Trp Val
        35                  40                  45

Ser Ala Ile Ser Gly Ser Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Tyr Cys
                85                  90                  95

Ala Arg Gly Tyr Ser Asp Ser Tyr Phe Tyr Gly Pro Tyr Tyr Thr Phe
            100                 105                 110

Asp Tyr Trp Gly Gln Gly Thr Leu Val Thr Val Ser Ser
        115                 120                 125

<210> SEQ ID NO 114
<211> LENGTH: 375
<212> TYPE: DNA
<213> ORGANISM: Artificial Sequence
<220> FEATURE:
<223> OTHER INFORMATION: Synthetic: VH54.0

<400> SEQUENCE: 114

| | |
|---|---|
| gaggtgcagc tggtggagtc tgggggaggc ttggtacagc ctggggggtc cctgagactc | 60 |
| tcctgtgcag cctctggatt cacctttagc agctatgcca tgagctggat ccgccaggct | 120 |
| ccagggaagg ggctggagtg ggtctcagct attagtggta gtggtggtag catatactac | 180 |
| gcagactccg tgaagggccg gttcaccatc tccagagaca attccaagaa cacgctgtat | 240 |
| ctgcaaatgg acagcctgag agccgaggac acggccgtgt attactgtgc gagggggttac | 300 |
| tctgattctt acttctacgg tccatactac acctttgatt actggggcca aggtaccctg | 360 |
| gtcactgtct ccagt | 375 |

<210> SEQ ID NO 115
<211> LENGTH: 125
<212> TYPE: PRT
<213> ORGANISM: Artificial Sequence
<220> FEATURE:
<223> OTHER INFORMATION: Synthetic: VH55

<400> SEQUENCE: 115

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Ile Arg Gln Ala Pro Gly Lys Gly Leu Glu Trp Ile
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Ser Asp Ser Tyr Tyr Tyr Gly Pro Tyr Tyr Thr Phe
            100                 105                 110

Asp Tyr Trp Gly Gln Gly Thr Leu Val Thr Val Ser Ser
        115                 120                 125
```

<210> SEQ ID NO 116
<211> LENGTH: 375
<212> TYPE: DNA
<213> ORGANISM: Artificial Sequence
<220> FEATURE:
<223> OTHER INFORMATION: Synthetic: VH55.0

<400> SEQUENCE: 116

```
gaggtgcagc tggtggagtc tgggggaggc ttggtacagc ctggggggtc cctgagactc      60
tcctgtgcag cctctggatt cacctttagc agctatgcca tgagctggat ccgccaggct     120
ccagggaagg ggctggagtg gatctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtgt attactgtgc gaggggttac     300
tctgattctt actactacgg tccatactac acctttgatt actggggcca aggtaccctg     360
gtcactgtct ccagt                                                      375
```

<210> SEQ ID NO 117
<211> LENGTH: 125
<212> TYPE: PRT
<213> ORGANISM: Artificial Sequence
<220> FEATURE:
<223> OTHER INFORMATION: Synthetic: VH56

<400> SEQUENCE: 117

```
Glu Val Gln Leu Val Glu Ser Gly Gly Gly Leu Val Gln Pro Gly Gly
1               5                   10                  15

Ser Leu Arg Leu Pro Cys Ala Ala Ser Gly Phe Thr Phe Ser Ser Tyr
            20                  25                  30

Ala Met Ser Trp Ile Arg Gln Ala Pro Gly Lys Gly Leu Glu Trp Val
        35                  40                  45

Ser Ala Ile Ser Gly Ser Gly Gly Ser Ile Tyr Tyr Ala Asp Ser Val
```

```
                    50                  55                  60
Lys Gly Arg Phe Thr Ile Ser Arg Asp Asn Ser Lys Asn Thr Leu Tyr
 65                  70                  75                  80

Leu Gln Met Asp Ser Leu Arg Ala Glu Asp Thr Ala Val Tyr Tyr Cys
                 85                  90                  95

Ala Arg Gly Tyr Ser Asp Ser Tyr Phe Tyr Gly Pro Tyr Tyr Thr Phe
             100                 105                 110

Asp Tyr Trp Gly Gln Gly Thr Leu Val Thr Val Ser Ser
         115                 120                 125

<210> SEQ ID NO 118
<211> LENGTH: 375
<212> TYPE: DNA
<213> ORGANISM: Artificial Sequence
<220> FEATURE:
<223> OTHER INFORMATION: Synthetic: VH56.0

<400> SEQUENCE: 118
gaggtgcagc tggtggagtc tgggggaggc ttggtacagc ctggggggtc cctgagactc        60
ccctgtgcag cctctggatt cacctttagc agctatgcca tgagctggat ccgccaggct       120
ccagggaagg gctggagtg gtctcagct attagtggta gtggtggtag catatactac         180
gcagactccg tgaagggccg gttcaccatc tccagagaca attccaagaa cacgctgtat       240
ctgcaaatgg acagcctgag agccgaggac acggccgtgt attactgtgc gaggggttac       300
tctgattctt acttctacgg tccatactac acctttgatt actggggcca aggtaccctg       360
gtcactgtct ccagt                                                        375

<210> SEQ ID NO 119
<211> LENGTH: 125
<212> TYPE: PRT
<213> ORGANISM: Artificial Sequence
<220> FEATURE:
<223> OTHER INFORMATION: Synthetic: VH57

<400> SEQUENCE: 119

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Ile Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asp Ser Leu Arg Ala Glu Asp Thr Ala Val Tyr Tyr Cys
                 85                  90                  95

Ala Arg Gly Tyr Ser Asp Ser Tyr Phe Tyr Gly Pro Tyr Tyr Thr Phe
             100                 105                 110

Asp Tyr Trp Gly Gln Gly Thr Leu Val Thr Val Ser Ser
         115                 120                 125

<210> SEQ ID NO 120
<211> LENGTH: 375
<212> TYPE: DNA
<213> ORGANISM: Artificial Sequence
<220> FEATURE:
<223> OTHER INFORMATION: Synthetic: VH57.0
```

```
<400> SEQUENCE: 120
gaggtgcagc tggtggagtc tgggggaggc ttggtacagc ctgggggtc cctgagactc      60 tcctgtgcag cctctggatt cacctttagc agctatgcca tgagctgggt ccgccaggct    120
ccagggaagg ggctggagtg ggtctcagct attagtggta gtggtggtag catatactac    180
gcagactccg tgaagggccg gttcaccatc tccagagaca attccaagaa cacgctgtat    240
ctgcaaatgg acagcctgag agccgaggac acggccgtgt attactgtgc gaggggttac    300
tctgattctt acttctacgg tccatactac acctttgact actggggcca aggtaccctg    360
gtcactgtct ccagt                                                     375

<210> SEQ ID NO 121
<211> LENGTH: 125
<212> TYPE: PRT
<213> ORGANISM: Artificial Sequence
<220> FEATURE:
<223> OTHER INFORMATION: Synthetic: VH58

<400> SEQUENCE: 121

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Ile Arg Gln Ala Pro Gly Arg Gly Leu Glu Trp Val
        35                  40                  45

Ser Ala Ile Ser Gly Ser Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Ser Asp Ser Tyr Phe Tyr Gly Pro Tyr Tyr Thr Phe
            100                 105                 110

Asp Tyr Trp Gly Gln Gly Thr Leu Val Thr Val Ser Ser
        115                 120                 125

<210> SEQ ID NO 122
<211> LENGTH: 375
<212> TYPE: DNA
<213> ORGANISM: Artificial Sequence
<220> FEATURE:
<223> OTHER INFORMATION: Synthetic: VH58.0

<400> SEQUENCE: 122
gaggtgcagc tggtggagtc tgggggaggc ttggtacagc ctgggggtc cctgagactc      60 tcctgtgcag cctctggatt cacctttagc agctatgcca tgagctggat ccgccaggct    120
ccagggaggg ggctggagtg ggtctcagct attagtggta gtggtggtag catatactac    180
gcagactccg tgaagggccg gttcaccatc tccagagaca attccaagaa cacgctgtat    240
ctgcaaatga acagcctgag agccgaggac acggccgtgt attactgtgc gaggggttac    300
tctgattctt acttctacgg tccatactac acctttgatt actggggcca aggtaccctg    360
gtcactgtct ccagt                                                     375

<210> SEQ ID NO 123
<211> LENGTH: 125
<212> TYPE: PRT
```

<213> ORGANISM: Artificial Sequence
<220> FEATURE:
<223> OTHER INFORMATION: Synthetic: VH59

<400> SEQUENCE: 123

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Ile Arg Gln Ala Pro Gly Lys Gly Leu Glu Trp Val
        35                  40                  45

Ser Ala Ile Ser Gly Ser Gly Gly Ser Ile Tyr Tyr Ala Asp Ser Val
    50                  55                  60

Lys Gly Arg Phe Thr Ile Ser Arg Asp Asn Pro Lys Asn Thr Leu Tyr
65                  70                  75                  80

Leu Gln Met Asp Ser Leu Arg Ala Glu Asp Ala Ala Val Tyr Tyr Cys
                85                  90                  95

Ala Arg Gly Tyr Ser Asp Ser Tyr Phe Tyr Gly Pro Tyr Tyr Thr Phe
            100                 105                 110

Asp Tyr Trp Gly Gln Gly Thr Leu Val Thr Val Ser Ser
        115                 120                 125
```

<210> SEQ ID NO 124
<211> LENGTH: 375
<212> TYPE: DNA
<213> ORGANISM: Artificial Sequence
<220> FEATURE:
<223> OTHER INFORMATION: Synthetic: VH59.0

<400> SEQUENCE: 124

```
gaggtgcagc tggtggagtc tgggggaggc ttggtacagc ctggggggtc cctgagactc      60
tcctgtgcag cctctggatt cacctttagc agctatgcca tgagctggat ccgccaggct     120
ccagggaagg gctggagtg gtctcagct attagtggta gtggtggtag catatactac       180
gcagactccg tgaagggccg gttcaccatc tccagagaca atcccaagaa cacgctgtat     240
ctgcaaatgg acagcctgag agccgaggac gcggccgtgt attactgtgc gagggggttac    300 tctgattctt acttctacgg tccatactac acctttgatt actggggcca aggtaccctg     360
gtcactgtct ccagt                                                      375
```

<210> SEQ ID NO 125
<211> LENGTH: 125
<212> TYPE: PRT
<213> ORGANISM: Artificial Sequence
<220> FEATURE:
<223> OTHER INFORMATION: Synthetic: VH60

<400> SEQUENCE: 125

```
Glu Val Gln Leu Val Glu Ser Gly Gly Gly Leu Val Gln Pro Gly Gly
1               5                   10                  15

Ser Leu Arg Leu Pro Cys Ala Ala Ser Gly Phe Thr Phe Ser Ser Tyr
            20                  25                  30

Ala Met Ser Trp Ile Arg Gln Ala Pro Gly Lys Gly Leu Glu Trp Val
        35                  40                  45

Ser Ala Ile Ser Gly Ser Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asp Ser Leu Arg Ala Glu Asp Thr Ala Met Tyr Tyr Cys
                85                  90                  95

Ala Arg Gly Tyr Ser Asp Ser Tyr Phe Tyr Gly Pro Tyr Tyr Thr Phe
            100                 105                 110

Asp Tyr Trp Gly Gln Gly Thr Leu Val Thr Val Ser Ser
        115                 120                 125

<210> SEQ ID NO 126
<211> LENGTH: 375
<212> TYPE: DNA
<213> ORGANISM: Artificial Sequence
<220> FEATURE:
<223> OTHER INFORMATION: Synthetic: VH60.0

<400> SEQUENCE: 126
gaggtgcagc tggtggagtc tgggggaggc ttggtacagc ctgggggtc cctgagactc       60 ccctgtgcag cctctggatt cacctttagc agctatgcca tgagctggat ccgccaggct     120
ccagggaagg gctggagtg gtctcagct attagtggta gtggtggtag catatactac       180
gcagactccg tgaagggccg gttcaccatc tccagagaca attccaagaa cacgctgtat    240
ctgcaaatgg acagcctgag agccgaggac acggccatgt attactgtgc gaggggttac   300
tctgattctt acttctacgg tccatactac acctttgatt actggggcca aggtaccctg   360
gtcactgtct ccagt                                                     375

<210> SEQ ID NO 127
<211> LENGTH: 8
<212> TYPE: PRT
<213> ORGANISM: Artificial Sequence
<220> FEATURE:
<223> OTHER INFORMATION: Synthetic: VH CDR1.1

<400> SEQUENCE: 127

Gly Phe Thr Phe Ser Ser Tyr Ala
1               5

<210> SEQ ID NO 128
<211> LENGTH: 8
<212> TYPE: PRT
<213> ORGANISM: Artificial Sequence
<220> FEATURE:
<223> OTHER INFORMATION: Synthetic: VH CDR1.2

<400> SEQUENCE: 128

Gly Phe Pro Phe Ser Ser Tyr Ala
1               5

<210> SEQ ID NO 129
<211> LENGTH: 8
<212> TYPE: PRT
<213> ORGANISM: Artificial Sequence
<220> FEATURE:
<223> OTHER INFORMATION: Synthetic: VH CDR1.3

<400> SEQUENCE: 129

Gly Ser Thr Phe Ser Ser Tyr Ala
1               5

<210> SEQ ID NO 130
<211> LENGTH: 8
<212> TYPE: PRT
<213> ORGANISM: Artificial Sequence
<220> FEATURE:
<223> OTHER INFORMATION: Synthetic: VH CDR1.5
```

```
<400> SEQUENCE: 130

Gly Phe Ala Phe Ile Ser Tyr Ala
1               5

<210> SEQ ID NO 131
<211> LENGTH: 8
<212> TYPE: PRT
<213> ORGANISM: Artificial Sequence
<220> FEATURE:
<223> OTHER INFORMATION: Synthetic: VH CDR1.6

<400> SEQUENCE: 131

Gly Phe Thr Phe Ser Ser Tyr Asp
1               5

<210> SEQ ID NO 132
<211> LENGTH: 8
<212> TYPE: PRT
<213> ORGANISM: Artificial Sequence
<220> FEATURE:
<223> OTHER INFORMATION: Synthetic: VH CDR2.1

<400> SEQUENCE: 132

Ile Ser Gly Ser Gly Gly Ser Thr
1               5

<210> SEQ ID NO 133
<211> LENGTH: 8
<212> TYPE: PRT
<213> ORGANISM: Artificial Sequence
<220> FEATURE:
<223> OTHER INFORMATION: Synthetic: VH CDR2.2

<400> SEQUENCE: 133

Thr Ser Gly Ser Gly Gly Ser Thr
1               5

<210> SEQ ID NO 134
<211> LENGTH: 8
<212> TYPE: PRT
<213> ORGANISM: Artificial Sequence
<220> FEATURE:
<223> OTHER INFORMATION: Synthetic: VH CDR2.3

<400> SEQUENCE: 134

Ile Ser Gly Ser Gly Gly Arg Thr
1               5

<210> SEQ ID NO 135
<211> LENGTH: 8
<212> TYPE: PRT
<213> ORGANISM: Artificial Sequence
<220> FEATURE:
<223> OTHER INFORMATION: Synthetic: VH CDR2.4

<400> SEQUENCE: 135

Ile Ser Gly Ser Gly Gly Ser Ala
1               5

<210> SEQ ID NO 136
<211> LENGTH: 8
<212> TYPE: PRT
<213> ORGANISM: Artificial Sequence
<220> FEATURE:
<223> OTHER INFORMATION: Synthetic: VH CDR2.5
```

```
<400> SEQUENCE: 136

Ile Ser Gly Ser Gly Arg Ser Thr
1               5

<210> SEQ ID NO 137
<211> LENGTH: 8
<212> TYPE: PRT
<213> ORGANISM: Artificial Sequence
<220> FEATURE:
<223> OTHER INFORMATION: Synthetic: VH CDR2.6

<400> SEQUENCE: 137

Ile Ser Gly Ser Gly Gly Ile Thr
1               5

<210> SEQ ID NO 138
<211> LENGTH: 8
<212> TYPE: PRT
<213> ORGANISM: Artificial Sequence
<220> FEATURE:
<223> OTHER INFORMATION: Synthetic: VH CDR2.7

<400> SEQUENCE: 138

Ile Ser Gly Ser Gly Gly Ser Ile
1               5

<210> SEQ ID NO 139
<211> LENGTH: 8
<212> TYPE: PRT
<213> ORGANISM: Artificial Sequence
<220> FEATURE:
<223> OTHER INFORMATION: Synthetic: VH CDR2.8

<400> SEQUENCE: 139

Ile Ser Gly Ser Gly Gly Gly Thr
1               5

<210> SEQ ID NO 140
<211> LENGTH: 8
<212> TYPE: PRT
<213> ORGANISM: Artificial Sequence
<220> FEATURE:
<223> OTHER INFORMATION: Synthetic: VH CDR2.9

<400> SEQUENCE: 140

Ile Ser Ser Ser Gly Gly Ser Thr
1               5

<210> SEQ ID NO 141
<211> LENGTH: 12
<212> TYPE: PRT
<213> ORGANISM: Artificial Sequence
<220> FEATURE:
<223> OTHER INFORMATION: Synthetic: VH CDR3.1

<400> SEQUENCE: 141

Ala Arg Gly Gly Leu Ile Pro Ser Gly Phe Asp Tyr
1               5                   10

<210> SEQ ID NO 142
<211> LENGTH: 12
<212> TYPE: PRT
<213> ORGANISM: Artificial Sequence
<220> FEATURE:
<223> OTHER INFORMATION: Synthetic: VH CDR3.2

<400> SEQUENCE: 142
```

Ala Arg Gly Gly Leu Ile Pro Ser Gly Phe Gly Tyr
1               5                   10

<210> SEQ ID NO 143
<211> LENGTH: 12
<212> TYPE: PRT
<213> ORGANISM: Artificial Sequence
<220> FEATURE:
<223> OTHER INFORMATION: Synthetic: VH CDR3.3

<400> SEQUENCE: 143

Ala Arg Gly Gly Tyr Leu Pro Asp Ala Phe Asp Tyr
1               5                   10

<210> SEQ ID NO 144
<211> LENGTH: 17
<212> TYPE: PRT
<213> ORGANISM: Artificial Sequence
<220> FEATURE:
<223> OTHER INFORMATION: Synthetic: VH CDR3.4

<400> SEQUENCE: 144

Ala Arg Gly Pro Gly Asp Met Tyr Leu Tyr Gly Asp Ser Phe Phe Asp
1               5                   10                  15

Tyr

<210> SEQ ID NO 145
<211> LENGTH: 17
<212> TYPE: PRT
<213> ORGANISM: Artificial Sequence
<220> FEATURE:
<223> OTHER INFORMATION: Synthetic: VH CDR3.5

<400> SEQUENCE: 145

Ala Arg Gly Pro Gly Tyr Met Tyr Leu Tyr Gly Asp Ser Phe Phe Asp
1               5                   10                  15

Tyr

<210> SEQ ID NO 146
<211> LENGTH: 17
<212> TYPE: PRT
<213> ORGANISM: Artificial Sequence
<220> FEATURE:
<223> OTHER INFORMATION: Synthetic: VH CDR3.6

<400> SEQUENCE: 146

Ala Arg Gly Pro Gly Tyr Met Tyr Leu Tyr Gly Asp Ser Phe Phe Glu
1               5                   10                  15

Tyr

<210> SEQ ID NO 147
<211> LENGTH: 17
<212> TYPE: PRT
<213> ORGANISM: Artificial Sequence
<220> FEATURE:
<223> OTHER INFORMATION: Synthetic: VH CDR3.6

<400> SEQUENCE: 147

Ala Arg Asp Tyr Tyr Leu Ser Asp Tyr Ile Thr Gln Thr Ser Phe Asp
1               5                   10                  15

Tyr

<210> SEQ ID NO 148

```
<211> LENGTH: 17
<212> TYPE: PRT
<213> ORGANISM: Artificial Sequence
<220> FEATURE:
<223> OTHER INFORMATION: Synthetic: VH CDR3.7

<400> SEQUENCE: 148

Ala Arg Asp Tyr Tyr Leu Phe Asp Tyr Ile Thr Gln Thr Ser Phe Asp
1               5                   10                  15
Tyr

<210> SEQ ID NO 149
<211> LENGTH: 17
<212> TYPE: PRT
<213> ORGANISM: Artificial Sequence
<220> FEATURE:
<223> OTHER INFORMATION: Synthetic: VH CDR3.8

<400> SEQUENCE: 149

Ala Arg Asp Tyr Tyr Leu Tyr Asp Tyr Ile Thr Gln Thr Ser Phe Asp
1               5                   10                  15
Tyr

<210> SEQ ID NO 150
<211> LENGTH: 18
<212> TYPE: PRT
<213> ORGANISM: Artificial Sequence
<220> FEATURE:
<223> OTHER INFORMATION: Synthetic: VH CDR3.9

<400> SEQUENCE: 150

Ala Arg Gly Tyr Ser Asp Ser Tyr Tyr Gly Pro Tyr Tyr Thr Phe
1               5                   10                  15
Asp Tyr

<210> SEQ ID NO 151
<211> LENGTH: 18
<212> TYPE: PRT
<213> ORGANISM: Artificial Sequence
<220> FEATURE:
<223> OTHER INFORMATION: Synthetic: VH CDR3.10

<400> SEQUENCE: 151

Ala Arg Gly Tyr Ser Asp Ser Tyr Phe Tyr Gly Pro Tyr Tyr Thr Phe
1               5                   10                  15
Asp Tyr

<210> SEQ ID NO 152
<211> LENGTH: 107
<212> TYPE: PRT
<213> ORGANISM: Artificial Sequence
<220> FEATURE:
<223> OTHER INFORMATION: Synthetic: VL1

<400> SEQUENCE: 152

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60
```

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys
            100                 105

<210> SEQ ID NO 153
<211> LENGTH: 321
<212> TYPE: DNA
<213> ORGANISM: Artificial Sequence
<220> FEATURE:
<223> OTHER INFORMATION: Synthetic: VL1.0

<400> SEQUENCE: 153
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta ccccgctcac gttcggccaa   300
gggaccaagg tggaaatcaa a                                              321

<210> SEQ ID NO 154
<211> LENGTH: 321
<212> TYPE: DNA
<213> ORGANISM: Artificial Sequence
<220> FEATURE:
<223> OTHER INFORMATION: Synthetic: VL1.4

<400> SEQUENCE: 154
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcagcag agttacagta ccccgctcac gttcggccaa   300
gggaccaagg tggaaatcaa a                                              321

<210> SEQ ID NO 155
<211> LENGTH: 107
<212> TYPE: PRT
<213> ORGANISM: Artificial Sequence
<220> FEATURE:
<223> OTHER INFORMATION: Synthetic: VL2

<400> SEQUENCE: 155

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Gly Thr Pro Leu
                85                  90                  95

Thr Phe Gly Gln Gly Thr Lys Val Glu Ile Lys
            100                 105

<210> SEQ ID NO 156
<211> LENGTH: 321
<212> TYPE: DNA
<213> ORGANISM: Artificial Sequence
<220> FEATURE:
<223> OTHER INFORMATION: Synthetic: VL2.0

<400> SEQUENCE: 156
gacatccaga tgacccagtc tccatcctcc ctgtccgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagatttcg caacttacta ctgtcaacag agttacggta ccccgctcac gttcggccaa   300
gggaccaagg tggaaatcaa a                                             321

<210> SEQ ID NO 157
<211> LENGTH: 107
<212> TYPE: PRT
<213> ORGANISM: Artificial Sequence
<220> FEATURE:
<223> OTHER INFORMATION: Synthetic: VL3

<400> SEQUENCE: 157

Gly Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Thr Pro Leu
                85                  90                  95

Thr Phe Gly Gln Gly Thr Lys Val Glu Ile Lys
            100                 105

<210> SEQ ID NO 158
<211> LENGTH: 321
<212> TYPE: DNA
<213> ORGANISM: Artificial Sequence
<220> FEATURE:
<223> OTHER INFORMATION: Synthetic: VL3.0

<400> SEQUENCE: 158
ggcatccaga tgacccagtc tccatcctcc ctgtctgcat ctgtaggaga cagagttacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240 gaagatttg caacttacta ctgtcaacag acgtacagta ccccgctcac gttcggccaa   300
gggaccaagg tggaaatcaa a                                              321

<210> SEQ ID NO 159
<211> LENGTH: 321
<212> TYPE: DNA
<213> ORGANISM: Artificial Sequence
<220> FEATURE:
<223> OTHER INFORMATION: Synthetic: VL3.1

<400> SEQUENCE: 159
ggcatccaga tgacccagtc tccatcctcc ctgtctgcat ctgtaggaga cagagtcacc       60
atcacttgcc gggcaagtca gagcattagc agctatttaa attggtatca gcagaaacca      120
gggaaagccc ctaagctcct gatctatgct gcatccagtt tgcaaagtgg ggtcccatca      180
aggttcagtg gcagtggatc tgggacagat ttcactctca ccatcagcag tctgcaacct      240
gaagattttg caacttacta ctgtcaacag acgtacagta ccccgctcac gttcggccaa      300
gggaccaagg tggaaatcaa a                                              321

<210> SEQ ID NO 160
<211> LENGTH: 107
<212> TYPE: PRT
<213> ORGANISM: Artificial Sequence
<220> FEATURE:
<223> OTHER INFORMATION: Synthetic: VL4

<400> SEQUENCE: 160

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Thr Pro Leu
                85                  90                  95

Thr Phe Gly Gln Gly Thr Lys Val Glu Ile Lys
            100                 105

<210> SEQ ID NO 161
<211> LENGTH: 321
<212> TYPE: DNA
<213> ORGANISM: Artificial Sequence
<220> FEATURE:
<223> OTHER INFORMATION: Synthetic: VL4.0

<400> SEQUENCE: 161
gacatccaga tgacccagtc tccatcctcc ctgtctgcat ctgtaggaga cagagtcacc       60
atcacttgcc gggcaagtca gagcattagc agctatttaa attggtatca gcagaaacca      120
gggaaagccc ctaagctcct gatctatgct gcatccagtt tgcaaagtgg ggtcccatca      180
aggttcagtg gcagtggatc tgggacagat ttcactctca ccatcagcag tctgcaacct      240
gaagattttg caacttacta ctgtcaacag acgtacagta ccccgctcac gttcggccaa      300
gggaccaagg tggaaatcaa a                                              321

<210> SEQ ID NO 162

```
<211> LENGTH: 107
<212> TYPE: PRT
<213> ORGANISM: Artificial Sequence
<220> FEATURE:
<223> OTHER INFORMATION: Synthetic: VL5

<400> SEQUENCE: 162

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Thr Pro Leu
                85                  90                  95

Thr Phe Gly Gln Gly Thr Lys Val Glu Ile Lys
            100                 105

<210> SEQ ID NO 163
<211> LENGTH: 321
<212> TYPE: DNA
<213> ORGANISM: Artificial Sequence
<220> FEATURE:
<223> OTHER INFORMATION: Synthetic: VL5.0

<400> SEQUENCE: 163
gacatccaga tgacccagtc tccatcctcc ctgtctgcat ctgtaggaga cagagtcacc      60
atcacttgcc gggcaagtca gagcattagc agctatttaa attggtatca gcagaaacca    120
gggaaagccc ctaagctcct gatctatgct gcatccagtt tgcaaagtgg gatcccatca    180
aggttcagtg gcagtggatc tgggacagat ttcactctca ccatcagcag tctgcaacct    240
gaggattttg caacttacta ctgtcaacag acgtacagta ccccgctcac gttcggccaa    300
gggaccaagg tggaaatcaa a                                              321

<210> SEQ ID NO 164
<211> LENGTH: 321
<212> TYPE: DNA
<213> ORGANISM: Artificial Sequence
<220> FEATURE:
<223> OTHER INFORMATION: Synthetic: VL5.1

<400> SEQUENCE: 164
gacatccaga tgacccagtc tccatcctcc ctgtctgcat ctgtaggaga cagagtcacc      60
atcacttgcc gggcaagcca gagcattagc agctatttaa attggtatca gcagaaacca    120
gggaaagccc ctaagctcct gatctatgct gcatccagtt tgcaaagtgg gatcccatca    180
aggttcagtg gcagtggatc tgggacagat ttcactctca ccatcagcag tctgcaacct    240
gaagattttg caacttacta ctgtcaacag acgtacagta ccccgctcac gttcggccaa    300
gggaccaagg tggaaatcaa a                                              321

<210> SEQ ID NO 165
<211> LENGTH: 107
<212> TYPE: PRT
<213> ORGANISM: Artificial Sequence
<220> FEATURE:
```

<223> OTHER INFORMATION: Synthetic: VL6

<400> SEQUENCE: 165

```
Asp Ile Gln Met Thr Gln Ser Pro Ser Ser Pro Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Leu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Thr Pro Leu
                85                  90                  95

Thr Phe Gly Gln Gly Thr Lys Val Glu Ile Lys
            100                 105
```

<210> SEQ ID NO 166
<211> LENGTH: 321
<212> TYPE: DNA
<213> ORGANISM: Artificial Sequence
<220> FEATURE:
<223> OTHER INFORMATION: Synthetic: VL6.0

<400> SEQUENCE: 166

```
gacatccaga tgacccagtc tccatcctcc ccgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgctaagtgg ggtcccatca   180
aggttcagtg gcagtggatc tgggacagat ttcactctca ccatcagcag tctgcaacct   240
gaagattttg caacttacta ctgtcaacag acgtacagta ccccgctcac gttcggccaa   300
gggaccaagg tggaaatcaa a                                             321
```

<210> SEQ ID NO 167
<211> LENGTH: 107
<212> TYPE: PRT
<213> ORGANISM: Artificial Sequence
<220> FEATURE:
<223> OTHER INFORMATION: Synthetic: VL7

<400> SEQUENCE: 167

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Leu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Ala Pro Leu
                85                  90                  95

Thr Phe Gly Gln Gly Thr Lys Val Glu Ile Lys
            100                 105
```

<210> SEQ ID NO 168
<211> LENGTH: 321
<212> TYPE: DNA
<213> ORGANISM: Artificial Sequence
<220> FEATURE:
<223> OTHER INFORMATION: Synthetic: VL7.0

<400> SEQUENCE: 168

```
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgctaagtgg ggtcccatca     180
aggttcagtg gcagtggatc tgggacagat ttcactctca ccatcagcag tctgcaacct     240
gaagattttg caacttacta ctgtcaacag acgtacagtg ccccgctcac gttcggccaa     300
gggaccaagg tggaaatcaa a                                                321
```

<210> SEQ ID NO 169
<211> LENGTH: 107
<212> TYPE: PRT
<213> ORGANISM: Artificial Sequence
<220> FEATURE:
<223> OTHER INFORMATION: Synthetic: VL8

<400> SEQUENCE: 169

Gly Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Ser Tyr
            20                  25                  30
Leu Asn Trp Tyr Gln Gln Lys Pro Gly Lys Ala Pro Lys Leu Leu Ile
        35                  40                  45
Tyr Ala Ala Ser Ser Leu Leu Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Thr Tyr Ser Thr Pro Leu
                85                  90                  95
Thr Phe Gly Gln Gly Thr Lys Val Glu Ile Lys
            100                 105

<210> SEQ ID NO 170
<211> LENGTH: 321
<212> TYPE: DNA
<213> ORGANISM: Artificial Sequence
<220> FEATURE:
<223> OTHER INFORMATION: Synthetic: VL8.0

<400> SEQUENCE: 170

```
ggcatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgctaagtgg ggtcccatca     180
aggttcagtg gcagtggatc tgggacagat ttcactctca ccatcagcag tctgcaacct     240
gaagattttg caacttacta ctgtcaacag acgtacagta ccccgctcac gttcggccaa     300
gggaccaagg tggaaatcaa a                                                321
```

<210> SEQ ID NO 171
<211> LENGTH: 107
<212> TYPE: PRT
<213> ORGANISM: Artificial Sequence
<220> FEATURE:
<223> OTHER INFORMATION: Synthetic: VL9

<400> SEQUENCE: 171

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Leu Ser Gly Val Pro Ser Arg Phe Ser Gly
50                  55                  60

Gly Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Thr Pro Leu
                85                  90                  95

Thr Phe Gly Gln Gly Thr Lys Val Glu Ile Lys
            100                 105

<210> SEQ ID NO 172
<211> LENGTH: 321
<212> TYPE: DNA
<213> ORGANISM: Artificial Sequence
<220> FEATURE:
<223> OTHER INFORMATION: Synthetic: VL9.0

<400> SEQUENCE: 172
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgctaagtgg ggtcccatca   180
aggttcagtg gcggtggatc tgggacagat ttcactctca ccatcagcag tctgcaacct   240
gaagattttg caacttacta ctgtcaacag acgtacagta ccccgctcac gttcggccaa   300
gggaccaagg tggaaatcaa a                                             321

<210> SEQ ID NO 173
<211> LENGTH: 107
<212> TYPE: PRT
<213> ORGANISM: Artificial Sequence
<220> FEATURE:
<223> OTHER INFORMATION: Synthetic: VL10

<400> SEQUENCE: 173

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Arg Pro Gly Arg Ala Pro Lys Leu Leu Ile
        35                  40                  45

Tyr Ala Ala Ser Ser Leu Leu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Thr Pro Leu
                85                  90                  95

Thr Phe Gly Gln Gly Thr Lys Val Glu Ile Lys
            100                 105

<210> SEQ ID NO 174
<211> LENGTH: 321
<212> TYPE: DNA
<213> ORGANISM: Artificial Sequence
<220> FEATURE:
<223> OTHER INFORMATION: Synthetic: VL10.0

<400> SEQUENCE: 174

```
gacatccaga tgacccagtc tccatcctcc ctgtctgcat ctgtaggaga cagagtcacc    60
atcacttgcc gggcaagtca gagcattagc agctatttaa attggtatca gcagagacca   120
gggagagccc ctaagctcct gatctatgct gcatccagtt tgctaagtgg ggtcccatca   180
aggttcagtg gcagtggatc tgggacagat ttcactctca ccatcagcag tctgcaacct   240
gaagattttg caacttacta ctgtcaacag acgtacagta ccccgctcac gttcggccaa   300
gggaccaagg tggaaatcaa a                                             321
```

<210> SEQ ID NO 175
<211> LENGTH: 107
<212> TYPE: PRT
<213> ORGANISM: Artificial Sequence
<220> FEATURE:
<223> OTHER INFORMATION: Synthetic: VL11

<400> SEQUENCE: 175

Asp Ile Gln Met Thr Gln Ser Pro Ser Ser Leu Ser Ala Ser Val Gly
1               5                   10                  15

Asp Arg Val Ala Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys
            100                 105

<210> SEQ ID NO 176
<211> LENGTH: 321
<212> TYPE: DNA
<213> ORGANISM: Artificial Sequence
<220> FEATURE:
<223> OTHER INFORMATION: Synthetic: VL11.0

<400> SEQUENCE: 176

```
gacatccaga tgacccagtc tccatcctcc ctgtctgcat ctgtaggaga cagagtcgcc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta ccccgctcac gttcggccaa   300
gggaccaagg tggaaatcaa a                                             321
```

<210> SEQ ID NO 177
<211> LENGTH: 107
<212> TYPE: PRT

<213> ORGANISM: Artificial Sequence
<220> FEATURE:
<223> OTHER INFORMATION: Synthetic: VL12

<400> SEQUENCE: 177

```
Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Thr Pro Leu
                85                  90                  95

Thr Phe Gly Gln Gly Thr Lys Val Glu Ile Lys
            100                 105
```

<210> SEQ ID NO 178
<211> LENGTH: 321
<212> TYPE: DNA
<213> ORGANISM: Artificial Sequence
<220> FEATURE:
<223> OTHER INFORMATION: Synthetic: VL12.0

<400> SEQUENCE: 178

```
gacatccaga tgacccagtc tccatcctcc ctgtctgcat ctgtaggaga cagagtcacc      60
atctcttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat tcactctcac catcagcagt ctgcaacct     240
gaagattttg cgacttacta ctgtcaacag acgtacagta ccccgctcac gttcggccaa     300
gggaccaagg tggaaatcaa a                                               321
```

<210> SEQ ID NO 179
<211> LENGTH: 107
<212> TYPE: PRT
<213> ORGANISM: Artificial Sequence
<220> FEATURE:
<223> OTHER INFORMATION: Synthetic: VL13

<400> SEQUENCE: 179

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Leu Ala Thr Tyr Tyr Cys Gln Gln Thr Tyr Ser Thr Pro Leu
                85                  90                  95

Thr Phe Gly Gln Gly Thr Lys Val Glu Ile Lys
            100                 105
```

<210> SEQ ID NO 180
<211> LENGTH: 321
<212> TYPE: DNA
<213> ORGANISM: Artificial Sequence
<220> FEATURE:
<223> OTHER INFORMATION: Synthetic: VL13.0

<400> SEQUENCE: 180

```
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagatttag caacttacta ctgtcaacag acgtacagta ccccgctcac gttcggccaa   300
gggaccaagg tggaaatcaa a                                             321
```

<210> SEQ ID NO 181
<211> LENGTH: 107
<212> TYPE: PRT
<213> ORGANISM: Artificial Sequence
<220> FEATURE:
<223> OTHER INFORMATION: Synthetic: VL14

<400> SEQUENCE: 181

Glu Ile Gln Met Thr Gln Ser Pro Ser Ser Leu Ser Ala Ser Val Gly
1               5                   10                  15
Gly Arg Val Thr Ile Thr Cys Arg Ala Ser Gln Ser Ile Ser Ser Tyr
            20                  25                  30
Leu Asn Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Thr Tyr Ser Thr Pro Leu
                85                  90                  95
Thr Phe Gly Gln Gly Thr Lys Val Glu Ile Lys
            100                 105

<210> SEQ ID NO 182
<211> LENGTH: 321
<212> TYPE: DNA
<213> ORGANISM: Artificial Sequence
<220> FEATURE:
<223> OTHER INFORMATION: Synthetic: VL14.0

<400> SEQUENCE: 182

```
gagatccaga tgacccagtc tccatcctcc ctgtctgcat ctgtaggagg cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag acgtacagta ccccgctcac gttcggccaa   300
gggaccaagg tggaaatcaa a                                             321
```

<210> SEQ ID NO 183
<211> LENGTH: 107

```
<212> TYPE: PRT
<213> ORGANISM: Artificial Sequence
<220> FEATURE:
<223> OTHER INFORMATION: Synthetic: VL15

<400> SEQUENCE: 183

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Ala Leu Thr Ile Ser Ser Leu Gln Pro
65                  70                  75                  80

Glu Asp Phe Ala Thr Tyr Tyr Cys Gln Gln Thr Tyr Ser Thr Pro Leu
                85                  90                  95

Thr Phe Gly Gln Gly Thr Lys Val Glu Ile Lys
            100                 105

<210> SEQ ID NO 184
<211> LENGTH: 321
<212> TYPE: DNA
<213> ORGANISM: Artificial Sequence
<220> FEATURE:
<223> OTHER INFORMATION: Synthetic: VL15.0

<400> SEQUENCE: 184
gacatccaga tgacccagtc tccatcctcc ctgtctgcat ctgtaggaga cagagtcacc        60
atcacttgcc gggcaagtca gagcattagc agctatttaa attggtatca gcagaaacca       120
gggaaagccc ctaagctcct gatctatgct gcatccagtt tgcaaagtgg ggtcccatca       180
aggttcagtg gcagtggatc tgggacagat ttcgccctca ccatcagcag tctgcaacct       240
gaagattttg caacttacta ctgtcaacag acgtacagta ccccgctcac gttcggccaa       300
gggaccaagg tggaaatcaa a                                                 321

<210> SEQ ID NO 185
<211> LENGTH: 107
<212> TYPE: PRT
<213> ORGANISM: Artificial Sequence
<220> FEATURE:
<223> OTHER INFORMATION: Synthetic: VL16

<400> SEQUENCE: 185

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Arg Phe Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Thr Pro Leu
                85                  90                  95

Thr Phe Gly Gln Gly Thr Lys Val Glu Ile Lys
```

<210> SEQ ID NO 186
<211> LENGTH: 321
<212> TYPE: DNA
<213> ORGANISM: Artificial Sequence
<220> FEATURE:
<223> OTHER INFORMATION: Synthetic: VL16.0

<400> SEQUENCE: 186

```
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaggttcct gatctatgct gcatccagtt tgcaaagtgg ggtcccatca   180
aggttcagtg gcagtggatc tgggacagat ttcactctca ccatcagcag tctgcaaccc   240
gaagattttg caacttacta ctgtcaacag acgtacagta ccccgctcac gttcggccaa   300
gggaccaagg tggaaattaa a                                              321
```

<210> SEQ ID NO 187
<211> LENGTH: 107
<212> TYPE: PRT
<213> ORGANISM: Artificial Sequence
<220> FEATURE:
<223> OTHER INFORMATION: Synthetic: VL17

<400> SEQUENCE: 187

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Glu Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Thr Pro Leu
                85                  90                  95

Thr Phe Gly Gln Gly Thr Lys Val Glu Ile Lys
            100                 105

<210> SEQ ID NO 188
<211> LENGTH: 321
<212> TYPE: DNA
<213> ORGANISM: Artificial Sequence
<220> FEATURE:
<223> OTHER INFORMATION: Synthetic: VL17.0

<400> SEQUENCE: 188

```
gacatccaga tgacccagtc tccatcctcc ctgtctgcat ctgtaggaga cagagtcacc    60
atcacttgcc gggcaagtca gagcattagc agctatttaa attggtatca gcaggaacca   120
gggaaagccc ctaagctcct gatctatgcc gcatccagtt tgcaaagtgg ggtcccatca   180
aggttcagtg gcagtggatc tgggacagat ttcactctca ccatcagcag tctgcaacct   240
gaagattttg caacttacta ctgtcaacag acgtacagta ccccgctcac gttcggccaa   300
gggaccaagg tggaaattaa a                                              321
```

<210> SEQ ID NO 189

<211> LENGTH: 321
<212> TYPE: DNA
<213> ORGANISM: Artificial Sequence
<220> FEATURE:
<223> OTHER INFORMATION: Synthetic: VL17.1

<400> SEQUENCE: 189

```
gacatccaaa tgacccagtc tccatcctcc ctgtctgcat ctgtaggaga cagagtcacc    60
atcacttgcc gggcaagtca gagcattagc agctatttaa attggtatca gcaggaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag acgtacagta ccccgctcac gttcggccaa   300
gggaccaagg tggaaatcaa a                                              321
```

<210> SEQ ID NO 190
<211> LENGTH: 107
<212> TYPE: PRT
<213> ORGANISM: Artificial Sequence
<220> FEATURE:
<223> OTHER INFORMATION: Synthetic: VL18

<400> SEQUENCE: 190

```
Asp Ile Gln Met Thr Gln Ser Pro Ser Ser Leu Ser Ala Ser Val Gly
1               5                   10                  15
Asp Arg Val Thr Ile Thr Cys Trp Ala Ser Gln Ser Ile Ser Ser Tyr
            20                  25                  30
Leu Asn Trp Tyr Gln Gln Glu Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Thr Tyr Ser Thr Pro Leu
                85                  90                  95
Thr Phe Gly Gln Gly Thr Lys Val Glu Ile Lys
            100                 105
```

<210> SEQ ID NO 191
<211> LENGTH: 321
<212> TYPE: DNA
<213> ORGANISM: Artificial Sequence
<220> FEATURE:
<223> OTHER INFORMATION: Synthetic: VL18.0

<400> SEQUENCE: 191

```
gacatccaaa tgacccagtc tccatcctcc ctgtctgcat ctgtaggaga cagagtcacc    60
atcacttgct gggcaagtca gagcattagc agctatttaa attggtatca gcaggaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag acgtacagta ccccgctcac gttcggccaa   300
gggaccaagg tggaaatcaa a                                              321
```

<210> SEQ ID NO 192
<211> LENGTH: 107
<212> TYPE: PRT
<213> ORGANISM: Artificial Sequence
<220> FEATURE:

<223> OTHER INFORMATION: Synthetic: VL19

<400> SEQUENCE: 192

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Gly Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys
            100                 105

<210> SEQ ID NO 193
<211> LENGTH: 321
<212> TYPE: DNA
<213> ORGANISM: Artificial Sequence
<220> FEATURE:
<223> OTHER INFORMATION: Synthetic: VL19.0

<400> SEQUENCE: 193
gacatccaga tgacccagtc tccatcctcc ctgtctgcat ctgtaggaga cagagtcacc    60
atcacttgcc gggcaagtca gagcattagc agctatttaa actggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcggcag tctgcaacct   240
gaagattttg caacttacta ctgtcaacag agttacagta ccccgctcac gttcggccaa   300
gggaccaagg tggaaatcaa a                                             321

<210> SEQ ID NO 194
<211> LENGTH: 107
<212> TYPE: PRT
<213> ORGANISM: Artificial Sequence
<220> FEATURE:
<223> OTHER INFORMATION: Synthetic: VL20

<400> SEQUENCE: 194

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Ala Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys
            100                 105

-continued

```
<210> SEQ ID NO 195
<211> LENGTH: 321
<212> TYPE: DNA
<213> ORGANISM: Artificial Sequence
<220> FEATURE:
<223> OTHER INFORMATION: Synthetic: VL20.0

<400> SEQUENCE: 195
gacatccaga tgacccagtc tccatcctcc ctgtccgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcgctctca ccatcagcag tctgcaacct     240
gaagattttg caacttacta ctgtcaacag agttacagta ccccgctcac gttcggccaa     300
gggaccaagg tggaaatcaa a                                                321

<210> SEQ ID NO 196
<211> LENGTH: 107
<212> TYPE: PRT
<213> ORGANISM: Artificial Sequence
<220> FEATURE:
<223> OTHER INFORMATION: Synthetic: VL21

<400> SEQUENCE: 196

Asp Ile Gln Met Thr Gln Ser Pro Ser Ser Leu Ser Ala Ser Val Gly
1               5                  10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ile Pro Leu
                85                  90                  95

Thr Phe Gly Gln Gly Thr Lys Val Glu Ile Lys
            100                 105

<210> SEQ ID NO 197
<211> LENGTH: 321
<212> TYPE: DNA
<213> ORGANISM: Artificial Sequence
<220> FEATURE:
<223> OTHER INFORMATION: Synthetic: VL21.0

<400> SEQUENCE: 197
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcaacag agttacagta tcccgctcac gttcggccaa     300
gggaccaagg tggagatcaa a                                                321

<210> SEQ ID NO 198
<211> LENGTH: 321
<212> TYPE: DNA
<213> ORGANISM: Artificial Sequence
```

<220> FEATURE:
<223> OTHER INFORMATION: Synthetic: VL21.1

<400> SEQUENCE: 198

```
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcaacag agttacagta tcccgctcac gttcggccaa     300
gggaccaagg tggaaatcaa a                                                321
```

<210> SEQ ID NO 199
<211> LENGTH: 107
<212> TYPE: PRT
<213> ORGANISM: Artificial Sequence
<220> FEATURE:
<223> OTHER INFORMATION: Synthetic: VL22

<400> SEQUENCE: 199

```
Asp Ile Gln Met Thr Gln Ser Pro Ser Ser Leu Ser Ala Ser Ile Gly
1               5                   10                  15
Asp Arg Val Thr Ile Thr Cys Arg Ala Ser Gln Ser Ile Ser Ser Tyr
            20                  25                  30
Leu Asn Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Tyr Ser Thr Pro Leu
                85                  90                  95
Thr Phe Gly Gln Gly Thr Lys Val Glu Ile Lys
            100                 105
```

<210> SEQ ID NO 200
<211> LENGTH: 321
<212> TYPE: DNA
<213> ORGANISM: Artificial Sequence
<220> FEATURE:
<223> OTHER INFORMATION: Synthetic: VL22.0

<400> SEQUENCE: 200

```
gacatccaga tgacccagtc tccatcctcc ctgtctgcat ctataggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcaacag agttacagta ccccgctcac gttcggccaa     300
gggaccaagg tggaaatcaa a                                                321
```

<210> SEQ ID NO 201
<211> LENGTH: 321
<212> TYPE: DNA
<213> ORGANISM: Artificial Sequence
<220> FEATURE:
<223> OTHER INFORMATION: Synthetic: VL22.1

<400> SEQUENCE: 201

```
gacatccaga tgacccagtc tccatcctcc ctgtctgcat ctataggaga tagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg cgacttacta ctgtcaacag agttacagta ccccgctcac gttcggccaa     300
gggaccaagg tggaaatcaa a                                               321
```

<210> SEQ ID NO 202
<211> LENGTH: 107
<212> TYPE: PRT
<213> ORGANISM: Artificial Sequence
<220> FEATURE:
<223> OTHER INFORMATION: Synthetic: VL23

<400> SEQUENCE: 202

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys
            100                 105
```

<210> SEQ ID NO 203
<211> LENGTH: 321
<212> TYPE: DNA
<213> ORGANISM: Artificial Sequence
<220> FEATURE:
<223> OTHER INFORMATION: Synthetic: VL23.0

<400> SEQUENCE: 203

```
gacatccaga tgacccagtc tccatcctcc ctgtctgcat ctgtaggaga cagagtcacc      60
atcacttgcc gggcgagtca gagcattagc aactatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcaacag agttacagta ccccgctcac gttcggccaa     300
gggaccaagg tggaaatcaa a                                               321
```

<210> SEQ ID NO 204
<211> LENGTH: 107
<212> TYPE: PRT
<213> ORGANISM: Artificial Sequence
<220> FEATURE:
<223> OTHER INFORMATION: Synthetic: VL24

<400> SEQUENCE: 204

```
Asp Ile Gln Met Ala Gln Ser Pro Ser Ser Leu Ser Ala Ser Val Gly
1               5                   10                  15
```

```
Asp Arg Val Thr Ile Thr Cys Arg Ala Ser Gln Gly Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ile Pro Leu
                85                  90                  95

Thr Phe Gly Gln Gly Thr Lys Val Glu Ile Lys
            100                 105

<210> SEQ ID NO 205
<211> LENGTH: 321
<212> TYPE: DNA
<213> ORGANISM: Artificial Sequence
<220> FEATURE:
<223> OTHER INFORMATION: Synthetic: VL24.0

<400> SEQUENCE: 205
gacatccaga tggcccagtc tccgtcctcc ctgtctgcat ctgtaggaga cagagtcacc      60
atcacttgcc gggcaagtca gggcattagc agctacttaa attggtatca gcagaaacca     120
gggaaagccc ctaagctcct gatctatgct gcatccagtt tgcaaagtga ggtcccatca     180
aggttcagtg gcagtggata tgggacagat ttcactctca ccatcagcag tctgcaacct     240
gaagattttg caacttacta ctgtcaacag agttacagta tcccgctcac gttcggccaa     300
gggaccaagg tggagatcaa a                                               321

<210> SEQ ID NO 206
<211> LENGTH: 107
<212> TYPE: PRT
<213> ORGANISM: Artificial Sequence
<220> FEATURE:
<223> OTHER INFORMATION: Synthetic: VL25

<400> SEQUENCE: 206

Asp Ile Gln Met Ala Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys
            100                 105

<210> SEQ ID NO 207
<211> LENGTH: 321
<212> TYPE: DNA
<213> ORGANISM: Artificial Sequence
<220> FEATURE:
<223> OTHER INFORMATION: Synthetic: VL25.0
```

```
<400> SEQUENCE: 207
gacatccaga tggcccagtc tccgtcctcc ctgtctgcat ctgtaggaga cagagtcacc    60
atcacttgcc gggcaagtca gggcattagc agctatttaa attggtatca gcagaaacca   120
gggaaagccc ctaagctcct gatctatgct gcatccagtt tgcaaagtgg ggtcccatca   180
aggttcagtg gcagtggata tgggacagat ttcactctca ccatcagcag tctgcaacct   240
gaagattttg caacttacta ctgtcaacag agttacagta ccccgctcac gttcggccaa   300
gggaccaagg tggagatcaa a                                             321

<210> SEQ ID NO 208
<211> LENGTH: 107
<212> TYPE: PRT
<213> ORGANISM: Artificial Sequence
<220> FEATURE:
<223> OTHER INFORMATION: Synthetic: VL26

<400> SEQUENCE: 208

Asp Ile Gln Met Ala Gln Ser Pro Thr Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys
            100                 105

<210> SEQ ID NO 209
<211> LENGTH: 321
<212> TYPE: DNA
<213> ORGANISM: Artificial Sequence
<220> FEATURE:
<223> OTHER INFORMATION: Synthetic: VL26.0

<400> SEQUENCE: 209
gacatccaga tggcccagtc tccaacctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta ccccgctcac gttcggccaa   300
gggaccaagg tggaaatcaa a                                             321

<210> SEQ ID NO 210
<211> LENGTH: 107
<212> TYPE: PRT
<213> ORGANISM: Artificial Sequence
<220> FEATURE:
<223> OTHER INFORMATION: Synthetic: VL27

<400> SEQUENCE: 210

Asp Ile Gln Met Thr Gln Ser Pro Ser Ser Leu Ser Ala Ser Val Gly
1               5                   10                  15
```

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Gly Gly
     50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys
            100                 105

<210> SEQ ID NO 211
<211> LENGTH: 321
<212> TYPE: DNA
<213> ORGANISM: Artificial Sequence
<220> FEATURE:
<223> OTHER INFORMATION: Synthetic: VL27.0

<400> SEQUENCE: 211
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcggtg gcagtggatc tgggacagat tcactctca ccatcagcag tctgcaacct     240
gaagattttg cgacttacta ctgtcaacag agttacagta ccccgctcac gttcggccaa     300
gggaccaagg tggaaatcaa a                                                321

<210> SEQ ID NO 212
<211> LENGTH: 107
<212> TYPE: PRT
<213> ORGANISM: Artificial Sequence
<220> FEATURE:
<223> OTHER INFORMATION: Synthetic: VL28

<400> SEQUENCE: 212

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asn Thr Pro Leu
                85                  90                  95

Thr Phe Gly Gln Gly Thr Lys Val Glu Ile Lys
            100                 105

<210> SEQ ID NO 213
<211> LENGTH: 321
<212> TYPE: DNA
<213> ORGANISM: Artificial Sequence
<220> FEATURE:
<223> OTHER INFORMATION: Synthetic: VL28.0

<400> SEQUENCE: 213

```
gacatccaga tgacccagtc tccatcctcc ctgtctgcat ctgtaggaga cagagtcacc        60
atcacttgcc gggcaagtca gagcattagc agctatttaa attggtatca gcagaaacca       120
gggaaagccc ctaagctcct gatctatgct gcatccagtt tgcaaagtgg ggtcccatca       180
aggttcagtg gcagtggatc tgggacagat tcactctca ccatcagcag tctgcaacct       240
gaagattttg caacttacta ctgtcaacag agttacaata ccccgctcac gttcggccaa      300
gggaccaagg tggaaatcaa a                                                 321
```

<210> SEQ ID NO 214
<211> LENGTH: 321
<212> TYPE: DNA
<213> ORGANISM: Artificial Sequence
<220> FEATURE:
<223> OTHER INFORMATION: Synthetic: VL28.1

<400> SEQUENCE: 214

```
gacatccaga tgacccagtc tccatcctcc ctgtctgcat ctgtaggaga cagagtcacc        60
atcacttgcc gggcaagtca gagcattagc agctatttaa attggtatca gcagaaacca       120
gggaaagccc ctaagctcct gatctacgct gcatccagtt tgcaaagtgg ggtcccatca       180
aggttcagtg gcagtggatc tgggacagat tcactctca ccatcagcag tctgcaacct       240
gaagattttg caacttacta ctgtcaacag agttacaata ccccgctcac gttcggccaa      300
gggaccaagg tggaaatcaa a                                                 321
```

<210> SEQ ID NO 215
<211> LENGTH: 107
<212> TYPE: PRT
<213> ORGANISM: Artificial Sequence
<220> FEATURE:
<223> OTHER INFORMATION: Synthetic: VL29

<400> SEQUENCE: 215

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys
            100                 105
```

<210> SEQ ID NO 216
<211> LENGTH: 321
<212> TYPE: DNA
<213> ORGANISM: Artificial Sequence
<220> FEATURE:
<223> OTHER INFORMATION: Synthetic: VL29.0

<400> SEQUENCE: 216

```
gacatccaga tgacccagtc tccatcctcc ctgtctgcat ctgtaggaga cagagtcacc        60
```

```
atcacttgcc gggcaagtcg gagcattagc agctatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacagta ccccgctcac gttcggccaa    300
gggaccaagg tggaaatcaa a                                              321
```

<210> SEQ ID NO 217
<211> LENGTH: 107
<212> TYPE: PRT
<213> ORGANISM: Artificial Sequence
<220> FEATURE:
<223> OTHER INFORMATION: Synthetic: VL30

<400> SEQUENCE: 217

```
Asp Ile Gln Met Thr Gln Ser Pro Ser Ser Leu Ser Ala Ser Ala Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys
            100                 105
```

<210> SEQ ID NO 218
<211> LENGTH: 321
<212> TYPE: DNA
<213> ORGANISM: Artificial Sequence
<220> FEATURE:
<223> OTHER INFORMATION: Synthetic: VL30.0

<400> SEQUENCE: 218

```
gacatccaga tgacccagtc tccatcctcc ctgtctgcat ctgcaggaga cagggtcacc    60
atcacttgcc gggcaagtca gagcattagc agctatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacagta ccccgctcac gttcggccaa    300
gggaccaagg tggaaatcaa a                                              321
```

<210> SEQ ID NO 219
<211> LENGTH: 107
<212> TYPE: PRT
<213> ORGANISM: Artificial Sequence
<220> FEATURE:
<223> OTHER INFORMATION: Synthetic: VL31

<400> SEQUENCE: 219

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30
```

Leu Asn Trp Tyr Gln Gln Lys Pro Gly Thr Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asn Thr Pro Leu
                85                  90                  95

Thr Phe Gly Gln Gly Thr Lys Val Glu Ile Lys
                100                 105

<210> SEQ ID NO 220
<211> LENGTH: 321
<212> TYPE: DNA
<213> ORGANISM: Artificial Sequence
<220> FEATURE:
<223> OTHER INFORMATION: Synthetic: VL31.0

<400> SEQUENCE: 220
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggacagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcaacag agttacaata ccccgctcac gttcggccaa     300
gggaccaagg tggaaatcaa a                                                321

<210> SEQ ID NO 221
<211> LENGTH: 107
<212> TYPE: PRT
<213> ORGANISM: Artificial Sequence
<220> FEATURE:
<223> OTHER INFORMATION: Synthetic: VL32

<400> SEQUENCE: 221

Asp Ile Gln Met Thr Gln Ser Ser Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asn Thr Pro Leu
                85                  90                  95

Thr Phe Gly Gln Gly Thr Lys Val Glu Ile Lys
                100                 105

<210> SEQ ID NO 222
<211> LENGTH: 321
<212> TYPE: DNA
<213> ORGANISM: Artificial Sequence
<220> FEATURE:
<223> OTHER INFORMATION: Synthetic: VL32.0

<400> SEQUENCE: 222

```
gacatccaga tgacccagtc ttcatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacaata ccccgctcac gttcggccaa   300
gggaccaagg tggaaatcaa a                                              321

<210> SEQ ID NO 223
<211> LENGTH: 107
<212> TYPE: PRT
<213> ORGANISM: Artificial Sequence
<220> FEATURE:
<223> OTHER INFORMATION: Synthetic: VL33

<400> SEQUENCE: 223

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Ser Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asn Thr Pro Leu
                85                  90                  95

Thr Phe Gly Gln Gly Thr Lys Val Glu Ile Lys
            100                 105

<210> SEQ ID NO 224
<211> LENGTH: 321
<212> TYPE: DNA
<213> ORGANISM: Artificial Sequence
<220> FEATURE:
<223> OTHER INFORMATION: Synthetic: VL33.0

<400> SEQUENCE: 224
gacatccaga tgacccagtc ttcatcctcc ctgtctgcat ctgtaggaga cagagtcacc    60
atcacctgcc gggcaagtca gggcattagc agctatttaa attggtatca gcagaaacca   120
gggaaagccc ccaagctcct gatctatgct gcatccagtt tgcaaagtgg ggtctcatca   180
aggttcagtg gcagtggatc tgggacagat ttcactctca ccatcagcag tctgcaacct   240
gaagattttg caacttacta ctgtcaacag agttacaata ccccgctcac gttcggccaa   300
gggaccaagg tggaaatcaa a                                              321

<210> SEQ ID NO 225
<211> LENGTH: 107
<212> TYPE: PRT
<213> ORGANISM: Artificial Sequence
<220> FEATURE:
<223> OTHER INFORMATION: Synthetic: VL34

<400> SEQUENCE: 225

Gly Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
```

```
                   20                  25                  30
Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                 70                  75                  80

Glu Asp Phe Ala Thr Tyr Tyr Cys Gln Gln Ser Tyr Asn Thr Pro Leu
                85                  90                  95

Thr Phe Gly Gln Gly Thr Lys Val Glu Ile Lys
            100                 105
```

<210> SEQ ID NO 226
<211> LENGTH: 321
<212> TYPE: DNA
<213> ORGANISM: Artificial Sequence
<220> FEATURE:
<223> OTHER INFORMATION: Synthetic: VL34.0

<400> SEQUENCE: 226

```
ggcatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacaata ccccgctcac gttcggccaa   300
gggaccaagg tggaaatcaa a                                             321
```

<210> SEQ ID NO 227
<211> LENGTH: 321
<212> TYPE: DNA
<213> ORGANISM: Artificial Sequence
<220> FEATURE:
<223> OTHER INFORMATION: Synthetic: VL34.1

<400> SEQUENCE: 227

```
ggcatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctacgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacaata ccccgctcac gttcggccaa   300
gggaccaagg tggaaatcaa a                                             321
```

<210> SEQ ID NO 228
<211> LENGTH: 107
<212> TYPE: PRT
<213> ORGANISM: Artificial Sequence
<220> FEATURE:
<223> OTHER INFORMATION: Synthetic: VL35

<400> SEQUENCE: 228

```
Asp Ile Gln Met Thr Gln Ser Pro Ser Ser Leu Ser Ala Ser Val Gly
  1               5                  10                  15

Asp Arg Val Thr Ile Ala Cys Arg Ala Ser Gln Ser Ile Ser Ser Tyr
             20                  25                  30

Leu Asn Trp Tyr Gln Gln Lys Pro Gly Lys Ala Pro Lys Leu Leu Ile
            35                  40                  45
```

```
Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asn Thr Pro Leu
                85                  90                  95

Thr Phe Gly Gln Gly Thr Lys Val Glu Ile Lys
            100                 105

<210> SEQ ID NO 229
<211> LENGTH: 321
<212> TYPE: DNA
<213> ORGANISM: Artificial Sequence
<220> FEATURE:
<223> OTHER INFORMATION: Synthetic: VL35

<400> SEQUENCE: 229
gacatccaga tgacccagtc tccatcctcc ctgtctgcat ctgtaggaga cagagtcacc      60
atcgcttgcc gggcaagtca gagcattagc agctatttaa attggtatca gcagaaacca    120
gggaaagccc ctaagctcct gatctatgct gcatccagtt tgcaaagtgg ggtcccatcg    180
aggttcagtg gcagtggatc tgggacagat tcactctca ccatcagcag tctgcaacct     240
gaagattttg caacttacta ctgtcaacag agttacaata ccccgctcac gttcggccaa    300
gggaccaagg tggaaatcaa a                                              321

<210> SEQ ID NO 230
<211> LENGTH: 107
<212> TYPE: PRT
<213> ORGANISM: Artificial Sequence
<220> FEATURE:
<223> OTHER INFORMATION: Synthetic: VL36

<400> SEQUENCE: 230

Gly Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys
            100                 105

<210> SEQ ID NO 231
<211> LENGTH: 321
<212> TYPE: DNA
<213> ORGANISM: Artificial Sequence
<220> FEATURE:
<223> OTHER INFORMATION: Synthetic: VL36.0

<400> SEQUENCE: 231
ggcatccaga tgacccagtc tccatcctcc ctgtctgcat ctgtaggaga cagagtcacc     60
atcacttgcc gggcaagtca gagcattagc agctatctaa attggtatca gcagaaacca   120
```

```
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacagta ccccgctcac gttcggccaa    300
gggaccaagg tggaaatcaa a                                              321
```

<210> SEQ ID NO 232
<211> LENGTH: 321
<212> TYPE: DNA
<213> ORGANISM: Artificial Sequence
<220> FEATURE:
<223> OTHER INFORMATION: Synthetic: VL36.1

<400> SEQUENCE: 232

```
ggcatccaga tgacccagtc tccatcctcc ctgtctgcat ctgtaggaga cagagtcacc     60
atcacttgcc gggcaagtca gagcattagc agctatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacagta ccccgctcac gttcggccaa    300
gggaccaagg tggaaatcaa a                                              321
```

<210> SEQ ID NO 233
<211> LENGTH: 107
<212> TYPE: PRT
<213> ORGANISM: Artificial Sequence
<220> FEATURE:
<223> OTHER INFORMATION: Synthetic: VL37

<400> SEQUENCE: 233

```
Gly Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Ser Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asn Thr Pro Leu
                85                  90                  95

Thr Phe Gly Gln Gly Thr Lys Val Glu Ile Lys
            100                 105
```

<210> SEQ ID NO 234
<211> LENGTH: 321
<212> TYPE: DNA
<213> ORGANISM: Artificial Sequence
<220> FEATURE:
<223> OTHER INFORMATION: Synthetic: VL37.0

<400> SEQUENCE: 234

```
ggcatccaga tgacccagtc tccatcctcc ctgtctgcat ctgtaggaga cagagtcacc     60
atcacctgcc gggcaagtca gggcattagc agctatttaa attggtatca gcagaaacca    120
gggaaagccc ccaagctcct gatctatgct gcatccagtt tgcaaagtgg ggtctcatca    180
aggttcagtg gcagtggatc tgggacagat ttcactctca ccatcagcag tctgcaacct    240
```

```
gaagattttg caacttacta ctgtcaacag agttacaata ccccgctcac gttcggccaa      300
gggaccaagg tggaaatcaa a                                                 321
```

<210> SEQ ID NO 235
<211> LENGTH: 107
<212> TYPE: PRT
<213> ORGANISM: Artificial Sequence
<220> FEATURE:
<223> OTHER INFORMATION: Synthetic: VL39

<400> SEQUENCE: 235

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asp Thr Pro Leu
                85                  90                  95

Thr Phe Gly Gln Gly Thr Lys Val Glu Ile Lys
            100                 105
```

<210> SEQ ID NO 236
<211> LENGTH: 321
<212> TYPE: DNA
<213> ORGANISM: Artificial Sequence
<220> FEATURE:
<223> OTHER INFORMATION: Synthetic: VL39.0

<400> SEQUENCE: 236

```
gacatccaga tgacccagtc tccatcctcc ctgtctgcat ctgtaggaga cagagtcacc       60
atcacttgcc gggcaagtca gagcattagc agctatttaa attggtatca gcagaaacca      120
gggaaagccc ctaagctcct gatctatgct gcatccagtt tgcaaagtgg ggtcccatca      180
aggttcagtg gcagtggatc tgggacagat tcactctca ccatcagcag tctgcaacct      240
gaagattttg caacttacta ctgtcaacag agttacgata ccccgctcac gttcggccaa      300
gggaccaagg tggaaatcaa a                                                 321
```

<210> SEQ ID NO 237
<211> LENGTH: 107
<212> TYPE: PRT
<213> ORGANISM: Artificial Sequence
<220> FEATURE:
<223> OTHER INFORMATION: Synthetic: VL41

<400> SEQUENCE: 237

```
Gly Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Ser Ser Arg Phe Ser Gly
    50                  55                  60
```

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asn Thr Pro Leu
                85                  90                  95

Thr Phe Gly Gln Gly Thr Lys Val Glu Ile Lys
            100                 105
```

<210> SEQ ID NO 238
<211> LENGTH: 321
<212> TYPE: DNA
<213> ORGANISM: Artificial Sequence
<220> FEATURE:
<223> OTHER INFORMATION: Synthetic: VL41.0

<400> SEQUENCE: 238

```
ggcatccaga tgacccagtc tccatcctcc ctgtctgcat ctgtaggaga cagagtcacc    60
atcacctgcc gggcaagtca gagcattagc agctatttaa attggtatca gcagaaacca   120
gggaaagccc ccaagctcct gatctatgct gcatccagtt tgcaaagtgg ggtctcatca   180
aggttcagtg gcagtggatc tgggacagat ttcactctca ccatcagcag tctgcaacct   240
gaagattttg caacttacta ctgtcaacag agttacaata ccccgctcac gttcggccaa   300
gggaccaagg tggaaatcaa a                                             321
```

<210> SEQ ID NO 239
<211> LENGTH: 107
<212> TYPE: PRT
<213> ORGANISM: Artificial Sequence
<220> FEATURE:
<223> OTHER INFORMATION: Synthetic: VL43

<400> SEQUENCE: 239

```
Gly Ile Gln Met Thr Gln Ser Pro Ser Ser Leu Ser Ala Ser Val Gly
1               5                   10                  15

Asp Arg Val Thr Ile Ala Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asn Thr Pro Leu
                85                  90                  95

Thr Phe Gly Gln Gly Thr Lys Val Glu Ile Lys
            100                 105
```

<210> SEQ ID NO 240
<211> LENGTH: 321
<212> TYPE: DNA
<213> ORGANISM: Artificial Sequence
<220> FEATURE:
<223> OTHER INFORMATION: Synthetic: VL43.0

<400> SEQUENCE: 240

```
ggcatccaga tgacccagtc tccatcctcc ctgtctgcat ctgtaggaga cagagtcacc    60
atcgcttgcc gggcaagtca gagcattagc agctatttaa attggtatca gcagaaacca   120
gggaaagccc ctaagctcct gatctacgct gcatccagtt tgcaaagtgg ggtcccatca   180
```

```
aggttcagtg gtagtggatc tgggacagat ttcactctca ccatcagcag tctgcaacct    240
gaagattttg caacttacta ctgtcaacag agttacaata ccccgctcac gttcggccaa    300
gggaccaagg tggaaatcaa a                                               321
```

<210> SEQ ID NO 241
<211> LENGTH: 107
<212> TYPE: PRT
<213> ORGANISM: Artificial Sequence
<220> FEATURE:
<223> OTHER INFORMATION: Synthetic: VL44

<400> SEQUENCE: 241

```
Gly Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Glu Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asp Thr Pro Leu
                85                  90                  95

Thr Phe Gly Gln Gly Thr Lys Val Glu Ile Lys
            100                 105
```

<210> SEQ ID NO 242
<211> LENGTH: 321
<212> TYPE: DNA
<213> ORGANISM: Artificial Sequence
<220> FEATURE:
<223> OTHER INFORMATION: Synthetic: VL44.0

<400> SEQUENCE: 242

```
ggcatccaga tgacccagtc tccatcctcc ctgtctgcat ctgtaggaga cagagtcacc    60
atcacttgcc gggcaagtca gagcattagc agctatttaa attggtatca gcagaaacca    120
ggggaagccc ctaagctcct gatctatgct gcatccagtt tgcaaagtgg ggtcccatca    180
aggttcagtg gcagtggatc tgggacagat ttcaccctca ccatcagcag tctgcaacct    240
gaagattttg caacttacta ctgtcaacag agttacgata ccccgctcac gttcggccaa    300
gggaccaagg tggaaatcaa a                                               321
```

<210> SEQ ID NO 243
<211> LENGTH: 107
<212> TYPE: PRT
<213> ORGANISM: Artificial Sequence
<220> FEATURE:
<223> OTHER INFORMATION: Synthetic: VL45

<400> SEQUENCE: 243

```
Gly Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Pro Gly Lys Ala Pro Lys Leu Leu Ile
        35                  40                  45

Tyr Ala Ala Ser Ser Leu Gln Ser Gly Val Pro Pro Arg Phe Ser Gly
```

```
                        50                    55                        60
Ser Gly Ser Gly Thr Asp Phe Thr Leu Thr Ile Ser Ser Leu Gln Pro
 65                         70                     75                         80

Glu Asp Phe Ala Thr Tyr Tyr Cys Gln Gln Ser Tyr Asn Ala Pro Leu
                         85                     90                      95

Thr Phe Gly Gln Gly Thr Lys Val Glu Ile Lys
                100                 105

<210> SEQ ID NO 244
<211> LENGTH: 321
<212> TYPE: DNA
<213> ORGANISM: Artificial Sequence
<220> FEATURE:
<223> OTHER INFORMATION: Synthetic: VL45.0

<400> SEQUENCE: 244
ggcatccaga tgacccagtc tccatcctcc ctgtctgcat ctgtaggaga cagagtcacc        60
atcacttgcc gggcaagtca gagcattagc agctatttaa attggtatca gcagcaacca      120
gggaaagccc ctaagctcct gatctacgct gcatccagtt tgcaaagtgg ggtcccacca      180
aggttcagtg gcagtggatc tgggacagat ttcactctca ccatcagcag tctgcaacct      240
gaagattttg caacttacta ctgtcaacag agttacaatg ccccgctcac gttcggccaa      300
gggaccaagg tggaaatcaa a                                                321

<210> SEQ ID NO 245
<211> LENGTH: 109
<212> TYPE: PRT
<213> ORGANISM: Artificial Sequence
<220> FEATURE:
<223> OTHER INFORMATION: Synthetic: VL46

<400> SEQUENCE: 245

Gln Ser Val Leu Thr Gln Pro Pro Ser Val Ser Gly Ala Pro Gly Gln
 1               5                  10                  15

Arg Val Thr Ile Ser Cys Thr Gly Ser Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
 50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Ser
                85                  90                  95

His Thr Val Phe Gly Gly Gly Thr Gln Leu Thr Val Leu
            100                 105

<210> SEQ ID NO 246
<211> LENGTH: 327
<212> TYPE: DNA
<213> ORGANISM: Artificial Sequence
<220> FEATURE:
<223> OTHER INFORMATION: Synthetic: VL46.0

<400> SEQUENCE: 246
cagtctgtgc tgacgcagcc gccctcagtg tctggggccc cagggcagag ggtcaccatc        60
tcctgcactg ggagcagctc caacatcggg gcaggttatg atgtacactg gtaccagcag      120
cttccaggaa cagccccaa actcctcatc tatggtaaca gcaatcggcc ctcaggggtc       180
```

```
cctgaccgat tctctggctc caagtctggc acctcagcct ccctggccat cactgggctc    240
caggctgagg atgaggctga ttactactgt cagtcttatg atagcagtca cactgtgttc    300
ggaggaggca cccagctgac cgtcctc                                        327
```

<210> SEQ ID NO 247
<211> LENGTH: 327
<212> TYPE: DNA
<213> ORGANISM: Artificial Sequence
<220> FEATURE:
<223> OTHER INFORMATION: Synthetic: VL46.1

<400> SEQUENCE: 247

```
cagtctgtgc tgacgcagcc gccctcagtg tctggggccc cagggcagag ggtcaccatc     60
tcctgcactg ggagcagctc aacatcggg gcaggttatg atgtacactg gtaccagcag    120
cttccaggaa cagcccccaa actcctcatc tatggtaaca gcaatcggcc ctcaggggtc    180
cctgacagat tctctggctc caagtctggc acctcagcct ccctggccat cactgggctc    240
caggctgagg atgaggctga ttactactgt cagtcttatg atagcagtca cactgtgttc    300
ggaggaggca cccagctgac cgtcctc                                        327
```

<210> SEQ ID NO 248
<211> LENGTH: 109
<212> TYPE: PRT
<213> ORGANISM: Artificial Sequence
<220> FEATURE:
<223> OTHER INFORMATION: Synthetic: VL47

<400> SEQUENCE: 248

```
Gln Ser Val Leu Thr Gln Pro Pro Ser Val Ser Gly Ala Pro Gly Gln
1               5                   10                  15

Arg Val Thr Ile Ser Cys Thr Gly Ser Asn Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

His Thr Val Phe Gly Gly Gly Thr Gln Leu Thr Val Leu
            100                 105
```

<210> SEQ ID NO 249
<211> LENGTH: 327
<212> TYPE: DNA
<213> ORGANISM: Artificial Sequence
<220> FEATURE:
<223> OTHER INFORMATION: Synthetic: VL47.0

<400> SEQUENCE: 249

```
cagtctgtgc tgacgcagcc gccctcagtg tctggggccc cagggcagag ggtcaccatc     60
tcctgcactg ggagcaactc aacatcggg gcaggttatg atgtacactg gtaccagcag    120
cttccaggaa cagcccccaa actcctcatc tatggtaaca gcaatcggcc ctcaggggtc    180
cctgaccgat tctctggctc caagtctggc acctcagcct ccctggccat cactgggctc    240
caggctgagg atgaggctga ttactactgt cagtcttatg atagcagtca cactgtgttc    300
```
ggaggaggca cccagctgac cgtcctc                                            327

<210> SEQ ID NO 250
<211> LENGTH: 109
<212> TYPE: PRT
<213> ORGANISM: Artificial Sequence
<220> FEATURE:
<223> OTHER INFORMATION: Synthetic: VL48

<400> SEQUENCE: 250

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Gln Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Gly Ser Ser
                85                  90                  95

His Thr Val Phe Gly Gly Gly Thr Gln Leu Thr Val Leu
            100                 105

<210> SEQ ID NO 251
<211> LENGTH: 327
<212> TYPE: DNA
<213> ORGANISM: Artificial Sequence
<220> FEATURE:
<223> OTHER INFORMATION: Synthetic: VL48.0

<400> SEQUENCE: 251
cagtctgtgc tgacgcagcc gccctcagtg tctggggccc cagggcagag ggtcaccatc     60
tcctgcactg ggagcagctc aaacatcggg gcaggttatg atgtacactg gtaccagcag    120
cttccaggaa cagcccccaa actcctcatc tatggtaaca gcaatcggcc ctcagggtc     180 cctgaccgat tctctggctc ccagtctggc acctcagcct ccctggccat cactgggctc    240
caggctgagg atgaggctga ttactactgt cagtcttatg gtagcagtca cactgtgttc    300
ggaggaggca cccagctgac cgtcctc                                         327

<210> SEQ ID NO 252
<211> LENGTH: 109
<212> TYPE: PRT
<213> ORGANISM: Artificial Sequence
<220> FEATURE:
<223> OTHER INFORMATION: Synthetic: VL49

<400> SEQUENCE: 252

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu

```
                65                  70                  75                  80
Gln Ala Glu Asp Gly Ala Asp Tyr Tyr Cys Gln Ser Tyr Asp Ser Ser
                    85                  90                  95

His Thr Val Phe Gly Gly Gly Thr Gln Leu Thr Val Leu
            100                 105
```

<210> SEQ ID NO 253
<211> LENGTH: 327
<212> TYPE: DNA
<213> ORGANISM: Artificial Sequence
<220> FEATURE:
<223> OTHER INFORMATION: Synthetic: VL49.0

<400> SEQUENCE: 253

```
cagtctgtgc tgacgcagcc gccctcagtg tctggggccc cagggcagag ggtcaccatc      60
tcctgcactg ggagcagctc caacatcggg gcaggttatg atgtacactg gtaccagcag     120
cttccaggaa cagcccccaa actcctcatc tatggtaaca gcaatcggcc ctcaggggtc     180
cctgaccgat tctctggctc caagtctggc acctcagcct ccctggccat cactgggctc     240
caggctgagg atggggctga ctactactgt cagtcttatg atagcagtca cactgtgttc     300
ggaggaggca cccagctgac cgtcctc                                         327
```

<210> SEQ ID NO 254
<211> LENGTH: 109
<212> TYPE: PRT
<213> ORGANISM: Artificial Sequence
<220> FEATURE:
<223> OTHER INFORMATION: Synthetic: VL50

<400> SEQUENCE: 254

```
Gln Ser Val Leu Thr Gln Pro Pro Ser Val Ser Gly Ala Pro Gly Gln
1               5                   10                  15

Arg Val Thr Ile Ser Cys Thr Gly Gly Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Gly Asn Ser Asp Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Gly
                85                  90                  95

His Thr Val Phe Gly Gly Gly Thr Gln Leu Thr Val Leu
            100                 105
```

<210> SEQ ID NO 255
<211> LENGTH: 327
<212> TYPE: DNA
<213> ORGANISM: Artificial Sequence
<220> FEATURE:
<223> OTHER INFORMATION: Synthetic: VL50.0

<400> SEQUENCE: 255

```
cagtctgtgc tgacgcagcc gccctcagtg tctggggccc cagggcagag ggtcaccatc      60
tcctgcactg ggggcagctc caacatcggg gcaggttatg atgtacactg gtaccagcag     120
cttccaggaa cagcccccaa actcctcatc tatggtaaca gcgatcggcc ctcaggggtc     180
cctgaccgat tctctggctc caagtctggc acctcagcct ccctggccat cactgggctc     240
```
caggctgagg atgaggctga ttactactgt cagtcttatg atagcggtca cactgtgttc    300
ggaggaggca cccagctgac cgtcctc    327

<210> SEQ ID NO 256
<211> LENGTH: 109
<212> TYPE: PRT
<213> ORGANISM: Artificial Sequence
<220> FEATURE:
<223> OTHER INFORMATION: Synthetic: VL51

<400> SEQUENCE: 256

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Gln Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

His Thr Val Phe Gly Gly Gly Thr Gln Leu Thr Val Leu
            100                 105

<210> SEQ ID NO 257
<211> LENGTH: 327
<212> TYPE: DNA
<213> ORGANISM: Artificial Sequence
<220> FEATURE:
<223> OTHER INFORMATION: Synthetic: VL51.0

<400> SEQUENCE: 257
cagtctgtgc tgacgcagcc gccctcagtg tctggggccc cagggcagag ggtcaccatc     60
tcctgcactg ggagcagctc caacatcggg gcaggttatg atgtacactg gtaccagcag    120
cttccaggaa cagccccaa actcctcatc tatggtaaca gcaatcggcc ctcaggggtc     180
cctgaccgat tctctggctc ccagtctggc acctcagcct ccctggccat cactgggctc    240
caggctgagg atgaggctga ttactactgt cagtcctatg atagcagtca cactgtgttc    300
ggaggaggca cccagctgac cgtcctc    327

<210> SEQ ID NO 258
<211> LENGTH: 109
<212> TYPE: PRT
<213> ORGANISM: Artificial Sequence
<220> FEATURE:
<223> OTHER INFORMATION: Synthetic: VL52

<400> SEQUENCE: 258

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

```
Ser Gly Ser Lys Ser Gly Thr Ser Ala Ser Leu Ala Ile Thr Gly Leu
 65                 70                  75                  80

Gln Ala Glu Asp Glu Ala Asp Tyr Tyr Cys Gln Ser Tyr Gly Ser Ser
                85                  90                  95

His Thr Val Phe Gly Gly Gly Thr Gln Leu Thr Val Leu
            100                 105
```

<210> SEQ ID NO 259
<211> LENGTH: 327
<212> TYPE: DNA
<213> ORGANISM: Artificial Sequence
<220> FEATURE:
<223> OTHER INFORMATION: Synthetic: VL52.0

<400> SEQUENCE: 259

```
cagtctgtgc tgacgcagcc gccctcagtg tctggggccc cagggcagag ggtcaccatc    60
tcctgcactg ggagcagctc aaacatcggg gcaggttatg atgtacactg gtaccagcag   120
cttccaggaa cagcccccaa actcctcatc tatggtaaca gcaatcggcc ctcaggggtc   180
cctgaccgat tctctggctc caagtctggc acctcagcct ccctggccat cactgggctc   240
caggctgagg atgaggctga ttactactgt cagtcttatg gtagcagtca cactgtgttc   300
ggaggaggca cccagctgac cgtcctc                                       327
```

<210> SEQ ID NO 260
<211> LENGTH: 109
<212> TYPE: PRT
<213> ORGANISM: Artificial Sequence
<220> FEATURE:
<223> OTHER INFORMATION: Synthetic: VL53

<400> SEQUENCE: 260

```
Gln Ser Val Leu Thr Gln Pro Pro Ser Val Ser Gly Ala Pro Gly Gln
  1               5                  10                  15

Arg Val Thr Ile Ser Cys Thr Gly Ser Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
     50                  55                  60

Ser Gly Ser Lys Ser Gly Thr Ser Ala Ser Leu Ala Ile Thr Gly Leu
 65                 70                  75                  80

Gln Ala Glu Asp Glu Ala Asp Tyr Tyr Cys Gln Ser Tyr Asp Ser Gly
                85                  90                  95

His Ser Val Phe Gly Gly Gly Thr Gln Leu Thr Val Leu
            100                 105
```

<210> SEQ ID NO 261
<211> LENGTH: 327
<212> TYPE: DNA
<213> ORGANISM: Artificial Sequence
<220> FEATURE:
<223> OTHER INFORMATION: Synthetic: VL53.0

<400> SEQUENCE: 261

```
cagtctgtgc tgacgcagcc gccctcagtg tctggggccc cagggcagag ggtcaccatc    60
tcctgcactg ggagcagctc aaacatcggg gcaggttatg atgtacactg gtaccagcag   120
cttccaggaa cagcccccaa actcctcatc tatggtaaca gcaatcggcc ctcaggggtc   180
cctgaccgat tctctggctc caagtctggc acctcagcct ccctggccat cactgggctc   240
```

```
caggctgagg atgaggctga ttactactgt cagtcttatg atagcggtca ctctgtgttc    300
ggaggaggca cccagctgac cgtcctc                                        327
```

<210> SEQ ID NO 262
<211> LENGTH: 109
<212> TYPE: PRT
<213> ORGANISM: Artificial Sequence
<220> FEATURE:
<223> OTHER INFORMATION: Synthetic: VL54

<400> SEQUENCE: 262

```
Gln Ser Val Leu Thr Gln Pro Pro Ser Val Ser Gly Ala Pro Gly Gln
1               5                   10                  15

Arg Val Thr Ile Pro Cys Thr Gly Ser Ser Asn Ile Gly Ala Gly
            20                  25                  30

Tyr Asp Val His Trp Tyr Gln Gln Leu Pro Gly Ala Ala Pro Lys Leu
            35                  40                  45

Leu Ile Tyr Gly Asn Ser Asn Arg Pro Ser Gly Val Pro Asp Arg Phe
    50                  55                  60

Ser Gly Ser Gln Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Gly
                85                  90                  95

His Thr Val Phe Gly Gly Gly Thr Gln Leu Thr Val Leu
            100                 105
```

<210> SEQ ID NO 263
<211> LENGTH: 327
<212> TYPE: DNA
<213> ORGANISM: Artificial Sequence
<220> FEATURE:
<223> OTHER INFORMATION: Synthetic: VL54.0

<400> SEQUENCE: 263

```
cagtctgtgc tgacgcagcc gccctcagtg tctggggccc cagggcagag ggtcaccatc    60
ccctgcactg ggagcagctc aacatcggg gcaggttatg atgtacactg gtaccagcag    120
cttccaggag cagcccccaa actcctcatc tatggtaaca gcaatcggcc ctcaggggtc    180
cctgaccgat tctctggctc ccagtctggc acctcagcct ccctggccat cactgggctc    240
caggctgagg atgaggctga ttactactgt cagtcctatg atagcggtca cactgtgttc    300
ggaggaggca cccagctgac cgtcctc                                        327
```

<210> SEQ ID NO 264
<211> LENGTH: 109
<212> TYPE: PRT
<213> ORGANISM: Artificial Sequence
<220> FEATURE:
<223> OTHER INFORMATION: Synthetic: VL55

<400> SEQUENCE: 264

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
    50                  55                  60
```

Ser Gly Ser Gln Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Gly
                85                  90                  95

His Thr Val Phe Gly Gly Gly Thr Gln Leu Thr Val Leu
            100                 105

<210> SEQ ID NO 265
<211> LENGTH: 327
<212> TYPE: DNA
<213> ORGANISM: Artificial Sequence
<220> FEATURE:
<223> OTHER INFORMATION: Synthetic: VL55.0

<400> SEQUENCE: 265
cagtctgtgc tgacgcagcc gccctcagtg tctggggccc cagggcagag ggtcaccatc    60
tcctgcactg ggagcagctc caacatcggg gcaggttatg atgtacactg gtaccagcag   120
cttccaggaa cagcccccaa actcctcatc tatggtaaca gcaatcggcc ctcagggatc   180
cctgaccgat tctctggctc ccagtctggc acctcagcct ccctggccat cactggactc   240
caggctgagg atgaggctga ttactactgt cagtcttatg atagcggtca cactgtgttc   300
ggaggaggca cccagctgac cgtcctc                                        327

<210> SEQ ID NO 266
<211> LENGTH: 327
<212> TYPE: DNA
<213> ORGANISM: Artificial Sequence
<220> FEATURE:
<223> OTHER INFORMATION: Synthetic: VL55.1

<400> SEQUENCE: 266
cagtctgtgc tgacgcagcc gccctcagtg tctggggccc cagggcagag ggtcaccatc    60
tcctgcactg ggagcagctc caacatcggg gcaggctatg atgtacactg gtaccagcag   120
cttccaggaa cagcccccaa actcctcatc tacggtaaca gcaatcggcc ctcaggggtc   180
cctgaccgat tctctggctc ccagtctggc acctcagcct ccctggccat cactggactc   240
caggctgagg atgaggctga ttactactgt cagtcttatg atagcggtca cactgtgttc   300
ggaggaggca cccagctgac cgtcctc                                        327

<210> SEQ ID NO 267
<211> LENGTH: 109
<212> TYPE: PRT
<213> ORGANISM: Artificial Sequence
<220> FEATURE:
<223> OTHER INFORMATION: Synthetic: VL56

<400> SEQUENCE: 267

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Gln Ser Gly Thr Ser Ala Ser Leu Ala Ile Thr Gly Leu
65                  70                  75                  80

```
Gln Ala Glu Asp Glu Ala Asp Tyr Tyr Cys Gln Ser Tyr Asn Ser Gly
                85                  90                  95

His Thr Val Phe Gly Gly Gly Thr Gln Leu Thr Val Leu
            100                 105
```

<210> SEQ ID NO 268
<211> LENGTH: 327
<212> TYPE: DNA
<213> ORGANISM: Artificial Sequence
<220> FEATURE:
<223> OTHER INFORMATION: Synthetic: VL56.0

<400> SEQUENCE: 268

```
cagtctgtgc tgacgcagcc gccctcagtg tctggggccc cagggcagag ggtcaccatc    60
tcctgcactg ggagcagctc caacatcggg gcaggttatg atgtacactg gtaccagcag   120
cttccaggaa cagcccccaa actcctcatc tatggtaaca gcaatcggcc ctcaggggtc   180
cctgaccgat tctccggctc ccagtctggc acctcagcct ccctggccat cactgggctc   240
caggctgagg atgaggctga ttactactgt cagtcttata atagcggtca cactgtgttc   300
ggaggaggca cccagctgac cgtcctc                                       327
```

<210> SEQ ID NO 269
<211> LENGTH: 109
<212> TYPE: PRT
<213> ORGANISM: Artificial Sequence
<220> FEATURE:
<223> OTHER INFORMATION: Synthetic: VL57

<400> SEQUENCE: 269

```
Gln Ser Ala Leu Thr Gln Pro Pro Ser Val Ser Gly Ala Pro Gly Gln
1               5                   10                  15

Arg Val Thr Ile Ser Cys Thr Gly Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Gly
                85                  90                  95

His Ser Val Phe Gly Gly Gly Thr Gln Leu Thr Val Leu
            100                 105
```

<210> SEQ ID NO 270
<211> LENGTH: 327
<212> TYPE: DNA
<213> ORGANISM: Artificial Sequence
<220> FEATURE:
<223> OTHER INFORMATION: Synthetic: VL57.0

<400> SEQUENCE: 270

```
cagtctgcgc tgacgcagcc gccctcagtg tctggggccc cagggcagag ggtcaccatc    60
tcctgcactg ggggcagctc caacatcggg gcaggttatg atgtacactg gtaccagcag   120
cttccaggaa cagcccccaa actcctcatc tatggtaaca gcaatcggcc ctcaggggtc   180
cctgaccgat tctctggctc ccagtctggc acctcagcct ccctggccat cactgggctc   240
caggctgagg atgaggctga ttactactgt cagtcttatg atagcggtca ctctgtgttc   300
```

```
ggaggaggca cccagctgac cgtcctc                                              327
```

```
<210> SEQ ID NO 271
<211> LENGTH: 109
<212> TYPE: PRT
<213> ORGANISM: Artificial Sequence
<220> FEATURE:
<223> OTHER INFORMATION: Synthetic: VL58

<400> SEQUENCE: 271
```

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Phe Gly Asn Ser Asn Arg Pro Ser Gly Val Pro Asp Arg Phe
    50                  55                  60

Ser Gly Ser Gln Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

His Ser Val Phe Gly Gly Gly Thr Gln Leu Thr Val Leu
            100                 105

```
<210> SEQ ID NO 272
<211> LENGTH: 327
<212> TYPE: DNA
<213> ORGANISM: Artificial Sequence
<220> FEATURE:
<223> OTHER INFORMATION: Synthetic: VL58.0

<400> SEQUENCE: 272
```

```
cagtctgtgc tgacgcagcc gccctcagtg tctggggccc cagggcagag ggtcaccatc    60
tcctgcactg ggagcagctc caacatcggg gcaggctatg atgtacactg gtaccagcag   120
cttccaggaa cagcccccaa actcctcatc tttggtaaca gcaatcggcc ctcaggggtc   180
cctgaccgat tctctggctc ccagtctggc acctcagcct ccctggccat cactgggctc   240
caggctgagg atgaggctga ttactactgt cagtcttatg atagcagtca ctctgtgttc   300
ggaggaggca cgcagctgac cgtcctc                                       327
```

```
<210> SEQ ID NO 273
<211> LENGTH: 6
<212> TYPE: PRT
<213> ORGANISM: Artificial Sequence
<220> FEATURE:
<223> OTHER INFORMATION: Synthetic: VL CDR1.1

<400> SEQUENCE: 273
```

Gln Ser Ile Ser Ser Tyr
1               5

```
<210> SEQ ID NO 274
<211> LENGTH: 6
<212> TYPE: PRT
<213> ORGANISM: Artificial Sequence
<220> FEATURE:
<223> OTHER INFORMATION: Synthetic: VL CDR1.2

<400> SEQUENCE: 274
```

Gln Ser Ile Ser Asn Tyr

```
1               5

<210> SEQ ID NO 275
<211> LENGTH: 6
<212> TYPE: PRT
<213> ORGANISM: Artificial Sequence
<220> FEATURE:
<223> OTHER INFORMATION: Synthetic: VL CDR1.3

<400> SEQUENCE: 275

Gln Gly Ile Ser Ser Tyr
1               5

<210> SEQ ID NO 276
<211> LENGTH: 6
<212> TYPE: PRT
<213> ORGANISM: Artificial Sequence
<220> FEATURE:
<223> OTHER INFORMATION: Synthetic: VL CDR1.4

<400> SEQUENCE: 276

Arg Ser Ile Ser Ser Tyr
1               5

<210> SEQ ID NO 277
<211> LENGTH: 9
<212> TYPE: PRT
<213> ORGANISM: Artificial Sequence
<220> FEATURE:
<223> OTHER INFORMATION: Synthetic: VL CDR1.5

<400> SEQUENCE: 277

Ser Ser Asn Ile Gly Ala Gly Tyr Asp
1               5

<210> SEQ ID NO 278
<211> LENGTH: 9
<212> TYPE: PRT
<213> ORGANISM: Artificial Sequence
<220> FEATURE:
<223> OTHER INFORMATION: Synthetic: VL CDR1.6

<400> SEQUENCE: 278

Asn Ser Asn Ile Gly Ala Gly Tyr Asp
1               5

<210> SEQ ID NO 279
<211> LENGTH: 3
<212> TYPE: PRT
<213> ORGANISM: Artificial Sequence
<220> FEATURE:
<223> OTHER INFORMATION: Synthetic: VL CDR2.1

<400> SEQUENCE: 279

Ala Ala Ser
1

<210> SEQ ID NO 280
<211> LENGTH: 3
<212> TYPE: PRT
<213> ORGANISM: Artificial Sequence
<220> FEATURE:
<223> OTHER INFORMATION: Synthetic: VL CDR2.2

<400> SEQUENCE: 280

Gly Asn Ser
1
```

```
<210> SEQ ID NO 281
<211> LENGTH: 9
<212> TYPE: PRT
<213> ORGANISM: Artificial Sequence
<220> FEATURE:
<223> OTHER INFORMATION: Synthetic: VL CDR3.1

<400> SEQUENCE: 281

Gln Gln Ser Tyr Ser Thr Pro Leu Thr
1               5

<210> SEQ ID NO 282
<211> LENGTH: 9
<212> TYPE: PRT
<213> ORGANISM: Artificial Sequence
<220> FEATURE:
<223> OTHER INFORMATION: Synthetic: VL CDR3.2

<400> SEQUENCE: 282

Gln Gln Ser Tyr Gly Thr Pro Leu Thr
1               5

<210> SEQ ID NO 283
<211> LENGTH: 9
<212> TYPE: PRT
<213> ORGANISM: Artificial Sequence
<220> FEATURE:
<223> OTHER INFORMATION: Synthetic: VL CDR3.3

<400> SEQUENCE: 283

Gln Gln Thr Tyr Ser Thr Pro Leu Thr
1               5

<210> SEQ ID NO 284
<211> LENGTH: 9
<212> TYPE: PRT
<213> ORGANISM: Artificial Sequence
<220> FEATURE:
<223> OTHER INFORMATION: Synthetic: VL CDR3.4

<400> SEQUENCE: 284

Gln Gln Thr Tyr Ser Ala Pro Leu Thr
1               5

<210> SEQ ID NO 285
<211> LENGTH: 9
<212> TYPE: PRT
<213> ORGANISM: Artificial Sequence
<220> FEATURE:
<223> OTHER INFORMATION: Synthetic: VL CDR3.5

<400> SEQUENCE: 285

Gln Gln Ser Tyr Ser Ile Pro Leu Thr
1               5

<210> SEQ ID NO 286
<211> LENGTH: 9
<212> TYPE: PRT
<213> ORGANISM: Artificial Sequence
<220> FEATURE:
<223> OTHER INFORMATION: Synthetic: VL CDR3.6

<400> SEQUENCE: 286

Gln Gln Ser Tyr Asn Thr Pro Leu Thr
1               5
```

```
<210> SEQ ID NO 287
<211> LENGTH: 9
<212> TYPE: PRT
<213> ORGANISM: Artificial Sequence
<220> FEATURE:
<223> OTHER INFORMATION: Synthetic: VL CDR3.7

<400> SEQUENCE: 287

Gln Gln Ser Tyr Asp Thr Pro Leu Thr
1               5

<210> SEQ ID NO 288
<211> LENGTH: 9
<212> TYPE: PRT
<213> ORGANISM: Artificial Sequence
<220> FEATURE:
<223> OTHER INFORMATION: Synthetic: VL CDR3.8

<400> SEQUENCE: 288

Gln Gln Ser Tyr Asn Ala Pro Leu Thr
1               5

<210> SEQ ID NO 289
<211> LENGTH: 9
<212> TYPE: PRT
<213> ORGANISM: Artificial Sequence
<220> FEATURE:
<223> OTHER INFORMATION: Synthetic: VL CDR3.9

<400> SEQUENCE: 289

Gln Ser Tyr Asp Ser Ser His Thr Val
1               5

<210> SEQ ID NO 290
<211> LENGTH: 9
<212> TYPE: PRT
<213> ORGANISM: Artificial Sequence
<220> FEATURE:
<223> OTHER INFORMATION: Synthetic: VL CDR3.10

<400> SEQUENCE: 290

Gln Ser Tyr Gly Ser Ser His Thr Val
1               5

<210> SEQ ID NO 291
<211> LENGTH: 9
<212> TYPE: PRT
<213> ORGANISM: Artificial Sequence
<220> FEATURE:
<223> OTHER INFORMATION: Synthetic: VL CDR3.11

<400> SEQUENCE: 291

Gln Ser Tyr Asp Ser Gly His Thr Val
1               5

<210> SEQ ID NO 292
<211> LENGTH: 9
<212> TYPE: PRT
<213> ORGANISM: Artificial Sequence
<220> FEATURE:
<223> OTHER INFORMATION: Synthetic: VL CDR3.12

<400> SEQUENCE: 292

Gln Ser Tyr Asp Ser Gly His Ser Val
1               5
```

```
<210> SEQ ID NO 293
<211> LENGTH: 9
<212> TYPE: PRT
<213> ORGANISM: Artificial Sequence
<220> FEATURE:
<223> OTHER INFORMATION: Synthetic: VL CDR3.13

<400> SEQUENCE: 293

Gln Ser Tyr Asn Ser Gly His Thr Val
1               5

<210> SEQ ID NO 294
<211> LENGTH: 9
<212> TYPE: PRT
<213> ORGANISM: Artificial Sequence
<220> FEATURE:
<223> OTHER INFORMATION: Synthetic: VL CDR3.14

<400> SEQUENCE: 294

Gln Ser Tyr Asp Ser Ser His Ser Val
1               5

<210> SEQ ID NO 295
<211> LENGTH: 107
<212> TYPE: PRT
<213> ORGANISM: Artificial Sequence
<220> FEATURE:
<223> OTHER INFORMATION: Synthetic: VL59

<400> SEQUENCE: 295

Gly Ile Gln Met Thr Gln Ser Pro Ser Ser Leu Ser Ala Ser Val Gly
1               5                   10                  15

Asp Arg Val Thr Ile Thr Cys Trp Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Leu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Ala Pro Leu
                85                  90                  95

Thr Phe Gly Gln Gly Thr Lys Val Glu Ile Lys
            100                 105

<210> SEQ ID NO 296
<211> LENGTH: 321
<212> TYPE: DNA
<213> ORGANISM: Artificial Sequence
<220> FEATURE:
<223> OTHER INFORMATION: Synthetic: VL59.0

<400> SEQUENCE: 296
ggcatccaga tgacccagtc tccatcctcc ctgtctgcat ctgtaggaga cagagtcacc      60
atcacttgct gggcaagtca gagcattagc agctatttaa attggtatca gcagaaacca     120
gggaaagccc ctaagctcct gatctatgct gcatccagtt tgctaagtgg ggtcccatca     180
aggttcagtg gcagtggatc tgggacagat tcactctca ccatcagcag tctgcaacct     240
gaagattttg caacttacta ctgtcaacag acgtacagtg ccccgctcac gttcggccaa     300
gggaccaagg tggaaatcaa a                                               321
```

<210> SEQ ID NO 297
<211> LENGTH: 109
<212> TYPE: PRT
<213> ORGANISM: Artificial Sequence
<220> FEATURE:
<223> OTHER INFORMATION: Synthetic: VL60

<400> SEQUENCE: 297

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Gln Ser Gly Thr Ser Pro Ser Leu Ala Ile Thr Gly Leu
65                  70                  75                  80

Gln Asp Glu Asp Glu Ala Asp Tyr Tyr Cys Gln Ser Tyr Gly Ser Ser
                85                  90                  95

His Thr Val Phe Gly Gly Gly Thr Gln Leu Thr Val Leu
            100                 105

<210> SEQ ID NO 298
<211> LENGTH: 327
<212> TYPE: DNA
<213> ORGANISM: Artificial Sequence
<220> FEATURE:
<223> OTHER INFORMATION: Synthetic: VL60.0

<400> SEQUENCE: 298
cagtctgtgc tgacgcagcc gccctcagtg tctggggccc cagggcagag ggtcaccatc      60
tcctgcactg ggagcagctc aacatcggg gcaggttatg atgtacactg gtaccagcag     120
cttccaggaa cagcccccaa actcctcatc tatggtaaca gcaatcggcc ctcaggggtc     180
cctgaccgat tctctggctc ccagtctggc acctcaccct ccctggccat cactgggctc     240
caggatgagg atgaggctga ttactactgt cagtcctatg gtagcagtca cactgtgttc     300
ggaggaggca cccagctgac cgtcctc                                         327

<210> SEQ ID NO 299
<211> LENGTH: 8
<212> TYPE: PRT
<213> ORGANISM: Artificial Sequence
<220> FEATURE:
<223> OTHER INFORMATION: Synthetic: VH CDR1 C1
<220> FEATURE:
<221> NAME/KEY: misc_feature
<222> LOCATION: (2)..(2)
<223> OTHER INFORMATION: X = F or S
<220> FEATURE:
<221> NAME/KEY: misc_feature
<222> LOCATION: (3)..(3)
<223> OTHER INFORMATION: X = T, P or A
<220> FEATURE:
<221> NAME/KEY: misc_feature
<222> LOCATION: (5)..(5)
<223> OTHER INFORMATION: X = S or I
<220> FEATURE:
<221> NAME/KEY: misc_feature
<222> LOCATION: (8)..(8)
<223> OTHER INFORMATION: X = A or D

<400> SEQUENCE: 299

Gly Xaa Xaa Phe Xaa Ser Tyr Xaa

```
1               5

<210> SEQ ID NO 300
<211> LENGTH: 8
<212> TYPE: PRT
<213> ORGANISM: Artificial Sequence
<220> FEATURE:
<223> OTHER INFORMATION: Synthetic: VH CDR1 C1a
<220> FEATURE:
<221> NAME/KEY: misc_feature
<222> LOCATION: (2)..(2)
<223> OTHER INFORMATION: X = any amino acid, optionally X = F or S
<220> FEATURE:
<221> NAME/KEY: misc_feature
<222> LOCATION: (3)..(3)
<223> OTHER INFORMATION: X = any amino acid, optionally X = T or P

<400> SEQUENCE: 300

Gly Xaa Xaa Phe Ser Ser Tyr Ala
1               5

<210> SEQ ID NO 301
<211> LENGTH: 8
<212> TYPE: PRT
<213> ORGANISM: Artificial Sequence
<220> FEATURE:
<223> OTHER INFORMATION: Synthetic: VH CDR1 C1b
<220> FEATURE:
<221> NAME/KEY: misc_feature
<222> LOCATION: (3)..(3)
<223> OTHER INFORMATION: X = any amino acid, optionally X = T or A
<220> FEATURE:
<221> NAME/KEY: misc_feature
<222> LOCATION: (5)..(5)
<223> OTHER INFORMATION: X = any amino acid, optionally X = S or I

<400> SEQUENCE: 301

Gly Phe Xaa Phe Xaa Ser Tyr Ala
1               5

<210> SEQ ID NO 302
<211> LENGTH: 8
<212> TYPE: PRT
<213> ORGANISM: Artificial Sequence
<220> FEATURE:
<223> OTHER INFORMATION: Synthetic: VH CDR1 C1c
<220> FEATURE:
<221> NAME/KEY: misc_feature
<222> LOCATION: (8)..(8)
<223> OTHER INFORMATION: X = any amino acid, optionally X = A or D

<400> SEQUENCE: 302

Gly Phe Thr Phe Ser Ser Tyr Xaa
1               5

<210> SEQ ID NO 303
<211> LENGTH: 8
<212> TYPE: PRT
<213> ORGANISM: Artificial Sequence
<220> FEATURE:
<223> OTHER INFORMATION: Synthetic: VH CDR2 C2
<220> FEATURE:
<221> NAME/KEY: misc_feature
<222> LOCATION: (1)..(1)
<223> OTHER INFORMATION: X = I or T
<220> FEATURE:
<221> NAME/KEY: misc_feature
<222> LOCATION: (3)..(3)
<223> OTHER INFORMATION: X = G or S
<220> FEATURE:
<221> NAME/KEY: misc_feature
<222> LOCATION: (6)..(6)
```

```
<223> OTHER INFORMATION: X = G or R
<220> FEATURE:
<221> NAME/KEY: misc_feature
<222> LOCATION: (7)..(7)
<223> OTHER INFORMATION: X = S, R, G or I
<220> FEATURE:
<221> NAME/KEY: misc_feature
<222> LOCATION: (8)..(8)
<223> OTHER INFORMATION: X = T, I or A

<400> SEQUENCE: 303

Xaa Ser Xaa Ser Gly Xaa Xaa Xaa
1               5

<210> SEQ ID NO 304
<211> LENGTH: 8
<212> TYPE: PRT
<213> ORGANISM: Artificial Sequence
<220> FEATURE:
<223> OTHER INFORMATION: Synthetic: VH CDR2 C2a
<220> FEATURE:
<221> NAME/KEY: misc_feature
<222> LOCATION: (1)..(1)
<223> OTHER INFORMATION: X = any amino acid, optionally X = I or T
<220> FEATURE:
<221> NAME/KEY: misc_feature
<222> LOCATION: (7)..(7)
<223> OTHER INFORMATION: X = any amino acid, optionally X = S or R

<400> SEQUENCE: 304

Xaa Ser Gly Ser Gly Gly Xaa Thr
1               5

<210> SEQ ID NO 305
<211> LENGTH: 8
<212> TYPE: PRT
<213> ORGANISM: Artificial Sequence
<220> FEATURE:
<223> OTHER INFORMATION: Synthetic: VH CDR2 C2b
<220> FEATURE:
<221> NAME/KEY: misc_feature
<222> LOCATION: (6)..(6)
<223> OTHER INFORMATION: X = any amino acid, optionally X = G or R
<220> FEATURE:
<221> NAME/KEY: misc_feature
<222> LOCATION: (8)..(8)
<223> OTHER INFORMATION: X = any amino acid, X = optionally T or A

<400> SEQUENCE: 305

Ile Ser Gly Ser Gly Xaa Ser Xaa
1               5

<210> SEQ ID NO 306
<211> LENGTH: 8
<212> TYPE: PRT
<213> ORGANISM: Artificial Sequence
<220> FEATURE:
<223> OTHER INFORMATION: Synthetic: VH CDR2 C2c
<220> FEATURE:
<221> NAME/KEY: misc_feature
<222> LOCATION: (3)..(3)
<223> OTHER INFORMATION: X = G or S
<220> FEATURE:
<221> NAME/KEY: misc_feature
<222> LOCATION: (7)..(7)
<223> OTHER INFORMATION: X = S, I or G
<220> FEATURE:
<221> NAME/KEY: misc_feature
<222> LOCATION: (8)..(8)
<223> OTHER INFORMATION: X = T or I

<400> SEQUENCE: 306
```

Ile Ser Xaa Ser Gly Gly Xaa Xaa
1               5

<210> SEQ ID NO 307
<211> LENGTH: 12
<212> TYPE: PRT
<213> ORGANISM: Artificial Sequence
<220> FEATURE:
<223> OTHER INFORMATION: Synthetic: VH CDR3 C3
<220> FEATURE:
<221> NAME/KEY: misc_feature
<222> LOCATION: (5)..(5)
<223> OTHER INFORMATION: X = L or Y
<220> FEATURE:
<221> NAME/KEY: misc_feature
<222> LOCATION: (6)..(6)
<223> OTHER INFORMATION: X = I or L
<220> FEATURE:
<221> NAME/KEY: misc_feature
<222> LOCATION: (8)..(8)
<223> OTHER INFORMATION: X = S or D
<220> FEATURE:
<221> NAME/KEY: misc_feature
<222> LOCATION: (9)..(9)
<223> OTHER INFORMATION: X = G or A
<220> FEATURE:
<221> NAME/KEY: misc_feature
<222> LOCATION: (11)..(11)
<223> OTHER INFORMATION: X = any amino acid, optionally X = D or G

<400> SEQUENCE: 307

Ala Arg Gly Gly Xaa Xaa Pro Xaa Xaa Phe Xaa Tyr
1               5                   10

<210> SEQ ID NO 308
<211> LENGTH: 12
<212> TYPE: PRT
<213> ORGANISM: Artificial Sequence
<220> FEATURE:
<223> OTHER INFORMATION: Synthetic: VH CDR3 C3a
<220> FEATURE:
<221> NAME/KEY: misc_feature
<222> LOCATION: (11)..(11)
<223> OTHER INFORMATION: X = any amino acid, X = optionally D or G

<400> SEQUENCE: 308

Ala Arg Gly Gly Leu Ile Pro Ser Gly Phe Xaa Tyr
1               5                   10

<210> SEQ ID NO 309
<211> LENGTH: 17
<212> TYPE: PRT
<213> ORGANISM: Artificial Sequence
<220> FEATURE:
<223> OTHER INFORMATION: Synthetic: VH CDR3 C4
<220> FEATURE:
<221> NAME/KEY: misc_feature
<222> LOCATION: (6)..(6)
<223> OTHER INFORMATION: X = any amino acid, optionally X = D or Y
<220> FEATURE:
<221> NAME/KEY: misc_feature
<222> LOCATION: (16)..(16)
<223> OTHER INFORMATION: X = any amino acid, X = optionally D or E

<400> SEQUENCE: 309

Ala Arg Gly Pro Gly Xaa Met Tyr Leu Tyr Gly Asp Ser Phe Phe Xaa
1               5                   10                  15

Tyr

<210> SEQ ID NO 310
<211> LENGTH: 17

```
<212> TYPE: PRT
<213> ORGANISM: Artificial Sequence
<220> FEATURE:
<223> OTHER INFORMATION: Synthetic: VH CDR3 C5
<220> FEATURE:
<221> NAME/KEY: misc_feature
<222> LOCATION: (7)..(7)
<223> OTHER INFORMATION: X = any amino acid, optionally X = S, F, or Y

<400> SEQUENCE: 310

Ala Arg Asp Tyr Tyr Leu Xaa Asp Tyr Ile Thr Gln Thr Ser Phe Asp
1               5                   10                  15

Tyr

<210> SEQ ID NO 311
<211> LENGTH: 18
<212> TYPE: PRT
<213> ORGANISM: Artificial Sequence
<220> FEATURE:
<223> OTHER INFORMATION: Synthetic: VH CDR3 C6
<220> FEATURE:
<221> NAME/KEY: misc_feature
<222> LOCATION: (9)..(9)
<223> OTHER INFORMATION: X = any amino acid, optionally X = Y or F

<400> SEQUENCE: 311

Ala Arg Gly Tyr Ser Asp Ser Tyr Xaa Tyr Gly Pro Tyr Tyr Thr Phe
1               5                   10                  15

Asp Tyr

<210> SEQ ID NO 312
<211> LENGTH: 6
<212> TYPE: PRT
<213> ORGANISM: Artificial Sequence
<220> FEATURE:
<223> OTHER INFORMATION: Synthetic: VL CDR1 C7
<220> FEATURE:
<221> NAME/KEY: misc_feature
<222> LOCATION: (1)..(1)
<223> OTHER INFORMATION: X = Q or R
<220> FEATURE:
<221> NAME/KEY: misc_feature
<222> LOCATION: (2)..(2)
<223> OTHER INFORMATION: X = S or G
<220> FEATURE:
<221> NAME/KEY: misc_feature
<222> LOCATION: (5)..(5)
<223> OTHER INFORMATION: X = S or N

<400> SEQUENCE: 312

Xaa Xaa Ile Ser Xaa Tyr
1               5

<210> SEQ ID NO 313
<211> LENGTH: 6
<212> TYPE: PRT
<213> ORGANISM: Artificial Sequence
<220> FEATURE:
<223> OTHER INFORMATION: Synthetic: VL CDR1 C7a
<220> FEATURE:
<221> NAME/KEY: misc_feature
<222> LOCATION: (2)..(2)
<223> OTHER INFORMATION: X = any amino acid, optionally X = S or G
<220> FEATURE:
<221> NAME/KEY: misc_feature
<222> LOCATION: (5)..(5)
<223> OTHER INFORMATION: X = any amino acid, optionally X = S or N

<400> SEQUENCE: 313

Gln Xaa Ile Ser Xaa Tyr
```

```
1               5
```

<210> SEQ ID NO 314
<211> LENGTH: 6
<212> TYPE: PRT
<213> ORGANISM: Artificial Sequence
<220> FEATURE:
<223> OTHER INFORMATION: Synthetic: VL CDR1 C7b
<220> FEATURE:
<221> NAME/KEY: misc_feature
<222> LOCATION: (1)..(1)
<223> OTHER INFORMATION: X = any amino acid, optionally X = Q or R
<220> FEATURE:
<221> NAME/KEY: misc_feature
<222> LOCATION: (2)..(2)
<223> OTHER INFORMATION: X = any amino acid, optionally X = S or G

<400> SEQUENCE: 314

```
Xaa Xaa Ile Ser Ser Tyr
1               5
```

<210> SEQ ID NO 315
<211> LENGTH: 9
<212> TYPE: PRT
<213> ORGANISM: Artificial Sequence
<220> FEATURE:
<223> OTHER INFORMATION: Synthetic: VL CDR1 C8
<220> FEATURE:
<221> NAME/KEY: misc_feature
<222> LOCATION: (1)..(1)
<223> OTHER INFORMATION: X = any amino acid, optionally X = S or N

<400> SEQUENCE: 315

```
Xaa Ser Asn Ile Gly Ala Gly Tyr Asp
1               5
```

<210> SEQ ID NO 316
<211> LENGTH: 3
<212> TYPE: PRT
<213> ORGANISM: Artificial Sequence
<220> FEATURE:
<223> OTHER INFORMATION: Synthetic: VL CDR2 C9
<220> FEATURE:
<221> NAME/KEY: misc_feature
<222> LOCATION: (1)..(1)
<223> OTHER INFORMATION: X = A or G
<220> FEATURE:
<221> NAME/KEY: misc_feature
<222> LOCATION: (2)..(2)
<223> OTHER INFORMATION: X = A or N

<400> SEQUENCE: 316

```
Xaa Xaa Ser
1
```

<210> SEQ ID NO 317
<211> LENGTH: 9
<212> TYPE: PRT
<213> ORGANISM: Artificial Sequence
<220> FEATURE:
<223> OTHER INFORMATION: Synthetic: VL CDR3 C10
<220> FEATURE:
<221> NAME/KEY: misc_feature
<222> LOCATION: (3)..(3)
<223> OTHER INFORMATION: X = S or T
<220> FEATURE:
<221> NAME/KEY: misc_feature
<222> LOCATION: (5)..(5)
<223> OTHER INFORMATION: X = S, G, N or D
<220> FEATURE:
<221> NAME/KEY: misc_feature
<222> LOCATION: (6)..(6)

```
<223> OTHER INFORMATION: X = T, A or I

<400> SEQUENCE: 317

Gln Gln Xaa Tyr Xaa Xaa Pro Leu Thr
1               5

<210> SEQ ID NO 318
<211> LENGTH: 9
<212> TYPE: PRT
<213> ORGANISM: Artificial Sequence
<220> FEATURE:
<223> OTHER INFORMATION: Synthetic: VL CDR3 C10a
<220> FEATURE:
<221> NAME/KEY: misc_feature
<222> LOCATION: (3)..(3)
<223> OTHER INFORMATION: X = S or T
<220> FEATURE:
<221> NAME/KEY: misc_feature
<222> LOCATION: (5)..(5)
<223> OTHER INFORMATION: X = S or G
<220> FEATURE:
<221> NAME/KEY: misc_feature
<222> LOCATION: (6)..(6)
<223> OTHER INFORMATION: X = T or A

<400> SEQUENCE: 318

Gln Gln Xaa Tyr Xaa Xaa Pro Leu Thr
1               5

<210> SEQ ID NO 319
<211> LENGTH: 9
<212> TYPE: PRT
<213> ORGANISM: Artificial Sequence
<220> FEATURE:
<223> OTHER INFORMATION: Synthetic: VL CDR3 C10b
<220> FEATURE:
<221> NAME/KEY: misc_feature
<222> LOCATION: (6)..(6)
<223> OTHER INFORMATION: X = any amino acid, optionally X = T or I

<400> SEQUENCE: 319

Gln Gln Ser Tyr Ser Xaa Pro Leu Thr
1               5

<210> SEQ ID NO 320
<211> LENGTH: 9
<212> TYPE: PRT
<213> ORGANISM: Artificial Sequence
<220> FEATURE:
<223> OTHER INFORMATION: Synthetic: VL CDR3 C10c
<220> FEATURE:
<221> NAME/KEY: misc_feature
<222> LOCATION: (5)..(5)
<223> OTHER INFORMATION: X = any amino acid, optionally X = S, N or D
<220> FEATURE:
<221> NAME/KEY: misc_feature
<222> LOCATION: (6)..(6)
<223> OTHER INFORMATION: X = any amino acid, optionally X = T or A

<400> SEQUENCE: 320

Gln Gln Ser Tyr Xaa Xaa Pro Leu Thr
1               5

<210> SEQ ID NO 321
<211> LENGTH: 9
<212> TYPE: PRT
<213> ORGANISM: Artificial Sequence
<220> FEATURE:
<223> OTHER INFORMATION: Synthetic: VL CDR3 C11
<220> FEATURE:
<221> NAME/KEY: misc_feature
```

```
<222> LOCATION: (4)..(4)
<223> OTHER INFORMATION: X = D, G or N
<220> FEATURE:
<221> NAME/KEY: misc_feature
<222> LOCATION: (6)..(6)
<223> OTHER INFORMATION: X = S or G
<220> FEATURE:
<221> NAME/KEY: misc_feature
<222> LOCATION: (8)..(8)
<223> OTHER INFORMATION: X = T or S

<400> SEQUENCE: 321

Gln Ser Tyr Xaa Ser Xaa His Xaa Val
1               5

<210> SEQ ID NO 322
<211> LENGTH: 330
<212> TYPE: PRT
<213> ORGANISM: Homo sapiens
<220> FEATURE:
<221> NAME/KEY: misc_feature
<222> LOCATION: (1)..(330)
<223> OTHER INFORMATION: Human IgG1 (UniProtKB Ref# P01857 IGHG1_HUMAN)

<400> SEQUENCE: 322

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270
```

```
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 323
<211> LENGTH: 327
<212> TYPE: PRT
<213> ORGANISM: Homo sapiens
<220> FEATURE:
<221> NAME/KEY: misc_feature
<222> LOCATION: (1)..(327)
<223> OTHER INFORMATION: Human IgG4 (UniProtKB Ref# P01861 IGHG4_HUMAN)

<400> SEQUENCE: 323

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
```

```
                290                 295                 300
Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 324
<211> LENGTH: 107
<212> TYPE: PRT
<213> ORGANISM: Homo sapiens
<220> FEATURE:
<221> NAME/KEY: misc_feature
<222> LOCATION: (1)..(107)
<223> OTHER INFORMATION: Human Ig kappa constant (UniProtKB Ref # P01834
      IGKC_HUMNAN)

<400> SEQUENCE: 324

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 325
<211> LENGTH: 106
<212> TYPE: PRT
<213> ORGANISM: Homo sapiens
<220> FEATURE:
<221> NAME/KEY: misc_feature
<222> LOCATION: (1)..(106)
<223> OTHER INFORMATION: Human Ig lambda constant (UniProtKB Ref# P0CG04
      IGLC1_HUMAN)

<400> SEQUENCE: 325

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 326
<211> LENGTH: 330
```

```
<212> TYPE: PRT
<213> ORGANISM: Homo sapiens
<220> FEATURE:
<221> NAME/KEY: misc_feature
<222> LOCATION: (1)..(330)
<223> OTHER INFORMATION: Human IgG1 Fc (LALA-PG sequence variation)

<400> SEQUENCE: 326

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Gly Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 327
<211> LENGTH: 98
<212> TYPE: PRT
<213> ORGANISM: Homo sapiens
<220> FEATURE:
<221> NAME/KEY: misc_feature
```

<222> LOCATION: (1)..(98)
<223> OTHER INFORMATION: Human IgG1 Fc (LALA-PG sequence variation) CH1
      domain

<400> SEQUENCE: 327

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 328
<211> LENGTH: 12
<212> TYPE: PRT
<213> ORGANISM: Homo sapiens
<220> FEATURE:
<221> NAME/KEY: misc_feature
<222> LOCATION: (1)..(12)
<223> OTHER INFORMATION: Human IgG1 Fc (LALA-PG sequence variation)
      hinge

<400> SEQUENCE: 328

Glu Pro Lys Ser Cys Asp Lys Thr His Thr Cys Pro
1               5                   10

<210> SEQ ID NO 329
<211> LENGTH: 113
<212> TYPE: PRT
<213> ORGANISM: Homo sapiens
<220> FEATURE:
<221> NAME/KEY: misc_feature
<222> LOCATION: (1)..(113)
<223> OTHER INFORMATION: Human IgG1 Fc (LALA-PG sequence variation) CH2
      domain

<400> SEQUENCE: 329

Pro Cys Pro Ala Pro Glu Ala Ala Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Gly Ala Pro Ile Glu Lys Thr Ile Ser Lys Ala
                100                 105                 110

Lys

```
<210> SEQ ID NO 330
<211> LENGTH: 107
<212> TYPE: PRT
<213> ORGANISM: Homo sapiens
<220> FEATURE:
<221> NAME/KEY: misc_feature
<222> LOCATION: (1)..(107)
<223> OTHER INFORMATION: Human IgG1 Fc (LALA-PG sequence variation) CH3
      domain

<400> SEQUENCE: 330
```

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

```
<210> SEQ ID NO 331
<211> LENGTH: 993
<212> TYPE: DNA
<213> ORGANISM: Artificial Sequence
<220> FEATURE:
<223> OTHER INFORMATION: Synthetic: hIgG1 Fc (LALA-PG sequence
      variation)

<400> SEQUENCE: 331
gctagcacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaagc tgcgggagga     360
ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcggaggga gcagtacaac     540
agcacgtacc gtgtggtcag cgtcctcacc gtcctgcacc aggactggct gaatggcaag     600
gagtacaagt gcaaggtctc caacaaagcc ctcggagccc catcgagaa aaccatctcc      660
aaagccaaag ggcagccccg agaaccacag gtgtacaccc tgcccccatc ccgggatgag     720
ctgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctac agcaagctca ccgtggacaa gagcaggtgg     900
cagcagggga acgtcttctc atgctccgtg atgcatgagg ctctgcacaa ccactacacg     960
cagaagagcc tctccctgtc tccgggtaaa tga                                  993
```

```
<210> SEQ ID NO 332
<211> LENGTH: 8
<212> TYPE: PRT
<213> ORGANISM: Artificial Sequence
<220> FEATURE:
<223> OTHER INFORMATION: Synthetic: FLAG tag

<400> SEQUENCE: 332

Asp Tyr Lys Asp Asp Asp Asp Lys
1               5

<210> SEQ ID NO 333
<211> LENGTH: 6
<212> TYPE: PRT
<213> ORGANISM: Artificial Sequence
<220> FEATURE:
<223> OTHER INFORMATION: Synthetic: 6-His tag

<400> SEQUENCE: 333

His His His His His His
1               5

<210> SEQ ID NO 334
<211> LENGTH: 9
<212> TYPE: PRT
<213> ORGANISM: Artificial Sequence
<220> FEATURE:
<223> OTHER INFORMATION: Synthetic: HA tag

<400> SEQUENCE: 334

Tyr Pro Tyr Asp Val Pro Asp Tyr Ala
1               5

<210> SEQ ID NO 335
<211> LENGTH: 225
<212> TYPE: PRT
<213> ORGANISM: Homo sapiens
<220> FEATURE:
<221> NAME/KEY: misc_feature
<222> LOCATION: (1)..(225)
<223> OTHER INFORMATION: Human CD161 (UniProtKB #: Q12918)

<400> SEQUENCE: 335

Met Asp Gln Gln Ala Ile Tyr Ala Glu Leu Asn Leu Pro Thr Asp Ser
1               5                   10                  15

Gly Pro Glu Ser Ser Pro Ser Leu Pro Arg Asp Val Cys Gln
            20                  25                  30

Gly Ser Pro Trp His Gln Phe Ala Leu Lys Leu Ser Cys Ala Gly Ile
        35                  40                  45

Ile Leu Leu Val Leu Val Val Thr Gly Leu Ser Val Ser Val Thr Ser
    50                  55                  60

Leu Ile Gln Lys Ser Ser Ile Glu Lys Cys Ser Val Asp Ile Gln Gln
65                  70                  75                  80

Ser Arg Asn Lys Thr Thr Glu Arg Pro Gly Leu Leu Asn Cys Pro Ile
                85                  90                  95

Tyr Trp Gln Gln Leu Arg Glu Lys Cys Leu Leu Phe Ser His Thr Val
            100                 105                 110

Asn Pro Trp Asn Asn Ser Leu Ala Asp Cys Ser Thr Lys Glu Ser Ser
        115                 120                 125

Leu Leu Leu Ile Arg Asp Lys Asp Glu Leu Ile His Thr Gln Asn Leu
    130                 135                 140

Ile Arg Asp Lys Ala Ile Leu Phe Trp Ile Gly Leu Asn Phe Ser Leu
145                 150                 155                 160
```

Ser Glu Lys Asn Trp Lys Trp Ile Asn Gly Ser Phe Leu Asn Ser Asn
            165                 170                 175

Asp Leu Glu Ile Arg Gly Asp Ala Lys Glu Asn Ser Cys Ile Ser Ile
        180                 185                 190

Ser Gln Thr Ser Val Tyr Ser Glu Tyr Cys Ser Thr Glu Ile Arg Trp
    195                 200                 205

Ile Cys Gln Lys Glu Leu Thr Pro Val Arg Asn Lys Val Tyr Pro Asp
210                 215                 220

Ser
225

<210> SEQ ID NO 336
<211> LENGTH: 227
<212> TYPE: PRT
<213> ORGANISM: Macaca fascicularis
<220> FEATURE:
<221> NAME/KEY: misc_feature
<222> LOCATION: (1)..(227)
<223> OTHER INFORMATION: Cynomolgus CD161 (UniProtKB #: A0A2K5WYI1)

<400> SEQUENCE: 336

Met Asp Gln Gln Met Met Tyr Ala Glu Leu Thr Leu Pro Lys Asp Ser
1               5                   10                  15

Gly Pro Glu Ser Ser Pro Ser Ser Leu Pro Arg Asp Val Cys Gln
            20                  25                  30

Gly Ser Pro Trp His Gln Phe Ala Leu Lys Leu Ser Cys Ala Gly Ile
        35                  40                  45

Ile Leu Leu Val Leu Val Val Thr Gly Leu Ser Val Leu Ser Val Ala Ser
    50                  55                  60

Leu Leu Gln Lys Pro Ser Ile Gly Lys Cys Ser Val Asp Ile Gln Gln
65                  70                  75                  80

Asn Arg Thr Lys Thr Thr Glu Arg Pro Asp Leu Leu Asn Cys Pro Ile
                85                  90                  95

Tyr Trp Gln Gln Val Gln Glu Lys Cys Leu Leu Phe Ser His Thr Val
            100                 105                 110

Asn Pro Trp Asn Asn Ser Leu Ala Asp Cys Ser Thr Lys Glu Ser Ser
        115                 120                 125

Leu Leu Leu Ile Gln Asp Lys Asp Glu Leu Thr Arg Thr Gln Asn Leu
130                 135                 140

Ile His Asp Lys Ala Ile Ser Phe Trp Ile Gly Leu Asn Phe Ser Leu
145                 150                 155                 160

Ser Glu Lys Asn Trp Lys Trp Ile Asn Gly Ser Phe Leu Ser Ser Asn
            165                 170                 175

Asp Leu Lys Ile Thr Gly Asp Ala Lys Glu Asn Ser Cys Val Tyr Ile
        180                 185                 190

Ser Gln Thr Ser Val Tyr Ser Glu Tyr Cys Ser Thr Glu Met Lys Trp
    195                 200                 205

Ile Cys Gln Lys Glu Leu Thr Leu Val Arg Asn Lys Val Ser Pro Asp
210                 215                 220

Ser Trp Leu
225

<210> SEQ ID NO 337
<211> LENGTH: 191
<212> TYPE: PRT
<213> ORGANISM: Homo sapiens
<220> FEATURE:

-continued

```
<221> NAME/KEY: misc_feature
<222> LOCATION: (1)..(191)
<223> OTHER INFORMATION: Human CLEC2D (UniProtKB #: Q9UHP7)

<400> SEQUENCE: 337
```

Met His Asp Ser Asn Asn Val Glu Lys Asp Ile Thr Pro Ser Glu Leu
1               5                   10                  15

Pro Ala Asn Pro Gly Cys Leu His Ser Lys Glu His Ser Ile Lys Ala
            20                  25                  30

Thr Leu Ile Trp Arg Leu Phe Phe Leu Ile Met Phe Leu Thr Ile Ile
        35                  40                  45

Val Cys Gly Met Val Ala Ala Leu Ser Ala Ile Arg Ala Asn Cys His
50                  55                  60

Gln Glu Pro Ser Val Cys Leu Gln Ala Ala Cys Pro Glu Ser Trp Ile
65                  70                  75                  80

Gly Phe Gln Arg Lys Cys Phe Tyr Phe Ser Asp Asp Thr Lys Asn Trp
                85                  90                  95

Thr Ser Ser Gln Arg Phe Cys Asp Ser Gln Asp Ala Asp Leu Ala Gln
            100                 105                 110

Val Glu Ser Phe Gln Glu Leu Asn Phe Leu Leu Arg Tyr Lys Gly Pro
        115                 120                 125

Ser Asp His Trp Ile Gly Leu Ser Arg Glu Gln Gly Gln Pro Trp Lys
    130                 135                 140

Trp Ile Asn Gly Thr Glu Trp Thr Arg Gln Phe Pro Ile Leu Gly Ala
145                 150                 155                 160

Gly Glu Cys Ala Tyr Leu Asn Asp Lys Gly Ala Ser Ser Ala Arg His
                165                 170                 175

Tyr Thr Glu Arg Lys Trp Ile Cys Ser Lys Ser Asp Ile His Val
            180                 185                 190

```
<210> SEQ ID NO 338
<211> LENGTH: 179
<212> TYPE: PRT
<213> ORGANISM: Homo sapiens
<220> FEATURE:
<221> NAME/KEY: misc_feature
<222> LOCATION: (1)..(179)
<223> OTHER INFORMATION: Human CD94 (UniProtKB #: Q13241)

<400> SEQUENCE: 338
```

Met Ala Val Phe Lys Thr Thr Leu Trp Arg Leu Ile Ser Gly Thr Leu
1               5                   10                  15

Gly Ile Ile Cys Leu Ser Leu Met Ser Thr Leu Gly Ile Leu Leu Lys
            20                  25                  30

Asn Ser Phe Thr Lys Leu Ser Ile Glu Pro Ala Phe Thr Pro Gly Pro
        35                  40                  45

Asn Ile Glu Leu Gln Lys Asp Ser Asp Cys Cys Ser Cys Gln Glu Lys
50                  55                  60

Trp Val Gly Tyr Arg Cys Asn Cys Tyr Phe Ile Ser Ser Glu Gln Lys
65                  70                  75                  80

Thr Trp Asn Glu Ser Arg His Leu Cys Ala Ser Gln Lys Ser Ser Leu
                85                  90                  95

Leu Gln Leu Gln Asn Thr Asp Glu Leu Asp Phe Met Ser Ser Ser Gln
            100                 105                 110

Gln Phe Tyr Trp Ile Gly Leu Ser Tyr Ser Glu Glu His Thr Ala Trp
        115                 120                 125

Leu Trp Glu Asn Gly Ser Ala Leu Ser Gln Tyr Leu Phe Pro Ser Phe

```
                130              135              140
Glu Thr Phe Asn Thr Lys Asn Cys Ile Ala Tyr Asn Pro Asn Gly Asn
145                 150                 155                 160

Ala Leu Asp Glu Ser Cys Glu Asp Lys Asn Arg Tyr Ile Cys Lys Gln
                165                 170                 175

Gln Leu Ile

<210> SEQ ID NO 339
<211> LENGTH: 207
<212> TYPE: PRT
<213> ORGANISM: Homo sapiens
<220> FEATURE:
<221> NAME/KEY: misc_feature
<222> LOCATION: (1)..(207)
<223> OTHER INFORMATION: Human KLRF2 (UniProtKB #: D3W0D1)

<400> SEQUENCE: 339

Met Glu Asn Glu Asp Gly Tyr Met Thr Leu Ser Phe Lys Asn Arg Cys
1               5                   10                  15

Lys Ser Lys Gln Lys Ser Lys Asp Phe Ser Leu Tyr Pro Gln Tyr Tyr
                20                  25                  30

Cys Leu Leu Leu Ile Phe Gly Cys Ile Val Leu Ile Phe Ile Met
                35                  40                  45

Thr Gly Ile Asp Leu Lys Phe Trp His Lys Lys Met Asp Phe Ser Gln
50                  55                  60

Asn Val Asn Val Ser Ser Leu Ser Gly His Asn Tyr Leu Cys Pro Asn
65                  70                  75                  80

Asp Trp Leu Leu Asn Glu Gly Lys Cys Tyr Trp Phe Ser Thr Ser Phe
                85                  90                  95

Lys Thr Trp Lys Glu Ser Gln Arg Asp Cys Thr Gln Leu Gln Ala His
                100                 105                 110

Leu Leu Val Ile Gln Asn Leu Asp Glu Leu Glu Phe Ile Gln Asn Ser
                115                 120                 125

Leu Lys Pro Gly His Phe Gly Trp Ile Gly Leu Tyr Val Thr Phe Gln
                130                 135                 140

Gly Asn Leu Trp Met Trp Ile Asp Glu His Phe Leu Val Pro Glu Leu
145                 150                 155                 160

Phe Ser Val Ile Gly Pro Thr Asp Asp Arg Ser Cys Ala Val Ile Thr
                165                 170                 175

Gly Asn Trp Val Tyr Ser Glu Asp Cys Ser Ser Thr Phe Lys Gly Ile
                180                 185                 190

Cys Gln Arg Asp Ala Ile Leu Thr His Asn Gly Thr Ser Gly Val
                195                 200                 205

<210> SEQ ID NO 340
<211> LENGTH: 276
<212> TYPE: PRT
<213> ORGANISM: Homo sapiens
<220> FEATURE:
<221> NAME/KEY: misc_feature
<222> LOCATION: (1)..(276)
<223> OTHER INFORMATION: Human Clec12B (UniProtKB #: D3W0D1)

<400> SEQUENCE: 340

Met Ser Glu Glu Val Thr Tyr Ala Thr Leu Thr Phe Gln Asp Ser Ala
1               5                   10                  15

Gly Ala Arg Asn Asn Arg Asp Gly Asn Asn Leu Arg Lys Arg Gly His
                20                  25                  30
```

```
Pro Ala Pro Ser Pro Ile Trp Arg His Ala Ala Leu Gly Leu Val Thr
         35                  40                  45

Leu Cys Leu Met Leu Leu Ile Gly Leu Val Thr Leu Gly Met Met Phe
 50                  55                  60

Leu Gln Ile Ser Asn Asp Ile Asn Ser Asp Ser Glu Lys Leu Ser Gln
 65                  70                  75                  80

Leu Gln Lys Thr Ile Gln Gln Gln Asp Asn Leu Ser Gln Gln Leu
             85                  90                  95

Gly Asn Ser Asn Asn Leu Ser Met Glu Glu Phe Leu Lys Ser Gln
            100                 105                 110

Ile Ser Ser Val Leu Lys Arg Gln Glu Gln Met Ala Ile Lys Leu Cys
            115                 120                 125

Gln Glu Leu Ile Ile His Thr Ser Asp His Arg Cys Asn Pro Cys Pro
130                 135                 140

Lys Met Trp Gln Trp Tyr Gln Asn Ser Cys Tyr Tyr Phe Thr Thr Asn
145                 150                 155                 160

Glu Glu Lys Thr Trp Ala Asn Ser Arg Lys Asp Cys Ile Asp Lys Asn
                165                 170                 175

Ser Thr Leu Val Lys Ile Asp Ser Leu Glu Glu Lys Asp Phe Leu Met
            180                 185                 190

Ser Gln Pro Leu Leu Met Phe Ser Phe Phe Trp Leu Gly Leu Ser Trp
        195                 200                 205

Asp Ser Ser Gly Arg Ser Trp Phe Trp Glu Asp Gly Ser Val Pro Ser
        210                 215                 220

Pro Ser Leu Phe Ser Thr Lys Glu Leu Asp Gln Ile Asn Gly Ser Lys
225                 230                 235                 240

Gly Cys Ala Tyr Phe Gln Lys Gly Asn Ile Tyr Ile Ser Arg Cys Ser
                245                 250                 255

Ala Glu Ile Phe Trp Ile Cys Glu Lys Thr Ala Ala Pro Val Lys Thr
                260                 265                 270

Glu Asp Leu Asp
        275

<210> SEQ ID NO 341
<211> LENGTH: 247
<212> TYPE: PRT
<213> ORGANISM: Homo sapiens
<220> FEATURE:
<221> NAME/KEY: misc_feature
<222> LOCATION: (1)..(247)
<223> OTHER INFORMATION: Human Clec7A (UniProtKB #: Q9BXN2)

<400> SEQUENCE: 341

Met Glu Tyr His Pro Asp Leu Glu Asn Leu Asp Glu Asp Gly Tyr Thr
 1               5                  10                  15

Gln Leu His Phe Asp Ser Gln Ser Asn Thr Arg Ile Ala Val Val Ser
             20                  25                  30

Glu Lys Gly Ser Cys Ala Ala Ser Pro Pro Trp Arg Leu Ile Ala Val
         35                  40                  45

Ile Leu Gly Ile Leu Cys Leu Val Ile Leu Val Ile Ala Val Val Leu
 50                  55                  60

Gly Thr Met Ala Ile Trp Arg Ser Asn Ser Gly Ser Asn Thr Leu Glu
 65                  70                  75                  80

Asn Gly Tyr Phe Leu Ser Arg Asn Lys Glu Asn His Ser Gln Pro Thr
             85                  90                  95

Gln Ser Ser Leu Glu Asp Ser Val Thr Pro Thr Lys Ala Val Lys Thr
```

```
                    100                 105                 110
Thr Gly Val Leu Ser Ser Pro Cys Pro Asn Trp Ile Ile Tyr Glu
            115                 120                 125
Lys Ser Cys Tyr Leu Phe Ser Met Ser Leu Asn Ser Trp Asp Gly Ser
130                 135                 140
Lys Arg Gln Cys Trp Gln Leu Gly Ser Asn Leu Leu Lys Ile Asp Ser
145                 150                 155                 160
Ser Asn Glu Leu Gly Phe Ile Val Lys Gln Val Ser Ser Gln Pro Asp
                    165                 170                 175
Asn Ser Phe Trp Ile Gly Leu Ser Arg Pro Gln Thr Glu Val Pro Trp
            180                 185                 190
Leu Trp Glu Asp Gly Ser Thr Phe Ser Ser Asn Leu Phe Gln Ile Arg
        195                 200                 205
Thr Thr Ala Thr Gln Glu Asn Pro Ser Pro Asn Cys Val Trp Ile His
            210                 215                 220
Val Ser Val Ile Tyr Asp Gln Leu Cys Ser Val Pro Ser Tyr Ser Ile
225                 230                 235                 240
Cys Glu Lys Lys Phe Ser Met
                    245

<210> SEQ ID NO 342
<211> LENGTH: 195
<212> TYPE: PRT
<213> ORGANISM: Homo sapiens
<220> FEATURE:
<221> NAME/KEY: misc_feature
<222> LOCATION: (1)..(195)
<223> OTHER INFORMATION: Human KLRG1 (UniProtKB #: Q96E93)

<400> SEQUENCE: 342

Met Thr Asp Ser Val Ile Tyr Ser Met Leu Glu Leu Pro Thr Ala Thr
1               5                   10                  15
Gln Ala Gln Asn Asp Tyr Gly Pro Gln Gln Lys Ser Ser Ser Ser Arg
                20                  25                  30
Pro Ser Cys Ser Cys Leu Val Ala Ile Ala Leu Gly Leu Leu Thr Ala
            35                  40                  45
Val Leu Leu Ser Val Leu Leu Tyr Gln Trp Ile Leu Cys Gln Gly Ser
        50                  55                  60
Asn Tyr Ser Thr Cys Ala Ser Cys Pro Ser Cys Pro Asp Arg Trp Met
65                  70                  75                  80
Lys Tyr Gly Asn His Cys Tyr Tyr Phe Ser Val Glu Glu Lys Asp Trp
                85                  90                  95
Asn Ser Ser Leu Glu Phe Cys Leu Ala Arg Asp Ser His Leu Leu Val
                100                 105                 110
Ile Thr Asp Asn Gln Glu Met Ser Leu Leu Gln Val Phe Leu Ser Glu
            115                 120                 125
Ala Phe Cys Trp Ile Gly Leu Arg Asn Asn Ser Gly Trp Arg Trp Glu
        130                 135                 140
Asp Gly Ser Pro Leu Asn Phe Ser Arg Ile Ser Ser Asn Ser Phe Val
145                 150                 155                 160
Gln Thr Cys Gly Ala Ile Asn Lys Asn Gly Leu Gln Ala Ser Ser Cys
                165                 170                 175
Glu Val Pro Leu His Trp Val Cys Lys Lys Cys Pro Phe Ala Asp Gln
            180                 185                 190
Ala Leu Phe
        195
```

<210> SEQ ID NO 343
<211> LENGTH: 273
<212> TYPE: PRT
<213> ORGANISM: Homo sapiens
<220> FEATURE:
<221> NAME/KEY: misc_feature
<222> LOCATION: (1)..(273)
<223> OTHER INFORMATION: Human OLR1 (UniProtKB #: P78380)

<400> SEQUENCE: 343

Met Thr Phe Asp Asp Leu Lys Ile Gln Thr Val Lys Asp Gln Pro Asp
1               5                   10                  15

Glu Lys Ser Asn Gly Lys Lys Ala Lys Gly Leu Gln Phe Leu Tyr Ser
            20                  25                  30

Pro Trp Trp Cys Leu Ala Ala Ala Thr Leu Gly Val Leu Cys Leu Gly
        35                  40                  45

Leu Val Val Thr Ile Met Val Leu Gly Met Gln Leu Ser Gln Val Ser
    50                  55                  60

Asp Leu Leu Thr Gln Glu Gln Ala Asn Leu Thr His Gln Lys Lys Lys
65                  70                  75                  80

Leu Glu Gly Gln Ile Ser Ala Arg Gln Gln Ala Glu Glu Ala Ser Gln
                85                  90                  95

Glu Ser Glu Asn Glu Leu Lys Glu Met Ile Glu Thr Leu Ala Arg Lys
            100                 105                 110

Leu Asn Glu Lys Ser Lys Glu Gln Met Glu Leu His His Gln Asn Leu
        115                 120                 125

Asn Leu Gln Glu Thr Leu Lys Arg Val Ala Asn Cys Ser Ala Pro Cys
    130                 135                 140

Pro Gln Asp Trp Ile Trp His Gly Glu Asn Cys Tyr Leu Phe Ser Ser
145                 150                 155                 160

Gly Ser Phe Asn Trp Glu Lys Ser Gln Glu Lys Cys Leu Ser Leu Asp
                165                 170                 175

Ala Lys Leu Leu Lys Ile Asn Ser Thr Ala Asp Leu Asp Phe Ile Gln
            180                 185                 190

Gln Ala Ile Ser Tyr Ser Ser Phe Pro Phe Trp Met Gly Leu Ser Arg
        195                 200                 205

Arg Asn Pro Ser Tyr Pro Trp Leu Trp Glu Asp Gly Ser Pro Leu Met
    210                 215                 220

Pro His Leu Phe Arg Val Arg Gly Ala Val Ser Gln Thr Tyr Pro Ser
225                 230                 235                 240

Gly Thr Cys Ala Tyr Ile Gln Arg Gly Ala Val Tyr Ala Glu Asn Cys
                245                 250                 255

Ile Leu Ala Ala Phe Ser Ile Cys Gln Lys Lys Ala Asn Leu Arg Ala
            260                 265                 270

Gln

<210> SEQ ID NO 344
<211> LENGTH: 188
<212> TYPE: PRT
<213> ORGANISM: Homo sapiens
<220> FEATURE:
<221> NAME/KEY: misc_feature
<222> LOCATION: (1)..(188)
<223> OTHER INFORMATION: Human Clec5A (UniProtKB #: Q9NY25)

<400> SEQUENCE: 344

Met Asn Trp His Met Ile Ile Ser Gly Leu Ile Val Val Val Leu Lys

```
  1               5                   10                  15
Val Val Gly Met Thr Leu Phe Leu Leu Tyr Phe Pro Gln Ile Phe Asn
                 20                  25                  30

Lys Ser Asn Asp Gly Phe Thr Thr Thr Arg Ser Tyr Gly Thr Val Ser
                 35                  40                  45

Gln Ile Phe Gly Ser Ser Ser Pro Ser Pro Asn Gly Phe Ile Thr Thr
     50                  55                  60

Arg Ser Tyr Gly Thr Val Cys Pro Lys Asp Trp Glu Phe Tyr Gln Ala
65                   70                  75                  80

Arg Cys Phe Phe Leu Ser Thr Ser Glu Ser Ser Trp Asn Glu Ser Arg
                 85                  90                  95

Asp Phe Cys Lys Gly Lys Gly Ser Thr Leu Ala Ile Val Asn Thr Pro
                 100                 105                 110

Glu Lys Leu Lys Phe Leu Gln Asp Ile Thr Asp Ala Glu Lys Tyr Phe
                 115                 120                 125

Ile Gly Leu Ile Tyr His Arg Glu Gly Lys Arg Trp Arg Trp Ile Asn
    130                  135                 140

Asn Ser Val Phe Asn Gly Asn Val Thr Asn Gln Asn Gln Asn Phe Asn
145                  150                 155                 160

Cys Ala Thr Ile Gly Leu Thr Lys Thr Phe Asp Ala Ala Ser Cys Asp
                 165                 170                 175

Ile Ser Tyr Arg Arg Ile Cys Glu Lys Asn Ala Lys
                 180                 185
```

<210> SEQ ID NO 345
<211> LENGTH: 241
<212> TYPE: PRT
<213> ORGANISM: Homo sapiens
<220> FEATURE:
<221> NAME/KEY: misc_feature
<222> LOCATION: (1)..(241)
<223> OTHER INFORMATION: Human Clec9A (UniProtKB #: Q6UXN8)

<400> SEQUENCE: 345

```
Met His Glu Glu Glu Ile Tyr Thr Ser Leu Gln Trp Asp Ser Pro Ala
1                5                  10                  15

Pro Asp Thr Tyr Gln Lys Cys Leu Ser Ser Asn Lys Cys Ser Gly Ala
                 20                  25                  30

Cys Cys Leu Val Met Val Ile Ser Cys Val Phe Cys Met Gly Leu Leu
                 35                  40                  45

Thr Ala Ser Ile Phe Leu Gly Val Lys Leu Leu Gln Val Ser Thr Ile
     50                  55                  60

Ala Met Gln Gln Gln Glu Lys Leu Ile Gln Gln Glu Arg Ala Leu Leu
65                   70                  75                  80

Asn Phe Thr Glu Trp Lys Arg Ser Cys Ala Leu Gln Met Lys Tyr Cys
                 85                  90                  95

Gln Ala Phe Met Gln Asn Ser Leu Ser Ser Ala His Asn Ser Ser Pro
                 100                 105                 110

Cys Pro Asn Asn Trp Ile Gln Asn Arg Glu Ser Cys Tyr Tyr Val Ser
                 115                 120                 125

Glu Ile Trp Ser Ile Trp His Thr Ser Gln Glu Asn Cys Leu Lys Glu
    130                  135                 140

Gly Ser Thr Leu Leu Gln Ile Glu Ser Lys Glu Glu Met Asp Phe Ile
145                  150                 155                 160

Thr Gly Ser Leu Arg Lys Ile Lys Gly Ser Tyr Asp Tyr Trp Val Gly
                 165                 170                 175
```

```
Leu Ser Gln Asp Gly His Ser Gly Arg Trp Leu Trp Gln Asp Gly Ser
            180                 185                 190

Ser Pro Ser Pro Gly Leu Leu Pro Ala Glu Arg Ser Gln Ser Ala Asn
            195                 200                 205

Gln Val Cys Gly Tyr Val Lys Ser Asn Ser Leu Leu Ser Ser Asn Cys
210                 215                 220

Ser Thr Trp Lys Tyr Phe Ile Cys Glu Lys Tyr Ala Leu Arg Ser Ser
225                 230                 235                 240

Val

<210> SEQ ID NO 346
<211> LENGTH: 404
<212> TYPE: PRT
<213> ORGANISM: Homo sapiens
<220> FEATURE:
<221> NAME/KEY: misc_feature
<222> LOCATION: (1)..(404)
<223> OTHER INFORMATION: Human CD209 (UniProtKB #: Q9NNX6)

<400> SEQUENCE: 346

Met Ser Asp Ser Lys Glu Pro Arg Leu Gln Gln Leu Gly Leu Leu Glu
1               5                   10                  15

Glu Glu Gln Leu Arg Gly Leu Gly Phe Arg Gln Thr Arg Gly Tyr Lys
            20                  25                  30

Ser Leu Ala Gly Cys Leu Gly His Gly Pro Leu Val Leu Gln Leu Leu
            35                  40                  45

Ser Phe Thr Leu Leu Ala Gly Leu Leu Val Gln Val Ser Lys Val Pro
50                  55                  60

Ser Ser Ile Ser Gln Glu Gln Ser Arg Gln Asp Ala Ile Tyr Gln Asn
65                  70                  75                  80

Leu Thr Gln Leu Lys Ala Ala Val Gly Glu Leu Ser Glu Lys Ser Lys
            85                  90                  95

Leu Gln Glu Ile Tyr Gln Glu Leu Thr Gln Leu Lys Ala Ala Val Gly
            100                 105                 110

Glu Leu Pro Glu Lys Ser Lys Leu Gln Glu Ile Tyr Gln Glu Leu Thr
            115                 120                 125

Arg Leu Lys Ala Ala Val Gly Glu Leu Pro Glu Lys Ser Lys Leu Gln
            130                 135                 140

Glu Ile Tyr Gln Glu Leu Thr Trp Leu Lys Ala Ala Val Gly Glu Leu
145                 150                 155                 160

Pro Glu Lys Ser Lys Met Gln Glu Ile Tyr Gln Glu Leu Thr Arg Leu
            165                 170                 175

Lys Ala Ala Val Gly Glu Leu Pro Glu Lys Ser Lys Gln Gln Glu Ile
            180                 185                 190

Tyr Gln Glu Leu Thr Arg Leu Lys Ala Ala Val Gly Glu Leu Pro Glu
            195                 200                 205

Lys Ser Lys Gln Gln Glu Ile Tyr Gln Glu Leu Thr Arg Leu Lys Ala
            210                 215                 220

Ala Val Gly Glu Leu Pro Glu Lys Ser Lys Gln Gln Glu Ile Tyr Gln
225                 230                 235                 240

Glu Leu Thr Gln Leu Lys Ala Ala Val Glu Arg Leu Cys His Pro Cys
            245                 250                 255

Pro Trp Glu Trp Thr Phe Phe Gln Gly Asn Cys Tyr Phe Met Ser Asn
            260                 265                 270

Ser Gln Arg Asn Trp His Asp Ser Ile Thr Ala Cys Lys Glu Val Gly
```

```
                275                 280                 285
Ala Gln Leu Val Val Ile Lys Ser Ala Glu Glu Gln Asn Phe Leu Gln
290                 295                 300

Leu Gln Ser Ser Arg Ser Asn Arg Phe Thr Trp Met Gly Leu Ser Asp
305                 310                 315                 320

Leu Asn Gln Glu Gly Thr Trp Gln Trp Val Asp Gly Ser Pro Leu Leu
                325                 330                 335

Pro Ser Phe Lys Gln Tyr Trp Asn Arg Gly Glu Pro Asn Asn Val Gly
                340                 345                 350

Glu Glu Asp Cys Ala Glu Phe Ser Gly Asn Gly Trp Asn Asp Asp Lys
                355                 360                 365

Cys Asn Leu Ala Lys Phe Trp Ile Cys Lys Lys Ser Ala Ala Ser Cys
370                 375                 380

Ser Arg Asp Glu Glu Gln Phe Leu Ser Pro Ala Pro Ala Thr Pro Asn
385                 390                 395                 400

Pro Pro Pro Ala

<210> SEQ ID NO 347
<211> LENGTH: 219
<212> TYPE: PRT
<213> ORGANISM: Homo sapiens
<220> FEATURE:
<221> NAME/KEY: misc_feature
<222> LOCATION: (1)..(219)
<223> OTHER INFORMATION: Human Clec4E (UniProtKB #: Q9ULY5)

<400> SEQUENCE: 347

Met Asn Ser Ser Lys Ser Ser Glu Thr Gln Cys Thr Glu Arg Gly Cys
1               5                   10                  15

Phe Ser Ser Gln Met Phe Leu Trp Thr Val Ala Gly Ile Pro Ile Leu
                20                  25                  30

Phe Leu Ser Ala Cys Phe Ile Thr Arg Cys Val Val Thr Phe Arg Ile
            35                  40                  45

Phe Gln Thr Cys Asp Glu Lys Lys Phe Gln Leu Pro Glu Asn Phe Thr
        50                  55                  60

Glu Leu Ser Cys Tyr Asn Tyr Gly Ser Gly Ser Val Lys Asn Cys Cys
65                  70                  75                  80

Pro Leu Asn Trp Glu Tyr Phe Gln Ser Ser Cys Tyr Phe Phe Ser Thr
                85                  90                  95

Asp Thr Ile Ser Trp Ala Leu Ser Leu Lys Asn Cys Ser Ala Met Gly
                100                 105                 110

Ala His Leu Val Val Ile Asn Ser Gln Glu Glu Gln Glu Phe Leu Ser
            115                 120                 125

Tyr Lys Lys Pro Lys Met Arg Glu Phe Phe Ile Gly Leu Ser Asp Gln
        130                 135                 140

Val Val Glu Gly Gln Trp Gln Trp Val Asp Gly Thr Pro Leu Thr Lys
145                 150                 155                 160

Ser Leu Ser Phe Trp Asp Val Gly Glu Pro Asn Asn Ile Ala Thr Leu
                165                 170                 175

Glu Asp Cys Ala Thr Met Arg Asp Ser Ser Asn Pro Arg Gln Asn Trp
                180                 185                 190

Asn Asp Val Thr Cys Phe Leu Asn Tyr Phe Arg Ile Cys Glu Met Val
            195                 200                 205

Gly Ile Asn Pro Leu Asn Lys Gly Lys Ser Leu
        210                 215
```

```
<210> SEQ ID NO 348
<211> LENGTH: 316
<212> TYPE: PRT
<213> ORGANISM: Homo sapiens
<220> FEATURE:
<221> NAME/KEY: misc_feature
<222> LOCATION: (1)..(316)
<223> OTHER INFORMATION: Human Clec10A (UniProtKB #: Q8IUN9)

<400> SEQUENCE: 348

Met Thr Arg Thr Tyr Glu Asn Phe Gln Tyr Leu Glu Asn Lys Val Lys
1               5                   10                  15

Val Gln Gly Phe Lys Asn Gly Pro Leu Pro Leu Gln Ser Leu Leu Gln
            20                  25                  30

Arg Leu Cys Ser Gly Pro Cys His Leu Leu Ser Leu Gly Leu Gly
        35                  40                  45

Leu Leu Leu Leu Val Ile Ile Cys Val Val Gly Phe Gln Asn Ser Lys
    50                  55                  60

Phe Gln Arg Asp Leu Val Thr Leu Arg Thr Asp Phe Ser Asn Phe Thr
65                  70                  75                  80

Ser Asn Thr Val Ala Glu Ile Gln Ala Leu Thr Ser Gln Gly Ser Ser
                85                  90                  95

Leu Glu Glu Thr Ile Ala Ser Leu Lys Ala Glu Val Glu Gly Phe Lys
            100                 105                 110

Gln Glu Arg Gln Ala Gly Val Ser Glu Leu Gln Glu His Thr Thr Gln
        115                 120                 125

Lys Ala His Leu Gly His Cys Pro His Cys Pro Ser Val Cys Val Pro
    130                 135                 140

Val His Ser Glu Met Leu Leu Arg Val Gln Gln Leu Val Gln Asp Leu
145                 150                 155                 160

Lys Lys Leu Thr Cys Gln Val Ala Thr Leu Asn Asn Asn Ala Ser Thr
                165                 170                 175

Glu Gly Thr Cys Cys Pro Val Asn Trp Val His Gln Asp Ser Cys
            180                 185                 190

Tyr Trp Phe Ser His Ser Gly Met Ser Trp Ala Glu Ala Glu Lys Tyr
        195                 200                 205

Cys Gln Leu Lys Asn Ala His Leu Val Val Ile Asn Ser Arg Glu Glu
    210                 215                 220

Gln Asn Phe Val Gln Lys Tyr Leu Gly Ser Ala Tyr Thr Trp Met Gly
225                 230                 235                 240

Leu Ser Asp Pro Glu Gly Ala Trp Lys Trp Val Asp Gly Thr Asp Tyr
                245                 250                 255

Ala Thr Gly Phe Gln Asn Trp Lys Pro Gly Gln Pro Asp Asp Trp Gln
            260                 265                 270

Gly His Gly Leu Gly Gly Gly Glu Asp Cys Ala His Phe His Pro Asp
        275                 280                 285

Gly Arg Trp Asn Asp Asp Val Cys Gln Arg Pro Tyr His Trp Val Cys
    290                 295                 300

Glu Ala Gly Leu Gly Gln Thr Ser Gln Glu Ser His
305                 310                 315

<210> SEQ ID NO 349
<211> LENGTH: 231
<212> TYPE: PRT
<213> ORGANISM: Homo sapiens
<220> FEATURE:
<221> NAME/KEY: misc_feature
```

<222> LOCATION: (1)..(231)
<223> OTHER INFORMATION: Human KLRF1 (UniProtKB #: Q9NZS2)

<400> SEQUENCE: 349

Met Gln Asp Glu Glu Arg Tyr Met Thr Leu Asn Val Gln Ser Lys Lys
1               5                   10                  15

Arg Ser Ser Ala Gln Thr Ser Gln Leu Thr Phe Lys Asp Tyr Ser Val
            20                  25                  30

Thr Leu His Trp Tyr Lys Ile Leu Leu Gly Ile Ser Gly Thr Val Asn
        35                  40                  45

Gly Ile Leu Thr Leu Thr Leu Ile Ser Leu Ile Leu Val Ser Gln
50                  55                  60

Gly Val Leu Leu Lys Cys Gln Lys Gly Ser Cys Ser Asn Ala Thr Gln
65                  70                  75                  80

Tyr Glu Asp Thr Gly Asp Leu Lys Val Asn Asn Gly Thr Arg Arg Asn
                85                  90                  95

Ile Ser Asn Lys Asp Leu Cys Ala Ser Arg Ser Ala Asp Gln Thr Val
            100                 105                 110

Leu Cys Gln Ser Glu Trp Leu Lys Tyr Gln Gly Lys Cys Tyr Trp Phe
        115                 120                 125

Ser Asn Glu Met Lys Ser Trp Ser Asp Ser Tyr Val Tyr Cys Leu Glu
130                 135                 140

Arg Lys Ser His Leu Leu Ile Ile His Asp Gln Leu Glu Met Ala Phe
145                 150                 155                 160

Ile Gln Lys Asn Leu Arg Gln Leu Asn Tyr Val Trp Ile Gly Leu Asn
                165                 170                 175

Phe Thr Ser Leu Lys Met Thr Trp Thr Trp Val Asp Gly Ser Pro Ile
            180                 185                 190

Asp Ser Lys Ile Phe Phe Ile Lys Gly Pro Ala Lys Glu Asn Ser Cys
        195                 200                 205

Ala Ala Ile Lys Glu Ser Lys Ile Phe Ser Glu Thr Cys Ser Ser Val
210                 215                 220

Phe Lys Trp Ile Cys Gln Tyr
225                 230

<210> SEQ ID NO 350
<211> LENGTH: 20
<212> TYPE: RNA
<213> ORGANISM: Artificial Sequence
<220> FEATURE:
<223> OTHER INFORMATION: Synthetic: TRAC gRNA spacer

<400> SEQUENCE: 350
ucaggguucu ggauaucugu                                           20

<210> SEQ ID NO 351
<211> LENGTH: 23
<212> TYPE: DNA
<213> ORGANISM: Artificial Sequence
<220> FEATURE:
<223> OTHER INFORMATION: Synthetic: TRAC target gene

<400> SEQUENCE: 351
tcagggttct ggatatctgt ggg                                       23

<210> SEQ ID NO 352
<211> LENGTH: 20
<212> TYPE: RNA
<213> ORGANISM: Artificial Sequence

```
<220> FEATURE:
<223> OTHER INFORMATION: Synthetic: KLRB1 gRNA spacer

<400> SEQUENCE: 352
aauuaaagcc acuuaccccg                                              20

<210> SEQ ID NO 353
<211> LENGTH: 23
<212> TYPE: DNA
<213> ORGANISM: Artificial Sequence
<220> FEATURE:
<223> OTHER INFORMATION: Synthetic: KLRB1 target gene

<400> SEQUENCE: 353
aattaaagcc acttaccccg agg                                          23

<210> SEQ ID NO 354
<211> LENGTH: 20
<212> TYPE: RNA
<213> ORGANISM: Artificial Sequence
<220> FEATURE:
<223> OTHER INFORMATION: Synthetic: LacZ gRNA spacer

<400> SEQUENCE: 354
gcugagcgcu cggagcgccu                                              20

<210> SEQ ID NO 355
<211> LENGTH: 20
<212> TYPE: DNA
<213> ORGANISM: Artificial Sequence
<220> FEATURE:
<223> OTHER INFORMATION: Synthetic: LacZ target gene

<400> SEQUENCE: 355
gctgagcgct cggagcgcct                                              20

<210> SEQ ID NO 356
<211> LENGTH: 1908
<212> TYPE: DNA
<213> ORGANISM: Artificial Sequence
<220> FEATURE:
<223> OTHER INFORMATION: Synthetic: NY-ESO-1 TCR

<400> SEQUENCE: 356
gccgccacca tggtaccgtg cacgctgctc ctgctgttgg cggccgccct ggctccgact    60
cagacccgcg cgaaaagtta tccttacgac gtgcccgact acgccggaaa gcaagaagtg   120
acacagatcc ctgccgctct gtctgtgcct gagggcgaaa acctggtgct gaactgcagc   180
ttcaccgaca gcgccatcta aacctgcag tggttcagac aggaccccgg caagggactg   240
acaagcctgc tgctgattca gagcagccag agagagcaga ccagcggcag actgaatgcc   300
agcctggata gtcctccgg cagaagcacc ctgtatatcg ccgcttctca gcctggcgat   360
agcgccacat atctgtgtgc cgtgcgacct ctgtacggcg gcagctacat ccctacattt   420
ggcagaggca ccagcctgat cgtgcacccc aacattcaaa atcctgatcc tgccgtgtac   480
cagctgagag acagcaagtc cagcgacaag agcgtgtgcc tgttcaccga cttcgacagc   540
cagaccaacg tgtcccagag caaggacagc gacgtgtaca tcaccgacaa gaccgtgctg   600
gacatgcgga gcatggactt caagagcaac agcgccgtgg cctggtccaa caagagcgat   660
ttcgcctgcg ccaacgcctt caacaacagc attatccccg aggacacatt cttcccaagt   720
cctgagagca gctgcgacgt gaagctggtg gaaaagagct cgagacagac accaaacctg   780
```

```
aactttcaaa acctgagcgt gatcggcttc cggatcctgc tgcttaaggt ggccggcttc        840
aacctgctga tgaccctgag actgtggtcc tctgagggca gaggcagcct gctgacctgc        900
ggcgacgtgg aggagaaccc cggccccatg gtaccgtgca cgctgctcct gctgttggcg        960
gccgccctgg ctccgactca gaccgcgcg gaggaccagg tggaccccag gctgatcgac         1020
ggcaagggca atgctggcgt cacccagaca cctaagttcc aggtgctgaa aaccggccag        1080
agcatgaccc tgcagtgcgc ccaggatatg aaccacgagt acatgtcctg gtatcggcag        1140
gaccctggaa tggggctgag actgatccac tactctgtcg gagccggcat caccgatcag        1200
ggcgaagtgc ctaatggcta caatgtgtcc cggtccacca ccgaggactt cccactgaga        1260
ctgctgtctg ctgcccctag ccagacctcc gtgtactttt gtgccagcag ctacgtgggc        1320
aacaccggcg agctgttttt tggcgagggc tccagactga ccgtgctcga ggacctgaag        1380
aacgtgttcc cacctgaggt ggccgtgttc gagccttctg aggccgagat cagccacaca        1440
cagaaagcca cactcgtgtg tctggccacc ggcttctatc ccgatcacgt ggaactgtct        1500
tggtgggtca acggcaaaga ggtgcacagc ggcgtcagca cagatcctca gcctctgaaa        1560
gagcagcccg ctctgaacga cagcagatac tgcctgagca gcagactgag agtgtccgcc        1620
accttctggc aaaatcctag aaaccacttc agatgccagg tgcagttcta cggcctgagc        1680
gagaacgatg agtggaccca ggatagagcc aagcctgtga ctcagatcgt gtctgccgaa        1740
gcctggggca gagccgattg tggctttacc agcgagagct accagcaggg cgttctgtct        1800
gccaccatcc tgtacgagat tctgctgggc aaagccactc tgtacgccgt gctggtgtct        1860
gccctggttc tgatggccat ggtcaagcgg aaggacagca gaggatga                    1908
```

<210> SEQ ID NO 357
<211> LENGTH: 9
<212> TYPE: DNA
<213> ORGANISM: Artificial Sequence
<220> FEATURE:
<223> OTHER INFORMATION: Synthetic: Kozak sequence

<400> SEQUENCE: 357

```
gccgccacc                                                                9
```

<210> SEQ ID NO 358
<211> LENGTH: 63
<212> TYPE: DNA
<213> ORGANISM: Artificial Sequence
<220> FEATURE:
<223> OTHER INFORMATION: Synthetic: Signal peptide1

<400> SEQUENCE: 358

```
atggtaccgt gcacgctgct cctgctgttg gcggccgccc tggctccgac tcagacccgc        60
gcg                                                                      63
```

<210> SEQ ID NO 359
<211> LENGTH: 27
<212> TYPE: DNA
<213> ORGANISM: Artificial Sequence
<220> FEATURE:
<223> OTHER INFORMATION: Synthetic: HA tag

<400> SEQUENCE: 359

```
tatccttacg acgtgcccga ctacgcc                                            27
```

<210> SEQ ID NO 360
<211> LENGTH: 342

```
<212> TYPE: DNA
<213> ORGANISM: Artificial Sequence
<220> FEATURE:
<223> OTHER INFORMATION: Synthetic: NY-ESO-1 TCR alpha-variable chain

<400> SEQUENCE: 360
aagcaagaag tgacacagat ccctgccgct ctgtctgtgc ctgagggcga aaacctggtg      60
ctgaactgca gcttcaccga cagcgccatc tacaacctgc agtggttcag acaggacccc    120
ggcaagggac tgcaagcct gctgctgatt cagagcagcc agagagagca gaccagcggc     180
agactgaatg ccagcctgga taagtcctcc ggcagaagca ccctgtatat cgccgcttct    240
cagcctggcg atagcgccac atatctgtgt gccgtgcgac tctgtacgg cggcagctac     300 atccctacat ttggcagagg caccagcctg atcgtgcacc cc                       342

<210> SEQ ID NO 361
<211> LENGTH: 423
<212> TYPE: DNA
<213> ORGANISM: Artificial Sequence
<220> FEATURE:
<223> OTHER INFORMATION: Synthetic: NY-ESO-1 TCR alpha-constant chain

<400> SEQUENCE: 361
aacattcaaa atcctgatcc tgccgtgtac cagctgagag acagcaagtc cagcgacaag      60
agcgtgtgcc tgttcaccga cttcgacagc cagaccaacg tgtcccagag caaggacagc    120
gacgtgtaca tcaccgacaa gaccgtgctg acatgcgga gcatggactt caagagcaac     180
agcgccgtgg cctggtccaa caagagcgat ttcgcctgcg ccaacgcctt caacaacagc    240
attatccccg aggacacatt cttcccaagt cctgagagca gctgcgacgt gaagctggtg    300
gaaaagagct tcgagacaga caccaacctg aactttcaaa acctgagcgt gatcggcttc    360
cggatcctgc tgcttaaggt ggccggcttc aacctgctga tgaccctgag actgtggtcc    420
tct                                                                  423

<210> SEQ ID NO 362
<211> LENGTH: 54
<212> TYPE: DNA
<213> ORGANISM: Artificial Sequence
<220> FEATURE:
<223> OTHER INFORMATION: Synthetic: T2A skip peptide

<400> SEQUENCE: 362
gagggcagag gcagcctgct gacctgcggc gacgtggagg agaaccccgg cccc          54

<210> SEQ ID NO 363
<211> LENGTH: 63
<212> TYPE: DNA
<213> ORGANISM: Artificial Sequence
<220> FEATURE:
<223> OTHER INFORMATION: Synthetic: TCR beta chain signal Peptide

<400> SEQUENCE: 363
atggtaccgt gcacgctgct cctgctgttg gcggccgccc tggctccgac tcagacccgc     60
gcg                                                                   63

<210> SEQ ID NO 364
<211> LENGTH: 36
<212> TYPE: DNA
<213> ORGANISM: Artificial Sequence
<220> FEATURE:
<223> OTHER INFORMATION: Synthetic: NY-ESO-1 TCR PC tag
```

-continued

<400> SEQUENCE: 364
gaggaccagg tggacccag gctgatcgac ggcaag  36

<210> SEQ ID NO 365
<211> LENGTH: 342
<212> TYPE: DNA
<213> ORGANISM: Artificial Sequence
<220> FEATURE:
<223> OTHER INFORMATION: Synthetic: NY-ESO-1 TCR beta-variable chain

<400> SEQUENCE: 365

```
ggcaatgctg gcgtcaccca gacacctaag ttccaggtgc tgaaaaccgg ccagagcatg    60
accctgcagt gcgcccagga tatgaaccac gagtacatgt cctggtatcg gcaggaccct   120
ggaatggggc tgagactgat ccactactct gtcggagccg gcatcaccga tcagggcgaa   180
gtgcctaatg gctacaatgt gtcccggtcc accaccgagg acttcccact gagactgctg   240
tctgctgccc ctagccagac ctccgtgtac ttttgtgcca gcagctacgt gggcaacacc   300
ggcgagctgt tttttggcga gggctccaga ctgaccgtgc tc                      342
```

<210> SEQ ID NO 366
<211> LENGTH: 537
<212> TYPE: DNA
<213> ORGANISM: Artificial Sequence
<220> FEATURE:
<223> OTHER INFORMATION: Synthetic: NY-ESO-1 TCR beta-constant chain

<400> SEQUENCE: 366

```
gaggacctga agaacgtgtt cccacctgag gtggccgtgt tcgagccttc tgaggccgag    60
atcagccaca cacagaaagc cacactcgtg tgtctggcca ccggcttcta tcccgatcac   120
gtggaactgt cttggtgggt caacggcaaa gaggtgcaca gcggcgtcag cacagatcct   180
cagcctctga agagcagcc cgctctgaac gacagcagat actgcctgag cagcagactg   240
agagtgtccg ccaccttctg gcaaaatcct agaaaccact tcagatgcca ggtgcagttc   300
tacggcctga gcgagaacga tgagtggacc caggatagag ccaagcctgt gactcagatc   360
gtgtctgccg aagcctgggg cagagccgat tgtggcttta ccagcgagag ctaccagcag   420
ggcgttctgt ctgccaccat cctgtacgag attctgctgg caaagccac tctgtacgcc   480
gtgctggtgt ctgccctggt tctgatggcc atggtcaagc ggaaggacag cagagga     537
```

<210> SEQ ID NO 367
<211> LENGTH: 3665
<212> TYPE: DNA
<213> ORGANISM: Artificial Sequence
<220> FEATURE:
<223> OTHER INFORMATION: Synthetic: NY-ESO-1 construct

<400> SEQUENCE: 367

```
gccgccacca tgcaggccga aggaagaggt acaggggggtt cgacgggcga tgctgatggc    60
ccaggaggcc ctggcattcc tgatggccca ggggggcaatg ctggtggacc aggagaggcg   120
ggtgccacgg gaggtagagg tccacgggga gcaggtgcag caagggcttc gggaccggga   180
ggaggtgccc cgcggggtcc gcatggtgga gcagcttcag gctgaatgg atgctgcaga   240
tgcggggcca gggggccgga gagccgcctg cttgagttct acctcgccat gccttttgcg   300
acacccatgg aagcagagct ggccgcagg agcctggccc aggatgcccc accgcttccc   360
gtgccagggg tgcttctgaa ggagttcact gtgtccggca acatactgac tatccgactg   420
actgctgcag accaccgcca actgcagctc tccatcagct cctgtctcca gcagctttcc   480
```

-continued

| | |
|---|---|
| ctgttgatgt ggatcacgca gtgctttctg cccgtgtttt tggctcagcc tccctcaggg | 540 |
| cagaggcgcg agggcagagg cagcctgctg acctgcggcg acgtggagga gaaccccggc | 600 |
| cccatggaag atgccaagaa catcaagaaa ggccctgccc ccttctaccc cctggaagat | 660 |
| ggcacagccg cgagcagct gcacaaggcc atgaagagat acgccctggt gcccggcacc | 720 |
| atcgccttca ccgacgccca catcgaggtg gacatcacct acgccgagta tttcgagatg | 780 |
| agcgtgcggc tggccgaggc catgaaacgc tacggcctga acaccaacca ccggatcgtg | 840 |
| gtgtgcagcg agaacagcct gcagttcttc atgcccgtgc tgggcgccct gttcatcggc | 900 |
| gtggccgtgg cccctgccaa cgacatctac aacgagcggg agctgctgaa cagcatgggc | 960 |
| atcagccagc ccaccgtggt gttcgtgagc aagaagggcc tgcagaaaat cctgaacgtg | 1020 |
| cagaagaagc tgcccatcat ccagaaaatc atcatcatgg acagcaagac cgactaccag | 1080 |
| ggcttccaga gcatgtacac cttcgtgacc agccacctgc ccctggcttc aacgagtac | 1140 |
| gacttcgtgc ccgagagctt cgaccgggac aagaccatcg ccctgatcat gaacagcagc | 1200 |
| ggcagcaccg gcctgcctaa aggcgtggcc ctgcctcacc ggaccgcctg cgtgcggttc | 1260 |
| agccacgccc gggaccccat cttcggcaac cagatcatcc ccgacaccgc catcctgagc | 1320 |
| gtggtgccct tccaccacgg cttcggcatg ttcaccaccc tgggctacct gatctgcggc | 1380 |
| ttccgggtgg tgctgatgta ccggttcgag gaagagctgt tcctgcggag cctgcaggac | 1440 |
| tacaagatcc agagcgccct gctggtgccc accctgttca gcttttttcgc caagagcacc | 1500 |
| ctgatcgaca gtacgacct gagcaacctg cacgagatcg ccagcggcgg agcccccctg | 1560 |
| tccaaagaag tgggcgaagc cgtcgccaag cggttccacc tgcccggcat ccggcagggc | 1620 |
| tatggcctga ccgagaccac aagcgccatt ctgatcaccc ccgagggcga cgacaagcct | 1680 |
| ggcgccgtgg gcaaggtggt gcctttcttc gaggccaagg tggtggacct ggacaccggc | 1740 |
| aagaccctgg gcgtgaacca gcggggcgag ctgtgcgtga ggggcccat gatcatgagc | 1800 |
| ggctacgtga acaaccccga ggccaccaac gccctgattg acaaggacgg ctggctgcac | 1860 |
| agcggcgaca tcgcctactg ggacgaggac gagcacttct tcatcgtgga ccggctgaag | 1920 |
| agcctgatca agtacaaggg ctaccaggtg gccccagccg agctggaaag catcctgctg | 1980 |
| cagcacccca acatcttcga tgccggggtg gccggactgc ccgacgacga tgccggcgag | 2040 |
| ctgcctgccg ccgtggtggt gctggaacac ggcaaaacca tgaccgagaa agaaatcgtg | 2100 |
| gactacgtgg ccagccaggt gaccaccgcc aagaaactga aggcggcgt ggtgtttgtg | 2160 |
| gacgaggtgc ccaagggcct gacaggcaag ctggacgccc ggaagatccg ggagatcctg | 2220 |
| atcaaggcca agaagggcgg caagtccaaa ttgtaatcta gaggatccct ccccccccc | 2280 |
| taacgttact ggccgaagcc gcttggaata aggccggtgt gcgtttgtct atatgttatt | 2340 |
| ttccaccata ttgccgtctt ttggcaatgt gagggcccgg aaacctggcc ctgtcttctt | 2400 |
| gacgagcatt cctaggggtc tttcccctct cgccaaagga atgcaaggtc tgttgaatgt | 2460 |
| cgtgaaggaa gcagttcctc tggaagcttc ttgaagacaa acaacgtctg tagcgaccct | 2520 |
| ttgcaggcag cggaaccccc cacctggcga caggtgcctc tgcggccaaa agccacgtgt | 2580 |
| ataagataca cctgcaaagg cggcacaacc ccagtgccac gttgtgagtt ggatagttgt | 2640 |
| ggaaagagtc aaatggctct cctcaagcgt attcaacaag ggctgaagg atgcccagaa | 2700 |
| ggtaccccat tgtatgggat ctgatctggg gcctcggtgc acatgcttta catgtgttta | 2760 |
| gtcgaggtta aaaaaacgtc taggccccccc gaaccacggg gacgtggttt tcctttgaaa | 2820 |

| | |
|---|---|
| aacacgatga taatatggcc acacatatgg ccacaaccat ggacgggccg cgcctgctgc | 2880 |
| tgttgctgct tctggggtg tcccttggag gtgccaagga ggcatgcccc acaggcctgt | 2940 |
| acacacacag cggtgagtgc tgcaaagcct gcaacctggg cgagggtgtg gcccagcctt | 3000 |
| gtggagccaa ccagaccgtg tgtgagccct gcctggacag cgtgacgttc tccgacgtgg | 3060 |
| tgagcgcgac cgagccgtgc aagccgtgca ccgagtgcgt ggggctccag agcatgtcgg | 3120 |
| cgccgtgcgt ggaggccgac gacgccgtgt gccgctgcgc ctacggctac taccaggatg | 3180 |
| agacgactgg gcgctgcgag gcgtgccgcg tgtgcgaggc gggctcgggc ctcgtgttct | 3240 |
| cctgccagga caagcagaac accgtgtgcg aggagtgccc cgacggcacg tattccgacg | 3300 |
| aggccaacca cgtggacccg tgcctgccct gcaccgtgtg cgaggacacc gagcgccagc | 3360 |
| tccgcgagtg cacacgctgg gccgacgccg agtgcgagga gatccctggc cgttggatta | 3420 |
| cacggtccac accccagag ggctcggaca gcacagcccc cagcacccag gagcctgagg | 3480 |
| cacctccaga caagacctc atagccagca cggtggcagg tgtggtgacc acagtgatgg | 3540 |
| gcagctccca gcccgtggtg acccgaggca ccaccgacaa cctcatccct gtctattgct | 3600 |
| ccatcctggc tgctgtggtt gtgggccttg tggcctacat agccttcaag aggtggaaca | 3660 |
| gttga | 3665 |

<210> SEQ ID NO 368
<211> LENGTH: 540
<212> TYPE: DNA
<213> ORGANISM: Artificial Sequence
<220> FEATURE:
<223> OTHER INFORMATION: Synthetic: NY-ESO-1 peptide

<400> SEQUENCE: 368

| | |
|---|---|
| atgcaggccg aaggaagagg tacaggggt tcgacgggcg atgctgatgg cccaggaggc | 60 |
| cctggcattc ctgatggccc aggggggcaat gctggtggac caggagaggc gggtgccacg | 120 |
| ggaggtagag gtccacgggg agcaggtgca gcaagggctt cgggaccggg aggaggtgcc | 180 |
| ccgcggggtc cgcatggtgg agcagcttca gggctgaatg gatgctgcag atgcggggcc | 240 |
| agggggccgg agagccgcct gcttgagttc tacctcgcca tgcctttcgc gacacccatg | 300 |
| gaagcagagc tggcccgcag gagcctggcc caggatgccc accgcttcc cgtgccaggg | 360 |
| gtgcttctga aggagttcac tgtgtccggc aacatactga ctatccgact gactgctgca | 420 |
| gaccaccgcc aactgcagct ctccatcagc tcctgtctcc agcagctttc cctgttgatg | 480 |
| tggatcacgc agtgctttct gcccgtgttt ttggctcagc ctccctcagg gcagaggcgc | 540 |

<210> SEQ ID NO 369
<211> LENGTH: 27
<212> TYPE: DNA
<213> ORGANISM: Artificial Sequence
<220> FEATURE:
<223> OTHER INFORMATION: Synthetic: 1G4 epitope

<400> SEQUENCE: 369

| | |
|---|---|
| tccctgttga tgtggatcac gcagtgc | 27 |

<210> SEQ ID NO 370
<211> LENGTH: 1653
<212> TYPE: DNA
<213> ORGANISM: Artificial Sequence
<220> FEATURE:
<223> OTHER INFORMATION: Synthetic: Luciferase

<400> SEQUENCE: 370

```
atggaagatg ccaagaacat caagaaaggc cctgccccct tctacccct  ggaagatggc      60 acagccggcg agcagctgca caaggccatg aagagatacg ccctggtgcc cggcaccatc     120
gccttcaccg acgcccacat cgaggtggac atcacctacg ccgagtattt cgagatgagc     180
gtgcggctgg ccgaggccat gaaacgctac ggcctgaaca ccaaccaccg gatcgtggtg     240
tgcagcgaga cagcctgca  gttcttcatg cccgtgctgg gcgccctgtt catcggcgtg     300
gccgtggccc ctgccaacga catctacaac gagcgggagc tgctgaacag catgggcatc     360
agccagccca ccgtggtgtt cgtgagcaag aagggcctgc agaaaatcct gaacgtgcag     420
aagaagctgc ccatcatcca gaaaatcatc atcatggaca gcaagaccga ctaccagggc     480
ttccagagca tgtacacctt cgtgaccagc cacctgcccc tggcttcaa  cgagtacgac     540 ttcgtgcccg agagcttcga ccgggacaag accatcgccc tgatcatgaa cagcagcggc     600
agcaccggcc tgcctaaagg cgtggccctg cctcaccgga ccgcctgcgt gcggttcagc     660
cacgcccggg accccatctt cggcaaccag atcatccccg acaccgccat cctgagcgtg     720
gtgcccttcc accacggctt cggcatgttc accaccctgg ctacctgat  ctgcggcttc     780 cgggtggtgc tgatgtaccg gttcgaggaa gagctgttcc tgcggagcct gcaggactac     840
aagatccaga gcgccctgct ggtgcccacc ctgttcagct ttttcgccaa gagcaccctg     900
atcgacaagt acgacctgag caacctgcac gagatcgcca gcggcggagc ccccctgtcc     960
aaagaagtgg gcgaagccgt cgccaagcgg ttccacctgc ccggcatccg gcagggctat    1020
ggcctgaccg agaccacaag cgccattctg atcaccccg  agggcgacga caagcctggc    1080
gccgtgggca aggtggtgcc tttcttcgag gccaaggtgg tggacctgga caccggcaag    1140
accctgggcg tgaaccagcg gggcgagctg tgcgtgaggg gccccatgat catgagcggc    1200
tacgtgaaca accccgaggc caccaacgcc ctgattgaca ggacggctg  gctgcacagc    1260 ggcgacatcg cctactggga cgaggacgag cacttcttca tcgtggaccg gctgaagagc    1320
ctgatcaagt acaagggcta ccaggtggcc ccagccgagc tggaaagcat cctgctgcag    1380 cacccccaaca tcttcgatgc cggggtggcc ggactgcccg acgacgatgc cggcgagctg    1440
cctgccgccg tggtggtgct ggaacacggc aaaaccatga ccgagaaaga aatcgtggac    1500
tacgtggcca gccaggtgac caccgccaag aaactgagag cggcgtggt  gtttgtggac    1560 gaggtgccca gggcctgac  aggcaagctg gacgcccgga gatccgggga gatcctgatc    1620
aaggccaaga agggcggcaa gtccaaattg taa                                 1653
```

<210> SEQ ID NO 371
<211> LENGTH: 568
<212> TYPE: DNA
<213> ORGANISM: Artificial Sequence
<220> FEATURE:
<223> OTHER INFORMATION: Synthetic: IRES

<400> SEQUENCE: 371

```
tccctccccc cccctaacg  ttactggccg aagccgcttg gaataaggcc ggtgtgcgtt      60
tgtctatatg ttattttcca ccatattgcc gtcttttggc aatgtgaggg cccggaaacc     120
tggccctgtc ttcttgacga gcattcctag gggtctttcc cctctcgcca aggaatgca      180 aggtctgttg aatgtcgtga aggaagcagt tcctctggaa gcttcttgaa gacaaacaac     240
gtctgtagcg accctttgca ggcagcggaa ccccccacct ggcgacaggt gcctctgcgg     300
ccaaaagcca cgtgtataag atacacctgc aaaggcggca acccccagt  gccacgttgt     360
```

```
gagttggata gttgtggaaa gagtcaaatg gctctcctca gcgtattca acaaggggct     420 gaaggatgcc cagaaggtac cccattgtat gggatctgat ctggggcctc ggtgcacatg     480
ctttacatgt gtttagtcga ggttaaaaaa acgtctaggc cccccgaacc acggggacgt     540
ggttttcctt tgaaaaacac gatgataa                                        568
```

```
<210> SEQ ID NO 372
<211> LENGTH: 69
<212> TYPE: DNA
<213> ORGANISM: Artificial Sequence
<220> FEATURE:
<223> OTHER INFORMATION: Synthetic: NY-ESO-1 construct Signal peptide

<400> SEQUENCE: 372
atggccacaa ccatggacgg gccgcgcctg ctgctgttgc tgcttctggg ggtgtccctt     60
ggaggtgcc                                                              69
```

```
<210> SEQ ID NO 373
<211> LENGTH: 666
<212> TYPE: DNA
<213> ORGANISM: Artificial Sequence
<220> FEATURE:
<223> OTHER INFORMATION: Synthetic: NY-ESO-1 construct  NGFR
      extracellular

<400> SEQUENCE: 373
aaggaggcat gccccacagg cctgtacaca cacagcggtg agtgctgcaa agcctgcaac     60
ctgggcgagg gtgtggccca gccttgtgga gccaaccaga ccgtgtgtga gccctgcctg     120
gacagcgtga cgttctccga cgtggtgagc gcgaccgagc cgtgcaagcc gtgcaccgag     180
tgcgtggggc tccagagcat gtcggcgccg tgcgtggagg ccgacgacgc cgtgtgccgc     240
tgcgcctacg gctactacca ggatgagacg actgggcgct gcgaggcgtg ccgcgtgtgc     300
gaggcgggct cgggcctcgt gttctcctgc caggacaagc agaacaccgt gtgcgaggag     360
tgccccgacg gcacgtattc cgacgaggcc aaccacgtgg accgtgcct gccctgcacc     420 gtgtgcgagg acaccgagcg ccagctccgc gagtgcacac gctgggccga cgccgagtgc     480
gaggagatcc ctggccgttg gattacacgg tccacacccc cagagggctc ggacagcaca     540 gccccccagca cccaggagcc tgaggcacct ccagaacaag acctcatagc cagcacggtg     600
gcaggtgtgg tgaccacagt gatgggcagc tcccagcccg tggtgacccg aggcaccacc     660
gacaac                                                                666
```

```
<210> SEQ ID NO 374
<211> LENGTH: 66
<212> TYPE: DNA
<213> ORGANISM: Artificial Sequence
<220> FEATURE:
<223> OTHER INFORMATION: Synthetic: NY-ESO-1 construct NGFR
      transmembrane

<400> SEQUENCE: 374
ctcatccctg tctattgctc catcctggct gctgtggttg tgggccttgt ggcctacata     60
gccttc                                                                66
```

```
<210> SEQ ID NO 375
<211> LENGTH: 15
<212> TYPE: DNA
<213> ORGANISM: Artificial Sequence
<220> FEATURE:
<223> OTHER INFORMATION: Synthetic: NY-ESO-1 construct NGFR cytoplasmic
``` tail

<400> SEQUENCE: 375
aagaggtgga acagt                                                       15

<210> SEQ ID NO 376
<211> LENGTH: 1227
<212> TYPE: DNA
<213> ORGANISM: Artificial Sequence
<220> FEATURE:
<223> OTHER INFORMATION: Synthetic: Monovalent CD161 (KLRB1)-Fc Fusion

<400> SEQUENCE: 376
gccgccacca tggtaccgtg cacgctgctc ctgctgttgg cggccgccct ggctccgact    60
cagacccgcg cgcagaaatc atcaatagaa aaatgcagtg tggacattca acagagcagg   120
aataaaacaa cagagagacc gggtctctta aactgcccaa tatattggca gcaactccga   180
gagaaatgct tgttattttc tcacactgtc aaccctcgga ataacagtct agctgattgt   240
tccaccaaag aatccagcct gctgcttatt cgagataagg atgaattgat acacacacag   300
aacctgatac gtgacaaagc aattctgttt tggattggat aaattttttc attatcagaa   360
aagaactgga agtggataaa cggctctttt ttaaattcta atgacttaga aattagaggt   420
gatgctaaag aaaacagctg tatttccatc tcacagacat ctgtgtattc tgagtactgt   480
agtacagaaa tcagatggat ctgccaaaaa gaactaacac ctgtgagaaa taaagtgtat   540
cctgactctg atcaggttg tccaccttgc ccagcacctg aactcctggg gggaccgtca   600
gtcttcctct tccccccaaa acccaaggac accctcatga tctcccggac ccctgaggtc   660
acatgcgtgg tggtggacgt gagccacgaa gaccctgagg tcaagttcaa ctggtacgtg   720
gacggcgtgg aggtgcataa tgccaagaca aagccgcggg aggagcagta caacagcacg   780
taccgtgtgg tcagcgtcct caccgtcctg caccaggact ggctgaatgg caaggagtac   840
aagtgcaagg tctccaacaa agccctccca gcccccatcg agaaaaccat ctccaaagcc   900
aaagggcagc cccgagaacc acaggtgtac accctgcccc catcccggga tgagctgacc   960
aagaaccagg tcagcctgac ctgcctggtc aaaggcttct atcccagcga catcgccgtg  1020
gagtgggaga gcaatgggca gccggagaac aactacaaga ccacgcctcc cgtgctggac  1080
tccgacggct ccttcttcct ctacagcaag ctcaccgtgg acaagagcag gtggcagcag  1140
gggaacgtct tctcatgctc cgtgatgcat gaggctctgc acaaccacta cacgcagaag  1200
agcctctccc tgtctccggg taaatga                                      1227

<210> SEQ ID NO 377
<211> LENGTH: 477
<212> TYPE: DNA
<213> ORGANISM: Artificial Sequence
<220> FEATURE:
<223> OTHER INFORMATION: Synthetic: CD161 (KLRB1) extracellular domain

<400> SEQUENCE: 377
cagaaatcat caatagaaaa atgcagtgtg gacattcaac agagcaggaa taaacaaca     60 gagagaccgg gtctcttaaa ctgcccaata tattggcagc aactccgaga gaaatgcttg   120
ttattttctc acactgtcaa cccttggaat aacagtctag ctgattgttc accaaagaa    180 tccagcctgc tgcttattcg agataaggat gaattgatac acacacagaa cctgatacgt   240
gacaaagcaa ttctgttttg gattggatta aattttttcat tatcagaaaa gaactggaag  300
tggataaacg ctctttttt aaattctaat gacttagaaa ttagaggtga tgctaaagaa   360

```
aacagctgta tttccatctc acagacatct gtgtattctg agtactgtag tacagaaatc    420
agatggatct gccaaaaaga actaacacct gtgagaaata agtgtatcc tgactct        477
```

<210> SEQ ID NO 378
<211> LENGTH: 9
<212> TYPE: DNA
<213> ORGANISM: Artificial Sequence
<220> FEATURE:
<223> OTHER INFORMATION: Synthetic: Flexible linker

<400> SEQUENCE: 378

```
ggatcaggt                                                              9
```

<210> SEQ ID NO 379
<211> LENGTH: 666
<212> TYPE: DNA
<213> ORGANISM: Homo sapiens
<220> FEATURE:
<221> NAME/KEY: misc_feature
<222> LOCATION: (1)..(666)
<223> OTHER INFORMATION: Human IgG1 heavy chain hinge and Fc region

<400> SEQUENCE: 379

```
tgtccacctt gcccagcacc tgaactcctg gggggaccgt cagtcttcct cttccccca     60 aaacccaagg acaccctcat gatctcccgg acccctgagg tcacatgcgt ggtggtggac   120
gtgagccacg aagaccctga ggtcaagttc aactggtacg tggacggcgt ggaggtgcat   180
aatgccaaga caaagccgcg ggaggagcag tacaacagca cgtaccgtgt ggtcagcgtc   240
ctcaccgtcc tgcaccagga ctggctgaat ggcaaggagt acaagtgcaa ggtctccaac   300
aaagccctcc cagcccccat cgagaaaacc atctccaaag ccaaagggca gccccgagaa   360
ccacaggtgt acaccctgcc cccatcccgg gatgagctga ccaagaacca ggtcagcctg   420
acctgcctgg tcaaaggctt ctatcccagc gacatcgccg tggagtggga gagcaatggg   480
cagccggaga acaactacaa gaccacgcct cccgtgctgg actccgacgg ctccttcttc   540
ctctacagca agctcaccgt ggacaagagc aggtggcagc aggggaacgt cttctcatgc   600
tccgtgatgc atgaggctct gcacaaccac tacacgcaga gagcctctc cctgtctccg   660 ggtaaa                                                                666
```

<210> SEQ ID NO 380
<211> LENGTH: 1227
<212> TYPE: DNA
<213> ORGANISM: Artificial Sequence
<220> FEATURE:
<223> OTHER INFORMATION: Synthetic: Monovalent CD161 (KLRB1)-Fc Fusion,
      substitution of free cysteine to serine

<400> SEQUENCE: 380

```
gccgccacca tggtaccgtg cacgctgctc ctgctgttgg cggccgccct ggctccgact    60
cagacccgcg cgcagaaatc atcaatagaa aaatccagtg tggacattca acagagcagg   120
aataaaacaa cagagagacc gggtctctta aactgcccaa tatattggca gcaactccga   180
gagaaatgct tgttattttc tcacactgtc aaccccttgga ataacagtct agctgattgt   240
tccaccaaag aatccagcct gctgcttatt cgagataagg atgaattgat acacacacag   300
aacctgatac gtgacaaagc aattctgttt tggattggat taaatttttc attatcagaa   360
aagaactgga gtggataaaa cggctctttt ttaaattcta atgacttaga aattagaggt   420
gatgctaaag aaaacagctg tatttccatc tcacagacat ctgtgtattc tgagtactgt   480
```

```
agtacagaaa tcagatggat ctgccaaaaa gaactaacac ctgtgagaaa taaagtgtat    540
cctgactctg gatcaggttg tccaccttgc ccagcacctg aactcctggg gggaccgtca    600
gtcttcctct tccccccaaa acccaaggac accctcatga tctcccggac ccctgaggtc    660
acatgcgtgg tggtggacgt gagccacgaa gaccctgagg tcaagttcaa ctggtacgtg    720
gacggcgtgg aggtgcataa tgccaagaca aagccgcggg aggagcagta caacagcacg    780
taccgtgtgg tcagcgtcct caccgtcctg caccaggact ggctgaatgg caaggagtac    840
aagtgcaagg tctccaacaa agccctccca gcccccatcg agaaaaccat ctccaaagcc    900
aaagggcagc cccgagaacc acaggtgtac accctgcccc catcccggga tgagctgacc    960
aagaaccagg tcagcctgac ctgcctggtc aaaggcttct atcccagcga catcgccgtg   1020
gagtgggaga gcaatgggca gccggagaac aactacaaga ccacgcctcc cgtgctggac   1080
tccgacggct ccttcttcct ctacagcaag ctcaccgtgg acaagagcag gtggcagcag   1140
gggaacgtct tctcatgctc cgtgatgcat gaggctctgc acaaccacta cacgcagaag   1200
agcctctccc tgtctccggg taaataa                                       1227
```

<210> SEQ ID NO 381
<211> LENGTH: 477
<212> TYPE: DNA
<213> ORGANISM: Homo sapiens
<220> FEATURE:
<221> NAME/KEY: misc_feature
<222> LOCATION: (1)..(477)
<223> OTHER INFORMATION: Extracellular domain human CD161 (KLRB1) (C29S)

<400> SEQUENCE: 381

```
cagaaatcat caatagaaaa atccagtgtg gacattcaac agagcaggaa taaaacaaca     60
gagagaccgg gtctcttaaa ctgcccaata tattggcagc aactccgaga gaaatgcttg    120
ttattttctc acactgtcaa cccttggaat aacagtctag ctgattgttc caccaaagaa    180
tccagcctgc tgcttattcg agataaggat gaattgatac acacacagaa cctgatacgt    240
gacaaagcaa ttctgttttg gattggatta aattttcat tatcagaaaa gaactggaag     300
tggataaacg gctctttttt aaattctaat gacttagaaa ttagaggtga tgctaaagaa    360
aacagctgta tttccatctc acagacatct gtgtattctg agtactgtag tacagaaatc    420
agatggatct gccaaaaaga actaacacct gtgagaaata aagtgtatcc tgactct       477
```

<210> SEQ ID NO 382
<211> LENGTH: 687
<212> TYPE: DNA
<213> ORGANISM: Homo sapiens
<220> FEATURE:
<221> NAME/KEY: misc_feature
<222> LOCATION: (1)..(687)
<223> OTHER INFORMATION: Full-length human CD161 (KLRB1)

<400> SEQUENCE: 382

```
gccgccacca tggatcaaca ggccatttat gccgaactca atcttccaac ggattctggc    60
ccggagagtt ctagcccctc cagcctgccg cgagatgtat gtcaaggtag cccttggcat   120
cagtttgcac tcaaacttag ttgcgcagga attatactgc tcgtgcttgt cgtaaccggg   180
ttgagcgtat cagtgactag tttgatccag aaatctagta tagagaagtg ttctgtagac   240
atccaacaaa gtagaaataa acaactgaa cggcctggcc tgcttaattg tccgatttat    300
tggcagcagc tccgcgagaa atgcctcctt ttcagtcata ccgttaatcc ttggaataac   360
```
agtctcgccg attgttccac aaaagaaagc tctcttctgc ttatccgcga taaggacgaa    420
ctgattcaca ctcaaaatct catccgggac aaggcaattc tcttctggat tggacttaat    480
tttagcctgt ccgagaagaa ttggaaatgg atcaacggtt catttctcaa ctctaacgac    540
cttgagattc gcggggatgc taagaaaat tcctgcatct ctataagcca gacgagcgtg    600
tattctgagt attgcagcac ggaaattcgc tggatatgcc aaaaagaatt gacaccagtt    660
cgaaataagg tctacccgga ctcctga                                        687

<210> SEQ ID NO 383
<211> LENGTH: 135
<212> TYPE: DNA
<213> ORGANISM: Homo sapiens
<220> FEATURE:
<221> NAME/KEY: misc_feature
<222> LOCATION: (1)..(135)
<223> OTHER INFORMATION: Human CD161 (KLRB1) cytoplasmic domain

<400> SEQUENCE: 383
atggatcaac aggccattta tgccgaactc aatcttccaa cggattctgg cccggagagt     60
tctagcccct ccagcctgcc gcgagatgta tgtcaaggta gcccttggca tcagtttgca    120
ctcaaactta gttgc                                                     135

<210> SEQ ID NO 384
<211> LENGTH: 63
<212> TYPE: DNA
<213> ORGANISM: Homo sapiens
<220> FEATURE:
<221> NAME/KEY: misc_feature
<222> LOCATION: (1)..(63)
<223> OTHER INFORMATION: Human CD161 (KLRB1) transmembrane region

<400> SEQUENCE: 384
gcaggaatta tactgctcgt gcttgtcgta accggggttga gcgtatcagt gactagtttg     60
atc                                                                   63

<210> SEQ ID NO 385
<211> LENGTH: 477
<212> TYPE: DNA
<213> ORGANISM: Homo sapiens
<220> FEATURE:
<221> NAME/KEY: misc_feature
<222> LOCATION: (1)..(477)
<223> OTHER INFORMATION: Human CD161 (KLRB1) Extracellular domain

<400> SEQUENCE: 385
cagaaatcta gtatagagaa gtgttctgta gacatccaac aaagtagaaa taaaacaact     60
gaacggcctg gcctgcttaa ttgtccgatt tattggcagc agctccgcga gaatgcctc    120 cttttcagtc ataccgttaa tccttggaat aacagtctcg ccgattgttc cacaaaagaa    180
agctctcttc tgcttatccg cgataaggac gaactgattc acactcaaaa tctcatccgg    240
gacaaggcaa ttctcttctg gattggactt aattttagcc tgtccgagaa gaattggaaa    300
tggatcaacg gttcatttct caactctaac gaccttgaga ttcgcgggga tgctaaagaa    360
aattcctgca tctctataag ccagacgagc gtgtattctg agtattgcag cacggaaatt    420
cgctggatat gccaaaaaga attgacacca gttcgaaata aggtctaccc ggactcc      477

<210> SEQ ID NO 386
<211> LENGTH: 1557
<212> TYPE: DNA
<213> ORGANISM: Artificial Sequence
<220> FEATURE:
<223> OTHER INFORMATION: Synthetic: Bivalent human CLEC2D-Fc Fusion

<400> SEQUENCE: 386

```
gccgccacca tggtaccgtg cacgctgctc ctgctgttgg cggccgccct ggctccgact      60
cagacccgcg cgagagctaa ctgccatcaa gagccatcag tatgtcttca agctgcatgc     120
ccagaaagct ggattggttt tcaaagaaag tgtttctatt tttctgatga caccaagaac     180
tggacatcaa gtcagaggtt ttgtgactca aagatgctga tcttgctca ggttgaaagc      240
ttccaggaac tgaatttcct gttgagatat aaaggcccat ctgatcactg gattgggctg     300
agcagagaac aaggccaacc atggaaatgg ataaatggta ctgaatggac aagacagttt     360
cctatcctgg gagcaggaga gtgtgcctat ttgaatgaca aggtgccag tagtgccagg      420
cactacacag agaggaagtg gatttgttcc aaatcagata tacatgtcgg atcaggcagc     480
ggaagagcga attgccatca ggagccatcc gtctgccttc aggccgcctg cccggagtcc     540
tggatagggt tccaacgcaa gtgtttttac ttcagtgacg acactaaaaa ttggacatct     600
tcacagagat tttgtgattc acaggacgct gacctggcgc aagtcgagtc atttcaggaa     660
cttaactttc tccttcggta caaagggcct tctgaccatt ggattggtct tagtcgcgaa     720
caggggcaac cttggaagtg gatcaatgga accgagtgga ctcggcagtt ccaatactg      780
ggggccgggg aatgtgcgta tcttaacgac aagggtgcct catcagcccg ccactacact     840
gagagaaaat ggatctgcag taaatccgac atccacgtgg ggagcggttg cccgccttgc     900
ccggccccag agctgctcgg cggtccgtcc gtattcctgt tcccacctaa gcctaaagat     960
acgttgatga ttagcagaac tcctgaagta acctgtgtag tggtagacgt ctctcacgag    1020
gaccccgaag taaagtttaa ctggtacgta gatggtgtcg aagtccacaa cgctaagacc    1080
aaaccaaggg aggagcaata taactctacc tatcgagtag tttccgtatt gacggtgctg    1140
catcaagact ggctgaacgg aaaggaatat aaatgcaagg tctccaataa agcgttgcct    1200
gctccgattg aaaagacgat atcaaaagca aggggcagc cgagagaacc tcaagtatat    1260
actctcccctc cgtcccgcga tgaactgact aaaaatcagg tatcactgac atgtttggtc    1320
aaagggttct atccctccga tattgctgtc gagtgggaat caaatggtca gccagaaaac    1380
aactacaaga ccactccacc tgtcctggat tcagatggtt cattctttct gtactcaaaa    1440
ttgaccgtcg ataagtcacg atggcagcaa gggaatgtat tcagttgctc cgtcatgcac    1500
gaagcactgc acaatcatta cacccagaaa agtctttcat tgtcacccgg taaataa     1557
```

<210> SEQ ID NO 387
<211> LENGTH: 396
<212> TYPE: DNA
<213> ORGANISM: Homo sapiens
<220> FEATURE:
<221> NAME/KEY: misc_feature
<222> LOCATION: (1)..(396)
<223> OTHER INFORMATION: Human extracellular domain CLEC2D copy 1

<400> SEQUENCE: 387

```
agagctaact gccatcaaga gccatcagta tgtcttcaag ctgcatgccc agaaagctgg     60
attggttttc aaagaaagtg tttctatttt tctgatgaca ccaagaactg gacatcaagt    120
cagaggtttt gtgactcaca agatgctgat cttgctcagg ttgaaagctt ccaggaactg    180
aatttcctgt tgagatataa aggcccatct gatcactgga ttgggctgag cagagaacaa    240
ggccaaccat ggaaatggat aaatggtact gaatggacaa gacagtttcc tatcctggga    300
```

```
gcaggagagt gtgcctattt gaatgacaaa ggtgccagta gtgccaggca ctacacagag    360
aggaagtgga tttgttccaa atcagatata catgtc                              396
```

<210> SEQ ID NO 388
<211> LENGTH: 15
<212> TYPE: DNA
<213> ORGANISM: Artificial Sequence
<220> FEATURE:
<223> OTHER INFORMATION: Synthetic: Flexible GSG linker

<400> SEQUENCE: 388

```
ggatcaggca gcgga                                                     15
```

<210> SEQ ID NO 389
<211> LENGTH: 396
<212> TYPE: DNA
<213> ORGANISM: Homo sapiens
<220> FEATURE:
<221> NAME/KEY: misc_feature
<222> LOCATION: (1)..(396)
<223> OTHER INFORMATION: Human extracellular domain CLEC2D copy 2

<400> SEQUENCE: 389

```
agagcgaatt gccatcagga gccatccgtc tgccttcagg ccgcctgccc ggagtcctgg    60 ataggggttcc aacgcaagtg tttttacttc agtgacgaca ctaaaaattg gacatcttca   120
cagagatttt gtgattcaca ggacgctgac ctggcgcaag tcgagtcatt tcaggaactt    180
aactttctcc ttcggtacaa agggccttct gaccattgga ttggtcttag tcgcgaacag    240 gggcaaacctt ggaagtggat caatggaacc gagtggactc ggcagtttcc aatactgggg   300
gccggggaat gtgcgtatct aacgacaag ggtgcctcat cagcccgcca ctacactgag     360
agaaaatgga tctgcagtaa atccgacatc cacgtg                              396
```

<210> SEQ ID NO 390
<211> LENGTH: 9
<212> TYPE: DNA
<213> ORGANISM: Artificial Sequence
<220> FEATURE:
<223> OTHER INFORMATION: Synthetic: Flexible linker

<400> SEQUENCE: 390

```
gggagcggt                                                             9
```

<210> SEQ ID NO 391
<211> LENGTH: 666
<212> TYPE: DNA
<213> ORGANISM: Artificial Sequence
<220> FEATURE:
<223> OTHER INFORMATION: Synthetic: Human IgG1 Fc  (used in bivalent
      CLEC2D-Fc construct)

<400> SEQUENCE: 391

```
tgcccgcctt gcccggcccc agagctgctc ggcggtccgt ccgtattcct gttcccacct    60
aagcctaaag atacgttgat gattagcaga actcctgaag taacctgtgt agtggtagac    120
gtctctcacg aggaccccga agtaaagttt aactggtacg tagatggtgt cgaagtccac    180
aacgctaaga ccaaaccaag ggaggagcaa tataactcta cctatcgagt agtttccgta    240
ttgacggtgc tgcatcaaga ctggctgaac ggaaaggaat ataaatgcaa ggtctccaat    300
aaagcgttgc ctgctccgat tgaaaagacg atatcaaaag caaggggggca gccgagagaa   360 cctcaagtat atactctccc tccgtcccgc gatgaactga ctaaaaatca ggtatcactg    420
```

```
acatgtttgg tcaaagggtt ctatccctcc gatattgctg tcgagtggga atcaaatggt    480
cagccagaaa acaactacaa gaccactcca cctgtcctgg attcagatgg ttcattcttt    540
ctgtactcaa aattgaccgt cgataagtca cgatggcagc aagggaatgt attcagttgc    600
tccgtcatgc acgaagcact gcacaatcat tacacccaga aaagtctttc attgtcaccc    660
ggtaaa                                                              666
```

```
<210> SEQ ID NO 392
<211> LENGTH: 9
<212> TYPE: PRT
<213> ORGANISM: Artificial Sequence
<220> FEATURE:
<223> OTHER INFORMATION: Synthetic: NY-ESO-1 1G4 peptide epitope

<400> SEQUENCE: 392

Ser Leu Leu Met Trp Ile Thr Gln Cys
1               5

<210> SEQ ID NO 393
<211> LENGTH: 107
<212> TYPE: PRT
<213> ORGANISM: Artificial Sequence
<220> FEATURE:
<223> OTHER INFORMATION: Synthetic: VL61

<400> SEQUENCE: 393

Gly Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Leu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Ala Pro Leu
                85                  90                  95

Thr Phe Gly Gln Gly Thr Lys Val Glu Ile Lys
            100                 105

<210> SEQ ID NO 394
<211> LENGTH: 321
<212> TYPE: DNA
<213> ORGANISM: Artificial Sequence
<220> FEATURE:
<223> OTHER INFORMATION: Synthetic: VL61.0

<400> SEQUENCE: 394
ggcatccaga tgacccagtc tccatcctcc ctgtctgcat ctgtaggaga cagagtcacc     60
atcacttgcc gggcaagtca gagcattagc agctatttaa attggtatca gcagaaacca    120
gggaaagccc ctaagctcct gatctatgct gcatccagtt tgctaagtgg ggtcccatca    180
aggttcagtg gcagtggatc tgggacagat tcactctcac catcagcagt ctgcaacct     240 gaagattttg caacttacta ctgtcaacag acgtacagtg ccccgctcac gttcggccaa    300
gggaccaagg tggaaatcaa a                                              321

<210> SEQ ID NO 395
<211> LENGTH: 107
```

```
<212> TYPE: PRT
<213> ORGANISM: Artificial Sequence
<220> FEATURE:
<223> OTHER INFORMATION: Synthetic: VL62

<400> SEQUENCE: 395

Gly Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asp Thr Pro Leu
                85                  90                  95

Thr Phe Gly Gln Gly Thr Lys Val Glu Ile Lys
                100                 105

<210> SEQ ID NO 396
<211> LENGTH: 321
<212> TYPE: DNA
<213> ORGANISM: Artificial Sequence
<220> FEATURE:
<223> OTHER INFORMATION: Synthetic: VL62.0

<400> SEQUENCE: 396
ggcatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcaacag agttacgata ccccgctcac gttcggccaa     300
gggaccaagg tggaaatcaa a                                              321
```